US012735710B2

(12) United States Patent
Brown et al.

(10) Patent No.: US 12,735,710 B2
(45) Date of Patent: Sep. 15, 2026

(54) COMPOSITIONS AND METHODS FOR INHIBITING ANGPTL3 EXPRESSION

(71) Applicant: Dicerna Pharmaceuticals, Inc., Lexington, MA (US)

(72) Inventors: Bob D. Brown, Lexington, MA (US); Henryk T. Dudek, Belmont, MA (US); Utsav Saxena, Watertown, MA (US); Marc Abrams, Natick, MA (US); Anton Turanov, Revere, MA (US)

(73) Assignee: Dicerna Pharmaceuticals, Inc., Cambridge, MA (US)

( * ) Notice: Subject to any disclaimer, the term of this patent is extended or adjusted under 35 U.S.C. 154(b) by 771 days.

(21) Appl. No.: 17/906,532

(22) PCT Filed: Mar. 18, 2021

(86) PCT No.: PCT/US2021/022967

§ 371 (c)(1),
(2) Date: Sep. 16, 2022

(87) PCT Pub. No.: WO2021/188795

PCT Pub. Date: Sep. 23, 2021

(65) Prior Publication Data

US 2023/0287425 A1 Sep. 14, 2023

Related U.S. Application Data

(60) Provisional application No. 62/991,335, filed on Mar. 18, 2020.

(51) Int. Cl.

| | |
|---|---|
| ***C07H 21/02*** | (2006.01) |
| ***A61K 31/713*** | (2006.01) |
| ***A61K 47/54*** | (2017.01) |
| ***C12N 15/113*** | (2010.01) |

(52) U.S. Cl.

CPC ........ *C12N 15/1136* (2013.01); *A61K 31/713* (2013.01); *A61K 47/549* (2017.08); *C12N 2310/14* (2013.01); *C12N 2310/315* (2013.01); *C12N 2310/321* (2013.01); *C12N 2310/322* (2013.01); *C12N 2310/351* (2013.01); *C12N 2310/531* (2013.01)

(58) Field of Classification Search

CPC .......................... C12N 15/113; C12N 2310/11
See application file for complete search history.

(56) References Cited

U.S. PATENT DOCUMENTS

| | | | | |
|---|---|---|---|---|
| 8,372,968 | B2 | 2/2013 | Tuschl et al. | |
| 8,513,207 | B2 | 8/2013 | Brown | |
| 8,653,047 | B2 | 2/2014 | Crooke et al. | |
| 8,883,996 | B2 | 11/2014 | Rossi et al. | |
| 8,927,705 | B2 | 1/2015 | Brown | |
| 9,012,138 | B2 | 4/2015 | Tuschl et al. | |
| 9,012,621 | B2 | 4/2015 | Tuschl et al. | |
| 9,193,753 | B2 | 11/2015 | Tuschl et al. | |
| 10,875,884 | B2 | 12/2020 | Prakash et al. | |
| 11,118,183 | B2 | 9/2021 | Freier et al. | |
| 12,173,286 | B2 * | 12/2024 | Khvorova | C12N 15/111 |

FOREIGN PATENT DOCUMENTS

| | | | | |
|---|---|---|---|---|
| CN | 103890000 | A | 6/2014 | |
| KR | 2021-0013730 | A | 2/2021 | |
| WO | WO-2010033225 | A2 | 3/2010 | |
| WO | WO-2012177784 | A2 | 12/2012 | |
| WO | 2013074974 | A2 | 5/2013 | |
| WO | WO-2015100394 | A1 * | 7/2015 | A61P 43/00 |
| WO | WO-2015168589 | A2 | 11/2015 | |
| WO | WO-2016100401 | A1 | 6/2016 | |
| WO | 2016168286 | A1 | 10/2016 | |
| WO | WO-2018045317 | A1 | 3/2018 | |
| WO | WO-2018154387 | A1 | 8/2018 | |
| WO | WO-2019055633 | A1 | 3/2019 | |
| WO | WO 2019/204021 | A1 | 10/2019 | |
| WO | 2021188795 | A1 | 9/2021 | |

OTHER PUBLICATIONS

Elbashir et al. (The EMBO Journal, vol. 20, No. 23, pp. 6877-6888, 2001).*
Bertrand et al. (Biochemical and Biophysical Research Communications, 296, 2002, 1000-1004).*
Calkins (2015, University of California, Dissertation, pp. 1-252).*
PCT International Search Report and Written Opinion from PCT/US2021/022967 dated May 28, 2021.
Invitation to Pay Additional Fees for Application No. PCT/US2021/022967, mailed Jun. 9, 2021.
International Preliminary Report on Patentability for Application No. PCT/US2021/022967, mailed Sep. 29, 2022.

* cited by examiner

*Primary Examiner* — Amy Rose Hudson
(74) *Attorney, Agent, or Firm* — Wolf, Greenfield & Sacks, P.C.

(57) ABSTRACT

Oligonucleotides are provided herein that inhibit angiopoietin-like protein 3 (ANGPTL3) expression. Also provided are compositions including the same and uses thereof, particularly uses relating to treating diseases, disorders and/or conditions associated with ANGPTL3 expression.

19 Claims, 14 Drawing Sheets

Specification includes a Sequence Listing.

COMPOSITIONS AND METHODS FOR INHIBITING ANGPTL3 EXPRESSION

RELATED APPLICATIONS

This application is a National Stage of International Application No. PCT/US2021/022967, filed Mar. 18, 2021, which claims the benefit under 35 U.S.C. § 119 (e) of U.S. Provisional Patent Application No. 62/991,335, filed Mar. 18, 2020, the contents of each of which are herein incorporated by reference in their entireties.

TECHNICAL FIELD

The disclosure relates to oligonucleotides that inhibit angiopoietin-like protein 3 (ANGPTL3) expression and uses thereof, particularly uses relating to treating diseases, disorders and/or conditions associated with ANGPTL3 expression.

REFERENCE TO THE SEQUENCE LISTING

The disclosure is being filed along with a Sequence Listing in electronic format. The Sequence Listing is provided as a file entitled 400930_182359_SL.txt, created on Mar. 18, 2021, having a file size of 371 KB. The information in electronic format of the Sequence Listing is incorporated herein by reference in its entirety.

BACKGROUND

Lipid metabolism disorders can result in elevated levels of serum lipids, such as triglycerides and/or cholesterol. Elevated serum lipids are strongly associated with high blood pressure, cardiovascular disease, diabetes and other pathological conditions. Despite treatment advances, there remains a very high, unmet, medical need for therapies to treat cardiovascular and metabolic diseases.

Hypertriglyceridemia is a lipid metabolism disorder characterized by an abnormally elevated concentration of triglyceride in the blood (e.g., >150 mg/dL). Hypertriglyceridemia has been associated with the development of cardiovascular diseases (e.g., arteriosclerosis). Severe hypertriglyceridemia (e.g., >500 mg/dL) may cause pancreatitis, eruptive xanthomas or lipemia retinalis. In some cases, extremely high levels of chylomicrons can cause chylomicronemia syndrome, which is characterized by recurrent abdominal pain, nausea, vomiting and pancreatitis (Pejic & Lee (2006) *J. Am. Board. Fam. Med.* 19:310-316). Hyperlipidemia is another lipid metabolism disorder that is characterized by elevated levels of any one or all lipids and/or lipoproteins in the blood.

ANGPTL3 is a member of the angiopoietin-like family of secreted proteins that regulates lipid metabolism and that is primarily expressed in the liver (Koishi et al. (2002) *Nat. Genet.* 30:151-157). ANGPTL3 inhibits lipoprotein lipase (LPL), which catalyzes the hydrolysis of triglycerides, and inhibits endothelial lipase (EL), which hydrolyzes high density lipoprotein (HDL) phospholipids.

BRIEF SUMMARY

Aspects of the disclosure relate to compositions and methods for treating a disease, disorder and/or condition related to ANGPTL3 expression. The disclosure is based, in part, on the discovery and development of oligonucleotides that selectively inhibit and/or reduce ANGPTL3 expression.

In some embodiments, the disclosure provides an oligonucleotide for reducing ANGPTL3 expression, where the oligonucleotide comprises an antisense strand comprising a sequence as set forth in any one of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, and 116.

In some embodiments, the disclosure provides an oligonucleotide for reducing ANGPTL3 expression, where the oligonucleotide comprises a sense strand comprising a sequence as set forth in any one of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, and 115.

In some embodiments, the oligonucleotide for reducing ANGPTL3 expression comprises an antisense strand of 15 to 30 nucleotides in length and a sense strand of 15 to 40 nucleotides in length, where the antisense strand has a region of complementarity to a target sequence of ANGPTL3 as set forth in any one of SEQ ID NOs: 125, 126, 127, 118, 119, 120, 121, 122, 123, 124, and 117, and where the region of complementarity is at least 15 contiguous nucleotides in length.

In some embodiments, the antisense strand is 19 to 27 nucleotides in length or 21 to 27 nucleotides in length. In some embodiments, the antisense strand is 22 nucleotides in length.

In some embodiments, the sense strand is 19 to 40 nucleotides in length. In some embodiments, the sense strand is 36 nucleotides in length.

In some embodiments, the oligonucleotide for reducing ANGPTL3 expression has a duplex region of at least 19 nucleotides in length or at least 21 nucleotides in length. In some embodiments, the duplex region is 20 nucleotides in length.

In some embodiments, the region of complementarity to ANGPTL3 is at least 19 contiguous nucleotides in length or at least 21 contiguous nucleotides in length.

In some embodiments, the oligonucleotide for reducing ANGPTL3 expression comprises on the sense strand at its 3' end a stem-loop set forth as: S1-L-S2, wherein S1 is complementary to S2, and where L forms a loop between S1 and S2 of 3 to 5 nucleotides in length.

In some embodiments, an oligonucleotide for reducing ANGPTL3 expression comprises an antisense strand and a sense strand, where the antisense strand is 21 to 27 nucleotides in length and has a region of complementarity to ANGPTL3, where the sense strand comprises at its 3' end a stem-loop set forth as: S1-L-S2, where S1 is complementary to S2, where L forms a loop between S1 and S2 of 3 to 5 nucleotides in length, and where the antisense strand and the sense strand form a duplex structure of at least 19 nucleotides in length but are not covalently linked.

In some embodiments, the loop L is a tetraloop. In some embodiments, L is 4 nucleotides in length. In some embodiments, L comprises a sequence GAAA.

In some embodiments, the oligonucleotide for reducing ANGPTL3 expression comprises an antisense strand that is 27 nucleotides in length and a sense strand that is 25 nucleotides in length. In some embodiments, the oligonucleotide comprises an antisense strand that is 22 nucleotides in length and a sense strand that is 36 nucleotides in length.

In some embodiments, an oligonucleotide with a duplex region comprises a 3'-overhang sequence on the antisense strand. In some embodiments, the 3'-overhang sequence on the antisense strand is 2 nucleotides in length.

In some embodiments, the oligonucleotide for reducing ANGPTL3 expression comprises an antisense strand and a sense strand that are each in a range of 21 to 23 nucleotides in length. In some embodiments, the oligonucleotide comprises a duplex structure in a range of 19 to 21 nucleotides in length. In some such embodiments, the oligonucleotide comprises a 3'-overhang sequence of one or more nucleotides in length, where the 3'-overhang sequence is present on the antisense strand, the sense strand, or the antisense strand and sense strand. In some embodiments, the 3'-overhang sequence of 2 nucleotides in length, where the 3'-overhang sequence is on the antisense strand, and where the sense strand is 21 nucleotides in length and the antisense strand is 23 nucleotides in length, such that the sense strand and antisense strand form a duplex of 21 nucleotides in length.

In some embodiments, the oligonucleotide for reducing ANGPTL3 expression comprises at least one modified nucleotide. In some embodiments, the modified nucleotide comprises a 2'-modification. In some embodiments, all of the nucleotides of the oligonucleotide are modified, for example with a 2'-modification.

In some embodiments, the oligonucleotide for reducing ANGPTL3 expression comprises at least one modified internucleotide linkage, preferably a phosphorothioate linkage.

In some embodiments, the 4'-carbon of the sugar of the 5'-nucleotide of the antisense strand comprises a phosphate analog, for example, an oxymethylphosphonate, vinylphosphonate or malonylphosphonate.

In some embodiments, at least one nucleotide of the oligonucleotide is conjugated to one or more targeting ligands, such as a carbohydrate, amino sugar, cholesterol, polypeptide or lipid. In some embodiments, the targeting ligand comprises a N-acetylgalactosamine (GalNAc) moiety. In some embodiments, the GalNAc moiety comprises a monovalent GalNAc moiety, a bivalent GalNAc moiety, a trivalent GalNAc moiety, or a tetravalent GalNAc moiety.

In some embodiments, the targeting ligand is conjugated to one or more nucleotides of L of the stem-loop. In some embodiments, up to 4 nucleotides of L of the stem-loop are each conjugated to a monovalent GalNAc moiety.

In some embodiments, the oligonucleotide for reducing ANGPTL3 expression is an RNAi oligonucleotide.

In another aspect, the disclosure provides a method of reducing ANGPTL3 expression in a cell, a population of cells or a subject by administering an oligonucleotide herein. In some embodiments, a method of for reducing ANGPTL3 expression in a cell, a population of cells or a subject comprises a step of contacting the cell or the population of cells or administering to the subject an effective amount of an oligonucleotide herein, or a pharmaceutical composition thereof. In some embodiments, the method for reducing ANGPTL3 expression comprises reducing an amount or a level of ANGPTL3 mRNA, an amount or a level of ANGPTL3 protein, or both.

In some embodiments, the disclosure provides a method for reducing an amount or level of triglyceride (TG) in a subject by administering to the subject an effective amount of an oligonucleotide herein, or a pharmaceutical composition thereof.

In some embodiments, the disclosure provides a method for reducing an amount or level of cholesterol in a subject by administering to the subject an effective amount of the oligonucleotide herein, or a pharmaceutical composition thereof.

In some embodiments, a subject for treatment with an oligonucleotide herein has a disease, disorder or condition associated with ANGPTL3 expression. In some embodiments, a method for treating a subject having a disease, disorder or condition associated with ANGPTL3 expression comprises administering to the subject in need thereof a therapeutically effective amount of an oligonucleotide herein, or a pharmaceutical composition thereof, thereby treating the subject.

In some embodiments, an oligonucleotide herein for administration comprises a sense strand of 15 to 50 nucleotides in length and an antisense strand of 15 to 30 nucleotides in length, where the sense strand forms a duplex region with the antisense strand, where the sense strand comprises a sequence as set forth in any one of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, and 115, and where the antisense strand comprises a complementary sequence selected from SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, and 116, or pharmaceutical composition thereof, thereby treating the subject.

In some embodiments, a method for treating a subject having a disease, disorder or condition associated with ANGPTL3 expression comprises administering to the subject in need thereof a therapeutically effective amount of an oligonucleotide comprising a pair of sense and antisense strands selected from a row of the table set forth in Table 5, or pharmaceutical composition thereof, thereby treating the subject.

In some embodiments, the disease, disorder or condition associated with ANGPTL3 expression is selected from the group consisting of hypertriglyceridemia, obesity, hyperlipidemia, abnormal lipid and/or cholesterol metabolism, atherosclerosis, type II diabetes mellitus, cardiovascular disease, coronary artery disease, non-alcoholic steatohepatitis (NASH), non-alcoholic fatty liver disease (NAFLD), homozygous and heterozygous familial hypercholesterolemia, and statin-resistant hypercholesterolemia.

In some embodiments, the disease, disorder or condition associated with ANGPTL3 expression is cardiovascular disease, type II diabetes mellitus, hypertriglyceridemia, NASH, obesity, or a combination thereof.

In some embodiments, the oligonucleotide, or pharmaceutical composition thereof, is administered in combination with a second therapeutic agent or composition thereof.

In a further aspect, the present disclosure provides use of any of the oligonucleotides of the present disclosure, or the pharmaceutical composition thereof, in the manufacture of a medicament for the treatment of a disease, disorder or condition associated with ANGPTL3 expression.

In some embodiments, the oligonucleotide of the disclosure, or the pharmaceutical composition of the disclosure, is for use, or adaptable for use, in the treatment of a disease, disorder or condition associated with ANGPTL3 expression.

In a further aspect, the oligonucleotide of the present disclosure is provided in the form of a kit for treating a disease, disorder or condition associated with ANGPTL3 expression. In some embodiments, the kit comprises an oligonucleotide herein, and a pharmaceutically acceptable carrier. In some embodiments, the kit further includes a package insert comprising instructions for administration to a subject having a disease, disorder or condition associated with ANGPTL3 expression.

In some embodiments of the use or kits, the disease, disorder or condition associated with ANGPTL3 expression is selected from the group consisting of hypertriglyceridemia, obesity, hyperlipidemia, abnormal lipid and/or cholesterol metabolism, atherosclerosis, type II diabetes mellitus, cardiovascular disease, coronary artery disease, NASH, NAFLD, homozygous and heterozygous familial hypercholesterolemia, and statin-resistant hypercholesterolemia.

In some embodiments of the use or kits, the disease, disorder or condition associated with ANGPTL3 expression is cardiovascular disease, type II diabetes mellitus, hypertriglyceridemia, NASH, obesity, or a combination thereof.

DETAILED DESCRIPTION

I. Definitions

Figure 1:
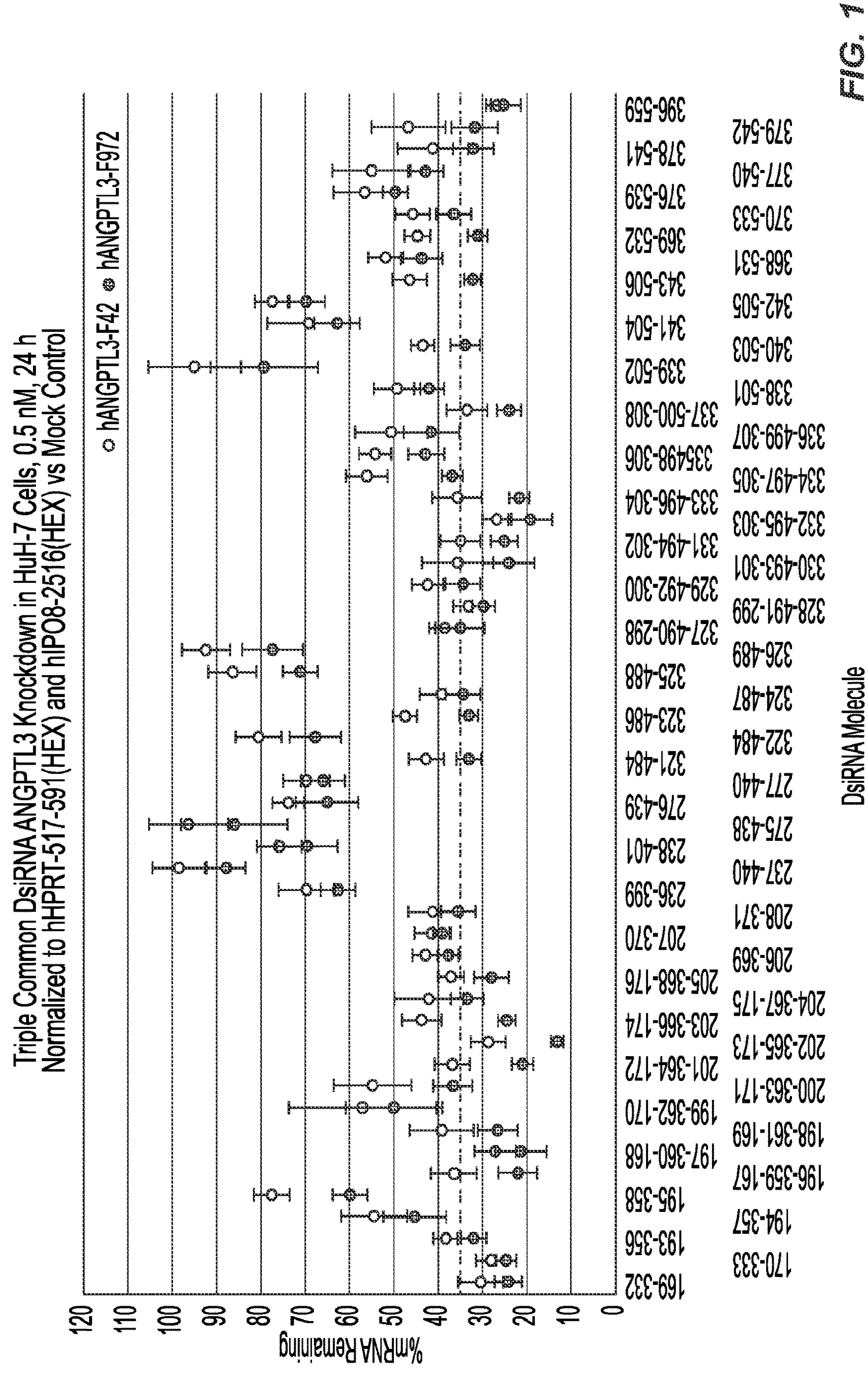
FIG. 1 provides a graph depicting the percent (%) of ANGPTL3 mRNA in HuH-7 cells transfected with the indicated DsiRNAs relative to the % of ANGPTL3 mRNA control mock-treated cells.
Figure 1:
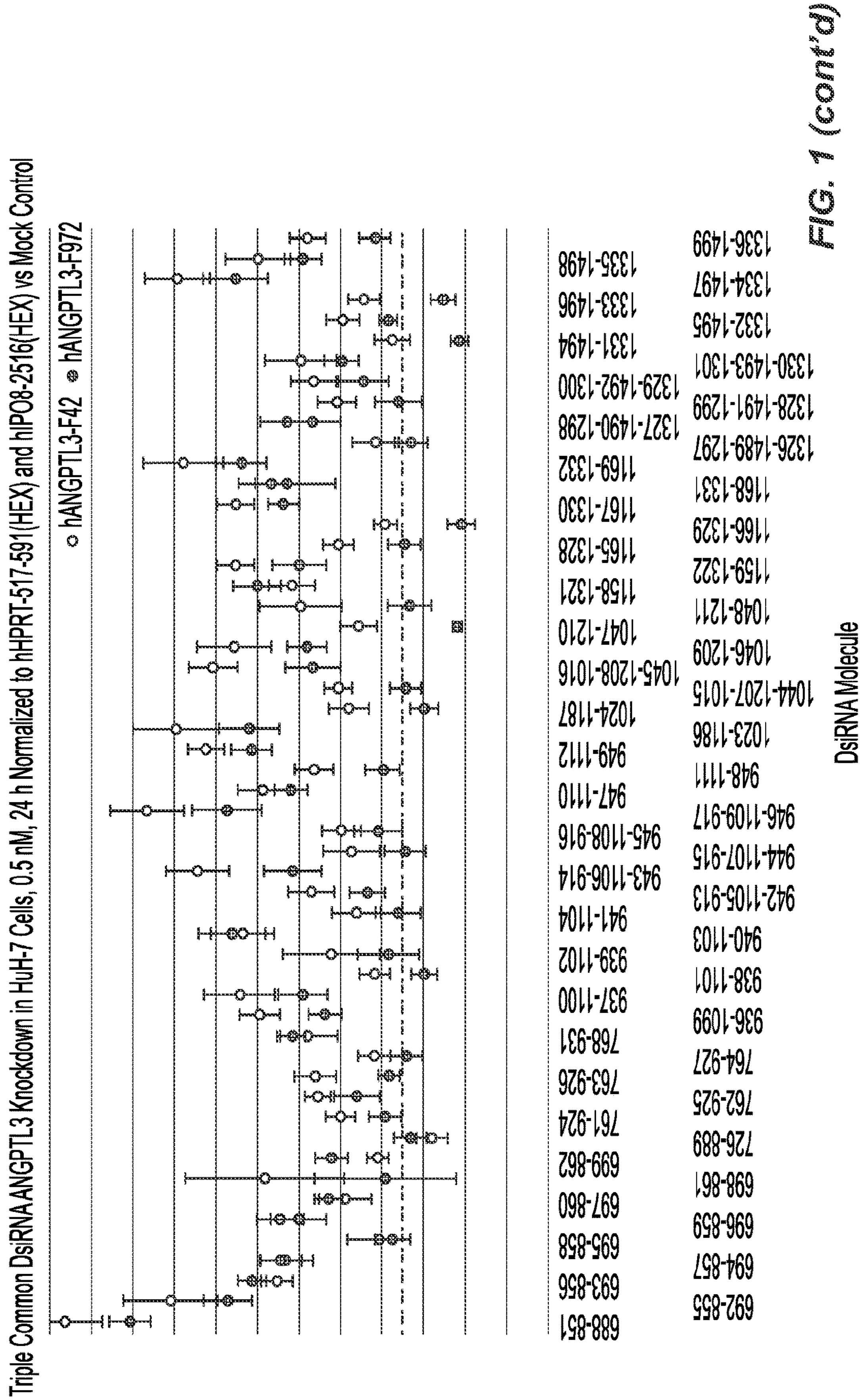

As used herein, “about,” as applied to one or more values of interest, refers to a value that is similar to a stated reference value. In certain embodiments, “about” refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1% or less in either direction (greater than or less than) of the stated reference value unless otherwise stated or otherwise evident from the context (except where such number would exceed 100% of a possible value).

As used herein, “administer,” “administering,” “administration” and the like refer to providing a substance (e.g., an oligonucleotide) to a subject in a manner that is pharmacologically useful (e.g., to treat a condition in the subject).

As used herein, “ANGPTL3” refers to angiopoietin-like protein 3, which is a member of the angiopoietin-like family of secreted polypeptides. ANGPTL3 is expressed predominantly in the liver of mammals, and the ANGPTL3 protein has the characteristic structure of angiopoietins, including a signal peptide, an N-terminal coiled-coil domain, and a C-terminal fibrinogen (FBN)-like domain. For the purposes of the disclosure, “ANGPTL3” refers to the ANGPTL3 from any vertebrate or mammal including, but not limited to, human, mouse, primate, monkey, bovine, chicken, rodent, rat, porcine, ovine and guinea pig. ANGPTL3 also refers to fragments and variants of native ANGPTL3 that maintain at least one in vivo or in vitro activity of a native ANGPTL3. ANGPTL3 encompasses full-length, unprocessed precursor forms of ANGPTL3, as well as mature forms resulting from post-translational cleavage of the signal peptide and forms resulting from proteolytic processing of the FBN-like domain. An exemplary sequence of a human ANGPTL3 mRNA transcript is publicly available (GenBank Accession No. GI: 41327750 (NM_014495.2)) and disclosed herein (SEQ ID NO: 128). An exemplary sequence of cynomolgus monkey ANGPTL3 mRNA is publicly available (GenBank Accession No. GI: 102136264 (XM_005543185.2)) and disclosed herein (SEQ ID NO: 129). An exemplary sequence of mouse ANGPTL3 mRNA is publicly available (GenBank Accession No. GI: 142388354 (NM_013913.3)) and disclosed herein (SEQ ID NO: 130). An exemplary sequence of rat ANGPTL3 is publicly available (GenBank Accession No. GI: 68163568 (NM_001025065.1) and disclosed herein (SEQ ID NO:131).

As used herein, “asialoglycoprotein receptor” or “ASGPR” refers to a bipartite C-type lectin formed by a major 48 kDa subunit (ASGPR-1) and minor 40 kDa subunit (ASGPR-2). ASGPR is primarily expressed on the sinusoidal surface of hepatocyte cells and has a major role in binding, internalizing and subsequent clearing of circulating glycoproteins that contain terminal galactose or GalNAc residues (asialoglycoproteins).

As used herein, “attenuate,” “attenuating,” “attenuation” and the like refer to reducing or effectively halting. As a non-limiting example, one or more of the treatments herein may reduce or effectively halt the onset or progression of dyslipidemia/hypertriglyceridemia/hyperlipidemia in a subject. This attenuation may be exemplified by, for example, a decrease in one or more aspects (e.g., symptoms, tissue characteristics, and cellular, inflammatory or immunological activity, etc.) of dyslipidemia/hypertriglyceridemia/hyperlipidemia, no detectable progression (worsening) of one or more aspects of dyslipidemia/hypertriglyceridemia/hyperlipidemia, or no detectable aspects of dyslipidemia/hypertriglyceridemia/hyperlipidemia in a subject when they might otherwise be expected.

As used herein, “complementary” refers to a structural relationship between two nucleotides (e.g., on two opposing nucleic acids or on opposing regions of a single nucleic acid strand) that permits the two nucleotides to form base pairs with one another. For example, a purine nucleotide of one nucleic acid that is complementary to a pyrimidine nucleotide of an opposing nucleic acid may base pair together by forming hydrogen bonds with one another. In some embodiments, complementary nucleotides can base pair in the Watson-Crick manner or in any other manner that allows for the formation of stable duplexes. In some embodiments, two nucleic acids may have regions of multiple nucleotides that are complementary with each other to form regions of complementarity, as described herein.

As used herein, "deoxyribonucleotide" refers to a nucleotide having a hydrogen in place of a hydroxyl at the 2' position of its pentose sugar when compared with a ribonucleotide. A modified deoxyribonucleotide is a deoxyribonucleotide having one or more modifications or substitutions of atoms other than at the 2' position, including modifications or substitutions in or of the sugar, phosphate group or base.

As used herein, "double-stranded oligonucleotide" or "ds oligonucleotide" refers to an oligonucleotide that is substantially in a duplex form. In some embodiments, the complementary base-pairing of duplex region(s) of a ds oligonucleotide is formed between antiparallel sequences of nucleotides of covalently separate nucleic acid strands. In some embodiments, complementary base-pairing of duplex region(s) of a ds oligonucleotide is formed between antiparallel sequences of nucleotides of nucleic acid strands that are covalently linked. In some embodiments, complementary base-pairing of duplex region(s) of a ds oligonucleotide is formed from single nucleic acid strand that is folded (e.g., via a hairpin) to provide complementary antiparallel sequences of nucleotides that base pair together. In some embodiments, a ds oligonucleotide comprises two covalently separate nucleic acid strands that are fully duplexed with one another. However, in some embodiments, a ds oligonucleotide comprises two covalently separate nucleic acid strands that are partially duplexed (e.g., having overhangs at one or both ends). In some embodiments, a ds oligonucleotide comprises antiparallel sequence of nucleotides that are partially complementary, and thus, may have one or more mismatches, which may include internal mismatches or end mismatches.

As used herein, "duplex," in reference to nucleic acids (e.g., oligonucleotides), refers to a structure formed through complementary base pairing of two antiparallel sequences of nucleotides.

As used herein, "excipient" refers to a non-therapeutic agent that may be included in a composition, for example, to provide or contribute to a desired consistency or stabilizing effect.

As used herein, "hepatocyte" or "hepatocytes" refers to cells of the parenchymal tissues of the liver. These cells make up about 70%-85% of the liver's mass and manufacture serum albumin, FBN and the prothrombin group of clotting factors (except for Factors 3 and 4). Markers for hepatocyte lineage cells include, but are not limited to, transthyretin (Ttr), glutamine synthetase (Glul), hepatocyte nuclear factor 1a (Hnf1a) and hepatocyte nuclear factor 4a (Hnf4a). Markers for mature hepatocytes may include, but are not limited to, cytochrome P450 (Cyp3a11), fumarylacetoacetate hydrolase (Fah), glucose 6-phosphate (G6p), albumin (Alb) and OC2-2F8. See, e.g., Huch et al. (2013) *Nature* 494:247-250.

As used herein, a "hepatotoxic agent" refers to a chemical compound, virus or other substance that is itself toxic to the liver or can be processed to form a metabolite that is toxic to the liver. Hepatotoxic agents may include, but are not limited to, carbon tetrachloride ($CCl_4$), acetaminophen (paracetamol), vinyl chloride, arsenic, chloroform, nonsteroidal anti-inflammatory drugs (such as aspirin and phenylbutazone).

As used herein, "labile linker" refers to a linker that can be cleaved (e.g., by acidic pH). A "fairly stable linker" refers to a linker that cannot be cleaved.

As used herein, "liver inflammation" or "hepatitis" refers to a physical condition in which the liver becomes swollen, dysfunctional and/or painful, especially as a result of injury or infection, as may be caused by exposure to a hepatotoxic agent. Symptoms may include jaundice (yellowing of the skin or eyes), fatigue, weakness, nausea, vomiting, appetite reduction and weight loss. Liver inflammation, if left untreated, may progress to fibrosis, cirrhosis, liver failure or liver cancer.

As used herein, "liver fibrosis" or "fibrosis of the liver" refers to an excessive accumulation in the liver of extracellular matrix proteins, which could include collagens (I, III, and IV), FBN, undulin, elastin, laminin, hyaluronan and proteoglycans resulting from inflammation and liver cell death. Liver fibrosis, if left untreated, may progress to cirrhosis, liver failure or liver cancer.

As used herein, "loop" refers to an unpaired region of a nucleic acid (e.g., oligonucleotide) that is flanked by two antiparallel regions of the nucleic acid that are sufficiently complementary to one another, such that under appropriate hybridization conditions (e.g., in a phosphate buffer, in a cells), the two antiparallel regions, which flank the unpaired region, hybridize to form a duplex (referred to as a "stem").

As used herein, "modified internucleotide linkage" refers to an internucleotide linkage having one or more chemical modifications when compared with a reference internucleotide linkage comprising a phosphodiester bond. In some embodiments, a modified nucleotide is a non-naturally occurring linkage. Typically, a modified internucleotide linkage confers one or more desirable properties to a nucleic acid in which the modified internucleotide linkage is present. For example, a modified nucleotide may improve thermal stability, resistance to degradation, nuclease resistance, solubility, bioavailability, bioactivity, reduced immunogenicity, etc.

As used herein, "modified nucleotide" refers to a nucleotide having one or more chemical modifications when compared with a corresponding reference nucleotide selected from: adenine ribonucleotide, guanine ribonucleotide, cytosine ribonucleotide, uracil ribonucleotide, adenine deoxyribonucleotide, guanine deoxyribonucleotide, cytosine deoxyribonucleotide and thymidine deoxyribonucleotide. In some embodiments, a modified nucleotide is a non-naturally occurring nucleotide. In some embodiments, a modified nucleotide has one or more chemical modification in its sugar, nucleobase and/or phosphate group. In some embodiments, a modified nucleotide has one or more chemical moieties conjugated to a corresponding reference nucleotide. Typically, a modified nucleotide confers one or more desirable properties to a nucleic acid in which the modified nucleotide is present. For example, a modified nucleotide may improve thermal stability, resistance to degradation, nuclease resistance, solubility, bioavailability, bioactivity, reduced immunogenicity, etc.

As used herein, "nicked tetraloop structure" refers to a structure of a RNAi oligonucleotide that is characterized by separate sense (passenger) and antisense (guide) strands, in which the sense strand has a region of complementarity with the antisense strand, and in which at least one of the strands, generally the sense strand, has a tetraloop configured to stabilize an adjacent stem region formed within the at least one strand.

As used herein, "oligonucleotide" refers to a short nucleic acid (e.g., less than about 100 nucleotides in length). An oligonucleotide may be single-stranded (ss) or ds. An oligonucleotide may or may not have duplex regions. As a set of non-limiting examples, an oligonucleotide may be, but is not limited to, a small interfering RNA (siRNA), microRNA (miRNA), short hairpin RNA (shRNA), dicer substrate interfering RNA (dsiRNA), antisense oligonucleotide, short siRNA or ss siRNA. In some embodiments, a ds oligonucleotide is an RNAi oligonucleotide.

As used herein, "overhang" refers to terminal non-base pairing nucleotide(s) resulting from one strand or region extending beyond the terminus of a complementary strand with which the one strand or region forms a duplex. In some embodiments, an overhang comprises one or more unpaired nucleotides extending from a duplex region at the 5' terminus or 3' terminus of a ds oligonucleotide. In certain embodiments, the overhang is a 3' or 5' overhang on the antisense strand or sense strand of a ds oligonucleotides.

As used herein, "phosphate analog" refers to a chemical moiety that mimics the electrostatic and/or steric properties of a phosphate group. In some embodiments, a phosphate analog is positioned at the 5' terminal nucleotide of an oligonucleotide in place of a 5'-phosphate, which is often susceptible to enzymatic removal. In some embodiments, a 5' phosphate analog contains a phosphatase-resistant linkage. Examples of phosphate analogs include, but are not limited to, 5' phosphonates, such as 5' methylenephosphonate (5'-MP) and 5'-(E)-vinylphosphonate (5'-VP). In some embodiments, an oligonucleotide has a phosphate analog at a 4'-carbon position of the sugar (referred to as a "4'-phosphate analog") at a 5'-terminal nucleotide. An example of a 4'-phosphate analog is oxymethylphosphonate, in which the oxygen atom of the oxymethyl group is bound to the sugar moiety (e.g., at its 4'-carbon) or analog thereof. See, e.g., U.S. Provisional Patent Application Nos. 62/383,207 (filed on 2 Sep. 2016) and 62/393,401 (filed on 12 Sep. 2016). Other modifications have been developed for the 5' end of oligonucleotides (see, e.g., Intl. Patent Application No. WO 2011/133871; U.S. Pat. No. 8,927,513; and Prakash et al. (2015) *Nucleic Acids Res.* 43:2993-3011).

As used herein, "reduced expression" of a gene (e.g., ANGPTL3) refers to a decrease in the amount or level of RNA transcript (e.g., ANGPTL3 mRNA) or protein encoded by the gene and/or a decrease in the amount or level of activity of the gene in a cell, a population of cells, a sample or a subject, when compared to an appropriate reference (e.g., a reference cell, population of cells, sample or subject). For example, the act of contacting a cell with an oligonucleotide herein (e.g., an oligonucleotide comprising an antisense strand having a nucleotide sequence that is complementary to a nucleotide sequence comprising ANGPTL3 mRNA) may result in a decrease in the amount or level of ANGPTL3 mRNA, protein and/or activity (e.g., via degradation of ANGPTL3 mRNA by the RNAi pathway) when compared to a cell that is not treated with the ds oligonucleotide. Similarly, and as used herein, "reducing expression" refers to an act that results in reduced expression of a gene (e.g., ANGPTL3). As used herein, "reduction of ANGPTL3 expression" refers to a decrease in the amount or level of ANGPTL3 mRNA, ANGPTL3 protein and/or ANGPTL3 activity in a cell, a population of cells, a sample or a subject when compared to an appropriate reference (e.g., a reference cell, population of cells, sample, or subject).

As used herein, "region of complementarity" refers to a sequence of nucleotides of a nucleic acid (e.g., a ds oligonucleotide) that is sufficiently complementary to an antiparallel sequence of nucleotides to permit hybridization between the two sequences of nucleotides under appropriate hybridization conditions (e.g., in a phosphate buffer, in a cell, etc.). In some embodiments, an oligonucleotide herein comprises a targeting sequence having a region of complementary to a mRNA target sequence.

As used herein, "ribonucleotide" refers to a nucleotide having a ribose as its pentose sugar, which contains a hydroxyl group at its 2' position. A modified ribonucleotide is a ribonucleotide having one or more modifications or substitutions of atoms other than at the 2' position, including modifications or substitutions in or of the ribose, phosphate group or base.

As used herein, "RNAi oligonucleotide" refers to either (a) a ds oligonucleotide having a sense strand (passenger) and antisense strand (guide), in which the antisense strand or part of the antisense strand is used by the Argonaute 2 (Ago2) endonuclease in the cleavage of a target mRNA or (b) a ss oligonucleotide having a single antisense strand, where that antisense strand (or part of that antisense strand) is used by the Ago2 endonuclease in the cleavage of a target mRNA.

As used herein, "strand" refers to a single, contiguous sequence of nucleotides linked together through internucleotide linkages (e.g., phosphodiester linkages or phosphorothioate linkages). In some embodiments, a strand has two free ends (e.g., a 5' end and a 3' end).

As used herein, "subject" means any mammal, including mice, rabbits and humans. In one embodiment, the subject is a human or NHP. Moreover, "individual" or "patient" may be used interchangeably with "subject."

As used herein, "synthetic" refers to a nucleic acid or other molecule that is artificially synthesized (e.g., using a machine (e.g., a solid-state nucleic acid synthesizer)) or that is otherwise not derived from a natural source (e.g., a cell or organism) that normally produces the molecule.

As used herein, "targeting ligand" refers to a molecule (e.g., a carbohydrate, amino sugar, cholesterol, polypeptide or lipid) that selectively binds to a cognate molecule (e.g., a receptor) of a tissue or cell of interest and that is conjugatable to another substance for purposes of targeting the other substance to the tissue or cell of interest. For example, in some embodiments, a targeting ligand may be conjugated to an oligonucleotide for purposes of targeting the oligonucleotide to a specific tissue or cell of interest. In some embodiments, a targeting ligand selectively binds to a cell surface receptor. Accordingly, in some embodiments, a targeting ligand when conjugated to an oligonucleotide facilitates delivery of the oligonucleotide into a particular cell through selective binding to a receptor expressed on the surface of the cell and endosomal internalization by the cell of the complex comprising the oligonucleotide, targeting ligand and receptor. In some embodiments, a targeting ligand is conjugated to an oligonucleotide via a linker that is cleaved following or during cellular internalization such that the oligonucleotide is released from the targeting ligand in the cell.

As used herein, "tetraloop" refers to a loop that increases stability of an adjacent duplex formed by hybridization of flanking sequences of nucleotides. The increase in stability is detectable as an increase in melting temperature ($T_m$) of an adjacent stem duplex that is higher than the $T_m$ of the adjacent stem duplex expected, on average, from a set of loops of comparable length consisting of randomly selected sequences of nucleotides. For example, a tetraloop can confer a $T_m$ of at least about 50° C., at least about 55° C., at least about 56° C., at least about 58° C., at least about 60° C., at least about 65° C., or at least about 75° C. in 10 mM $NaHPO_4$ to a hairpin comprising a duplex of at least 2 base pairs (bp) in length. In some embodiments, a tetraloop may stabilize a bp in an adjacent stem duplex by stacking interactions. In addition, interactions among the nucleotides in a tetraloop include, but are not limited to, non-Watson-Crick base pairing, stacking interactions, hydrogen bonding and contact interactions (Cheong et al. (1990) *Nature* 346:

680-682; Heus & Pardi (1991) *Science* 253:191-194). In some embodiments, a tetraloop comprises or consists of 3 to 6 nucleotides and is typically 4 to 5 nucleotides. In certain embodiments, a tetraloop comprises or consists of 3, 4, 5 or 6 nucleotides, which may or may not be modified (e.g., which may or may not be conjugated to a targeting moiety). In one embodiment, a tetraloop consists of 4 nucleotides. Any nucleotide may be used in the tetraloop and standard IUPAC-IUB symbols for such nucleotides may be used as described in Cornish-Bowden (1985) *Nucleic Acids Res.* 13:3021-3030. For example, the letter "N" may be used to mean that any base may be in that position, the letter "R" may be used to show that A (adenine) or G (guanine) may be in that position, and "B" may be used to show that C (cytosine), G (guanine), or T (thymine) may be in that position. Examples of tetraloops include the UNCG family of tetraloops (e.g., UUCG), the GNRA family of tetraloops (e.g., GAAA), and the CUUG tetraloop (Woese et al. (1990) *Proc. Natl. Acad. Sci. USA* 87:8467-8471; Antao et al. (1991) *Nucleic Acids Res.* 19:5901-5905). Examples of DNA tetraloops include the d(GNNA) family of tetraloops (e.g., d(GTTA), the d(GNRA)) family of tetraloops, the d(GNAB) family of tetraloops, the d(CNNG) family of tetraloops, and the d(TNCG) family of tetraloops (e.g., d(TTCG)). See, e.g., Nakano et al. (2002) *Biochem.* 41:4281-14292; Shinji et al. (2000) *Nippon Kagakkai Koen Yokoshu* 78:731. In some embodiments, the tetraloop is contained within a nicked tetraloop structure.

As used herein, "treat" or "treating" refers to the act of providing care to a subject in need thereof, for example, by administering a therapeutic agent (e.g., an oligonucleotide herein) to the subject, for purposes of improving the health and/or well-being of the subject with respect to an existing condition (e.g., a disease, disorder) or to prevent or decrease the likelihood of the occurrence of a condition. In some embodiments, treatment involves reducing the frequency or severity of at least one sign, symptom or contributing factor of a condition (e.g., disease, disorder) experienced by a subject.

II. Oligonucleotide Inhibitors of ANGPTL3 Expression

The disclosure provides, inter alia, oligonucleotides that inhibit ANGPTL3 expression. In some embodiments, an oligonucleotide that inhibits ANGPTL3 expression herein is targeted to an ANGPTL3 mRNA.

i. ANGPTL3 Target Sequences

In some embodiments, the oligonucleotide is targeted to a target sequence comprising an ANGPTL3 mRNA. In some embodiments, the oligonucleotide, or a portion, fragment or strand thereof (e.g., an antisense strand or a guide strand of a ds oligonucleotide) binds or anneals to a target sequence comprising an ANGPTL3 mRNA, thereby inhibiting ANGPTL3 expression. In some embodiments, the oligonucleotide is targeted to an ANGPTL3 target sequence for the purpose of inhibiting ANGPTL3 expression in vivo. In some embodiments, the amount or extent of inhibition of ANGPTL3 expression by an oligonucleotide targeted to an ANGPTL3 target sequence correlates with the potency of the oligonucleotide. In some embodiments, the amount or extent of inhibition of ANGPTL3 expression by an oligonucleotide targeted to an ANGPTL3 target sequence correlates with the amount or extent of therapeutic benefit in a subject or patient having a disease, disorder or condition associated with the expression of ANGPTL3 treated with the oligonucleotide.

Through examination of the nucleotide sequence of mRNAs encoding ANGPTL3, including mRNAs of multiple different species (e.g., human, cynomolgus monkey, mouse, and rat; see, e.g., Example 1) and as a result of in vitro and in vivo testing (see, e.g., Example 2 and Example 3), it has been discovered that certain nucleotide sequences of ANGPTL3 mRNA are more amenable than others to oligonucleotide-based inhibition and are thus useful as target sequences for the oligonucleotides herein. In some embodiments, a sense strand of an oligonucleotide (e.g., a ds oligonucleotide) described herein (e.g., in Table 5) comprises an ANGPTL3 target sequence. In some embodiments, a portion or region of the sense strand of a ds oligonucleotide described herein (e.g., in Table 5) comprises an ANGPTL3 target sequence. In some embodiments, an ANGPTL3 target sequence comprises, or consists of, a sequence of any one of SEQ ID NOs: 117, 118, 119, 120, 121, 122, 123, 124, 125, 126 and 127.

ii. ANGPTL3-Targeting Sequences

In some embodiments, the oligonucleotides herein have regions of complementarity to ANGPTL3 mRNA (e.g., within a target sequence of ANGPTL3 mRNA) for purposes of targeting the mRNA in cells and inhibiting its expression. In some embodiments, the oligonucleotides herein comprise an ANGPTL3 targeting sequence (e.g., an antisense strand or a guide strand of a ds oligonucleotide) having a region of complementarity that binds or anneals to an ANGPTL3 target sequence by complementary (Watson-Crick) base pairing. The targeting sequence or region of complementarity is generally of a suitable length and base content to enable binding or annealing of the oligonucleotide (or a strand thereof) to an ANGPTL3 mRNA for purposes of inhibiting its expression. In some embodiments, the targeting sequence or region of complementarity is at least about 12, at least about 13, at least about 14, at least about 15, at least about 16, at least about 17, at least about 18, at least about 19, at least about 20, at least about 21, at least about 22, at least about 23, at least about 24, at least about 25, at least about 26, at least about 27, at least about 28, at least about 29, or at least about 30 nucleotides in length. In some embodiments, the targeting sequence or region of complementarity is about 12 to about 30 (e.g., 12 to 30, 12 to 22, 15 to 25, 17 to 21, 18 to 27, 19 to 27, or 15 to 30) nucleotides in length. In some embodiments, the targeting sequence or region of complementarity is about 12, 13, 14, 15, 16, 17, 18, 19, 20, 21, 22, 23, 24, 25, 26, 27, 28, 29, or 30 nucleotides in length. In some embodiments, the targeting sequence or region of complementarity is 18 nucleotides in length. In some embodiments, the targeting sequence or region of complementarity is 19 nucleotides in length. In some embodiments, the targeting sequence or region of complementarity is 20 nucleotides in length. In some embodiments, the targeting sequence or region of complementarity is 21 nucleotides in length. In some embodiments, the targeting sequence or region of complementarity is 22 nucleotides in length. In some embodiments, the targeting sequence or region of complementarity is 23 nucleotides in length. In some embodiments, the targeting sequence or region of complementarity is 24 nucleotides in length.

In some embodiments, an oligonucleotide herein comprises a targeting sequence or a region of complementarity (e.g., an antisense strand or a guide strand of a double-stranded oligonucleotide) that is fully complementary to an ANGPTL3 target sequence. In some embodiments, the targeting sequence or region of complementarity is partially complementary to an ANGPTL3 target sequence. In some embodiments, the oligonucleotide comprises a targeting sequence or region of complementarity that is fully complementary to a sequence of any one of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, and 115. In some embodiments, the oligonucleotide comprises a targeting sequence or region of complementarity that is partially complementary to a sequence of any one of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, and 115.

In some embodiments, the oligonucleotide herein comprises a targeting sequence or region of complementarity that is complementary to a contiguous sequence of nucleotides comprising an ANGPTL3 mRNA, where the contiguous sequence of nucleotides is about 12 to about 30 nucleotides in length (e.g., 12 to 30, 12 to 28, 12 to 26, 12 to 24, 12 to 20, 12 to 18, 12 to 16, 14 to 22, 16 to 20, 18 to 20, or 18 to 19 nucleotides in length). In some embodiments, the oligonucleotide comprises a targeting sequence or region of complementarity that is complementary to a contiguous sequence of nucleotides comprising an ANGPTL3 mRNA, wherein the contiguous sequence of nucleotides is 10, 11, 12, 13, 14, 15, 16, 17, 18, 19, or 20 nucleotides in length. In some embodiments, the oligonucleotide comprises a targeting sequence or region of complementarity that is complementary to a contiguous sequence of nucleotides comprising an ANGPTL3 mRNA, where the contiguous sequence of nucleotides is 19 nucleotides in length. In some embodiments, the oligonucleotide comprises a targeting sequence or a region of complementarity that is complementary to a contiguous sequence of nucleotides of any one of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, and 115, optionally where the contiguous sequence of nucleotides is 19 nucleotides in length.

In some embodiments, a targeting sequence or region of complementarity of an oligonucleotide that is complementary to contiguous nucleotides of a sequence as set forth in any one of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, and 115 spans the entire length of an antisense strand. In some embodiments, a region of complementarity of an oligonucleotide that is complementary to contiguous nucleotides of a sequence as set forth in any one of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, and 115 spans a portion of the entire length of an antisense strand. In some embodiments, an oligonucleotide herein comprises a region of complementarity (e.g., on an antisense strand of a ds oligonucleotide) that is at least partially (e.g., fully) complementary to a contiguous stretch of nucleotides spanning nucleotides 1-20 of a sequence as set forth in any one of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, and 115.

In some embodiments, an oligonucleotide herein comprises a targeting sequence or region of complementarity having one or more bp mismatches with the corresponding ANGPTL3 target sequence. In some embodiments, the targeting sequence or region of complementarity may have up to about 1, up to about 2, up to about 3, up to about 4, up to about 5, etc. mismatches with the corresponding ANGPTL3 target sequence provided that the ability of the targeting sequence or region of complementarity to bind or anneal to the ANGPTL3 mRNA under appropriate hybridization conditions and/or the ability of the oligonucleotide to inhibit ANGPTL3 expression is maintained. Alternatively, the targeting sequence or region of complementarity may have no more than 1, no more than 2, no more than 3, no more than 4, or no more than 5 mismatches with the corresponding ANGPTL3 target sequence provided that the ability of the targeting sequence or region of complementarity to bind or anneal to the ANGPTL3 mRNA under appropriate hybridization conditions and/or the ability of the oligonucleotide to inhibit ANGPTL3 expression is maintained. In some embodiments, the oligonucleotide comprises a targeting sequence or region of complementarity having 1 mismatch with the corresponding target sequence. In some embodiments, the oligonucleotide comprises a targeting sequence or region of complementarity having 2 mismatches with the corresponding target sequence. In some embodiments, the oligonucleotide comprises a targeting sequence or region of complementarity having 3 mismatches with the corresponding target sequence. In some embodiments, the oligonucleotide comprises a targeting sequence or region of complementarity having 4 mismatches with the corresponding target sequence. In some embodiments, the oligonucleotide comprises a targeting sequence or region of complementarity having 5 mismatches with the corresponding target sequence. In some embodiments, the oligonucleotide comprises a targeting sequence or region of complementarity more than one mismatch (e.g., 2, 3, 4, 5 or more mismatches) with the corresponding target sequence, wherein at least 2 (e.g., all) of the mismatches are positioned consecutively (e.g., 2, 3, 4, 5 or more mismatches in a row), or where in the mismatches are interspersed throughout the targeting sequence or region of complementarity.

iii. Types of Oligonucleotides

A variety of oligonucleotide types and/or structures are useful for targeting ANGPTL3 in the methods herein including, but not limited to, RNAi oligonucleotides, antisense oligonucleotides, miRNAs, etc. Any of the oligonucleotide types described herein or elsewhere are contemplated for use as a framework to incorporate an ANGPTL3 targeting sequence herein.

In some embodiments, the oligonucleotides herein inhibit ANGPTL3 expression by engaging with RNA interference (RNAi) pathways upstream or downstream of Dicer involvement. For example, RNAi oligonucleotides have been developed with each strand having sizes of about 19-25 nucleotides with at least one 3' overhang of 1 to 5 nucleotides (see, e.g., U.S. Pat. No. 8,372,968). Longer oligonucleotides also have been developed that are processed by Dicer to generate active RNAi products (see, e.g., U.S. Pat. No. 8,883,996). Further work produced extended ds oligonucleotides where at least one end of at least one strand is extended beyond a duplex targeting region, including structures where one of the strands includes a thermodynamically-stabilizing tetraloop structure (see, e.g., U.S. Pat. Nos. 8,513,207 and 8,927,705, as well as Intl. Patent Application Publication No. WO 2010/033225). Such structures may include ss extensions (on one or both sides of the molecule) as well as ds extensions.

In some embodiments, the oligonucleotides herein engage with the RNAi pathway downstream of the involvement of Dicer (e.g., Dicer cleavage). In some embodiments, the oligonucleotide has an overhang (e.g., of 1, 2, or 3 nucleotides in length) in the 3' end of the sense strand. In some embodiments, the oligonucleotide (e.g., siRNA) comprises a 21-nucleotide guide strand that is antisense to a target RNA and a complementary passenger strand, in which both strands anneal to form a 19-bp duplex and 2 nucleotide overhangs at either or both 3' ends. Longer oligonucleotide designs also are available including oligonucleotides having a guide strand of 23 nucleotides and a passenger strand of 21 nucleotides, where there is a blunt end on the right side of the molecule (3' end of passenger strand/5' end of guide strand) and a two nucleotide 3'-guide strand overhang on the left side of the molecule (5' end of the passenger strand/3' end of the guide strand). In such molecules, there is a 21 bp duplex region. See, e.g., U.S. Pat. Nos. 9,012,138; 9,012,621 and 9,193,753.

In some embodiments, the oligonucleotides herein comprise sense and antisense strands that are both in the range of about 17 to 26 (e.g., 17 to 26, 20 to 25 or 21-23) nucleotides in length. In some embodiments, an oligonucleotide herein comprises a sense and antisense strand that are both in the range of about 19-22 nucleotides in length. In some embodiments, the sense and antisense strands are of equal length. In some embodiments, an oligonucleotide comprises sense and antisense strands, such that there is a 3'-overhang on either the sense strand or the antisense strand, or both the sense and antisense strand. In some embodiments, for oligonucleotides that have sense and antisense strands that are both in the range of about 21-23 nucleotides in length, a 3' overhang on the sense, antisense, or both sense and antisense strands is 1 or 2 nucleotides in length. In some embodiments, the oligonucleotide has a guide strand of 22 nucleotides and a passenger strand of 20 nucleotides, where there is a blunt end on the right side of the molecule (3' end of passenger strand/5' end of guide strand) and a 2 nucleotide 3'-guide strand overhang on the left side of the molecule (5' end of the passenger strand/3' end of the guide strand). In such molecules, there is a 20 bp duplex region.

Other oligonucleotide designs for use with the compositions and methods herein include: 16-mer siRNAs (see, e.g., NUCLEIC ACIDS IN CHEMISTRY AND BIOLOGY. Blackburn (ed.), Royal Society of Chemistry, 2006), shRNAs (e.g., having 19 bp or shorter stems; see, e.g., Moore et al. (2010) *Methods Mol. Biol.* 629:141-158), blunt siRNAs (e.g., of 19 bps in length; see, e.g., Kraynack & Baker (2006) *RNA* 12:163-176), asymmetrical siRNAs (aiRNA; see, e.g., Sun et al. (2008) *Nat. Biotechnol.* 26:1379-1382), asymmetric shorter-duplex siRNA (see, e.g., Chang et al. (2009) *Mol. Ther.* 17:725-732), fork siRNAs (see, e.g., Hohjoh (2004) *FEBS Lett.* 557:193-198), ss siRNAs (Elsner (2012) *Nat. Biotechnol.* 30:1063), dumbbell-shaped circular siRNAs (see, e.g., Abe et al. (2007) *J. Am. Chem. Soc.* 129:15108-15109), and small internally segmented interfering RNA (siRNA; see, e.g., Bramsen et al. (2007) *Nucleic Acids Res.* 35:5886-5897). Further non-limiting examples of an oligonucleotide structures that may be used in some embodiments to reduce or inhibit the expression of ANGPTL3 are microRNA (miRNA), short hairpin RNA (shRNA) and short siRNA (see, e.g., Hamilton et al. (2002) *EMBO J.* 21:4671-4679; see also, US Patent Application Publication No. 2009/0099115).

Still, in some embodiments, an oligonucleotide for reducing or inhibiting ANGPTL3 expression herein is ss. Such structures may include but are not limited to ss RNAi molecules. Recent efforts have demonstrated the activity of ss RNAi molecules (see, e.g., Matsui et al. (2016) *Mol. Ther.* 24:946-955). However, in some embodiments, oligonucleotides herein are antisense oligonucleotides (ASOs). An antisense oligonucleotide is a ss oligonucleotide that has a nucleobase sequence which, when written in the 5' to 3' direction, comprises the reverse complement of a targeted segment of a particular nucleic acid and is suitably modified (e.g., as a gapmer) so as to induce RNaseH-mediated cleavage of its target RNA in cells or (e.g., as a mixmer) so as to inhibit translation of the target mRNA in cells. ASOs for use herein may be modified in any suitable manner known in the art including, for example, as shown in U.S. Pat. No. 9,567,587 (including, e.g., length, sugar moieties of the nucleobase (pyrimidine, purine), and alterations of the heterocyclic portion of the nucleobase). Further, ASOs have been used for decades to reduce expression of specific target genes (see, e.g., Bennett et al. (2017) *Annu. Rev. Pharmacol.* 57:81-105).

iv. Double-Stranded Oligonucleotides

The disclosure provides ds oligonucleotides for targeting ANGPTL3 mRNA and inhibiting ANGPTL3 expression (e.g., via the RNAi pathway) comprising a sense strand (also referred to herein as a passenger strand) and an antisense strand (also referred to herein as a guide strand). In some embodiments, the sense strand and antisense strand are separate strands and are not covalently linked. In some embodiments, the sense strand and antisense strand are covalently linked.

In some embodiments, the sense strand has a first region (R1) and a second region (R2), wherein R2 comprises a first subregion (S1), a tetraloop (L) or triloop (triL), and a second subregion (S2), wherein L or triL is located between S1 and S2, and wherein S1 and S2 form a second duplex (D2). D2 may have various length. In some embodiments, D2 is about 1-6 bp in length. In some embodiments, D2 is 2-6, 3-6, 4-6, 5-6, 1-5, 2-5, 3-5 or 4-5 bp in length. In some embodiments, D2 is 1, 2, 3, 4, 5 or 6 bp in length. In some embodiments, D2 is 6 bp in length.

In some embodiments, R1 of the sense strand and the antisense strand form a first duplex (D1). In some embodiments, D1 is at least about 15 (e.g., at least 15, at least 16, at least 17, at least 18, at least 19, at least 20, or at least 21) nucleotides in length. In some embodiments, D1 is in the range of about 12 to 30 nucleotides in length (e.g., 12 to 30, 12 to 27, 15 to 22, 18 to 22, 18 to 25, 18 to 27, 18 to 30, or 21 to 30 nucleotides in length). In some embodiments, D1 is at least 12 nucleotides in length (e.g., at least 12, at least 15, at least 20, at least 25, or at least 30 nucleotides in length). In some embodiments, D1 is 12, 13, 14, 15, 16, 17, 18, 19, 20, 21, 22, 23, 24, 25, 26, 27, 28, 29 or 30 nucleotides in length. In some embodiments, D1 is 20 nucleotides in length. In some embodiments, D1 comprising sense strand and antisense strand does not span the entire length of the sense strand and/or antisense strand. In some embodiments, D1 comprising the sense strand and antisense strand spans the entire length of either the sense strand or antisense strand or both. In certain embodiments, D1 comprising the sense strand and antisense strand spans the entire length of both the sense strand and the antisense strand.

In some embodiments, a ds oligonucleotide herein comprises a sense strand having a sequence of any one of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, and 115 and an antisense strand comprising a complementary sequence selected from SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, and 116, as is arranged Table 3. In some embodiments, the sense strand comprises the sequence of SEQ ID NO: 99 and the antisense strand comprises the sequence of SEQ ID NO: 100.

In some embodiments, a ds oligonucleotide herein comprises a sense strand comprising a sequence of any one of SEQ ID NOs: 19, 25, 49, 71, 73, 75, 79, 99, 101, 103, and 113 and an antisense strand comprising a complementary sequence selected from SEQ ID NOs: 20, 26, 50, 72, 74, 76, 80, 100, 102, 104, and 114, as is arranged Table 4. In some embodiments, the sense strand comprises the sequence of SEQ ID NO: 99 and the antisense strand comprises the sequence of SEQ ID NO: 100.

It should be appreciated that, in some embodiments, sequences presented in the Sequence Listing may be referred to in describing the structure of an oligonucleotide or other nucleic acid. In such embodiments, the actual oligonucleotide or other nucleic acid may have one or more alternative nucleotides (e.g., an RNA counterpart of a DNA nucleotide or a DNA counterpart of an RNA nucleotide) and/or one or more modified nucleotides and/or one or more modified internucleotide linkages and/or one or more other modification when compared with the specified sequence while retaining essentially same or similar complementary properties as the specified sequence.

In some embodiments, a ds oligonucleotide herein comprises a 25-nucleotide sense strand and a 27-nucleotide antisense strand that when acted upon by a Dicer enzyme results in an antisense strand that is incorporated into the mature RISC. In some embodiments, the sense strand of the ds oligonucleotide is longer than 27 nucleotides (e.g., 28, 29, 30, 31, 32, 33, 34, 35, 36, 37, 38, 39 or 40 nucleotides). In some embodiments, the sense strand of the ds oligonucleotide is longer than 25 nucleotides (e.g., 26, 27, 28, 29 or 30 nucleotides).

In some embodiments, oligonucleotides herein have one 5' end that is thermodynamically less stable when compared to the other 5' end. In some embodiments, an asymmetry oligonucleotide is provided that includes a blunt end at the 3' end of a sense strand and a 3'-overhang at the 3' end of an antisense strand. In some embodiments, the 3'-overhang on the antisense strand is about 1-8 nucleotides in length (e.g., 1, 2, 3, 4, 5, 6, 7 or 8 nucleotides in length). Typically, an oligonucleotide for RNAi has a two-nucleotide overhang on the 3' end of the antisense (guide) strand. However, other overhangs are possible. In some embodiments, an overhang is a 3'-overhang comprising a length of between 1 and 6 nucleotides, optionally 1 to 5, 1 to 4, 1 to 3, 1 to 2, 2 to 6, 2 to 5, 2 to 4, 2 to 3, 3 to 6, 3 to 5, 3 to 4, 4 to 6, 4 to 5, 5 to 6 nucleotides, or 1, 2, 3, 4, 5 or 6 nucleotides. However, in some embodiments, the overhang is a 5'-overhang comprising a length of between 1 and 6 nucleotides, optionally 1 to 5, 1 to 4, 1 to 3, 1 to 2, 2 to 6, 2 to 5, 2 to 4, 2 to 3, 3 to 6, 3 to 5, 3 to 4, 4 to 6, 4 to 5, 5 to 6 nucleotides, or 1, 2, 3, 4, 5 or 6 nucleotides.

In some embodiments, two terminal nucleotides on the 3' end of an antisense strand are modified. In some embodiments, the two terminal nucleotides on the 3' end of the antisense strand are complementary with the target. In some embodiments, the two terminal nucleotides on the 3' end of the antisense strand are not complementary with the target. In some embodiments, two terminal nucleotides on each 3' end of an oligonucleotide in the nicked tetraloop structure are GG. Typically, one or both of the two terminal GG nucleotides on each 3' end of an oligonucleotide is not complementary with the target.

In some embodiments, there is one or more (e.g., 1, 2, 3, 4 or 5) mismatch between a sense and antisense strand. If there is more than one mismatch between a sense and antisense strand, they may be positioned consecutively (e.g., 2, 3 or more in a row), or interspersed throughout the region of complementarity. In some embodiments, the 3' end of the sense strand contains one or more mismatches. In one embodiment, two mismatches are incorporated at the 3' end of the sense strand. In some embodiments, base mismatches or destabilization of segments at the 3' end of the sense strand of the oligonucleotide improved the potency of synthetic duplexes in RNAi, possibly through facilitating processing by Dicer.

a. Antisense Strands

In some embodiments, an oligonucleotide disclosed herein for targeting ANGPTL3 comprises an antisense strand comprising or consisting of a sequence as set forth in any one of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, and 116. In some embodiments, an oligonucleotide comprises an antisense strand comprising or consisting of at least about 12 (e.g., at least 12, at least 13, at least 14, at least 15, at least 16, at least 17, at least 18, at least 19, at least 20, at least 21, at least 22, or at least 23) contiguous nucleotides of a sequence as set forth in any one of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, and 116.

In some embodiments, a ds oligonucleotide comprises an antisense strand of up to about 40 nucleotides in length (e.g., up to 40, up to 35, up to 30, up to 27, up to 25, up to 21, up to 19, up to 17, or up to 12 nucleotides in length). In some embodiments, an oligonucleotide may have an antisense strand of at least about 12 nucleotides in length (e.g., at least 12, at least 15, at least 19, at least 21, at least 22, at least 25, at least 27, at least 30, at least 35, or at least 38 nucleotides in length). In some embodiments, an oligonucleotide may have an antisense strand in a range of about 12 to about 40 (e.g., 12 to 40, 12 to 36, 12 to 32, 12 to 28, 15 to 40, 15 to 36, 15 to 32, 15 to 28, 17 to 22, 17 to 25, 19 to 27, 19 to 30, 20 to 40, 22 to 40, 25 to 40, or 32 to 40) nucleotides in length. In some embodiments, an oligonucleotide may have an antisense strand of 12, 13, 14, 15, 16, 17, 18, 19, 20, 21, 22, 23, 24, 25, 26, 27, 28, 29, 30, 31, 32, 33, 34, 35, 36, 37, 38, 39 or 40 nucleotides in length.

In some embodiments, an antisense strand of an oligonucleotide may be referred to as a "guide strand." For example, if an antisense strand can engage with RNA-induced silencing complex (RISC) and bind to an Argonaute protein such as Ago2, or engage with or bind to one or more similar factors, and direct silencing of a target gene, it may be referred to as a guide strand. In some embodiments, a sense strand complementary to a guide strand may be referred to as a "passenger strand."

b. Sense Strands

In some embodiments, an oligonucleotide herein for targeting ANGPTL3 comprises or consists of a sense strand sequence as set forth in in any one of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, and 115. In some embodiments, an oligonucleotide has a sense strand that comprises or consists of at least about 12 (e.g., at least 13, at least 14, at least 15, at least 16, at least 17, at least 18, at least 19, at least 20, at least 21, at least 22, or at least 23) contiguous nucleotides of a sequence as set forth in in any one of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, and 115.

In some embodiments, an oligonucleotide comprises a sense strand (or passenger strand) of up to about 40 nucleotides in length (e.g., up to 40, up to 36, up to 30, up to 27, up to 25, up to 21, up to 19, up to 17, or up to 12 nucleotides in length). In some embodiments, an oligonucleotide may have a sense strand of at least about 12 nucleotides in length (e.g., at least 12, at least 15, at least 19, at least 21, at least 25, at least 27, at least 30, at least 36, or at least 38 nucleotides in length). In some embodiments, an oligonucleotide may have a sense strand in a range of about 12 to about 40 (e.g., 12 to 40, 12 to 36, 12 to 32, 12 to 28, 15 to 40, 15 to 36, 15 to 32, 15 to 28, 17 to 21, 17 to 25, 19 to 27, 19 to 30, 20 to 40, 22 to 40, 25 to 40, or 32 to 40) nucleotides in length. In some embodiments, an oligonucleotide may have a sense strand of 12, 13, 14, 15, 16, 17, 18, 19, 20, 21, 22, 23, 24, 25, 26, 27, 28, 29, 30, 31, 32, 33, 34, 35, 36, 37, 38, 39 or 40 nucleotides in length.

Figure 3:
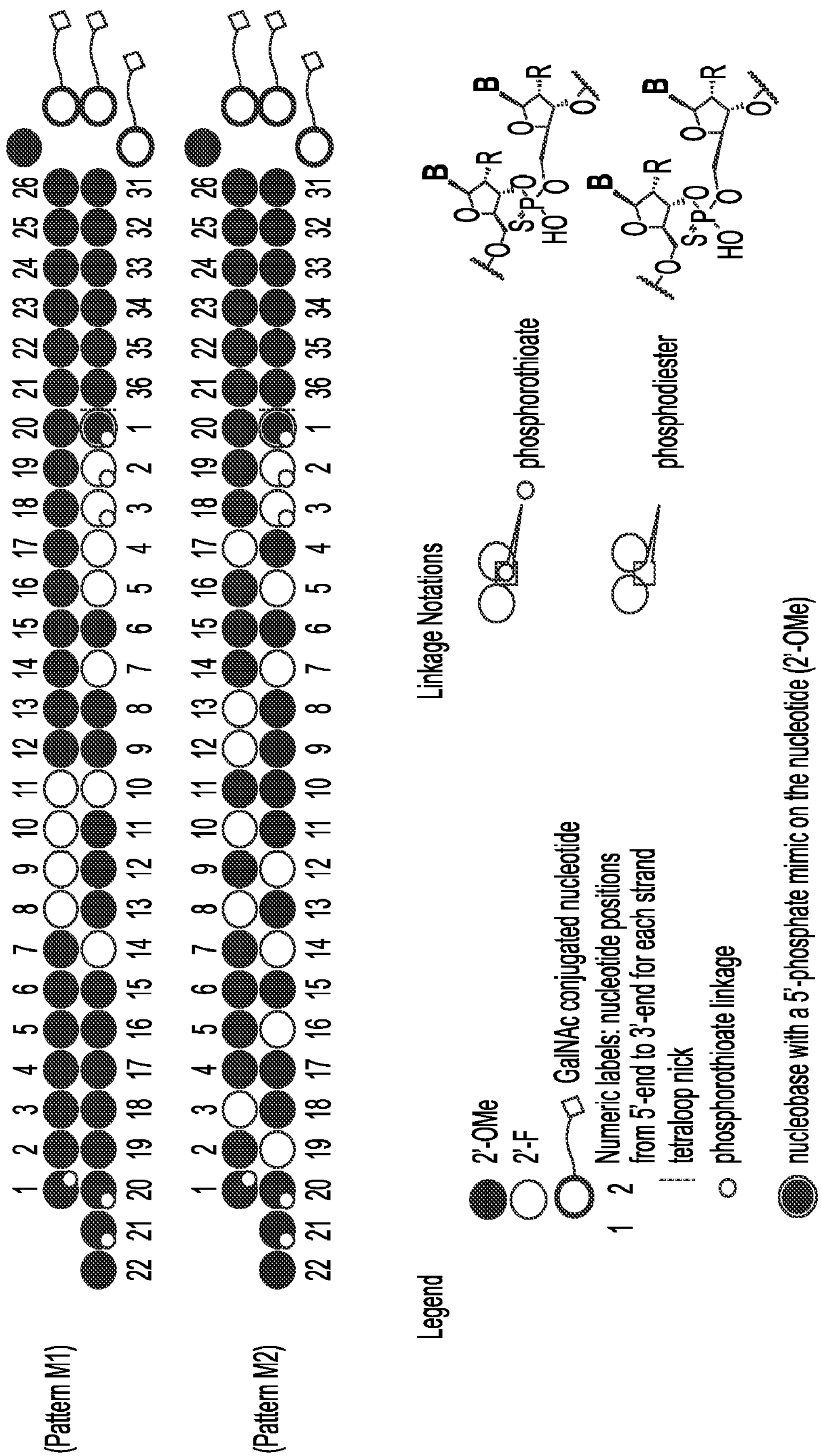
FIG. 3 provides a schematic depicting the structure and chemical modification patterns of generic GalNAc-conjugated ANGPTL3 oligonucleotides.

In some embodiments, a sense strand comprises a stem-loop structure at its 3' end. In some embodiments, a sense strand comprises a stem-loop structure at its 5' end. In some embodiments, a stem is a duplex of 2, 3, 4, 5, 6, 7, 8, 9, 10, 11, 12, 13 or 14 bp in length. In some embodiments, a stem-loop provides the molecule protection against degradation (e.g., enzymatic degradation) and facilitates targeting characteristics for delivery to a target cell. For example, in some embodiments, a loop provides added nucleotides on which modification can be made without substantially affecting the gene expression inhibition activity of an oligonucleotide. In certain embodiments, an oligonucleotide is herein in which the sense strand comprises (e.g., at its 3' end) a stem-loop set forth as: S1-L-S2, in which S1 is complementary to S2, and in which L forms a loop between S1 and S2 of up to about 10 nucleotides in length (e.g., 3, 4, 5, 6, 7, 8, 9 or 10 nucleotides in length). FIG. 3 depicts a non-limiting example of such an oligonucleotide.

In some embodiments, a loop (F) of a stem-loop is a tetraloop (e.g., within a nicked tetraloop structure). A tetraloop may contain ribonucleotides, deoxyribonucleotides, modified nucleotides and combinations thereof. Typically, a tetraloop has 4 to 5 nucleotides.

v. Oligonucleotide Modifications a. Sugar Modifications

In some embodiments, a modified sugar (also referred herein to a sugar analog) includes a modified deoxyribose or ribose moiety in which, for example, one or more modifications occur at the 2', 3', 4' and/or 5' carbon position of the sugar. In some embodiments, a modified sugar may also include non-natural alternative carbon structures such as those present in locked nucleic acids ("LNA"; see, e.g., Koshkin et al. (1998) *Tetrahedron* 54:3607-3630), unlocked nucleic acids ("UNA"; see, e.g., Snead et al. (2013) *Mol. Ther-Nucl. Acids* 2:e103), and bridged nucleic acids ("BNA"; see, e.g., Imanishi & Obika (2002) *Chem Commun*. (*Camb*) 21:1653-1659).

In some embodiments, a nucleotide modification in a sugar comprises a 2'-modification. In some embodiments, a 2'-modification may be 2'-O-propargyl, 2'-O-propylamin, 2'-amino, 2'-ethyl, 2'-fluoro (2'-F), 2'-aminoethyl (EA), 2'-O-methyl (2'-OMe), 2'-O-methoxyethyl (2'-MOE), 2'-O-[2-(methylamino)-2-oxoethyl] (2'-O-NMA), or 2'-deoxy-2'-fluoro-β-d-arabinonucleic acid (2'-FANA). In some embodiments, the modification is 2'-F, 2'-OMe or 2'-MOE. In some embodiments, a modification in a sugar comprises a modification of the sugar ring, which may comprise modification of one or more carbons of the sugar ring. For example, a modification of a sugar of a nucleotide may comprise a 2'-oxygen of a sugar is linked to a 1'-carbon or 4'-carbon of the sugar, or a 2'-oxygen is linked to the 1'-carbon or 4'-carbon via an ethylene or methylene bridge. In some embodiments, a modified nucleotide has an acyclic sugar that lacks a 2'-carbon to 3'-carbon bond. In some embodiments, a modified nucleotide has a thiol group, e.g., in the 4' position of the sugar.

In some embodiments, the oligonucleotide described herein comprises at least about 1 modified nucleotide (e.g., at least 1, at least 5, at least 10, at least 15, at least 20, at least 25, at least 30, at least 35, at least 40, at least 45, at least 50, at least 55, at least 60, or more). In some embodiments, the sense strand of the oligonucleotide comprises at least about 1 modified nucleotide (e.g., at least 1, at least 5, at least 10, at least 15, at least 20, at least 25, at least 30, at least 35, or more). In some embodiments, the antisense strand of the oligonucleotide comprises at least about 1 modified nucleotide (e.g., at least 1, at least 5, at least 10, at least 15, at least 20, or more).

In some embodiments, all the nucleotides of the sense strand of the oligonucleotide are modified. In some embodiments, all the nucleotides of the antisense strand of the oligonucleotide are modified. In some embodiments, all the nucleotides of the oligonucleotide (i.e., both the sense strand and the antisense strand) are modified. In some embodiments, the modified nucleotide comprises a 2'-modification (e.g., a 2'-F or 2'-OMe, 2'-MOE, and 2'-deoxy-2'-fluoro-β-d-arabinonucleic acid). In some embodiments, the modified nucleotide comprises a 2'-modification (e.g., a 2'-F or 2'-OMe).

The disclosure provides oligonucleotides having different modification patterns. In some embodiments, the modified oligonucleotides comprise a sense strand sequence having a modification pattern as set forth in any one of Tables 3 and 4 (as well as FIG. 3) and an antisense strand having a modification pattern as set forth in any one of Tables 3 and 4 (as well as FIG. 3). In some embodiments, for these oligonucleotides, one or more of positions 8, 9, 10 or 11 of the sense strand is modified with a 2'-F group. In other embodiments, for these oligonucleotides, the sugar moiety at each of nucleotides at positions 1-7 and 12-20 in the sense strand is modified with a 2'-OMe.

In some embodiments, the present invention provide an oligonucleotide, which is, or comprises, a modified or unmodified sense strand selected from those listed in Table A. In some embodiments, the present invention provide an oligonucleotide, which is, or comprises, a modified or unmodified antisense strand selected from those listed in Table A. In some embodiments, the present invention provide a modified or unmodified double-stranded oligonucleotide selected from those listed in Table A. In some embodiments, the present invention provide a sense strand modification pattern selected from those listed in Table A. In some embodiments, the present invention provide an antisense strand modification pattern selected from those listed in Table A.

In some embodiments, the antisense strand has 3 nucleotides that are modified at the 2'-position of the sugar moiety with a 2'-F. In some embodiments, the sugar moiety at positions 2, 5 and 14 and optionally up to 3 of the nucleotides at positions 1, 3, 7 and 10 of the antisense strand are modified with a 2'-F. In other embodiments, the sugar moiety at each of the positions at positions 2, 5 and 14 of the antisense strand is modified with the 2'-F. In other embodiments, the sugar moiety at each of the positions at positions 1, 2, 5 and 14 of the antisense strand is modified with the 2'-F. In still other embodiments, the sugar moiety at each of the positions at positions 1, 2, 3, 5, 7 and 14 of the antisense strand is modified with the 2'-F. In yet another embodiment, the sugar moiety at each of the positions at positions 1, 2, 3, 5, 10 and 14 of the antisense strand is modified with the 2'-F. In another embodiment, the sugar moiety at each of the positions at positions 2, 3, 5, 7, 10 and 14 of the antisense strand is modified with the 2'-F.

b. 5' Terminal Phosphates

In some embodiments, 5'-terminal phosphate groups of oligonucleotides enhance the interaction with Ago2. However, oligonucleotides comprising a 5'-phosphate group may be susceptible to degradation via phosphatases or other enzymes, which can limit their bioavailability in vivo. In some embodiments, oligonucleotides include analogs of 5' phosphates that are resistant to such degradation. In some embodiments, a phosphate analog may be oxymethylphosphonate, vinylphosphonate or malonylphosphonate. In certain embodiments, the 1' end of an oligonucleotide strand is attached to chemical moiety that mimics the electrostatic and steric properties of a natural 5'-phosphate group ("phosphate mimic").

In some embodiments, an oligonucleotide has a phosphate analog at a 4'-carbon position of the sugar (referred to as a "4'-phosphate analog"). See, e.g., Intl. Patent Application Publication No. WO 2018/045317. In some embodiments, an oligonucleotide herein comprises a 4'-phosphate analog at a 5'-terminal nucleotide. In some embodiments, a phosphate analog is an oxymethylphosphonate, in which the oxygen atom of the oxymethyl group is bound to the sugar moiety (e.g., at its 4'-carbon) or analog thereof. In other embodiments, a 4'-phosphate analog is a thiomethylphosphonate or an aminomethylphosphonate, in which the sulfur atom of the thiomethyl group or the nitrogen atom of the amino methyl group is bound to the 4'-carbon of the sugar moiety or analog thereof. In certain embodiments, a 4'-phosphate analog is an oxymethylphosphonate. In some embodiments, an oxymethylphosphonate is represented by the formula $-O-CH_2-PO(OH)_2$ or $-O-CH_2-PO(OR)_2$, in which R is independently selected from H, $CH_3$, an alkyl group, $CH_2CH_2CN$, $CH_2OCOC(CH_3)_3$, $CH_2OCH_2CH_2Si(CH_3)_3$ or a protecting group. In certain embodiments, the alkyl group is $CH_2CH_3$. More typically, R is independently selected from H, $CH_3$ or $CH_2CH_3$.

c. Modified Intranucleoside Linkages

In some embodiments, an oligonucleotide may comprise a modified internucleoside linkage. In some embodiments, phosphate modifications or substitutions may result in an oligonucleotide that comprises at least about 1 (e.g., at least 1, at least 2, at least 3 or at least 5) modified internucleotide linkage. In some embodiments, any one of the oligonucleotides disclosed herein comprises about 1 to about 10 (e.g., 1 to 10, 2 to 8, 4 to 6, 3 to 10, 5 to 10, 1 to 5, 1 to 3, or 1 to 2) modified internucleotide linkages. In some embodiments, any one of the oligonucleotides disclosed herein comprises 1, 2, 3, 4, 5, 6, 7, 8, 9 or 10 modified internucleotide linkages.

A modified internucleotide linkage may be a phosphorodithioate linkage, a phosphorothioate linkage, a phosphotriester linkage, a thionoalkylphosphonate linkage, a thionalkylphosphotriester linkage, a phosphoramidite linkage, a phosphonate linkage or a boranophosphate linkage. In some embodiments, at least one modified internucleotide linkage of any one of the oligonucleotides as disclosed herein is a phosphorothioate linkage.

In some embodiments, the oligonucleotide described herein has a phosphorothioate linkage between one or more of positions 1 and 2 of the sense strand, positions 1 and 2 of the antisense strand, positions 2 and 3 of the antisense strand, positions 3 and 4 of the antisense strand, positions 20 and 21 of the antisense strand, and positions 21 and 22 of the antisense strand. In some embodiments, the oligonucleotide described herein has a phosphorothioate linkage between each of positions 1 and 2 of the sense strand, positions 1 and 2 of the antisense strand, positions 2 and 3 of the antisense strand, positions 20 and 21 of the antisense strand, and positions 21 and 22 of the antisense strand.

d. Base Modifications

In some embodiments, oligonucleotides herein have one or more modified nucleobases. In some embodiments, modified nucleobases (also referred to herein as base analogs) are linked at the 1' position of a nucleotide sugar moiety. In certain embodiments, a modified nucleobase is a nitrogenous base. In certain embodiments, a modified nucleobase does not contain nitrogen atom. See, e.g., US Patent Application Publication No. 2008/0274462. In some embodiments, a modified nucleotide comprises a universal base. However, in certain embodiments, a modified nucleotide does not contain a nucleobase (abasic).

In some embodiments, a universal base is a heterocyclic moiety located at the 1' position of a nucleotide sugar moiety in a modified nucleotide, or the equivalent position in a nucleotide sugar moiety substitution, that, when present in a duplex, can be positioned opposite more than one type of base without substantially altering structure of the duplex. In some embodiments, compared to a reference single-stranded nucleic acid (e.g., oligonucleotide) that is fully complementary to a target nucleic acid, a single-stranded nucleic acid containing a universal base forms a duplex with the target nucleic acid that has a lower $T_m$ than a duplex formed with the complementary nucleic acid. However, in some embodiments, when compared to a reference single-stranded nucleic acid in which the universal base has been replaced with a base to generate a single mismatch, the single-stranded nucleic acid containing the universal base forms a duplex with the target nucleic acid that has a higher $T_m$ than a duplex formed with the nucleic acid comprising the mismatched base.

Non-limiting examples of universal-binding nucleotides include, but are not limited to, inosine, 1-β-D-ribofuranosyl-5-nitroindole and/or 1-β-D-ribofuranosyl-3-nitropyrrole (see, US Patent Application Publication No. 2007/0254362; Van Aerschot et al. (1995) *Nucleic Acids Res.* 23:4363-4370; Loakes et al. (1995) *Nucleic Acids Res.* 23:2361-2366; and Loakes & Brown (1994) *Nucleic Acids Res.* 22:4039-4043).

e. Reversible Modifications

While certain modifications to protect an oligonucleotide from the in vivo environment before reaching target cells can be made, they can reduce the potency or activity of the oligonucleotide once it reaches the cytosol of the target cell. Reversible modifications can be made such that the molecule retains desirable properties outside of the cell, which are then removed upon entering the cytosolic environment of the cell. Reversible modification can be removed, for example, by the action of an intracellular enzyme or by the chemical conditions inside of a cell (e.g., through reduction by intracellular glutathione).

In some embodiments, a reversibly modified nucleotide comprises a glutathione-sensitive moiety. Typically, nucleic acid molecules have been chemically modified with cyclic disulfide moieties to mask the negative charge created by the internucleotide diphosphate linkages and improve cellular uptake and nuclease resistance. See US Patent Application Publication No. 2011/0294869, Intl. Patent Application Publication Nos. WO 2014/088920 and WO 2015/188197, and Meade et al. (2014) *Nat. Biotechnol.* 32:1256-1263. This reversible modification of the internucleotide diphosphate linkages is designed to be cleaved intracellularly by the reducing environment of the cytosol (e.g., glutathione). Earlier examples include neutralizing phosphotriester modifications that were reported to be cleavable inside cells (see, Dellinger et al. (2003) *J. Am. Chem. Soc.* 125:940-950).

In some embodiments, such a reversible modification allows protection during in vivo administration (e.g., transit through the blood and/or lysosomal/endosomal compartments of a cell) where the oligonucleotide will be exposed to nucleases and other harsh environmental conditions (e.g., pH). When released into the cytosol of a cell where the levels of glutathione are higher compared to extracellular space, the modification is reversed, and the result is a cleaved oligonucleotide. Using reversible, glutathione-sensitive moieties, it is possible to introduce sterically larger chemical groups into the oligonucleotide of interest when compared to the options available using irreversible chemical modifications. This is because these larger chemical groups will be removed in the cytosol and, therefore, should not interfere with the biological activity of the oligonucleotides inside the cytosol of a cell. As a result, these larger chemical groups can be engineered to confer various advantages to the nucleotide or oligonucleotide, such as nuclease resistance, lipophilicity, charge, thermal stability, specificity and reduced immunogenicity. In some embodiments, the structure of the glutathione-sensitive moiety can be engineered to modify the kinetics of its release.

In some embodiments, a glutathione-sensitive moiety is attached to the sugar of the nucleotide. In some embodiments, a glutathione-sensitive moiety is attached to the 2'-carbon of the sugar of a modified nucleotide. In some embodiments, the glutathione-sensitive moiety is located at the 5'-carbon of a sugar, particularly when the modified nucleotide is the 5'-terminal nucleotide of the oligonucleotide. In some embodiments, the glutathione-sensitive moiety is located at the 3'-carbon of sugar, particularly when the modified nucleotide is the 3'-terminal nucleotide of the oligonucleotide. In some embodiments, the glutathione-sensitive moiety comprises a sulfonyl group. See, e.g., U.S. Provisional Patent Application No. 62/378,635, entitled Compositions Comprising Reversibly Modified Oligonucleotides and Uses Thereof, which was filed on Aug. 23, 2016.

vi. Targeting Ligands

In some embodiments, it is desirable to target the oligonucleotides of the disclosure to one or more cells or one or more organs. Such a strategy can help to avoid undesirable effects in other organs or avoid undue loss of the oligonucleotide to cells, tissue or organs that would not benefit from the oligonucleotide. Accordingly, in some embodiments, oligonucleotides disclosed herein are modified to facilitate targeting and/or delivery of a particular tissue, cell or organ (e.g., to facilitate delivery of the oligonucleotide to the liver). In certain embodiments, oligonucleotides disclosed herein are modified to facilitate delivery of the oligonucleotide to the hepatocytes of the liver. In some embodiments, an oligonucleotide comprises at least one nucleotide (e.g., 1, 2, 3, 4, 5, 6 or more nucleotides) conjugated to one or more targeting ligand(s).

In some embodiments, the targeting ligand comprises a carbohydrate, amino sugar, cholesterol, peptide, polypeptide, protein or part of a protein (e.g., an antibody or antibody fragment), or lipid. In some embodiments, the targeting ligand is an aptamer. For example, a targeting ligand may be an RGD peptide that is used to target tumor vasculature or glioma cells, CREKA peptide to target tumor vasculature or stoma, transferring, lactoferrin, or an aptamer to target transferrin receptors expressed on CNS vasculature, or an anti-EGFR antibody to target EGFR on glioma cells. In certain embodiments, the targeting ligand is one or more GalNAc moieties.

In some embodiments, 1 or more (e.g., 1, 2, 3, 4, 5 or 6) nucleotides of an oligonucleotide are each conjugated to a separate targeting ligand. In some embodiments, 2 to 4 nucleotides of an oligonucleotide are each conjugated to a separate targeting ligand. In some embodiments, targeting ligands are conjugated to 2 to 4 nucleotides at either ends of the sense or antisense strand (e.g., targeting ligands are conjugated to a 2 to 4 nucleotide overhang or extension on the 5' or 3' end of the sense or antisense strand) such that the targeting ligands resemble bristles of a toothbrush and the oligonucleotide resembles a toothbrush. For example, an oligonucleotide may comprise a stem-loop at either the 5' or 3' end of the sense strand and 1, 2, 3 or 4 nucleotides of the loop of the stem may be individually conjugated to a targeting ligand. In some embodiments, an oligonucleotide (e.g., a ds oligonucleotide) provided by the disclosure comprises a stem-loop at the 3' end of the sense strand, wherein the loop of the stem-loop comprises a triloop or a tetraloop, and wherein the 3 or 4 nucleotides comprising the triloop or tetraloop, respectfully, are individually conjugated to a targeting ligand.

GalNAc is a high affinity ligand for the ASGPR, which is primarily expressed on the sinusoidal surface of hepatocyte cells and has a major role in binding, internalizing and subsequent clearing circulating glycoproteins that contain terminal galactose or GalNAc residues (asialoglycoproteins). Conjugation (either indirect or direct) of GalNAc moieties to oligonucleotides of the instant disclosure can be used to target these oligonucleotides to the ASGPR expressed on cells. In some embodiments, an oligonucleotide of the instant disclosure is conjugated to at least one or more GalNAc moieties, wherein the GalNAc moieties target the oligonucleotide to an ASGPR expressed on human liver cells (e.g., human hepatocytes). In some embodiments, the GalNAc moiety target the oligonucleotide to the liver.

In some embodiments, an oligonucleotide of the instant disclosure is conjugated directly or indirectly to a monovalent GalNAc. In some embodiments, the oligonucleotide is conjugated directly or indirectly to more than one monovalent GalNAc (i.e., is conjugated to 2, 3 or 4 monovalent GalNAc moieties, and is typically conjugated to 3 or 4 monovalent GalNAc moieties). In some embodiments, an oligonucleotide is conjugated to one or more bivalent GalNAc, trivalent GalNAc or tetravalent GalNAc moieties.

In some embodiments, 1 or more (e.g., 1, 2, 3, 4, 5 or 6) nucleotides of an oligonucleotide are each conjugated to a GalNAc moiety. In some embodiments, 2 to 4 nucleotides of a tetraloop are each conjugated to a separate GalNAc. In some embodiments, 1 to 3 nucleotides of a triloop are each conjugated to a separate GalNAc. In some embodiments, targeting ligands are conjugated to 2 to 4 nucleotides at either ends of the sense or antisense strand (e.g., ligands are conjugated to a 2 to 4 nucleotide overhang or extension on the 5' or 3' end of the sense or antisense strand) such that the GalNAc moieties resemble bristles of a toothbrush and the oligonucleotide resembles a toothbrush. In some embodiments, GalNAc moieties are conjugated to a nucleotide of the sense strand. For example, 4 GalNAc moieties can be conjugated to nucleotides in the tetraloop of the sense strand where each GalNAc moiety is conjugated to 1 nucleotide.

In some embodiments, an oligonucleotide herein comprises a monovalent GalNAc attached to a guanine nucleotide referred to as [ademG-GalNAc] or 2'-aminodiethoxymethanol-Guanine-GalNAc, as depicted below:

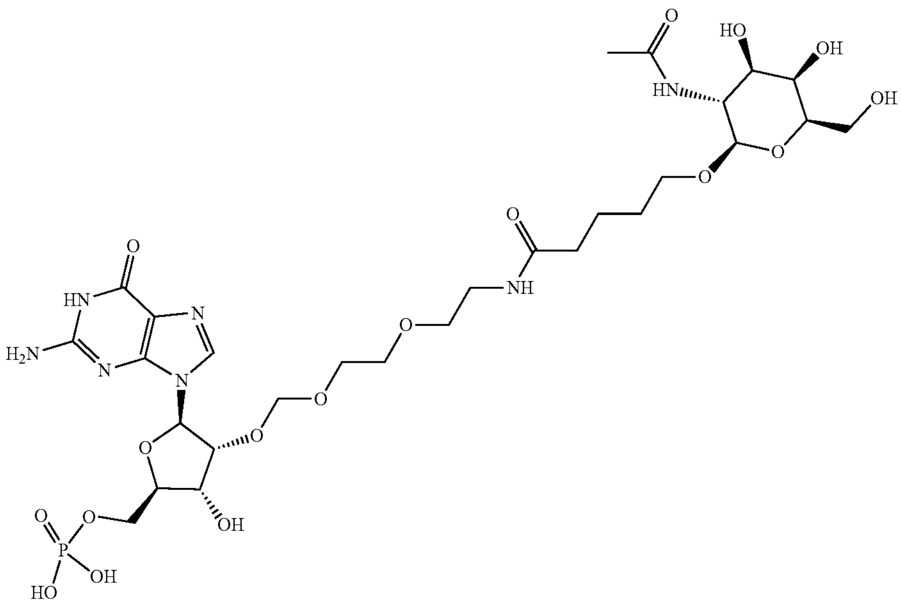 [SMILES: CC(=O)N[C@H]1[C@H](OCCCCC(=O)NCCOCCOCO[C@@H]2[C@H](O)[C@@H](COP(=O)(O)O)O[C@H]2n2cnc3c(=O)[nH]c(N)nc32)O[C@H](CO)[C@H](O)[C@@H]1O]
In some embodiments, an oligonucleotide herein comprises a monovalent GalNAc attached to an adenine nucleotide, referred to as [ademA-GalNAc] or 2'-aminodiethoxymethanol-Adenine-GalNAc, as depicted below:
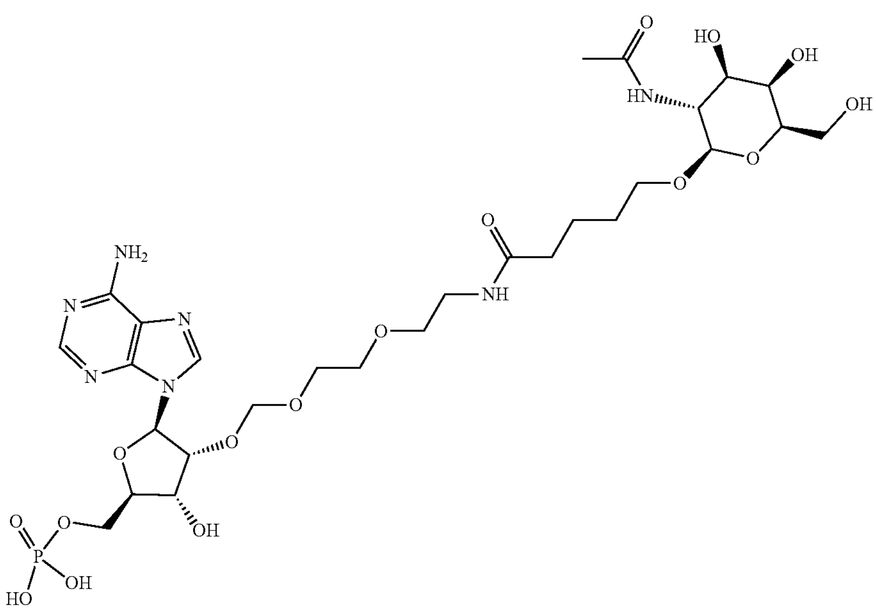

An example of such conjugation is shown below for a loop comprising from 5' to 3' the nucleotide sequence GAAA (L=linker, X=heteroatom) stem attachment points are shown. Such a loop may be present, for example, at positions 27-30 of the sense strand listed in Table 5 and as shown in FIG. 3. In the chemical formula,

is used to describe an attachment point to the oligonucleotide strand.

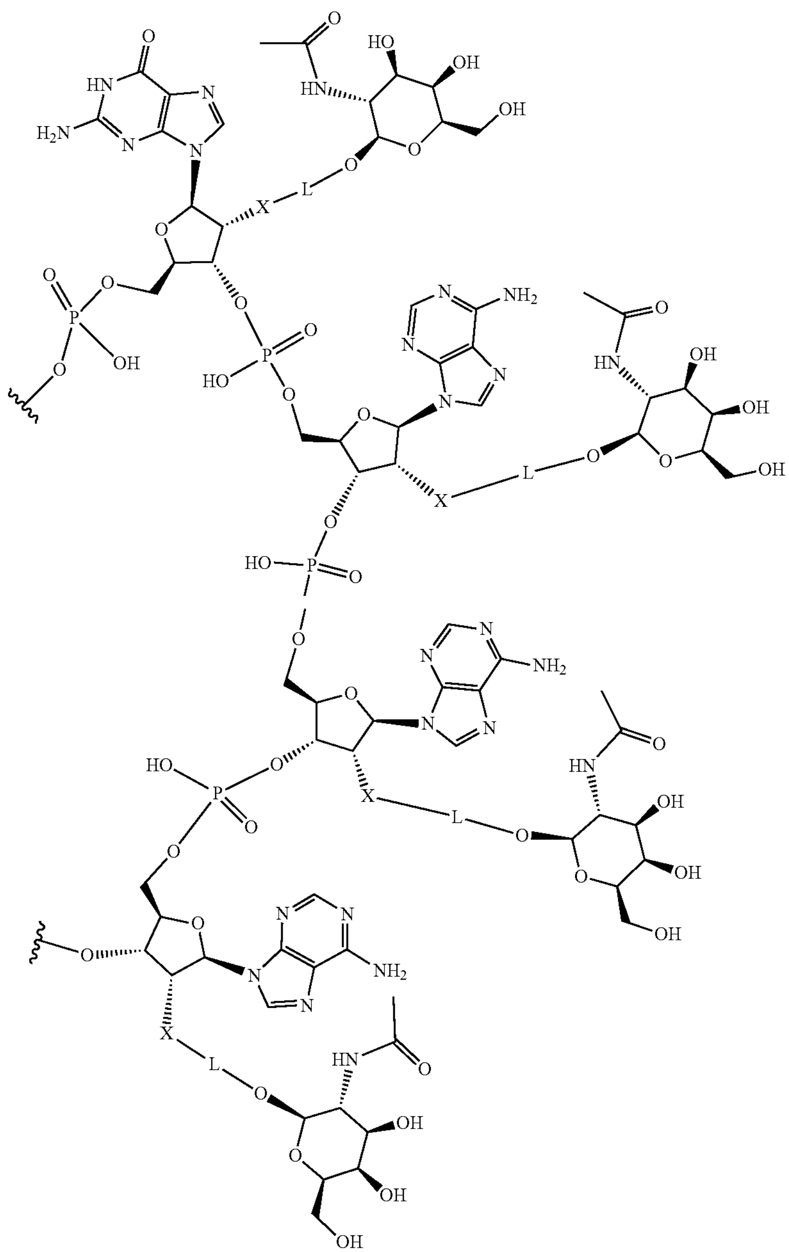

Appropriate methods or chemistry (e.g., click chemistry) can be used to link a targeting ligand to a nucleotide. In some embodiments, a targeting ligand is conjugated to a nucleotide using a click linker. In some embodiments, an acetal-based linker is used to conjugate a targeting ligand to a nucleotide of any one of the oligonucleotides described herein. Acetal-based linkers are disclosed, for example, in Intl. Patent Application Publication No. WO 2016/100401. In some embodiments, the linker is a labile linker. However, in other embodiments, the linker is stable. An example is shown below for a loop comprising from 5' to 3' the nucleotides GAAA, in which GalNAc moieties are attached to nucleotides of the loop using an acetal linker. Such a loop may be present, for example, at positions 27-30 of the any one of the sense strand listed in Table 5 and as shown in FIG. 3. In the chemical formula,

is an attachment point to the oligonucleotide strand.

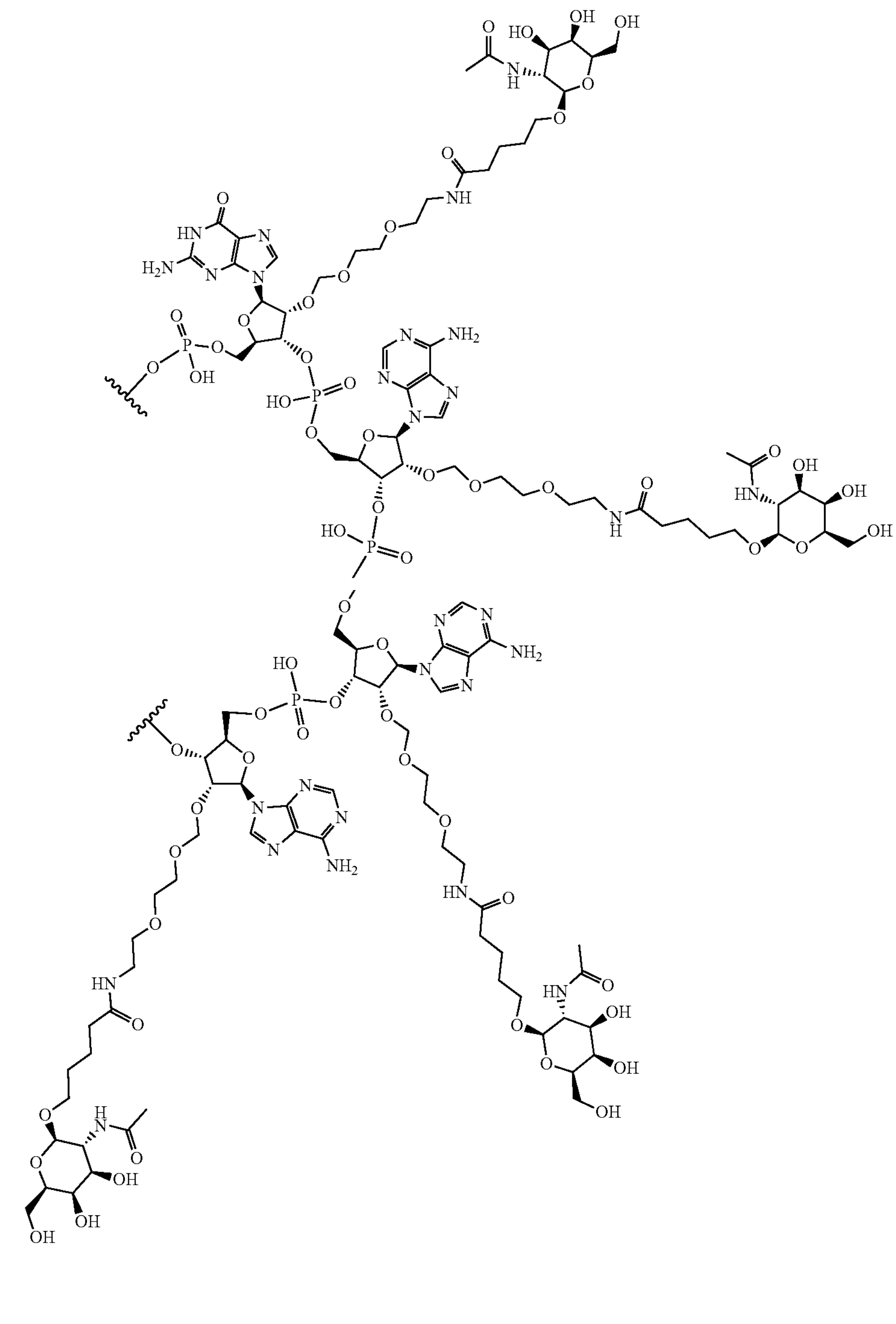 [SMILES: *O[C@H]1[C@@H](OCOCCOCCNC(=O)CCCCO[C@@H]2O[C@H](CO)[C@H](O)[C@H](O)[C@H]2NC(C)=O)[C@H](n2cnc3c(N)ncnc32)O[C@@H]1COP(=O)(O)O[C@H]1[C@@H](OCOCCOCCNC(=O)CCCCO[C@@H]2O[C@H](CO)[C@H](O)[C@H](O)[C@H]2NC(C)=O)[C@H](n2cnc3c(N)ncnc32)O[C@@H]1COP(=O)(O)O[C@H]1[C@@H](OCOCCOCCNC(=O)CCCCO[C@@H]2O[C@H](CO)[C@H](O)[C@H](O)[C@H]2NC(C)=O)[C@H](n2cnc3c(N)ncnc32)O[C@@H]1COP(=O)(O)O[C@H]1[C@@H](OCOCCOCCNC(=O)CCCCO[C@@H]2O[C@H](CO)[C@H](O)[C@H](O)[C@H]2NC(C)=O)[C@H](n2cnc3c(=O)[nH]c(N)nc32)O[C@@H]1COP(=O)(O)O*]

As mentioned, various appropriate methods or chemistry synthetic techniques (e.g., click chemistry) can be used to link a targeting ligand to a nucleotide. In some embodiments, a targeting ligand is conjugated to a nucleotide using a click linker. In some embodiments, an acetal-based linker is used to conjugate a targeting ligand to a nucleotide of any one of the oligonucleotides described herein. Acetal-based linkers are disclosed, for example, in Intl. Patent Application Publication No. WO 2016/100401. In some embodiments, the linker is a labile linker. However, in other embodiments, the linker is a stable linker.

In some embodiments, a duplex extension (e.g., of up to 3, 4, 5 or 6 bp in length) is provided between a targeting ligand (e.g., a GalNAc moiety) and a ds oligonucleotide. In some embodiments, the oligonucleotides herein do not have a GalNAc conjugated thereto.

III. Formulations

Various formulations have been developed to facilitate oligonucleotide use. For example, oligonucleotides can be delivered to a subject or a cellular environment using a formulation that minimizes degradation, facilitates delivery and/or uptake, or provides another beneficial property to the oligonucleotides in the formulation. In some embodiments, an oligonucleotide is formulated in buffer solutions such as phosphate buffered saline solutions, liposomes, micellar structures and capsids.

Formulations of oligonucleotides with cationic lipids can be used to facilitate transfection of the oligonucleotides into cells. For example, cationic lipids, such as lipofectin, cationic glycerol derivatives, and polycationic molecules (e.g., polylysine, can be used. Suitable lipids include Oligofectamine, Lipofectamine (Life Technologies), NC388 (Ribozyme Pharmaceuticals, Inc., Boulder, Colo.), or FuGene 6 (Roche) all of which can be used according to the manufacturer's instructions.

Accordingly, in some embodiments, a formulation comprises a lipid nanoparticle. In some embodiments, an excipient comprises a liposome, a lipid, a lipid complex, a microsphere, a microparticle, a nanosphere or a nanoparticle, or may be otherwise formulated for administration to the cells, tissues, organs, or body of a subject in need thereof (see, e.g., Remington: THE SCIENCE AND PRACTICE OF PHARMACY, 22nd edition, Pharmaceutical Press, 2013).

In some embodiments, the formulations herein comprise an excipient. In some embodiments, an excipient confers to a composition improved stability, improved absorption, improved solubility and/or therapeutic enhancement of the active ingredient. In some embodiments, an excipient is a buffering agent (e.g., sodium citrate, sodium phosphate, a tris base, or sodium hydroxide) or a vehicle (e.g., a buffered solution, petrolatum, dimethyl sulfoxide or mineral oil). In some embodiments, an oligonucleotide is lyophilized for extending its shelf-life and then made into a solution before use (e.g., administration to a subject). Accordingly, an excipient in a composition comprising any one of the oligonucleotides described herein may be a lyoprotectant (e.g., mannitol, lactose, polyethylene glycol or polyvinylpyrrolidone) or a collapse temperature modifier (e.g., dextran, Ficoll™ or gelatin).

In some embodiments, a pharmaceutical composition is formulated to be compatible with its intended route of administration. Examples of routes of administration include parenteral (e.g., intravenous, intramuscular, intraperitoneal, intradermal, subcutaneous), oral (e.g., inhalation), transdermal (e.g., topical), transmucosal and rectal administration.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.), or phosphate buffered saline (PBS). The carrier can be a solvent or dispersion medium containing, for example, water, ethanol, polyol (e.g., glycerol, propylene glycol, and liquid polyethylene glycol, and the like), and suitable mixtures thereof. In many cases, it will be preferable to include isotonic agents, for example, sugars, polyalcohols such as mannitol, sorbitol, sodium chloride in the composition. Sterile injectable solutions can be prepared by incorporating the oligonucleotides in a required amount in a selected solvent with one or a combination of ingredients enumerated above, as required, followed by filtered sterilization.

In some embodiments, a composition may contain at least about 0.1% of the therapeutic agent or more, although the percentage of the active ingredient(s) may be between about 1% to about 80% or more of the weight or volume of the total composition. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

Even though several embodiments are directed to liver-targeted delivery of any of the oligonucleotides herein, targeting of other tissues is also contemplated.

IV. Methods of Use i. Reducing ANGPTL3 Expression in Cells

The disclosure provides methods for contacting or delivering to a cell or population of cells an effective amount any one of oligonucleotides herein for purposes of reducing ANGPTL3 expression. The methods can include the steps described herein, and these maybe be, but not necessarily, carried out in the sequence as described. Other sequences, however, also are conceivable. Moreover, individual or multiple steps bay be carried out either in parallel and/or overlapping in time and/or individually or in multiply repeated steps. Furthermore, the methods may include additional, unspecified steps.

Methods herein are useful in any appropriate cell type. In some embodiments, a cell is any cell that expresses mRNA (e.g., hepatocytes, macrophages, monocyte-derived cells, prostate cancer cells, cells of the brain, endocrine tissue, bone marrow, lymph nodes, lung, gall bladder, liver, duodenum, small intestine, pancreas, kidney, gastrointestinal tract, bladder, adipose, and soft tissue and skin). In some embodiments, the cell is a primary cell obtained from a subject. In some embodiments, the primary cell has undergone a limited number of passages such that the cell substantially maintains is natural phenotypic properties. In some embodiments, a cell to which the oligonucleotide is delivered is ex vivo or in vitro (i.e., can be delivered to a cell in culture or to an organism in which the cell resides).

In some embodiments, the oligonucleotides herein are delivered using appropriate nucleic acid delivery methods including, but not limited to, injection of a solution containing the oligonucleotides, bombardment by particles covered by the oligonucleotides, exposing the cell or population of cells to a solution containing the oligonucleotides, or electroporation of cell membranes in the presence of the oligonucleotides. Other appropriate methods for delivering oligonucleotides to cells may be used, such as lipid-mediated carrier transport, chemical-mediated transport, and cationic liposome transfection such as calcium phosphate, and others.

In some embodiments, reduction of ANGPTL3 expression can be determined by an appropriate assay or technique to evaluate one or more properties or characteristics of a cell or population of cells associated with ANGPTL3 expression (e.g., using an ANGPTL3 expression biomarker) or by an assay or technique that evaluates molecules that are directly indicative of ANGPTL3 expression (e.g., ANGPTL3 mRNA or ANGPTL3 protein). In some embodiments, the extent to which an oligonucleotide herein reduces ANGPTL3 expression is evaluated by comparing ANGPTL3 expression in a cell or population of cells contacted with the oligonucleotide to an appropriate control (e.g., an appropriate cell or population of cells not contacted with the oligonucleotide or contacted with a control oligonucleotide). In some embodiments, an appropriate control level of mRNA expression into protein, after delivery of a RNAi molecule may be a predetermined level or value, such that a control level need not be measured every time. The predetermined level or value can take a variety of forms. In some embodiments, a predetermined level or value can be single cut-off value, such as a median or mean.

In some embodiments, administration of an oligonucleotide herein results in a reduction in ANGPTL3 expression in a cell or population of cells. In some embodiments, the reduction in ANGPTL3 expression is about 1% or lower, about 5% or lower, about 10% or lower, about 15% or lower, about 20% or lower, about 25% or lower, about 30% or lower, about 35% or lower, about 40% or lower, about 45% or lower, about 50% or lower, about 55% or lower, about 60% or lower, about 70% or lower, about 80% or lower, or about 90% or lower when compared with an appropriate control level of mRNA. The appropriate control level may be a level of mRNA expression and/or protein translation in a cell or population of cells that has not been contacted with an oligonucleotide herein. In some embodiments, the effect of delivery of an oligonucleotide to a cell according to a method herein is assessed after a finite period. For example, levels of mRNA may be analyzed in a cell at least about 8 hours, about 12 hours, about 18 hours, or about 24 hours; or at least about 1, 2, 3, 4, 5, 6, 7 or even up to 14 days after introduction of the oligonucleotide into the cell.

In some embodiments, an oligonucleotide is delivered in the form of a transgene that is engineered to express in a cell the oligonucleotide or strands comprising the oligonucleotide (e.g., its sense and antisense strands). In some embodiments, an oligonucleotide is delivered using a transgene engineered to express any oligonucleotide disclosed herein. Transgenes may be delivered using viral vectors (e.g., adenovirus, retrovirus, vaccinia virus, poxvirus, adeno-associated virus or herpes simplex virus) or non-viral vectors (e.g., plasmids or synthetic mRNAs). In some embodiments, transgenes can be injected directly to a subject.

ii. Medical Use

The disclosure also provides oligonucleotides for use, or adaptable for use, to treat a subject (e.g., a human having a disease, disorder or condition associated with ANGPTL3 expression) that would benefit from reducing ANGPTL3 expression. In some respects, the disclosure provides oligonucleotides for use, or adapted for use, to treat a subject having a disease, disorder or condition associated with expression of ANGPTL3. The disclosure also provides oligonucleotides for use, or adaptable for use, in the manufacture of a medicament or pharmaceutical composition for treating a disease, disorder or condition associated with ANGPTL3 expression. In some embodiments, the oligonucleotides for use, or adaptable for use, target ANGPTL3 mRNA and reduce ANGPTL3 expression (e.g., via the RNAi pathway). In some embodiments, the oligonucleotides for use, or adaptable for use, target ANGPTL3 mRNA and reduce the amount or level of ANGPTL3 mRNA, ANGPTL3 protein and/or ANGPTL3 activity.

In addition, the methods below can include selecting a subject having a disease, disorder or condition associated with ANGPTL3 expression or is predisposed to the same. In some instances, the methods can include selecting an individual having a marker for ANGPTL3 expression such as elevated TG or cholesterol (or even altered LPL and/or EL activity) or is predisposed to the same.

Likewise, and as detailed below, the methods also may include steps such as measuring or obtaining a baseline value for a marker of ANGPTL3 expression, and then comparing such obtained value to one or more other baseline values or values obtained after being administered the oligonucleotide to assess the effectiveness of treatment.

iii. Methods of Treatment

The disclosure also provides methods of treating a subject having, suspected of having, or at risk of developing a disease, disorder or condition with an oligonucleotide herein. In some aspects, the disclosure provides methods of treating or attenuating the onset or progression of a disease, disorder or condition associated with ANGPTL3 expression using the oligonucleotides herein. In other aspects, the disclosure provides methods to achieve one or more therapeutic benefits in a subject having a disease, disorder or condition associated with ANGPTL3 expression using the oligonucleotides herein. In some embodiments of the methods herein, the subject is treated by administering a therapeutically effective amount of any one or more of the oligonucleotides herein. In some embodiments, treatment comprises reducing ANGPTL3 expression. In some embodiments, the subject is treated therapeutically. In some embodiments, the subject is treated prophylactically.

In some embodiments of the methods herein, an oligonucleotide herein, or a pharmaceutical composition comprising the oligonucleotide, is administered to a subject having a disease, disorder or condition associated with ANGPTL3 expression such that ANGPTL3 expression is reduced in the subject, thereby treating the subject. In some embodiments, an amount or level of ANGPTL3 mRNA is reduced in the subject. In some embodiments, an amount or level of ANGPTL3 protein is reduced in the subject. In some embodiments, an amount or level of ANGPTL3 activity is reduced in the subject. In some embodiments, an amount or level of triglyceride (TG) (e.g., one or more TG(s) or total TGs) is reduced in the subject. In some embodiments, an amount or level of cholesterol (e.g., total cholesterol, LDL cholesterol, and/or HDL cholesterol) is reduced in the subject. In some embodiments, an amount or level of low-density lipoprotein (LDL) cholesterol is reduced in the subject. In some embodiments, an amount or activity of LPL is altered in the subject. In some embodiments, an amount or activity of EL is altered in the subject. In some embodiments, any combination of the following is reduced or altered in the subject: ANGPTL3 expression, an amount or level of ANGPTL3 mRNA, an amount or level of ANGPTL3 protein, an amount or level of ANGPTL3 activity, an amount or level of TG, an amount or level of cholesterol, and/or an amount or activity of LPL and/or EL.

In some embodiments of the methods herein, an oligonucleotide herein, or a pharmaceutical composition comprising the oligonucleotide, is administered to a subject having a disease, disorder or condition associated with ANGPTL3 such that ANGPTL3 expression is reduced in the subject by at least about 30%, about 35%, about 40%, about 45%, about 50%, about 55%, about 60%, about 65%, about 70%, about 75%, about 80%, about 85%, about 90%, about 95%, about 99%, or greater than 99% when compared to ANGPTL3 expression prior to administration of the oligonucleotide or pharmaceutical composition. In some embodiments, ANGPTL3 expression is reduced in the subject by at least about 30%, about 35%, about 40%, about 45%, about 50%, about 55%, about 60%, about 65%, about 70%, about 75%, about 80%, about 85%, about 90%, about 95%, about 99%, or greater than 99% when compared to ANGPTL3 expression in a subject (e.g., a reference or control subject) not receiving the oligonucleotide or pharmaceutical composition or receiving a control oligonucleotide, pharmaceutical composition or treatment.

In some embodiments of the methods herein, an oligonucleotide herein, or a pharmaceutical composition comprising the oligonucleotide, is administered to a subject having a disease, disorder or condition associated with ANGPTL3 expression such that an amount or level of ANGPTL3 mRNA is reduced in the subject by at least about 30%, about 35%, about 40%, about 45%, about 50%, about 55%, about 60%, about 65%, about 70%, about 75%, about 80%, about 85%, about 90%, about 95%, about 99%, or greater than 99% when compared to the amount or level of ANGPTL3 mRNA prior to administration of the oligonucleotide or pharmaceutical composition. In some embodiments, an amount or level of ANGPTL3 mRNA is reduced in the subject by at least about 30%, about 35%, about 40%, about 45%, about 50%, about 55%, about 60%, about 65%, about 70%, about 75%, about 80%, about 85%, about 90%, about 95%, about 99%, or greater than 99% when compared to an amount or level of ANGPTL3 mRNA in a subject (e.g., a reference or control subject) not receiving the oligonucleotide or pharmaceutical composition or receiving a control oligonucleotide, pharmaceutical composition or treatment.

In some embodiments of the methods herein, an oligonucleotide herein, or a pharmaceutical composition comprising the oligonucleotide, is administered to a subject having a disease, disorder or condition associated with ANGPTL3 expression such that an amount or level of ANGPTL3 protein is reduced in the subject by at least about 30%, about 35%, about 40%, about 45%, about 50%, about 55%, about 60%, about 65%, about 70%, about 75%, about 80%, about 85%, about 90%, about 95%, about 99%, or greater than 99% when compared to the amount or level of ANGPTL3 protein prior to administration of the oligonucleotide or pharmaceutical composition. In some embodiments, an amount or level of ANGPTL3 protein is reduced in the subject by at least about 30%, about 35%, about 40%, about 45%, about 50%, about 55%, about 60%, about 65%, about 70%, about 75%, about 80%, about 85%, about 90%, about 95%, about 99%, or greater than 99% when compared to an amount or level of ANGPTL3 protein in a subject (e.g., a reference or control subject) not receiving the oligonucleotide or pharmaceutical composition or receiving a control oligonucleotide, pharmaceutical composition or treatment.

In some embodiments of the methods herein, an oligonucleotide herein, or a pharmaceutical composition comprising the oligonucleotide, is administered to a subject having a disease, disorder or condition associated with ANGPTL3 such that an amount or level of ANGPTL3 activity/expression is reduced in the subject by at least about 30%, about 35%, about 40%, about 45%, about 50%, about 55%, about 60%, about 65%, about 70%, about 75%, about 80%, about 85%, about 90%, about 95%, about 99%, or greater than 99% when compared to the amount or level of ANGPTL3 activity prior to administration of the oligonucleotide or pharmaceutical composition. In some embodiments, an amount or level of ANGPTL3 activity is reduced in the subject by at least about 30%, about 35%, about 40%, about 45%, about 50%, about 55%, about 60%, about 65%, about 70%, about 75%, about 80%, about 85%, about 90%, about 95%, about 99%, or greater than 99% when compared to an amount or level of ANGPTL3 activity in a subject (e.g., a reference or control subject) not receiving the oligonucleotide or pharmaceutical composition or receiving a control oligonucleotide, pharmaceutical composition or treatment.

In some embodiments of the methods herein, an oligonucleotide herein, or a pharmaceutical composition comprising the oligonucleotide, is administered to a subject having a disease, disorder or condition associated with ANGPTL3 expression such that an amount or level of TG (e.g., one or more TGs or total TGs) is reduced in the subject by at least about 30%, about 35%, about 40%, about 45%, about 50%, about 55%, about 60%, about 65%, about 70%, about 75%, about 80%, about 85%, about 90%, about 95%, about 99%, or greater than 99% when compared to the amount or level of TG prior to administration of the oligonucleotide or pharmaceutical composition. In some embodiments, an amount or level of TG is reduced in the subject by at least about 30%, about 35%, about 40%, about 45%, about 50%, about 55%, about 60%, about 65%, about 70%, about 75%, about 80%, about 85%, about 90%, about 95%, about 99%, or greater than 99% when compared to an amount or level of TG in a subject (e.g., a reference or control subject) not receiving the oligonucleotide or pharmaceutical composition or receiving a control oligonucleotide, pharmaceutical composition or treatment.

Generally, a normal or desirable TG range for a human subject is <150 mg/dL of blood, with <100 mg/dL being considered ideal. In some embodiments, the subject selected for treatment or treated is identified or determined to have an amount or level of TG of ≥150 mg/dL. In some embodiments, the subject selected for treatment or treated is identified or determined to have an amount or level of TG in the range of 150 mg/dL to 199 mg/dL, which is considered borderline high TG levels. In some embodiments, the subject selected for treatment or treated is identified or determined to have an amount or level of TG in the range of 200 to 499 mg/dL, which is considered high TG levels. In some embodiments, the subject selected for treatment or treated is identified or determined to have an amount or level of TG in the range of 500 mg/dL or higher (i.e., ≥500 mg/dL), which is considered very high TG levels. In some embodiments, the subject selected for treatment or treated is identified or determined to have an amount or level of TG which is ≥150 mg/dL, ≥200 mg/dL or ≥500 mg/dL. In some embodiments, the subject selected for treatment or treated is identified or determined to have an amount of level of TG of 200 mg/dL to 499 mg/dL, or 500 mg/dL or higher. In some embodiments, the patient selected for treatment or treated is identified or determined to have an amount or level of TG which is ≥200 mg/dL.

In some embodiments of the methods herein, an oligonucleotide herein, or a pharmaceutical composition comprising the oligonucleotide, is administered to a subject having a disease, disorder or condition associated with ANGPTL3 expression such that an amount or level of cholesterol (e.g., total cholesterol, LDL cholesterol, and/or HDL cholesterol) is reduced in the subject by at least about 30%, about 35%, about 40%, about 45%, about 50%, about 55%, about 60%, about 65%, about 70%, about 75%, about 80%, about 85%, about 90%, about 95%, about 99%, or greater than 99% when compared to the amount or level of cholesterol prior to administration of the oligonucleotide or pharmaceutical composition. In some embodiments, an amount or level of cholesterol is reduced in the subject by at least about 30%, about 35%, about 40%, about 45%, about 50%, about 55%, about 60%, about 65%, about 70%, about 75%, about 80%, about 85%, about 90%, about 95%, about 99%, or greater than 99% when compared to an amount or level of cholesterol in a subject (e.g., a reference or control subject) not receiving the oligonucleotide or pharmaceutical composition or receiving a control oligonucleotide, pharmaceutical composition or treatment.

Generally, a normal or desirable cholesterol range (total cholesterol) for an adult human patient is <200 mg/dL of blood. In some embodiments, the patient selected for treatment or treated is identified or determined to have an amount or level of cholesterol of ≥200 mg/dL. In some embodiments, the patient selected for treatment or treated is identified or determined to have an amount or level of cholesterol in the range of 200 mg/dL to 239 mg/dL, which is considered borderline high cholesterol levels. In some embodiments, the patient selected for treatment or treated is identified or determined to have an amount or level of cholesterol in the range of 240 mg/dL and higher (i.e., ≥240 mg/dL), which is considered high cholesterol levels. In some embodiments, the patient selected from treatment or treated is identified or determined to have an amount or level of cholesterol of 200 mg/dL to 239 mg/dL, or 240 mg/dL or higher. In some embodiments, the patient selected for treatment or treated is identified or determined to have an amount or level of cholesterol which is ≥200 mg/dL or ≥240 mg/dL or higher.

In some embodiments of the methods herein, an oligonucleotide herein, or a pharmaceutical composition comprising the oligonucleotide, is administered to a subject having a disease, disorder, or condition associated with ANGPTL3 expression such that an amount or level of LDL cholesterol is reduced in the subject by at least about 30%, about 35%, about 40%, about 45%, about 50%, about 55%, about 60%, about 65%, about 70%, about 75%, about 80%, about 85%, about 90%, about 95%, about 99%, or greater than 99% when compared to the amount or level of LDL cholesterol prior to administration of the oligonucleotide or pharmaceutical composition. In some embodiments, an amount or level of LDL cholesterol is reduced in the subject by at least about 30%, about 35%, about 40%, about 45%, about 50%, about 55%, about 60%, about 65%, about 70%, about 75%, about 80%, about 85%, about 90%, about 95%, about 99%, or greater than 99% when compared to an amount or level of LDL cholesterol in a subject (e.g., a reference or control subject) not receiving the oligonucleotide or pharmaceutical composition or receiving a control oligonucleotide, pharmaceutical composition or treatment.

Generally, a normal or desirable LDL cholesterol range for an adult human subject is <100 mg/dL of blood. In some embodiments, the subject selected for treatment or treated is identified or determined to have an amount or level of cholesterol of ≥100 mg/dL. In some embodiments, the subject selected for treatment or treated is identified or determined to have an amount or level of LDL cholesterol in the range of 100 mg/dL to 129 mg/dL, which is considered above optimal. In some embodiments, the subject selected for treatment or treated is identified or determined to have an amount or level of LDL cholesterol in the range of 130 mg/dL to 159 mg/dL, which is considered borderline high levels. In some embodiments, the subject selected for treatment or treated is identified or determined to have an amount or level of LDL cholesterol in the range of 160 mg/dL to 189 mg/dL, which is considered high LDL cholesterol levels. In some embodiments, the subject selected for treatment or treated is identified or determined to have an amount or level of LDL cholesterol in the range of 190 mg/dL and higher (i.e., ≥190 mg/dL), which is considered very high LDL cholesterol levels. In some embodiments, the subject selected for treatment or treated is identified or determined to have an amount or level of LDL cholesterol which is ≥100 mg/dL, ≥130 mg/dL, ≥160 mg/dL, or ≥190 mg/dL or higher, preferably ≥160 mg/dL, or ≥190 mg/dL or higher. In some embodiments, the subject selected for treatment or treated is identified or determined to have an amount or level of LDL cholesterol of 100 mg/dL to 129 mg/dL, 130 mg/dL to 159 mg/dL, 160 mg/dL to 189 mg/dL, or 190 mg/dL and higher.

Suitable methods for determining ANGPTL3 expression, the amount or level of ANGPTL3 mRNA, ANGPTL3 protein, ANGPTL3 activity, TG and/or LDL cholesterol, LPL and/or EL amount or activity in the subject, or in a sample from the subject, are known in the art. Further, the Examples set forth herein illustrate methods for determining ANGPTL3 expression.

In some embodiments, ANGPTL3 expression, the amount or level of ANGPTL3 mRNA, ANGPTL3 protein, ANGPTL3 activity, TG, LDL cholesterol, LPL protein, LPL activity, EL protein, EL activity or any combination thereof, is reduced in a cell (e.g., a hepatocyte), a population or a group of cells (e.g., an organoid), an organ (e.g., liver), blood or a fraction thereof (e.g., plasma), a tissue (e.g., liver tissue), a sample (e.g., a liver biopsy sample), or any other appropriate biological material obtained or isolated from the subject. In some embodiments, ANGPTL3 expression, the amount or level of ANGPTL3 mRNA, ANGPTL3 protein, ANGPTL3 activity, TG, LDL cholesterol, LPL protein, LPL activity, EL protein, EL activity or any combination thereof, is reduced in more than one type of cell (e.g., a hepatocyte and one or more other type(s) of cell), more than one groups of cells, more than one organ (e.g., liver and one or more other organ(s)), more than one fraction of blood (e.g., plasma and one or more other blood fraction(s)), more than one type of tissue (e.g., liver tissue and one or more other type(s) of tissue), more than one type of sample (e.g., a liver biopsy sample and one or more other type(s) of biopsy sample) isolated or other.

Examples of a disease, disorder or condition associated with ANGPTL3 expression include, but are not limited to, hypertriglyceridemia, obesity, hyperlipidemia, abnormal lipid and/or cholesterol metabolism, atherosclerosis, type II diabetes mellitus (T2D), cardiovascular disease, chronic kidney disease, coronary artery disease, NASH, NAFLD, homozygous and heterozygous familial hypercholesterolemia, statin-resistant hypercholesterolemia and other ANGPTL3-associated metabolic-related disorders and diseases. Of particular interest herein are cardiovascular disease, T2D, hypertriglyceridemia, NASH, obesity or a combination thereof.

Because of their high specificity, the oligonucleotides herein specifically target mRNAs of target genes of diseased cells and tissues. In preventing disease, the target gene may be one that is required for initiation or maintenance of the disease or that has been identified as being associated with a higher risk of contracting the disease. In treating disease, the oligonucleotide can be brought into contact with the cells or tissue exhibiting the disease. For example, an oligonucleotide substantially identical to all or part of a wild-type (i.e., native) or mutated gene associated with a disorder or condition associated with ANGPTL3 expression may be brought into contact with or introduced into a cell or tissue type of interest such as a hepatocyte or other liver cell.

In some embodiments, the target gene may be a target gene from any mammal, such as a human. Any gene may be silenced according to the method described herein.

Methods described herein are typically involve administering to a subject in an effective amount of an oligonucleotide, that is, an amount capable of producing a desirable therapeutic result. A therapeutically acceptable amount may be an amount that can therapeutically treat a disease or disorder. The appropriate dosage for any one subject will depend on certain factors, including the subject's size, body surface area, age, the particular composition to be administered, the active ingredient(s) in the composition, time and route of administration, general health, and other drugs being administered concurrently.

In some embodiments, a subject is administered any one of the compositions herein either enterally (e.g., orally, by gastric feeding tube, by duodenal feeding tube, via gastrostomy or rectally), parenterally (e.g., subcutaneous injection, intravenous injection or infusion, intra-arterial injection or infusion, intraosseous infusion, intramuscular injection, intracerebral injection, intracerebroventricular injection, intrathecal), topically (e.g., epicutaneous, inhalational, via eye drops, or through a mucous membrane), or by direct injection into a target organ (e.g., the liver of a subject). Typically, oligonucleotides herein are administered intravenously or subcutaneously.

As a non-limiting set of examples, the oligonucleotides herein would typically be administered quarterly (once every three months), bi-monthly (once every two months), monthly or weekly. For example, the oligonucleotides may be administered every week or at intervals of two, or three weeks. Alternatively, the oligonucleotides may be administered daily. In some embodiments, a subject is administered one or more loading doses of the oligonucleotide followed by one or more maintenance doses of the oligonucleotide.

In some embodiments, the subject to be treated is a human or non-human primate or other mammalian subject. Other exemplary subjects include domesticated animals such as dogs and cats; livestock such as horses, cattle, pigs, sheep, goats, and chickens; and animals such as mice, rats, guinea pigs, and hamsters.

V. Kits

In some embodiments, the disclosure provides a kit comprising an oligonucleotide herein, and instructions for use. In some embodiments, the kit comprises an oligonucleotide herein, and a package insert containing instructions for use of the kit and/or any component thereof. In some embodiments, the kit comprises, in a suitable container, an oligonucleotide herein, one or more controls, and various buffers, reagents, enzymes, and other standard ingredients well known in the art. In some embodiments, the container comprises at least one vial, well, test tube, flask, bottle, syringe or other container means, into which the oligonucleotide is placed, and in some instances, suitably aliquoted. In some embodiments where an additional component is provided, the kit contains additional containers into which this component is placed. The kits can also include a means for containing the oligonucleotide and any other reagent in close confinement for commercial sale. Such containers may include injection or blow-molded plastic containers into which the desired vials are retained. Containers and/or kits can include labeling with instructions for use and/or warnings.

In some embodiments, a kit comprises an oligonucleotide herein, and a pharmaceutically acceptable carrier, or a pharmaceutical composition comprising the oligonucleotide and instructions for treating or delaying progression of a disease, disorder or condition associated with ANGPTL3 expression in a subject in need thereof.

EXAMPLES

While the disclosure has been described with reference to the specific embodiments set forth in the following Examples, it should be understood by those skilled in the art that various changes may be made, and equivalents may be substituted without departing from the true spirit and scope of the disclosure. Further, the following Examples are offered by way of illustration and are not intended to limit the scope of the disclosure in any manner. In addition, modifications may be made to adapt to a particular situation, material, composition of matter, process, process step or steps, to the objective, spirit and scope of the disclosure. All such modifications are intended to be within the scope of the disclosure. Standard techniques well known in the art or the techniques specifically described below are utilized.

Example 1: Preparation of Double-Stranded RNAi Oligonucleotides

Oligonucleotide Synthesis and Purification

The ds RNAi oligonucleotides described in the foregoing Examples are chemically synthesized using methods described herein. Generally, ds RNAi oligonucleotides are synthesized using solid phase oligonucleotide synthesis methods as described for 19-23mer siRNAs (see, e.g., Scaringe et al. (1990) *Nucleic Acids Res.* 18:5433-5441 and Usman et al. (1987) *J. Am. Chem. Soc.* 109:7845-7845; see also, U.S. Pat. Nos. 5,804,683; 5,831,071; 5,998,203; 6,008,400; 6,111,086; 6,117,657; 6,353,098; 6,362,323; 6,437,117 and 6,469,158).

Individual RNA strands are synthesized and HPLC purified according to standard methods (Integrated DNA Technologies; Coralville, IA). For example, RNA oligonucleotides are synthesized using solid phase phosphoramidite chemistry, deprotected and desalted on NAP-5 columns (Amersham Pharmacia Biotech; Piscataway, NJ) using standard techniques (Damha & Olgivie (1993) *Methods Mol. Biol.* 20:81-114; Wincott et al. (1995) *Nucleic Acids Res.* 23:2677-2684). The oligomers are purified using ion-exchange high performance liquid chromatography (IE-HPLC) on an Amersham Source 15Q column (1.0 cm×25 cm; Amersham Pharmacia Biotech) using a 15 min step-linear gradient. The gradient varies from 90:10 Buffers A:B to 52:48 Buffers A:B, where Buffer A is 100 mM Tris pH 8.5 and Buffer B is 100 mM Tris pH 8.5, 1 M NaCl. Samples are monitored at 260 nm and peaks corresponding to the full-length oligonucleotide species are collected, pooled, desalted on NAP-5 columns, and lyophilized.

The purity of each oligomer is determined by capillary electrophoresis (CE) on a Beckman PACE 5000 (Beckman Coulter, Inc.; Fullerton, CA). The CE capillaries have a 100 μm inner diameter and contain ssDNA 100R Gel (Beckman-Coulter). Typically, about 0.6 nmole of oligonucleotide is injected into a capillary, is run in an electric field of 444 V/cm and is detected by UV absorbance at 260 nm. Denaturing Tris-Borate-7 M-urea running buffer is purchased from Beckman-Coulter. Oligoribonucleotides are obtained that are at least 90% pure as assessed by CE for use in experiments described below. Compound identity is verified by matrix-assisted laser desorption ionization time-of-flight (MALDI-TOF) mass spectroscopy on a Voyager DE™ Biospectometry Work Station (Applied Biosystems; Foster City, CA) following the manufacturer's recommended protocol. Relative molecular masses of all oligomers are obtained, often within 0.2% of expected molecular mass.

Preparation of Duplexes ssRNA oligomers are resuspended (e.g., at 100 μM concentration) in duplex buffer consisting of 100 mM potassium acetate, 30 mM HEPES, pH 7.5. Complementary sense and antisense strands are mixed in equal molar amounts to yield a final solution of, for example, 50 μM duplex. Samples are heated to 100° C. for 5' in RNA buffer (IDT) and are allowed to cool to room temperature before use. The ds RNA oligonucleotides are stored at −20° C. ss RNA oligomers are stored lyophilized or in nuclease-free water at −80° C.

Example 2: RNAi Oligonucleotide Inhibition of ANGPTL3 Expression In Vitro

ANGPTL3 Target Sequence Identification

To identify RNAi oligonucleotide inhibitors of ANGPTL3 expression, a computer-based algorithm is used to computationally generate ANGPTL3 target sequences suitable for assaying inhibition of ANGPTL3 expression by the RNAi pathway. The algorithm provides RNAi oligonucleotide guide strand sequences that are complementary to suitable ANGPTL3 target sequences of human ANGPTL3 mRNA (e.g., SEQ ID NO: 128; Table 1). Exemplary target sequences of human ANGPTL3 mRNA are provided in Table 2. Some of the guide strand sequences identified by the algorithm are also complementary to the corresponding ANGPTL3 target sequence of monkey and/or mouse ANGPTL3 mRNA (SEQ ID NO: 129 and 130, respectively; Table 1). 384 ds RNAi oligonucleotides (formatted as DsiRNA oligonucleotides) are generated, each with a unique guide strand having a region of complementarity to an ANGPTL3 target sequence identified by the algorithm.

TABLE 1

Sequences of Human, Monkey and Mouse ANGPTL3 mRNA

| Species | GenBank Ref Seq # | SEQ ID NO |
|---|---|---|
| Human (Hs) | NM_014495.4 | 128 |
| Cynomolgus monkey (Mf) | XM_005543185.2 | 129 |
| Mouse (Mm) | NM_013913.4 | 130 |
| Rat (Rn) | NM_001025065.1 | 131 |

TABLE 2

Exemplary Human ANGPTL3 mRNA Target Sequences

| Target Sequence | SEQ ID NO |
|---|---|
| CUCAACAUAUUUGAUCAGU | 117 |
| AGAGCCAAAAUCAAGAUUU | 118 |
| CAAAAUCAAGAUUUGCUAU | 119 |
| GAGAAGAACUACAUAUAAA | 120 |
| GUAGAAAAACAAGAUAAUA | 121 |
| UAGAAAAACAAGAUAAUAG | 122 |
| AGAAAAACAAGAUAAUAGC | 123 |
| AACAGCAUAGUCAAAUAAA | 124 |
| UCAAAAUGGAAGGUUAUAC* | 125 |
| AAAUGGAAGGUUAUACUCU | 126 |
| GAAGGUUAUACUCUAUAAA | 127 |

In Vitro Cell-Based Assays

The ability of each of the 384 DsiRNAs above to inhibit ANGPTL3 expression is determined using in vitro cell-based assays. Briefly, HuH-7 human liver cells stably expressing ANGPTL3 are transfected with each of the DsiRNAs (0.5 nM) in separate wells of a multi-well cell-culture plate. Cells are maintained for 24 hr following transfection, and then levels of remaining ANGPTL3 mRNA from the transfected cells are determined using TAQMAN®-based qPCR assays. Two qPCR assays, a 3' assay and a 5' assay, are used to determine mRNA levels as measured by HEX and FAM probes, respectively.

Figure 2:
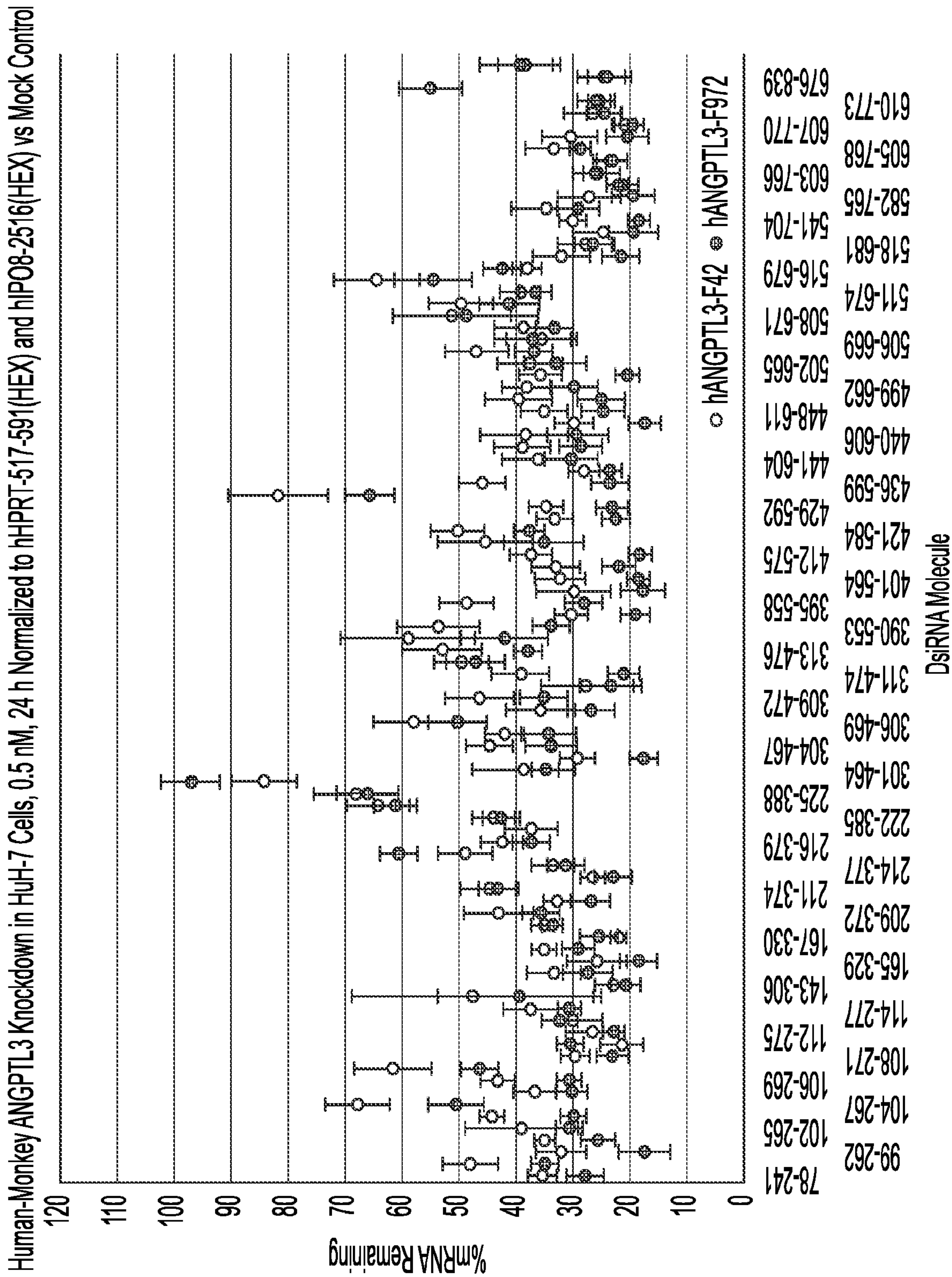
FIG. 2 provides a graph depicting the percent (%) of ANGPTL3 mRNA in HuH-7 cells transfected with the indicated DsiRNAs relative to the % of ANGPTL3 mRNA control mock-treated cells.
Figure 2:
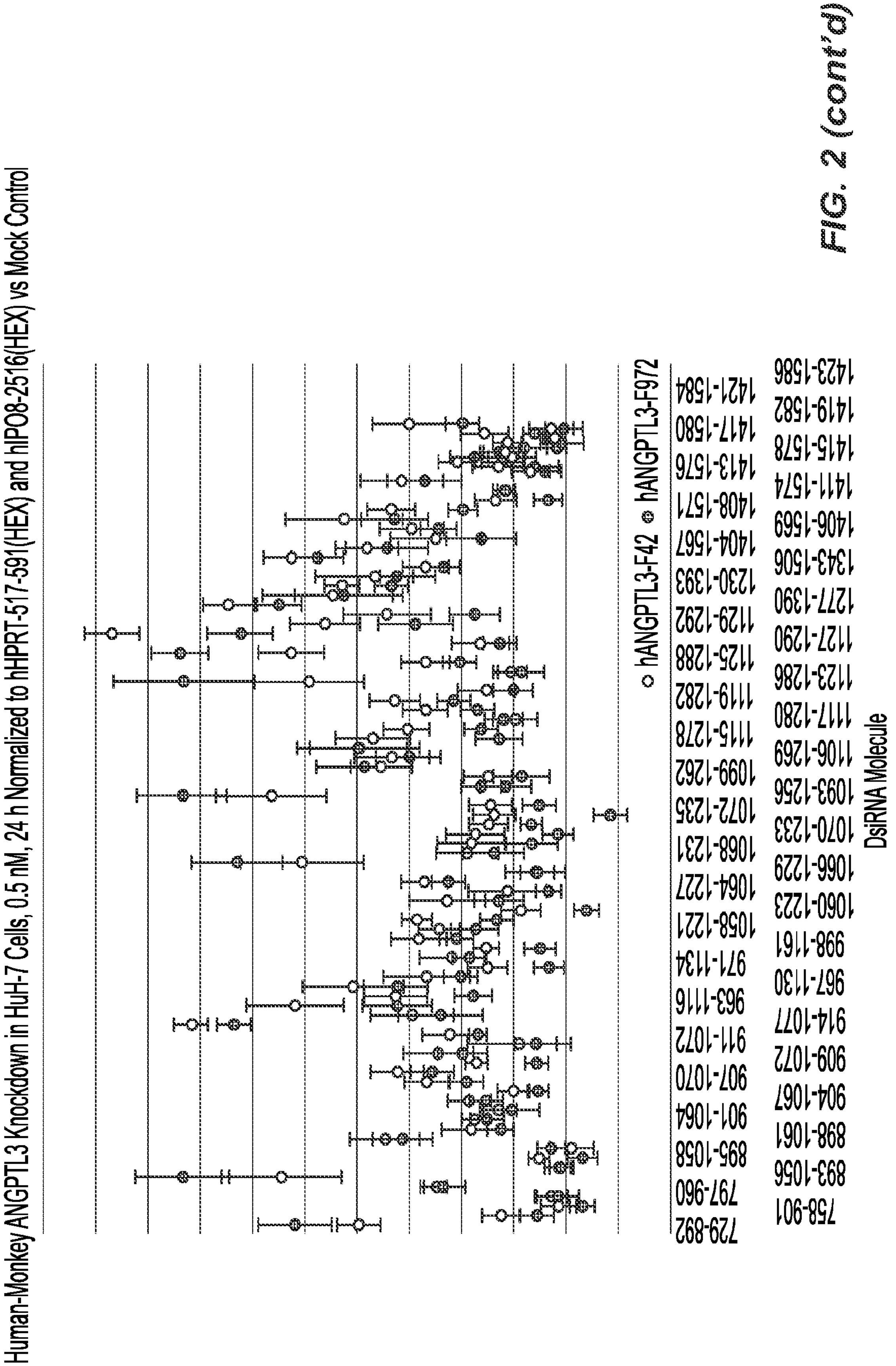
Figure 2:
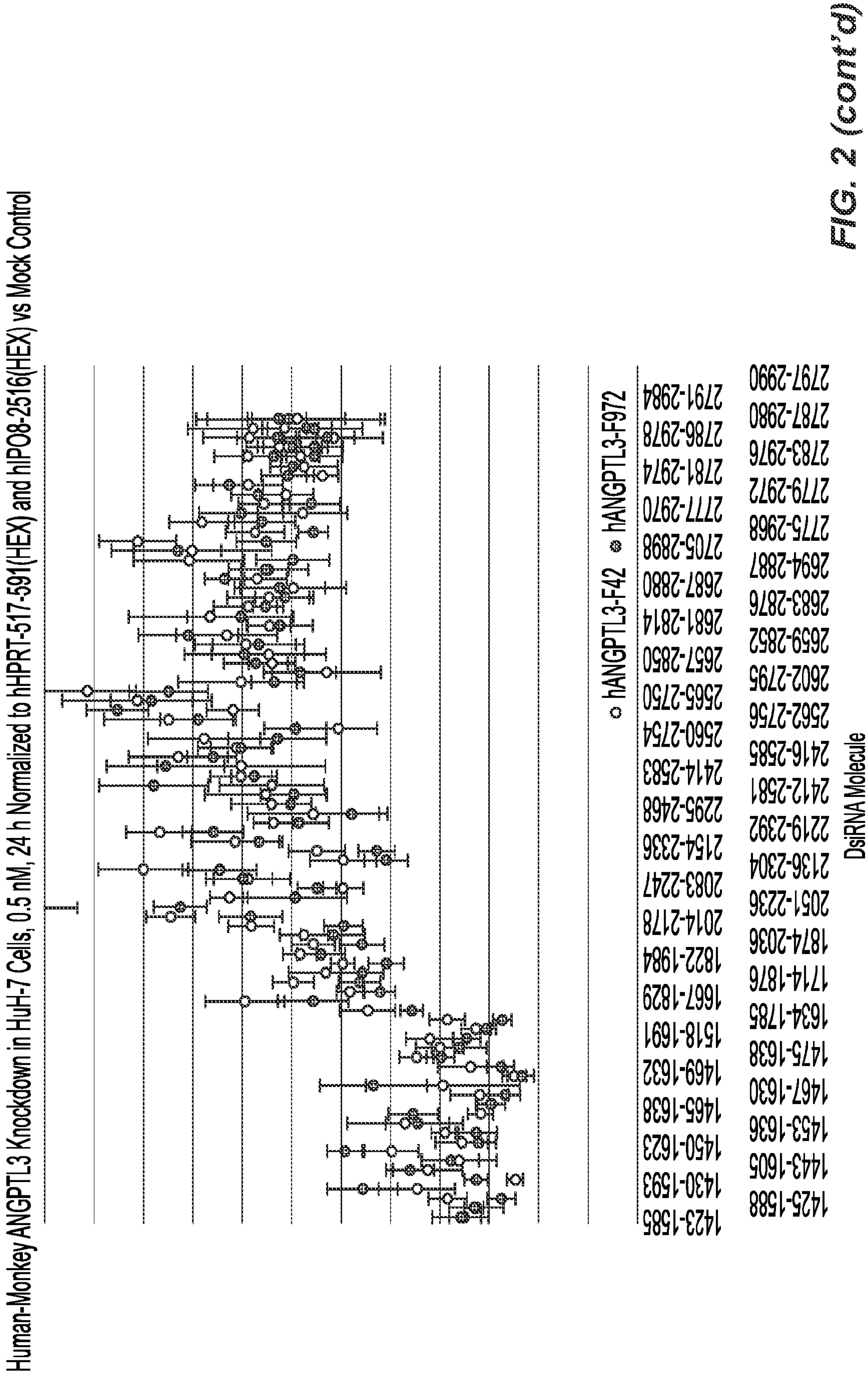

The results of the HuH-7 cell-based assay with the 384 DsiRNAs are shown in FIG. 1 and FIG. 2. FIG. 1 shows the results of the HuH-7 cell-based assay with 109 DsiRNAs that have guide strands that are complementary to human, monkey and mouse ANGPTL3 mRNA ("triple common"). Transfection of a triple common DsiRNA that results in less than or equal to 35% ANGPTL3 mRNA remaining in the cells when compared to negative controls is considered a candidate ANGPTL3 expression inhibitor (referred to herein as a "hit"). FIG. 2 shows the results of the HuH-7 cell-based assay with 275 DsiRNAs that have guide strands that are complementary to human and monkey ANGPTL3 mRNA ("human-monkey"). Human-monkey DsiRNAs resulting in less than or equal to 30% ANGPTL3 mRNA remaining when compared to negative controls are also considered hits. In FIG. 1 and FIG. 2, the percent mRNA remaining is shown for each of the 3' assay (circle shapes) and the 5' assay (diamond shapes).

These results show that DsiRNAs designed to target human ANGPTL3 mRNA inhibit ANGPTL3 expression in cells (as determined by a reduced amount of ANGPTL3 mRNA in DsiRNA-transfected cells) and that the nucleotide sequences comprising the DsiRNA hits are useful for generating RNAi oligonucleotides to inhibit ANGPTL3 expression. Further, these results demonstrate that multiple ANGPTL3 target sequences are suitable for the RNAi-mediated inhibition of ANGPTL3 expression.

Example 3: RNAi Oligonucleotide Inhibition of ANGPTL3 Expression In Vivo

Of the 384 DsiRNAs screened in the HuH-7 cell-based assays described in Example 2, the nucleotide sequences of 55 DsiRNAs hits (Table 3) are selected for further evaluation in vivo. Briefly, the nucleotide sequences of the 55 selected DsiRNAs are used to generate 55 corresponding double-stranded RNAi oligonucleotides comprising a nicked tetraloop GalNAc-conjugated structure (referred to herein as "GalNAc-conjugated ANGPTL3 oligonucleotides") having a 36-mer passenger strand and a 22-mer guide strand. Further, the nucleotide sequences comprising the passenger strand and guide strand of the GalNAc-conjugated ANGPTL3 oligonucleotides have a distinct pattern of modified nucleotides and phosphorothioate linkages (see, e.g., FIG. 3 for a schematic of the generic structure and chemical modification patterns of the GalNAc-conjugated ANGPTL3 oligonucleotides). The three adenosine nucleotides comprising the tetraloop are each conjugated to a GalNAc moiety (CAS #: 14131-60-3).

TABLE 3

GalNAc-Conjugated ANGPTL3 Oligonucleotides Evaluated in Mice

| Oligonucleotide | DP# | SEQ ID NO (Sense) | SEQ ID NO (Antisense) |
|---|---|---|---|
| ANGPTL3-0099-M1 | DP14993P:DP14992G | 1 | 2 |
| ANGPTL3-0108-M1 | DP14995P:DP14994G | 3 | 4 |
| ANGPTL3-0111-M1 | DP14997P:DP14996G | 5 | 6 |
| ANGPTL3-0112-M1 | DP14999P:DP14998G | 7 | 8 |
| ANGPTL3-0143-M1 | DP15001P:DP15000G | 9 | 10 |
| ANGPTL3-0165-M1 | DP15003P:DP15002G | 11 | 12 |
| ANGPTL3-0167-M1 | DP15005P:DP15004G | 13 | 14 |
| ANGPTL3-0170-M1 | DP15007P:DP15006G | 15 | 16 |
| ANGPTL3-0196-M1 | DP15009P:DP15008G | 17 | 18 |
| ANGPTL3-0197-M1 | DP15011P:DP15010G | 19 | 20 |
| ANGPTL3-0198-M1 | DP15013P:DP15012G | 21 | 22 |
| ANGPTL3-0201-M1 | DP15015P:DP15014G | 23 | 24 |
| ANGPTL3-0202-M1 | DP15017P:DP15016G | 25 | 26 |
| ANGPTL3-0203-M1 | DP15019P:DP15018G | 27 | 28 |
| ANGPTL3-0212-M1 | DP15021P:DP15020G | 29 | 30 |
| ANGPTL3-0303-M1 | DP15023P:DP15022G | 31 | 32 |
| ANGPTL3-0310-M1 | DP15025P:DP15024G | 33 | 34 |
| ANGPTL3-0330-M1 | DP15027P:DP15026G | 35 | 36 |
| ANGPTL3-0332-M1 | DP15029P:DP15028G | 37 | 38 |
| ANGPTL3-0333-M1 | DP15031P:DP15030G | 39 | 40 |
| ANGPTL3-0337-M1 | DP15033P:DP15032G | 41 | 42 |
| ANGPTL3-0394-M1 | DP15035P:DP15034G | 43 | 44 |
| ANGPTL3-0396-M1 | DP15037P:DP15036G | 45 | 46 |
| ANGPTL3-0400-M1 | DP15039P:DP15038G | 47 | 48 |
| ANGPTL3-0401-M1 | DP15041P:DP15040G | 49 | 50 |
| ANGPTL3-0437-M1 | DP15043P:DP15042G | 51 | 52 |
| ANGPTL3-0447-M1 | DP15045P:DP15044G | 53 | 54 |
| ANGPTL3-0517-M1 | DP15047P:DP15046G | 55 | 56 |
| ANGPTL3-0518-M1 | DP15049P:DP15048G | 57 | 58 |
| ANGPTL3-0532-M1 | DP15051P:DP15050G | 59 | 60 |
| ANGPTL3-0541-M1 | DP15053P:DP15052G | 61 | 62 |
| ANGPTL3-0582-M1 | DP15055P:DP15054G | 63 | 64 |
| ANGPTL3-0602-M1 | DP15057P:DP15056G | 65 | 66 |
| ANGPTL3-0603-M1 | DP15059P:DP15058G | 67 | 68 |
| ANGPTL3-0604-M1 | DP15061P:DP15060G | 69 | 70 |
| ANGPTL3-0606-M1 | DP15063P:DP15062G | 71 | 72 |
| ANGPTL3-0607-M1 | DP15065P:DP15064G | 73 | 74 |
| ANGPTL3-0608-M1 | DP15067P:DP15066G | 75 | 76 |
| ANGPTL3-0610-M1 | DP15069P:DP15068G | 77 | 78 |
| ANGPTL3-0676-M1 | DP15071P:DP15070G | 79 | 80 |
| ANGPTL3-0738-M1 | DP15073P:DP15072G | 81 | 82 |
| ANGPTL3-0796-M1 | DP15075P:DP15074G | 83 | 84 |
| ANGPTL3-0893-M1 | DP15077P:DP15076G | 85 | 86 |
| ANGPTL3-0894-M1 | DP15079P:DP15078G | 87 | 88 |
| ANGPTL3-0895-M1 | DP15081P:DP15080G | 89 | 90 |
| ANGPTL3-1059-M1 | DP15083P:DP15082G | 91 | 92 |
| ANGPTL3-1062-M1 | DP15085P:DP15084G | 93 | 94 |
| ANGPTL3-1065-M1 | DP15087P:DP15086G | 95 | 96 |
| ANGPTL3-1071-M1 | DP15089P:DP15088G | 97 | 98 |
| ANGPTL3-1412-M1 | DP15091P:DP15090G | 99 | 100 |
| ANGPTL3-1415-M1 | DP15093P:DP15092G | 101 | 102 |
| ANGPTL3-1420-M1 | DP15095P:DP15094G | 103 | 104 |
| ANGPTL3-1421-M1 | DP15097P:DP15096G | 105 | 106 |
| ANGPTL3-1422-M1 | DP15099P:DP15098G | 107 | 108 |

TABLE 3-continued

GalNAc-Conjugated ANGPTL3 Oligonucleotides Evaluated in Mice

| Oligonucleotide | DP# | SEQ ID NO (Sense) | SEQ ID NO (Antisense) |
|---|---|---|---|
| ANGPTL3-1468-M1 | DP15101P:DP15100G | 109 | 110 |
| ANGPTL3-0204-M2 | DP13439P:DP13438G | 111 | 112 |
| ANGPTL3-0327-M2 | DP13443P:DP13442G | 113 | 114 |
| ANGPTL3-1327-M2 | DP13465P:DP13464G | 115 | 116 |

Mouse Studies

The GalNAc-conjugated ANGPTL3 oligonucleotides listed in Table 3 are evaluated in mice engineered to transiently express human ANGPTL3 mRNA in hepatocytes. Three GalNAc-conjugated ANGPTL3 oligonucleotides (ANGPTL3-0204-M2, ANGPTL3-0327-M2 and ANGPTL3-1327-M2) are used as benchmark controls. Briefly, 6-8-week-old female CD-1 mice are treated subcutaneously with a GalNAc-conjugated ANGPTL3 oligonucleotide at a dose level of 1 mg/kg. Three days later (72 h), the mice are hydrodynamically injected with a DNA plasmid encoding the full human ANGPTL3 gene under control of a ubiquitous cytomegalovirus (CMV) promoter sequence. One day after introduction of the plasmid, liver samples are collected. Total RNA derived from these mice are subjected to qRT-PCR analysis for ANGPTL3 mRNA, relative to mice treated only with an identical volume of PBS. The values are normalized for transfection efficiency using the NeoR gene included on the plasmid.

Figure 4:
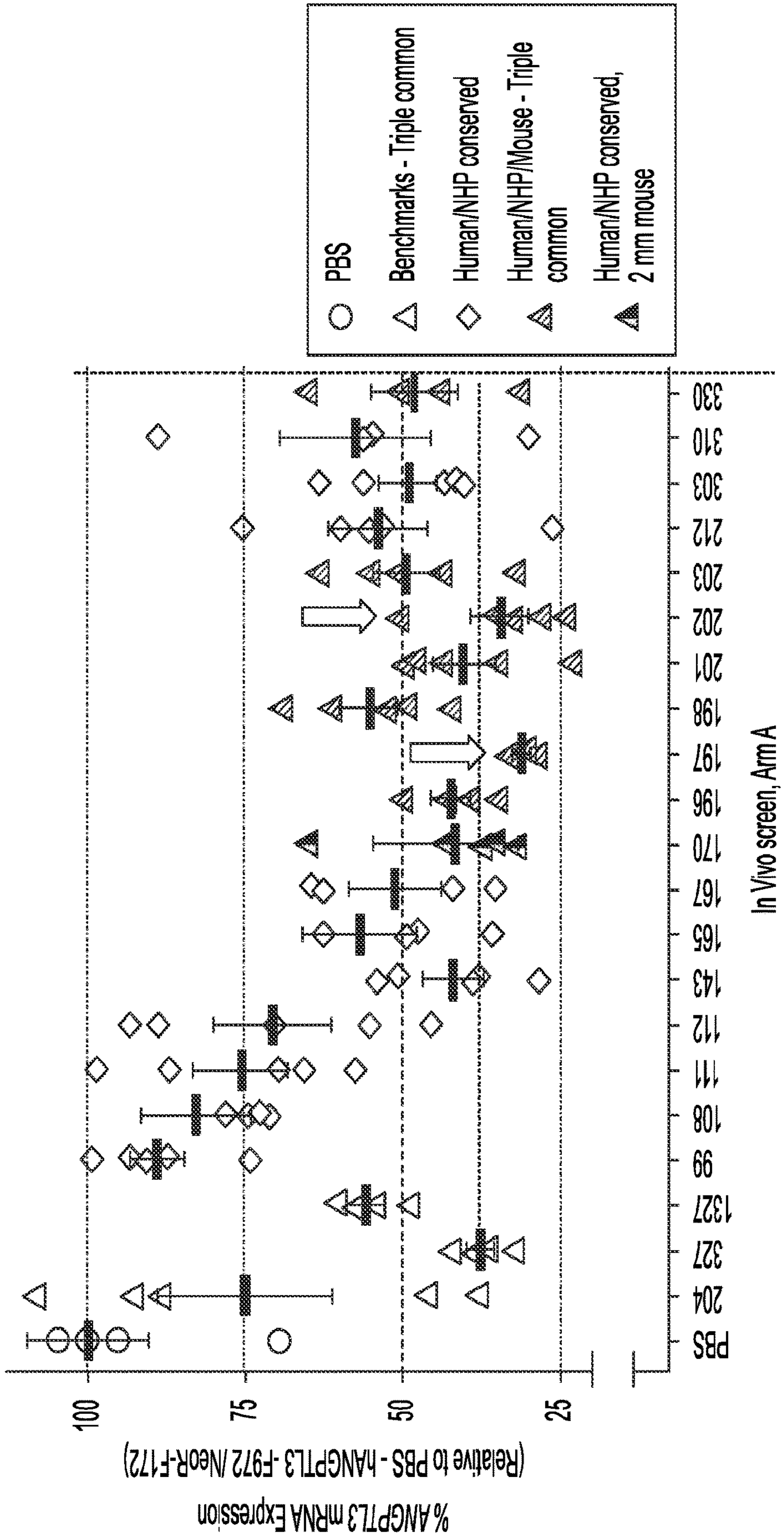
FIG. 4 provides a graph depicting the percent (%) of ANGPTL3 mRNA in liver samples from mice treated with the indicated GalNAc-conjugated ANGPTL3 oligonucleotides relative to mice treated with phosphate buffered saline (PBS).
Figure 4:
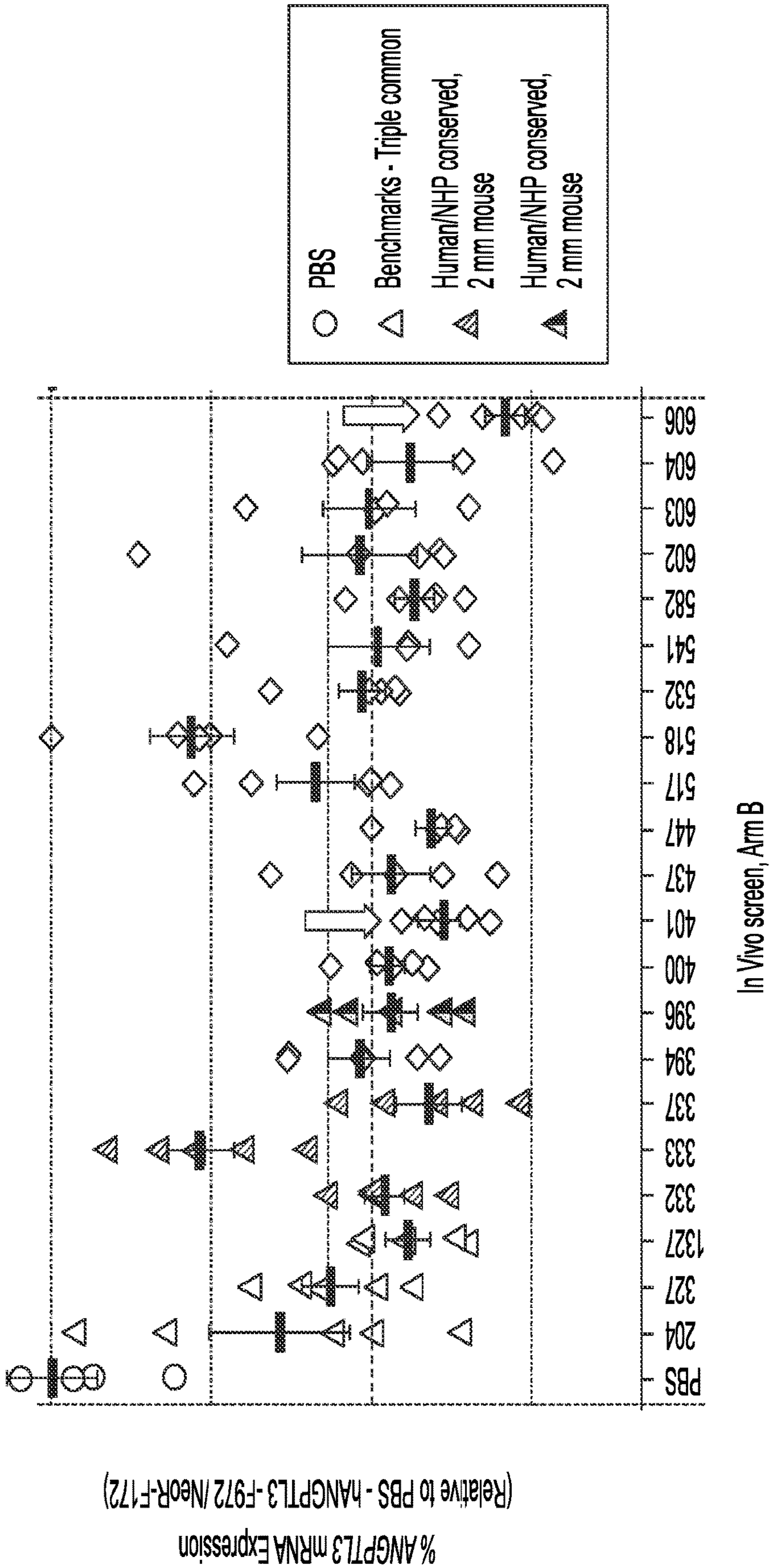
Figure 4:
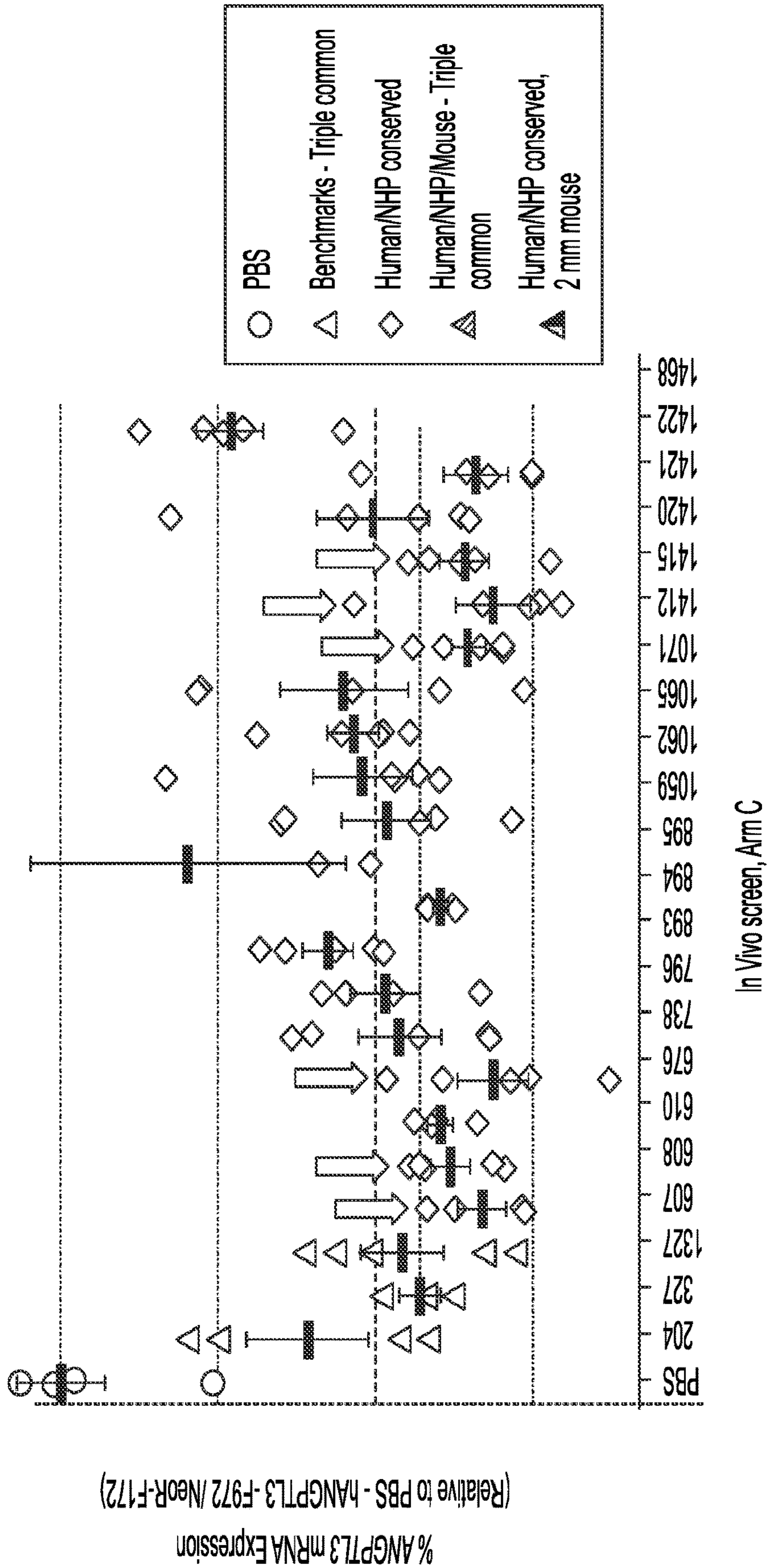

As shown in FIG. 4, all the GalNAc-conjugated ANGPTL3 oligonucleotides tested inhibit ANGPTL3 expression, as determined by a reduced amount of ANGPTL3 mRNA in liver samples from oligonucleotide-treated mice relative to mice treated with PBS. The mean % of remaining ANGPTL3 mRNA in liver samples of mice treated with the benchmark GalNAc-conjugated ANGPTL3 oligonucleotide ANGPTL3-0327 relative to mice treated with PBS is shown as a solid bar. FIG. 4 shows that 26 out of the 55 GalNAc-conjugated ANGPTL3 oligonucleotides tested inhibit ANGPTL3 expression to a greater extent than the benchmark GalNAc-conjugated ANGPTL3 oligonucleotide ANGPTL3-0327. Based on these results, 10 of the 55 GalNAc-conjugated ANGPTL3 oligonucleotides, indicated by arrows in FIG. 4 and listed in Table 4, are selected for evaluation of their ability to inhibit ANGPTL3 expression in NHPs. The 10 GalNAc-conjugated ANGPTL3 oligonucleotides listed in Table 4 comprise chemically modified nucleotides having either pattern M1 or M2 as described in FIG. 3.

TABLE 4

GalNAc-Conjugated ANGPTL3 Oligonucleotides Evaluated in NHPs

| Oligonucleotide | DP# | SEQ ID NO (Sense) | SEQ ID NO (Antisense) |
|---|---|---|---|
| ANGPTL3-0327-M2 | DP13443P:DP13442G | 113 | 114 |
| ANGPTL3-0197-M1 | DP15011P:DP15010G | 19 | 20 |
| ANGPTL3-0202-M1 | DP15017P:DP15016G | 25 | 26 |
| ANGPTL3-0401-M1 | DP15041P:DP15040G | 49 | 50 |
| ANGPTL3-0606-M1 | DP15063P:DP15062G | 71 | 72 |
| ANGPTL3-0607-M1 | DP15065P:DP15064G | 73 | 74 |
| ANGPTL3-0608-M1 | DP15067P:DP15066G | 75 | 76 |
| ANGPTL3-0676-M1 | DP15071P:DP15070G | 79 | 80 |

TABLE 4-continued

GalNAc-Conjugated ANGPTL3 Oligonucleotides Evaluated in NHPs

| Oligonucleotide | DP# | SEQ ID NO (Sense) | SEQ ID NO (Antisense) |
|---|---|---|---|
| ANGPTL3-1412-M1 | DP15091P:DP15090G | 99 | 100 |
| ANGPTL3-1415-M1 | DP15093P:DP15092G | 101 | 102 |
| ANGPTL3-1420-M1 | DP15095P:DP15094G | 103 | 104 |

TABLE A

Sequence information for the oligonucleotides in Tables 3 and 4.

| DP number passenger: Guide | Modification Pattern | Sequence with Modifications | Corresponding unmodified sequence |
|---|---|---|---|
| DP14993P:DP14992G | {MS}MMMMMMFFFFMMMMMMMMMMMMMMMM[adem-GalNAc][adem-GalNAc][adem-GalNAc]MMMMMM | [mAs][mU][mA][mA][mA][mA][mA][fU][fG][fU][fU][mC][mA][mC][mA][mA][mU][mU][mA][mA][mG][mC][mA][mG][mC][mC][mG][ademA-GalNAc][ademA-GalNAc][ademA-GalNAc][mG][mG][mC][mU][mG][mC] (SEQ ID NO: 132) | AUAAAAAUGUUCACAAUUAAGCAGCCGAAAGGCUGC (SEQ ID NO: 1) |
| | M{MS}{MS}MMMMMFMMMFMMFMFF{FS}{FS}{Px-MS} | [MePhosphonate-4O-mUs][fUs][fAs][fA][fU][mU][fG][mU][mG][fA][mA][mG] (SEQ ID NO: 133) | UUAAUUGUGAACAUUUUUAUGG (SEQ ID NO: 2) |
| DP14995P:DP14994G | {MS}MMMMMMFFFFMMMMMMMMMMMMMMMM[adem-GalNAc][adem-GalNAc][adem-GalNAc]MMMMMM | [mUs][mU][mC][mA][mC][mA][mA][fU][fU][fA][fA][mG][mC][mU][mC][mC][mU][mU][mC][mA][mG][mC][mA][mG][mC][mC][mG][ademA-GalNAc][ademA-GalNAc][ademA-GalNAc][mG][mG][mC][mU][mG][mC] (SEQ ID NO: 134) | UUCACAAUUAAGCUCCUUCAGCAGCCGAAAGGCUGC (SEQ ID NO: 3) |
| | M{MS}{MS}MMMMMFMMMFMMFMFF{FS}{FS}{Px-MS} | [MePhosphonate-4O-mA][mA][fU][mU][mG][mU][mG][mA][mAs][mGs][mG] (SEQ ID NO: 135) | UGAAGGAGCUUAAUUGUGAAGG (SEQ ID NO: 4) |
| DP14997P:DP14996G | {MS}MMMMMMFFFFMMMMMMMMMMMMMMMM[adem-GalNAc][adem-GalNAc][adem-GalNAc]MMMMMM | [mAs][mC][mA][mA][mU][mU][mA][fA][fG][fC][fU][mC][mC][mU][mU][mC][mU][mU][mU][mA][mG][mC][mA][mG][mC][mC][mG][ademA-GalNAc][ademA-GalNAc][ademA-GalNAc][mG][mG][mC][mU][mG][mC] (SEQ ID NO: 136) | ACAAUUAAGCUCCUUCUUUAGCAGCCGAAAGGCUGC (SEQ ID NO: 5) |
| | M{MS}{MS}MMMMMFMMMFMMFMFF{FS}{FS}{Px-MS} | [MePhosphonate-4O-mUs][fAs][fAs][fA][fG][mA][fA][mG][mG][fA][mG][mC][mU][fU][mA][mA][mU][mU][mG][mUs][mGs][mG] (SEQ ID NO: 137) | UAAAGAAGGAGCUUAAUUGUGG (SEQ ID NO: 6) |
| DP14999P:DP14998G | {MS}MMMMMMFFFFMMMMMMMMMMMM[adem-GalNAc][adem-GalNAc][adem-GalNAc]MMMMMM | [mCs][mA][mA][mU][mU][mA][mA][fG][fC][fU][fC][mC][mU][mU][mC][mU][mU][mU][mU][mA][mG][mC][mA][mG][mC][mC][mG][ademA-GalNAc][ademA-GalNAc][ademA-GalNAc][mG][mG][mC][mU][mG][mC] (SEQ ID NO: 138) | CAAUUAAGCUCCUUCUUUUAGCAGCCGAAAGGCUGC (SEQ ID NO: 7) |
| | M{MS}{MS}MMMMMFMMMFMMFMFF{FS}{FS}{Px-MS} | [MePhosphonate-4O-mUs][fAs][fAs][fA][fA][mG][fA][mA][mG][fG][mA][mG][mC][fU][mU][mA][mA][mU][mU][mGs][mGs][mG] (SEQ ID NO: 139) | UAAAAGAAGGAGCUUAAUUGGG (SEQ ID NO: 8) |
| DP15001P:DP15000G | {MS}MMMMMMFFFFMMMMMMMMMMMMMMMM[adem-GalNAc][adem-GalNAc][adem-GalNAc]MMMMMM | [mAs][mG][mU][mU][mA][mU][mU][fU][C][C][fU][mC][mC][mA][mG][mA][mA][mU][mU][mA][mG][mC][mA][mG][mC][mC][mG][ademA-GalNAc][ademA-GalNAc][ademA-GalNAc][mG][mG][mC][mU][mG][mC] (SEQ ID NO: 140) | AGUUAUUUCCUCCAGAAUUAGCAGCCGAAAGGCUGC (SEQ ID NO: 9) |
| | M{MS}{MS}MMMMMFMMMFMMFMFF{FS}{FS}{Px-MS} | [MePhosphonate-4O-mUs][fAs][fAs][fU][fU][mC][fU][mG][mG][fA][mG][mG][mA][fA][mA][mU][mA][mA][mC][mUs][mGs][mG] (SEQ ID NO: 141) | UAAUUCUGGAGGAAUAACUGG (SEQ ID NO: 10) |

TABLE A-continued

| Sequence information for the oligonucleotides in Tables 3 and 4. | | | |
|---|---|---|---|
| DP number passenger: Guide | Modification Pattern | Sequence with Modifications | Corresponding unmodified sequence |
| DP1500 3P:DP1 5002G | {MS}MMMMMMFFFF MMMMMMMMMMM MMMMM[adem-GalNAc][adem-GalNAc][adem-GalNAc]MMMMMM | [mCs][mA][mA][mG][mA][mC][mA][fA][fU][fU][fC] [mA][mU][mC][mA][mU][mU][mU][mG][mA][mG][m C][mA][mG][mC][mC][mG][ademA-GalNAc][ademA-GaINAc][ademA-GalNAc][mG][mG][mC][mU][mG][mC] (SEQ ID NO: 142) | CAAGACAAUUCAU CAUUUGAGCAGCC GAAAGGCUGC (SEQ ID NO: 11) |
| | M{MS}{MS}MMMMM FMMMFMMFMFF{FS} {FS}{Px-MS} | [MePhosphonate-4O-mUs][fCs][fAs][fA][fA][mU][fG][mA][mU][fG][mA] [mA][mU][fU][mG][mU][mC][mU][mU][mGs][mGs] [mG] (SEQ ID NO: 143) | UCAAAUGAUGAAU UGUCUUGGG (SEQ ID NO: 12) |
| DP1500 5P:DP1 5004G | {MS}MMMMMMFFFF MMMMMMMMMMM MMMMM[adem-GalNAc][adem-GalNAc][adem-GalNAc]MMMMMM | [mAs][mG][mA][mC][mA][mA][mU][fU][fC][fA][fU] [mC][mA][mU][mU][mU][mG][mA][mU][mA][mG] [mC][mA][mG][mC][mC][mG][ademA-GalNAc][ademA-GalNAc][ademA-GalNAc][mG][mG][mC][mU][mG][mC] (SEQ ID NO: 144) | AGACAAUUCAUCA UUUGAUAGCAGCC GAAAGGCUGC (SEQ ID NO: 13) |
| | M{MS}{MS}MMMMM FMMMFMMFMFF{FS} {FS}{Px-MS} | [MePhosphonate-4O-mUs][fAs][fUs][fC][[A][mA][fA][mU][mG][fA][mU] [mG][mA][fA][mU][mU][mG][mU][mC][mUs][mGs] [mG] (SEQ ID NO: 145) | UAUCAAAUGAUGA AUUGUCUGG (SEQ ID NO: 14) |
| DP1500 7P:DP1 5006G | {MS}MMMMMMFFFF MMMMMMMMMMM MMMMM[adem-GalNAc][adem-GalNAc][adem-GalNAc]MMMMMM | [mCs][mA][mA][mU][mU][mC][mA][fU][fC][fA][fU] [mU][mU][mG][mA][mU][mU][mC][mU][mA][mG] [mC][mA][mG][mC][mC][mG][ademA-GalNAc][ademA-GalNAc][ademA-GalNAc][mG][mG][mC][mU][mG][mC] (SEQ ID NO: 146) | CAAUUCAUCAUUU GAUUCUAGCAGCC GAAAGGCUGC (SEQ ID NO: 15) |
| | M{MS}{MS}MMMMM FMMMFMMFMFF{FS} {FS}{Px-MS} | [MePhosphonate-4O-mUs][fAs][fGs][fA][fA][mU][fC][mA][mA][fA][mU] [mG][mA][fU][mG][mA][mA][mU][mU][mGs][mGs] [mG] (SEQ ID NO: 147) | UAGAAUCAAAUGA UGAAUUGGG (SEQ ID NO: 16) |
| DP1500 9P:DP1 5008G | {MS}MMMMMMFFFF MMMMMMMMMMM MMMMM[adem-GalNAc][adem-GalNAc][adem-GalNAc]MMMMMM | [mCs][mA][mG][mA][mG][mC][mC][fA][[A][fA][fA] [mU][mC][mA][mA][mG][mA][mU][mU][mA][mG] [mC][mA][mG][mC][mC][mG][ademA-GalNAc][ademA-GalNAc][ademA-GalNAc][mG][mG][mC][mU][mG][mC] (SEQ ID NO: 148) | CAGAGCCAAAAUC AAGAUUAGCAGCC GAAAGGCUGC (SEQ ID NO: 17) |
| | M{MS}{MS}MMMMM FMMMFMMFMFF{FS} {FS}{Px-MS} | [MePhosphonate-4O-mUs][fAs][fAs][fU][fC][mU][fU][mG][mA][fU][mU] [mU][mU][fG][mG][mC][mU][mC][mU][mGs][mGs] [mG] (SEQ ID NO: 149) | UAAUCUUGAUUUU GGCUCUGGG (SEQ ID NO: 18) |
| DP1501 1P:DP1 5010G | {MS}MMMMMMFFFF MMMMMMMMMMM MMMMM[adem-GalNAc][adem-GalNAc][adem-GalNAc]MMMMMM | [mAs][mG][mA][mG][mC][mC][mA][fA][A][fA][fU] [mC][mA][mA][mG][mA][mU][mU][mU][mA][mG] [mC][mA][mG][mC][mC][mG][ademA-GalNAc][ademA-GalNAc][ademA-GalNAc][mG][mG][mC][mU][mG][mC] (SEQ ID NO: 150) | AGAGCCAAAAUCA AGAUUUAGCAGCC GAAAGGCUGC (SEQ ID NO: 19) |
| | M{MS}{MS}MMMMM FMMMFMMFMFF{FS} {FS}{Px-MS} | [MePhosphonate-4O-mUs][fAs][fAs][fA][fU][mC][fU][mU][mG][fA][mU] [mU][mU][fU][mG][mG][mC][mU][mC][mUs][mGs] [mG] (SEQ ID NO: 151) | UAAAUCUUGAUUU UGGCUCUGG (SEQ ID NO: 20) |
| DP1501 3P:DP1 5012G | {MS}MMMMMMFFFF MMMMMMMMMMM MMMMM[adem-GalNAc][adem-GalNAc][adem-GalNAc]MMMMMM | [mGs][mA][mG][mC][mC][mA][mA][fA][A][fU][fC] [mA][mA][mG][mA][mU][mU][mU][mG][mA][mG] [mC][mA][mG][mC][mC][mG][ademA-GalNAc][ademA-GaINAc][ademA-GalNAc][mG][mG][mC][mU][mG][mC] (SEQ ID NO: 152) | GAGCCAAAAUCAA GAUUUGAGCAGCC GAAAGGCUGC (SEQ ID NO: 21) |
| | M{MS}{MS}MMMMM FMMMFMMFMFF{FS} {FS}{Px-MS} | [MePhosphonate-4O-mUs][fCs][fAs][fA][fA][mU][fC][mU][mU][fG][mA] [mU][mU][fU][mU][mG][mG][mC][mU][mCs][mGs] [mG] (SEQ ID NO: 153) | UCAAAUCUUGAUU UUGGCUCGG (SEQ ID NO: 22) |

TABLE A-continued

| DP number passenger: Guide | Modification Pattern | Sequence with Modifications | Corresponding unmodified sequence |
|---|---|---|---|
| DP1501 5P:DP1 5014G | {MS}MMMMMMFFFF MMMMMMMMMMM MMMMM[adem-GalNAc][adem-GalNAc][adem-GalNAc]MMMMMM | [mCs][mC][mA][mA][mA][mA][mU][fC][fA][[A][fG] [mA][mU][mU][mU][mG][mC][mU][mA][mA][mG] [mC][mA][mG][mC][mC][mG][ademA-GalNAc][ademA-GalNAc][ademA-GalNAc][mG][mG][mC][mU][mG][mC] (SEQ ID NO: 154) | CCAAAAUCAAGAU UUGCUAAGCAGCC GAAAGGCUGC (SEQ ID NO: 23) |
| | M{MS}{MS}MMMMM FMMMFMMFMFF{FS} {FS}{Px-MS} | [MePhosphonate-4O-mUs][fUs][fAs][fG][fC][mA][fA][mA][mU][fC][mU] [mU][mG][fA][mU][mU][mU][mU][mG][mGs][mGs] [mG] (SEQ ID NO: 155) | UUAGCAAAUCUUG AUUUUGGGG (SEQ ID NO: 24) |
| DP1501 7P:DP1 5016G | {MS}MMMMMMFFFF MMMMMMMMMMM MMMMM[adem-GalNAc][adem-GalNAc][adem-GalNAc]MMMMMM | [mCs][mA][mA][mA][mA][mU][mC][fA][fA][fG][fA] [mU][mU][mU][mG][mC][mU][mA][mU][mA][mG] [mC][mA][mG][mC][mC][mG][ademA-GalNAc][ademA-GalNAc][ademA-GalNAc][mG][mG][mC][mU][mG][mC] (SEQ ID NO: 156) | CAAAAUCAAGAUU UGCUAUAGCAGCC GAAAGGCUGC (SEQ ID NO: 25) |
| | M{MS}{MS}MMMMM FMMMFMMFMFF{FS} {FS}{Px-MS} | [MePhosphonate-4O-mUs][fAs][fUs][fA][fG][mC][fA][mA][mA][fU][mC] [mU][mU][fG][mA][mU][mU][mU][mU][mGs][mGs] [mG] (SEQ ID NO: 157) | UAUAGCAAAUCUU GAUUUUGGG (SEQ ID NO: 26) |
| DP1501 9P:DP1 5018G | {MS}MMMMMMFFFF MMMMMMMMMMM MMMMM[adem-GalNAc][adem-GalNAc][adem-GalNAc]MMMMMM | [mAs][mA][mA][mA][mU][mC][mA][fA][fG][fA][fU] [mU][mU][mG][mC][mU][mA][mU][mG][mA][mG] [mC][mA][mG][mC][mC][mG][ademA-GalNAc][ademA-GaINAc][ademA-GalNAc][mG][mG][mC][mU][mG][mC] (SEQ ID NO: 158) | AAAAUCAAGAUUU GCUAUGAGCAGCC GAAAGGCUGC (SEQ ID NO: 27) |
| | M{MS}{MS}MMMMM FMMMFMMFMFF{FS} {FS}{Px-MS} | [MePhosphonate-4O-mUs][fCs][fAs][fU][fA][mG][fC][mA][mA][fA][mU] [mC][mU][fU][mG][mA][mU][mU][mU][mUs][mGs] [mG] (SEQ ID NO: 159) | UCAUAGCAAAUCU UGAUUUUGG (SEQ ID NO: 28) |
| DP1502 1P:DP1 5020G | {MS}MMMMMMFFFF MMMMMMMMMMM MMMMM[adem-GalNAc][adem-GalNAc][adem-GalNAc]MMMMMM | [mAs][mU][mU][mU][mG][mC][mU][fA][fU][fG][fU] [mU][mA][mG][mA][mC][mG][mA][mU][mA][mG] [mC][mA][mG][mC][mC][mG][ademA-GalNAc][ademA-GalNAc][ademA-GalNAc][mG][mG][mC][mU][mG][mC] (SEQ ID NO: 160) | AUUUGCUAUGUUA GACGAUAGCAGCC GAAAGGCUGC (SEQ ID NO: 29) |
| | M{MS}{MS}MMMMM FMMMFMMFMFF{FS} {FS}{Px-MS} | [MePhosphonate-4O-mUs][fAs][fUs][fC][fG][mU][fC][mU][mA][fA][mC] [mA][mU][fA][mG][mC][mA][mA][mA][mUs][mGs] [mG] (SEQ ID NO: 161) | UAUCGUCUAACAU AGCAAAUGG (SEQ ID NO: 30) |
| DP1502 3P:DP1 5022G | {MS}MMMMMMFFFF MMMMMMMMMMM MMMMM[adem-GalNAc][adem-GalNAc][adem-GalNAc]MMMMMM | [mCs][mA][mA][mA][mU][mU][mA][fA][fU][fG][fA] [mC][mA][mU][mA][mU][mU][mU][mC][mA][mG] [mC][mA][mG][mC][mC][mG][ademA-GalNAc][ademA-GalNAc][ademA-GalNAc][mG][mG][mC][mU][mG][mC] (SEQ ID NO: 162) | CAAAUUAAUGACA UAUUUCAGCAGCC GAAAGGCUGC (SEQ ID NO: 31) |
| | M{MS}{MS}MMMMM FMMMFMMFMFF{FS} {FS}{Px-MS} | [MePhosphonate-4O-mUs][fGs][fAs][fA][fA][mU][fA][mU][mG][fU][mC] [mA][mU][fU][mA][mA][mU][mU][mU][mGs][mGs] [mG] (SEQ ID NO: 163) | UGAAAUAUGUCAU UAAUUUGGG (SEQ ID NO: 32) |
| DP1502 5P:DP1 5024G | {MS}MMMMMMFFFF MMMMMMMMMMM MMMMM[adem-GalNAc][adem-GalNAc][adem-GalNAc]MMMMMM | [mAs][mU][mG][mA][mC][mA][mU][A][fU][fU][fU] [mC][mA][mA][mA][mA][mA][mC][mU][mA][mG] [mC][mA][mG][mC][mC][mG][ademA-GalNAc][ademA-GalNAc][ademA-GalNAc][mG][mG][mC][mU][mG][mC] (SEQ ID NO: 164) | AUGACAUAUUUCA AAAACUAGCAGCC GAAAGGCUGC (SEQ ID NO: 33) |
| | M{MS}{MS}MMMMM FMMMFMMFMFF{FS} {FS}{Px-MS} | [MePhosphonate-4O-mUs][fAs][fGs][fU][fU][mU][fU][mU][mG][fA][mA] [mA][mU][fA][mU][mG][mU][mC][mA][mUs][mGs] [mG] (SEQ ID NO: 165) | UAGUUUUUGAAAU AUGUCAUGG (SEQ ID NO: 34) |

Sequence information for the oligonucleotides in Tables 3 and 4.

TABLE A-continued

Sequence information for the oligonucleotides in Tables 3 and 4.

| DP number passenger: Guide | Modification Pattern | Sequence with Modifications | Corresponding unmodified sequence |
|---|---|---|---|
| DP15027P:DP15026G | {MS}MMMMMMFFFF-MMMMMMMMMMM-MMMMM[adem-GalNAc][adem-GalNAc][adem-GalNAc]MMMMMM | [mAs][mA][mC][mA][mU][mA][mU][fU][fU][fG][fA][mU][mC][mA][mG][mU][mC][mU][mU][mA][mG][mC][mA][mG][mC][mC][mG][ademA-GalNAc][ademA-GalNAc][ademA-GalNAc][mG][mG][mC][mU][mG][mC] (SEQ ID NO: 166) | AACAUAUUUGAUCAGUCUUAGCAGCCGAAAGGCUGC (SEQ ID NO: 35) |
| | M{MS}{MS}MMMMM-FMMMFMMFMFF{FS}{FS}{Px-MS} | [MePhosphonate-4O-mUs][fAs][fAs][fG][A][mC][fU][mG][mA][fU][mC][mA][mA][fA][mU][mA][mU][mG][mU][mUs][mGs][mG] (SEQ ID NO: 167) | UAAGACUGAUCAAAUAUGUUGG (SEQ ID NO: 36) |
| DP15029P:DP15028G | {MS}MMMMMMFFFFMMMMMMMMMMMMMMMM[adem-GalNAc][adem-GalNAc][adem-GalNAc]MMMMMM | [mCs][mA][mU][mA][mU][mU][mU][G][A][fU][fC][mA][mG][mU][mC][mU][mU][mU][mU][mA][mG][mC][mA][mG][mC][mC][mG][ademA-GalNAc][ademA-GalNAc][ademA-GalNAc][mG][mG][mC][mU][mG][mC] (SEQ ID NO: 168) | CAUAUUUGAUCAGUCUUUUAGCAGCCGAAAGGCUGC (SEQ ID NO: 37) |
| | M{MS}{MS}MMMMMFMMMFMMFMFF{FS}{FS}{Px-MS} | [MePhosphonate-4O-mUs][fAs][fAs][fA][fA][mG][fA][mC][mU][fG][mA][mU][mC][fA][mA][mA][mU][mA][mU][mGs][mGs][mG] (SEQ ID NO: 169) | UAAAAGACUGAUCAAAUAUGGG (SEQ ID NO: 38) |
| DP15031P:DP15030G | {MS}MMMMMMFFFFMMMMMMMMMMMMMMMM[adem-GalNAc][adem-GalNAc][adem-GalNAc]MMMMMM | [mAs][mU][mA][mU][mU][mU][mG][fA][fU][fC][fA][mG][mU][mC][mU][mU][mU][mU][mU][mA][mG][mC][mA][mG][mC][mC][mG][ademA-GalNAc][ademA-GalNAc][ademA-GalNAc][mG][mG][mC][mU][mG][mC] (SEQ ID NO: 170) | AUAUUUGAUCAGUCUUUUUAGCAGCCGAAAGGCUGC (SEQ ID NO: 39) |
| | M{MS}{MS}MMMMMFMMMFMMFMFF{FS}{FS}{Px-MS} | [MePhosphonate-4O-mUs][fAs][fAs][fA][fA][mA][fG][mA][mC][fU][mG][mA][mU][fC][mA][mA][mA][mU][mA][mUs][mGs][mG] (SEQ ID NO: 171) | UAAAAAGACUGAUCAAAUAUGG (SEQ ID NO: 40) |
| DP15033P:DP15032G | {MS}MMMMMMFFFFMMMMMMMMMMMMMMMM[adem-GalNAc][adem-GalNAc][adem-GalNAc]MMMMMM | [mUs][mU][mG][mA][mU][mC][mA][fG][fU][fC][fU][mU][mU][mU][mU][mA][mU][mG][mA][mA][mG][mC][mA][mG][mC][mC][mG][ademA-GalNAc][ademA-GalNAc][ademA-GalNAc][mG][mG][mC][mU][mG][mC] (SEQ ID NO: 172) | UUGAUCAGUCUUUUUAUGAAGCAGCCGAAAGGCUGC (SEQ ID NO: 41) |
| | M{MS}{MS}MMMMMFMMMFMMFMFF{FS}{FS}{Px-MS} | [MePhosphonate-4O-mUs][fUs][fCs][fA][fU][mA][fA][mA][mA][fA][mG][mA][mC][fU][mG][mA][mU][mC][mA][mAs][mGs][mG] (SEQ ID NO: 173) | UUCAUAAAAAGACUGAUCAAGG (SEQ ID NO: 42) |
| DP15035P:DP15034G | {MS}MMMMMMFFFFMMMMMMMMMMMMMMMM[adem-GalNAc][adem-GalNAc][adem-GalNAc]MMMMMM | [mAs][mG][mG][mA][mA][mC][mU][fG][fA][fG][fA][mA][mG][mA][mA][mC][mU][mA][mC][mA][mG][mC][mA][mG][mC][mC][mG][ademA-GalNAc][ademA-GalNAc][ademA-GalNAc][mG][mG][mC][mU][mG][mC] (SEQ ID NO: 174) | AGGAACUGAGAAGAACUACAGCAGCCGAAAGGCUGC (SEQ ID NO: 43) |
| | M{MS}{MS}MMMMMFMMMFMMFMFF{FS}{FS}{Px-MS} | [MePhosphonate-4O-mUs][fGs][fUs][fA][fG][mU][fU][mC][mU][fU][mC][mU][mC][fA][mG][mU][mU][mC][mC][mUs][mGs][mG] (SEQ ID NO: 175) | UGUAGUUCUUCUCAGUUCCUGG (SEQ ID NO: 44) |
| DP15037P:DP15036G | {MS}MMMMMMFFFFMMMMMMMMMMMMMMMM[adem-GalNAc][adem-GaINAc][adem-GalNAc]MMMMMM | [mGs][mA][mA][mC][mU][mG][mA][fG][fA][[A][fG][mA][mA][mC][mU][mA][mC][mA][mU][mA][mG][mC][mA][mG][mC][mC][mG][ademA-GalNAc][ademA-GalNAc][ademA-GalNAc][mG][mG][mC][mU][mG][mC] (SEQ ID NO: 176) | GAACUGAGAAGAACUACAUAGCAGCCGAAAGGCUGC (SEQ ID NO: 45) |
| | M{MS}{MS}MMMMMFMMMFMMFMFF{FS}{FS}{Px-MS} | [MePhosphonate-4O-mUs][fAs][fUs][fG][fU][mA][fG][mU][mU][fC][mU][mG] (SEQ ID NO: 177) | UAUGUAGUUCUUCUCAGUUCGG (SEQ ID NO: 46) |

TABLE A-continued

Sequence information for the oligonucleotides in Tables 3 and 4.

| DP number passenger: Guide | Modification Pattern | Sequence with Modifications | Corresponding unmodified sequence |
|---|---|---|---|
| DP15039P:DP15038G | {MS}MMMMMMFFFFMMMMMMMMMMMMMMMM[adem-GalNAc][adem-GalNAc][adem-GalNAc]MMMMMM | [mUs][mG][mA][mG][mA][mA][mG][fA][fA][fC][fU][mA][mC][mA][mU][mA][mU][mA][mA][mA][mG][mC][mA][mG][mC][mC][mG][ademA-GalNAc][ademA-GalNAc][ademA-GalNAc][mG][mG][mC][mU][mG][mC] (SEQ ID NO: 178) | UGAGAAGAACUACAUAUAAAGCAGCCGAAAGGCUGC (SEQ ID NO: 47) |
| | M{MS}{MS}MMMMMFMMMFMMFMFF{FS}{FS}{Px-MS} | [MePhosphonate-4O-mUs][fUs][fUs][fA][fU][mA][fU][mG][mU][fA][mG][mU][mU][fC][mU][mU][mC][mU][mC][mAs][mGs][mG] (SEQ ID NO: 179) | UUUAUAUGUAGUUCUUCUCAGG (SEQ ID NO: 48) |
| DP15041P:DP15040G | {MS}MMMMMMFFFFMMMMMMMMMMMMMMMM[adem-GalNAc][adem-GalNAc][adem-GalNAc]MMMMMM | [mGs][mA][mG][mA][mA][mG][mA][fA][fC][fU][fA][mC][mA][mU][mA][mU][mA][mA][mA][mA][mG][mC][mA][mG][mC][mC][mG][ademA-GalNAc][ademA-GalNAc][ademA-GalNAc][mG][mG][mC][mU][mG][mC] (SEQ ID NO: 180) | GAGAAGAACUACAUAUAAAAGCAGCCGAAAGGCUGC (SEQ ID NO: 49) |
| | M{MS}{MS}MMMMMFMMMFMMFMFF{FS}{FS}{Px-MS} | [MePhosphonate-4O-mUs][fUs][fUs][fU][A][mU][fA][mU][mG][fU][mA][mG][mU][fU][mC][mU][mU][mC][mU][mCs][mGs][mG] (SEQ ID NO: 181) | UUUUAUAUGUAGUUCUUCUCGG (SEQ ID NO: 50) |
| DP15043P:DP15042G | {MS}MMMMMMFFFFMMMMMMMMMMMMMMMM[adem-GalNAc][adem-GalNAc][adem-GalNAc]MMMMMM | [mAs][mG][mA][mG][mG][mU][mA][fA][fA][fG][fA][mA][mU][mA][mU][mG][mU][mC][mA][mA][mG][mC][mA][mG][mC][mC][mG][ademA-GalNAc][ademA-GalNAc][ademA-GalNAc][mG][mG][mC][mU][mG][mC] (SEQ ID NO: 182) | AGAGGUAAAGAAUAUGUCAAGCAGCCGAAAGGCUGC (SEQ ID NO: 51) |
| | M{MS}{MS}MMMMMFMMMFMMFMFF{FS}{FS}{Px-MS} | [MePhosphonate-4O-mU][mU][fU][mA][mC][mC][mU][mC][mUs][mGs][mG] (SEQ ID NO: 183) | UUGACAUAUUCUUUACCUCUGG (SEQ ID NO: 52) |
| DP15045P:DP15044G | {MS}MMMMMMFFFFMMMMMMMMMMMMMMMM[adem-GalNAc][adem-GalNAc][adem-GalNAc]MMMMMM | [mAs][mA][mU][mA][mU][mG][mU][fC][A][fC][fU][mU][mG][mA][mA][mC][mU][mC][mA][mA][mG][mC][mA][mG][mC][mC][mG][ademA-GalNAc][ademA-GalNAc][ademA-GalNAc][mG][mG][mC][mU][mG][mC] (SEQ ID NO: 184) | AAUAUGUCACUUGAACUCAAGCAGCCGAAAGGCUGC (SEQ ID NO: 53) |
| | M{MS}{MS}MMMMMFMMMFMMFMFF{FS}{FS}{Px-MS} | [MePhosphonate-4O-mUs][fUs][fGs][fA][fG][mU][fU][mC][mA][fA][mG][mU][mG][fA][mC][mA][mU][mA][mU][mUs][mGs][mG] (SEQ ID NO: 185) | UUGAGUUCAAGUGACAUAUUGG (SEQ ID NO: 54) |
| DP15047P:DP15046G | {MS}MMMMMMFFFFMMMMMMMMMMMMMMMM[adem-GalNAc][adem-GalNAc][adem-GalNAc]MMMMMM | [mUs][mG][mA][mA][mA][mU][mA][fU][fU][fU][fA][mG][mA][mA][mG][mA][mG][mC][mA][mA][mG][mC][mA][mG][mC][mC][mG][ademA-GalNAc][ademA-GalNAc][ademA-GalNAc][mG][mG][mC][mU][mG][mC] (SEQ ID NO: 186) | UGAAAUAUUUAGAAGAGCAAGCAGCCGAAAGGCUGC (SEQ ID NO: 55) |
| | M{MS}{MS}MMMMMFMMMFMMFMFF{FS}{FS}{Px-MS} | [MePhosphonate-4O-mA][mA][fU][mA][mU][mU][mU][mC][mAs][mGs][mG] (SEQ ID NO: 187) | UUGCUCUUCUAAAUAUUUCAGG (SEQ ID NO: 56) |
| DP15049P:DP15048G | {MS}MMMMMMFFFFMMMMMMMMMMMMMMMM[adem-GalNAc][adem-GalNAc][adem-GalNAc]MMMMMM | [mAs][mA][mU][mA][mU][mG][mU][fC][fA][fC][fU][mA][mA][mG][mA][mG][mC][mA][mA][mA][mG][mC][mA][mG][mC][mC][mG][ademA-GalNAc][ademA-GalNAc][ademA-GalNAc][mG][mG][mC][mU][mG][mC] (SEQ ID NO: 188) | GAAAUAUUUAGAAGAGCAAAGCAGCCGAAAGGCUGC (SEQ ID NO: 57) |
| | M{MS}{MS}MMMMMFMMMFMMFMFF{FS}{FS}{Px-MS} | [MePhosphonate-4O-mUs][fUs][fUs][fG][fC][mU][fC][mU][mU][fC][mU][mA][mA][fA][mU][mA][mU][mU][mU][mCs][mGs][mG] (SEQ ID NO: 189) | UUUGCUCUUCUAAAUAUUUCGG (SEQ ID NO: 58) |
| DP15051P:DP15050G | {MS}MMMMMMFFFFMMMMMMMMMMMMMMMM[adem- | [mAs][mG][mC][mA][mA][mC][mU][fA][fA][fC][fU][mA][mA][mC][mU][mU][mA][mA][mU][mA][mG][mC][mA][mG][mC][mC][mG][ademA- | AGCAACUAACUAACUUAAUAGCAGCCGAAAGGCUGC |

TABLE A-continued

Sequence information for the oligonucleotides in Tables 3 and 4.

| DP number passenger: Guide | Modification Pattern | Sequence with Modifications | Corresponding unmodified sequence |
|---|---|---|---|
| | GalNAc][adem-GalNAc][adem-GalNAc]MMMMMM | GalNAc][ademA-GalNAc][ademA-GalNAc][mG][mG][mC][mU][mG][mC] (SEQ ID NO: 190) | (SEQ ID NO: 59) |
| | M{MS}{MS}MMMMM FMMMFMMFMFF{FS}{FS}{Px-MS} | [MePhosphonate-4O-mUs][fAs][fUs][fU][fA][mA][fG][mU][mU][fA][mG][mU][mU][fA][mG][mU][mU][mG][mC][mUs][mGs][mG] (SEQ ID NO: 191) | UAUUAAGUUAGUUAGUUGCUGG (SEQ ID NO: 60) |
| DP15053P:DP15052G | {MS}MMMMMMFFFF MMMMMMMMMMM MMMMM[adem-GalNAc][adem-GalNAc][adem-GalNAc]MMMMMM | [mCs][mU][mA][mA][mC][mU][mU][fA][fA][fU][fU][mC][mA][mA][mA][mA][mU][mC][mA][mA][mG][mC][mA][mG][mC][mC][mG][ademA-GalNAc][ademA-GalNAc][ademA-GalNAc][mG][mG][mC][mU][mG][mC] (SEQ ID NO: 192) | CUAACUUAAUUCAAAAUCAAGCAGCCGAAAGGCUGC (SEQ ID NO: 61) |
| | M{MS}{MS}MMMMM FMMMFMMFMFF{FS}{FS}{Px-MS} | [MePhosphonate-4O-mUs][fUs][fGs][fA][fU][mU][fU][mU][mG][fA][mA][mU][mU][fA][mA][mG][mU][mU][mA][mGs][mGs][mG] (SEQ ID NO: 193) | UUGAUUUUGAAUUAAGUUAGGG (SEQ ID NO: 62) |
| DP15055P:DP15054G | {MS}MMMMMMFFFF MMMMMMMMMMM MMMMM[adem-GalNAc][adem-GalNAc][adem-GalNAc]MMMMMM | [mGs][mA][mA][mG][mU][mA][mA][fC][fU][fU][fC][mA][mC][mU][mU][mA][mA][mA][mA][mA][mG][mC][mA][mG][mC][mC][mG][ademA-GalNAc][ademA-GalNAc][ademA-GalNAc][mG][mG][mC][mU][mG][mC] (SEQ ID NO: 194) | GAAGUAACUUCACUUAAAAAGCAGCCGAAAGGCUGC (SEQ ID NO: 63) |
| | M{MS}{MS}MMMMM FMMMFMMFMFF{FS}{FS}{Px-MS} | [MePhosphonate-4O-mUs][fUs][fUs][fU][fU][mA][fA][mG][mU][fG][mA][mA][mG][fU][mU][mA][mC][mU][mU][mCs][mGs][mG] (SEQ ID NO: 195) | UUUUUAAGUGAAGUUACUUCGG (SEQ ID NO: 64) |
| DP15057P:DP15056G | {MS}MMMMMMFFFF MMMMMMMMMMM MMMMM[adem-GalNAc][adem-GalNAc][adem-GalNAc]MMMMMM | [mUs][mU][mU][mU][mG][mU][mA][G][fA][fA][fA][mA][mA][mC][mA][mA][mG][mA][mU][mA][mG][mC][mA][mG][mC][mC][mG][ademA-GalNAc][ademA-GalNAc][ademA-GalNAc][mG][mG][mC][mU][mG][mC] (SEQ ID NO: 196) | UUUUGUAGAAAAACAAGAUAGCAGCCGAAAGGCUGC (SEQ ID NO: 65) |
| | M{MS}{MS}MMMMM FMMMFMMFMFF{FS}{FS}{Px-MS} | [MePhosphonate-4O-mUs][fAs][fUs][fC][fU][mU][fG][mU][mU][fU][mU][mU][mC][fU][mA][mC][mA][mA][mA][mAs][mGs][mG] (SEQ ID NO: 197) | UAUCUUGUUUUUCUACAAAAGG (SEQ ID NO: 66) |
| DP15059P:DP15058G | {MS}MMMMMMFFFF MMMMMMMMMMM MMMMM[adem-GalNAc][adem-GalNAc][adem-GalNAc]MMMMMM | [mUs][mU][mU][mG][mU][mA][mG][fA][fA][fA][fA][mA][mC][mA][mA][mG][mA][mU][mA][mA][mG][mC][mA][mG][mC][mC][mG][ademA-GalNAc][ademA-GalNAc][ademA-GalNAc[mG][mG][mC][mU][mG][mC] (SEQ ID NO: 198) | UUUGUAGAAAAACAAGAUAAGCAGCCGAAAGGCUGC (SEQ ID NO: 67) |
| | M{MS}{MS}MMMMM FMMMFMMFMFF{FS}{FS}{Px-MS} | [MePhosphonate-4O-mUs][fUs][fAs][fU][fC][mU][fU][mG][mU][fU][mU][mU][mU][fC][mU][mA][mC][mA][mA][mAs][mGs][mG] (SEQ ID NO: 199) | UUAUCUUGUUUUUCUACAAAGG (SEQ ID NO: 68) |
| DP15061P:DP15060G | {MS}MMMMMMFFFF MMMMMMMMMMM MMMMM[adem-GalNAc][adem-GalNAc][adem-GalNAc]MMMMMM | [mUs][mU][mG][mU][mA][mG][mA][fA][fA][A][fA][mC][mA][mA][mG][mA][mU][mA][mA][mA][mG][mC][mA][mG][mC][mC][mG][ademA-GalNAc][ademA-GalNAc][ademA-GalNAc][mG][mG][mC][mU][mG][mC] (SEQ ID NO: 200) | UUGUAGAAAAACAAGAUAAAGCAGCCGAAAGGCUGC (SEQ ID NO: 69) |
| | M{MS}{MS}MMMMM FMMMFMMFMFF{FS}{FS}{Px-MS} | [MePhosphonate-4O-mU][mU][fU][mC][mU][mA][mC][mA][mAs][mGs][mG] (SEQ ID NO: 201) | UUUAUCUUGUUUUUCUACAAGG (SEQ ID NO: 70) |

TABLE A-continued

Sequence information for the oligonucleotides in Tables 3 and 4.

| DP number passenger: Guide | Modification Pattern | Sequence with Modifications | Corresponding unmodified sequence |
|---|---|---|---|
| DP15063P:DP15062G | {MS}MMMMMMFFFFMMMMMMMMMMMMMMMM[adem-GalNAc][adem-GalNAc][adem-GalNAc]MMMMMM | [mGs][mU][mA][mG][mA][mA][mA][fA][fA][fC][fA][mA][mG][mA][mU][mA][mA][mU][mA][mA][mG][mC][mA][mG][mC][mC][mG][ademA-GalNAc][ademA-GalNAc][ademA-GalNAc][mG][mG][mC][mU][mG][mC] (SEQ ID NO: 202) | GUAGAAAAACAAGAUAAUAAGCAGCCGAAAGGCUGC (SEQ ID NO: 71) |
| | M{MS}{MS}MMMMMFMMMFMMFMFF{FS}{FS}{Px-MS} | [MePhosphonate-4O-mUs][fUs][fAs][fU][fU][mA][fU][mC][mU][fU][mG][mU][mU][fU][mU][mU][mC][mU][mA][mCs][mGs][mG] (SEQ ID NO: 203) | UUAUUAUCUUGUUUUCUACGG (SEQ ID NO: 72) |
| DP15065P:DP15064G | {MS}MMMMMMFFFFMMMMMMMMMMMMMMMM[adem-GalNAc][adem-GalNAc][adem-GalNAc]MMMMMM | [mUs][mA][mG][mA][mA][mA][mA][fA][fC][fA][fA][mG][mA][mU][mA][mA][mU][mA][mG][mA][mG][mC][mA][mG][mC][mC][mG][ademA-GalNAc][ademA-GalNAc][ademA-GalNAc][mG][mG][mC][mU][mG][mC] (SEQ ID NO: 204) | UAGAAAAACAAGAUAAUAGAGCAGCCGAAAGGCUGC (SEQ ID NO: 73) |
| | M{MS}{MS}MMMMMFMMMFMMFMFF{FS}{FS}{Px-MS} | [MePhosphonate-4O-mUs][fCs][fUs][fA][fU][mU][fA][mU][mC][fU][mU][mG][mU][fU][mU][mU][mC][mU][mAs][mGs][mG] (SEQ ID NO: 205) | UCUAUUAUCUUGUUUUUCUAGG (SEQ ID NO: 74) |
| DP15067P:DP15066G | {MS}MMMMMMFFFFMMMMMMMMMMMMMMMM[adem-GalNAc][adem-GalNAc][adem-GalNAc]MMMMMM | [mAs][mG][mA][mA][mA][mA][mA][fC][fA][fA][fG][mA][mU][mA][mA][mU][mA][mG][mC][mA][mG][mC][mA][mG][mC][mC][mG][ademA-GalNAc][ademA-GalNAc][ademA-GalNAc][mG][mG][mC][mU][mG][mC] (SEQ ID NO: 206) | AGAAAAACAAGAUAAUAGCAGCAGCCGAAAGGCUGC (SEQ ID NO: 75) |
| | M{MS}{MS}MMMMMFMMMFMMFMFF{FS}{FS}{Px-MS} | [MePhosphonate-4O-mUs][fGs][fCs][fU][fA][mU][fU][mA][mU][fC][mU][mU][mG][fU][mU][mU][mU][mU][mC][mUs][mGs][mG] (SEQ ID NO: 207) | UGCUAUUAUCUUGUUUUUCUGG (SEQ ID NO: 76) |
| DP15069P:DP15068G | {MS}MMMMMMFFFFMMMMMMMMMMMMMMMM[adem-GalNAc][adem-GalNAc][adem-GalNAc]MMMMMM | [mAs][mA][mA][mA][mA][mC][mA][fA][fG][fA][fU][mA][mA][mU][mA][mG][mC][mA][mU][mA][mG][mC][mA][mG][mC][mC][mG][ademA-GalNAc][ademA-GalNAc][ademA-GalNAc][mG][mG][mC][mU][mG][mC] (SEQ ID NO: 208) | AAAAACAAGAUAAUAGCAUAGCAGCCGAAAGGCUGC (SEQ ID NO: 77) |
| | M{MS}{MS}MMMMMFMMMFMMFMFF{FS}{FS}{Px-MS} | [MePhosphonate-4O-mUs][fAs][fUs][fG][fC][mU][fA][mU][mU][fA][mU][mC][mU][fU][mG][mU][mU][mU][mU][mUs][mGs][mG] (SEQ ID NO: 209) | UAUGCUAUUAUCUUGUUUUUGG (SEQ ID NO: 78) |
| DP15071P:DP15070G | {MS}MMMMMMFFFFMMMMMMMMMMMMMMMM[adem-GalNAc][adem-GalNAc][adem-GalNAc]MMMMMM | [mAs][mA][mC][mA][mG][mC][mA][fU][fA][fG][fU][mC][mA][mA][mA][mU][mA][mA][mA][mA][mG][mC][mA][mG][mC][mC][mG][ademA-GalNAc][ademA-GalNAc][ademA-GalNAc][mG][mG][mC][mU][mG][mC] (SEQ ID NO: 210) | AACAGCAUAGUCAAAUAAAAGCAGCCGAAAGGCUGC (SEQ ID NO: 79) |
| | M{MS}{MS}MMMMMFMMMFMMFMFF{FS}{FS}{Px-MS} | [MePhosphonate-4O-mU][mA][fU][mG][mC][mU][mG][mU][mUs][mGs][mG] (SEQ ID NO: 211) | UUUUAUUUGACUAUGCUGUUGG (SEQ ID NO: 80) |
| DP15073P:DP15072G | {MS}MMMMMMFFFFMMMMMMMMMMMMMMMM[adem-GalNAc][adem-GalNAc][adem-GalNAc]MMMMMM | [mAs][mC][mA][mG][mA][mA][mA][fU][fU][fU][fC][mU][mC][mU][mA][mU][mC][mU][mU][mA][mG][mC][mA][mG][mC][mC][mG][ademA-GalNAc][ademA-GalNAc][ademA-GalNAc][mG][mG][mC][mU][mG][mC] (SEQ ID NO: 212) | ACAGAAAUUUCUCUAUCUUAGCAGCCGAAAGGCUGC (SEQ ID NO: 81) |
| | M{MS}{MS}MMMMMFMMMFMMFMFF{FS}{FS}{Px-MS} | [MePhosphonate-4O-mUs][fAs][fAs][fG][fA][mU][fA][mG][mA][fG][mA][mA][mA][fU][mU][mU][mC][mU][mG][mUs][mGs][mG] (SEQ ID NO: 213) | UAAGAUAGAGAAAUUUCUGUGG (SEQ ID NO: 82) |

TABLE A-continued

| Sequence information for the oligonucleotides in Tables 3 and 4. | | | |
|---|---|---|---|
| DP number passenger: Guide | Modification Pattern | Sequence with Modifications | Corresponding unmodified sequence |
| DP15075P:DP15074G | {MS}MMMMMMFFFF MMMMMMMMMMM MMMMM[adem-GalNAc][adem-GalNAc][adem-GalNAc]MMMMMM | [mUs][mG][mA][mA][mU][mG][mA][fA][fA][fU][fA][mA][mG][mA][mA][mA][mU][mG][mU][mA][mG][mC][mA][mG][mC][mC][mG][ademA-GalNAc][ademA-GalNAc][ademA-GalNAc][mG][mG][mC][mU][mG][mC] (SEQ ID NO: 214) | UGAAUGAAAUAAGAAAUGUAGCAGCCGAAAGGCUGC (SEQ ID NO: 83) |
| | M{MS}{MS}MMMMM FMMMFMMFMFF{FS}{FS}{Px-MS} | [MePhosphonate-4O-mUs][fAs][fCs][fA][fU][mU][fU][mC][mU][fU][mA][mU][mU][fU][mC][mA][mU][mU][mC][mAs][mGs][mG] (SEQ ID NO: 215) | UACAUUUCUUAUUUCAUUCAGG (SEQ ID NO: 84) |
| DP15077P:DP15076G | {MS}MMMMMMFFFF MMMMMMMMMMM MMMMM[adem-GalNAc][adem-GalNAc][adem-GalNAc]MMMMMM | [mAs][mC][mC][mC][mA][mG][mC][fA][fA][fC][fU][mC][mU][mC][mA][mA][mG][mU][mU][mA][mG][mC][mA][mG][mC][mC][mG][ademA-GalNAc][ademA-GalNAc][ademA-GalNAc][mG][mG][mC][mU][mG][mC] (SEQ ID NO: 216) | ACCCAGCAACUCUCAAGUUAGCAGCCGAAAGGCUGC (SEQ ID NO: 85) |
| | M{MS}{MS}MMMMM FMMMFMMFMFF{FS}{FS}{Px-MS} | [MePhosphonate-4O-mUs][fAs][fAs][fC][fU][mU][fG][mA][mG][fA][mG][mU][mU][fG][mC][mU][mG][mG][mG][mUs][mGs][mG] (SEQ ID NO: 217) | UAACUUGAGAGUUGCUGGGUGG (SEQ ID NO: 86) |
| DP15079P:DP15078G | {MS}MMMMMMFFFF MMMMMMMMMMM MMMMM[adem-GalNAc][adem-GalNAc][adem-GalNAc]MMMMMM | [mCs][mC][mC][mA][mG][mC][mA][fA][fC][fU][fC][mU][mC][mA][mA][mG][mU][mU][mU][mA][mG][mC][mA][mG][mC][mC][mG][ademA-GalNAc][ademA-GalNAc][ademA-GalNAc][mG][mG][mC][mU][mG][mC] (SEQ ID NO: 218) | CCCAGCAACUCUCAAGUUUAGCAGCCGAAAGGCUGC (SEQ ID NO: 87) |
| | M{MS}{MS}MMMMM FMMMFMMFMFF{FS}{FS}{Px-MS} | [MePhosphonate-4O-mUs][fAs][fAs][fA][fC][mU][fU][mG][mA][fG][mA][mG][mU][fU][mG][mC][mU][mG][mG][mGs][mGs][mG] (SEQ ID NO: 219) | UAAACUUGAGAGUUGCUGGGGG (SEQ ID NO: 88) |
| DP15081P:DP15080G | {MS}MMMMMMFFFF MMMMMMMMMMM MMMMM[adem-GalNAc][adem-GalNAc][adem-GalNAc]MMMMMM | [mCs][mC][mA][mG][mC][mA][mA][fC][fU][fC][fU][mC][mA][mA][mG][mU][mU][mU][mU][mA][mG][mC][mA][mG][mC][mC][mG][ademA-GalNAc][ademA-GalNAc][ademA-GalNAc][G][G][mC][mu][mG][mC] (SEQ ID NO: 220) | CCAGCAACUCUCAAGUUUUAGCAGCCGAAAGGCUGC (SEQ ID NO: 89) |
| | M{MS}{MS}MMMMM FMMMFMMFMFF{FS}{FS}{Px-MS} | [MePhosphonate-4O-mUs][fAs][fAs][fA][fA][mC][fU][mU][mG][fA][mG][mA][mG][fU][mU][mG][mC][mU][mG][mGs][mGs][mG] (SEQ ID NO: 221) | UAAAACUUGAGAGUUGCUGGGG (SEQ ID NO: 90) |
| DP15083P:DP15082G | {MS}MMMMMMFFFF MMMMMMMMMMM MMMMM[adem-GalNAc][adem-GalNAc][adem-GalNAc]MMMMMM | [mAs][mA][mG][mA][mU][mA][mU][fA][fC][fU][fC][mC][mA][mU][mA][mG][mU][mG][mA][mA][mG][mC][mA][mG][mC][mC][mG][ademA-GalNAc][ademA-GalNAc][ademA-GalNAc][mG][mG][mC][mU][mG][mC] (SEQ ID NO: 222) | AAGAUAUACUCCAUAGUGAAGCAGCCGAAAGGCUGC (SEQ ID NO: 91) |
| | M{MS}{MS}MMMMM FMMMFMMFMFF{FS}{FS}{Px-MS} | [MePhosphonate-4O-mUs][fUs][fCs][fA][fC][mU][fA][mU][mG][fG][mA][mG][mU][fA][mU][mA][mU][mC][mU][mUs][mGs][mG] (SEQ ID NO: 223) | UUCACUAUGGAGUAUAUCUUGG (SEQ ID NO: 92) |
| DP15085P:DP15084G | {MS}MMMMMMFFFF MMMMMMMMMMM MMMMM[adem-GalNAc][adem-GalNAc][adem-GalNAc]MMMMMM | [mAs][mU][mA][mU][mA][mC][mU][fC][fC][fA][fU][mA][mG][mU][mG][mA][mA][mG][mC][mA][mG][mC][mA][mG][mC][mC][mG][ademA-GalNAc][ademA-GalNAc][ademA-GalNAc][mG][mG][mC][mU][mG][mC] (SEQ ID NO: 224) | AUAUACUCCAUAGUGAAGCAGCAGCCGAAAGGCUGC (SEQ ID NO: 93) |
| | M{MS}{MS}MMMMM FMMMFMMFMFF{FS}{FS}{Px-MS} | [MePhosphonate-4O-mUs][fGs][fCs][fU][fU][mC][[A][mC][mU][fA][mU][mG][mG][fA][mG][mU][mA][mU][mA][mUs][mGs][mG] (SEQ ID NO: 225) | UGCUUCACUAUGGAGUAUAUGG (SEQ ID NO: 94) |

TABLE A-continued

Sequence information for the oligonucleotides in Tables 3 and 4.

| DP number passenger: Guide | Modification Pattern | Sequence with Modifications | Corresponding unmodified sequence |
|---|---|---|---|
| DP15087P:DP15086G | {MS}MMMMMMFFFFMMMMMMMMMMMMMMMM[adem-GalNAc][adem-GalNAc][adem-GalNAc]MMMMMM | [mUs][mA][mC][mU][mC][mC][mA][fU][A][fG][fU][mG][mA][mA][mG][mC][mA][mA][mU][mA][mG][mC][mA][mG][mC][mC][mG][ademA-GalNAc][ademA-GalNAc][ademA-GalNAc][mG][mG][mC][mU][mG][mC] (SEQ ID NO: 226) | UACUCCAUAGUGAAGCAAUAGCAGCCGAAAGGCUGC (SEQ ID NO: 95) |
| | M{MS}{MS}MMMMMFMMMFMMFMFF{FS}{FS}{Px-MS} | [MePhosphonate-4O-mUs][fAs][fUs][fU][fG][mC][fU][mU][mC][fA][mC][mU][mA][fU][mG][mG][mA][mG][mU][mAs][mGs][mG] (SEQ ID NO: 227) | UAUUGCUUCACUAUGGAGUAGG (SEQ ID NO: 96) |
| DP15089P:DP15088G | {MS}MMMMMMFFFFMMMMMMMMMMMMMMMM[adem-GalNAc][adem-GalNAc][adem-GalNAc]MMMMMM | [mAs][mU][mA][mG][mU][mG][mA][fA][fG][fC][fA][mA][mU][mC][mU][mA][mA][mU][mU][mA][mG][mC][mA][mG][mC][mC][mG][ademA-GalNAc][ademA-GalNAc][ademA-GalNAc][mG][mG][mC][mU][mG][mC] (SEQ ID NO: 228) | AUAGUGAAGCAAUCUAAUUAGCAGCCGAAAGGCUGC (SEQ ID NO: 97) |
| | M{MS}{MS}MMMMMFMMMFMMFMFF{FS}{FS}{Px-MS} | [MePhosphonate-4O-mUs][fAs][fAs][fU][fU][mA][fG][mA][mU][fU][mG][mC][mU][fU][mC][mA][mC][mU][mA][mUs][mGs][mG] (SEQ ID NO: 229) | UAAUUAGAUUGCUUCACUAUGG (SEQ ID NO: 98) |
| DP15091P:DP15090G | {MS}MMMMMMFFFFMMMMMMMMMMMMMMMM[adem-GalNAc][adem-GalNAc][adem-GalNAc]MMMMMM | [mUs][mC][mA][mA][mA][mA][mU][fG][fG][fA][fA][mG][mG][mU][mU][mA][mU][mA][mC][mA][mG][mC][mA][mG][mC][mC][mG][ademA-GalNAc][ademA-GalNAc][ademA-GalNAc][mG][mG][mC][mU][mG][mC] (SEQ ID NO: 230) | UCAAAAUGGAAGGUUAUACAGCAGCCGAAAGGCUGC (SEQ ID NO: 99) |
| | M{MS}{MS}MMMMMFMMMFMMFMFF{FS}{FS}{Px-MS} | [MePhosphonate-4O-mUs][fGs][fUs][fA][fU][mA][fA][mC][mC][fU][mU][mC][mC][fA][mU][mU][mU][mU][mG][mAs][mGs][mG] (SEQ ID NO: 231) | UGUAUAACCUUCCAUUUUGAGG (SEQ ID NO: 100) |
| DP15093P:DP15092G | {MS}MMMMMMFFFFMMMMMMMMMMMMMMMM[adem-GalNAc][adem-GalNAc][adem-GalNAc]MMMMMM | [mAs][mA][mA][mU][mG][mG][mA][fA][fG][fG][fU][mU][mA][mU][mA][mC][mU][mC][mU][mA][mG][mC][mA][mG][mC][mC][mG][ademA-GalNAc][ademA-GalNAc][ademA-GalNAc][mG][mG][mC][mU][mG][mC] (SEQ ID NO: 232) | AAAUGGAAGGUUAUACUCUAGCAGCCGAAAGGCUGC (SEQ ID NO: 101) |
| | M{MS}{MS}MMMMMFMMMFMMFMFF{FS}{FS}{Px-MS} | [MePhosphonate-4O-mUs][fAs][fGs][fA][fG][mU][fA][mU][mA][fA][mC][mC][mU][fU][mC][mC][mA][mU][mU][mUs][mGs][mG] (SEQ ID NO: 233) | UAGAGUAUAACCUUCCAUUUGG (SEQ ID NO: 102) |
| DP15095P:DP15094G | {MS}MMMMMMFFFFMMMMMMMMMMMMMMMM[adem-GalNAc][adem-GalNAc][adem-GalNAc]MMMMMM | [mGs][mA][mA][mG][mG][mU][mU][fA][fU][fA][fC][mU][mC][mU][mA][mU][mA][mA][mA][mA][mG][mC][mA][mG][mC][mC][mG][ademA-GalNAc][ademA-GalNAc][ademA-GalNAc][mG][mG][mC][mU][mG][mC] (SEQ ID NO: 234) | GAAGGUUAUACUCUAUAAAAGCAGCCGAAAGGCUGC (SEQ ID NO: 103) |
| | M{MS}{MS}MMMMMFMMMFMMFMFF{FS}{FS}{Px-MS} | [MePhosphonate-4O-mUs][fUs][fUs][fU][fA][mU][fA][mG][mA][fG][mU][mA][mU][fA][mA][mC][mC][mU][mU][mCs][mGs][mG] (SEQ ID NO: 235) | UUUUAUAGAGUAUAACCUUCGG (SEQ ID NO: 104) |
| DP15097P:DP15096G | {MS}MMMMMMFFFFMMMMMMMMMMMMMMMM[adem-GalNAc][adem-GalNAc][adem-GalNAc]MMMMMM | [mAs][mA][mG][mG][mU][mU][mA][fU][A][fC][fU][mC][mU][mA][mU][mA][mA][mA][mA][mA][mG][mC][mA][mG][mC][mC][mG][ademA-GalNAc][ademA-GalNAc][ademA-GalNAc][mG][mG][mC][mU][mG][mC] (SEQ ID NO: 236) | AAGGUUAUACUCUAUAAAAAGCAGCCGAAAGGCUGC (SEQ ID NO: 105) |
| | M{MS}{MS}MMMMMFMMMFMMFMFF{FS}{FS}{Px-MS} | [MePhosphonate-4O-mUs][fUs][fUs][fU][fU][mA][fU][mA][mG][fA][mG][mU][mA][fU][mA][mA][mC][mC][mU][mUs][mGs][mG] (SEQ ID NO: 237) | UUUUUAUAGAGUAUAACCUUGG (SEQ ID NO: 106) |

TABLE A-continued

Sequence information for the oligonucleotides in Tables 3 and 4.

| DP number passenger: Guide | Modification Pattern | Sequence with Modifications | Corresponding unmodified sequence |
|---|---|---|---|
| DP15099P:DP15098G | {MS}MMMMMMFFFFMMMMMMMMMMMMMMMM[adem-GalNAc][adem-GalNAc][adem-GalNAc]MMMMMM | [mAs][mG][mG][mU][mU][mA][mU][fA][fC][fU][fC][mU][mA][mU][mA][mA][mA][mA][mU][mA][mG][mC][mA][mG][mC][mC][mG][ademA-GalNAc][ademA-GalNAc][ademA-GalNAc][mG][mG][mC][mU][mG][mC] (SEQ ID NO: 238) | AGGUUAUACUCUAUAAAAUAGCAGCCGAAAGGCUGC (SEQ ID NO: 107) |
| | M{MS}{MS}MMMMMFMMMFMMFMFF{FS}(FS}{Px-MS} | [MePhosphonate-4O-mUs][fAs][fUs][fU][fU][mU][fA][mU][mA][fG][mA][mG][mU][fA][mU][mA][mA][mC][mC][mUs][mGs][mG] (SEQ ID NO: 239) | UAUUUUAUAGAGUAUAACCUGG (SEQ ID NO: 108) |
| DP15101P:DP15100G | {MS}MMMMMMFFFFMMMMMMMMMMMMMMMM[adem-GalNAc][adem-GalNAc][adem-GalNAc]MMMMMM | [mAs][mU][mU][mC][mA][mG][mA][fA][fA][fG][fC][mU][mU][mU][mG][mA][mA][mU][mG][mA][mG][mC][mA][mG][mC][mC][mG][ademA-GalNAc][ademA-GalNAc][ademA-GalNAc][mG][mG][mC][mU][mG][mC] (SEQ ID NO: 240) | AUUCAGAAAGCUUUGAAUGAGCAGCCGAAAGGCUGC (SEQ ID NO: 109) |
| | M{MS}{MS}MMMMMFMMMFMMFMFF{FS}{FS}{Px-MS} | [MePhosphonate-4O-mUs][fCs][fAs][fU][fU][mC][fA][mA][mA][fG][mC][mU][mU][fU][mC][mU][mG][mA][mA][mUs][mGs][mG] (SEQ ID NO: 241) | UCAUUCAAAGCUUUCUGAAUGG (SEQ ID NO: 110) |
| DP13439P:DP13438G | {MS}MFMMMMFMFMFFMMMFMMMMMMMMM[adem-GalNAc][adem-GalNAc][adem-GalNAc]MMMMMM | [mAs][mA][fA][mU][mC][mA][mA][fG][mA][fU][mU][fU][fG][mC][mU][mA][fU][mG][mU][mA][mG][mC][mA][mG][mC][mC][mG][ademA-GalNAc][ademA-GalNAc][ademA-GalNAc][mG][mG][mC][mU][mG][mC] (SEQ ID NO: 242) | AAAUCAAGAUUUGCUAUGUAGCAGCCGAAAGGCUGC (SEQ ID NO: 111) |
| | M{MS}{MS}FMMFMFMFMMMMFMFM{FS}{FS}{Px-MS} | [MePhosphonate-4O-mUs][fAs][fCs][mA][fU][mA][fG][mC][mA][mA][mA][fU][mC][fU][mU][fG][mA][mU][fU][mUs][mGs][mG] (SEQ ID NO: 243) | UACAUAGCAAAUCUUGAUUUGG (SEQ ID NO: 112) |
| DP13443P:DP13442G | {MS}MFMMMMFMFMFFMMMFMMMMMMMMM[adem-GalNAc][adem-GalNAc][adem-GalNAc]MMMMMM | [mCs][mU][fC][mA][mA][mC][mA][fU][mA][fU][mU][fU][fG][mA][mU][mC][fA][mG][mU][mA][mG][mC][mA][mG][mC][mC][mG][ademA-GalNAc][ademA-GalNAc][ademA-GalNAc][mG][mG][mC][mU][mG][mC] (SEQ ID NO: 244) | CUCAACAUAUUUGAUCAGUAGCAGCCGAAAGGCUGC (SEQ ID NO: 113) |
| | M{MS}{MS}FMMFMFMFMMMMFMFM{FS}{FS}{Px-MS} | [MePhosphonate-4O-mUs][fAs][fCs][mU][fG][mA][fU][mC][mA][mA][mA][fU][mA][fU][mG][fU][mU][mG][fA][mGs][mGs][mG] (SEQ ID NO: 245) | UACUGAUCAAAUAUGUUGAGGG (SEQ ID NO: 114) |
| DP13465P:DP13464G | {MS}MFMMMMFMFMFFMMMFMMMMMMMMM[adem-GalNAc][adem-GalNAc][adem-GalNAc]MMMMMM | [mGs][mU][fG][mG][mA][mG][mA][fA][mA][fA][mC][fA][fA][mC][mC][mU][fA][MA][mA][mA][mG][mC][mA][mG][mC][mC][mG][ademA-GalNAc][ademA-GalNAc][ademA-GalNAc][mG][mG][mC][mU][mG][mC] (SEQ ID NO: 246) | GUGGAGAAAACAACCUAAAAGCAGCCGAAAGGCUGC (SEQ ID NO: 115) |
| | M{MS}{MS}FMMFMFMFMMMMFMFM{FS}{FS}{Px-MS} | [MePhosphonate-4O-mUs][fUs][fUs][mU][fA][mG][fG][mU][mU][mG][mU] (SEQ ID NO: 247) | UUUUAGGUUGUUUUCUCCACGG (SEQ ID NO: 116) |

In the modification patterns of Table A:
"M" refers to a 2'-OMe modified nucleotide;
"F" refers to a 2'-F modified nucleotide;
"S" refers to a nucleotide with a 3'-phosphorothioate linkage;
"{MS}" refers to a 2'-OMe modified nucleotide with a 3'-phosphorothioate linkage;
"{FS}" refers to a 2'-F modified nucleotide with a 3'-phosphorothioate linkage;
"[adem-GalNAc]" refers to a nucleotide having a 2'-GalNAc conjugate:

TABLE A-continued

Sequence information for the oligonucleotides in Tables 3 and 4.

| DP number passenger: Guide | Modification Pattern | Sequence with Modifications | Corresponding unmodified sequence |
|---|---|---|---|

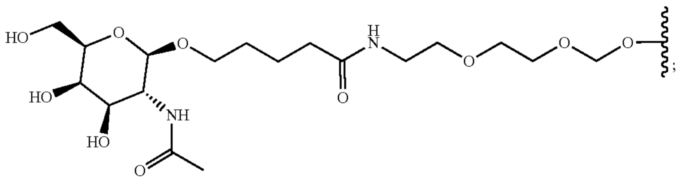 [SMILES: *OCOCCOCCNC(=O)CCCCO[C@@H]1O[C@H](CO)[C@H](O)[C@H](O)[C@H]1NC(C)=O]

;

"{Px-MS}" refers to a 2'-OMe modified nucleotide with a 3'-phosphorothioate linkage, and 5' phosphonate.

In the modified sequences of Table A:

"[mN]" refers to a 2'-OMe modified nucleotide;

"[fN]" refers to a 2'-F modified nucleotide;

"[mNs]" refers to a 2'-OMe modified nucleotide with a 3'-phosphorothioate linkage;

"[fNs]" refers to a 2'-F modified nucleotide with a 3'-phosphorothioate linkage;

"[ademG-GalNAc]" refers to a G nucleotide having a 2'-GalNAc conjugate:

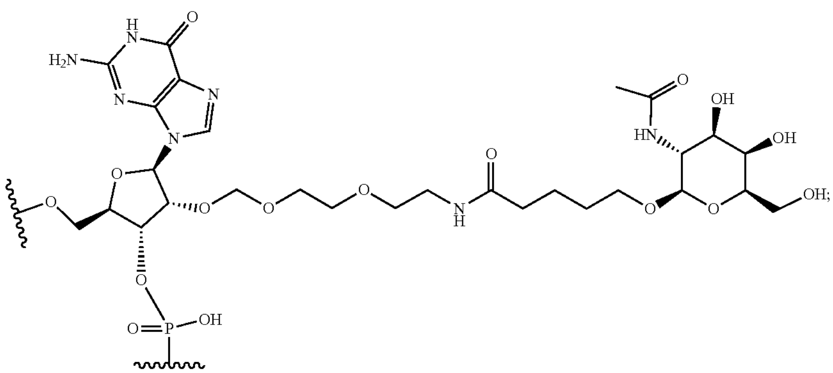 [SMILES: *OC[C@H]1O[C@@H](n2cnc3c(=O)[nH]c(N)nc32)[C@H](OCOCCOCCNC(=O)CCCCO[C@@H]2O[C@H](CO)[C@H](O)[C@H](O)[C@H]2NC(C)=O)[C@@H]1OP(*)(=O)O]

;

"[ademA-GalNAc]" refers to an A nucleotide having a 2'-GalNAc conjugate:

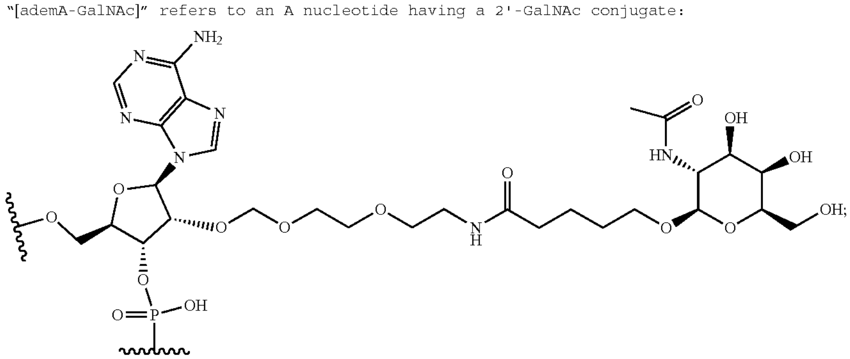

;

"[MePhosphonate-4O-mUs]" refers to a 5'-phosphonate-4'-Oxy-2'-OMe uridine with a 3'-phosphorothioate linkage:

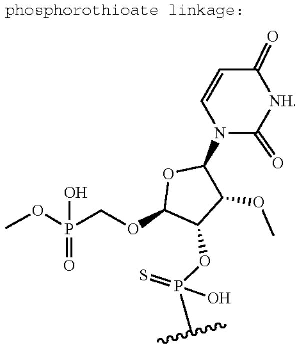

.

Non-Human Primate (NHP) Studies

Figure 5A:
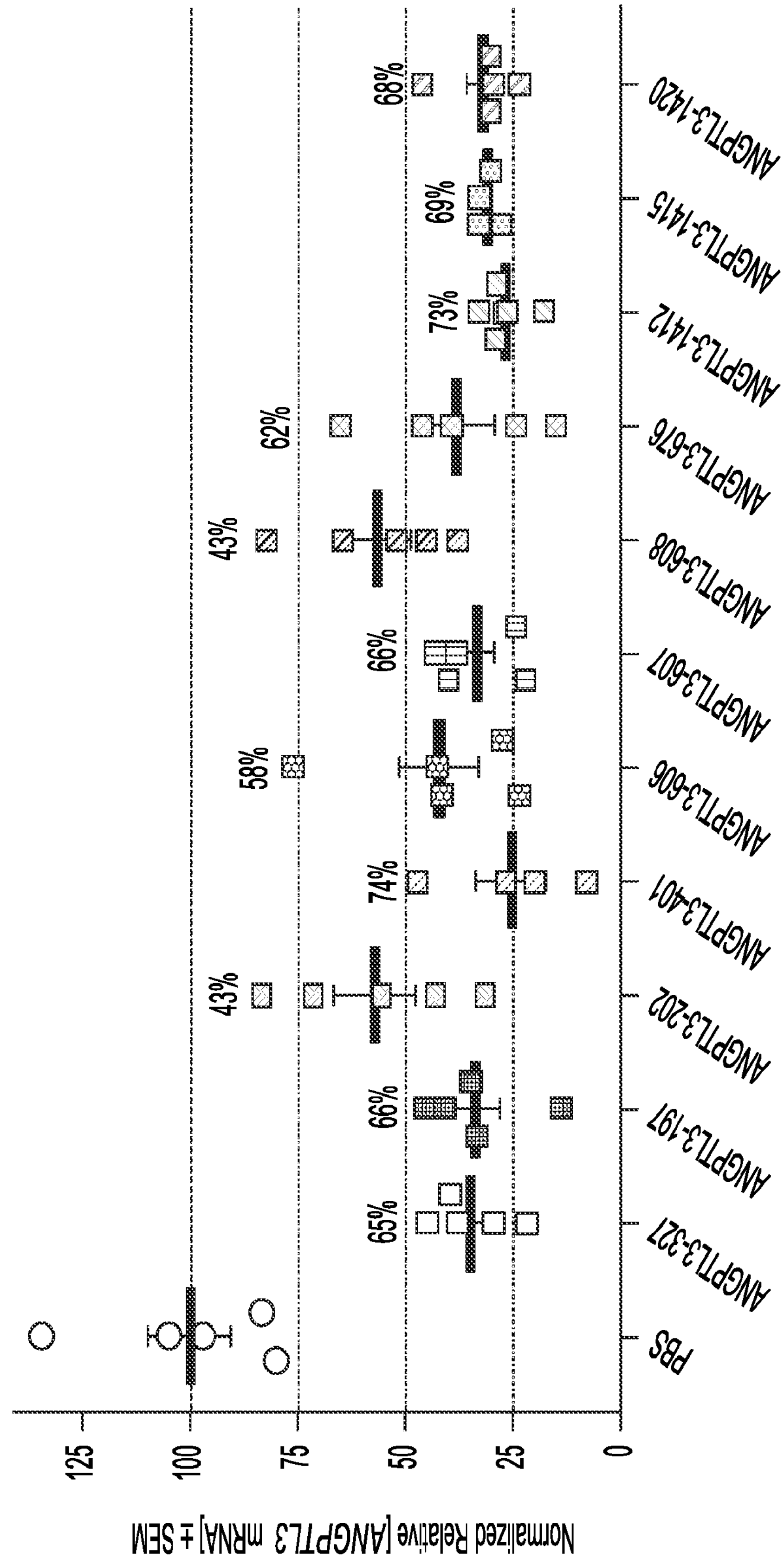
FIG. 5A-5C provides graphs depicting the percent (%) of ANGPTL3 mRNA in liver samples from non-human primates (NHPs) treated with the indicated GalNAc-conjugated ANGPTL3 oligonucleotides relative to NHPs treated with PBS on day 28 (FIG. 5A), day 56 (FIG. 5B) and day 84 (FIG. 5C) following treatment.
Figure 5B:
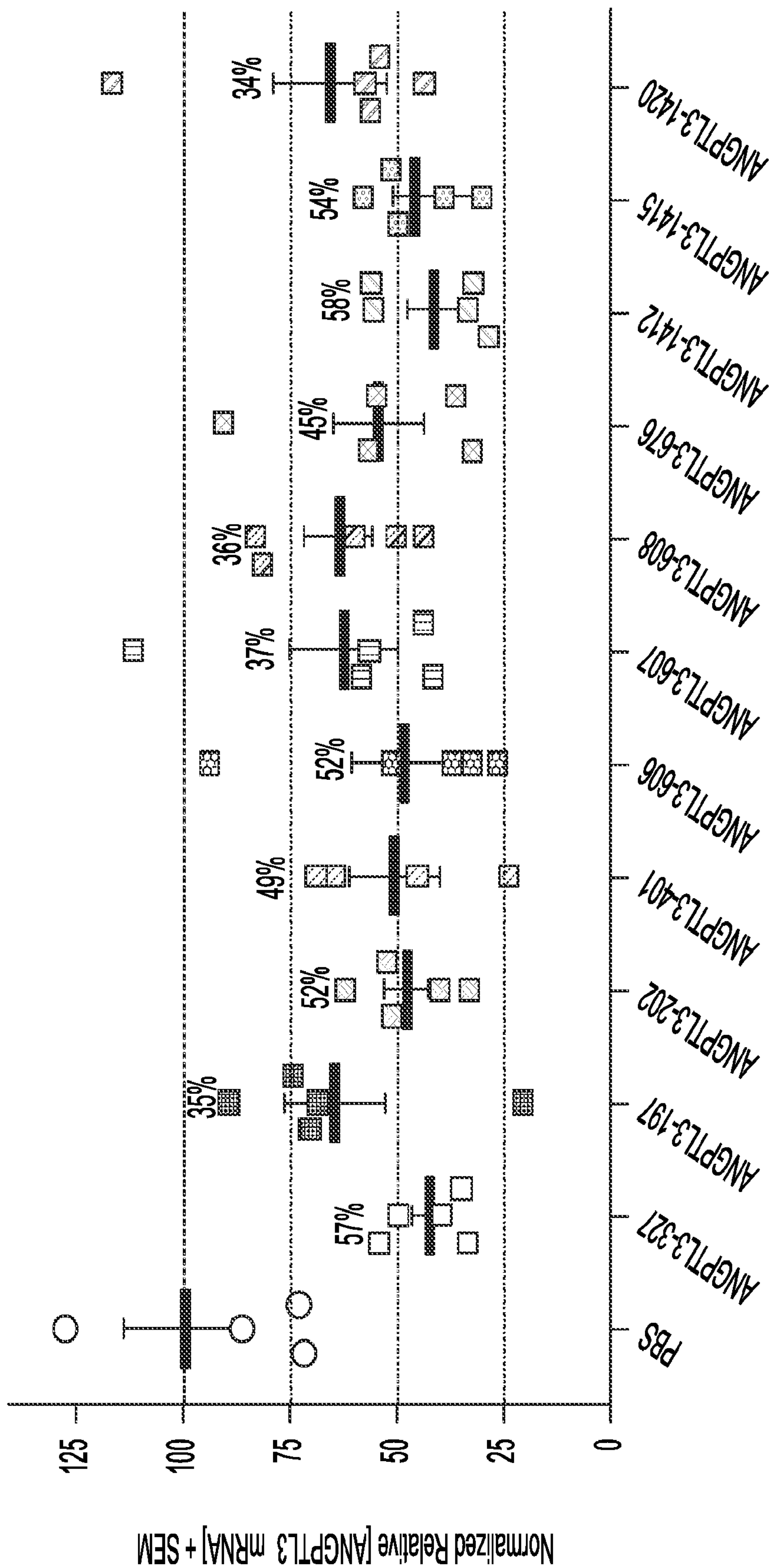
Figure 5C:
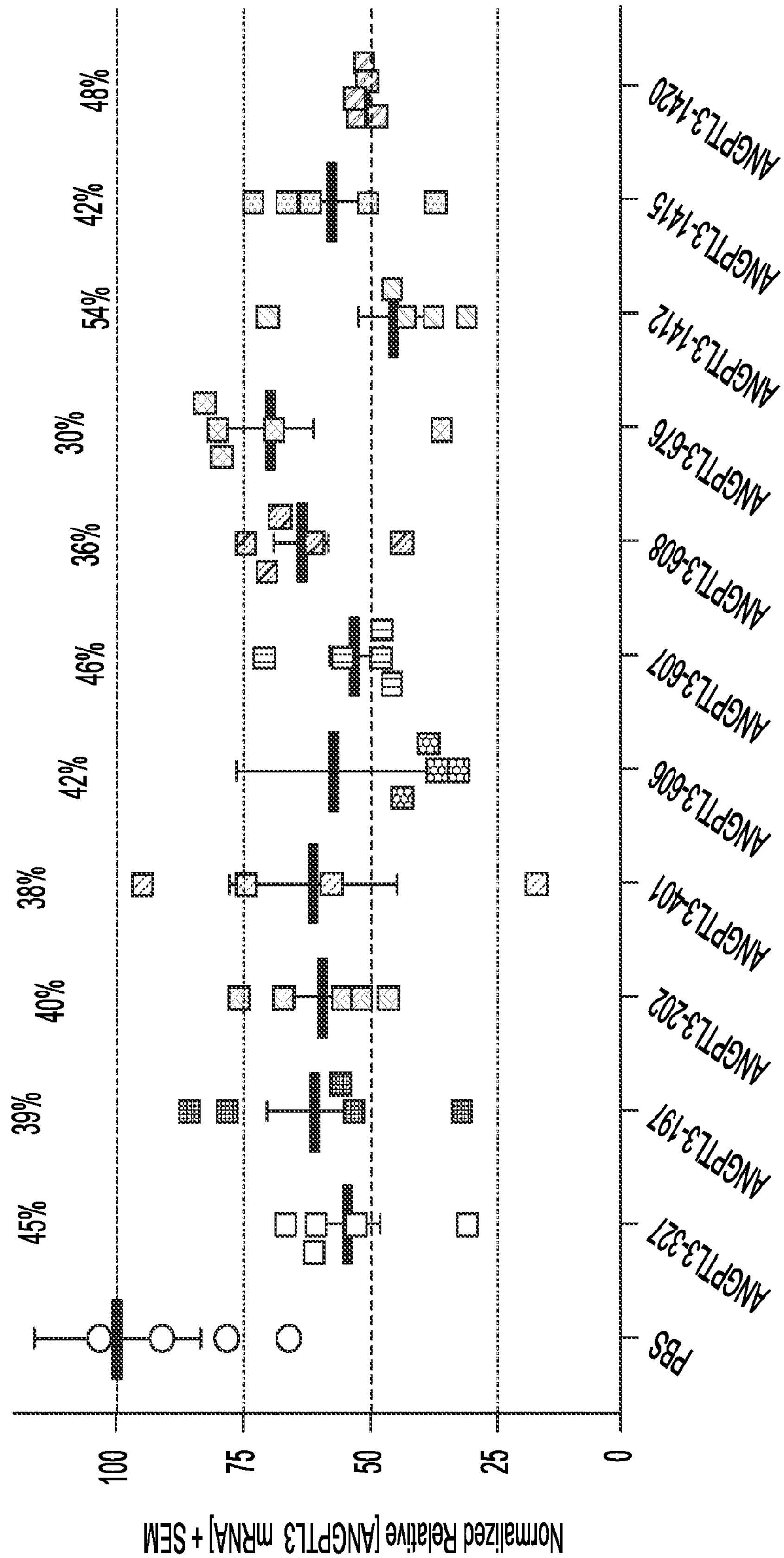
Figure 6:
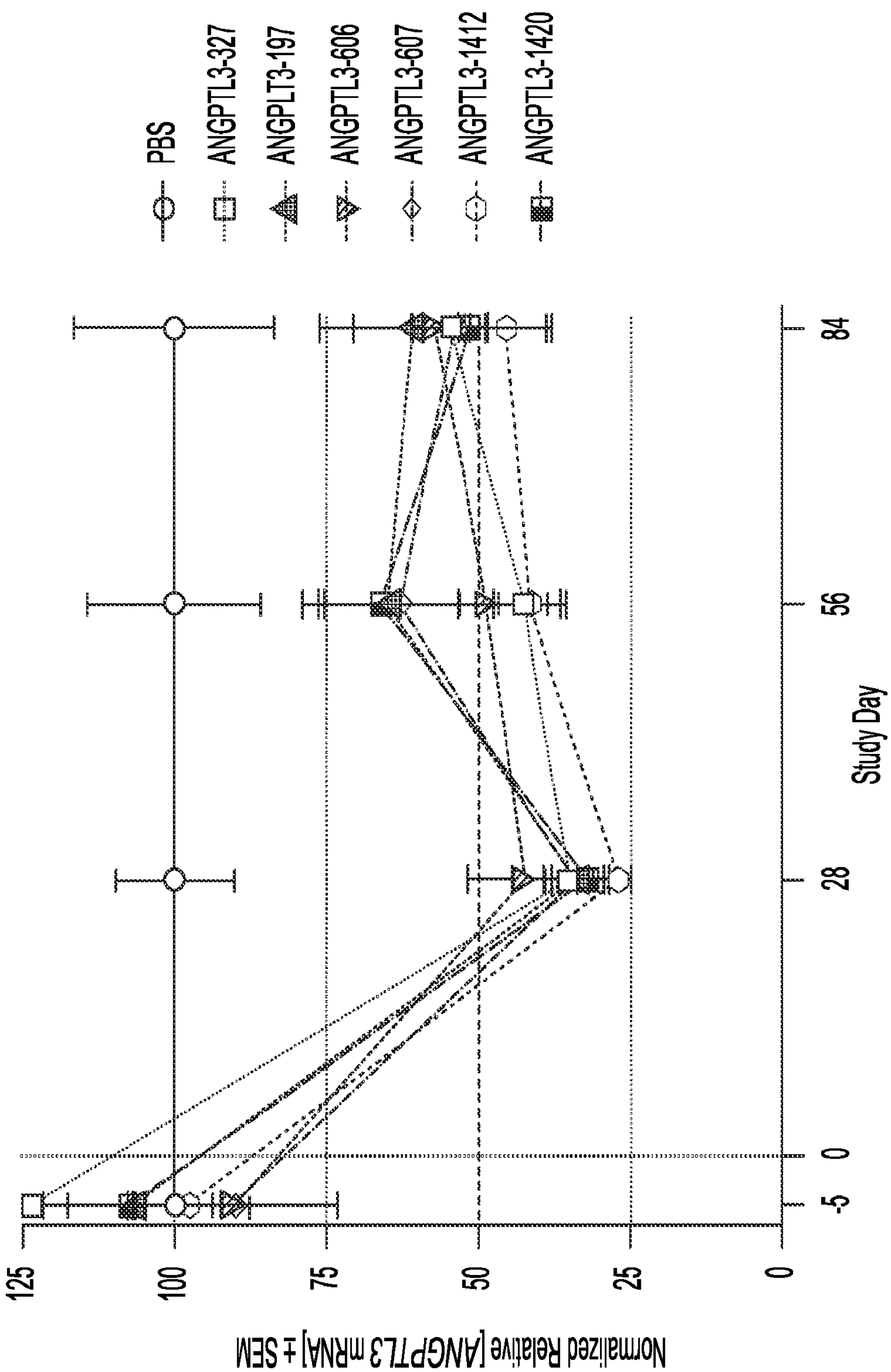
FIG. 6 provides a graph depicting the mean percent (%) of ANGPTL3 mRNA in liver samples from NHPs treated with the indicated GalNAc-conjugated ANGPTL3 oligonucleotides relative to NHPs treated with PBS over time.
Figure 7:
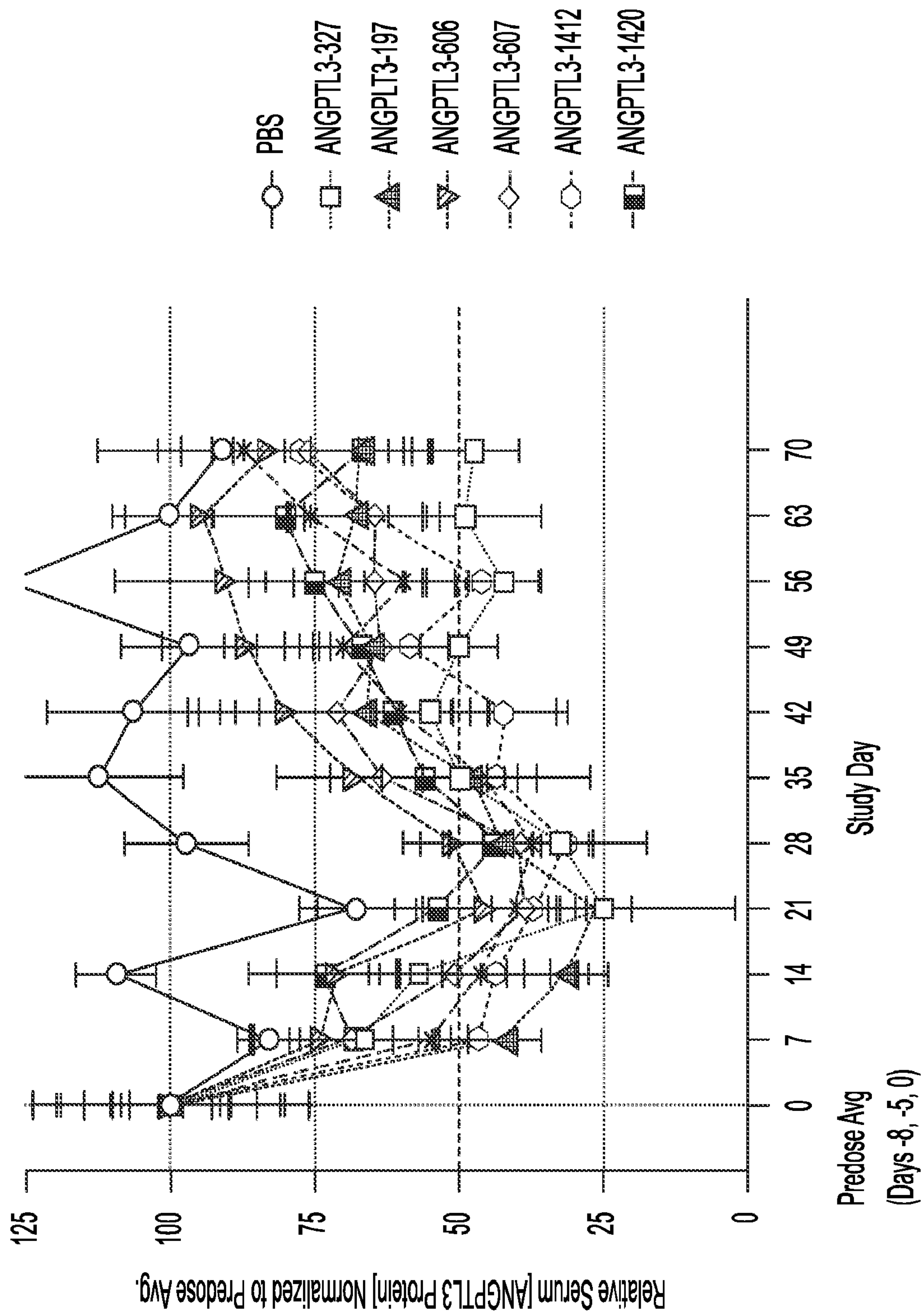
FIG. 7 provides a graph depicting the mean percent (%) of ANGPTL3 protein in serum from NHPs treated with the indicated GalNAc-conjugated ANGPTL3 oligonucleotides relative to NHPs treated with PBS over time.

The GalNAc-conjugated ANGPTL3 oligonucleotides listed in Table 4 are evaluated in cynomolgus monkeys (*Macaca fascicularis*). In this study, the NHPs are grouped so that their mean body weights (about 5.4 kg) are comparable between the control and experimental groups. Each cohort contains two male and three female subjects. The GalNAc-conjugated ANGPTL3 oligonucleotides are administered subcutaneously on Study Day 0. Blood samples are collected on Study Days −8, −5 and 0, and weekly after dosing. Ultrasound-guided core needle liver biopsies are collected on Study Days 28, 56 and 84. At each time point, total RNA derived from the liver biopsy samples is subjected to qRT-PCR analysis to measure ANGPTL3 mRNA in oligonucleotide-treated NHPs relative to NHPs treated with a comparable volume of PBS. To normalize the data, the measurements are made relative to the geometric mean of two reference genes, PPIB and 18S rRNA. As shown in FIG. 5A (Day 28), FIG. 5B (Day 56), and FIG. 5C (Day 84), treating NHPs with the GalNAc-conjugated ANGPTL3 oligonucleotides listed in Table 4 inhibits ANGPTL3 expression in the liver, as determined by a reduced amount of ANGPTL3 mRNA in liver samples from oligonucleotide-treated NHPs relative to NHPs treated with PBS. The mean percent reduction of ANGPTL3 mRNA in the liver samples of treated NHPs is indicated above the set of data points for each treatment group and a plot of the mean values over times is shown in FIG. 6. For all time points evaluated, ANGPTL3-1412 inhibits ANGPTL3 expression to a greater extent than the benchmark GalNAc-conjugated ANGPTL3 oligonucleotide ANGPTL3-0327. From the same NHP study, inhibition of ANGPTL3 expression is also determined by measuring ANGPTL3 protein in serum prepared from the pre-dose and weekly blood samples by ELISA. As shown in FIG. 7, a significant reduction in serum ANGPTL3 protein is observed in NHPs treated with GalNAc-conjugated ANGPTL3 oligonucleotides compared to NHPs treated with PBS. Values from three pre-dose samples are averaged and set to 100%, and data are reported as relative values compared to the pre-dose average. Taken together, these results demonstrate that treating NHPs with GalNAc-conjugated ANGPTL3 oligonucleotides reduces the amount of ANGPTL3 mRNA in the liver and concomitantly reduces the amount of ANGPTL3 protein in the serum.

[1] Taken together, these results show that GalNAc-conjugated ANGPTL3 oligonucleotides designed to target human ANGPTL3 mRNA inhibit ANGPTL3 expression in vivo (as determined by the reduction of the amount of ANGPTL3 mRNA and ANGPTL3 protein in treated animals).

Sequence Listing

The following nucleic and/or amino acid sequences are referred to in the disclosure above and are provided below for reference.

TABLE 5

ANGPTL3 Oligonucleotide Sequences (Unmodified)

| Oligo-nucleotide | DP# | Sequence (Sense Strand) | SEQ ID NO | Sequence (Antisense Strand) | SEQ ID NO |
|---|---|---|---|---|---|
| ANGPTL3-0099 | DP14993P: DP14992G | AUAAAAAUGUUCACAAUUAAGCAGCCGAAAGGCUGC | 1 | UUAAUUGUGAACAUUUUUAUGG | 2 |
| ANGPTL3-0108 | DP14995P: DP14994G | UUCACAAUUAAGCUCCUUCAGCAGCCGAAAGGCUGC | 3 | UGAAGGAGCUUAAUUGUGAAGG | 4 |
| ANGPTL3-0111 | DP14997P: DP14996G | ACAAUUAAGCUCCUUCUUUAGCAGCCGAAAGGCUGC | 5 | UAAAGAAGGAGCUUAAUUGUGG | 6 |
| ANGPTL3-0112 | DP14999P: DP14998G | CAAUUAAGCUCCUUCUUUUAGCAGCCGAAAGGCUGC | 7 | UAAAAGAAGGAGCUUAAUUGGG | 8 |
| ANGPTL3-0143 | DP15001P: DP15000G | AGUUAUUUCCUCCAGAAUUAGCAGCCGAAAGGCUGC | 9 | UAAUUCUGGAGGAAAUAACUGG | 10 |
| ANGPTL3-0165 | DP15003P: DP15002G | UGAGCAGCCGAAAGGCUCAAGACAAUUCAUCAUUGC | 11 | UCAAAUGAUGAAUUGUCUUGGG | 12 |
| ANGPTL3-0167 | DP15005P: DP15004G | AGACAAUUCAUCAUUUGAUAGCAGCCGAAAGGCUGC | 13 | UAUCAAAUGAUGAAUUGUCUGG | 14 |
| ANGPTL3-0170 | DP15007P: DP15006G | CAAUUCAUCAUUUGAUUCUAGCAGCCGAAAGGCUGC | 15 | UAGAAUCAAAUGAUGAAUUGGG | 16 |
| ANGPTL3-0196 | DP15009P: DP15008G | CAGAGCCAAAAUCAAGAUUAGCAGCCGAAAGGCUGC | 17 | UAAUCUUGAUUUUGGCUCUGGG | 18 |

TABLE 5-continued

ANGPTL3 Oligonucleotide Sequences (Unmodified)

| Oligo-nucleotide | DP# | Sequence (Sense Strand) | SEQ ID NO | Sequence (Antisense Strand) | SEQ ID NO |
|---|---|---|---|---|---|
| ANGPTL3-0197 | DP15011P: DP15010G | AGAGCCAAAAUCAAGAUUUAGCAGCCGAAAGGCUGC | 19 | UAAAUCUUGAUUUUGGCUCUGG | 20 |
| ANGPTL3-0198 | DP15013P: DP15012G | UGAGCAGCCGAAAGGCUGAGCCAAAAUCAAGAUUGC | 21 | UCAAAUCUUGAUUUUGGCUCGG | 22 |
| ANGPTL3-0201 | DP15015P: DP15014G | CCAAAAUCAAGAUUUGCUAAGCAGCCGAAAGGCUGC | 23 | UUAGCAAAUCUUGAUUUUGGGG | 24 |
| ANGPTL3-0202 | DP15017P: DP15016G | CAAAAUCAAGAUUUGCUAUAGCAGCCGAAAGGCUGC | 25 | UAUAGCAAAUCUUGAUUUUGGG | 26 |
| ANGPTL3-0203 | DP15019P: DP15018G | UGAGCAGCCGAAAGGCUAAAAUCAAGAUUUGCUAGC | 27 | UCAUAGCAAAUCUUGAUUUUGG | 28 |
| ANGPTL3-0212 | DP15021P: DP15020G | AUUUGCUAUGUUAGACGAUAGCAGCCGAAAGGCUGC | 29 | UAUCGUCUAACAUAGCAAAUGG | 30 |
| ANGPTL3-0303 | DP15023P: DP15022G | CAAAUUAAUGACAUAUUUCAGCAGCCGAAAGGCUGC | 31 | UGAAAUAUGUCAUUAAUUUGGG | 32 |
| ANGPTL3-0310 | DP15025P: DP15024G | AUGACAUAUUUCAAAAACUAGCAGCCGAAAGGCUGC | 33 | UAGUUUUUGAAAUAUGUCAUGG | 34 |
| ANGPTL3-0330 | DP15027P: DP15026G | AACAUAUUUGAUCAGUCUUAGCAGCCGAAAGGCUGC | 35 | UAAGACUGAUCAAAUAUGUUGG | 36 |
| ANGPTL3-0332 | DP15029P: DP15028G | UUAGCAGCCGAAAGGCUCAUAUUUGAUCAGUCUUGC | 37 | UAAAAGACUGAUCAAAUAUGGG | 38 |
| ANGPTL3-0333 | DP15031P: DP15030G | AUAUUUGAUCAGUCUUUUUAGCAGCCGAAAGGCUGC | 39 | UAAAAAGACUGAUCAAAUAUGG | 40 |
| ANGPTL3-0337 | DP15033P: DP15032G | UUGAUCAGUCUUUUUAUGAAGCAGCCGAAAGGCUGC | 41 | UUCAUAAAAAGACUGAUCAAGG | 42 |
| ANGPTL3-0394 | DP15035P: DP15034G | ACAGCAGCCGAAAGGCUAGGAACUGAGAAGAACUGC | 43 | UGUAGUUCUUCUCAGUUCCUGG | 44 |
| ANGPTL3-0396 | DP15037P: DP15036G | GAACUGAGAAGAACUACAUAGCAGCCGAAAGGCUGC | 45 | UAUGUAGUUCUUCUCAGUUCGG | 46 |
| ANGPTL3-0400 | DP15039P: DP15038G | UGAGAAGAACUACAUAUAAAGCAGCCGAAAGGCUGC | 47 | UUUAUAUGUAGUUCUUCUCAGG | 48 |
| ANGPTL3-0401 | DP15041P: DP15040G | AAAGCAGCCGAAAGGCUGAGAAGAACUACAUAUAGC | 49 | UUUUAUAUGUAGUUCUUCUCGG | 50 |
| ANGPTL3-0437 | DP15043P: DP15042G | AGAGGUAAAGAAUAUGUCAAGCAGCCGAAAGGCUGC | 51 | UUGACAUAUUCUUUACCUCUGG | 52 |
| ANGPTL3-0447 | DP15045P: DP15044G | AAUAUGUCACUUGAACUCAAGCAGCCGAAAGGCUGC | 53 | UUGAGUUCAAGUGACAUAUUGG | 54 |

TABLE 5-continued

ANGPTL3 Oligonucleotide Sequences (Unmodified)

| Oligo-nucleotide | DP# | Sequence (Sense Strand) | SEQ ID NO | Sequence (Antisense Strand) | SEQ ID NO |
|---|---|---|---|---|---|
| ANGPTL3-0517 | DP15047P:<br>DP15046G | UGAAAUAUUUAGAAGAG<br>CAAGCAGCCGAAAGGCU<br>GC | 55 | UUGCUCUUCUAAAUAUU<br>UCAGG | 56 |
| ANGPTL3-0518 | DP15049P:<br>DP15048G | AAAGCAGCCGAAAGGCU<br>GAAAUAUUUAGAAGAGC<br>GC | 56 | UUUGCUCUUCUAAAUAU<br>UUCGG | 58 |
| ANGPTL3-0532 | DP15051P:<br>DP15050G | AGCAACUAACUAACUUA<br>AUAGCAGCCGAAAGGCU<br>GC | 59 | UAUUAAGUUAGUUAGUU<br>GCUGG | 60 |
| ANGPTL3-0541 | DP15053P:<br>DP15052G | CUAACUUAAUUCAAAAU<br>CAAGCAGCCGAAAGGCU<br>GC | 51 | UUGAUUUUGAAUUAAGU<br>UAGGG | 62 |
| ANGPTL3-0582 | DP15055P:<br>DP15054G | GAAGUAACUUCACUUAA<br>AAAGCAGCCGAAAGGCU<br>GC | 63 | UUUUUAAGUGAAGUUAC<br>UUCGG | 64 |
| ANGPTL3-0602 | DP15057P:<br>DP15056G | UUUUGUAGAAAAACAAG<br>AUAGCAGCCGAAAGGCU<br>GC | 65 | UAUCUUGUUUUUCUACA<br>AAAGG | 66 |
| ANGPTL3-0603 | DP15059P:<br>DP15058G | UUUGUAGAAAAACAAGA<br>UAAGCAGCCGAAAGGCU<br>GC | 67 | UUAUCUUGUUUUUCUAC<br>AAAGG | 68 |
| ANGPTL3-0604 | DP15061P:<br>DP15060G | UUGUAGAAAAACAAGAU<br>AAAGCAGCCGAAAGGCU<br>GC | 69 | UUUAUCUUGUUUUUCUA<br>CAAGG | 70 |
| ANGPTL3-0606 | DP15063P:<br>DP15062G | GUAGAAAAACAAGAUAA<br>UAAGCAGCCGAAAGGCU<br>GC | 71 | UUAUUAUCUUGUUUUUC<br>UACGG | 72 |
| ANGPTL3-0607 | DP15065P:<br>DP15064G | UAGAAAAACAAGAUAAU<br>AGAGCAGCCGAAAGGCU<br>GC | 73 | UCUAUUAUCUUGUUUUU<br>CUAGG | 74 |
| ANGPTL3-0608 | DP15067P:<br>DP15066G | AGAAAAACAAGAUAAUA<br>GCAGCAGCCGAAAGGCU<br>GC | 75 | UGCUAUUAUCUUGUUUU<br>UCUGG | 76 |
| ANGPTL3-0610 | DP15069P:<br>DP15068G | AAAAACAAGAUAAUAGC<br>AUAGCAGCCGAAAGGCU<br>GC | 77 | UAUGCUAUUAUCUUGUU<br>UUUGG | 78 |
| ANGPTL3-0676 | DP15071P:<br>DP15070G | AACAGCAUAGUCAAAUA<br>AAAGCAGCCGAAAGGCU<br>GC | 79 | UUUUAUUUGACUAUGCU<br>GUUGG | 80 |
| ANGPTL3-0738 | DP15073P:<br>DP15072G | ACAGAAAUUUCUCUAUC<br>UUAGCAGCCGAAAGGCU<br>GC | 81 | JUAAGAUAGAGAAAUUUC<br>UGUGG | 82 |
| ANGPTL3-0796 | DP15075P:<br>DP15074G | UGAAUGAAAUAAGAAAU<br>GUAGCAGCCGAAAGGCU<br>GC | 83 | UACAUUUCUUAUUUCAU<br>UCAGG | 84 |
| ANGPTL3-0893 | DP15077P:<br>DP15076G | ACCCAGCAACUCUCAAG<br>UUAGCAGCCGAAAGGCU<br>GC | 85 | UAACUUGAGAGUUGCUG<br>GGUGG | 86 |
| ANGPTL3-0894 | DP15079P:<br>DP15078G | UUAGCAGCCGAAAGGCU<br>CCCAGCAACUCUCAAGU<br>GC | 87 | UAAACUUGAGAGUUGCU<br>GGGGG | 88 |
| ANGPTL3-0895 | DP15081P:<br>DP15080G | CCAGCAACUCUCAAGUU<br>UUAGCAGCCGAAAGGCU<br>GC | 89 | UAAAACUUGAGAGUUGC<br>UGGGG | 90 |

TABLE 5-continued

ANGPTL3 Oligonucleotide Sequences (Unmodified)

| Oligo-nucleotide | DP# | Sequence (Sense Strand) | SEQ ID NO | Sequence (Antisense Strand) | SEQ ID NO |
|---|---|---|---|---|---|
| ANGPTL3-1059 | DP15083P: DP15082G | AAGAUAUACUCCAUAGU GAAGCAGCCGAAAGGCU GC | 91 | UUCACUAUGGAGUAUAU CUUGG | 92 |
| ANGPTL3-1062 | DP15085P: DP15084G | AUAUACUCCAUAGUGAA GCAGCAGCCGAAAGGCU GC | 93 | UGCUUCACUAUGGAGUA UAUGG | 94 |
| ANGPTL3-1065 | DP15087P: DP15086G | UACUCCAUAGUGAAGCA AUAGCAGCCGAAAGGCU GC | 95 | UAUUGCUUCACUAUGGA GUAGG | 96 |
| ANGPTL3-1071 | DP15089P: DP15088G | AUAGUGAAGCAAUCUAA UUAGCAGCCGAAAGGCU GC | 97 | UAAUUAGAUUGCUUCAC UAUGG | 98 |
| ANGPTL3-1412 | DP15091P: DP15090G | UCAAAAUGGAAGGUUAU ACAGCAGCCGAAAGGCU GC | 99 | UGUAUAACCUUCCAUUU UGAGG | 100 |
| ANGPTL3-1415 | DP15093P: DP15092G | AAAUGGAAGGUUAUACU CUAGCAGCCGAAAGGCU GC | 101 | UAGAGUAUAACCUUCCA UUUGG | 102 |
| ANGPTL3-1420 | DP15095P: DP15094G | GAAGGUUAUACUCUAUA AAAGCAGCCGAAAGGCU GC | 103 | JUUUUAUAGAGUAUAACC UUCGG | 104 |
| ANGPTL3-1421 | DP15097P: DP15096G | AAGGUUAUACUCUAUAA AAAGCAGCCGAAAGGCU GC | 105 | UUUUUAUAGAGUAUAAC CUUGG | 106 |
| ANGPTL3-1422 | DP15099P: DP15098G | AGGUUAUACUCUAUAAA AUAGCAGCCGAAAGGCU GC | 107 | UAUUUUAUAGAGUAUAA CCUGG | 108 |
| ANGPTL3-1468 | DP15101P: DP15100G | AUUCAGAAAGCUUUGAA UGAGCAGCCGAAAGGCU GC | 109 | UCAUUCAAAGCUUUCUG AAUGG | 110 |
| ANGPTL3-0204 | DP13439P: DP13438G | AAAUCAAGAUUUGCUAU GUAGCAGCCGAAAGGCU GC | 111 | JUACAUAGCAAAUCUUGA UUUGG | 112 |
| ANGPTL3-0327 | DP13443P: DP13442G | CUCAACAUAUUUGAUCA GUAGCAGCCGAAAGGCU GC | 113 | UACUGAUCAAAUAUGUU GAGGG | 114 |
| ANGPTL3-1327 | DP13465P: DP13464G | GUGGAGAAAACAACCUA AAAGCAGCCGAAAGGCU GC | 115 | UUUUAGGUUGUUUUCUC CACGG | 116 |

What is claimed is:

1. An RNAi oligonucleotide for reducing angiopoietin-like protein 3 (ANGPTL3) expression, the RNAi oligonucleotide comprising a sense strand forming a duplex region with an antisense strand, wherein:

the sense strand comprises a nucleotide sequence as set forth in sequence: 5'-UCAAAAUGGAAGGUUAUACAGCAGCCGAAAGGCUGC-3' (SEQ ID NO: 99); and the antisense strand comprises a nucleotide sequence as set forth in sequence: 5'-UGUAUAACCUUCCAUUUUGAGG-3' (SEQ ID NO: 100).

2. The RNAi oligonucleotide of claim 1, wherein the RNAi oligonucleotide comprises at least one modified nucleotide.

3. The RNAi oligonucleotide of claim 2, wherein at least one modified nucleotide comprises a 2'-modification.

4. The RNAi oligonucleotide of claim 2, wherein all nucleotides of the oligonucleotide are modified.

5. The RNAi oligonucleotide of claim 1, wherein the RNAi oligonucleotide comprises at least one modified internucleotide linkage.

6. The RNAi oligonucleotide of claim 5, wherein the at least one modified internucleotide linkage is a phosphorothioate linkage.

7. The RNAi oligonucleotide of claim 1, wherein the 4'-carbon of the sugar of the 5'-nucleotide of the antisense strand comprises a phosphate analog.

8. The RNAi oligonucleotide of claim 7, wherein the phosphate analog is oxymethylphosphonate, vinylphosphonate, or malonylphosphonate.

9. The RNAi oligonucleotide of claim 1, wherein at least one nucleotide of the RNAi oligonucleotide is conjugated to one or more targeting ligands.

10. The RNAi oligonucleotide of claim 9, wherein each targeting ligand comprises a N-acetylgalactosamine (GalNAc) moiety.

11. The RNAi oligonucleotide of claim 10, wherein the GalNac moiety is a monovalent GalNAc moiety, a bivalent GalNAc moiety, a trivalent GalNAc moiety, or a tetravalent GalNAc moiety.

12. The RNAi oligonucleotide of claim 11, wherein up to 4 nucleotides of a stem-loop of the RNAi oligonucleotide are each conjugated to a monovalent GalNAc moiety.

13. A pharmaceutical composition comprising:

(i) the RNAi oligonucleotide of claim 1; and (ii) a pharmaceutically acceptable carrier, delivery agent, or excipient.

14. The RNAi oligonucleotide of claim 3, wherein the 2'-modification is a modification selected from 2'-aminoethyl, 2'-fluoro, 2'-O-methyl, 2'O-methoxyethyl, and 2'-deoxy-2'-fluoro-β-d-arabinonucleic acid.

15. The RNAi oligonucleotide of claim 14, wherein the 2'-modification is selected from the group consisting of 2'-fluoro (2'-F) and 2'-O-methyl (2'-OMe).

16. The RNAi oligonucleotide of claim 7, wherein the phosphate analog is a 4'-phosphate analog comprising 5'-methoxyphosphonate-4'-oxy.

17. The RNAi oligonucleotide of claim 9, wherein each targeting ligand comprises a carbohydrate, amino sugar, cholesterol, polypeptide, or lipid.

18. The pharmaceutical composition of claim 13, wherein the pharmaceutically acceptable carrier comprises water.

19. The pharmaceutical composition of claim 13, wherein the pharmaceutically acceptable carrier comprises phosphate buffered saline.

* * * * *

SEQUENCE LISTING

<160> NUMBER OF SEQ ID NOS: 248

<210> SEQ ID NO 1
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 1
auaaaaaugu ucacaauuaa gcagccgaaa ggcugc 36

<210> SEQ ID NO 2
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 2
uuaauuguga acauuuuuau gg 22

<210> SEQ ID NO 3
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 3
uucacaauua agcuccuuca gcagccgaaa ggcugc 36

<210> SEQ ID NO 4
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 4
ugaaggagcu uaauugugaa gg 22

<210> SEQ ID NO 5
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 5
acaauuaagc uccuucuuua gcagccgaaa ggcugc 36

<210> SEQ ID NO 6
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 6
uaaagaagga gcuuaauugu gg 22

<210> SEQ ID NO 7
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 7
caauuaagcu ccuucuuuua gcagccgaaa ggcugc 36

<210> SEQ ID NO 8
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 8
uaaaagaagg agcuuaauug gg 22

<210> SEQ ID NO 9
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 9
aguuauuucc uccagaauua gcagccgaaa ggcugc 36

<210> SEQ ID NO 10
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 10
uaauucugga ggaaauaacu gg 22

<210> SEQ ID NO 11
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 11
caagacaauu caucauuuga gcagccgaaa ggcugc 36

<210> SEQ ID NO 12
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 12
ucaaaugaug aauugucuug gg 22

<210> SEQ ID NO 13
<211> LENGTH: 36

<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 13
agacaauuca ucauuugaua gcagccgaaa ggcugc 36

<210> SEQ ID NO 14
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 14
uaucaaauga ugaauugucu gg 22

<210> SEQ ID NO 15
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 15
caauucauca uuugauucua gcagccgaaa ggcugc 36

<210> SEQ ID NO 16
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 16
uagaaucaaa ugaugaauug gg 22

<210> SEQ ID NO 17
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 17
cagagccaaa aucaagauua gcagccgaaa ggcugc 36

<210> SEQ ID NO 18
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 18

-continued uaaucuugau uuuggcucug gg 22

<210> SEQ ID NO 19
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 19
agagccaaaa ucaagauuua gcagccgaaa ggcugc 36

<210> SEQ ID NO 20
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 20
uaaaucuuga uuuuggcucu gg 22

<210> SEQ ID NO 21
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 21
gagccaaaau caagauuuga gcagccgaaa ggcugc 36

<210> SEQ ID NO 22
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 22
ucaaaucuug auuuuggcuc gg 22

<210> SEQ ID NO 23
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 23
ccaaaaucaa gauuugcuaa gcagccgaaa ggcugc 36

<210> SEQ ID NO 24
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 24
uuagcaaauc uugauuuugg gg                                          22

<210> SEQ ID NO 25
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 25
caaaaucaag auuugcuaua gcagccgaaa ggcugc                           36

<210> SEQ ID NO 26
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 26
uauagcaaau cuugauuuug gg                                          22

<210> SEQ ID NO 27
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 27
aaaaucaaga uuugcuauga gcagccgaaa ggcugc                           36

<210> SEQ ID NO 28
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 28
ucauagcaaa ucuugauuuu gg                                          22

<210> SEQ ID NO 29
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 29
auuugcuaug uuagacgaua gcagccgaaa ggcugc                           36

<210> SEQ ID NO 30

-continued

<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 30
uaucgucuaa cauagcaaau gg 22

<210> SEQ ID NO 31
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 31
caaauuaaug acauauuuca gcagccgaaa ggcugc 36

<210> SEQ ID NO 32
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 32
ugaaauaugu cauuaauuug gg 22

<210> SEQ ID NO 33
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 33
augacauauu ucaaaaacua gcagccgaaa ggcugc 36

<210> SEQ ID NO 34
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 34
uaguuuuuga aauaugucau gg 22

<210> SEQ ID NO 35
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 35
aacauauuug aucagucuua gcagccgaaa ggcugc 36

<210> SEQ ID NO 36
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 36
uaagacugau caaauauguu gg 22

<210> SEQ ID NO 37
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 37
cauauuugau cagucuuuua gcagccgaaa ggcugc 36

<210> SEQ ID NO 38
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 38
uaaaagacug aucaaauaug gg 22

<210> SEQ ID NO 39
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 39
auauuugauc agucuuuuua gcagccgaaa ggcugc 36

<210> SEQ ID NO 40
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 40
uaaaaagacu gaucaaauau gg 22

<210> SEQ ID NO 41
<211> LENGTH: 36
<212> TYPE: RNA
<213> ORGANISM: Artificial Sequence
<220> FEATURE:

<221> NAME/KEY: source
<223> OTHER INFORMATION: /note="Description of Artificial Sequence:
      Synthetic oligonucleotide"

<400> SEQUENCE: 41
uugaucaguc uuuuuaugaa gcagccgaaa ggcugc 36

<210> SEQ ID NO 42
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 42
uucauaaaaa gacugaucaa gg 22

<210> SEQ ID NO 43
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 43
aggaacugag aagaacuaca gcagccgaaa ggcugc 36

<210> SEQ ID NO 44
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 44
uguaguucuu cucaguuccu gg 22

<210> SEQ ID NO 45
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 45
gaacugagaa gaacuacaua gcagccgaaa ggcugc 36

<210> SEQ ID NO 46
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 46
uauguaguuc uucucaguuc gg 22

-continued

<210> SEQ ID NO 47
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 47
ugagaagaac uacauauaaa gcagccgaaa ggcugc 36

<210> SEQ ID NO 48
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 48
uuuauaugua guucuucuca gg 22

<210> SEQ ID NO 49
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 49
gagaagaacu acauauaaaa gcagccgaaa ggcugc 36

<210> SEQ ID NO 50
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 50
uuuuauaugu aguucuucuc gg 22

<210> SEQ ID NO 51
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 51
agagguaaag aauaugucaa gcagccgaaa ggcugc 36

<210> SEQ ID NO 52
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 52
uugacauauu cuuuaccucu gg 22

<210> SEQ ID NO 53
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 53
aauaugucac uugaacucaa gcagccgaaa ggcugc 36

<210> SEQ ID NO 54
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 54
uugaguucaa gugacauauu gg 22

<210> SEQ ID NO 55
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 55
ugaaauauuu agaagagcaa gcagccgaaa ggcugc 36

<210> SEQ ID NO 56
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 56
uugcucuucu aaauauuuca gg 22

<210> SEQ ID NO 57
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 57
gaaauauuua gaagagcaaa gcagccgaaa ggcugc 36

<210> SEQ ID NO 58
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 58
uuugcucuuc uaaauauuuc gg 22

<210> SEQ ID NO 59
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 59
agcaacuaac uaacuuaaua gcagccgaaa ggcugc 36

<210> SEQ ID NO 60
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 60
uauuaaguua guuaguugcu gg 22

<210> SEQ ID NO 61
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 61
cuaacuuaau ucaaaaucaa gcagccgaaa ggcugc 36

<210> SEQ ID NO 62
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 62
uugauuuuga auuaaguuag gg 22

<210> SEQ ID NO 63
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 63
gaaguaacuu cacuuaaaaa gcagccgaaa ggcugc 36

<210> SEQ ID NO 64
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 64
uuuuuaagug aaguuacuuc gg 22

<210> SEQ ID NO 65
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 65
uuuuguagaa aaacaagaua gcagccgaaa ggcugc 36

<210> SEQ ID NO 66
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 66
uaucuuguuu uucuacaaaa gg 22

<210> SEQ ID NO 67
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 67
uuuguagaaa aacaagauaa gcagccgaaa ggcugc 36

<210> SEQ ID NO 68
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 68
uuaucuuguu uuucuacaaa gg 22

<210> SEQ ID NO 69
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 69
uuguagaaaa acaagauaaa gcagccgaaa ggcugc 36

<210> SEQ ID NO 70
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 70
uuuaucuugu uuuucuacaa gg 22

<210> SEQ ID NO 71
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 71
guagaaaaac aagauaauaa gcagccgaaa ggcugc 36

<210> SEQ ID NO 72
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 72
uuauuaucuu guuuuucuac gg 22

<210> SEQ ID NO 73
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 73
uagaaaaaca agauaauaga gcagccgaaa ggcugc 36

<210> SEQ ID NO 74
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 74
ucuauuaucu uguuuuucua gg 22

<210> SEQ ID NO 75
<211> LENGTH: 36
<212> TYPE: RNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 75

agaaaaacaa gauaauagca gcagccgaaa ggcugc                          36


<210> SEQ ID NO 76
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 76

ugcuauuauc uuguuuuucu gg                                         22


<210> SEQ ID NO 77
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 77

aaaaacaaga uaauagcaua gcagccgaaa ggcugc                          36


<210> SEQ ID NO 78
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 78

uaugcuauua ucuuguuuuu gg                                         22


<210> SEQ ID NO 79
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 79

aacagcauag ucaaauaaaa gcagccgaaa ggcugc                          36


<210> SEQ ID NO 80
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 80

uuuuauuuga cuaugcuguu gg                                         22
```

<210> SEQ ID NO 81
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 81
acagaaauuu cucuaucuua gcagccgaaa ggcugc 36

<210> SEQ ID NO 82
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 82
uaagauagag aaauuucugu gg 22

<210> SEQ ID NO 83
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 83
ugaaugaaau aagaaaugua gcagccgaaa ggcugc 36

<210> SEQ ID NO 84
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 84
uacauuucuu auuucauuca gg 22

<210> SEQ ID NO 85
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 85
acccagcaac ucucaaguua gcagccgaaa ggcugc 36

<210> SEQ ID NO 86
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 86
uaacuugaga guugcugggu gg 22

<210> SEQ ID NO 87
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 87
cccagcaacu cucaaguuua gcagccgaaa ggcugc 36

<210> SEQ ID NO 88
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 88
uaaacuugag aguugcuggg gg 22

<210> SEQ ID NO 89
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 89
ccagcaacuc ucaaguuuua gcagccgaaa ggcugc 36

<210> SEQ ID NO 90
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 90
uaaaacuuga gaguugcugg gg 22

<210> SEQ ID NO 91
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 91
aagauauacu ccauagugaa gcagccgaaa ggcugc 36

<210> SEQ ID NO 92
<211> LENGTH: 22

-continued

<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 92
uucacuaugg aguauaucuu gg                                              22

<210> SEQ ID NO 93
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 93
auauacucca uagugaagca gcagccgaaa ggcugc                               36

<210> SEQ ID NO 94
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 94
ugcuucacua uggaguauau gg                                              22

<210> SEQ ID NO 95
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 95
uacuccauag ugaagcaaua gcagccgaaa ggcugc                               36

<210> SEQ ID NO 96
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 96
uauugcuuca cuauggagua gg                                              22

<210> SEQ ID NO 97
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 97

-continued

```
auagugaagc aaucuaauua gcagccgaaa ggcugc                        36


<210> SEQ ID NO 98
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 98

uaauuagauu gcuucacuau gg                                       22


<210> SEQ ID NO 99
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 99

ucaaaaugga agguuauaca gcagccgaaa ggcugc                        36


<210> SEQ ID NO 100
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 100

uguauaaccu uccauuuuga gg                                       22


<210> SEQ ID NO 101
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 101

aaauggaagg uuauacucua gcagccgaaa ggcugc                        36


<210> SEQ ID NO 102
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 102

uagaguauaa ccuuccauuu gg                                       22


<210> SEQ ID NO 103
<211> LENGTH: 36
<212> TYPE: RNA
<213> ORGANISM: Artificial Sequence
<220> FEATURE:
<221> NAME/KEY: source
```

<223> OTHER INFORMATION: /note="Description of Artificial Sequence:
Synthetic oligonucleotide"

<400> SEQUENCE: 103
gaagguuaua cucuauaaaa gcagccgaaa ggcugc 36

<210> SEQ ID NO 104
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 104
uuuuauagag uauaaccuuc gg 22

<210> SEQ ID NO 105
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 105
aagguuauac ucuauaaaaa gcagccgaaa ggcugc 36

<210> SEQ ID NO 106
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 106
uuuuuauaga guauaaccuu gg 22

<210> SEQ ID NO 107
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 107
agguuauacu cuauaaaaua gcagccgaaa ggcugc 36

<210> SEQ ID NO 108
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 108
uauuuuauag aguauaaccu gg 22

<210> SEQ ID NO 109

<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 109
auucagaaag cuuugaauga gcagccgaaa ggcugc 36

<210> SEQ ID NO 110
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 110
ucauucaaag cuuucugaau gg 22

<210> SEQ ID NO 111
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 111
aaaucaagau uugcuaugua gcagccgaaa ggcugc 36

<210> SEQ ID NO 112
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 112
uacauagcaa aucuugauuu gg 22

<210> SEQ ID NO 113
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 113
cucaacauau uugaucagua gcagccgaaa ggcugc 36

<210> SEQ ID NO 114
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 114

```
uacugaucaa auauguugag gg                                          22


<210> SEQ ID NO 115
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 115

guggagaaaa caaccuaaaa gcagccgaaa ggcugc                           36


<210> SEQ ID NO 116
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 116

uuuuagguug uuuucuccac gg                                          22


<210> SEQ ID NO 117
<211> LENGTH: 19
<212> TYPE: RNA
<213> ORGANISM: Homo sapiens

<400> SEQUENCE: 117

cucaacauau uugaucagu                                              19


<210> SEQ ID NO 118
<211> LENGTH: 19
<212> TYPE: RNA
<213> ORGANISM: Homo sapiens

<400> SEQUENCE: 118

agagccaaaa ucaagauuu                                              19


<210> SEQ ID NO 119
<211> LENGTH: 19
<212> TYPE: RNA
<213> ORGANISM: Homo sapiens

<400> SEQUENCE: 119

caaaaucaag auuugcuau                                              19


<210> SEQ ID NO 120
<211> LENGTH: 19
<212> TYPE: RNA
<213> ORGANISM: Homo sapiens

<400> SEQUENCE: 120

gagaagaacu acauauaaa                                              19


<210> SEQ ID NO 121
<211> LENGTH: 19
<212> TYPE: RNA
<213> ORGANISM: Homo sapiens

<400> SEQUENCE: 121
```

-continued guagaaaaac aagauaaua 19

<210> SEQ ID NO 122
<211> LENGTH: 19
<212> TYPE: RNA
<213> ORGANISM: Homo sapiens

<400> SEQUENCE: 122
uagaaaaaca agauaauag 19

<210> SEQ ID NO 123
<211> LENGTH: 19
<212> TYPE: RNA
<213> ORGANISM: Homo sapiens

<400> SEQUENCE: 123
agaaaaacaa gauaauagc 19

<210> SEQ ID NO 124
<211> LENGTH: 19
<212> TYPE: RNA
<213> ORGANISM: Homo sapiens

<400> SEQUENCE: 124
aacagcauag ucaaauaaa 19

<210> SEQ ID NO 125
<211> LENGTH: 19
<212> TYPE: RNA
<213> ORGANISM: Homo sapiens

<400> SEQUENCE: 125
ucaaaaugga agguuauac 19

<210> SEQ ID NO 126
<211> LENGTH: 19
<212> TYPE: RNA
<213> ORGANISM: Homo sapiens

<400> SEQUENCE: 126
aaauggaagg uuauacucu 19

<210> SEQ ID NO 127
<211> LENGTH: 19
<212> TYPE: RNA
<213> ORGANISM: Homo sapiens

<400> SEQUENCE: 127
gaagguuaua cucuauaaa 19

<210> SEQ ID NO 128
<211> LENGTH: 2926
<212> TYPE: DNA
<213> ORGANISM: Homo sapiens

<400> SEQUENCE: 128
agaagaaaac agttccacgt tgcttgaaat tgaaaatcaa gataaaaatg ttcacaatta 60
agctccttct ttttattgtt cctctagtta tttcctccag aattgatcaa gacaattcat 120
catttgattc tctatctcca gagccaaaat caagatttgc tatgttagac gatgtaaaaa 180
ttttagccaa tggcctcctt cagttgggac atggtcttaa agactttgtc cataagacga 240
agggccaaat taatgacata tttcaaaaac tcaacatatt tgatcagtct tttatgatc 300

-continued

```
tatcgctgca aaccagtgaa atcaaagaag aagaaaagga actgagaaga actacatata    360
aactacaagt caaaaatgaa gaggtaaaga atatgtcact tgaactcaac tcaaaacttg    420
aaagcctcct agaagaaaaa attctacttc aacaaaaagt gaaatattta gaagagcaac    480
taactaactt aattcaaaat caacctgaaa ctccagaaca cccagaagta acttcactta    540
aaacttttgt agaaaaacaa gataatagca tcaaagacct tctccagacc gtggaagacc    600
aatataaaca attaaaccaa cagcatagtc aaataaaaga aatagaaaat cagctcagaa    660
ggactagtat tcaagaaccc acagaaattt ctctatcttc caagccaaga gcaccaagaa    720
ctactccctt tcttcagttg aatgaaataa gaaatgtaaa acatgatggc attcctgctg    780
aatgtaccac catttataac agaggtgaac atacaagtgg catgtatgcc atcagaccca    840
gcaactctca agtttttcat gtctactgtg atgttatatc aggtagtcca tggacattaa    900
ttcaacatcg aatagatgga tcacaaaact tcaatgaaac gtgggagaac tacaaatatg    960
gttttgggag gcttgatgga gaattttggt tgggcctaga gaagatatac tccatagtga   1020
agcaatctaa ttatgtttta cgaattgagt tggaagactg gaaagacaac aaacattata   1080
ttgaatattc tttttacttg ggaaatcacg aaaccaacta tacgctacat ctagttgcga   1140
ttactggcaa tgtccccaat gcaatcccgg aaaacaaaga tttggtgttt tctacttggg   1200
atcacaaagc aaaaggacac ttcaactgtc cagagggtta ttcaggaggc tggtggtggc   1260
atgatgagtg tggagaaaac aacctaaatg gtaaatataa caaaccaaga gcaaaatcta   1320
agccagagag gagaagagga ttatcttgga agtctcaaaa tggaaggtta tactctataa   1380
aatcaaccaa aatgttgatc catccaacag attcagaaag ctttgaatga actgaggcaa   1440
atttaaaagg caataattta aacattaacc tcattccaag ttaatgtggt ctaataatct   1500
ggtattaaat ccttaagaga aagcttgaga aatagatttt ttttatctta aagtcactgt   1560
ctatttaaga ttaaacatac aatcacataa ccttaaagaa taccgtttac atttctcaat   1620
caaaattctt ataatactat ttgttttaaa ttttgtgatg tgggaatcaa ttttagatgg   1680
tcacaatcta gattataatc aataggtgaa cttattaaat aactttttcta aataaaaaat   1740
ttagagactt ttattttaaa aggcatcata tgagctaata tcacaacttt cccagtttaa   1800
aaaactagta ctcttgttaa aactctaaac ttgactaaat acagaggact ggtaattgta   1860
cagttcttaa atgttgtagt attaatttca aaactaaaaa tcgtcagcac agagtatgtg   1920
taaaaatctg taatacaaat ttttaaactg atgcttcatt ttgctacaaa ataatttgga   1980
gtaaatgttt gatatgattt atttatgaaa cctaatgaag cagaattaaa tactgtatta   2040
aaataagttc gctgtcttta aacaaatgga gatgactact aagtcacatt gactttaaca   2100
tgaggtatca ctataccttta tttgttaaaa tatatactgt atacatttta tatattttaa   2160
cacttaatac tatgaaaaca aataattgta aaggaatctt gtcagattac agtaagaatg   2220
aacatatttg tggcatcgag ttaaagttta tatttcccct aaatatgctg tgattctaat   2280
acattcgtgt aggttttcaa gtagaaataa acctcgtaac aagttactga acgtttaaac   2340
agcctgacaa gcatgtatat atgtttaaaa ttcaataaac aaagacccag tccctaaatt   2400
atagaaattt aaattattct tgcatgttta tcgacatcac aacagatccc taaatcccta   2460
aatccctaaa gattagatac aaattttttta ccacagtatc acttgtcaga atttattttt   2520
aaatatgatt ttttaaaact gccagtaaga aattttaaat taaacccatt tgttaaagga   2580
tatagtgccc aagttatatg gtgacctacc tttgtcaata cttagcatta tgtatttcaa   2640
```

```
attatccaat atacatgtca tatatatttt tatatgtcac atatataaaa gatatgtatg   2700

atctatgtga atcctaagta aatattttgt tccagaaaag tacaaaataa taaaggtaaa   2760

aataatctat aattttcagg accacagact aagctgtcga aattaacgct gattttttta   2820

gggccagaat accaaaatgg ctcctctctt cccccaaaat tggacaattt caaatgcaaa   2880

ataattcatt atttaatata tgagttgctt cctctatttg gtttcc                 2926


<210> SEQ ID NO 129
<211> LENGTH: 2995
<212> TYPE: DNA
<213> ORGANISM: Macaca fascicularis

<400> SEQUENCE: 129

tacaatttca aattacctat taagttagtt gctcatttct ttgatttcat ttagcattga     60

tgtaactcaa tgtggaagaa ggttacattc gtgcaagtta acatggctta atgattaact    120

atattcacct gccaaccttg ccttttctgt ggcaaatatt ggtatatata gagttaagaa    180

gtctaggtct gcttccagaa gaacacagtt ccacgctgct tgaaattgaa aatcaggata    240

aaaatgttca caattaagct ccttcttttt attgttcctc tagttatttc ctccagaatt    300

gaccaagaca attcatcatt tgattctgta tctccagagc caaaatcaag atttgctatg    360

ttagacgatg taaaaatttt agccaatggc ctccttcagt tgggacatgg tcttaaagac    420

tttgtccata agactaaggg ccaaattaat gacatatttc aaaaactcaa catatttgat    480

cagtcttttt atgatctatc actgcaaacc agtgaaatca aagaagaaga aaaggaactg    540

agaagaacta catataaact acaagtcaaa aatgaagagg taaagaatat gtcacttgaa    600

ctcaactcaa aacttgaaag cctcctagaa gaaaaaattc tacttcaaca aaaagtgaaa    660

tatttagaag agcaactaac taacttaatt caaaatcaac ctgcaactcc agaacatcca    720

gaagtaactt cacttaaaag ttttgtagaa aaacaagata atagcatcaa agaccttctc    780

cagactgtgg aagaacaata taagcaatta aaccaacagc atagtcaaat aaaagaaata    840

gaaaatcagc tcagaatgac taatattcaa gaacccacag aaatttctct atcttccaag    900

ccaagagcac caagaactac tccctttctt cagctgaatg aaataagaaa tgtaaaacat    960

gatggcattc ctgctgattg taccaccatt tacaatagag gtgaacatat aagtggcacg   1020

tatgccatca gacccagcaa ctctcaagtt tttcatgtct actgtgatgt tgtatcaggt   1080

agtccatgga cattaattca acatcgaata gatggatcac aaaacttcaa tgaaacgtgg   1140

gagaactaca aatatggttt cgggaggctt gatggagaat tctggttggg cctagagaag   1200

atatactcca tagtgaagca atctaattac gttttacgaa ttgagttgga agactggaaa   1260

gacaacaaac attatattga atattctttt tacttgggaa atcacgaaac caactatacg   1320

ctacatgtag ttaagattac tggcaatgtc cccaatgcaa tcccggaaaa caaagatttg   1380

gtgttttcta cttgggatca caaagcaaaa ggacacttca gctgtccaga gagttattca   1440

ggaggctggt ggtggcatga tgagtgtgga gaaaacaacc taaatggtaa atataacaaa   1500

ccaagaacaa aatctaagcc agagcggaga agaggattat cctggaagtc tcaaaatgga   1560

aggttatact ctataaaatc aaccaaaatg ttgatccatc caacagattc agaaagcttt   1620

gaatgaactg aggcaaattt aaaaggcaat aaattaaaca ttaaactcat tccaagttaa   1680

tgtggtttaa taatctggta ttaaatcctt aagagaaggc ttgagaaata gattttttta   1740

tcttaaagtc actgtcaatt taagattaaa catacaatca cataacctta aagaatacca   1800

tttacatttc tcaatcaaaa ttcttacaac actatttgtt ttatattttg tgatgtggga   1860
```

atcaatttta gatggtcgca atctaaatta taatcaacag gtgaacttac taaataactt 1920
ttctaaataa aaaacttaga gactttaatt ttaaaagtca tcatatgagc taatatcaca 1980
attttcccag tttaaaaaac tagttttctt gttaaaactc taaacttgac taaataaaga 2040
ggactgataa ttatacagtt cttaaatttg ttgtaatatt aatttcaaaa ctaaaaattg 2100
tcagcacaga gtatgtgtaa aaatctgtaa tataaatttt taaactgatg cctcattttg 2160
ctacaaaata atctggagta aatttttgat aggatttatt tatgaaacct aatgaagcag 2220
gattaaatac tgtattaaaa taggttcgct gtcttttaaa caaatggaga tgatgattac 2280
taagtcacat tgactttaat atgaggtatc actatacctt aacatatttg ttaaaacgta 2340
tactgtatac attttgtgta ttttaatact taatactatg aaaacaagta attgtaaacg 2400
tatcttgtca gattacaata ggaatgaaca tattggtgac atcgagttaa agtttatatt 2460
tcccctaaat atgctgcgat tccaatatat tcatgtaggt tttcaagcag aaataaacct 2520
tgtaacaagt tactgactaa acagcctgac aagtatgtat atatgtttaa aattcaataa 2580
ataaagaccc agtcttctaa attataaaaa tttaaattag tcttgcacaa attaaattat 2640
tcatcacaaa agatgtattg ttatttttaa gtcatttaag ccctaaatcc ctaaagatta 2700
gatataaatt tttttgccca gagtataaat tgtcagaatt tatttttaaa tatatttttt 2760
aaaactacca gtaagaaatt ttaaattaaa cccatttgtt aaaggatata gtgcccaagt 2820
tatacggtga cctacctttg tcaatattta gcattatgta tttcaaatta tccaatatac 2880
atgtcatata tatttttata tgttgcatat ataaaagata tacacgattt atgtgaatcc 2940
tatgtaaata ttttgttcca gaaaagtaca aaataataaa ggtaaaaata atcca 2995

<210> SEQ ID NO 130
<211> LENGTH: 1609
<212> TYPE: DNA
<213> ORGANISM: Mus musculus

<400> SEQUENCE: 130
acaggaggga gaagttccaa attgcttaaa attgaataat tgagacaaaa aatgcacaca 60
attaaattat tcctttttgt tgttccttta gtaattgcat ccagagtgga tccagacctt 120
tcatcatttg attctgcacc ttcagagcca aaatcaagat ttgctatgtt ggatgatgtc 180
aaaattttag cgaatggcct cctgcagctg ggtcatggac ttaaagattt tgtccataag 240
actaagggac aaattaacga catatttcag aagctcaaca tatttgatca gtctttttat 300
gacctatcac ttcgaaccaa tgaaatcaaa gaagaggaaa aggagctaag aagaactaca 360
tctacactac aagttaaaaa cgaggaggtg aagaacatgt cagtagaact gaactcaaag 420
cttgagagtc tgctggaaga gaagacagcc cttcaacaca aggtcagggc tttggaggag 480
cagctaacca acttaattct aagcccagct ggggctcagg agcacccaga agtaacatca 540
ctcaaaagtt ttgtagaaca gcaagacaac agcataagag aactcctcca gagtgtggaa 600
gaacagtata aacaattaag tcaacagcac atgcagataa aagaaataga aaagcagctc 660
agaaagactg gtattcaaga accctcagaa aattctcttt cttctaaatc aagagcacca 720
agaactactc cccctcttca actgaacgaa acagaaaata cagaacaaga tgaccttcct 780
gccgactgct ctgccgttta taacagaggc gaacatacaa gtggcgtgta cactattaaa 840
ccaagaaact cccaagggtt taatgtctac tgtgataccc aatcaggcag tccatggaca 900
ttaattcaac accggaaaga tggctcacag gacttcaacg aaacatggga aaactacgaa 960

-continued

```
aagggctttg ggaggctcga tggagaattt tggttgggcc tagagaagat ctatgctata   1020

gtccaacagt ctaactacat tttacgactc gagctacaag actggaaaga cagcaagcac   1080

tacgttgaat actcctttca cctgggcagt cacgaaacca actacacgct acatgtggct   1140

gagattgctg gcaatatccc tggggccctc ccagagcaca cagacctgat gttttctaca   1200

tggaatcaca gagcaaaggg acagctctac tgtccagaaa gttactcagg tggctggtgg   1260

tggaatgaca tatgtggaga aaacaaccta aatggaaaat acaacaaacc cagaaccaaa   1320

tccagaccag agagaagaag agggatctac tggagacctc agagcagaaa gctctatgct   1380

atcaaatcat ccaaaatgat gctccagccc accacctaag aagcttcaac tgaactgaga   1440

caaaataaaa gatcaataaa ttaaatatta aagtcctccc gatcactgta gtaatctggt   1500

attaaaattt taatggaaag cttgagaatt gaatttcaat taggtttaaa ctcattgtta   1560

agatcagata tcaccgaatc aacgtaaaca aaatttatct ttttcaatc              1609
```

<210> SEQ ID NO 131
<211> LENGTH: 1785
<212> TYPE: DNA
<213> ORGANISM: Rattus norvegicus

<400> SEQUENCE: 131

```
gacgttccaa attgcttgaa attgaataat tgaaacaaaa atgcacacaa ttaagctgct     60

ccttttttgtt gttcctctag taatttcgtc cagagttgat ccagaccttt cgccatttga    120

ttctgtaccg tcagagccaa aatcaagatt tgctatgttg gatgatgtca aaattttagc    180

caatggcctc ctgcagctgg gtcatggtct taaagatttt gtccataaga caaagggaca    240

aattaatgac atatttcaga agctcaacat atttgatcag tgtttttatg acctatcact    300

tcaaaccaat gaaatcaaag aagaggaaaa ggagctaaga agaaccacat ctaaactaca    360

agttaaaaac gaagaggtga agaatatgtc acttgaactg aactcaaagc ttgaaagtct    420

actggaggag aagatggcgc tccaacacag agtcagggct ttggaggaac agctgaccag    480

cttggttcag aacccgcctg ggctcggga gcacccagag gtaacgtcac ttaaaagttt    540

tgtagaacag caagataaca gcataagaga actcctccag agtgtggaag aacaatataa    600

acaactaagt caacagcaca ttcagataaa agaaatagaa aatcagctca gaaagactgg    660

cattcaagaa cccactgaaa attctcttta ttctaaacca agagcaccaa gaactactcc    720

ccctcttcat ctgaaggaag caaaaaaatat agaacaagat gatctgcctg ctgactgctc    780

tgccatttat aacagaggtg aacatacaag tggcgtgtat actattagac caagcagctc    840

tcaagtgttt aatgtctact gtgacaccca atcaggcact ccacggacat taattcaaca    900

ccggaaagat ggctctcaaa acttcaacca aacgtgggaa aactacgaaa agggttttgg    960

gaggcttgat ggtaaagtga tttccttgca tcactcactt atctgttgat ttaatagtat   1020

tagttgggtg tgttgacaca ggcctgagac catagcgctt ttgggcaagg ggggaggagg   1080

agcagcaggt gaattgaaag ttcaagacca gtctgggcca cacattgata ctccttctcg   1140

acattaagaa ttataaatta agcagcaatt ataaaatggg ctgtggaaat gtaacaataa   1200

gcaaaagcag accccagtct tcataaaact gattggtaaa tattatccat gatagcaact   1260

gcaatgatct cattgtactt atcactactg catgcctgca gtatgcttgt tgaaacttaa   1320

ttctatagtt catggttatc ataagtctta ttaaggaaca tagtatacgc cattggctct   1380

agtgaggggc catgctacaa atgagctgca aagatagcag tatagagctc tttcagtgat   1440

atcctaagca caacgtaaca caggtgaaat gggctggagg cacagttgtg gtggaacacg   1500
```

```
cggccagcag gacactggga ctgatcccca gcagcacaaa gaaagtgata ggaacacaga   1560

gcgagagtta gaagggacag ggtcaccgtc agagatacgg tgtctaactc ctgcaaccct   1620

acctgtaatt attccatatt ataaacatat actatataac tgtgggtctc tgcatgttct   1680

agaatatgaa ttctatttga ttgtaaaaca aaactataaa aataagtaaa aaaataaaaa   1740

ataaacagat acttaaaatc aaaaaaaaaa aaaaaaaaaa aaaaa                   1785


<210> SEQ ID NO 132
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: misc_feature
<222> LOCATION: (1)..(1)
<223> OTHER INFORMATION: /note="2'-OMe modified nucleotide with a
      3'-phosphorothioate linkage"
<220> FEATURE:
<221> NAME/KEY: misc_feature
<222> LOCATION: (2)..(2)
<223> OTHER INFORMATION: /note="2'-OMe modified nucleotide"
<220> FEATURE:
<221> NAME/KEY: misc_feature
<222> LOCATION: (3)..(3)
<223> OTHER INFORMATION: /note="2'-OMe modified nucleotide"
<220> FEATURE:
<221> NAME/KEY: misc_feature
<222> LOCATION: (4)..(4)
<223> OTHER INFORMATION: /note="2'-OMe modified nucleotide"
<220> FEATURE:
<221> NAME/KEY: misc_feature
<222> LOCATION: (5)..(5)
<223> OTHER INFORMATION: /note="2'-OMe modified nucleotide"
<220> FEATURE:
<221> NAME/KEY: misc_feature
<222> LOCATION: (6)..(6)
<223> OTHER INFORMATION: /note="2'-OMe modified nucleotide"
<220> FEATURE:
<221> NAME/KEY: misc_feature
<222> LOCATION: (7)..(7)
<223> OTHER INFORMATION: /note="2'-OMe modified nucleotide"
<220> FEATURE:
<221> NAME/KEY: misc_feature
<222> LOCATION: (8)..(8)
<223> OTHER INFORMATION: /note="2'-F modified nucleotide"
<220> FEATURE:
<221> NAME/KEY: misc_feature
<222> LOCATION: (9)..(9)
<223> OTHER INFORMATION: /note="2'-F modified nucleotide"
<220> FEATURE:
<221> NAME/KEY: misc_feature
<222> LOCATION: (10)..(10)
<223> OTHER INFORMATION: /note="2'-F modified nucleotide"
<220> FEATURE:
<221> NAME/KEY: misc_feature
<222> LOCATION: (11)..(11)
<223> OTHER INFORMATION: /note="2'-F modified nucleotide"
<220> FEATURE:
<221> NAME/KEY: misc_feature
<222> LOCATION: (12)..(12)
<223> OTHER INFORMATION: /note="2'-OMe modified nucleotide"
<220> FEATURE:
<221> NAME/KEY: misc_feature
<222> LOCATION: (13)..(13)
<223> OTHER INFORMATION: /note="2'-OMe modified nucleotide"
<220> FEATURE:
<221> NAME/KEY: misc_feature
<222> LOCATION: (14)..(14)
<223> OTHER INFORMATION: /note="2'-OMe modified nucleotide"
<220> FEATURE:
<221> NAME/KEY: misc_feature
```

<222> LOCATION: (15)..(15)
<223> OTHER INFORMATION: /note="2'-OMe modified nucleotide"
<220> FEATURE:
<221> NAME/KEY: misc_feature
<222> LOCATION: (16)..(16)
<223> OTHER INFORMATION: /note="2'-OMe modified nucleotide"
<220> FEATURE:
<221> NAME/KEY: misc_feature
<222> LOCATION: (17)..(17)
<223> OTHER INFORMATION: /note="2'-OMe modified nucleotide"
<220> FEATURE:
<221> NAME/KEY: misc_feature
<222> LOCATION: (18)..(18)
<223> OTHER INFORMATION: /note="2'-OMe modified nucleotide"
<220> FEATURE:
<221> NAME/KEY: misc_feature
<222> LOCATION: (19)..(19)
<223> OTHER INFORMATION: /note="2'-OMe modified nucleotide"
<220> FEATURE:
<221> NAME/KEY: misc_feature
<222> LOCATION: (20)..(20)
<223> OTHER INFORMATION: /note="2'-OMe modified nucleotide"
<220> FEATURE:
<221> NAME/KEY: misc_feature
<222> LOCATION: (21)..(21)
<223> OTHER INFORMATION: /note="2'-OMe modified nucleotide"
<220> FEATURE:
<221> NAME/KEY: misc_feature
<222> LOCATION: (22)..(22)
<223> OTHER INFORMATION: /note="2'-OMe modified nucleotide"
<220> FEATURE:
<221> NAME/KEY: misc_feature
<222> LOCATION: (23)..(23)
<223> OTHER INFORMATION: /note="2'-OMe modified nucleotide"
<220> FEATURE:
<221> NAME/KEY: misc_feature
<222> LOCATION: (24)..(24)
<223> OTHER INFORMATION: /note="2'-OMe modified nucleotide"
<220> FEATURE:
<221> NAME/KEY: misc_feature
<222> LOCATION: (25)..(25)
<223> OTHER INFORMATION: /note="2'-OMe modified nucleotide"
<220> FEATURE:
<221> NAME/KEY: misc_feature
<222> LOCATION: (26)..(26)
<223> OTHER INFORMATION: /note="2'-OMe modified nucleotide"
<220> FEATURE:
<221> NAME/KEY: misc_feature
<222> LOCATION: (27)..(27)
<223> OTHER INFORMATION: /note="2'-OMe modified nucleotide"
<220> FEATURE:
<221> NAME/KEY: misc_feature
<222> LOCATION: (28)..(28)
<223> OTHER INFORMATION: /note="ademA-GalNAc"
<220> FEATURE:
<221> NAME/KEY: misc_feature
<222> LOCATION: (29)..(29)
<223> OTHER INFORMATION: /note="ademA-GalNAc"
<220> FEATURE:
<221> NAME/KEY: misc_feature
<222> LOCATION: (30)..(30)
<223> OTHER INFORMATION: /note="ademA-GalNAc"
<220> FEATURE:
<221> NAME/KEY: misc_feature
<222> LOCATION: (31)..(31)
<223> OTHER INFORMATION: /note="2'-OMe modified nucleotide"
<220> FEATURE:
<221> NAME/KEY: misc_feature
<222> LOCATION: (32)..(32)
<223> OTHER INFORMATION: /note="2'-OMe modified nucleotide"
<220> FEATURE:
<221> NAME/KEY: misc_feature
<222> LOCATION: (33)..(33)
<223> OTHER INFORMATION: /note="2'-OMe modified nucleotide"
<220> FEATURE:
<221> NAME/KEY: misc_feature
<222> LOCATION: (34)..(34)
<223> OTHER INFORMATION: /note="2'-OMe modified nucleotide"
<220> FEATURE:

<221> NAME/KEY: misc_feature
<222> LOCATION: (35)..(35)
<223> OTHER INFORMATION: /note="2'-OMe modified nucleotide"
<220> FEATURE:
<221> NAME/KEY: misc_feature
<222> LOCATION: (36)..(36)
<223> OTHER INFORMATION: /note="2'-OMe modified nucleotide"

<400> SEQUENCE: 132
auaaaaaugu ucacaauuaa gcagccgaaa ggcugc 36

<210> SEQ ID NO 133
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: misc_feature
<222> LOCATION: (1)..(1)
<223> OTHER INFORMATION: /note="MePhosphonate-4O-mUs"
<220> FEATURE:
<221> NAME/KEY: misc_feature
<222> LOCATION: (2)..(2)
<223> OTHER INFORMATION: /note="2'-F modified nucleotide with a 3'-phosphorothioate linkage"
<220> FEATURE:
<221> NAME/KEY: misc_feature
<222> LOCATION: (3)..(3)
<223> OTHER INFORMATION: /note="2'-F modified nucleotide with a 3'-phosphorothioate linkage"
<220> FEATURE:
<221> NAME/KEY: misc_feature
<222> LOCATION: (4)..(4)
<223> OTHER INFORMATION: /note="2'-F modified nucleotide"
<220> FEATURE:
<221> NAME/KEY: misc_feature
<222> LOCATION: (5)..(5)
<223> OTHER INFORMATION: /note="2'-F modified nucleotide"
<220> FEATURE:
<221> NAME/KEY: misc_feature
<222> LOCATION: (6)..(6)
<223> OTHER INFORMATION: /note="2'-OMe modified nucleotide"
<220> FEATURE:
<221> NAME/KEY: misc_feature
<222> LOCATION: (7)..(7)
<223> OTHER INFORMATION: /note="2'-F modified nucleotide"
<220> FEATURE:
<221> NAME/KEY: misc_feature
<222> LOCATION: (8)..(8)
<223> OTHER INFORMATION: /note="2'-OMe modified nucleotide"
<220> FEATURE:
<221> NAME/KEY: misc_feature
<222> LOCATION: (9)..(9)
<223> OTHER INFORMATION: /note="2'-OMe modified nucleotide"
<220> FEATURE:
<221> NAME/KEY: misc_feature
<222> LOCATION: (10)..(10)
<223> OTHER INFORMATION: /note="2'-F modified nucleotide"
<220> FEATURE:
<221> NAME/KEY: misc_feature
<222> LOCATION: (11)..(11)
<223> OTHER INFORMATION: /note="2'-OMe modified nucleotide"
<220> FEATURE:
<221> NAME/KEY: misc_feature
<222> LOCATION: (12)..(12)
<223> OTHER INFORMATION: /note="2'-OMe modified nucleotide"
<220> FEATURE:
<221> NAME/KEY: misc_feature
<222> LOCATION: (13)..(13)
<223> OTHER INFORMATION: /note="2'-OMe modified nucleotide"
<220> FEATURE:
<221> NAME/KEY: misc_feature
<222> LOCATION: (14)..(14)
<223> OTHER INFORMATION: /note="2'-F modified nucleotide"

<220> FEATURE:
<221> NAME/KEY: misc_feature
<222> LOCATION: (15)..(15)
<223> OTHER INFORMATION: /note="2'-OMe modified nucleotide"
<220> FEATURE:
<221> NAME/KEY: misc_feature
<222> LOCATION: (16)..(16)
<223> OTHER INFORMATION: /note="2'-OMe modified nucleotide"
<220> FEATURE:
<221> NAME/KEY: misc_feature
<222> LOCATION: (17)..(17)
<223> OTHER INFORMATION: /note="2'-OMe modified nucleotide"
<220> FEATURE:
<221> NAME/KEY: misc_feature
<222> LOCATION: (18)..(18)
<223> OTHER INFORMATION: /note="2'-OMe modified nucleotide"
<220> FEATURE:
<221> NAME/KEY: misc_feature
<222> LOCATION: (19)..(19)
<223> OTHER INFORMATION: /note="2'-OMe modified nucleotide"
<220> FEATURE:
<221> NAME/KEY: misc_feature
<222> LOCATION: (20)..(20)
<223> OTHER INFORMATION: /note="2'-OMe modified nucleotide with a 3'-phosphorothioate linkage"
<220> FEATURE:
<221> NAME/KEY: misc_feature
<222> LOCATION: (21)..(21)
<223> OTHER INFORMATION: /note="2'-OMe modified nucleotide with a 3'-phosphorothioate linkage"
<220> FEATURE:
<221> NAME/KEY: misc_feature
<222> LOCATION: (22)..(22)
<223> OTHER INFORMATION: /note="2'-OMe modified nucleotide"

<400> SEQUENCE: 133
uuaauuguga acauuuuuau gg 22

<210> SEQ ID NO 134
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: misc_feature
<222> LOCATION: (1)..(1)
<223> OTHER INFORMATION: /note="2'-OMe modified nucleotide with a 3'-phosphorothioate linkage"
<220> FEATURE:
<221> NAME/KEY: misc_feature
<222> LOCATION: (2)..(2)
<223> OTHER INFORMATION: /note="2'-OMe modified nucleotide"
<220> FEATURE:
<221> NAME/KEY: misc_feature
<222> LOCATION: (3)..(3)
<223> OTHER INFORMATION: /note="2'-OMe modified nucleotide"
<220> FEATURE:
<221> NAME/KEY: misc_feature
<222> LOCATION: (4)..(4)
<223> OTHER INFORMATION: /note="2'-OMe modified nucleotide"
<220> FEATURE:
<221> NAME/KEY: misc_feature
<222> LOCATION: (5)..(5)
<223> OTHER INFORMATION: /note="2'-OMe modified nucleotide"
<220> FEATURE:
<221> NAME/KEY: misc_feature
<222> LOCATION: (6)..(6)
<223> OTHER INFORMATION: /note="2'-OMe modified nucleotide"
<220> FEATURE:
<221> NAME/KEY: misc_feature
<222> LOCATION: (7)..(7)
<223> OTHER INFORMATION: /note="2'-OMe modified nucleotide"
<220> FEATURE:
<221> NAME/KEY: misc_feature
<222> LOCATION: (8)..(8)
<223> OTHER INFORMATION: /note="2'-F modified nucleotide"
<220> FEATURE:
<221> NAME/KEY: misc_feature
<222> LOCATION: (9)..(9)
<223> OTHER INFORMATION: /note="2'-F modified nucleotide"
<220> FEATURE:
<221> NAME/KEY: misc_feature
<222> LOCATION: (10)..(10)
<223> OTHER INFORMATION: /note="2'-F modified nucleotide"
<220> FEATURE:
<221> NAME/KEY: misc_feature
<222> LOCATION: (11)..(11)
<223> OTHER INFORMATION: /note="2'-F modified nucleotide"
<220> FEATURE:
<221> NAME/KEY: misc_feature
<222> LOCATION: (12)..(12)
<223> OTHER INFORMATION: /note="2'-OMe modified nucleotide"
<220> FEATURE:
<221> NAME/KEY: misc_feature
<222> LOCATION: (13)..(13)
<223> OTHER INFORMATION: /note="2'-OMe modified nucleotide"
<220> FEATURE:
<221> NAME/KEY: misc_feature
<222> LOCATION: (14)..(14)
<223> OTHER INFORMATION: /note="2'-OMe modified nucleotide"
<220> FEATURE:
<221> NAME/KEY: misc_feature
<222> LOCATION: (15)..(15)
<223> OTHER INFORMATION: /note="2'-OMe modified nucleotide"
<220> FEATURE:
<221> NAME/KEY: misc_feature
<222> LOCATION: (16)..(16)
<223> OTHER INFORMATION: /note="2'-OMe modified nucleotide"
<220> FEATURE:
<221> NAME/KEY: misc_feature
<222> LOCATION: (17)..(17)
<223> OTHER INFORMATION: /note="2'-OMe modified nucleotide"
<220> FEATURE:
<221> NAME/KEY: misc_feature
<222> LOCATION: (18)..(18)
<223> OTHER INFORMATION: /note="2'-OMe modified nucleotide"
<220> FEATURE:
<221> NAME/KEY: misc_feature
<222> LOCATION: (19)..(19)
<223> OTHER INFORMATION: /note="2'-OMe modified nucleotide"
<220> FEATURE:
<221> NAME/KEY: misc_feature
<222> LOCATION: (20)..(20)
<223> OTHER INFORMATION: /note="2'-OMe modified nucleotide"
<220> FEATURE:
<221> NAME/KEY: misc_feature
<222> LOCATION: (21)..(21)
<223> OTHER INFORMATION: /note="2'-OMe modified nucleotide"
<220> FEATURE:
<221> NAME/KEY: misc_feature
<222> LOCATION: (22)..(22)
<223> OTHER INFORMATION: /note="2'-OMe modified nucleotide"
<220> FEATURE:
<221> NAME/KEY: misc_feature
<222> LOCATION: (23)..(23)
<223> OTHER INFORMATION: /note="2'-OMe modified nucleotide"
<220> FEATURE:
<221> NAME/KEY: misc_feature
<222> LOCATION: (24)..(24)
<223> OTHER INFORMATION: /note="2'-OMe modified nucleotide"
<220> FEATURE:
<221> NAME/KEY: misc_feature
<222> LOCATION: (25)..(25)
<223> OTHER INFORMATION: /note="2'-OMe modified nucleotide"
<220> FEATURE:
<221> NAME/KEY: misc_feature
<222> LOCATION: (26)..(26)
<223> OTHER INFORMATION: /note="2'-OMe modified nucleotide"
<220> FEATURE:
<221> NAME/KEY: misc_feature
<222> LOCATION: (27)..(27)
<223> OTHER INFORMATION: /note="2'-OMe modified nucleotide"
<220> FEATURE:

<221> NAME/KEY: misc_feature
<222> LOCATION: (28)..(28)
<223> OTHER INFORMATION: /note="ademA-GalNAc"
<220> FEATURE:
<221> NAME/KEY: misc_feature
<222> LOCATION: (29)..(29)
<223> OTHER INFORMATION: /note="ademA-GalNAc"
<220> FEATURE:
<221> NAME/KEY: misc_feature
<222> LOCATION: (30)..(30)
<223> OTHER INFORMATION: /note="ademA-GalNAc"
<220> FEATURE:
<221> NAME/KEY: misc_feature
<222> LOCATION: (31)..(31)
<223> OTHER INFORMATION: /note="2'-OMe modified nucleotide"
<220> FEATURE:
<221> NAME/KEY: misc_feature
<222> LOCATION: (32)..(32)
<223> OTHER INFORMATION: /note="2'-OMe modified nucleotide"
<220> FEATURE:
<221> NAME/KEY: misc_feature
<222> LOCATION: (33)..(33)
<223> OTHER INFORMATION: /note="2'-OMe modified nucleotide"
<220> FEATURE:
<221> NAME/KEY: misc_feature
<222> LOCATION: (34)..(34)
<223> OTHER INFORMATION: /note="2'-OMe modified nucleotide"
<220> FEATURE:
<221> NAME/KEY: misc_feature
<222> LOCATION: (35)..(35)
<223> OTHER INFORMATION: /note="2'-OMe modified nucleotide"
<220> FEATURE:
<221> NAME/KEY: misc_feature
<222> LOCATION: (36)..(36)
<223> OTHER INFORMATION: /note="2'-OMe modified nucleotide"

<400> SEQUENCE: 134
uucacaauua agcuccuuca gcagccgaaa ggcugc 36

<210> SEQ ID NO 135
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: misc_feature
<222> LOCATION: (1)..(1)
<223> OTHER INFORMATION: /note="MePhosphonate-4O-mUs"
<220> FEATURE:
<221> NAME/KEY: misc_feature
<222> LOCATION: (2)..(2)
<223> OTHER INFORMATION: /note="2'-F modified nucleotide with a
3'-phosphorothioate linkage"
<220> FEATURE:
<221> NAME/KEY: misc_feature
<222> LOCATION: (3)..(3)
<223> OTHER INFORMATION: /note="2'-F modified nucleotide with a
3'-phosphorothioate linkage"
<220> FEATURE:
<221> NAME/KEY: misc_feature
<222> LOCATION: (4)..(4)
<223> OTHER INFORMATION: /note="2'-F modified nucleotide"
<220> FEATURE:
<221> NAME/KEY: misc_feature
<222> LOCATION: (5)..(5)
<223> OTHER INFORMATION: /note="2'-F modified nucleotide"
<220> FEATURE:
<221> NAME/KEY: misc_feature
<222> LOCATION: (6)..(6)
<223> OTHER INFORMATION: /note="2'-OMe modified nucleotide"
<220> FEATURE:
<221> NAME/KEY: misc_feature
<222> LOCATION: (7)..(7)
<223> OTHER INFORMATION: /note="2'-F modified nucleotide"

<220> FEATURE:
<221> NAME/KEY: misc_feature
<222> LOCATION: (8)..(8)
<223> OTHER INFORMATION: /note="2'-OMe modified nucleotide"
<220> FEATURE:
<221> NAME/KEY: misc_feature
<222> LOCATION: (9)..(9)
<223> OTHER INFORMATION: /note="2'-OMe modified nucleotide"
<220> FEATURE:
<221> NAME/KEY: misc_feature
<222> LOCATION: (10)..(10)
<223> OTHER INFORMATION: /note="2'-F modified nucleotide"
<220> FEATURE:
<221> NAME/KEY: misc_feature
<222> LOCATION: (11)..(11)
<223> OTHER INFORMATION: /note="2'-OMe modified nucleotide"
<220> FEATURE:
<221> NAME/KEY: misc_feature
<222> LOCATION: (12)..(12)
<223> OTHER INFORMATION: /note="2'-OMe modified nucleotide"
<220> FEATURE:
<221> NAME/KEY: misc_feature
<222> LOCATION: (13)..(13)
<223> OTHER INFORMATION: /note="2'-OMe modified nucleotide"
<220> FEATURE:
<221> NAME/KEY: misc_feature
<222> LOCATION: (14)..(14)
<223> OTHER INFORMATION: /note="2'-F modified nucleotide"
<220> FEATURE:
<221> NAME/KEY: misc_feature
<222> LOCATION: (15)..(15)
<223> OTHER INFORMATION: /note="2'-OMe modified nucleotide"
<220> FEATURE:
<221> NAME/KEY: misc_feature
<222> LOCATION: (16)..(16)
<223> OTHER INFORMATION: /note="2'-OMe modified nucleotide"
<220> FEATURE:
<221> NAME/KEY: misc_feature
<222> LOCATION: (17)..(17)
<223> OTHER INFORMATION: /note="2'-OMe modified nucleotide"
<220> FEATURE:
<221> NAME/KEY: misc_feature
<222> LOCATION: (18)..(18)
<223> OTHER INFORMATION: /note="2'-OMe modified nucleotide"
<220> FEATURE:
<221> NAME/KEY: misc_feature
<222> LOCATION: (19)..(19)
<223> OTHER INFORMATION: /note="2'-OMe modified nucleotide"
<220> FEATURE:
<221> NAME/KEY: misc_feature
<222> LOCATION: (20)..(20)
<223> OTHER INFORMATION: /note="2'-OMe modified nucleotide with a
3'-phosphorothioate linkage"
<220> FEATURE:
<221> NAME/KEY: misc_feature
<222> LOCATION: (21)..(21)
<223> OTHER INFORMATION: /note="2'-OMe modified nucleotide with a
3'-phosphorothioate linkage"
<220> FEATURE:
<221> NAME/KEY: misc_feature
<222> LOCATION: (22)..(22)
<223> OTHER INFORMATION: /note="2'-OMe modified nucleotide"

<400> SEQUENCE: 135
ugaaggagcu uaauugugaa gg 22

<210> SEQ ID NO 136
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: misc_feature
<222> LOCATION: (1)..(1)

<223> OTHER INFORMATION: /note="2'-OMe modified nucleotide with a
3'-phosphorothioate linkage"
<220> FEATURE:
<221> NAME/KEY: misc_feature
<222> LOCATION: (2)..(2)
<223> OTHER INFORMATION: /note="2'-OMe modified nucleotide"
<220> FEATURE:
<221> NAME/KEY: misc_feature
<222> LOCATION: (3)..(3)
<223> OTHER INFORMATION: /note="2'-OMe modified nucleotide"
<220> FEATURE:
<221> NAME/KEY: misc_feature
<222> LOCATION: (4)..(4)
<223> OTHER INFORMATION: /note="2'-OMe modified nucleotide"
<220> FEATURE:
<221> NAME/KEY: misc_feature
<222> LOCATION: (5)..(5)
<223> OTHER INFORMATION: /note="2'-OMe modified nucleotide"
<220> FEATURE:
<221> NAME/KEY: misc_feature
<222> LOCATION: (6)..(6)
<223> OTHER INFORMATION: /note="2'-OMe modified nucleotide"
<220> FEATURE:
<221> NAME/KEY: misc_feature
<222> LOCATION: (7)..(7)
<223> OTHER INFORMATION: /note="2'-OMe modified nucleotide"
<220> FEATURE:
<221> NAME/KEY: misc_feature
<222> LOCATION: (8)..(8)
<223> OTHER INFORMATION: /note="2'-F modified nucleotide"
<220> FEATURE:
<221> NAME/KEY: misc_feature
<222> LOCATION: (9)..(9)
<223> OTHER INFORMATION: /note="2'-F modified nucleotide"
<220> FEATURE:
<221> NAME/KEY: misc_feature
<222> LOCATION: (10)..(10)
<223> OTHER INFORMATION: /note="2'-F modified nucleotide"
<220> FEATURE:
<221> NAME/KEY: misc_feature
<222> LOCATION: (11)..(11)
<223> OTHER INFORMATION: /note="2'-F modified nucleotide"
<220> FEATURE:
<221> NAME/KEY: misc_feature
<222> LOCATION: (12)..(12)
<223> OTHER INFORMATION: /note="2'-OMe modified nucleotide"
<220> FEATURE:
<221> NAME/KEY: misc_feature
<222> LOCATION: (13)..(13)
<223> OTHER INFORMATION: /note="2'-OMe modified nucleotide"
<220> FEATURE:
<221> NAME/KEY: misc_feature
<222> LOCATION: (14)..(14)
<223> OTHER INFORMATION: /note="2'-OMe modified nucleotide"
<220> FEATURE:
<221> NAME/KEY: misc_feature
<222> LOCATION: (15)..(15)
<223> OTHER INFORMATION: /note="2'-OMe modified nucleotide"
<220> FEATURE:
<221> NAME/KEY: misc_feature
<222> LOCATION: (16)..(16)
<223> OTHER INFORMATION: /note="2'-OMe modified nucleotide"
<220> FEATURE:
<221> NAME/KEY: misc_feature
<222> LOCATION: (17)..(17)
<223> OTHER INFORMATION: /note="2'-OMe modified nucleotide"
<220> FEATURE:
<221> NAME/KEY: misc_feature
<222> LOCATION: (18)..(18)
<223> OTHER INFORMATION: /note="2'-OMe modified nucleotide"
<220> FEATURE:
<221> NAME/KEY: misc_feature
<222> LOCATION: (19)..(19)
<223> OTHER INFORMATION: /note="2'-OMe modified nucleotide"
<220> FEATURE:
<221> NAME/KEY: misc_feature
<222> LOCATION: (20)..(20)
<223> OTHER INFORMATION: /note="2'-OMe modified nucleotide"
<220> FEATURE:

<221> NAME/KEY: misc_feature
<222> LOCATION: (21)..(21)
<223> OTHER INFORMATION: /note="2'-OMe modified nucleotide"
<220> FEATURE:
<221> NAME/KEY: misc_feature
<222> LOCATION: (22)..(22)
<223> OTHER INFORMATION: /note="2'-OMe modified nucleotide"
<220> FEATURE:
<221> NAME/KEY: misc_feature
<222> LOCATION: (23)..(23)
<223> OTHER INFORMATION: /note="2'-OMe modified nucleotide"
<220> FEATURE:
<221> NAME/KEY: misc_feature
<222> LOCATION: (24)..(24)
<223> OTHER INFORMATION: /note="2'-OMe modified nucleotide"
<220> FEATURE:
<221> NAME/KEY: misc_feature
<222> LOCATION: (25)..(25)
<223> OTHER INFORMATION: /note="2'-OMe modified nucleotide"
<220> FEATURE:
<221> NAME/KEY: misc_feature
<222> LOCATION: (26)..(26)
<223> OTHER INFORMATION: /note="2'-OMe modified nucleotide"
<220> FEATURE:
<221> NAME/KEY: misc_feature
<222> LOCATION: (27)..(27)
<223> OTHER INFORMATION: /note="2'-OMe modified nucleotide"
<220> FEATURE:
<221> NAME/KEY: misc_feature
<222> LOCATION: (28)..(28)
<223> OTHER INFORMATION: /note="ademA-GalNAc"
<220> FEATURE:
<221> NAME/KEY: misc_feature
<222> LOCATION: (29)..(29)
<223> OTHER INFORMATION: /note="ademA-GalNAc"
<220> FEATURE:
<221> NAME/KEY: misc_feature
<222> LOCATION: (30)..(30)
<223> OTHER INFORMATION: /note="ademA-GalNAc"
<220> FEATURE:
<221> NAME/KEY: misc_feature
<222> LOCATION: (31)..(31)
<223> OTHER INFORMATION: /note="2'-OMe modified nucleotide"
<220> FEATURE:
<221> NAME/KEY: misc_feature
<222> LOCATION: (32)..(32)
<223> OTHER INFORMATION: /note="2'-OMe modified nucleotide"
<220> FEATURE:
<221> NAME/KEY: misc_feature
<222> LOCATION: (33)..(33)
<223> OTHER INFORMATION: /note="2'-OMe modified nucleotide"
<220> FEATURE:
<221> NAME/KEY: misc_feature
<222> LOCATION: (34)..(34)
<223> OTHER INFORMATION: /note="2'-OMe modified nucleotide"
<220> FEATURE:
<221> NAME/KEY: misc_feature
<222> LOCATION: (35)..(35)
<223> OTHER INFORMATION: /note="2'-OMe modified nucleotide"
<220> FEATURE:
<221> NAME/KEY: misc_feature
<222> LOCATION: (36)..(36)
<223> OTHER INFORMATION: /note="2'-OMe modified nucleotide"

<400> SEQUENCE: 136
acaauuaagc uccuucuuua gcagccgaaa ggcugc 36

<210> SEQ ID NO 137
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: misc_feature

```
<222> LOCATION: (1)..(1)
<223> OTHER INFORMATION: /note="MePhosphonate-4O-mUs"
<220> FEATURE:
<221> NAME/KEY: misc_feature
<222> LOCATION: (2)..(2)
<223> OTHER INFORMATION: /note="2'-F modified nucleotide with a
      3'-phosphorothioate linkage"
<220> FEATURE:
<221> NAME/KEY: misc_feature
<222> LOCATION: (3)..(3)
<223> OTHER INFORMATION: /note="2'-F modified nucleotide with a
      3'-phosphorothioate linkage"
<220> FEATURE:
<221> NAME/KEY: misc_feature
<222> LOCATION: (4)..(4)
<223> OTHER INFORMATION: /note="2'-F modified nucleotide"
<220> FEATURE:
<221> NAME/KEY: misc_feature
<222> LOCATION: (5)..(5)
<223> OTHER INFORMATION: /note="2'-F modified nucleotide"
<220> FEATURE:
<221> NAME/KEY: misc_feature
<222> LOCATION: (6)..(6)
<223> OTHER INFORMATION: /note="2'-OMe modified nucleotide"
<220> FEATURE:
<221> NAME/KEY: misc_feature
<222> LOCATION: (7)..(7)
<223> OTHER INFORMATION: /note="2'-F modified nucleotide"
<220> FEATURE:
<221> NAME/KEY: misc_feature
<222> LOCATION: (8)..(8)
<223> OTHER INFORMATION: /note="2'-OMe modified nucleotide"
<220> FEATURE:
<221> NAME/KEY: misc_feature
<222> LOCATION: (9)..(9)
<223> OTHER INFORMATION: /note="2'-OMe modified nucleotide"
<220> FEATURE:
<221> NAME/KEY: misc_feature
<222> LOCATION: (10)..(10)
<223> OTHER INFORMATION: /note="2'-F modified nucleotide"
<220> FEATURE:
<221> NAME/KEY: misc_feature
<222> LOCATION: (11)..(11)
<223> OTHER INFORMATION: /note="2'-OMe modified nucleotide"
<220> FEATURE:
<221> NAME/KEY: misc_feature
<222> LOCATION: (12)..(12)
<223> OTHER INFORMATION: /note="2'-OMe modified nucleotide"
<220> FEATURE:
<221> NAME/KEY: misc_feature
<222> LOCATION: (13)..(13)
<223> OTHER INFORMATION: /note="2'-OMe modified nucleotide"
<220> FEATURE:
<221> NAME/KEY: misc_feature
<222> LOCATION: (14)..(14)
<223> OTHER INFORMATION: /note="2'-F modified nucleotide"
<220> FEATURE:
<221> NAME/KEY: misc_feature
<222> LOCATION: (15)..(15)
<223> OTHER INFORMATION: /note="2'-OMe modified nucleotide"
<220> FEATURE:
<221> NAME/KEY: misc_feature
<222> LOCATION: (16)..(16)
<223> OTHER INFORMATION: /note="2'-OMe modified nucleotide"
<220> FEATURE:
<221> NAME/KEY: misc_feature
<222> LOCATION: (17)..(17)
<223> OTHER INFORMATION: /note="2'-OMe modified nucleotide"
<220> FEATURE:
<221> NAME/KEY: misc_feature
<222> LOCATION: (18)..(18)
<223> OTHER INFORMATION: /note="2'-OMe modified nucleotide"
<220> FEATURE:
<221> NAME/KEY: misc_feature
<222> LOCATION: (19)..(19)
<223> OTHER INFORMATION: /note="2'-OMe modified nucleotide"
<220> FEATURE:
<221> NAME/KEY: misc_feature
<222> LOCATION: (20)..(20)
```

<223> OTHER INFORMATION: /note="2'-OMe modified nucleotide with a
      3'-phosphorothioate linkage"
<220> FEATURE:
<221> NAME/KEY: misc_feature
<222> LOCATION: (21)..(21)
<223> OTHER INFORMATION: /note="2'-OMe modified nucleotide with a
      3'-phosphorothioate linkage"
<220> FEATURE:
<221> NAME/KEY: misc_feature
<222> LOCATION: (22)..(22)
<223> OTHER INFORMATION: /note="2'-OMe modified nucleotide"

<400> SEQUENCE: 137
uaaagaagga gcuuaauugu gg 22

<210> SEQ ID NO 138
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: misc_feature
<222> LOCATION: (1)..(1)
<223> OTHER INFORMATION: /note="2'-OMe modified nucleotide with a
      3'-phosphorothioate linkage"
<220> FEATURE:
<221> NAME/KEY: misc_feature
<222> LOCATION: (2)..(2)
<223> OTHER INFORMATION: /note="2'-OMe modified nucleotide"
<220> FEATURE:
<221> NAME/KEY: misc_feature
<222> LOCATION: (3)..(3)
<223> OTHER INFORMATION: /note="2'-OMe modified nucleotide"
<220> FEATURE:
<221> NAME/KEY: misc_feature
<222> LOCATION: (4)..(4)
<223> OTHER INFORMATION: /note="2'-OMe modified nucleotide"
<220> FEATURE:
<221> NAME/KEY: misc_feature
<222> LOCATION: (5)..(5)
<223> OTHER INFORMATION: /note="2'-OMe modified nucleotide"
<220> FEATURE:
<221> NAME/KEY: misc_feature
<222> LOCATION: (6)..(6)
<223> OTHER INFORMATION: /note="2'-OMe modified nucleotide"
<220> FEATURE:
<221> NAME/KEY: misc_feature
<222> LOCATION: (7)..(7)
<223> OTHER INFORMATION: /note="2'-OMe modified nucleotide"
<220> FEATURE:
<221> NAME/KEY: misc_feature
<222> LOCATION: (8)..(8)
<223> OTHER INFORMATION: /note="2'-F modified nucleotide"
<220> FEATURE:
<221> NAME/KEY: misc_feature
<222> LOCATION: (9)..(9)
<223> OTHER INFORMATION: /note="2'-F modified nucleotide"
<220> FEATURE:
<221> NAME/KEY: misc_feature
<222> LOCATION: (10)..(10)
<223> OTHER INFORMATION: /note="2'-F modified nucleotide"
<220> FEATURE:
<221> NAME/KEY: misc_feature
<222> LOCATION: (11)..(11)
<223> OTHER INFORMATION: /note="2'-F modified nucleotide"
<220> FEATURE:
<221> NAME/KEY: misc_feature
<222> LOCATION: (12)..(12)
<223> OTHER INFORMATION: /note="2'-OMe modified nucleotide"
<220> FEATURE:
<221> NAME/KEY: misc_feature
<222> LOCATION: (13)..(13)
<223> OTHER INFORMATION: /note="2'-OMe modified nucleotide"
<220> FEATURE:

<221> NAME/KEY: misc_feature
<222> LOCATION: (14)..(14)
<223> OTHER INFORMATION: /note="2'-OMe modified nucleotide"
<220> FEATURE:
<221> NAME/KEY: misc_feature
<222> LOCATION: (15)..(15)
<223> OTHER INFORMATION: /note="2'-OMe modified nucleotide"
<220> FEATURE:
<221> NAME/KEY: misc_feature
<222> LOCATION: (16)..(16)
<223> OTHER INFORMATION: /note="2'-OMe modified nucleotide"
<220> FEATURE:
<221> NAME/KEY: misc_feature
<222> LOCATION: (17)..(17)
<223> OTHER INFORMATION: /note="2'-OMe modified nucleotide"
<220> FEATURE:
<221> NAME/KEY: misc_feature
<222> LOCATION: (18)..(18)
<223> OTHER INFORMATION: /note="2'-OMe modified nucleotide"
<220> FEATURE:
<221> NAME/KEY: misc_feature
<222> LOCATION: (19)..(19)
<223> OTHER INFORMATION: /note="2'-OMe modified nucleotide"
<220> FEATURE:
<221> NAME/KEY: misc_feature
<222> LOCATION: (20)..(20)
<223> OTHER INFORMATION: /note="2'-OMe modified nucleotide"
<220> FEATURE:
<221> NAME/KEY: misc_feature
<222> LOCATION: (21)..(21)
<223> OTHER INFORMATION: /note="2'-OMe modified nucleotide"
<220> FEATURE:
<221> NAME/KEY: misc_feature
<222> LOCATION: (22)..(22)
<223> OTHER INFORMATION: /note="2'-OMe modified nucleotide"
<220> FEATURE:
<221> NAME/KEY: misc_feature
<222> LOCATION: (23)..(23)
<223> OTHER INFORMATION: /note="2'-OMe modified nucleotide"
<220> FEATURE:
<221> NAME/KEY: misc_feature
<222> LOCATION: (24)..(24)
<223> OTHER INFORMATION: /note="2'-OMe modified nucleotide"
<220> FEATURE:
<221> NAME/KEY: misc_feature
<222> LOCATION: (25)..(25)
<223> OTHER INFORMATION: /note="2'-OMe modified nucleotide"
<220> FEATURE:
<221> NAME/KEY: misc_feature
<222> LOCATION: (26)..(26)
<223> OTHER INFORMATION: /note="2'-OMe modified nucleotide"
<220> FEATURE:
<221> NAME/KEY: misc_feature
<222> LOCATION: (27)..(27)
<223> OTHER INFORMATION: /note="2'-OMe modified nucleotide"
<220> FEATURE:
<221> NAME/KEY: misc_feature
<222> LOCATION: (28)..(28)
<223> OTHER INFORMATION: /note="ademA-GalNAc"
<220> FEATURE:
<221> NAME/KEY: misc_feature
<222> LOCATION: (29)..(29)
<223> OTHER INFORMATION: /note="ademA-GalNAc"
<220> FEATURE:
<221> NAME/KEY: misc_feature
<222> LOCATION: (30)..(30)
<223> OTHER INFORMATION: /note="ademA-GalNAc"
<220> FEATURE:
<221> NAME/KEY: misc_feature
<222> LOCATION: (31)..(31)
<223> OTHER INFORMATION: /note="2'-OMe modified nucleotide"
<220> FEATURE:
<221> NAME/KEY: misc_feature
<222> LOCATION: (32)..(32)
<223> OTHER INFORMATION: /note="2'-OMe modified nucleotide"
<220> FEATURE:
<221> NAME/KEY: misc_feature
<222> LOCATION: (33)..(33)
<223> OTHER INFORMATION: /note="2'-OMe modified nucleotide"

<220> FEATURE:
<221> NAME/KEY: misc_feature
<222> LOCATION: (34)..(34)
<223> OTHER INFORMATION: /note="2'-OMe modified nucleotide"
<220> FEATURE:
<221> NAME/KEY: misc_feature
<222> LOCATION: (35)..(35)
<223> OTHER INFORMATION: /note="2'-OMe modified nucleotide"
<220> FEATURE:
<221> NAME/KEY: misc_feature
<222> LOCATION: (36)..(36)
<223> OTHER INFORMATION: /note="2'-OMe modified nucleotide"

<400> SEQUENCE: 138
caauuaagcu ccuucuuuua gcagccgaaa ggcugc 36

<210> SEQ ID NO 139
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: misc_feature
<222> LOCATION: (1)..(1)
<223> OTHER INFORMATION: /note="MePhosphonate-4O-mUs"
<220> FEATURE:
<221> NAME/KEY: misc_feature
<222> LOCATION: (2)..(2)
<223> OTHER INFORMATION: /note="2'-F modified nucleotide with a 3'-phosphorothioate linkage"
<220> FEATURE:
<221> NAME/KEY: misc_feature
<222> LOCATION: (3)..(3)
<223> OTHER INFORMATION: /note="2'-F modified nucleotide with a 3'-phosphorothioate linkage"
<220> FEATURE:
<221> NAME/KEY: misc_feature
<222> LOCATION: (4)..(4)
<223> OTHER INFORMATION: /note="2'-F modified nucleotide"
<220> FEATURE:
<221> NAME/KEY: misc_feature
<222> LOCATION: (5)..(5)
<223> OTHER INFORMATION: /note="2'-F modified nucleotide"
<220> FEATURE:
<221> NAME/KEY: misc_feature
<222> LOCATION: (6)..(6)
<223> OTHER INFORMATION: /note="2'-OMe modified nucleotide"
<220> FEATURE:
<221> NAME/KEY: misc_feature
<222> LOCATION: (7)..(7)
<223> OTHER INFORMATION: /note="2'-F modified nucleotide"
<220> FEATURE:
<221> NAME/KEY: misc_feature
<222> LOCATION: (8)..(8)
<223> OTHER INFORMATION: /note="2'-OMe modified nucleotide"
<220> FEATURE:
<221> NAME/KEY: misc_feature
<222> LOCATION: (9)..(9)
<223> OTHER INFORMATION: /note="2'-OMe modified nucleotide"
<220> FEATURE:
<221> NAME/KEY: misc_feature
<222> LOCATION: (10)..(10)
<223> OTHER INFORMATION: /note="2'-F modified nucleotide"
<220> FEATURE:
<221> NAME/KEY: misc_feature
<222> LOCATION: (11)..(11)
<223> OTHER INFORMATION: /note="2'-OMe modified nucleotide"
<220> FEATURE:
<221> NAME/KEY: misc_feature
<222> LOCATION: (12)..(12)
<223> OTHER INFORMATION: /note="2'-OMe modified nucleotide"
<220> FEATURE:
<221> NAME/KEY: misc_feature
<222> LOCATION: (13)..(13)

<223> OTHER INFORMATION: /note="2'-OMe modified nucleotide"
<220> FEATURE:
<221> NAME/KEY: misc_feature
<222> LOCATION: (14)..(14)
<223> OTHER INFORMATION: /note="2'-F modified nucleotide"
<220> FEATURE:
<221> NAME/KEY: misc_feature
<222> LOCATION: (15)..(15)
<223> OTHER INFORMATION: /note="2'-OMe modified nucleotide"
<220> FEATURE:
<221> NAME/KEY: misc_feature
<222> LOCATION: (16)..(16)
<223> OTHER INFORMATION: /note="2'-OMe modified nucleotide"
<220> FEATURE:
<221> NAME/KEY: misc_feature
<222> LOCATION: (17)..(17)
<223> OTHER INFORMATION: /note="2'-OMe modified nucleotide"
<220> FEATURE:
<221> NAME/KEY: misc_feature
<222> LOCATION: (18)..(18)
<223> OTHER INFORMATION: /note="2'-OMe modified nucleotide"
<220> FEATURE:
<221> NAME/KEY: misc_feature
<222> LOCATION: (19)..(19)
<223> OTHER INFORMATION: /note="2'-OMe modified nucleotide"
<220> FEATURE:
<221> NAME/KEY: misc_feature
<222> LOCATION: (20)..(20)
<223> OTHER INFORMATION: /note="2'-OMe modified nucleotide with a
3'-phosphorothioate linkage"
<220> FEATURE:
<221> NAME/KEY: misc_feature
<222> LOCATION: (21)..(21)
<223> OTHER INFORMATION: /note="2'-OMe modified nucleotide with a
3'-phosphorothioate linkage"
<220> FEATURE:
<221> NAME/KEY: misc_feature
<222> LOCATION: (22)..(22)
<223> OTHER INFORMATION: /note="2'-OMe modified nucleotide"

<400> SEQUENCE: 139
uaaaagaagg agcuuaauug gg 22

<210> SEQ ID NO 140
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: misc_feature
<222> LOCATION: (1)..(1)
<223> OTHER INFORMATION: /note="2'-OMe modified nucleotide with a
3'-phosphorothioate linkage"
<220> FEATURE:
<221> NAME/KEY: misc_feature
<222> LOCATION: (2)..(2)
<223> OTHER INFORMATION: /note="2'-OMe modified nucleotide"
<220> FEATURE:
<221> NAME/KEY: misc_feature
<222> LOCATION: (3)..(3)
<223> OTHER INFORMATION: /note="2'-OMe modified nucleotide"
<220> FEATURE:
<221> NAME/KEY: misc_feature
<222> LOCATION: (4)..(4)
<223> OTHER INFORMATION: /note="2'-OMe modified nucleotide"
<220> FEATURE:
<221> NAME/KEY: misc_feature
<222> LOCATION: (5)..(5)
<223> OTHER INFORMATION: /note="2'-OMe modified nucleotide"
<220> FEATURE:
<221> NAME/KEY: misc_feature
<222> LOCATION: (6)..(6)
<223> OTHER INFORMATION: /note="2'-OMe modified nucleotide"
<220> FEATURE:

<221> NAME/KEY: misc_feature
<222> LOCATION: (7)..(7)
<223> OTHER INFORMATION: /note="2'-OMe modified nucleotide"
<220> FEATURE:
<221> NAME/KEY: misc_feature
<222> LOCATION: (8)..(8)
<223> OTHER INFORMATION: /note="2'-F modified nucleotide"
<220> FEATURE:
<221> NAME/KEY: misc_feature
<222> LOCATION: (9)..(9)
<223> OTHER INFORMATION: /note="2'-F modified nucleotide"
<220> FEATURE:
<221> NAME/KEY: misc_feature
<222> LOCATION: (10)..(10)
<223> OTHER INFORMATION: /note="2'-F modified nucleotide"
<220> FEATURE:
<221> NAME/KEY: misc_feature
<222> LOCATION: (11)..(11)
<223> OTHER INFORMATION: /note="2'-F modified nucleotide"
<220> FEATURE:
<221> NAME/KEY: misc_feature
<222> LOCATION: (12)..(12)
<223> OTHER INFORMATION: /note="2'-OMe modified nucleotide"
<220> FEATURE:
<221> NAME/KEY: misc_feature
<222> LOCATION: (13)..(13)
<223> OTHER INFORMATION: /note="2'-OMe modified nucleotide"
<220> FEATURE:
<221> NAME/KEY: misc_feature
<222> LOCATION: (14)..(14)
<223> OTHER INFORMATION: /note="2'-OMe modified nucleotide"
<220> FEATURE:
<221> NAME/KEY: misc_feature
<222> LOCATION: (15)..(15)
<223> OTHER INFORMATION: /note="2'-OMe modified nucleotide"
<220> FEATURE:
<221> NAME/KEY: misc_feature
<222> LOCATION: (16)..(16)
<223> OTHER INFORMATION: /note="2'-OMe modified nucleotide"
<220> FEATURE:
<221> NAME/KEY: misc_feature
<222> LOCATION: (17)..(17)
<223> OTHER INFORMATION: /note="2'-OMe modified nucleotide"
<220> FEATURE:
<221> NAME/KEY: misc_feature
<222> LOCATION: (18)..(18)
<223> OTHER INFORMATION: /note="2'-OMe modified nucleotide"
<220> FEATURE:
<221> NAME/KEY: misc_feature
<222> LOCATION: (19)..(19)
<223> OTHER INFORMATION: /note="2'-OMe modified nucleotide"
<220> FEATURE:
<221> NAME/KEY: misc_feature
<222> LOCATION: (20)..(20)
<223> OTHER INFORMATION: /note="2'-OMe modified nucleotide"
<220> FEATURE:
<221> NAME/KEY: misc_feature
<222> LOCATION: (21)..(21)
<223> OTHER INFORMATION: /note="2'-OMe modified nucleotide"
<220> FEATURE:
<221> NAME/KEY: misc_feature
<222> LOCATION: (22)..(22)
<223> OTHER INFORMATION: /note="2'-OMe modified nucleotide"
<220> FEATURE:
<221> NAME/KEY: misc_feature
<222> LOCATION: (23)..(23)
<223> OTHER INFORMATION: /note="2'-OMe modified nucleotide"
<220> FEATURE:
<221> NAME/KEY: misc_feature
<222> LOCATION: (24)..(24)
<223> OTHER INFORMATION: /note="2'-OMe modified nucleotide"
<220> FEATURE:
<221> NAME/KEY: misc_feature
<222> LOCATION: (25)..(25)
<223> OTHER INFORMATION: /note="2'-OMe modified nucleotide"
<220> FEATURE:
<221> NAME/KEY: misc_feature
<222> LOCATION: (26)..(26)
<223> OTHER INFORMATION: /note="2'-OMe modified nucleotide"

<220> FEATURE:
<221> NAME/KEY: misc_feature
<222> LOCATION: (27)..(27)
<223> OTHER INFORMATION: /note="2'-OMe modified nucleotide"
<220> FEATURE:
<221> NAME/KEY: misc_feature
<222> LOCATION: (28)..(28)
<223> OTHER INFORMATION: /note="ademA-GalNAc"
<220> FEATURE:
<221> NAME/KEY: misc_feature
<222> LOCATION: (29)..(29)
<223> OTHER INFORMATION: /note="ademA-GalNAc"
<220> FEATURE:
<221> NAME/KEY: misc_feature
<222> LOCATION: (30)..(30)
<223> OTHER INFORMATION: /note="ademA-GalNAc"
<220> FEATURE:
<221> NAME/KEY: misc_feature
<222> LOCATION: (31)..(31)
<223> OTHER INFORMATION: /note="2'-OMe modified nucleotide"
<220> FEATURE:
<221> NAME/KEY: misc_feature
<222> LOCATION: (32)..(32)
<223> OTHER INFORMATION: /note="2'-OMe modified nucleotide"
<220> FEATURE:
<221> NAME/KEY: misc_feature
<222> LOCATION: (33)..(33)
<223> OTHER INFORMATION: /note="2'-OMe modified nucleotide"
<220> FEATURE:
<221> NAME/KEY: misc_feature
<222> LOCATION: (34)..(34)
<223> OTHER INFORMATION: /note="2'-OMe modified nucleotide"
<220> FEATURE:
<221> NAME/KEY: misc_feature
<222> LOCATION: (35)..(35)
<223> OTHER INFORMATION: /note="2'-OMe modified nucleotide"
<220> FEATURE:
<221> NAME/KEY: misc_feature
<222> LOCATION: (36)..(36)
<223> OTHER INFORMATION: /note="2'-OMe modified nucleotide"

<400> SEQUENCE: 140
aguuauuucc uccagaauua gcagccgaaa ggcugc 36

<210> SEQ ID NO 141
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: misc_feature
<222> LOCATION: (1)..(1)
<223> OTHER INFORMATION: /note="MePhosphonate-4O-mUs"
<220> FEATURE:
<221> NAME/KEY: misc_feature
<222> LOCATION: (2)..(2)
<223> OTHER INFORMATION: /note="2'-F modified nucleotide with a 3'-phosphorothioate linkage"
<220> FEATURE:
<221> NAME/KEY: misc_feature
<222> LOCATION: (3)..(3)
<223> OTHER INFORMATION: /note="2'-F modified nucleotide with a 3'-phosphorothioate linkage"
<220> FEATURE:
<221> NAME/KEY: misc_feature
<222> LOCATION: (4)..(4)
<223> OTHER INFORMATION: /note="2'-F modified nucleotide"
<220> FEATURE:
<221> NAME/KEY: misc_feature
<222> LOCATION: (5)..(5)
<223> OTHER INFORMATION: /note="2'-F modified nucleotide"
<220> FEATURE:
<221> NAME/KEY: misc_feature
<222> LOCATION: (6)..(6)

<223> OTHER INFORMATION: /note="2'-OMe modified nucleotide"
<220> FEATURE:
<221> NAME/KEY: misc_feature
<222> LOCATION: (7)..(7)
<223> OTHER INFORMATION: /note="2'-F modified nucleotide"
<220> FEATURE:
<221> NAME/KEY: misc_feature
<222> LOCATION: (8)..(8)
<223> OTHER INFORMATION: /note="2'-OMe modified nucleotide"
<220> FEATURE:
<221> NAME/KEY: misc_feature
<222> LOCATION: (9)..(9)
<223> OTHER INFORMATION: /note="2'-OMe modified nucleotide"
<220> FEATURE:
<221> NAME/KEY: misc_feature
<222> LOCATION: (10)..(10)
<223> OTHER INFORMATION: /note="2'-F modified nucleotide"
<220> FEATURE:
<221> NAME/KEY: misc_feature
<222> LOCATION: (11)..(11)
<223> OTHER INFORMATION: /note="2'-OMe modified nucleotide"
<220> FEATURE:
<221> NAME/KEY: misc_feature
<222> LOCATION: (12)..(12)
<223> OTHER INFORMATION: /note="2'-OMe modified nucleotide"
<220> FEATURE:
<221> NAME/KEY: misc_feature
<222> LOCATION: (13)..(13)
<223> OTHER INFORMATION: /note="2'-OMe modified nucleotide"
<220> FEATURE:
<221> NAME/KEY: misc_feature
<222> LOCATION: (14)..(14)
<223> OTHER INFORMATION: /note="2'-F modified nucleotide"
<220> FEATURE:
<221> NAME/KEY: misc_feature
<222> LOCATION: (15)..(15)
<223> OTHER INFORMATION: /note="2'-OMe modified nucleotide"
<220> FEATURE:
<221> NAME/KEY: misc_feature
<222> LOCATION: (16)..(16)
<223> OTHER INFORMATION: /note="2'-OMe modified nucleotide"
<220> FEATURE:
<221> NAME/KEY: misc_feature
<222> LOCATION: (17)..(17)
<223> OTHER INFORMATION: /note="2'-OMe modified nucleotide"
<220> FEATURE:
<221> NAME/KEY: misc_feature
<222> LOCATION: (18)..(18)
<223> OTHER INFORMATION: /note="2'-OMe modified nucleotide"
<220> FEATURE:
<221> NAME/KEY: misc_feature
<222> LOCATION: (19)..(19)
<223> OTHER INFORMATION: /note="2'-OMe modified nucleotide"
<220> FEATURE:
<221> NAME/KEY: misc_feature
<222> LOCATION: (20)..(20)
<223> OTHER INFORMATION: /note="2'-OMe modified nucleotide with a
      3'-phosphorothioate linkage"
<220> FEATURE:
<221> NAME/KEY: misc_feature
<222> LOCATION: (21)..(21)
<223> OTHER INFORMATION: /note="2'-OMe modified nucleotide with a
      3'-phosphorothioate linkage"
<220> FEATURE:
<221> NAME/KEY: misc_feature
<222> LOCATION: (22)..(22)
<223> OTHER INFORMATION: /note="2'-OMe modified nucleotide"

<400> SEQUENCE: 141
uaauucugga ggaaauaacu gg 22

<210> SEQ ID NO 142
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: misc_feature
<222> LOCATION: (1)..(1)
<223> OTHER INFORMATION: /note="2'-OMe modified nucleotide with a
      3'-phosphorothioate linkage"
<220> FEATURE:
<221> NAME/KEY: misc_feature
<222> LOCATION: (2)..(2)
<223> OTHER INFORMATION: /note="2'-OMe modified nucleotide"
<220> FEATURE:
<221> NAME/KEY: misc_feature
<222> LOCATION: (3)..(3)
<223> OTHER INFORMATION: /note="2'-OMe modified nucleotide"
<220> FEATURE:
<221> NAME/KEY: misc_feature
<222> LOCATION: (4)..(4)
<223> OTHER INFORMATION: /note="2'-OMe modified nucleotide"
<220> FEATURE:
<221> NAME/KEY: misc_feature
<222> LOCATION: (5)..(5)
<223> OTHER INFORMATION: /note="2'-OMe modified nucleotide"
<220> FEATURE:
<221> NAME/KEY: misc_feature
<222> LOCATION: (6)..(6)
<223> OTHER INFORMATION: /note="2'-OMe modified nucleotide"
<220> FEATURE:
<221> NAME/KEY: misc_feature
<222> LOCATION: (7)..(7)
<223> OTHER INFORMATION: /note="2'-OMe modified nucleotide"
<220> FEATURE:
<221> NAME/KEY: misc_feature
<222> LOCATION: (8)..(8)
<223> OTHER INFORMATION: /note="2'-F modified nucleotide"
<220> FEATURE:
<221> NAME/KEY: misc_feature
<222> LOCATION: (9)..(9)
<223> OTHER INFORMATION: /note="2'-F modified nucleotide"
<220> FEATURE:
<221> NAME/KEY: misc_feature
<222> LOCATION: (10)..(10)
<223> OTHER INFORMATION: /note="2'-F modified nucleotide"
<220> FEATURE:
<221> NAME/KEY: misc_feature
<222> LOCATION: (11)..(11)
<223> OTHER INFORMATION: /note="2'-F modified nucleotide"
<220> FEATURE:
<221> NAME/KEY: misc_feature
<222> LOCATION: (12)..(12)
<223> OTHER INFORMATION: /note="2'-OMe modified nucleotide"
<220> FEATURE:
<221> NAME/KEY: misc_feature
<222> LOCATION: (13)..(13)
<223> OTHER INFORMATION: /note="2'-OMe modified nucleotide"
<220> FEATURE:
<221> NAME/KEY: misc_feature
<222> LOCATION: (14)..(14)
<223> OTHER INFORMATION: /note="2'-OMe modified nucleotide"
<220> FEATURE:
<221> NAME/KEY: misc_feature
<222> LOCATION: (15)..(15)
<223> OTHER INFORMATION: /note="2'-OMe modified nucleotide"
<220> FEATURE:
<221> NAME/KEY: misc_feature
<222> LOCATION: (16)..(16)
<223> OTHER INFORMATION: /note="2'-OMe modified nucleotide"
<220> FEATURE:
<221> NAME/KEY: misc_feature
<222> LOCATION: (17)..(17)
<223> OTHER INFORMATION: /note="2'-OMe modified nucleotide"
<220> FEATURE:
<221> NAME/KEY: misc_feature
<222> LOCATION: (18)..(18)
<223> OTHER INFORMATION: /note="2'-OMe modified nucleotide"
<220> FEATURE:
<221> NAME/KEY: misc_feature
<222> LOCATION: (19)..(19)
<223> OTHER INFORMATION: /note="2'-OMe modified nucleotide"

<220> FEATURE:
<221> NAME/KEY: misc_feature
<222> LOCATION: (20)..(20)
<223> OTHER INFORMATION: /note="2'-OMe modified nucleotide"
<220> FEATURE:
<221> NAME/KEY: misc_feature
<222> LOCATION: (21)..(21)
<223> OTHER INFORMATION: /note="2'-OMe modified nucleotide"
<220> FEATURE:
<221> NAME/KEY: misc_feature
<222> LOCATION: (22)..(22)
<223> OTHER INFORMATION: /note="2'-OMe modified nucleotide"
<220> FEATURE:
<221> NAME/KEY: misc_feature
<222> LOCATION: (23)..(23)
<223> OTHER INFORMATION: /note="2'-OMe modified nucleotide"
<220> FEATURE:
<221> NAME/KEY: misc_feature
<222> LOCATION: (24)..(24)
<223> OTHER INFORMATION: /note="2'-OMe modified nucleotide"
<220> FEATURE:
<221> NAME/KEY: misc_feature
<222> LOCATION: (25)..(25)
<223> OTHER INFORMATION: /note="2'-OMe modified nucleotide"
<220> FEATURE:
<221> NAME/KEY: misc_feature
<222> LOCATION: (26)..(26)
<223> OTHER INFORMATION: /note="2'-OMe modified nucleotide"
<220> FEATURE:
<221> NAME/KEY: misc_feature
<222> LOCATION: (27)..(27)
<223> OTHER INFORMATION: /note="2'-OMe modified nucleotide"
<220> FEATURE:
<221> NAME/KEY: misc_feature
<222> LOCATION: (28)..(28)
<223> OTHER INFORMATION: /note="ademA-GalNAc"
<220> FEATURE:
<221> NAME/KEY: misc_feature
<222> LOCATION: (29)..(29)
<223> OTHER INFORMATION: /note="ademA-GalNAc"
<220> FEATURE:
<221> NAME/KEY: misc_feature
<222> LOCATION: (30)..(30)
<223> OTHER INFORMATION: /note="ademA-GalNAc"
<220> FEATURE:
<221> NAME/KEY: misc_feature
<222> LOCATION: (31)..(31)
<223> OTHER INFORMATION: /note="2'-OMe modified nucleotide"
<220> FEATURE:
<221> NAME/KEY: misc_feature
<222> LOCATION: (32)..(32)
<223> OTHER INFORMATION: /note="2'-OMe modified nucleotide"
<220> FEATURE:
<221> NAME/KEY: misc_feature
<222> LOCATION: (33)..(33)
<223> OTHER INFORMATION: /note="2'-OMe modified nucleotide"
<220> FEATURE:
<221> NAME/KEY: misc_feature
<222> LOCATION: (34)..(34)
<223> OTHER INFORMATION: /note="2'-OMe modified nucleotide"
<220> FEATURE:
<221> NAME/KEY: misc_feature
<222> LOCATION: (35)..(35)
<223> OTHER INFORMATION: /note="2'-OMe modified nucleotide"
<220> FEATURE:
<221> NAME/KEY: misc_feature
<222> LOCATION: (36)..(36)
<223> OTHER INFORMATION: /note="2'-OMe modified nucleotide"

<400> SEQUENCE: 142
caagacaauu caucauuuga gcagccgaaa ggcugc 36

<210> SEQ ID NO 143
<211> LENGTH: 22
<212> TYPE: RNA
<213> ORGANISM: Artificial Sequence
<220> FEATURE:

-continued

<221> NAME/KEY: source
<223> OTHER INFORMATION: /note="Description of Artificial Sequence: Synthetic oligonucleotide"
<220> FEATURE:
<221> NAME/KEY: misc_feature
<222> LOCATION: (1)..(1)
<223> OTHER INFORMATION: /note="MePhosphonate-4O-mUs"
<220> FEATURE:
<221> NAME/KEY: misc_feature
<222> LOCATION: (2)..(2)
<223> OTHER INFORMATION: /note="2'-F modified nucleotide with a 3'-phosphorothioate linkage"
<220> FEATURE:
<221> NAME/KEY: misc_feature
<222> LOCATION: (3)..(3)
<223> OTHER INFORMATION: /note="2'-F modified nucleotide with a 3'-phosphorothioate linkage"
<220> FEATURE:
<221> NAME/KEY: misc_feature
<222> LOCATION: (4)..(4)
<223> OTHER INFORMATION: /note="2'-F modified nucleotide"
<220> FEATURE:
<221> NAME/KEY: misc_feature
<222> LOCATION: (5)..(5)
<223> OTHER INFORMATION: /note="2'-F modified nucleotide"
<220> FEATURE:
<221> NAME/KEY: misc_feature
<222> LOCATION: (6)..(6)
<223> OTHER INFORMATION: /note="2'-OMe modified nucleotide"
<220> FEATURE:
<221> NAME/KEY: misc_feature
<222> LOCATION: (7)..(7)
<223> OTHER INFORMATION: /note="2'-F modified nucleotide"
<220> FEATURE:
<221> NAME/KEY: misc_feature
<222> LOCATION: (8)..(8)
<223> OTHER INFORMATION: /note="2'-OMe modified nucleotide"
<220> FEATURE:
<221> NAME/KEY: misc_feature
<222> LOCATION: (9)..(9)
<223> OTHER INFORMATION: /note="2'-OMe modified nucleotide"
<220> FEATURE:
<221> NAME/KEY: misc_feature
<222> LOCATION: (10)..(10)
<223> OTHER INFORMATION: /note="2'-F modified nucleotide"
<220> FEATURE:
<221> NAME/KEY: misc_feature
<222> LOCATION: (11)..(11)
<223> OTHER INFORMATION: /note="2'-OMe modified nucleotide"
<220> FEATURE:
<221> NAME/KEY: misc_feature
<222> LOCATION: (12)..(12)
<223> OTHER INFORMATION: /note="2'-OMe modified nucleotide"
<220> FEATURE:
<221> NAME/KEY: misc_feature
<222> LOCATION: (13)..(13)
<223> OTHER INFORMATION: /note="2'-OMe modified nucleotide"
<220> FEATURE:
<221> NAME/KEY: misc_feature
<222> LOCATION: (14)..(14)
<223> OTHER INFORMATION: /note="2'-F modified nucleotide"
<220> FEATURE:
<221> NAME/KEY: misc_feature
<222> LOCATION: (15)..(15)
<223> OTHER INFORMATION: /note="2'-OMe modified nucleotide"
<220> FEATURE:
<221> NAME/KEY: misc_feature
<222> LOCATION: (16)..(16)
<223> OTHER INFORMATION: /note="2'-OMe modified nucleotide"
<220> FEATURE:
<221> NAME/KEY: misc_feature
<222> LOCATION: (17)..(17)
<223> OTHER INFORMATION: /note="2'-OMe modified nucleotide"
<220> FEATURE:
<221> NAME/KEY: misc_feature
<222> LOCATION: (18)..(18)
<223> OTHER INFORMATION: /note="2'-OMe modified nucleotide"
<220> FEATURE:
<221> NAME/KEY: misc_feature

```
<222> LOCATION: (19)..(19)
<223> OTHER INFORMATION: /note="2'-OMe modified nucleotide"
<220> FEATURE:
<221> NAME/KEY: misc_feature
<222> LOCATION: (20)..(20)
<223> OTHER INFORMATION: /note="2'-OMe modified nucleotide with a
      3'-phosphorothioate linkage"
<220> FEATURE:
<221> NAME/KEY: misc_feature
<222> LOCATION: (21)..(21)
<223> OTHER INFORMATION: /note="2'-OMe modified nucleotide with a
      3'-phosphorothioate linkage"
<220> FEATURE:
<221> NAME/KEY: misc_feature
<222> LOCATION: (22)..(22)
<223> OTHER INFORMATION: /note="2'-OMe modified nucleotide"

<400> SEQUENCE: 143

ucaaaugaug aauugucuug gg                                          22


<210> SEQ ID NO 144
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: misc_feature
<222> LOCATION: (1)..(1)
<223> OTHER INFORMATION: /note="2'-OMe modified nucleotide with a
      3'-phosphorothioate linkage"
<220> FEATURE:
<221> NAME/KEY: misc_feature
<222> LOCATION: (2)..(2)
<223> OTHER INFORMATION: /note="2'-OMe modified nucleotide"
<220> FEATURE:
<221> NAME/KEY: misc_feature
<222> LOCATION: (3)..(3)
<223> OTHER INFORMATION: /note="2'-OMe modified nucleotide"
<220> FEATURE:
<221> NAME/KEY: misc_feature
<222> LOCATION: (4)..(4)
<223> OTHER INFORMATION: /note="2'-OMe modified nucleotide"
<220> FEATURE:
<221> NAME/KEY: misc_feature
<222> LOCATION: (5)..(5)
<223> OTHER INFORMATION: /note="2'-OMe modified nucleotide"
<220> FEATURE:
<221> NAME/KEY: misc_feature
<222> LOCATION: (6)..(6)
<223> OTHER INFORMATION: /note="2'-OMe modified nucleotide"
<220> FEATURE:
<221> NAME/KEY: misc_feature
<222> LOCATION: (7)..(7)
<223> OTHER INFORMATION: /note="2'-OMe modified nucleotide"
<220> FEATURE:
<221> NAME/KEY: misc_feature
<222> LOCATION: (8)..(8)
<223> OTHER INFORMATION: /note="2'-F modified nucleotide"
<220> FEATURE:
<221> NAME/KEY: misc_feature
<222> LOCATION: (9)..(9)
<223> OTHER INFORMATION: /note="2'-F modified nucleotide"
<220> FEATURE:
<221> NAME/KEY: misc_feature
<222> LOCATION: (10)..(10)
<223> OTHER INFORMATION: /note="2'-F modified nucleotide"
<220> FEATURE:
<221> NAME/KEY: misc_feature
<222> LOCATION: (11)..(11)
<223> OTHER INFORMATION: /note="2'-F modified nucleotide"
<220> FEATURE:
<221> NAME/KEY: misc_feature
<222> LOCATION: (12)..(12)
<223> OTHER INFORMATION: /note="2'-OMe modified nucleotide"
```

```
<220> FEATURE:
<221> NAME/KEY: misc_feature
<222> LOCATION: (13)..(13)
<223> OTHER INFORMATION: /note="2'-OMe modified nucleotide"
<220> FEATURE:
<221> NAME/KEY: misc_feature
<222> LOCATION: (14)..(14)
<223> OTHER INFORMATION: /note="2'-OMe modified nucleotide"
<220> FEATURE:
<221> NAME/KEY: misc_feature
<222> LOCATION: (15)..(15)
<223> OTHER INFORMATION: /note="2'-OMe modified nucleotide"
<220> FEATURE:
<221> NAME/KEY: misc_feature
<222> LOCATION: (16)..(16)
<223> OTHER INFORMATION: /note="2'-OMe modified nucleotide"
<220> FEATURE:
<221> NAME/KEY: misc_feature
<222> LOCATION: (17)..(17)
<223> OTHER INFORMATION: /note="2'-OMe modified nucleotide"
<220> FEATURE:
<221> NAME/KEY: misc_feature
<222> LOCATION: (18)..(18)
<223> OTHER INFORMATION: /note="2'-OMe modified nucleotide"
<220> FEATURE:
<221> NAME/KEY: misc_feature
<222> LOCATION: (19)..(19)
<223> OTHER INFORMATION: /note="2'-OMe modified nucleotide"
<220> FEATURE:
<221> NAME/KEY: misc_feature
<222> LOCATION: (20)..(20)
<223> OTHER INFORMATION: /note="2'-OMe modified nucleotide"
<220> FEATURE:
<221> NAME/KEY: misc_feature
<222> LOCATION: (21)..(21)
<223> OTHER INFORMATION: /note="2'-OMe modified nucleotide"
<220> FEATURE:
<221> NAME/KEY: misc_feature
<222> LOCATION: (22)..(22)
<223> OTHER INFORMATION: /note="2'-OMe modified nucleotide"
<220> FEATURE:
<221> NAME/KEY: misc_feature
<222> LOCATION: (23)..(23)
<223> OTHER INFORMATION: /note="2'-OMe modified nucleotide"
<220> FEATURE:
<221> NAME/KEY: misc_feature
<222> LOCATION: (24)..(24)
<223> OTHER INFORMATION: /note="2'-OMe modified nucleotide"
<220> FEATURE:
<221> NAME/KEY: misc_feature
<222> LOCATION: (25)..(25)
<223> OTHER INFORMATION: /note="2'-OMe modified nucleotide"
<220> FEATURE:
<221> NAME/KEY: misc_feature
<222> LOCATION: (26)..(26)
<223> OTHER INFORMATION: /note="2'-OMe modified nucleotide"
<220> FEATURE:
<221> NAME/KEY: misc_feature
<222> LOCATION: (27)..(27)
<223> OTHER INFORMATION: /note="2'-OMe modified nucleotide"
<220> FEATURE:
<221> NAME/KEY: misc_feature
<222> LOCATION: (28)..(28)
<223> OTHER INFORMATION: /note="ademA-GalNAc"
<220> FEATURE:
<221> NAME/KEY: misc_feature
<222> LOCATION: (29)..(29)
<223> OTHER INFORMATION: /note="ademA-GalNAc"
<220> FEATURE:
<221> NAME/KEY: misc_feature
<222> LOCATION: (30)..(30)
<223> OTHER INFORMATION: /note="ademA-GalNAc"
<220> FEATURE:
<221> NAME/KEY: misc_feature
<222> LOCATION: (31)..(31)
<223> OTHER INFORMATION: /note="2'-OMe modified nucleotide"
<220> FEATURE:
<221> NAME/KEY: misc_feature
<222> LOCATION: (32)..(32)
```

-continued

<223> OTHER INFORMATION: /note="2'-OMe modified nucleotide"
<220> FEATURE:
<221> NAME/KEY: misc_feature
<222> LOCATION: (33)..(33)
<223> OTHER INFORMATION: /note="2'-OMe modified nucleotide"
<220> FEATURE:
<221> NAME/KEY: misc_feature
<222> LOCATION: (34)..(34)
<223> OTHER INFORMATION: /note="2'-OMe modified nucleotide"
<220> FEATURE:
<221> NAME/KEY: misc_feature
<222> LOCATION: (35)..(35)
<223> OTHER INFORMATION: /note="2'-OMe modified nucleotide"
<220> FEATURE:
<221> NAME/KEY: misc_feature
<222> LOCATION: (36)..(36)
<223> OTHER INFORMATION: /note="2'-OMe modified nucleotide"

<400> SEQUENCE: 144
agacaauuca ucauuugaua gcagccgaaa ggcugc 36

<210> SEQ ID NO 145
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: misc_feature
<222> LOCATION: (1)..(1)
<223> OTHER INFORMATION: /note="MePhosphonate-4O-mUs"
<220> FEATURE:
<221> NAME/KEY: misc_feature
<222> LOCATION: (2)..(2)
<223> OTHER INFORMATION: /note="2'-F modified nucleotide with a 3'-phosphorothioate linkage"
<220> FEATURE:
<221> NAME/KEY: misc_feature
<222> LOCATION: (3)..(3)
<223> OTHER INFORMATION: /note="2'-F modified nucleotide with a 3'-phosphorothioate linkage"
<220> FEATURE:
<221> NAME/KEY: misc_feature
<222> LOCATION: (4)..(4)
<223> OTHER INFORMATION: /note="2'-F modified nucleotide"
<220> FEATURE:
<221> NAME/KEY: misc_feature
<222> LOCATION: (5)..(5)
<223> OTHER INFORMATION: /note="2'-F modified nucleotide"
<220> FEATURE:
<221> NAME/KEY: misc_feature
<222> LOCATION: (6)..(6)
<223> OTHER INFORMATION: /note="2'-OMe modified nucleotide"
<220> FEATURE:
<221> NAME/KEY: misc_feature
<222> LOCATION: (7)..(7)
<223> OTHER INFORMATION: /note="2'-F modified nucleotide"
<220> FEATURE:
<221> NAME/KEY: misc_feature
<222> LOCATION: (8)..(8)
<223> OTHER INFORMATION: /note="2'-OMe modified nucleotide"
<220> FEATURE:
<221> NAME/KEY: misc_feature
<222> LOCATION: (9)..(9)
<223> OTHER INFORMATION: /note="2'-OMe modified nucleotide"
<220> FEATURE:
<221> NAME/KEY: misc_feature
<222> LOCATION: (10)..(10)
<223> OTHER INFORMATION: /note="2'-F modified nucleotide"
<220> FEATURE:
<221> NAME/KEY: misc_feature
<222> LOCATION: (11)..(11)
<223> OTHER INFORMATION: /note="2'-OMe modified nucleotide"
<220> FEATURE:
<221> NAME/KEY: misc_feature
<222> LOCATION: (12)..(12)
<223> OTHER INFORMATION: /note="2'-OMe modified nucleotide"
<220> FEATURE:
<221> NAME/KEY: misc_feature
<222> LOCATION: (13)..(13)
<223> OTHER INFORMATION: /note="2'-OMe modified nucleotide"
<220> FEATURE:
<221> NAME/KEY: misc_feature
<222> LOCATION: (14)..(14)
<223> OTHER INFORMATION: /note="2'-F modified nucleotide"
<220> FEATURE:
<221> NAME/KEY: misc_feature
<222> LOCATION: (15)..(15)
<223> OTHER INFORMATION: /note="2'-OMe modified nucleotide"
<220> FEATURE:
<221> NAME/KEY: misc_feature
<222> LOCATION: (16)..(16)
<223> OTHER INFORMATION: /note="2'-OMe modified nucleotide"
<220> FEATURE:
<221> NAME/KEY: misc_feature
<222> LOCATION: (17)..(17)
<223> OTHER INFORMATION: /note="2'-OMe modified nucleotide"
<220> FEATURE:
<221> NAME/KEY: misc_feature
<222> LOCATION: (18)..(18)
<223> OTHER INFORMATION: /note="2'-OMe modified nucleotide"
<220> FEATURE:
<221> NAME/KEY: misc_feature
<222> LOCATION: (19)..(19)
<223> OTHER INFORMATION: /note="2'-OMe modified nucleotide"
<220> FEATURE:
<221> NAME/KEY: misc_feature
<222> LOCATION: (20)..(20)
<223> OTHER INFORMATION: /note="2'-OMe modified nucleotide with a
3'-phosphorothioate linkage"
<220> FEATURE:
<221> NAME/KEY: misc_feature
<222> LOCATION: (21)..(21)
<223> OTHER INFORMATION: /note="2'-OMe modified nucleotide with a
3'-phosphorothioate linkage"
<220> FEATURE:
<221> NAME/KEY: misc_feature
<222> LOCATION: (22)..(22)
<223> OTHER INFORMATION: /note="2'-OMe modified nucleotide"

<400> SEQUENCE: 145
uaucaaauga ugaauugucu gg 22

<210> SEQ ID NO 146
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: misc_feature
<222> LOCATION: (1)..(1)
<223> OTHER INFORMATION: /note="2'-OMe modified nucleotide with a
3'-phosphorothioate linkage"
<220> FEATURE:
<221> NAME/KEY: misc_feature
<222> LOCATION: (2)..(2)
<223> OTHER INFORMATION: /note="2'-OMe modified nucleotide"
<220> FEATURE:
<221> NAME/KEY: misc_feature
<222> LOCATION: (3)..(3)
<223> OTHER INFORMATION: /note="2'-OMe modified nucleotide"
<220> FEATURE:
<221> NAME/KEY: misc_feature
<222> LOCATION: (4)..(4)
<223> OTHER INFORMATION: /note="2'-OMe modified nucleotide"
<220> FEATURE:
<221> NAME/KEY: misc_feature
<222> LOCATION: (5)..(5)
<223> OTHER INFORMATION: /note="2'-OMe modified nucleotide"

-continued

```
<220> FEATURE:
<221> NAME/KEY: misc_feature
<222> LOCATION: (6)..(6)
<223> OTHER INFORMATION: /note="2'-OMe modified nucleotide"
<220> FEATURE:
<221> NAME/KEY: misc_feature
<222> LOCATION: (7)..(7)
<223> OTHER INFORMATION: /note="2'-OMe modified nucleotide"
<220> FEATURE:
<221> NAME/KEY: misc_feature
<222> LOCATION: (8)..(8)
<223> OTHER INFORMATION: /note="2'-F modified nucleotide"
<220> FEATURE:
<221> NAME/KEY: misc_feature
<222> LOCATION: (9)..(9)
<223> OTHER INFORMATION: /note="2'-F modified nucleotide"
<220> FEATURE:
<221> NAME/KEY: misc_feature
<222> LOCATION: (10)..(10)
<223> OTHER INFORMATION: /note="2'-F modified nucleotide"
<220> FEATURE:
<221> NAME/KEY: misc_feature
<222> LOCATION: (11)..(11)
<223> OTHER INFORMATION: /note="2'-F modified nucleotide"
<220> FEATURE:
<221> NAME/KEY: misc_feature
<222> LOCATION: (12)..(12)
<223> OTHER INFORMATION: /note="2'-OMe modified nucleotide"
<220> FEATURE:
<221> NAME/KEY: misc_feature
<222> LOCATION: (13)..(13)
<223> OTHER INFORMATION: /note="2'-OMe modified nucleotide"
<220> FEATURE:
<221> NAME/KEY: misc_feature
<222> LOCATION: (14)..(14)
<223> OTHER INFORMATION: /note="2'-OMe modified nucleotide"
<220> FEATURE:
<221> NAME/KEY: misc_feature
<222> LOCATION: (15)..(15)
<223> OTHER INFORMATION: /note="2'-OMe modified nucleotide"
<220> FEATURE:
<221> NAME/KEY: misc_feature
<222> LOCATION: (16)..(16)
<223> OTHER INFORMATION: /note="2'-OMe modified nucleotide"
<220> FEATURE:
<221> NAME/KEY: misc_feature
<222> LOCATION: (17)..(17)
<223> OTHER INFORMATION: /note="2'-OMe modified nucleotide"
<220> FEATURE:
<221> NAME/KEY: misc_feature
<222> LOCATION: (18)..(18)
<223> OTHER INFORMATION: /note="2'-OMe modified nucleotide"
<220> FEATURE:
<221> NAME/KEY: misc_feature
<222> LOCATION: (19)..(19)
<223> OTHER INFORMATION: /note="2'-OMe modified nucleotide"
<220> FEATURE:
<221> NAME/KEY: misc_feature
<222> LOCATION: (20)..(20)
<223> OTHER INFORMATION: /note="2'-OMe modified nucleotide"
<220> FEATURE:
<221> NAME/KEY: misc_feature
<222> LOCATION: (21)..(21)
<223> OTHER INFORMATION: /note="2'-OMe modified nucleotide"
<220> FEATURE:
<221> NAME/KEY: misc_feature
<222> LOCATION: (22)..(22)
<223> OTHER INFORMATION: /note="2'-OMe modified nucleotide"
<220> FEATURE:
<221> NAME/KEY: misc_feature
<222> LOCATION: (23)..(23)
<223> OTHER INFORMATION: /note="2'-OMe modified nucleotide"
<220> FEATURE:
<221> NAME/KEY: misc_feature
<222> LOCATION: (24)..(24)
<223> OTHER INFORMATION: /note="2'-OMe modified nucleotide"
<220> FEATURE:
<221> NAME/KEY: misc_feature
<222> LOCATION: (25)..(25)
```

<223> OTHER INFORMATION: /note="2'-OMe modified nucleotide"
<220> FEATURE:
<221> NAME/KEY: misc_feature
<222> LOCATION: (26)..(26)
<223> OTHER INFORMATION: /note="2'-OMe modified nucleotide"
<220> FEATURE:
<221> NAME/KEY: misc_feature
<222> LOCATION: (27)..(27)
<223> OTHER INFORMATION: /note="2'-OMe modified nucleotide"
<220> FEATURE:
<221> NAME/KEY: misc_feature
<222> LOCATION: (28)..(28)
<223> OTHER INFORMATION: /note="ademA-GalNAc"
<220> FEATURE:
<221> NAME/KEY: misc_feature
<222> LOCATION: (29)..(29)
<223> OTHER INFORMATION: /note="ademA-GalNAc"
<220> FEATURE:
<221> NAME/KEY: misc_feature
<222> LOCATION: (30)..(30)
<223> OTHER INFORMATION: /note="ademA-GalNAc"
<220> FEATURE:
<221> NAME/KEY: misc_feature
<222> LOCATION: (31)..(31)
<223> OTHER INFORMATION: /note="2'-OMe modified nucleotide"
<220> FEATURE:
<221> NAME/KEY: misc_feature
<222> LOCATION: (32)..(32)
<223> OTHER INFORMATION: /note="2'-OMe modified nucleotide"
<220> FEATURE:
<221> NAME/KEY: misc_feature
<222> LOCATION: (33)..(33)
<223> OTHER INFORMATION: /note="2'-OMe modified nucleotide"
<220> FEATURE:
<221> NAME/KEY: misc_feature
<222> LOCATION: (34)..(34)
<223> OTHER INFORMATION: /note="2'-OMe modified nucleotide"
<220> FEATURE:
<221> NAME/KEY: misc_feature
<222> LOCATION: (35)..(35)
<223> OTHER INFORMATION: /note="2'-OMe modified nucleotide"
<220> FEATURE:
<221> NAME/KEY: misc_feature
<222> LOCATION: (36)..(36)
<223> OTHER INFORMATION: /note="2'-OMe modified nucleotide"

<400> SEQUENCE: 146
caauucauca uuugauucua gcagccgaaa ggcugc 36

<210> SEQ ID NO 147
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: misc_feature
<222> LOCATION: (1)..(1)
<223> OTHER INFORMATION: /note="MePhosphonate-4O-mUs"
<220> FEATURE:
<221> NAME/KEY: misc_feature
<222> LOCATION: (2)..(2)
<223> OTHER INFORMATION: /note="2'-F modified nucleotide with a 3'-phosphorothioate linkage"
<220> FEATURE:
<221> NAME/KEY: misc_feature
<222> LOCATION: (3)..(3)
<223> OTHER INFORMATION: /note="2'-F modified nucleotide with a 3'-phosphorothioate linkage"
<220> FEATURE:
<221> NAME/KEY: misc_feature
<222> LOCATION: (4)..(4)
<223> OTHER INFORMATION: /note="2'-F modified nucleotide"
<220> FEATURE:
<221> NAME/KEY: misc_feature
<222> LOCATION: (5)..(5)
<223> OTHER INFORMATION: /note="2'-F modified nucleotide"
<220> FEATURE:
<221> NAME/KEY: misc_feature
<222> LOCATION: (6)..(6)
<223> OTHER INFORMATION: /note="2'-OMe modified nucleotide"
<220> FEATURE:
<221> NAME/KEY: misc_feature
<222> LOCATION: (7)..(7)
<223> OTHER INFORMATION: /note="2'-F modified nucleotide"
<220> FEATURE:
<221> NAME/KEY: misc_feature
<222> LOCATION: (8)..(8)
<223> OTHER INFORMATION: /note="2'-OMe modified nucleotide"
<220> FEATURE:
<221> NAME/KEY: misc_feature
<222> LOCATION: (9)..(9)
<223> OTHER INFORMATION: /note="2'-OMe modified nucleotide"
<220> FEATURE:
<221> NAME/KEY: misc_feature
<222> LOCATION: (10)..(10)
<223> OTHER INFORMATION: /note="2'-F modified nucleotide"
<220> FEATURE:
<221> NAME/KEY: misc_feature
<222> LOCATION: (11)..(11)
<223> OTHER INFORMATION: /note="2'-OMe modified nucleotide"
<220> FEATURE:
<221> NAME/KEY: misc_feature
<222> LOCATION: (12)..(12)
<223> OTHER INFORMATION: /note="2'-OMe modified nucleotide"
<220> FEATURE:
<221> NAME/KEY: misc_feature
<222> LOCATION: (13)..(13)
<223> OTHER INFORMATION: /note="2'-OMe modified nucleotide"
<220> FEATURE:
<221> NAME/KEY: misc_feature
<222> LOCATION: (14)..(14)
<223> OTHER INFORMATION: /note="2'-F modified nucleotide"
<220> FEATURE:
<221> NAME/KEY: misc_feature
<222> LOCATION: (15)..(15)
<223> OTHER INFORMATION: /note="2'-OMe modified nucleotide"
<220> FEATURE:
<221> NAME/KEY: misc_feature
<222> LOCATION: (16)..(16)
<223> OTHER INFORMATION: /note="2'-OMe modified nucleotide"
<220> FEATURE:
<221> NAME/KEY: misc_feature
<222> LOCATION: (17)..(17)
<223> OTHER INFORMATION: /note="2'-OMe modified nucleotide"
<220> FEATURE:
<221> NAME/KEY: misc_feature
<222> LOCATION: (18)..(18)
<223> OTHER INFORMATION: /note="2'-OMe modified nucleotide"
<220> FEATURE:
<221> NAME/KEY: misc_feature
<222> LOCATION: (19)..(19)
<223> OTHER INFORMATION: /note="2'-OMe modified nucleotide"
<220> FEATURE:
<221> NAME/KEY: misc_feature
<222> LOCATION: (20)..(20)
<223> OTHER INFORMATION: /note="2'-OMe modified nucleotide with a
3'-phosphorothioate linkage"
<220> FEATURE:
<221> NAME/KEY: misc_feature
<222> LOCATION: (21)..(21)
<223> OTHER INFORMATION: /note="2'-OMe modified nucleotide with a
3'-phosphorothioate linkage"
<220> FEATURE:
<221> NAME/KEY: misc_feature
<222> LOCATION: (22)..(22)
<223> OTHER INFORMATION: /note="2'-OMe modified nucleotide"

<400> SEQUENCE: 147
uagaaucaaa ugaugaauug gg 22

<210> SEQ ID NO 148

```
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: misc_feature
<222> LOCATION: (1)..(1)
<223> OTHER INFORMATION: /note="2'-OMe modified nucleotide with a
      3'-phosphorothioate linkage"
<220> FEATURE:
<221> NAME/KEY: misc_feature
<222> LOCATION: (2)..(2)
<223> OTHER INFORMATION: /note="2'-OMe modified nucleotide"
<220> FEATURE:
<221> NAME/KEY: misc_feature
<222> LOCATION: (3)..(3)
<223> OTHER INFORMATION: /note="2'-OMe modified nucleotide"
<220> FEATURE:
<221> NAME/KEY: misc_feature
<222> LOCATION: (4)..(4)
<223> OTHER INFORMATION: /note="2'-OMe modified nucleotide"
<220> FEATURE:
<221> NAME/KEY: misc_feature
<222> LOCATION: (5)..(5)
<223> OTHER INFORMATION: /note="2'-OMe modified nucleotide"
<220> FEATURE:
<221> NAME/KEY: misc_feature
<222> LOCATION: (6)..(6)
<223> OTHER INFORMATION: /note="2'-OMe modified nucleotide"
<220> FEATURE:
<221> NAME/KEY: misc_feature
<222> LOCATION: (7)..(7)
<223> OTHER INFORMATION: /note="2'-OMe modified nucleotide"
<220> FEATURE:
<221> NAME/KEY: misc_feature
<222> LOCATION: (8)..(8)
<223> OTHER INFORMATION: /note="2'-F modified nucleotide"
<220> FEATURE:
<221> NAME/KEY: misc_feature
<222> LOCATION: (9)..(9)
<223> OTHER INFORMATION: /note="2'-F modified nucleotide"
<220> FEATURE:
<221> NAME/KEY: misc_feature
<222> LOCATION: (10)..(10)
<223> OTHER INFORMATION: /note="2'-F modified nucleotide"
<220> FEATURE:
<221> NAME/KEY: misc_feature
<222> LOCATION: (11)..(11)
<223> OTHER INFORMATION: /note="2'-F modified nucleotide"
<220> FEATURE:
<221> NAME/KEY: misc_feature
<222> LOCATION: (12)..(12)
<223> OTHER INFORMATION: /note="2'-OMe modified nucleotide"
<220> FEATURE:
<221> NAME/KEY: misc_feature
<222> LOCATION: (13)..(13)
<223> OTHER INFORMATION: /note="2'-OMe modified nucleotide"
<220> FEATURE:
<221> NAME/KEY: misc_feature
<222> LOCATION: (14)..(14)
<223> OTHER INFORMATION: /note="2'-OMe modified nucleotide"
<220> FEATURE:
<221> NAME/KEY: misc_feature
<222> LOCATION: (15)..(15)
<223> OTHER INFORMATION: /note="2'-OMe modified nucleotide"
<220> FEATURE:
<221> NAME/KEY: misc_feature
<222> LOCATION: (16)..(16)
<223> OTHER INFORMATION: /note="2'-OMe modified nucleotide"
<220> FEATURE:
<221> NAME/KEY: misc_feature
<222> LOCATION: (17)..(17)
<223> OTHER INFORMATION: /note="2'-OMe modified nucleotide"
<220> FEATURE:
<221> NAME/KEY: misc_feature
<222> LOCATION: (18)..(18)
```

<223> OTHER INFORMATION: /note="2'-OMe modified nucleotide"
<220> FEATURE:
<221> NAME/KEY: misc_feature
<222> LOCATION: (19)..(19)
<223> OTHER INFORMATION: /note="2'-OMe modified nucleotide"
<220> FEATURE:
<221> NAME/KEY: misc_feature
<222> LOCATION: (20)..(20)
<223> OTHER INFORMATION: /note="2'-OMe modified nucleotide"
<220> FEATURE:
<221> NAME/KEY: misc_feature
<222> LOCATION: (21)..(21)
<223> OTHER INFORMATION: /note="2'-OMe modified nucleotide"
<220> FEATURE:
<221> NAME/KEY: misc_feature
<222> LOCATION: (22)..(22)
<223> OTHER INFORMATION: /note="2'-OMe modified nucleotide"
<220> FEATURE:
<221> NAME/KEY: misc_feature
<222> LOCATION: (23)..(23)
<223> OTHER INFORMATION: /note="2'-OMe modified nucleotide"
<220> FEATURE:
<221> NAME/KEY: misc_feature
<222> LOCATION: (24)..(24)
<223> OTHER INFORMATION: /note="2'-OMe modified nucleotide"
<220> FEATURE:
<221> NAME/KEY: misc_feature
<222> LOCATION: (25)..(25)
<223> OTHER INFORMATION: /note="2'-OMe modified nucleotide"
<220> FEATURE:
<221> NAME/KEY: misc_feature
<222> LOCATION: (26)..(26)
<223> OTHER INFORMATION: /note="2'-OMe modified nucleotide"
<220> FEATURE:
<221> NAME/KEY: misc_feature
<222> LOCATION: (27)..(27)
<223> OTHER INFORMATION: /note="2'-OMe modified nucleotide"
<220> FEATURE:
<221> NAME/KEY: misc_feature
<222> LOCATION: (28)..(28)
<223> OTHER INFORMATION: /note="ademA-GalNAc"
<220> FEATURE:
<221> NAME/KEY: misc_feature
<222> LOCATION: (29)..(29)
<223> OTHER INFORMATION: /note="ademA-GalNAc"
<220> FEATURE:
<221> NAME/KEY: misc_feature
<222> LOCATION: (30)..(30)
<223> OTHER INFORMATION: /note="ademA-GalNAc"
<220> FEATURE:
<221> NAME/KEY: misc_feature
<222> LOCATION: (31)..(31)
<223> OTHER INFORMATION: /note="2'-OMe modified nucleotide"
<220> FEATURE:
<221> NAME/KEY: misc_feature
<222> LOCATION: (32)..(32)
<223> OTHER INFORMATION: /note="2'-OMe modified nucleotide"
<220> FEATURE:
<221> NAME/KEY: misc_feature
<222> LOCATION: (33)..(33)
<223> OTHER INFORMATION: /note="2'-OMe modified nucleotide"
<220> FEATURE:
<221> NAME/KEY: misc_feature
<222> LOCATION: (34)..(34)
<223> OTHER INFORMATION: /note="2'-OMe modified nucleotide"
<220> FEATURE:
<221> NAME/KEY: misc_feature
<222> LOCATION: (35)..(35)
<223> OTHER INFORMATION: /note="2'-OMe modified nucleotide"
<220> FEATURE:
<221> NAME/KEY: misc_feature
<222> LOCATION: (36)..(36)
<223> OTHER INFORMATION: /note="2'-OMe modified nucleotide"

<400> SEQUENCE: 148
cagagccaaa aucaagauua gcagccgaaa ggcugc 36

-continued

<210> SEQ ID NO 149
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: misc_feature
<222> LOCATION: (1)..(1)
<223> OTHER INFORMATION: /note="MePhosphonate-4O-mUs"
<220> FEATURE:
<221> NAME/KEY: misc_feature
<222> LOCATION: (2)..(2)
<223> OTHER INFORMATION: /note="2'-F modified nucleotide with a 3'-phosphorothioate linkage"
<220> FEATURE:
<221> NAME/KEY: misc_feature
<222> LOCATION: (3)..(3)
<223> OTHER INFORMATION: /note="2'-F modified nucleotide with a 3'-phosphorothioate linkage"
<220> FEATURE:
<221> NAME/KEY: misc_feature
<222> LOCATION: (4)..(4)
<223> OTHER INFORMATION: /note="2'-F modified nucleotide"
<220> FEATURE:
<221> NAME/KEY: misc_feature
<222> LOCATION: (5)..(5)
<223> OTHER INFORMATION: /note="2'-F modified nucleotide"
<220> FEATURE:
<221> NAME/KEY: misc_feature
<222> LOCATION: (6)..(6)
<223> OTHER INFORMATION: /note="2'-OMe modified nucleotide"
<220> FEATURE:
<221> NAME/KEY: misc_feature
<222> LOCATION: (7)..(7)
<223> OTHER INFORMATION: /note="2'-F modified nucleotide"
<220> FEATURE:
<221> NAME/KEY: misc_feature
<222> LOCATION: (8)..(8)
<223> OTHER INFORMATION: /note="2'-OMe modified nucleotide"
<220> FEATURE:
<221> NAME/KEY: misc_feature
<222> LOCATION: (9)..(9)
<223> OTHER INFORMATION: /note="2'-OMe modified nucleotide"
<220> FEATURE:
<221> NAME/KEY: misc_feature
<222> LOCATION: (10)..(10)
<223> OTHER INFORMATION: /note="2'-F modified nucleotide"
<220> FEATURE:
<221> NAME/KEY: misc_feature
<222> LOCATION: (11)..(11)
<223> OTHER INFORMATION: /note="2'-OMe modified nucleotide"
<220> FEATURE:
<221> NAME/KEY: misc_feature
<222> LOCATION: (12)..(12)
<223> OTHER INFORMATION: /note="2'-OMe modified nucleotide"
<220> FEATURE:
<221> NAME/KEY: misc_feature
<222> LOCATION: (13)..(13)
<223> OTHER INFORMATION: /note="2'-OMe modified nucleotide"
<220> FEATURE:
<221> NAME/KEY: misc_feature
<222> LOCATION: (14)..(14)
<223> OTHER INFORMATION: /note="2'-F modified nucleotide"
<220> FEATURE:
<221> NAME/KEY: misc_feature
<222> LOCATION: (15)..(15)
<223> OTHER INFORMATION: /note="2'-OMe modified nucleotide"
<220> FEATURE:
<221> NAME/KEY: misc_feature
<222> LOCATION: (16)..(16)
<223> OTHER INFORMATION: /note="2'-OMe modified nucleotide"
<220> FEATURE:
<221> NAME/KEY: misc_feature
<222> LOCATION: (17)..(17)
<223> OTHER INFORMATION: /note="2'-OMe modified nucleotide"
<220> FEATURE:

<221> NAME/KEY: misc_feature
<222> LOCATION: (18)..(18)
<223> OTHER INFORMATION: /note="2'-OMe modified nucleotide"
<220> FEATURE:
<221> NAME/KEY: misc_feature
<222> LOCATION: (19)..(19)
<223> OTHER INFORMATION: /note="2'-OMe modified nucleotide"
<220> FEATURE:
<221> NAME/KEY: misc_feature
<222> LOCATION: (20)..(20)
<223> OTHER INFORMATION: /note="2'-OMe modified nucleotide with a
3'-phosphorothioate linkage"
<220> FEATURE:
<221> NAME/KEY: misc_feature
<222> LOCATION: (21)..(21)
<223> OTHER INFORMATION: /note="2'-OMe modified nucleotide with a
3'-phosphorothioate linkage"
<220> FEATURE:
<221> NAME/KEY: misc_feature
<222> LOCATION: (22)..(22)
<223> OTHER INFORMATION: /note="2'-OMe modified nucleotide"

<400> SEQUENCE: 149
uaaucuugau uuuggcucug gg 22

<210> SEQ ID NO 150
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: misc_feature
<222> LOCATION: (1)..(1)
<223> OTHER INFORMATION: /note="2'-OMe modified nucleotide with a
3'-phosphorothioate linkage"
<220> FEATURE:
<221> NAME/KEY: misc_feature
<222> LOCATION: (2)..(2)
<223> OTHER INFORMATION: /note="2'-OMe modified nucleotide"
<220> FEATURE:
<221> NAME/KEY: misc_feature
<222> LOCATION: (3)..(3)
<223> OTHER INFORMATION: /note="2'-OMe modified nucleotide"
<220> FEATURE:
<221> NAME/KEY: misc_feature
<222> LOCATION: (4)..(4)
<223> OTHER INFORMATION: /note="2'-OMe modified nucleotide"
<220> FEATURE:
<221> NAME/KEY: misc_feature
<222> LOCATION: (5)..(5)
<223> OTHER INFORMATION: /note="2'-OMe modified nucleotide"
<220> FEATURE:
<221> NAME/KEY: misc_feature
<222> LOCATION: (6)..(6)
<223> OTHER INFORMATION: /note="2'-OMe modified nucleotide"
<220> FEATURE:
<221> NAME/KEY: misc_feature
<222> LOCATION: (7)..(7)
<223> OTHER INFORMATION: /note="2'-OMe modified nucleotide"
<220> FEATURE:
<221> NAME/KEY: misc_feature
<222> LOCATION: (8)..(8)
<223> OTHER INFORMATION: /note="2'-F modified nucleotide"
<220> FEATURE:
<221> NAME/KEY: misc_feature
<222> LOCATION: (9)..(9)
<223> OTHER INFORMATION: /note="2'-F modified nucleotide"
<220> FEATURE:
<221> NAME/KEY: misc_feature
<222> LOCATION: (10)..(10)
<223> OTHER INFORMATION: /note="2'-F modified nucleotide"
<220> FEATURE:
<221> NAME/KEY: misc_feature
<222> LOCATION: (11)..(11)

<223> OTHER INFORMATION: /note="2'-F modified nucleotide"
<220> FEATURE:
<221> NAME/KEY: misc_feature
<222> LOCATION: (12)..(12)
<223> OTHER INFORMATION: /note="2'-OMe modified nucleotide"
<220> FEATURE:
<221> NAME/KEY: misc_feature
<222> LOCATION: (13)..(13)
<223> OTHER INFORMATION: /note="2'-OMe modified nucleotide"
<220> FEATURE:
<221> NAME/KEY: misc_feature
<222> LOCATION: (14)..(14)
<223> OTHER INFORMATION: /note="2'-OMe modified nucleotide"
<220> FEATURE:
<221> NAME/KEY: misc_feature
<222> LOCATION: (15)..(15)
<223> OTHER INFORMATION: /note="2'-OMe modified nucleotide"
<220> FEATURE:
<221> NAME/KEY: misc_feature
<222> LOCATION: (16)..(16)
<223> OTHER INFORMATION: /note="2'-OMe modified nucleotide"
<220> FEATURE:
<221> NAME/KEY: misc_feature
<222> LOCATION: (17)..(17)
<223> OTHER INFORMATION: /note="2'-OMe modified nucleotide"
<220> FEATURE:
<221> NAME/KEY: misc_feature
<222> LOCATION: (18)..(18)
<223> OTHER INFORMATION: /note="2'-OMe modified nucleotide"
<220> FEATURE:
<221> NAME/KEY: misc_feature
<222> LOCATION: (19)..(19)
<223> OTHER INFORMATION: /note="2'-OMe modified nucleotide"
<220> FEATURE:
<221> NAME/KEY: misc_feature
<222> LOCATION: (20)..(20)
<223> OTHER INFORMATION: /note="2'-OMe modified nucleotide"
<220> FEATURE:
<221> NAME/KEY: misc_feature
<222> LOCATION: (21)..(21)
<223> OTHER INFORMATION: /note="2'-OMe modified nucleotide"
<220> FEATURE:
<221> NAME/KEY: misc_feature
<222> LOCATION: (22)..(22)
<223> OTHER INFORMATION: /note="2'-OMe modified nucleotide"
<220> FEATURE:
<221> NAME/KEY: misc_feature
<222> LOCATION: (23)..(23)
<223> OTHER INFORMATION: /note="2'-OMe modified nucleotide"
<220> FEATURE:
<221> NAME/KEY: misc_feature
<222> LOCATION: (24)..(24)
<223> OTHER INFORMATION: /note="2'-OMe modified nucleotide"
<220> FEATURE:
<221> NAME/KEY: misc_feature
<222> LOCATION: (25)..(25)
<223> OTHER INFORMATION: /note="2'-OMe modified nucleotide"
<220> FEATURE:
<221> NAME/KEY: misc_feature
<222> LOCATION: (26)..(26)
<223> OTHER INFORMATION: /note="2'-OMe modified nucleotide"
<220> FEATURE:
<221> NAME/KEY: misc_feature
<222> LOCATION: (27)..(27)
<223> OTHER INFORMATION: /note="2'-OMe modified nucleotide"
<220> FEATURE:
<221> NAME/KEY: misc_feature
<222> LOCATION: (28)..(28)
<223> OTHER INFORMATION: /note="ademA-GalNAc"
<220> FEATURE:
<221> NAME/KEY: misc_feature
<222> LOCATION: (29)..(29)
<223> OTHER INFORMATION: /note="ademA-GalNAc"
<220> FEATURE:
<221> NAME/KEY: misc_feature
<222> LOCATION: (30)..(30)
<223> OTHER INFORMATION: /note="ademA-GalNAc"
<220> FEATURE:
<221> NAME/KEY: misc_feature
<222> LOCATION: (31)..(31)
<223> OTHER INFORMATION: /note="2'-OMe modified nucleotide"
<220> FEATURE:
<221> NAME/KEY: misc_feature
<222> LOCATION: (32)..(32)
<223> OTHER INFORMATION: /note="2'-OMe modified nucleotide"
<220> FEATURE:
<221> NAME/KEY: misc_feature
<222> LOCATION: (33)..(33)
<223> OTHER INFORMATION: /note="2'-OMe modified nucleotide"
<220> FEATURE:
<221> NAME/KEY: misc_feature
<222> LOCATION: (34)..(34)
<223> OTHER INFORMATION: /note="2'-OMe modified nucleotide"
<220> FEATURE:
<221> NAME/KEY: misc_feature
<222> LOCATION: (35)..(35)
<223> OTHER INFORMATION: /note="2'-OMe modified nucleotide"
<220> FEATURE:
<221> NAME/KEY: misc_feature
<222> LOCATION: (36)..(36)
<223> OTHER INFORMATION: /note="2'-OMe modified nucleotide"

<400> SEQUENCE: 150
agagccaaaa ucaagauuua gcagccgaaa ggcugc 36

<210> SEQ ID NO 151
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: misc_feature
<222> LOCATION: (1)..(1)
<223> OTHER INFORMATION: /note="MePhosphonate-4O-mUs"
<220> FEATURE:
<221> NAME/KEY: misc_feature
<222> LOCATION: (2)..(2)
<223> OTHER INFORMATION: /note="2'-F modified nucleotide with a 3'-phosphorothioate linkage"
<220> FEATURE:
<221> NAME/KEY: misc_feature
<222> LOCATION: (3)..(3)
<223> OTHER INFORMATION: /note="2'-F modified nucleotide with a 3'-phosphorothioate linkage"
<220> FEATURE:
<221> NAME/KEY: misc_feature
<222> LOCATION: (4)..(4)
<223> OTHER INFORMATION: /note="2'-F modified nucleotide"
<220> FEATURE:
<221> NAME/KEY: misc_feature
<222> LOCATION: (5)..(5)
<223> OTHER INFORMATION: /note="2'-F modified nucleotide"
<220> FEATURE:
<221> NAME/KEY: misc_feature
<222> LOCATION: (6)..(6)
<223> OTHER INFORMATION: /note="2'-OMe modified nucleotide"
<220> FEATURE:
<221> NAME/KEY: misc_feature
<222> LOCATION: (7)..(7)
<223> OTHER INFORMATION: /note="2'-F modified nucleotide"
<220> FEATURE:
<221> NAME/KEY: misc_feature
<222> LOCATION: (8)..(8)
<223> OTHER INFORMATION: /note="2'-OMe modified nucleotide"
<220> FEATURE:
<221> NAME/KEY: misc_feature
<222> LOCATION: (9)..(9)
<223> OTHER INFORMATION: /note="2'-OMe modified nucleotide"
<220> FEATURE:
<221> NAME/KEY: misc_feature
<222> LOCATION: (10)..(10)
<223> OTHER INFORMATION: /note="2'-F modified nucleotide"
<220> FEATURE:

```
<221> NAME/KEY: misc_feature
<222> LOCATION: (11)..(11)
<223> OTHER INFORMATION: /note="2'-OMe modified nucleotide"
<220> FEATURE:
<221> NAME/KEY: misc_feature
<222> LOCATION: (12)..(12)
<223> OTHER INFORMATION: /note="2'-OMe modified nucleotide"
<220> FEATURE:
<221> NAME/KEY: misc_feature
<222> LOCATION: (13)..(13)
<223> OTHER INFORMATION: /note="2'-OMe modified nucleotide"
<220> FEATURE:
<221> NAME/KEY: misc_feature
<222> LOCATION: (14)..(14)
<223> OTHER INFORMATION: /note="2'-F modified nucleotide"
<220> FEATURE:
<221> NAME/KEY: misc_feature
<222> LOCATION: (15)..(15)
<223> OTHER INFORMATION: /note="2'-OMe modified nucleotide"
<220> FEATURE:
<221> NAME/KEY: misc_feature
<222> LOCATION: (16)..(16)
<223> OTHER INFORMATION: /note="2'-OMe modified nucleotide"
<220> FEATURE:
<221> NAME/KEY: misc_feature
<222> LOCATION: (17)..(17)
<223> OTHER INFORMATION: /note="2'-OMe modified nucleotide"
<220> FEATURE:
<221> NAME/KEY: misc_feature
<222> LOCATION: (18)..(18)
<223> OTHER INFORMATION: /note="2'-OMe modified nucleotide"
<220> FEATURE:
<221> NAME/KEY: misc_feature
<222> LOCATION: (19)..(19)
<223> OTHER INFORMATION: /note="2'-OMe modified nucleotide"
<220> FEATURE:
<221> NAME/KEY: misc_feature
<222> LOCATION: (20)..(20)
<223> OTHER INFORMATION: /note="2'-OMe modified nucleotide with a
      3'-phosphorothioate linkage"
<220> FEATURE:
<221> NAME/KEY: misc_feature
<222> LOCATION: (21)..(21)
<223> OTHER INFORMATION: /note="2'-OMe modified nucleotide with a
      3'-phosphorothioate linkage"
<220> FEATURE:
<221> NAME/KEY: misc_feature
<222> LOCATION: (22)..(22)
<223> OTHER INFORMATION: /note="2'-OMe modified nucleotide"

<400> SEQUENCE: 151

uaaaucuuga uuuuggcucu gg                                          22


<210> SEQ ID NO 152
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: misc_feature
<222> LOCATION: (1)..(1)
<223> OTHER INFORMATION: /note="2'-OMe modified nucleotide with a
      3'-phosphorothioate linkage"
<220> FEATURE:
<221> NAME/KEY: misc_feature
<222> LOCATION: (2)..(2)
<223> OTHER INFORMATION: /note="2'-OMe modified nucleotide"
<220> FEATURE:
<221> NAME/KEY: misc_feature
<222> LOCATION: (3)..(3)
<223> OTHER INFORMATION: /note="2'-OMe modified nucleotide"
<220> FEATURE:
<221> NAME/KEY: misc_feature
<222> LOCATION: (4)..(4)
```

<223> OTHER INFORMATION: /note="2'-OMe modified nucleotide"
<220> FEATURE:
<221> NAME/KEY: misc_feature
<222> LOCATION: (5)..(5)
<223> OTHER INFORMATION: /note="2'-OMe modified nucleotide"
<220> FEATURE:
<221> NAME/KEY: misc_feature
<222> LOCATION: (6)..(6)
<223> OTHER INFORMATION: /note="2'-OMe modified nucleotide"
<220> FEATURE:
<221> NAME/KEY: misc_feature
<222> LOCATION: (7)..(7)
<223> OTHER INFORMATION: /note="2'-OMe modified nucleotide"
<220> FEATURE:
<221> NAME/KEY: misc_feature
<222> LOCATION: (8)..(8)
<223> OTHER INFORMATION: /note="2'-F modified nucleotide"
<220> FEATURE:
<221> NAME/KEY: misc_feature
<222> LOCATION: (9)..(9)
<223> OTHER INFORMATION: /note="2'-F modified nucleotide"
<220> FEATURE:
<221> NAME/KEY: misc_feature
<222> LOCATION: (10)..(10)
<223> OTHER INFORMATION: /note="2'-F modified nucleotide"
<220> FEATURE:
<221> NAME/KEY: misc_feature
<222> LOCATION: (11)..(11)
<223> OTHER INFORMATION: /note="2'-F modified nucleotide"
<220> FEATURE:
<221> NAME/KEY: misc_feature
<222> LOCATION: (12)..(12)
<223> OTHER INFORMATION: /note="2'-OMe modified nucleotide"
<220> FEATURE:
<221> NAME/KEY: misc_feature
<222> LOCATION: (13)..(13)
<223> OTHER INFORMATION: /note="2'-OMe modified nucleotide"
<220> FEATURE:
<221> NAME/KEY: misc_feature
<222> LOCATION: (14)..(14)
<223> OTHER INFORMATION: /note="2'-OMe modified nucleotide"
<220> FEATURE:
<221> NAME/KEY: misc_feature
<222> LOCATION: (15)..(15)
<223> OTHER INFORMATION: /note="2'-OMe modified nucleotide"
<220> FEATURE:
<221> NAME/KEY: misc_feature
<222> LOCATION: (16)..(16)
<223> OTHER INFORMATION: /note="2'-OMe modified nucleotide"
<220> FEATURE:
<221> NAME/KEY: misc_feature
<222> LOCATION: (17)..(17)
<223> OTHER INFORMATION: /note="2'-OMe modified nucleotide"
<220> FEATURE:
<221> NAME/KEY: misc_feature
<222> LOCATION: (18)..(18)
<223> OTHER INFORMATION: /note="2'-OMe modified nucleotide"
<220> FEATURE:
<221> NAME/KEY: misc_feature
<222> LOCATION: (19)..(19)
<223> OTHER INFORMATION: /note="2'-OMe modified nucleotide"
<220> FEATURE:
<221> NAME/KEY: misc_feature
<222> LOCATION: (20)..(20)
<223> OTHER INFORMATION: /note="2'-OMe modified nucleotide"
<220> FEATURE:
<221> NAME/KEY: misc_feature
<222> LOCATION: (21)..(21)
<223> OTHER INFORMATION: /note="2'-OMe modified nucleotide"
<220> FEATURE:
<221> NAME/KEY: misc_feature
<222> LOCATION: (22)..(22)
<223> OTHER INFORMATION: /note="2'-OMe modified nucleotide"
<220> FEATURE:
<221> NAME/KEY: misc_feature
<222> LOCATION: (23)..(23)
<223> OTHER INFORMATION: /note="2'-OMe modified nucleotide"
<220> FEATURE:
<221> NAME/KEY: misc_feature
<222> LOCATION: (24)..(24)
<223> OTHER INFORMATION: /note="2'-OMe modified nucleotide"
<220> FEATURE:
<221> NAME/KEY: misc_feature
<222> LOCATION: (25)..(25)
<223> OTHER INFORMATION: /note="2'-OMe modified nucleotide"
<220> FEATURE:
<221> NAME/KEY: misc_feature
<222> LOCATION: (26)..(26)
<223> OTHER INFORMATION: /note="2'-OMe modified nucleotide"
<220> FEATURE:
<221> NAME/KEY: misc_feature
<222> LOCATION: (27)..(27)
<223> OTHER INFORMATION: /note="2'-OMe modified nucleotide"
<220> FEATURE:
<221> NAME/KEY: misc_feature
<222> LOCATION: (28)..(28)
<223> OTHER INFORMATION: /note="ademA-GalNAc"
<220> FEATURE:
<221> NAME/KEY: misc_feature
<222> LOCATION: (29)..(29)
<223> OTHER INFORMATION: /note="ademA-GalNAc"
<220> FEATURE:
<221> NAME/KEY: misc_feature
<222> LOCATION: (30)..(30)
<223> OTHER INFORMATION: /note="ademA-GalNAc"
<220> FEATURE:
<221> NAME/KEY: misc_feature
<222> LOCATION: (31)..(31)
<223> OTHER INFORMATION: /note="2'-OMe modified nucleotide"
<220> FEATURE:
<221> NAME/KEY: misc_feature
<222> LOCATION: (32)..(32)
<223> OTHER INFORMATION: /note="2'-OMe modified nucleotide"
<220> FEATURE:
<221> NAME/KEY: misc_feature
<222> LOCATION: (33)..(33)
<223> OTHER INFORMATION: /note="2'-OMe modified nucleotide"
<220> FEATURE:
<221> NAME/KEY: misc_feature
<222> LOCATION: (34)..(34)
<223> OTHER INFORMATION: /note="2'-OMe modified nucleotide"
<220> FEATURE:
<221> NAME/KEY: misc_feature
<222> LOCATION: (35)..(35)
<223> OTHER INFORMATION: /note="2'-OMe modified nucleotide"
<220> FEATURE:
<221> NAME/KEY: misc_feature
<222> LOCATION: (36)..(36)
<223> OTHER INFORMATION: /note="2'-OMe modified nucleotide"

<400> SEQUENCE: 152
gagccaaaau caagauuuga gcagccgaaa ggcugc 36

<210> SEQ ID NO 153
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: misc_feature
<222> LOCATION: (1)..(1)
<223> OTHER INFORMATION: /note="MePhosphonate-4O-mUs"
<220> FEATURE:
<221> NAME/KEY: misc_feature
<222> LOCATION: (2)..(2)
<223> OTHER INFORMATION: /note="2'-F modified nucleotide with a 3'-phosphorothioate linkage"
<220> FEATURE:
<221> NAME/KEY: misc_feature
<222> LOCATION: (3)..(3)
<223> OTHER INFORMATION: /note="2'-F modified nucleotide with a 3'-phosphorothioate linkage"
<220> FEATURE:

<221> NAME/KEY: misc_feature
<222> LOCATION: (4)..(4)
<223> OTHER INFORMATION: /note="2'-F modified nucleotide"
<220> FEATURE:
<221> NAME/KEY: misc_feature
<222> LOCATION: (5)..(5)
<223> OTHER INFORMATION: /note="2'-F modified nucleotide"
<220> FEATURE:
<221> NAME/KEY: misc_feature
<222> LOCATION: (6)..(6)
<223> OTHER INFORMATION: /note="2'-OMe modified nucleotide"
<220> FEATURE:
<221> NAME/KEY: misc_feature
<222> LOCATION: (7)..(7)
<223> OTHER INFORMATION: /note="2'-F modified nucleotide"
<220> FEATURE:
<221> NAME/KEY: misc_feature
<222> LOCATION: (8)..(8)
<223> OTHER INFORMATION: /note="2'-OMe modified nucleotide"
<220> FEATURE:
<221> NAME/KEY: misc_feature
<222> LOCATION: (9)..(9)
<223> OTHER INFORMATION: /note="2'-OMe modified nucleotide"
<220> FEATURE:
<221> NAME/KEY: misc_feature
<222> LOCATION: (10)..(10)
<223> OTHER INFORMATION: /note="2'-F modified nucleotide"
<220> FEATURE:
<221> NAME/KEY: misc_feature
<222> LOCATION: (11)..(11)
<223> OTHER INFORMATION: /note="2'-OMe modified nucleotide"
<220> FEATURE:
<221> NAME/KEY: misc_feature
<222> LOCATION: (12)..(12)
<223> OTHER INFORMATION: /note="2'-OMe modified nucleotide"
<220> FEATURE:
<221> NAME/KEY: misc_feature
<222> LOCATION: (13)..(13)
<223> OTHER INFORMATION: /note="2'-OMe modified nucleotide"
<220> FEATURE:
<221> NAME/KEY: misc_feature
<222> LOCATION: (14)..(14)
<223> OTHER INFORMATION: /note="2'-F modified nucleotide"
<220> FEATURE:
<221> NAME/KEY: misc_feature
<222> LOCATION: (15)..(15)
<223> OTHER INFORMATION: /note="2'-OMe modified nucleotide"
<220> FEATURE:
<221> NAME/KEY: misc_feature
<222> LOCATION: (16)..(16)
<223> OTHER INFORMATION: /note="2'-OMe modified nucleotide"
<220> FEATURE:
<221> NAME/KEY: misc_feature
<222> LOCATION: (17)..(17)
<223> OTHER INFORMATION: /note="2'-OMe modified nucleotide"
<220> FEATURE:
<221> NAME/KEY: misc_feature
<222> LOCATION: (18)..(18)
<223> OTHER INFORMATION: /note="2'-OMe modified nucleotide"
<220> FEATURE:
<221> NAME/KEY: misc_feature
<222> LOCATION: (19)..(19)
<223> OTHER INFORMATION: /note="2'-OMe modified nucleotide"
<220> FEATURE:
<221> NAME/KEY: misc_feature
<222> LOCATION: (20)..(20)
<223> OTHER INFORMATION: /note="2'-OMe modified nucleotide with a 3'-phosphorothioate linkage"
<220> FEATURE:
<221> NAME/KEY: misc_feature
<222> LOCATION: (21)..(21)
<223> OTHER INFORMATION: /note="2'-OMe modified nucleotide with a 3'-phosphorothioate linkage"
<220> FEATURE:
<221> NAME/KEY: misc_feature
<222> LOCATION: (22)..(22)
<223> OTHER INFORMATION: /note="2'-OMe modified nucleotide"

<400> SEQUENCE: 153
ucaaaucuug auuuuggcuc gg 22

<210> SEQ ID NO 154
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: misc_feature
<222> LOCATION: (1)..(1)
<223> OTHER INFORMATION: /note="2'-OMe modified nucleotide with a 3'-phosphorothioate linkage"
<220> FEATURE:
<221> NAME/KEY: misc_feature
<222> LOCATION: (2)..(2)
<223> OTHER INFORMATION: /note="2'-OMe modified nucleotide"
<220> FEATURE:
<221> NAME/KEY: misc_feature
<222> LOCATION: (3)..(3)
<223> OTHER INFORMATION: /note="2'-OMe modified nucleotide"
<220> FEATURE:
<221> NAME/KEY: misc_feature
<222> LOCATION: (4)..(4)
<223> OTHER INFORMATION: /note="2'-OMe modified nucleotide"
<220> FEATURE:
<221> NAME/KEY: misc_feature
<222> LOCATION: (5)..(5)
<223> OTHER INFORMATION: /note="2'-OMe modified nucleotide"
<220> FEATURE:
<221> NAME/KEY: misc_feature
<222> LOCATION: (6)..(6)
<223> OTHER INFORMATION: /note="2'-OMe modified nucleotide"
<220> FEATURE:
<221> NAME/KEY: misc_feature
<222> LOCATION: (7)..(7)
<223> OTHER INFORMATION: /note="2'-OMe modified nucleotide"
<220> FEATURE:
<221> NAME/KEY: misc_feature
<222> LOCATION: (8)..(8)
<223> OTHER INFORMATION: /note="2'-F modified nucleotide"
<220> FEATURE:
<221> NAME/KEY: misc_feature
<222> LOCATION: (9)..(9)
<223> OTHER INFORMATION: /note="2'-F modified nucleotide"
<220> FEATURE:
<221> NAME/KEY: misc_feature
<222> LOCATION: (10)..(10)
<223> OTHER INFORMATION: /note="2'-F modified nucleotide"
<220> FEATURE:
<221> NAME/KEY: misc_feature
<222> LOCATION: (11)..(11)
<223> OTHER INFORMATION: /note="2'-F modified nucleotide"
<220> FEATURE:
<221> NAME/KEY: misc_feature
<222> LOCATION: (12)..(12)
<223> OTHER INFORMATION: /note="2'-OMe modified nucleotide"
<220> FEATURE:
<221> NAME/KEY: misc_feature
<222> LOCATION: (13)..(13)
<223> OTHER INFORMATION: /note="2'-OMe modified nucleotide"
<220> FEATURE:
<221> NAME/KEY: misc_feature
<222> LOCATION: (14)..(14)
<223> OTHER INFORMATION: /note="2'-OMe modified nucleotide"
<220> FEATURE:
<221> NAME/KEY: misc_feature
<222> LOCATION: (15)..(15)
<223> OTHER INFORMATION: /note="2'-OMe modified nucleotide"
<220> FEATURE:
<221> NAME/KEY: misc_feature
<222> LOCATION: (16)..(16)
<223> OTHER INFORMATION: /note="2'-OMe modified nucleotide"
<220> FEATURE:
<221> NAME/KEY: misc_feature -continued
<222> LOCATION: (17)..(17)
<223> OTHER INFORMATION: /note="2'-OMe modified nucleotide"
<220> FEATURE:
<221> NAME/KEY: misc_feature
<222> LOCATION: (18)..(18)
<223> OTHER INFORMATION: /note="2'-OMe modified nucleotide"
<220> FEATURE:
<221> NAME/KEY: misc_feature
<222> LOCATION: (19)..(19)
<223> OTHER INFORMATION: /note="2'-OMe modified nucleotide"
<220> FEATURE:
<221> NAME/KEY: misc_feature
<222> LOCATION: (20)..(20)
<223> OTHER INFORMATION: /note="2'-OMe modified nucleotide"
<220> FEATURE:
<221> NAME/KEY: misc_feature
<222> LOCATION: (21)..(21)
<223> OTHER INFORMATION: /note="2'-OMe modified nucleotide"
<220> FEATURE:
<221> NAME/KEY: misc_feature
<222> LOCATION: (22)..(22)
<223> OTHER INFORMATION: /note="2'-OMe modified nucleotide"
<220> FEATURE:
<221> NAME/KEY: misc_feature
<222> LOCATION: (23)..(23)
<223> OTHER INFORMATION: /note="2'-OMe modified nucleotide"
<220> FEATURE:
<221> NAME/KEY: misc_feature
<222> LOCATION: (24)..(24)
<223> OTHER INFORMATION: /note="2'-OMe modified nucleotide"
<220> FEATURE:
<221> NAME/KEY: misc_feature
<222> LOCATION: (25)..(25)
<223> OTHER INFORMATION: /note="2'-OMe modified nucleotide"
<220> FEATURE:
<221> NAME/KEY: misc_feature
<222> LOCATION: (26)..(26)
<223> OTHER INFORMATION: /note="2'-OMe modified nucleotide"
<220> FEATURE:
<221> NAME/KEY: misc_feature
<222> LOCATION: (27)..(27)
<223> OTHER INFORMATION: /note="2'-OMe modified nucleotide"
<220> FEATURE:
<221> NAME/KEY: misc_feature
<222> LOCATION: (28)..(28)
<223> OTHER INFORMATION: /note="ademA-GalNAc"
<220> FEATURE:
<221> NAME/KEY: misc_feature
<222> LOCATION: (29)..(29)
<223> OTHER INFORMATION: /note="ademA-GalNAc"
<220> FEATURE:
<221> NAME/KEY: misc_feature
<222> LOCATION: (30)..(30)
<223> OTHER INFORMATION: /note="ademA-GalNAc"
<220> FEATURE:
<221> NAME/KEY: misc_feature
<222> LOCATION: (31)..(31)
<223> OTHER INFORMATION: /note="2'-OMe modified nucleotide"
<220> FEATURE:
<221> NAME/KEY: misc_feature
<222> LOCATION: (32)..(32)
<223> OTHER INFORMATION: /note="2'-OMe modified nucleotide"
<220> FEATURE:
<221> NAME/KEY: misc_feature
<222> LOCATION: (33)..(33)
<223> OTHER INFORMATION: /note="2'-OMe modified nucleotide"
<220> FEATURE:
<221> NAME/KEY: misc_feature
<222> LOCATION: (34)..(34)
<223> OTHER INFORMATION: /note="2'-OMe modified nucleotide"
<220> FEATURE:
<221> NAME/KEY: misc_feature
<222> LOCATION: (35)..(35)
<223> OTHER INFORMATION: /note="2'-OMe modified nucleotide"
<220> FEATURE:
<221> NAME/KEY: misc_feature
<222> LOCATION: (36)..(36)
<223> OTHER INFORMATION: /note="2'-OMe modified nucleotide"

<400> SEQUENCE: 154
ccaaaaucaa gauuugcuaa gcagccgaaa ggcugc 36

<210> SEQ ID NO 155
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: misc_feature
<222> LOCATION: (1)..(1)
<223> OTHER INFORMATION: /note="MePhosphonate-4O-mUs"
<220> FEATURE:
<221> NAME/KEY: misc_feature
<222> LOCATION: (2)..(2)
<223> OTHER INFORMATION: /note="2'-F modified nucleotide with a 3'-phosphorothioate linkage"
<220> FEATURE:
<221> NAME/KEY: misc_feature
<222> LOCATION: (3)..(3)
<223> OTHER INFORMATION: /note="2'-F modified nucleotide with a 3'-phosphorothioate linkage"
<220> FEATURE:
<221> NAME/KEY: misc_feature
<222> LOCATION: (4)..(4)
<223> OTHER INFORMATION: /note="2'-F modified nucleotide"
<220> FEATURE:
<221> NAME/KEY: misc_feature
<222> LOCATION: (5)..(5)
<223> OTHER INFORMATION: /note="2'-F modified nucleotide"
<220> FEATURE:
<221> NAME/KEY: misc_feature
<222> LOCATION: (6)..(6)
<223> OTHER INFORMATION: /note="2'-OMe modified nucleotide"
<220> FEATURE:
<221> NAME/KEY: misc_feature
<222> LOCATION: (7)..(7)
<223> OTHER INFORMATION: /note="2'-F modified nucleotide"
<220> FEATURE:
<221> NAME/KEY: misc_feature
<222> LOCATION: (8)..(8)
<223> OTHER INFORMATION: /note="2'-OMe modified nucleotide"
<220> FEATURE:
<221> NAME/KEY: misc_feature
<222> LOCATION: (9)..(9)
<223> OTHER INFORMATION: /note="2'-OMe modified nucleotide"
<220> FEATURE:
<221> NAME/KEY: misc_feature
<222> LOCATION: (10)..(10)
<223> OTHER INFORMATION: /note="2'-F modified nucleotide"
<220> FEATURE:
<221> NAME/KEY: misc_feature
<222> LOCATION: (11)..(11)
<223> OTHER INFORMATION: /note="2'-OMe modified nucleotide"
<220> FEATURE:
<221> NAME/KEY: misc_feature
<222> LOCATION: (12)..(12)
<223> OTHER INFORMATION: /note="2'-OMe modified nucleotide"
<220> FEATURE:
<221> NAME/KEY: misc_feature
<222> LOCATION: (13)..(13)
<223> OTHER INFORMATION: /note="2'-OMe modified nucleotide"
<220> FEATURE:
<221> NAME/KEY: misc_feature
<222> LOCATION: (14)..(14)
<223> OTHER INFORMATION: /note="2'-F modified nucleotide"
<220> FEATURE:
<221> NAME/KEY: misc_feature
<222> LOCATION: (15)..(15)
<223> OTHER INFORMATION: /note="2'-OMe modified nucleotide"
<220> FEATURE:
<221> NAME/KEY: misc_feature
<222> LOCATION: (16)..(16)
<223> OTHER INFORMATION: /note="2'-OMe modified nucleotide"

<220> FEATURE:
<221> NAME/KEY: misc_feature
<222> LOCATION: (17)..(17)
<223> OTHER INFORMATION: /note="2'-OMe modified nucleotide"
<220> FEATURE:
<221> NAME/KEY: misc_feature
<222> LOCATION: (18)..(18)
<223> OTHER INFORMATION: /note="2'-OMe modified nucleotide"
<220> FEATURE:
<221> NAME/KEY: misc_feature
<222> LOCATION: (19)..(19)
<223> OTHER INFORMATION: /note="2'-OMe modified nucleotide"
<220> FEATURE:
<221> NAME/KEY: misc_feature
<222> LOCATION: (20)..(20)
<223> OTHER INFORMATION: /note="2'-OMe modified nucleotide with a 3'-phosphorothioate linkage"
<220> FEATURE:
<221> NAME/KEY: misc_feature
<222> LOCATION: (21)..(21)
<223> OTHER INFORMATION: /note="2'-OMe modified nucleotide with a 3'-phosphorothioate linkage"
<220> FEATURE:
<221> NAME/KEY: misc_feature
<222> LOCATION: (22)..(22)
<223> OTHER INFORMATION: /note="2'-OMe modified nucleotide"

<400> SEQUENCE: 155
uuagcaaauc uugauuuugg gg 22

<210> SEQ ID NO 156
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: misc_feature
<222> LOCATION: (1)..(1)
<223> OTHER INFORMATION: /note="2'-OMe modified nucleotide with a 3'-phosphorothioate linkage"
<220> FEATURE:
<221> NAME/KEY: misc_feature
<222> LOCATION: (2)..(2)
<223> OTHER INFORMATION: /note="2'-OMe modified nucleotide"
<220> FEATURE:
<221> NAME/KEY: misc_feature
<222> LOCATION: (3)..(3)
<223> OTHER INFORMATION: /note="2'-OMe modified nucleotide"
<220> FEATURE:
<221> NAME/KEY: misc_feature
<222> LOCATION: (4)..(4)
<223> OTHER INFORMATION: /note="2'-OMe modified nucleotide"
<220> FEATURE:
<221> NAME/KEY: misc_feature
<222> LOCATION: (5)..(5)
<223> OTHER INFORMATION: /note="2'-OMe modified nucleotide"
<220> FEATURE:
<221> NAME/KEY: misc_feature
<222> LOCATION: (6)..(6)
<223> OTHER INFORMATION: /note="2'-OMe modified nucleotide"
<220> FEATURE:
<221> NAME/KEY: misc_feature
<222> LOCATION: (7)..(7)
<223> OTHER INFORMATION: /note="2'-OMe modified nucleotide"
<220> FEATURE:
<221> NAME/KEY: misc_feature
<222> LOCATION: (8)..(8)
<223> OTHER INFORMATION: /note="2'-F modified nucleotide"
<220> FEATURE:
<221> NAME/KEY: misc_feature
<222> LOCATION: (9)..(9)
<223> OTHER INFORMATION: /note="2'-F modified nucleotide"
<220> FEATURE:
<221> NAME/KEY: misc_feature
<222> LOCATION: (10)..(10)
<223> OTHER INFORMATION: /note="2'-F modified nucleotide"
<220> FEATURE:
<221> NAME/KEY: misc_feature
<222> LOCATION: (11)..(11)
<223> OTHER INFORMATION: /note="2'-F modified nucleotide"
<220> FEATURE:
<221> NAME/KEY: misc_feature
<222> LOCATION: (12)..(12)
<223> OTHER INFORMATION: /note="2'-OMe modified nucleotide"
<220> FEATURE:
<221> NAME/KEY: misc_feature
<222> LOCATION: (13)..(13)
<223> OTHER INFORMATION: /note="2'-OMe modified nucleotide"
<220> FEATURE:
<221> NAME/KEY: misc_feature
<222> LOCATION: (14)..(14)
<223> OTHER INFORMATION: /note="2'-OMe modified nucleotide"
<220> FEATURE:
<221> NAME/KEY: misc_feature
<222> LOCATION: (15)..(15)
<223> OTHER INFORMATION: /note="2'-OMe modified nucleotide"
<220> FEATURE:
<221> NAME/KEY: misc_feature
<222> LOCATION: (16)..(16)
<223> OTHER INFORMATION: /note="2'-OMe modified nucleotide"
<220> FEATURE:
<221> NAME/KEY: misc_feature
<222> LOCATION: (17)..(17)
<223> OTHER INFORMATION: /note="2'-OMe modified nucleotide"
<220> FEATURE:
<221> NAME/KEY: misc_feature
<222> LOCATION: (18)..(18)
<223> OTHER INFORMATION: /note="2'-OMe modified nucleotide"
<220> FEATURE:
<221> NAME/KEY: misc_feature
<222> LOCATION: (19)..(19)
<223> OTHER INFORMATION: /note="2'-OMe modified nucleotide"
<220> FEATURE:
<221> NAME/KEY: misc_feature
<222> LOCATION: (20)..(20)
<223> OTHER INFORMATION: /note="2'-OMe modified nucleotide"
<220> FEATURE:
<221> NAME/KEY: misc_feature
<222> LOCATION: (21)..(21)
<223> OTHER INFORMATION: /note="2'-OMe modified nucleotide"
<220> FEATURE:
<221> NAME/KEY: misc_feature
<222> LOCATION: (22)..(22)
<223> OTHER INFORMATION: /note="2'-OMe modified nucleotide"
<220> FEATURE:
<221> NAME/KEY: misc_feature
<222> LOCATION: (23)..(23)
<223> OTHER INFORMATION: /note="2'-OMe modified nucleotide"
<220> FEATURE:
<221> NAME/KEY: misc_feature
<222> LOCATION: (24)..(24)
<223> OTHER INFORMATION: /note="2'-OMe modified nucleotide"
<220> FEATURE:
<221> NAME/KEY: misc_feature
<222> LOCATION: (25)..(25)
<223> OTHER INFORMATION: /note="2'-OMe modified nucleotide"
<220> FEATURE:
<221> NAME/KEY: misc_feature
<222> LOCATION: (26)..(26)
<223> OTHER INFORMATION: /note="2'-OMe modified nucleotide"
<220> FEATURE:
<221> NAME/KEY: misc_feature
<222> LOCATION: (27)..(27)
<223> OTHER INFORMATION: /note="2'-OMe modified nucleotide"
<220> FEATURE:
<221> NAME/KEY: misc_feature
<222> LOCATION: (28)..(28)
<223> OTHER INFORMATION: /note="ademA-GalNAc"
<220> FEATURE:
<221> NAME/KEY: misc_feature
<222> LOCATION: (29)..(29)
<223> OTHER INFORMATION: /note="ademA-GalNAc"
<220> FEATURE:

<221> NAME/KEY: misc_feature
<222> LOCATION: (30)..(30)
<223> OTHER INFORMATION: /note="ademA-GalNAc"
<220> FEATURE:
<221> NAME/KEY: misc_feature
<222> LOCATION: (31)..(31)
<223> OTHER INFORMATION: /note="2'-OMe modified nucleotide"
<220> FEATURE:
<221> NAME/KEY: misc_feature
<222> LOCATION: (32)..(32)
<223> OTHER INFORMATION: /note="2'-OMe modified nucleotide"
<220> FEATURE:
<221> NAME/KEY: misc_feature
<222> LOCATION: (33)..(33)
<223> OTHER INFORMATION: /note="2'-OMe modified nucleotide"
<220> FEATURE:
<221> NAME/KEY: misc_feature
<222> LOCATION: (34)..(34)
<223> OTHER INFORMATION: /note="2'-OMe modified nucleotide"
<220> FEATURE:
<221> NAME/KEY: misc_feature
<222> LOCATION: (35)..(35)
<223> OTHER INFORMATION: /note="2'-OMe modified nucleotide"
<220> FEATURE:
<221> NAME/KEY: misc_feature
<222> LOCATION: (36)..(36)
<223> OTHER INFORMATION: /note="2'-OMe modified nucleotide"

<400> SEQUENCE: 156
caaaaucaag auuugcuaua gcagccgaaa ggcugc 36

<210> SEQ ID NO 157
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: misc_feature
<222> LOCATION: (1)..(1)
<223> OTHER INFORMATION: /note="MePhosphonate-4O-mUs"
<220> FEATURE:
<221> NAME/KEY: misc_feature
<222> LOCATION: (2)..(2)
<223> OTHER INFORMATION: /note="2'-F modified nucleotide with a 3'-phosphorothioate linkage"
<220> FEATURE:
<221> NAME/KEY: misc_feature
<222> LOCATION: (3)..(3)
<223> OTHER INFORMATION: /note="2'-F modified nucleotide with a 3'-phosphorothioate linkage"
<220> FEATURE:
<221> NAME/KEY: misc_feature
<222> LOCATION: (4)..(4)
<223> OTHER INFORMATION: /note="2'-F modified nucleotide"
<220> FEATURE:
<221> NAME/KEY: misc_feature
<222> LOCATION: (5)..(5)
<223> OTHER INFORMATION: /note="2'-F modified nucleotide"
<220> FEATURE:
<221> NAME/KEY: misc_feature
<222> LOCATION: (6)..(6)
<223> OTHER INFORMATION: /note="2'-OMe modified nucleotide"
<220> FEATURE:
<221> NAME/KEY: misc_feature
<222> LOCATION: (7)..(7)
<223> OTHER INFORMATION: /note="2'-F modified nucleotide"
<220> FEATURE:
<221> NAME/KEY: misc_feature
<222> LOCATION: (8)..(8)
<223> OTHER INFORMATION: /note="2'-OMe modified nucleotide"
<220> FEATURE:
<221> NAME/KEY: misc_feature
<222> LOCATION: (9)..(9)
<223> OTHER INFORMATION: /note="2'-OMe modified nucleotide"

<220> FEATURE:
<221> NAME/KEY: misc_feature
<222> LOCATION: (10)..(10)
<223> OTHER INFORMATION: /note="2'-F modified nucleotide"
<220> FEATURE:
<221> NAME/KEY: misc_feature
<222> LOCATION: (11)..(11)
<223> OTHER INFORMATION: /note="2'-OMe modified nucleotide"
<220> FEATURE:
<221> NAME/KEY: misc_feature
<222> LOCATION: (12)..(12)
<223> OTHER INFORMATION: /note="2'-OMe modified nucleotide"
<220> FEATURE:
<221> NAME/KEY: misc_feature
<222> LOCATION: (13)..(13)
<223> OTHER INFORMATION: /note="2'-OMe modified nucleotide"
<220> FEATURE:
<221> NAME/KEY: misc_feature
<222> LOCATION: (14)..(14)
<223> OTHER INFORMATION: /note="2'-F modified nucleotide"
<220> FEATURE:
<221> NAME/KEY: misc_feature
<222> LOCATION: (15)..(15)
<223> OTHER INFORMATION: /note="2'-OMe modified nucleotide"
<220> FEATURE:
<221> NAME/KEY: misc_feature
<222> LOCATION: (16)..(16)
<223> OTHER INFORMATION: /note="2'-OMe modified nucleotide"
<220> FEATURE:
<221> NAME/KEY: misc_feature
<222> LOCATION: (17)..(17)
<223> OTHER INFORMATION: /note="2'-OMe modified nucleotide"
<220> FEATURE:
<221> NAME/KEY: misc_feature
<222> LOCATION: (18)..(18)
<223> OTHER INFORMATION: /note="2'-OMe modified nucleotide"
<220> FEATURE:
<221> NAME/KEY: misc_feature
<222> LOCATION: (19)..(19)
<223> OTHER INFORMATION: /note="2'-OMe modified nucleotide"
<220> FEATURE:
<221> NAME/KEY: misc_feature
<222> LOCATION: (20)..(20)
<223> OTHER INFORMATION: /note="2'-OMe modified nucleotide with a 3'-phosphorothioate linkage"
<220> FEATURE:
<221> NAME/KEY: misc_feature
<222> LOCATION: (21)..(21)
<223> OTHER INFORMATION: /note="2'-OMe modified nucleotide with a 3'-phosphorothioate linkage"
<220> FEATURE:
<221> NAME/KEY: misc_feature
<222> LOCATION: (22)..(22)
<223> OTHER INFORMATION: /note="2'-OMe modified nucleotide"

<400> SEQUENCE: 157
uauagcaaau cuugauuuug gg 22

<210> SEQ ID NO 158
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: misc_feature
<222> LOCATION: (1)..(1)
<223> OTHER INFORMATION: /note="2'-OMe modified nucleotide with a 3'-phosphorothioate linkage"
<220> FEATURE:
<221> NAME/KEY: misc_feature
<222> LOCATION: (2)..(2)
<223> OTHER INFORMATION: /note="2'-OMe modified nucleotide"
<220> FEATURE:
<221> NAME/KEY: misc_feature
<222> LOCATION: (3)..(3)
<223> OTHER INFORMATION: /note="2'-OMe modified nucleotide"
<220> FEATURE:
<221> NAME/KEY: misc_feature
<222> LOCATION: (4)..(4)
<223> OTHER INFORMATION: /note="2'-OMe modified nucleotide"
<220> FEATURE:
<221> NAME/KEY: misc_feature
<222> LOCATION: (5)..(5)
<223> OTHER INFORMATION: /note="2'-OMe modified nucleotide"
<220> FEATURE:
<221> NAME/KEY: misc_feature
<222> LOCATION: (6)..(6)
<223> OTHER INFORMATION: /note="2'-OMe modified nucleotide"
<220> FEATURE:
<221> NAME/KEY: misc_feature
<222> LOCATION: (7)..(7)
<223> OTHER INFORMATION: /note="2'-OMe modified nucleotide"
<220> FEATURE:
<221> NAME/KEY: misc_feature
<222> LOCATION: (8)..(8)
<223> OTHER INFORMATION: /note="2'-F modified nucleotide"
<220> FEATURE:
<221> NAME/KEY: misc_feature
<222> LOCATION: (9)..(9)
<223> OTHER INFORMATION: /note="2'-F modified nucleotide"
<220> FEATURE:
<221> NAME/KEY: misc_feature
<222> LOCATION: (10)..(10)
<223> OTHER INFORMATION: /note="2'-F modified nucleotide"
<220> FEATURE:
<221> NAME/KEY: misc_feature
<222> LOCATION: (11)..(11)
<223> OTHER INFORMATION: /note="2'-F modified nucleotide"
<220> FEATURE:
<221> NAME/KEY: misc_feature
<222> LOCATION: (12)..(12)
<223> OTHER INFORMATION: /note="2'-OMe modified nucleotide"
<220> FEATURE:
<221> NAME/KEY: misc_feature
<222> LOCATION: (13)..(13)
<223> OTHER INFORMATION: /note="2'-OMe modified nucleotide"
<220> FEATURE:
<221> NAME/KEY: misc_feature
<222> LOCATION: (14)..(14)
<223> OTHER INFORMATION: /note="2'-OMe modified nucleotide"
<220> FEATURE:
<221> NAME/KEY: misc_feature
<222> LOCATION: (15)..(15)
<223> OTHER INFORMATION: /note="2'-OMe modified nucleotide"
<220> FEATURE:
<221> NAME/KEY: misc_feature
<222> LOCATION: (16)..(16)
<223> OTHER INFORMATION: /note="2'-OMe modified nucleotide"
<220> FEATURE:
<221> NAME/KEY: misc_feature
<222> LOCATION: (17)..(17)
<223> OTHER INFORMATION: /note="2'-OMe modified nucleotide"
<220> FEATURE:
<221> NAME/KEY: misc_feature
<222> LOCATION: (18)..(18)
<223> OTHER INFORMATION: /note="2'-OMe modified nucleotide"
<220> FEATURE:
<221> NAME/KEY: misc_feature
<222> LOCATION: (19)..(19)
<223> OTHER INFORMATION: /note="2'-OMe modified nucleotide"
<220> FEATURE:
<221> NAME/KEY: misc_feature
<222> LOCATION: (20)..(20)
<223> OTHER INFORMATION: /note="2'-OMe modified nucleotide"
<220> FEATURE:
<221> NAME/KEY: misc_feature
<222> LOCATION: (21)..(21)
<223> OTHER INFORMATION: /note="2'-OMe modified nucleotide"
<220> FEATURE:
<221> NAME/KEY: misc_feature
<222> LOCATION: (22)..(22)
<223> OTHER INFORMATION: /note="2'-OMe modified nucleotide"
<220> FEATURE:

<221> NAME/KEY: misc_feature
<222> LOCATION: (23)..(23)
<223> OTHER INFORMATION: /note="2'-OMe modified nucleotide"
<220> FEATURE:
<221> NAME/KEY: misc_feature
<222> LOCATION: (24)..(24)
<223> OTHER INFORMATION: /note="2'-OMe modified nucleotide"
<220> FEATURE:
<221> NAME/KEY: misc_feature
<222> LOCATION: (25)..(25)
<223> OTHER INFORMATION: /note="2'-OMe modified nucleotide"
<220> FEATURE:
<221> NAME/KEY: misc_feature
<222> LOCATION: (26)..(26)
<223> OTHER INFORMATION: /note="2'-OMe modified nucleotide"
<220> FEATURE:
<221> NAME/KEY: misc_feature
<222> LOCATION: (27)..(27)
<223> OTHER INFORMATION: /note="2'-OMe modified nucleotide"
<220> FEATURE:
<221> NAME/KEY: misc_feature
<222> LOCATION: (28)..(28)
<223> OTHER INFORMATION: /note="ademA-GalNAc"
<220> FEATURE:
<221> NAME/KEY: misc_feature
<222> LOCATION: (29)..(29)
<223> OTHER INFORMATION: /note="ademA-GalNAc"
<220> FEATURE:
<221> NAME/KEY: misc_feature
<222> LOCATION: (30)..(30)
<223> OTHER INFORMATION: /note="ademA-GalNAc"
<220> FEATURE:
<221> NAME/KEY: misc_feature
<222> LOCATION: (31)..(31)
<223> OTHER INFORMATION: /note="2'-OMe modified nucleotide"
<220> FEATURE:
<221> NAME/KEY: misc_feature
<222> LOCATION: (32)..(32)
<223> OTHER INFORMATION: /note="2'-OMe modified nucleotide"
<220> FEATURE:
<221> NAME/KEY: misc_feature
<222> LOCATION: (33)..(33)
<223> OTHER INFORMATION: /note="2'-OMe modified nucleotide"
<220> FEATURE:
<221> NAME/KEY: misc_feature
<222> LOCATION: (34)..(34)
<223> OTHER INFORMATION: /note="2'-OMe modified nucleotide"
<220> FEATURE:
<221> NAME/KEY: misc_feature
<222> LOCATION: (35)..(35)
<223> OTHER INFORMATION: /note="2'-OMe modified nucleotide"
<220> FEATURE:
<221> NAME/KEY: misc_feature
<222> LOCATION: (36)..(36)
<223> OTHER INFORMATION: /note="2'-OMe modified nucleotide"

<400> SEQUENCE: 158
aaaaucaaga uuugcuauga gcagccgaaa ggcugc 36

<210> SEQ ID NO 159
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: misc_feature
<222> LOCATION: (1)..(1)
<223> OTHER INFORMATION: /note="MePhosphonate-4O-mUs"
<220> FEATURE:
<221> NAME/KEY: misc_feature
<222> LOCATION: (2)..(2)
<223> OTHER INFORMATION: /note="2'-F modified nucleotide with a 3'-phosphorothioate linkage"
<220> FEATURE:

<221> NAME/KEY: misc_feature
<222> LOCATION: (3)..(3)
<223> OTHER INFORMATION: /note="2'-F modified nucleotide with a 3'-phosphorothioate linkage"
<220> FEATURE:
<221> NAME/KEY: misc_feature
<222> LOCATION: (4)..(4)
<223> OTHER INFORMATION: /note="2'-F modified nucleotide"
<220> FEATURE:
<221> NAME/KEY: misc_feature
<222> LOCATION: (5)..(5)
<223> OTHER INFORMATION: /note="2'-F modified nucleotide"
<220> FEATURE:
<221> NAME/KEY: misc_feature
<222> LOCATION: (6)..(6)
<223> OTHER INFORMATION: /note="2'-OMe modified nucleotide"
<220> FEATURE:
<221> NAME/KEY: misc_feature
<222> LOCATION: (7)..(7)
<223> OTHER INFORMATION: /note="2'-F modified nucleotide"
<220> FEATURE:
<221> NAME/KEY: misc_feature
<222> LOCATION: (8)..(8)
<223> OTHER INFORMATION: /note="2'-OMe modified nucleotide"
<220> FEATURE:
<221> NAME/KEY: misc_feature
<222> LOCATION: (9)..(9)
<223> OTHER INFORMATION: /note="2'-OMe modified nucleotide"
<220> FEATURE:
<221> NAME/KEY: misc_feature
<222> LOCATION: (10)..(10)
<223> OTHER INFORMATION: /note="2'-F modified nucleotide"
<220> FEATURE:
<221> NAME/KEY: misc_feature
<222> LOCATION: (11)..(11)
<223> OTHER INFORMATION: /note="2'-OMe modified nucleotide"
<220> FEATURE:
<221> NAME/KEY: misc_feature
<222> LOCATION: (12)..(12)
<223> OTHER INFORMATION: /note="2'-OMe modified nucleotide"
<220> FEATURE:
<221> NAME/KEY: misc_feature
<222> LOCATION: (13)..(13)
<223> OTHER INFORMATION: /note="2'-OMe modified nucleotide"
<220> FEATURE:
<221> NAME/KEY: misc_feature
<222> LOCATION: (14)..(14)
<223> OTHER INFORMATION: /note="2'-F modified nucleotide"
<220> FEATURE:
<221> NAME/KEY: misc_feature
<222> LOCATION: (15)..(15)
<223> OTHER INFORMATION: /note="2'-OMe modified nucleotide"
<220> FEATURE:
<221> NAME/KEY: misc_feature
<222> LOCATION: (16)..(16)
<223> OTHER INFORMATION: /note="2'-OMe modified nucleotide"
<220> FEATURE:
<221> NAME/KEY: misc_feature
<222> LOCATION: (17)..(17)
<223> OTHER INFORMATION: /note="2'-OMe modified nucleotide"
<220> FEATURE:
<221> NAME/KEY: misc_feature
<222> LOCATION: (18)..(18)
<223> OTHER INFORMATION: /note="2'-OMe modified nucleotide"
<220> FEATURE:
<221> NAME/KEY: misc_feature
<222> LOCATION: (19)..(19)
<223> OTHER INFORMATION: /note="2'-OMe modified nucleotide"
<220> FEATURE:
<221> NAME/KEY: misc_feature
<222> LOCATION: (20)..(20)
<223> OTHER INFORMATION: /note="2'-OMe modified nucleotide with a 3'-phosphorothioate linkage"
<220> FEATURE:
<221> NAME/KEY: misc_feature
<222> LOCATION: (21)..(21)
<223> OTHER INFORMATION: /note="2'-OMe modified nucleotide with a 3'-phosphorothioate linkage"
<220> FEATURE:

<221> NAME/KEY: misc_feature
<222> LOCATION: (22)..(22)
<223> OTHER INFORMATION: /note="2'-OMe modified nucleotide"

<400> SEQUENCE: 159
ucauagcaaa ucuugauuuu gg 22

<210> SEQ ID NO 160
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: misc_feature
<222> LOCATION: (1)..(1)
<223> OTHER INFORMATION: /note="2'-OMe modified nucleotide with a
3'-phosphorothioate linkage"
<220> FEATURE:
<221> NAME/KEY: misc_feature
<222> LOCATION: (2)..(2)
<223> OTHER INFORMATION: /note="2'-OMe modified nucleotide"
<220> FEATURE:
<221> NAME/KEY: misc_feature
<222> LOCATION: (3)..(3)
<223> OTHER INFORMATION: /note="2'-OMe modified nucleotide"
<220> FEATURE:
<221> NAME/KEY: misc_feature
<222> LOCATION: (4)..(4)
<223> OTHER INFORMATION: /note="2'-OMe modified nucleotide"
<220> FEATURE:
<221> NAME/KEY: misc_feature
<222> LOCATION: (5)..(5)
<223> OTHER INFORMATION: /note="2'-OMe modified nucleotide"
<220> FEATURE:
<221> NAME/KEY: misc_feature
<222> LOCATION: (6)..(6)
<223> OTHER INFORMATION: /note="2'-OMe modified nucleotide"
<220> FEATURE:
<221> NAME/KEY: misc_feature
<222> LOCATION: (7)..(7)
<223> OTHER INFORMATION: /note="2'-OMe modified nucleotide"
<220> FEATURE:
<221> NAME/KEY: misc_feature
<222> LOCATION: (8)..(8)
<223> OTHER INFORMATION: /note="2'-F modified nucleotide"
<220> FEATURE:
<221> NAME/KEY: misc_feature
<222> LOCATION: (9)..(9)
<223> OTHER INFORMATION: /note="2'-F modified nucleotide"
<220> FEATURE:
<221> NAME/KEY: misc_feature
<222> LOCATION: (10)..(10)
<223> OTHER INFORMATION: /note="2'-F modified nucleotide"
<220> FEATURE:
<221> NAME/KEY: misc_feature
<222> LOCATION: (11)..(11)
<223> OTHER INFORMATION: /note="2'-F modified nucleotide"
<220> FEATURE:
<221> NAME/KEY: misc_feature
<222> LOCATION: (12)..(12)
<223> OTHER INFORMATION: /note="2'-OMe modified nucleotide"
<220> FEATURE:
<221> NAME/KEY: misc_feature
<222> LOCATION: (13)..(13)
<223> OTHER INFORMATION: /note="2'-OMe modified nucleotide"
<220> FEATURE:
<221> NAME/KEY: misc_feature
<222> LOCATION: (14)..(14)
<223> OTHER INFORMATION: /note="2'-OMe modified nucleotide"
<220> FEATURE:
<221> NAME/KEY: misc_feature
<222> LOCATION: (15)..(15)
<223> OTHER INFORMATION: /note="2'-OMe modified nucleotide"
<220> FEATURE:

<221> NAME/KEY: misc_feature
<222> LOCATION: (16)..(16)
<223> OTHER INFORMATION: /note="2'-OMe modified nucleotide"
<220> FEATURE:
<221> NAME/KEY: misc_feature
<222> LOCATION: (17)..(17)
<223> OTHER INFORMATION: /note="2'-OMe modified nucleotide"
<220> FEATURE:
<221> NAME/KEY: misc_feature
<222> LOCATION: (18)..(18)
<223> OTHER INFORMATION: /note="2'-OMe modified nucleotide"
<220> FEATURE:
<221> NAME/KEY: misc_feature
<222> LOCATION: (19)..(19)
<223> OTHER INFORMATION: /note="2'-OMe modified nucleotide"
<220> FEATURE:
<221> NAME/KEY: misc_feature
<222> LOCATION: (20)..(20)
<223> OTHER INFORMATION: /note="2'-OMe modified nucleotide"
<220> FEATURE:
<221> NAME/KEY: misc_feature
<222> LOCATION: (21)..(21)
<223> OTHER INFORMATION: /note="2'-OMe modified nucleotide"
<220> FEATURE:
<221> NAME/KEY: misc_feature
<222> LOCATION: (22)..(22)
<223> OTHER INFORMATION: /note="2'-OMe modified nucleotide"
<220> FEATURE:
<221> NAME/KEY: misc_feature
<222> LOCATION: (23)..(23)
<223> OTHER INFORMATION: /note="2'-OMe modified nucleotide"
<220> FEATURE:
<221> NAME/KEY: misc_feature
<222> LOCATION: (24)..(24)
<223> OTHER INFORMATION: /note="2'-OMe modified nucleotide"
<220> FEATURE:
<221> NAME/KEY: misc_feature
<222> LOCATION: (25)..(25)
<223> OTHER INFORMATION: /note="2'-OMe modified nucleotide"
<220> FEATURE:
<221> NAME/KEY: misc_feature
<222> LOCATION: (26)..(26)
<223> OTHER INFORMATION: /note="2'-OMe modified nucleotide"
<220> FEATURE:
<221> NAME/KEY: misc_feature
<222> LOCATION: (27)..(27)
<223> OTHER INFORMATION: /note="2'-OMe modified nucleotide"
<220> FEATURE:
<221> NAME/KEY: misc_feature
<222> LOCATION: (28)..(28)
<223> OTHER INFORMATION: /note="ademA-GalNAc"
<220> FEATURE:
<221> NAME/KEY: misc_feature
<222> LOCATION: (29)..(29)
<223> OTHER INFORMATION: /note="ademA-GalNAc"
<220> FEATURE:
<221> NAME/KEY: misc_feature
<222> LOCATION: (30)..(30)
<223> OTHER INFORMATION: /note="ademA-GalNAc"
<220> FEATURE:
<221> NAME/KEY: misc_feature
<222> LOCATION: (31)..(31)
<223> OTHER INFORMATION: /note="2'-OMe modified nucleotide"
<220> FEATURE:
<221> NAME/KEY: misc_feature
<222> LOCATION: (32)..(32)
<223> OTHER INFORMATION: /note="2'-OMe modified nucleotide"
<220> FEATURE:
<221> NAME/KEY: misc_feature
<222> LOCATION: (33)..(33)
<223> OTHER INFORMATION: /note="2'-OMe modified nucleotide"
<220> FEATURE:
<221> NAME/KEY: misc_feature
<222> LOCATION: (34)..(34)
<223> OTHER INFORMATION: /note="2'-OMe modified nucleotide"
<220> FEATURE:
<221> NAME/KEY: misc_feature
<222> LOCATION: (35)..(35)
<223> OTHER INFORMATION: /note="2'-OMe modified nucleotide"

```
<220> FEATURE:
<221> NAME/KEY: misc_feature
<222> LOCATION: (36)..(36)
<223> OTHER INFORMATION: /note="2'-OMe modified nucleotide"

<400> SEQUENCE: 160

auuugcuaug uuagacgaua gcagccgaaa ggcugc                          36


<210> SEQ ID NO 161
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: misc_feature
<222> LOCATION: (1)..(1)
<223> OTHER INFORMATION: /note="MePhosphonate-4O-mUs"
<220> FEATURE:
<221> NAME/KEY: misc_feature
<222> LOCATION: (2)..(2)
<223> OTHER INFORMATION: /note="2'-F modified nucleotide with a
      3'-phosphorothioate linkage"
<220> FEATURE:
<221> NAME/KEY: misc_feature
<222> LOCATION: (3)..(3)
<223> OTHER INFORMATION: /note="2'-F modified nucleotide with a
      3'-phosphorothioate linkage"
<220> FEATURE:
<221> NAME/KEY: misc_feature
<222> LOCATION: (4)..(4)
<223> OTHER INFORMATION: /note="2'-F modified nucleotide"
<220> FEATURE:
<221> NAME/KEY: misc_feature
<222> LOCATION: (5)..(5)
<223> OTHER INFORMATION: /note="2'-F modified nucleotide"
<220> FEATURE:
<221> NAME/KEY: misc_feature
<222> LOCATION: (6)..(6)
<223> OTHER INFORMATION: /note="2'-OMe modified nucleotide"
<220> FEATURE:
<221> NAME/KEY: misc_feature
<222> LOCATION: (7)..(7)
<223> OTHER INFORMATION: /note="2'-F modified nucleotide"
<220> FEATURE:
<221> NAME/KEY: misc_feature
<222> LOCATION: (8)..(8)
<223> OTHER INFORMATION: /note="2'-OMe modified nucleotide"
<220> FEATURE:
<221> NAME/KEY: misc_feature
<222> LOCATION: (9)..(9)
<223> OTHER INFORMATION: /note="2'-OMe modified nucleotide"
<220> FEATURE:
<221> NAME/KEY: misc_feature
<222> LOCATION: (10)..(10)
<223> OTHER INFORMATION: /note="2'-F modified nucleotide"
<220> FEATURE:
<221> NAME/KEY: misc_feature
<222> LOCATION: (11)..(11)
<223> OTHER INFORMATION: /note="2'-OMe modified nucleotide"
<220> FEATURE:
<221> NAME/KEY: misc_feature
<222> LOCATION: (12)..(12)
<223> OTHER INFORMATION: /note="2'-OMe modified nucleotide"
<220> FEATURE:
<221> NAME/KEY: misc_feature
<222> LOCATION: (13)..(13)
<223> OTHER INFORMATION: /note="2'-OMe modified nucleotide"
<220> FEATURE:
<221> NAME/KEY: misc_feature
<222> LOCATION: (14)..(14)
<223> OTHER INFORMATION: /note="2'-F modified nucleotide"
<220> FEATURE:
<221> NAME/KEY: misc_feature
<222> LOCATION: (15)..(15)
```

<223> OTHER INFORMATION: /note="2'-OMe modified nucleotide"
<220> FEATURE:
<221> NAME/KEY: misc_feature
<222> LOCATION: (16)..(16)
<223> OTHER INFORMATION: /note="2'-OMe modified nucleotide"
<220> FEATURE:
<221> NAME/KEY: misc_feature
<222> LOCATION: (17)..(17)
<223> OTHER INFORMATION: /note="2'-OMe modified nucleotide"
<220> FEATURE:
<221> NAME/KEY: misc_feature
<222> LOCATION: (18)..(18)
<223> OTHER INFORMATION: /note="2'-OMe modified nucleotide"
<220> FEATURE:
<221> NAME/KEY: misc_feature
<222> LOCATION: (19)..(19)
<223> OTHER INFORMATION: /note="2'-OMe modified nucleotide"
<220> FEATURE:
<221> NAME/KEY: misc_feature
<222> LOCATION: (20)..(20)
<223> OTHER INFORMATION: /note="2'-OMe modified nucleotide with a 3'-phosphorothioate linkage"
<220> FEATURE:
<221> NAME/KEY: misc_feature
<222> LOCATION: (21)..(21)
<223> OTHER INFORMATION: /note="2'-OMe modified nucleotide with a 3'-phosphorothioate linkage"
<220> FEATURE:
<221> NAME/KEY: misc_feature
<222> LOCATION: (22)..(22)
<223> OTHER INFORMATION: /note="2'-OMe modified nucleotide"

<400> SEQUENCE: 161
uaucgucuaa cauagcaaau gg 22

<210> SEQ ID NO 162
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: misc_feature
<222> LOCATION: (1)..(1)
<223> OTHER INFORMATION: /note="2'-OMe modified nucleotide with a 3'-phosphorothioate linkage"
<220> FEATURE:
<221> NAME/KEY: misc_feature
<222> LOCATION: (2)..(2)
<223> OTHER INFORMATION: /note="2'-OMe modified nucleotide"
<220> FEATURE:
<221> NAME/KEY: misc_feature
<222> LOCATION: (3)..(3)
<223> OTHER INFORMATION: /note="2'-OMe modified nucleotide"
<220> FEATURE:
<221> NAME/KEY: misc_feature
<222> LOCATION: (4)..(4)
<223> OTHER INFORMATION: /note="2'-OMe modified nucleotide"
<220> FEATURE:
<221> NAME/KEY: misc_feature
<222> LOCATION: (5)..(5)
<223> OTHER INFORMATION: /note="2'-OMe modified nucleotide"
<220> FEATURE:
<221> NAME/KEY: misc_feature
<222> LOCATION: (6)..(6)
<223> OTHER INFORMATION: /note="2'-OMe modified nucleotide"
<220> FEATURE:
<221> NAME/KEY: misc_feature
<222> LOCATION: (7)..(7)
<223> OTHER INFORMATION: /note="2'-OMe modified nucleotide"
<220> FEATURE:
<221> NAME/KEY: misc_feature
<222> LOCATION: (8)..(8)
<223> OTHER INFORMATION: /note="2'-F modified nucleotide"
<220> FEATURE:

<221> NAME/KEY: misc_feature
<222> LOCATION: (9)..(9)
<223> OTHER INFORMATION: /note="2'-F modified nucleotide"
<220> FEATURE:
<221> NAME/KEY: misc_feature
<222> LOCATION: (10)..(10)
<223> OTHER INFORMATION: /note="2'-F modified nucleotide"
<220> FEATURE:
<221> NAME/KEY: misc_feature
<222> LOCATION: (11)..(11)
<223> OTHER INFORMATION: /note="2'-F modified nucleotide"
<220> FEATURE:
<221> NAME/KEY: misc_feature
<222> LOCATION: (12)..(12)
<223> OTHER INFORMATION: /note="2'-OMe modified nucleotide"
<220> FEATURE:
<221> NAME/KEY: misc_feature
<222> LOCATION: (13)..(13)
<223> OTHER INFORMATION: /note="2'-OMe modified nucleotide"
<220> FEATURE:
<221> NAME/KEY: misc_feature
<222> LOCATION: (14)..(14)
<223> OTHER INFORMATION: /note="2'-OMe modified nucleotide"
<220> FEATURE:
<221> NAME/KEY: misc_feature
<222> LOCATION: (15)..(15)
<223> OTHER INFORMATION: /note="2'-OMe modified nucleotide"
<220> FEATURE:
<221> NAME/KEY: misc_feature
<222> LOCATION: (16)..(16)
<223> OTHER INFORMATION: /note="2'-OMe modified nucleotide"
<220> FEATURE:
<221> NAME/KEY: misc_feature
<222> LOCATION: (17)..(17)
<223> OTHER INFORMATION: /note="2'-OMe modified nucleotide"
<220> FEATURE:
<221> NAME/KEY: misc_feature
<222> LOCATION: (18)..(18)
<223> OTHER INFORMATION: /note="2'-OMe modified nucleotide"
<220> FEATURE:
<221> NAME/KEY: misc_feature
<222> LOCATION: (19)..(19)
<223> OTHER INFORMATION: /note="2'-OMe modified nucleotide"
<220> FEATURE:
<221> NAME/KEY: misc_feature
<222> LOCATION: (20)..(20)
<223> OTHER INFORMATION: /note="2'-OMe modified nucleotide"
<220> FEATURE:
<221> NAME/KEY: misc_feature
<222> LOCATION: (21)..(21)
<223> OTHER INFORMATION: /note="2'-OMe modified nucleotide"
<220> FEATURE:
<221> NAME/KEY: misc_feature
<222> LOCATION: (22)..(22)
<223> OTHER INFORMATION: /note="2'-OMe modified nucleotide"
<220> FEATURE:
<221> NAME/KEY: misc_feature
<222> LOCATION: (23)..(23)
<223> OTHER INFORMATION: /note="2'-OMe modified nucleotide"
<220> FEATURE:
<221> NAME/KEY: misc_feature
<222> LOCATION: (24)..(24)
<223> OTHER INFORMATION: /note="2'-OMe modified nucleotide"
<220> FEATURE:
<221> NAME/KEY: misc_feature
<222> LOCATION: (25)..(25)
<223> OTHER INFORMATION: /note="2'-OMe modified nucleotide"
<220> FEATURE:
<221> NAME/KEY: misc_feature
<222> LOCATION: (26)..(26)
<223> OTHER INFORMATION: /note="2'-OMe modified nucleotide"
<220> FEATURE:
<221> NAME/KEY: misc_feature
<222> LOCATION: (27)..(27)
<223> OTHER INFORMATION: /note="2'-OMe modified nucleotide"
<220> FEATURE:
<221> NAME/KEY: misc_feature
<222> LOCATION: (28)..(28)
<223> OTHER INFORMATION: /note="ademA-GalNAc"

<220> FEATURE:
<221> NAME/KEY: misc_feature
<222> LOCATION: (29)..(29)
<223> OTHER INFORMATION: /note="ademA-GalNAc"
<220> FEATURE:
<221> NAME/KEY: misc_feature
<222> LOCATION: (30)..(30)
<223> OTHER INFORMATION: /note="ademA-GalNAc"
<220> FEATURE:
<221> NAME/KEY: misc_feature
<222> LOCATION: (31)..(31)
<223> OTHER INFORMATION: /note="2'-OMe modified nucleotide"
<220> FEATURE:
<221> NAME/KEY: misc_feature
<222> LOCATION: (32)..(32)
<223> OTHER INFORMATION: /note="2'-OMe modified nucleotide"
<220> FEATURE:
<221> NAME/KEY: misc_feature
<222> LOCATION: (33)..(33)
<223> OTHER INFORMATION: /note="2'-OMe modified nucleotide"
<220> FEATURE:
<221> NAME/KEY: misc_feature
<222> LOCATION: (34)..(34)
<223> OTHER INFORMATION: /note="2'-OMe modified nucleotide"
<220> FEATURE:
<221> NAME/KEY: misc_feature
<222> LOCATION: (35)..(35)
<223> OTHER INFORMATION: /note="2'-OMe modified nucleotide"
<220> FEATURE:
<221> NAME/KEY: misc_feature
<222> LOCATION: (36)..(36)
<223> OTHER INFORMATION: /note="2'-OMe modified nucleotide"

<400> SEQUENCE: 162
caaauuaaug acauauuuca gcagccgaaa ggcugc 36

<210> SEQ ID NO 163
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: misc_feature
<222> LOCATION: (1)..(1)
<223> OTHER INFORMATION: /note="MePhosphonate-4O-mUs"
<220> FEATURE:
<221> NAME/KEY: misc_feature
<222> LOCATION: (2)..(2)
<223> OTHER INFORMATION: /note="2'-F modified nucleotide with a
3'-phosphorothioate linkage"
<220> FEATURE:
<221> NAME/KEY: misc_feature
<222> LOCATION: (3)..(3)
<223> OTHER INFORMATION: /note="2'-F modified nucleotide with a
3'-phosphorothioate linkage"
<220> FEATURE:
<221> NAME/KEY: misc_feature
<222> LOCATION: (4)..(4)
<223> OTHER INFORMATION: /note="2'-F modified nucleotide"
<220> FEATURE:
<221> NAME/KEY: misc_feature
<222> LOCATION: (5)..(5)
<223> OTHER INFORMATION: /note="2'-F modified nucleotide"
<220> FEATURE:
<221> NAME/KEY: misc_feature
<222> LOCATION: (6)..(6)
<223> OTHER INFORMATION: /note="2'-OMe modified nucleotide"
<220> FEATURE:
<221> NAME/KEY: misc_feature
<222> LOCATION: (7)..(7)
<223> OTHER INFORMATION: /note="2'-F modified nucleotide"
<220> FEATURE:
<221> NAME/KEY: misc_feature
<222> LOCATION: (8)..(8)

<223> OTHER INFORMATION: /note="2'-OMe modified nucleotide"
<220> FEATURE:
<221> NAME/KEY: misc_feature
<222> LOCATION: (9)..(9)
<223> OTHER INFORMATION: /note="2'-OMe modified nucleotide"
<220> FEATURE:
<221> NAME/KEY: misc_feature
<222> LOCATION: (10)..(10)
<223> OTHER INFORMATION: /note="2'-F modified nucleotide"
<220> FEATURE:
<221> NAME/KEY: misc_feature
<222> LOCATION: (11)..(11)
<223> OTHER INFORMATION: /note="2'-OMe modified nucleotide"
<220> FEATURE:
<221> NAME/KEY: misc_feature
<222> LOCATION: (12)..(12)
<223> OTHER INFORMATION: /note="2'-OMe modified nucleotide"
<220> FEATURE:
<221> NAME/KEY: misc_feature
<222> LOCATION: (13)..(13)
<223> OTHER INFORMATION: /note="2'-OMe modified nucleotide"
<220> FEATURE:
<221> NAME/KEY: misc_feature
<222> LOCATION: (14)..(14)
<223> OTHER INFORMATION: /note="2'-F modified nucleotide"
<220> FEATURE:
<221> NAME/KEY: misc_feature
<222> LOCATION: (15)..(15)
<223> OTHER INFORMATION: /note="2'-OMe modified nucleotide"
<220> FEATURE:
<221> NAME/KEY: misc_feature
<222> LOCATION: (16)..(16)
<223> OTHER INFORMATION: /note="2'-OMe modified nucleotide"
<220> FEATURE:
<221> NAME/KEY: misc_feature
<222> LOCATION: (17)..(17)
<223> OTHER INFORMATION: /note="2'-OMe modified nucleotide"
<220> FEATURE:
<221> NAME/KEY: misc_feature
<222> LOCATION: (18)..(18)
<223> OTHER INFORMATION: /note="2'-OMe modified nucleotide"
<220> FEATURE:
<221> NAME/KEY: misc_feature
<222> LOCATION: (19)..(19)
<223> OTHER INFORMATION: /note="2'-OMe modified nucleotide"
<220> FEATURE:
<221> NAME/KEY: misc_feature
<222> LOCATION: (20)..(20)
<223> OTHER INFORMATION: /note="2'-OMe modified nucleotide with a
3'-phosphorothioate linkage"
<220> FEATURE:
<221> NAME/KEY: misc_feature
<222> LOCATION: (21)..(21)
<223> OTHER INFORMATION: /note="2'-OMe modified nucleotide with a
3'-phosphorothioate linkage"
<220> FEATURE:
<221> NAME/KEY: misc_feature
<222> LOCATION: (22)..(22)
<223> OTHER INFORMATION: /note="2'-OMe modified nucleotide"

<400> SEQUENCE: 163
ugaaauaugu cauuaauuug gg 22

<210> SEQ ID NO 164
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: misc_feature
<222> LOCATION: (1)..(1)
<223> OTHER INFORMATION: /note="2'-OMe modified nucleotide with a
3'-phosphorothioate linkage"
<220> FEATURE:

<221> NAME/KEY: misc_feature
<222> LOCATION: (2)..(2)
<223> OTHER INFORMATION: /note="2'-OMe modified nucleotide"
<220> FEATURE:
<221> NAME/KEY: misc_feature
<222> LOCATION: (3)..(3)
<223> OTHER INFORMATION: /note="2'-OMe modified nucleotide"
<220> FEATURE:
<221> NAME/KEY: misc_feature
<222> LOCATION: (4)..(4)
<223> OTHER INFORMATION: /note="2'-OMe modified nucleotide"
<220> FEATURE:
<221> NAME/KEY: misc_feature
<222> LOCATION: (5)..(5)
<223> OTHER INFORMATION: /note="2'-OMe modified nucleotide"
<220> FEATURE:
<221> NAME/KEY: misc_feature
<222> LOCATION: (6)..(6)
<223> OTHER INFORMATION: /note="2'-OMe modified nucleotide"
<220> FEATURE:
<221> NAME/KEY: misc_feature
<222> LOCATION: (7)..(7)
<223> OTHER INFORMATION: /note="2'-OMe modified nucleotide"
<220> FEATURE:
<221> NAME/KEY: misc_feature
<222> LOCATION: (8)..(8)
<223> OTHER INFORMATION: /note="2'-F modified nucleotide"
<220> FEATURE:
<221> NAME/KEY: misc_feature
<222> LOCATION: (9)..(9)
<223> OTHER INFORMATION: /note="2'-F modified nucleotide"
<220> FEATURE:
<221> NAME/KEY: misc_feature
<222> LOCATION: (10)..(10)
<223> OTHER INFORMATION: /note="2'-F modified nucleotide"
<220> FEATURE:
<221> NAME/KEY: misc_feature
<222> LOCATION: (11)..(11)
<223> OTHER INFORMATION: /note="2'-F modified nucleotide"
<220> FEATURE:
<221> NAME/KEY: misc_feature
<222> LOCATION: (12)..(12)
<223> OTHER INFORMATION: /note="2'-OMe modified nucleotide"
<220> FEATURE:
<221> NAME/KEY: misc_feature
<222> LOCATION: (13)..(13)
<223> OTHER INFORMATION: /note="2'-OMe modified nucleotide"
<220> FEATURE:
<221> NAME/KEY: misc_feature
<222> LOCATION: (14)..(14)
<223> OTHER INFORMATION: /note="2'-OMe modified nucleotide"
<220> FEATURE:
<221> NAME/KEY: misc_feature
<222> LOCATION: (15)..(15)
<223> OTHER INFORMATION: /note="2'-OMe modified nucleotide"
<220> FEATURE:
<221> NAME/KEY: misc_feature
<222> LOCATION: (16)..(16)
<223> OTHER INFORMATION: /note="2'-OMe modified nucleotide"
<220> FEATURE:
<221> NAME/KEY: misc_feature
<222> LOCATION: (17)..(17)
<223> OTHER INFORMATION: /note="2'-OMe modified nucleotide"
<220> FEATURE:
<221> NAME/KEY: misc_feature
<222> LOCATION: (18)..(18)
<223> OTHER INFORMATION: /note="2'-OMe modified nucleotide"
<220> FEATURE:
<221> NAME/KEY: misc_feature
<222> LOCATION: (19)..(19)
<223> OTHER INFORMATION: /note="2'-OMe modified nucleotide"
<220> FEATURE:
<221> NAME/KEY: misc_feature
<222> LOCATION: (20)..(20)
<223> OTHER INFORMATION: /note="2'-OMe modified nucleotide"
<220> FEATURE:
<221> NAME/KEY: misc_feature
<222> LOCATION: (21)..(21)
<223> OTHER INFORMATION: /note="2'-OMe modified nucleotide"

<220> FEATURE:
<221> NAME/KEY: misc_feature
<222> LOCATION: (22)..(22)
<223> OTHER INFORMATION: /note="2'-OMe modified nucleotide"
<220> FEATURE:
<221> NAME/KEY: misc_feature
<222> LOCATION: (23)..(23)
<223> OTHER INFORMATION: /note="2'-OMe modified nucleotide"
<220> FEATURE:
<221> NAME/KEY: misc_feature
<222> LOCATION: (24)..(24)
<223> OTHER INFORMATION: /note="2'-OMe modified nucleotide"
<220> FEATURE:
<221> NAME/KEY: misc_feature
<222> LOCATION: (25)..(25)
<223> OTHER INFORMATION: /note="2'-OMe modified nucleotide"
<220> FEATURE:
<221> NAME/KEY: misc_feature
<222> LOCATION: (26)..(26)
<223> OTHER INFORMATION: /note="2'-OMe modified nucleotide"
<220> FEATURE:
<221> NAME/KEY: misc_feature
<222> LOCATION: (27)..(27)
<223> OTHER INFORMATION: /note="2'-OMe modified nucleotide"
<220> FEATURE:
<221> NAME/KEY: misc_feature
<222> LOCATION: (28)..(28)
<223> OTHER INFORMATION: /note="ademA-GalNAc"
<220> FEATURE:
<221> NAME/KEY: misc_feature
<222> LOCATION: (29)..(29)
<223> OTHER INFORMATION: /note="ademA-GalNAc"
<220> FEATURE:
<221> NAME/KEY: misc_feature
<222> LOCATION: (30)..(30)
<223> OTHER INFORMATION: /note="ademA-GalNAc"
<220> FEATURE:
<221> NAME/KEY: misc_feature
<222> LOCATION: (31)..(31)
<223> OTHER INFORMATION: /note="2'-OMe modified nucleotide"
<220> FEATURE:
<221> NAME/KEY: misc_feature
<222> LOCATION: (32)..(32)
<223> OTHER INFORMATION: /note="2'-OMe modified nucleotide"
<220> FEATURE:
<221> NAME/KEY: misc_feature
<222> LOCATION: (33)..(33)
<223> OTHER INFORMATION: /note="2'-OMe modified nucleotide"
<220> FEATURE:
<221> NAME/KEY: misc_feature
<222> LOCATION: (34)..(34)
<223> OTHER INFORMATION: /note="2'-OMe modified nucleotide"
<220> FEATURE:
<221> NAME/KEY: misc_feature
<222> LOCATION: (35)..(35)
<223> OTHER INFORMATION: /note="2'-OMe modified nucleotide"
<220> FEATURE:
<221> NAME/KEY: misc_feature
<222> LOCATION: (36)..(36)
<223> OTHER INFORMATION: /note="2'-OMe modified nucleotide"

<400> SEQUENCE: 164
augacauauu ucaaaaacua gcagccgaaa ggcugc 36

<210> SEQ ID NO 165
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: misc_feature
<222> LOCATION: (1)..(1)
<223> OTHER INFORMATION: /note="MePhosphonate-4O-mUs"
<220> FEATURE:

<221> NAME/KEY: misc_feature
<222> LOCATION: (2)..(2)
<223> OTHER INFORMATION: /note="2'-F modified nucleotide with a 3'-phosphorothioate linkage"
<220> FEATURE:
<221> NAME/KEY: misc_feature
<222> LOCATION: (3)..(3)
<223> OTHER INFORMATION: /note="2'-F modified nucleotide with a 3'-phosphorothioate linkage"
<220> FEATURE:
<221> NAME/KEY: misc_feature
<222> LOCATION: (4)..(4)
<223> OTHER INFORMATION: /note="2'-F modified nucleotide"
<220> FEATURE:
<221> NAME/KEY: misc_feature
<222> LOCATION: (5)..(5)
<223> OTHER INFORMATION: /note="2'-F modified nucleotide"
<220> FEATURE:
<221> NAME/KEY: misc_feature
<222> LOCATION: (6)..(6)
<223> OTHER INFORMATION: /note="2'-OMe modified nucleotide"
<220> FEATURE:
<221> NAME/KEY: misc_feature
<222> LOCATION: (7)..(7)
<223> OTHER INFORMATION: /note="2'-F modified nucleotide"
<220> FEATURE:
<221> NAME/KEY: misc_feature
<222> LOCATION: (8)..(8)
<223> OTHER INFORMATION: /note="2'-OMe modified nucleotide"
<220> FEATURE:
<221> NAME/KEY: misc_feature
<222> LOCATION: (9)..(9)
<223> OTHER INFORMATION: /note="2'-OMe modified nucleotide"
<220> FEATURE:
<221> NAME/KEY: misc_feature
<222> LOCATION: (10)..(10)
<223> OTHER INFORMATION: /note="2'-F modified nucleotide"
<220> FEATURE:
<221> NAME/KEY: misc_feature
<222> LOCATION: (11)..(11)
<223> OTHER INFORMATION: /note="2'-OMe modified nucleotide"
<220> FEATURE:
<221> NAME/KEY: misc_feature
<222> LOCATION: (12)..(12)
<223> OTHER INFORMATION: /note="2'-OMe modified nucleotide"
<220> FEATURE:
<221> NAME/KEY: misc_feature
<222> LOCATION: (13)..(13)
<223> OTHER INFORMATION: /note="2'-OMe modified nucleotide"
<220> FEATURE:
<221> NAME/KEY: misc_feature
<222> LOCATION: (14)..(14)
<223> OTHER INFORMATION: /note="2'-F modified nucleotide"
<220> FEATURE:
<221> NAME/KEY: misc_feature
<222> LOCATION: (15)..(15)
<223> OTHER INFORMATION: /note="2'-OMe modified nucleotide"
<220> FEATURE:
<221> NAME/KEY: misc_feature
<222> LOCATION: (16)..(16)
<223> OTHER INFORMATION: /note="2'-OMe modified nucleotide"
<220> FEATURE:
<221> NAME/KEY: misc_feature
<222> LOCATION: (17)..(17)
<223> OTHER INFORMATION: /note="2'-OMe modified nucleotide"
<220> FEATURE:
<221> NAME/KEY: misc_feature
<222> LOCATION: (18)..(18)
<223> OTHER INFORMATION: /note="2'-OMe modified nucleotide"
<220> FEATURE:
<221> NAME/KEY: misc_feature
<222> LOCATION: (19)..(19)
<223> OTHER INFORMATION: /note="2'-OMe modified nucleotide"
<220> FEATURE:
<221> NAME/KEY: misc_feature
<222> LOCATION: (20)..(20)
<223> OTHER INFORMATION: /note="2'-OMe modified nucleotide with a 3'-phosphorothioate linkage"
<220> FEATURE:

<221> NAME/KEY: misc_feature
<222> LOCATION: (21)..(21)
<223> OTHER INFORMATION: /note="2'-OMe modified nucleotide with a
 3'-phosphorothioate linkage"
<220> FEATURE:
<221> NAME/KEY: misc_feature
<222> LOCATION: (22)..(22)
<223> OTHER INFORMATION: /note="2'-OMe modified nucleotide"

<400> SEQUENCE: 165
uaguuuuuga aauaugucau gg 22

<210> SEQ ID NO 166
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence:
 Synthetic oligonucleotide"
<220> FEATURE:
<221> NAME/KEY: misc_feature
<222> LOCATION: (1)..(1)
<223> OTHER INFORMATION: /note="2'-OMe modified nucleotide with a
 3'-phosphorothioate linkage"
<220> FEATURE:
<221> NAME/KEY: misc_feature
<222> LOCATION: (2)..(2)
<223> OTHER INFORMATION: /note="2'-OMe modified nucleotide"
<220> FEATURE:
<221> NAME/KEY: misc_feature
<222> LOCATION: (3)..(3)
<223> OTHER INFORMATION: /note="2'-OMe modified nucleotide"
<220> FEATURE:
<221> NAME/KEY: misc_feature
<222> LOCATION: (4)..(4)
<223> OTHER INFORMATION: /note="2'-OMe modified nucleotide"
<220> FEATURE:
<221> NAME/KEY: misc_feature
<222> LOCATION: (5)..(5)
<223> OTHER INFORMATION: /note="2'-OMe modified nucleotide"
<220> FEATURE:
<221> NAME/KEY: misc_feature
<222> LOCATION: (6)..(6)
<223> OTHER INFORMATION: /note="2'-OMe modified nucleotide"
<220> FEATURE:
<221> NAME/KEY: misc_feature
<222> LOCATION: (7)..(7)
<223> OTHER INFORMATION: /note="2'-OMe modified nucleotide"
<220> FEATURE:
<221> NAME/KEY: misc_feature
<222> LOCATION: (8)..(8)
<223> OTHER INFORMATION: /note="2'-F modified nucleotide"
<220> FEATURE:
<221> NAME/KEY: misc_feature
<222> LOCATION: (9)..(9)
<223> OTHER INFORMATION: /note="2'-F modified nucleotide"
<220> FEATURE:
<221> NAME/KEY: misc_feature
<222> LOCATION: (10)..(10)
<223> OTHER INFORMATION: /note="2'-F modified nucleotide"
<220> FEATURE:
<221> NAME/KEY: misc_feature
<222> LOCATION: (11)..(11)
<223> OTHER INFORMATION: /note="2'-F modified nucleotide"
<220> FEATURE:
<221> NAME/KEY: misc_feature
<222> LOCATION: (12)..(12)
<223> OTHER INFORMATION: /note="2'-OMe modified nucleotide"
<220> FEATURE:
<221> NAME/KEY: misc_feature
<222> LOCATION: (13)..(13)
<223> OTHER INFORMATION: /note="2'-OMe modified nucleotide"
<220> FEATURE:
<221> NAME/KEY: misc_feature
<222> LOCATION: (14)..(14)
<223> OTHER INFORMATION: /note="2'-OMe modified nucleotide"

<220> FEATURE:
<221> NAME/KEY: misc_feature
<222> LOCATION: (15)..(15)
<223> OTHER INFORMATION: /note="2'-OMe modified nucleotide"
<220> FEATURE:
<221> NAME/KEY: misc_feature
<222> LOCATION: (16)..(16)
<223> OTHER INFORMATION: /note="2'-OMe modified nucleotide"
<220> FEATURE:
<221> NAME/KEY: misc_feature
<222> LOCATION: (17)..(17)
<223> OTHER INFORMATION: /note="2'-OMe modified nucleotide"
<220> FEATURE:
<221> NAME/KEY: misc_feature
<222> LOCATION: (18)..(18)
<223> OTHER INFORMATION: /note="2'-OMe modified nucleotide"
<220> FEATURE:
<221> NAME/KEY: misc_feature
<222> LOCATION: (19)..(19)
<223> OTHER INFORMATION: /note="2'-OMe modified nucleotide"
<220> FEATURE:
<221> NAME/KEY: misc_feature
<222> LOCATION: (20)..(20)
<223> OTHER INFORMATION: /note="2'-OMe modified nucleotide"
<220> FEATURE:
<221> NAME/KEY: misc_feature
<222> LOCATION: (21)..(21)
<223> OTHER INFORMATION: /note="2'-OMe modified nucleotide"
<220> FEATURE:
<221> NAME/KEY: misc_feature
<222> LOCATION: (22)..(22)
<223> OTHER INFORMATION: /note="2'-OMe modified nucleotide"
<220> FEATURE:
<221> NAME/KEY: misc_feature
<222> LOCATION: (23)..(23)
<223> OTHER INFORMATION: /note="2'-OMe modified nucleotide"
<220> FEATURE:
<221> NAME/KEY: misc_feature
<222> LOCATION: (24)..(24)
<223> OTHER INFORMATION: /note="2'-OMe modified nucleotide"
<220> FEATURE:
<221> NAME/KEY: misc_feature
<222> LOCATION: (25)..(25)
<223> OTHER INFORMATION: /note="2'-OMe modified nucleotide"
<220> FEATURE:
<221> NAME/KEY: misc_feature
<222> LOCATION: (26)..(26)
<223> OTHER INFORMATION: /note="2'-OMe modified nucleotide"
<220> FEATURE:
<221> NAME/KEY: misc_feature
<222> LOCATION: (27)..(27)
<223> OTHER INFORMATION: /note="2'-OMe modified nucleotide"
<220> FEATURE:
<221> NAME/KEY: misc_feature
<222> LOCATION: (28)..(28)
<223> OTHER INFORMATION: /note="ademA-GalNAc"
<220> FEATURE:
<221> NAME/KEY: misc_feature
<222> LOCATION: (29)..(29)
<223> OTHER INFORMATION: /note="ademA-GalNAc"
<220> FEATURE:
<221> NAME/KEY: misc_feature
<222> LOCATION: (30)..(30)
<223> OTHER INFORMATION: /note="ademA-GalNAc"
<220> FEATURE:
<221> NAME/KEY: misc_feature
<222> LOCATION: (31)..(31)
<223> OTHER INFORMATION: /note="2'-OMe modified nucleotide"
<220> FEATURE:
<221> NAME/KEY: misc_feature
<222> LOCATION: (32)..(32)
<223> OTHER INFORMATION: /note="2'-OMe modified nucleotide"
<220> FEATURE:
<221> NAME/KEY: misc_feature
<222> LOCATION: (33)..(33)
<223> OTHER INFORMATION: /note="2'-OMe modified nucleotide"
<220> FEATURE:
<221> NAME/KEY: misc_feature
<222> LOCATION: (34)..(34)

<223> OTHER INFORMATION: /note="2'-OMe modified nucleotide"
<220> FEATURE:
<221> NAME/KEY: misc_feature
<222> LOCATION: (35)..(35)
<223> OTHER INFORMATION: /note="2'-OMe modified nucleotide"
<220> FEATURE:
<221> NAME/KEY: misc_feature
<222> LOCATION: (36)..(36)
<223> OTHER INFORMATION: /note="2'-OMe modified nucleotide"

<400> SEQUENCE: 166
aacauauuug aucagucuua gcagccgaaa ggcugc 36

<210> SEQ ID NO 167
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: misc_feature
<222> LOCATION: (1)..(1)
<223> OTHER INFORMATION: /note="MePhosphonate-4O-mUs"
<220> FEATURE:
<221> NAME/KEY: misc_feature
<222> LOCATION: (2)..(2)
<223> OTHER INFORMATION: /note="2'-F modified nucleotide with a 3'-phosphorothioate linkage"
<220> FEATURE:
<221> NAME/KEY: misc_feature
<222> LOCATION: (3)..(3)
<223> OTHER INFORMATION: /note="2'-F modified nucleotide with a 3'-phosphorothioate linkage"
<220> FEATURE:
<221> NAME/KEY: misc_feature
<222> LOCATION: (4)..(4)
<223> OTHER INFORMATION: /note="2'-F modified nucleotide"
<220> FEATURE:
<221> NAME/KEY: misc_feature
<222> LOCATION: (5)..(5)
<223> OTHER INFORMATION: /note="2'-F modified nucleotide"
<220> FEATURE:
<221> NAME/KEY: misc_feature
<222> LOCATION: (6)..(6)
<223> OTHER INFORMATION: /note="2'-OMe modified nucleotide"
<220> FEATURE:
<221> NAME/KEY: misc_feature
<222> LOCATION: (7)..(7)
<223> OTHER INFORMATION: /note="2'-F modified nucleotide"
<220> FEATURE:
<221> NAME/KEY: misc_feature
<222> LOCATION: (8)..(8)
<223> OTHER INFORMATION: /note="2'-OMe modified nucleotide"
<220> FEATURE:
<221> NAME/KEY: misc_feature
<222> LOCATION: (9)..(9)
<223> OTHER INFORMATION: /note="2'-OMe modified nucleotide"
<220> FEATURE:
<221> NAME/KEY: misc_feature
<222> LOCATION: (10)..(10)
<223> OTHER INFORMATION: /note="2'-F modified nucleotide"
<220> FEATURE:
<221> NAME/KEY: misc_feature
<222> LOCATION: (11)..(11)
<223> OTHER INFORMATION: /note="2'-OMe modified nucleotide"
<220> FEATURE:
<221> NAME/KEY: misc_feature
<222> LOCATION: (12)..(12)
<223> OTHER INFORMATION: /note="2'-OMe modified nucleotide"
<220> FEATURE:
<221> NAME/KEY: misc_feature
<222> LOCATION: (13)..(13)
<223> OTHER INFORMATION: /note="2'-OMe modified nucleotide"
<220> FEATURE:
<221> NAME/KEY: misc_feature
<222> LOCATION: (14)..(14)
<223> OTHER INFORMATION: /note="2'-F modified nucleotide"
<220> FEATURE:
<221> NAME/KEY: misc_feature
<222> LOCATION: (15)..(15)
<223> OTHER INFORMATION: /note="2'-OMe modified nucleotide"
<220> FEATURE:
<221> NAME/KEY: misc_feature
<222> LOCATION: (16)..(16)
<223> OTHER INFORMATION: /note="2'-OMe modified nucleotide"
<220> FEATURE:
<221> NAME/KEY: misc_feature
<222> LOCATION: (17)..(17)
<223> OTHER INFORMATION: /note="2'-OMe modified nucleotide"
<220> FEATURE:
<221> NAME/KEY: misc_feature
<222> LOCATION: (18)..(18)
<223> OTHER INFORMATION: /note="2'-OMe modified nucleotide"
<220> FEATURE:
<221> NAME/KEY: misc_feature
<222> LOCATION: (19)..(19)
<223> OTHER INFORMATION: /note="2'-OMe modified nucleotide"
<220> FEATURE:
<221> NAME/KEY: misc_feature
<222> LOCATION: (20)..(20)
<223> OTHER INFORMATION: /note="2'-OMe modified nucleotide with a 3'-phosphorothioate linkage"
<220> FEATURE:
<221> NAME/KEY: misc_feature
<222> LOCATION: (21)..(21)
<223> OTHER INFORMATION: /note="2'-OMe modified nucleotide with a 3'-phosphorothioate linkage"
<220> FEATURE:
<221> NAME/KEY: misc_feature
<222> LOCATION: (22)..(22)
<223> OTHER INFORMATION: /note="2'-OMe modified nucleotide"

<400> SEQUENCE: 167
uaagacugau caaauauguu gg 22

<210> SEQ ID NO 168
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: misc_feature
<222> LOCATION: (1)..(1)
<223> OTHER INFORMATION: /note="2'-OMe modified nucleotide with a 3'-phosphorothioate linkage"
<220> FEATURE:
<221> NAME/KEY: misc_feature
<222> LOCATION: (2)..(2)
<223> OTHER INFORMATION: /note="2'-OMe modified nucleotide"
<220> FEATURE:
<221> NAME/KEY: misc_feature
<222> LOCATION: (3)..(3)
<223> OTHER INFORMATION: /note="2'-OMe modified nucleotide"
<220> FEATURE:
<221> NAME/KEY: misc_feature
<222> LOCATION: (4)..(4)
<223> OTHER INFORMATION: /note="2'-OMe modified nucleotide"
<220> FEATURE:
<221> NAME/KEY: misc_feature
<222> LOCATION: (5)..(5)
<223> OTHER INFORMATION: /note="2'-OMe modified nucleotide"
<220> FEATURE:
<221> NAME/KEY: misc_feature
<222> LOCATION: (6)..(6)
<223> OTHER INFORMATION: /note="2'-OMe modified nucleotide"
<220> FEATURE:
<221> NAME/KEY: misc_feature
<222> LOCATION: (7)..(7)
<223> OTHER INFORMATION: /note="2'-OMe modified nucleotide"

<220> FEATURE:
<221> NAME/KEY: misc_feature
<222> LOCATION: (8)..(8)
<223> OTHER INFORMATION: /note="2'-F modified nucleotide"
<220> FEATURE:
<221> NAME/KEY: misc_feature
<222> LOCATION: (9)..(9)
<223> OTHER INFORMATION: /note="2'-F modified nucleotide"
<220> FEATURE:
<221> NAME/KEY: misc_feature
<222> LOCATION: (10)..(10)
<223> OTHER INFORMATION: /note="2'-F modified nucleotide"
<220> FEATURE:
<221> NAME/KEY: misc_feature
<222> LOCATION: (11)..(11)
<223> OTHER INFORMATION: /note="2'-F modified nucleotide"
<220> FEATURE:
<221> NAME/KEY: misc_feature
<222> LOCATION: (12)..(12)
<223> OTHER INFORMATION: /note="2'-OMe modified nucleotide"
<220> FEATURE:
<221> NAME/KEY: misc_feature
<222> LOCATION: (13)..(13)
<223> OTHER INFORMATION: /note="2'-OMe modified nucleotide"
<220> FEATURE:
<221> NAME/KEY: misc_feature
<222> LOCATION: (14)..(14)
<223> OTHER INFORMATION: /note="2'-OMe modified nucleotide"
<220> FEATURE:
<221> NAME/KEY: misc_feature
<222> LOCATION: (15)..(15)
<223> OTHER INFORMATION: /note="2'-OMe modified nucleotide"
<220> FEATURE:
<221> NAME/KEY: misc_feature
<222> LOCATION: (16)..(16)
<223> OTHER INFORMATION: /note="2'-OMe modified nucleotide"
<220> FEATURE:
<221> NAME/KEY: misc_feature
<222> LOCATION: (17)..(17)
<223> OTHER INFORMATION: /note="2'-OMe modified nucleotide"
<220> FEATURE:
<221> NAME/KEY: misc_feature
<222> LOCATION: (18)..(18)
<223> OTHER INFORMATION: /note="2'-OMe modified nucleotide"
<220> FEATURE:
<221> NAME/KEY: misc_feature
<222> LOCATION: (19)..(19)
<223> OTHER INFORMATION: /note="2'-OMe modified nucleotide"
<220> FEATURE:
<221> NAME/KEY: misc_feature
<222> LOCATION: (20)..(20)
<223> OTHER INFORMATION: /note="2'-OMe modified nucleotide"
<220> FEATURE:
<221> NAME/KEY: misc_feature
<222> LOCATION: (21)..(21)
<223> OTHER INFORMATION: /note="2'-OMe modified nucleotide"
<220> FEATURE:
<221> NAME/KEY: misc_feature
<222> LOCATION: (22)..(22)
<223> OTHER INFORMATION: /note="2'-OMe modified nucleotide"
<220> FEATURE:
<221> NAME/KEY: misc_feature
<222> LOCATION: (23)..(23)
<223> OTHER INFORMATION: /note="2'-OMe modified nucleotide"
<220> FEATURE:
<221> NAME/KEY: misc_feature
<222> LOCATION: (24)..(24)
<223> OTHER INFORMATION: /note="2'-OMe modified nucleotide"
<220> FEATURE:
<221> NAME/KEY: misc_feature
<222> LOCATION: (25)..(25)
<223> OTHER INFORMATION: /note="2'-OMe modified nucleotide"
<220> FEATURE:
<221> NAME/KEY: misc_feature
<222> LOCATION: (26)..(26)
<223> OTHER INFORMATION: /note="2'-OMe modified nucleotide"
<220> FEATURE:
<221> NAME/KEY: misc_feature
<222> LOCATION: (27)..(27)

<223> OTHER INFORMATION: /note="2'-OMe modified nucleotide"
<220> FEATURE:
<221> NAME/KEY: misc_feature
<222> LOCATION: (28)..(28)
<223> OTHER INFORMATION: /note="ademA-GalNAc"
<220> FEATURE:
<221> NAME/KEY: misc_feature
<222> LOCATION: (29)..(29)
<223> OTHER INFORMATION: /note="ademA-GalNAc"
<220> FEATURE:
<221> NAME/KEY: misc_feature
<222> LOCATION: (30)..(30)
<223> OTHER INFORMATION: /note="ademA-GalNAc"
<220> FEATURE:
<221> NAME/KEY: misc_feature
<222> LOCATION: (31)..(31)
<223> OTHER INFORMATION: /note="2'-OMe modified nucleotide"
<220> FEATURE:
<221> NAME/KEY: misc_feature
<222> LOCATION: (32)..(32)
<223> OTHER INFORMATION: /note="2'-OMe modified nucleotide"
<220> FEATURE:
<221> NAME/KEY: misc_feature
<222> LOCATION: (33)..(33)
<223> OTHER INFORMATION: /note="2'-OMe modified nucleotide"
<220> FEATURE:
<221> NAME/KEY: misc_feature
<222> LOCATION: (34)..(34)
<223> OTHER INFORMATION: /note="2'-OMe modified nucleotide"
<220> FEATURE:
<221> NAME/KEY: misc_feature
<222> LOCATION: (35)..(35)
<223> OTHER INFORMATION: /note="2'-OMe modified nucleotide"
<220> FEATURE:
<221> NAME/KEY: misc_feature
<222> LOCATION: (36)..(36)
<223> OTHER INFORMATION: /note="2'-OMe modified nucleotide"

<400> SEQUENCE: 168
cauauuugau cagucuuuua gcagccgaaa ggcugc 36

<210> SEQ ID NO 169
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: misc_feature
<222> LOCATION: (1)..(1)
<223> OTHER INFORMATION: /note="MePhosphonate-4O-mUs"
<220> FEATURE:
<221> NAME/KEY: misc_feature
<222> LOCATION: (2)..(2)
<223> OTHER INFORMATION: /note="2'-F modified nucleotide with a 3'-phosphorothioate linkage"
<220> FEATURE:
<221> NAME/KEY: misc_feature
<222> LOCATION: (3)..(3)
<223> OTHER INFORMATION: /note="2'-F modified nucleotide with a 3'-phosphorothioate linkage"
<220> FEATURE:
<221> NAME/KEY: misc_feature
<222> LOCATION: (4)..(4)
<223> OTHER INFORMATION: /note="2'-F modified nucleotide"
<220> FEATURE:
<221> NAME/KEY: misc_feature
<222> LOCATION: (5)..(5)
<223> OTHER INFORMATION: /note="2'-F modified nucleotide"
<220> FEATURE:
<221> NAME/KEY: misc_feature
<222> LOCATION: (6)..(6)
<223> OTHER INFORMATION: /note="2'-OMe modified nucleotide"
<220> FEATURE:
<221> NAME/KEY: misc_feature
<222> LOCATION: (7)..(7)
<223> OTHER INFORMATION: /note="2'-F modified nucleotide"
<220> FEATURE:
<221> NAME/KEY: misc_feature
<222> LOCATION: (8)..(8)
<223> OTHER INFORMATION: /note="2'-OMe modified nucleotide"
<220> FEATURE:
<221> NAME/KEY: misc_feature
<222> LOCATION: (9)..(9)
<223> OTHER INFORMATION: /note="2'-OMe modified nucleotide"
<220> FEATURE:
<221> NAME/KEY: misc_feature
<222> LOCATION: (10)..(10)
<223> OTHER INFORMATION: /note="2'-F modified nucleotide"
<220> FEATURE:
<221> NAME/KEY: misc_feature
<222> LOCATION: (11)..(11)
<223> OTHER INFORMATION: /note="2'-OMe modified nucleotide"
<220> FEATURE:
<221> NAME/KEY: misc_feature
<222> LOCATION: (12)..(12)
<223> OTHER INFORMATION: /note="2'-OMe modified nucleotide"
<220> FEATURE:
<221> NAME/KEY: misc_feature
<222> LOCATION: (13)..(13)
<223> OTHER INFORMATION: /note="2'-OMe modified nucleotide"
<220> FEATURE:
<221> NAME/KEY: misc_feature
<222> LOCATION: (14)..(14)
<223> OTHER INFORMATION: /note="2'-F modified nucleotide"
<220> FEATURE:
<221> NAME/KEY: misc_feature
<222> LOCATION: (15)..(15)
<223> OTHER INFORMATION: /note="2'-OMe modified nucleotide"
<220> FEATURE:
<221> NAME/KEY: misc_feature
<222> LOCATION: (16)..(16)
<223> OTHER INFORMATION: /note="2'-OMe modified nucleotide"
<220> FEATURE:
<221> NAME/KEY: misc_feature
<222> LOCATION: (17)..(17)
<223> OTHER INFORMATION: /note="2'-OMe modified nucleotide"
<220> FEATURE:
<221> NAME/KEY: misc_feature
<222> LOCATION: (18)..(18)
<223> OTHER INFORMATION: /note="2'-OMe modified nucleotide"
<220> FEATURE:
<221> NAME/KEY: misc_feature
<222> LOCATION: (19)..(19)
<223> OTHER INFORMATION: /note="2'-OMe modified nucleotide"
<220> FEATURE:
<221> NAME/KEY: misc_feature
<222> LOCATION: (20)..(20)
<223> OTHER INFORMATION: /note="2'-OMe modified nucleotide with a
3'-phosphorothioate linkage"
<220> FEATURE:
<221> NAME/KEY: misc_feature
<222> LOCATION: (21)..(21)
<223> OTHER INFORMATION: /note="2'-OMe modified nucleotide with a
3'-phosphorothioate linkage"
<220> FEATURE:
<221> NAME/KEY: misc_feature
<222> LOCATION: (22)..(22)
<223> OTHER INFORMATION: /note="2'-OMe modified nucleotide"

<400> SEQUENCE: 169
uaaaagacug aucaaauaug gg 22

<210> SEQ ID NO 170
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:

-continued

<221> NAME/KEY: misc_feature
<222> LOCATION: (1)..(1)
<223> OTHER INFORMATION: /note="2'-OMe modified nucleotide with a 3'-phosphorothioate linkage"
<220> FEATURE:
<221> NAME/KEY: misc_feature
<222> LOCATION: (2)..(2)
<223> OTHER INFORMATION: /note="2'-OMe modified nucleotide"
<220> FEATURE:
<221> NAME/KEY: misc_feature
<222> LOCATION: (3)..(3)
<223> OTHER INFORMATION: /note="2'-OMe modified nucleotide"
<220> FEATURE:
<221> NAME/KEY: misc_feature
<222> LOCATION: (4)..(4)
<223> OTHER INFORMATION: /note="2'-OMe modified nucleotide"
<220> FEATURE:
<221> NAME/KEY: misc_feature
<222> LOCATION: (5)..(5)
<223> OTHER INFORMATION: /note="2'-OMe modified nucleotide"
<220> FEATURE:
<221> NAME/KEY: misc_feature
<222> LOCATION: (6)..(6)
<223> OTHER INFORMATION: /note="2'-OMe modified nucleotide"
<220> FEATURE:
<221> NAME/KEY: misc_feature
<222> LOCATION: (7)..(7)
<223> OTHER INFORMATION: /note="2'-OMe modified nucleotide"
<220> FEATURE:
<221> NAME/KEY: misc_feature
<222> LOCATION: (8)..(8)
<223> OTHER INFORMATION: /note="2'-F modified nucleotide"
<220> FEATURE:
<221> NAME/KEY: misc_feature
<222> LOCATION: (9)..(9)
<223> OTHER INFORMATION: /note="2'-F modified nucleotide"
<220> FEATURE:
<221> NAME/KEY: misc_feature
<222> LOCATION: (10)..(10)
<223> OTHER INFORMATION: /note="2'-F modified nucleotide"
<220> FEATURE:
<221> NAME/KEY: misc_feature
<222> LOCATION: (11)..(11)
<223> OTHER INFORMATION: /note="2'-F modified nucleotide"
<220> FEATURE:
<221> NAME/KEY: misc_feature
<222> LOCATION: (12)..(12)
<223> OTHER INFORMATION: /note="2'-OMe modified nucleotide"
<220> FEATURE:
<221> NAME/KEY: misc_feature
<222> LOCATION: (13)..(13)
<223> OTHER INFORMATION: /note="2'-OMe modified nucleotide"
<220> FEATURE:
<221> NAME/KEY: misc_feature
<222> LOCATION: (14)..(14)
<223> OTHER INFORMATION: /note="2'-OMe modified nucleotide"
<220> FEATURE:
<221> NAME/KEY: misc_feature
<222> LOCATION: (15)..(15)
<223> OTHER INFORMATION: /note="2'-OMe modified nucleotide"
<220> FEATURE:
<221> NAME/KEY: misc_feature
<222> LOCATION: (16)..(16)
<223> OTHER INFORMATION: /note="2'-OMe modified nucleotide"
<220> FEATURE:
<221> NAME/KEY: misc_feature
<222> LOCATION: (17)..(17)
<223> OTHER INFORMATION: /note="2'-OMe modified nucleotide"
<220> FEATURE:
<221> NAME/KEY: misc_feature
<222> LOCATION: (18)..(18)
<223> OTHER INFORMATION: /note="2'-OMe modified nucleotide"
<220> FEATURE:
<221> NAME/KEY: misc_feature
<222> LOCATION: (19)..(19)
<223> OTHER INFORMATION: /note="2'-OMe modified nucleotide"
<220> FEATURE:
<221> NAME/KEY: misc_feature
<222> LOCATION: (20)..(20)

<223> OTHER INFORMATION: /note="2'-OMe modified nucleotide"
<220> FEATURE:
<221> NAME/KEY: misc_feature
<222> LOCATION: (21)..(21)
<223> OTHER INFORMATION: /note="2'-OMe modified nucleotide"
<220> FEATURE:
<221> NAME/KEY: misc_feature
<222> LOCATION: (22)..(22)
<223> OTHER INFORMATION: /note="2'-OMe modified nucleotide"
<220> FEATURE:
<221> NAME/KEY: misc_feature
<222> LOCATION: (23)..(23)
<223> OTHER INFORMATION: /note="2'-OMe modified nucleotide"
<220> FEATURE:
<221> NAME/KEY: misc_feature
<222> LOCATION: (24)..(24)
<223> OTHER INFORMATION: /note="2'-OMe modified nucleotide"
<220> FEATURE:
<221> NAME/KEY: misc_feature
<222> LOCATION: (25)..(25)
<223> OTHER INFORMATION: /note="2'-OMe modified nucleotide"
<220> FEATURE:
<221> NAME/KEY: misc_feature
<222> LOCATION: (26)..(26)
<223> OTHER INFORMATION: /note="2'-OMe modified nucleotide"
<220> FEATURE:
<221> NAME/KEY: misc_feature
<222> LOCATION: (27)..(27)
<223> OTHER INFORMATION: /note="2'-OMe modified nucleotide"
<220> FEATURE:
<221> NAME/KEY: misc_feature
<222> LOCATION: (28)..(28)
<223> OTHER INFORMATION: /note="ademA-GalNAc"
<220> FEATURE:
<221> NAME/KEY: misc_feature
<222> LOCATION: (29)..(29)
<223> OTHER INFORMATION: /note="ademA-GalNAc"
<220> FEATURE:
<221> NAME/KEY: misc_feature
<222> LOCATION: (30)..(30)
<223> OTHER INFORMATION: /note="ademA-GalNAc"
<220> FEATURE:
<221> NAME/KEY: misc_feature
<222> LOCATION: (31)..(31)
<223> OTHER INFORMATION: /note="2'-OMe modified nucleotide"
<220> FEATURE:
<221> NAME/KEY: misc_feature
<222> LOCATION: (32)..(32)
<223> OTHER INFORMATION: /note="2'-OMe modified nucleotide"
<220> FEATURE:
<221> NAME/KEY: misc_feature
<222> LOCATION: (33)..(33)
<223> OTHER INFORMATION: /note="2'-OMe modified nucleotide"
<220> FEATURE:
<221> NAME/KEY: misc_feature
<222> LOCATION: (34)..(34)
<223> OTHER INFORMATION: /note="2'-OMe modified nucleotide"
<220> FEATURE:
<221> NAME/KEY: misc_feature
<222> LOCATION: (35)..(35)
<223> OTHER INFORMATION: /note="2'-OMe modified nucleotide"
<220> FEATURE:
<221> NAME/KEY: misc_feature
<222> LOCATION: (36)..(36)
<223> OTHER INFORMATION: /note="2'-OMe modified nucleotide"

<400> SEQUENCE: 170
auauuugauc agucuuuuua gcagccgaaa ggcugc 36

<210> SEQ ID NO 171
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

```
<220> FEATURE:
<221> NAME/KEY: misc_feature
<222> LOCATION: (1)..(1)
<223> OTHER INFORMATION: /note="MePhosphonate-4O-mUs"
<220> FEATURE:
<221> NAME/KEY: misc_feature
<222> LOCATION: (2)..(2)
<223> OTHER INFORMATION: /note="2'-F modified nucleotide with a
      3'-phosphorothioate linkage"
<220> FEATURE:
<221> NAME/KEY: misc_feature
<222> LOCATION: (3)..(3)
<223> OTHER INFORMATION: /note="2'-F modified nucleotide with a
      3'-phosphorothioate linkage"
<220> FEATURE:
<221> NAME/KEY: misc_feature
<222> LOCATION: (4)..(4)
<223> OTHER INFORMATION: /note="2'-F modified nucleotide"
<220> FEATURE:
<221> NAME/KEY: misc_feature
<222> LOCATION: (5)..(5)
<223> OTHER INFORMATION: /note="2'-F modified nucleotide"
<220> FEATURE:
<221> NAME/KEY: misc_feature
<222> LOCATION: (6)..(6)
<223> OTHER INFORMATION: /note="2'-OMe modified nucleotide"
<220> FEATURE:
<221> NAME/KEY: misc_feature
<222> LOCATION: (7)..(7)
<223> OTHER INFORMATION: /note="2'-F modified nucleotide"
<220> FEATURE:
<221> NAME/KEY: misc_feature
<222> LOCATION: (8)..(8)
<223> OTHER INFORMATION: /note="2'-OMe modified nucleotide"
<220> FEATURE:
<221> NAME/KEY: misc_feature
<222> LOCATION: (9)..(9)
<223> OTHER INFORMATION: /note="2'-OMe modified nucleotide"
<220> FEATURE:
<221> NAME/KEY: misc_feature
<222> LOCATION: (10)..(10)
<223> OTHER INFORMATION: /note="2'-F modified nucleotide"
<220> FEATURE:
<221> NAME/KEY: misc_feature
<222> LOCATION: (11)..(11)
<223> OTHER INFORMATION: /note="2'-OMe modified nucleotide"
<220> FEATURE:
<221> NAME/KEY: misc_feature
<222> LOCATION: (12)..(12)
<223> OTHER INFORMATION: /note="2'-OMe modified nucleotide"
<220> FEATURE:
<221> NAME/KEY: misc_feature
<222> LOCATION: (13)..(13)
<223> OTHER INFORMATION: /note="2'-OMe modified nucleotide"
<220> FEATURE:
<221> NAME/KEY: misc_feature
<222> LOCATION: (14)..(14)
<223> OTHER INFORMATION: /note="2'-F modified nucleotide"
<220> FEATURE:
<221> NAME/KEY: misc_feature
<222> LOCATION: (15)..(15)
<223> OTHER INFORMATION: /note="2'-OMe modified nucleotide"
<220> FEATURE:
<221> NAME/KEY: misc_feature
<222> LOCATION: (16)..(16)
<223> OTHER INFORMATION: /note="2'-OMe modified nucleotide"
<220> FEATURE:
<221> NAME/KEY: misc_feature
<222> LOCATION: (17)..(17)
<223> OTHER INFORMATION: /note="2'-OMe modified nucleotide"
<220> FEATURE:
<221> NAME/KEY: misc_feature
<222> LOCATION: (18)..(18)
<223> OTHER INFORMATION: /note="2'-OMe modified nucleotide"
<220> FEATURE:
<221> NAME/KEY: misc_feature
<222> LOCATION: (19)..(19)
<223> OTHER INFORMATION: /note="2'-OMe modified nucleotide"
<220> FEATURE:
```

<221> NAME/KEY: misc_feature
<222> LOCATION: (20)..(20)
<223> OTHER INFORMATION: /note="2'-OMe modified nucleotide with a 3'-phosphorothioate linkage"
<220> FEATURE:
<221> NAME/KEY: misc_feature
<222> LOCATION: (21)..(21)
<223> OTHER INFORMATION: /note="2'-OMe modified nucleotide with a 3'-phosphorothioate linkage"
<220> FEATURE:
<221> NAME/KEY: misc_feature
<222> LOCATION: (22)..(22)
<223> OTHER INFORMATION: /note="2'-OMe modified nucleotide"

<400> SEQUENCE: 171
uaaaaagacu gaucaaauau gg 22

<210> SEQ ID NO 172
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: misc_feature
<222> LOCATION: (1)..(1)
<223> OTHER INFORMATION: /note="2'-OMe modified nucleotide with a 3'-phosphorothioate linkage"
<220> FEATURE:
<221> NAME/KEY: misc_feature
<222> LOCATION: (2)..(2)
<223> OTHER INFORMATION: /note="2'-OMe modified nucleotide"
<220> FEATURE:
<221> NAME/KEY: misc_feature
<222> LOCATION: (3)..(3)
<223> OTHER INFORMATION: /note="2'-OMe modified nucleotide"
<220> FEATURE:
<221> NAME/KEY: misc_feature
<222> LOCATION: (4)..(4)
<223> OTHER INFORMATION: /note="2'-OMe modified nucleotide"
<220> FEATURE:
<221> NAME/KEY: misc_feature
<222> LOCATION: (5)..(5)
<223> OTHER INFORMATION: /note="2'-OMe modified nucleotide"
<220> FEATURE:
<221> NAME/KEY: misc_feature
<222> LOCATION: (6)..(6)
<223> OTHER INFORMATION: /note="2'-OMe modified nucleotide"
<220> FEATURE:
<221> NAME/KEY: misc_feature
<222> LOCATION: (7)..(7)
<223> OTHER INFORMATION: /note="2'-OMe modified nucleotide"
<220> FEATURE:
<221> NAME/KEY: misc_feature
<222> LOCATION: (8)..(8)
<223> OTHER INFORMATION: /note="2'-F modified nucleotide"
<220> FEATURE:
<221> NAME/KEY: misc_feature
<222> LOCATION: (9)..(9)
<223> OTHER INFORMATION: /note="2'-F modified nucleotide"
<220> FEATURE:
<221> NAME/KEY: misc_feature
<222> LOCATION: (10)..(10)
<223> OTHER INFORMATION: /note="2'-F modified nucleotide"
<220> FEATURE:
<221> NAME/KEY: misc_feature
<222> LOCATION: (11)..(11)
<223> OTHER INFORMATION: /note="2'-F modified nucleotide"
<220> FEATURE:
<221> NAME/KEY: misc_feature
<222> LOCATION: (12)..(12)
<223> OTHER INFORMATION: /note="2'-OMe modified nucleotide"
<220> FEATURE:
<221> NAME/KEY: misc_feature
<222> LOCATION: (13)..(13)

<223> OTHER INFORMATION: /note="2'-OMe modified nucleotide"
<220> FEATURE:
<221> NAME/KEY: misc_feature
<222> LOCATION: (14)..(14)
<223> OTHER INFORMATION: /note="2'-OMe modified nucleotide"
<220> FEATURE:
<221> NAME/KEY: misc_feature
<222> LOCATION: (15)..(15)
<223> OTHER INFORMATION: /note="2'-OMe modified nucleotide"
<220> FEATURE:
<221> NAME/KEY: misc_feature
<222> LOCATION: (16)..(16)
<223> OTHER INFORMATION: /note="2'-OMe modified nucleotide"
<220> FEATURE:
<221> NAME/KEY: misc_feature
<222> LOCATION: (17)..(17)
<223> OTHER INFORMATION: /note="2'-OMe modified nucleotide"
<220> FEATURE:
<221> NAME/KEY: misc_feature
<222> LOCATION: (18)..(18)
<223> OTHER INFORMATION: /note="2'-OMe modified nucleotide"
<220> FEATURE:
<221> NAME/KEY: misc_feature
<222> LOCATION: (19)..(19)
<223> OTHER INFORMATION: /note="2'-OMe modified nucleotide"
<220> FEATURE:
<221> NAME/KEY: misc_feature
<222> LOCATION: (20)..(20)
<223> OTHER INFORMATION: /note="2'-OMe modified nucleotide"
<220> FEATURE:
<221> NAME/KEY: misc_feature
<222> LOCATION: (21)..(21)
<223> OTHER INFORMATION: /note="2'-OMe modified nucleotide"
<220> FEATURE:
<221> NAME/KEY: misc_feature
<222> LOCATION: (22)..(22)
<223> OTHER INFORMATION: /note="2'-OMe modified nucleotide"
<220> FEATURE:
<221> NAME/KEY: misc_feature
<222> LOCATION: (23)..(23)
<223> OTHER INFORMATION: /note="2'-OMe modified nucleotide"
<220> FEATURE:
<221> NAME/KEY: misc_feature
<222> LOCATION: (24)..(24)
<223> OTHER INFORMATION: /note="2'-OMe modified nucleotide"
<220> FEATURE:
<221> NAME/KEY: misc_feature
<222> LOCATION: (25)..(25)
<223> OTHER INFORMATION: /note="2'-OMe modified nucleotide"
<220> FEATURE:
<221> NAME/KEY: misc_feature
<222> LOCATION: (26)..(26)
<223> OTHER INFORMATION: /note="2'-OMe modified nucleotide"
<220> FEATURE:
<221> NAME/KEY: misc_feature
<222> LOCATION: (27)..(27)
<223> OTHER INFORMATION: /note="2'-OMe modified nucleotide"
<220> FEATURE:
<221> NAME/KEY: misc_feature
<222> LOCATION: (28)..(28)
<223> OTHER INFORMATION: /note="ademA-GalNAc"
<220> FEATURE:
<221> NAME/KEY: misc_feature
<222> LOCATION: (29)..(29)
<223> OTHER INFORMATION: /note="ademA-GalNAc"
<220> FEATURE:
<221> NAME/KEY: misc_feature
<222> LOCATION: (30)..(30)
<223> OTHER INFORMATION: /note="ademA-GalNAc"
<220> FEATURE:
<221> NAME/KEY: misc_feature
<222> LOCATION: (31)..(31)
<223> OTHER INFORMATION: /note="2'-OMe modified nucleotide"
<220> FEATURE:
<221> NAME/KEY: misc_feature
<222> LOCATION: (32)..(32)
<223> OTHER INFORMATION: /note="2'-OMe modified nucleotide"
<220> FEATURE:
<221> NAME/KEY: misc_feature

```
<222> LOCATION: (33)..(33)
<223> OTHER INFORMATION: /note="2'-OMe modified nucleotide"
<220> FEATURE:
<221> NAME/KEY: misc_feature
<222> LOCATION: (34)..(34)
<223> OTHER INFORMATION: /note="2'-OMe modified nucleotide"
<220> FEATURE:
<221> NAME/KEY: misc_feature
<222> LOCATION: (35)..(35)
<223> OTHER INFORMATION: /note="2'-OMe modified nucleotide"
<220> FEATURE:
<221> NAME/KEY: misc_feature
<222> LOCATION: (36)..(36)
<223> OTHER INFORMATION: /note="2'-OMe modified nucleotide"

<400> SEQUENCE: 172

uugaucaguc uuuuuaugaa gcagccgaaa ggcugc                              36


<210> SEQ ID NO 173
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: misc_feature
<222> LOCATION: (1)..(1)
<223> OTHER INFORMATION: /note="MePhosphonate-4O-mUs"
<220> FEATURE:
<221> NAME/KEY: misc_feature
<222> LOCATION: (2)..(2)
<223> OTHER INFORMATION: /note="2'-F modified nucleotide with a
      3'-phosphorothioate linkage"
<220> FEATURE:
<221> NAME/KEY: misc_feature
<222> LOCATION: (3)..(3)
<223> OTHER INFORMATION: /note="2'-F modified nucleotide with a
      3'-phosphorothioate linkage"
<220> FEATURE:
<221> NAME/KEY: misc_feature
<222> LOCATION: (4)..(4)
<223> OTHER INFORMATION: /note="2'-F modified nucleotide"
<220> FEATURE:
<221> NAME/KEY: misc_feature
<222> LOCATION: (5)..(5)
<223> OTHER INFORMATION: /note="2'-F modified nucleotide"
<220> FEATURE:
<221> NAME/KEY: misc_feature
<222> LOCATION: (6)..(6)
<223> OTHER INFORMATION: /note="2'-OMe modified nucleotide"
<220> FEATURE:
<221> NAME/KEY: misc_feature
<222> LOCATION: (7)..(7)
<223> OTHER INFORMATION: /note="2'-F modified nucleotide"
<220> FEATURE:
<221> NAME/KEY: misc_feature
<222> LOCATION: (8)..(8)
<223> OTHER INFORMATION: /note="2'-OMe modified nucleotide"
<220> FEATURE:
<221> NAME/KEY: misc_feature
<222> LOCATION: (9)..(9)
<223> OTHER INFORMATION: /note="2'-OMe modified nucleotide"
<220> FEATURE:
<221> NAME/KEY: misc_feature
<222> LOCATION: (10)..(10)
<223> OTHER INFORMATION: /note="2'-F modified nucleotide"
<220> FEATURE:
<221> NAME/KEY: misc_feature
<222> LOCATION: (11)..(11)
<223> OTHER INFORMATION: /note="2'-OMe modified nucleotide"
<220> FEATURE:
<221> NAME/KEY: misc_feature
<222> LOCATION: (12)..(12)
<223> OTHER INFORMATION: /note="2'-OMe modified nucleotide"
<220> FEATURE:
```

<221> NAME/KEY: misc_feature
<222> LOCATION: (13)..(13)
<223> OTHER INFORMATION: /note="2'-OMe modified nucleotide"
<220> FEATURE:
<221> NAME/KEY: misc_feature
<222> LOCATION: (14)..(14)
<223> OTHER INFORMATION: /note="2'-F modified nucleotide"
<220> FEATURE:
<221> NAME/KEY: misc_feature
<222> LOCATION: (15)..(15)
<223> OTHER INFORMATION: /note="2'-OMe modified nucleotide"
<220> FEATURE:
<221> NAME/KEY: misc_feature
<222> LOCATION: (16)..(16)
<223> OTHER INFORMATION: /note="2'-OMe modified nucleotide"
<220> FEATURE:
<221> NAME/KEY: misc_feature
<222> LOCATION: (17)..(17)
<223> OTHER INFORMATION: /note="2'-OMe modified nucleotide"
<220> FEATURE:
<221> NAME/KEY: misc_feature
<222> LOCATION: (18)..(18)
<223> OTHER INFORMATION: /note="2'-OMe modified nucleotide"
<220> FEATURE:
<221> NAME/KEY: misc_feature
<222> LOCATION: (19)..(19)
<223> OTHER INFORMATION: /note="2'-OMe modified nucleotide"
<220> FEATURE:
<221> NAME/KEY: misc_feature
<222> LOCATION: (20)..(20)
<223> OTHER INFORMATION: /note="2'-OMe modified nucleotide with a
3'-phosphorothioate linkage"
<220> FEATURE:
<221> NAME/KEY: misc_feature
<222> LOCATION: (21)..(21)
<223> OTHER INFORMATION: /note="2'-OMe modified nucleotide with a
3'-phosphorothioate linkage"
<220> FEATURE:
<221> NAME/KEY: misc_feature
<222> LOCATION: (22)..(22)
<223> OTHER INFORMATION: /note="2'-OMe modified nucleotide"

<400> SEQUENCE: 173
uucauaaaaa gacugaucaa gg 22

<210> SEQ ID NO 174
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: misc_feature
<222> LOCATION: (1)..(1)
<223> OTHER INFORMATION: /note="2'-OMe modified nucleotide with a
3'-phosphorothioate linkage"
<220> FEATURE:
<221> NAME/KEY: misc_feature
<222> LOCATION: (2)..(2)
<223> OTHER INFORMATION: /note="2'-OMe modified nucleotide"
<220> FEATURE:
<221> NAME/KEY: misc_feature
<222> LOCATION: (3)..(3)
<223> OTHER INFORMATION: /note="2'-OMe modified nucleotide"
<220> FEATURE:
<221> NAME/KEY: misc_feature
<222> LOCATION: (4)..(4)
<223> OTHER INFORMATION: /note="2'-OMe modified nucleotide"
<220> FEATURE:
<221> NAME/KEY: misc_feature
<222> LOCATION: (5)..(5)
<223> OTHER INFORMATION: /note="2'-OMe modified nucleotide"
<220> FEATURE:
<221> NAME/KEY: misc_feature
<222> LOCATION: (6)..(6)

<223> OTHER INFORMATION: /note="2'-OMe modified nucleotide"
<220> FEATURE:
<221> NAME/KEY: misc_feature
<222> LOCATION: (7)..(7)
<223> OTHER INFORMATION: /note="2'-OMe modified nucleotide"
<220> FEATURE:
<221> NAME/KEY: misc_feature
<222> LOCATION: (8)..(8)
<223> OTHER INFORMATION: /note="2'-F modified nucleotide"
<220> FEATURE:
<221> NAME/KEY: misc_feature
<222> LOCATION: (9)..(9)
<223> OTHER INFORMATION: /note="2'-F modified nucleotide"
<220> FEATURE:
<221> NAME/KEY: misc_feature
<222> LOCATION: (10)..(10)
<223> OTHER INFORMATION: /note="2'-F modified nucleotide"
<220> FEATURE:
<221> NAME/KEY: misc_feature
<222> LOCATION: (11)..(11)
<223> OTHER INFORMATION: /note="2'-F modified nucleotide"
<220> FEATURE:
<221> NAME/KEY: misc_feature
<222> LOCATION: (12)..(12)
<223> OTHER INFORMATION: /note="2'-OMe modified nucleotide"
<220> FEATURE:
<221> NAME/KEY: misc_feature
<222> LOCATION: (13)..(13)
<223> OTHER INFORMATION: /note="2'-OMe modified nucleotide"
<220> FEATURE:
<221> NAME/KEY: misc_feature
<222> LOCATION: (14)..(14)
<223> OTHER INFORMATION: /note="2'-OMe modified nucleotide"
<220> FEATURE:
<221> NAME/KEY: misc_feature
<222> LOCATION: (15)..(15)
<223> OTHER INFORMATION: /note="2'-OMe modified nucleotide"
<220> FEATURE:
<221> NAME/KEY: misc_feature
<222> LOCATION: (16)..(16)
<223> OTHER INFORMATION: /note="2'-OMe modified nucleotide"
<220> FEATURE:
<221> NAME/KEY: misc_feature
<222> LOCATION: (17)..(17)
<223> OTHER INFORMATION: /note="2'-OMe modified nucleotide"
<220> FEATURE:
<221> NAME/KEY: misc_feature
<222> LOCATION: (18)..(18)
<223> OTHER INFORMATION: /note="2'-OMe modified nucleotide"
<220> FEATURE:
<221> NAME/KEY: misc_feature
<222> LOCATION: (19)..(19)
<223> OTHER INFORMATION: /note="2'-OMe modified nucleotide"
<220> FEATURE:
<221> NAME/KEY: misc_feature
<222> LOCATION: (20)..(20)
<223> OTHER INFORMATION: /note="2'-OMe modified nucleotide"
<220> FEATURE:
<221> NAME/KEY: misc_feature
<222> LOCATION: (21)..(21)
<223> OTHER INFORMATION: /note="2'-OMe modified nucleotide"
<220> FEATURE:
<221> NAME/KEY: misc_feature
<222> LOCATION: (22)..(22)
<223> OTHER INFORMATION: /note="2'-OMe modified nucleotide"
<220> FEATURE:
<221> NAME/KEY: misc_feature
<222> LOCATION: (23)..(23)
<223> OTHER INFORMATION: /note="2'-OMe modified nucleotide"
<220> FEATURE:
<221> NAME/KEY: misc_feature
<222> LOCATION: (24)..(24)
<223> OTHER INFORMATION: /note="2'-OMe modified nucleotide"
<220> FEATURE:
<221> NAME/KEY: misc_feature
<222> LOCATION: (25)..(25)
<223> OTHER INFORMATION: /note="2'-OMe modified nucleotide"
<220> FEATURE:
<221> NAME/KEY: misc_feature
<222> LOCATION: (26)..(26)
<223> OTHER INFORMATION: /note="2'-OMe modified nucleotide"
<220> FEATURE:
<221> NAME/KEY: misc_feature
<222> LOCATION: (27)..(27)
<223> OTHER INFORMATION: /note="2'-OMe modified nucleotide"
<220> FEATURE:
<221> NAME/KEY: misc_feature
<222> LOCATION: (28)..(28)
<223> OTHER INFORMATION: /note="ademA-GalNAc"
<220> FEATURE:
<221> NAME/KEY: misc_feature
<222> LOCATION: (29)..(29)
<223> OTHER INFORMATION: /note="ademA-GalNAc"
<220> FEATURE:
<221> NAME/KEY: misc_feature
<222> LOCATION: (30)..(30)
<223> OTHER INFORMATION: /note="ademA-GalNAc"
<220> FEATURE:
<221> NAME/KEY: misc_feature
<222> LOCATION: (31)..(31)
<223> OTHER INFORMATION: /note="2'-OMe modified nucleotide"
<220> FEATURE:
<221> NAME/KEY: misc_feature
<222> LOCATION: (32)..(32)
<223> OTHER INFORMATION: /note="2'-OMe modified nucleotide"
<220> FEATURE:
<221> NAME/KEY: misc_feature
<222> LOCATION: (33)..(33)
<223> OTHER INFORMATION: /note="2'-OMe modified nucleotide"
<220> FEATURE:
<221> NAME/KEY: misc_feature
<222> LOCATION: (34)..(34)
<223> OTHER INFORMATION: /note="2'-OMe modified nucleotide"
<220> FEATURE:
<221> NAME/KEY: misc_feature
<222> LOCATION: (35)..(35)
<223> OTHER INFORMATION: /note="2'-OMe modified nucleotide"
<220> FEATURE:
<221> NAME/KEY: misc_feature
<222> LOCATION: (36)..(36)
<223> OTHER INFORMATION: /note="2'-OMe modified nucleotide"

<400> SEQUENCE: 174
aggaacugag aagaacuaca gcagccgaaa ggcugc 36

<210> SEQ ID NO 175
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: misc_feature
<222> LOCATION: (1)..(1)
<223> OTHER INFORMATION: /note="MePhosphonate-4O-mUs"
<220> FEATURE:
<221> NAME/KEY: misc_feature
<222> LOCATION: (2)..(2)
<223> OTHER INFORMATION: /note="2'-F modified nucleotide with a
3'-phosphorothioate linkage"
<220> FEATURE:
<221> NAME/KEY: misc_feature
<222> LOCATION: (3)..(3)
<223> OTHER INFORMATION: /note="2'-F modified nucleotide with a
3'-phosphorothioate linkage"
<220> FEATURE:
<221> NAME/KEY: misc_feature
<222> LOCATION: (4)..(4)
<223> OTHER INFORMATION: /note="2'-F modified nucleotide"
<220> FEATURE:
<221> NAME/KEY: misc_feature
<222> LOCATION: (5)..(5)
<223> OTHER INFORMATION: /note="2'-F modified nucleotide"
<220> FEATURE:

<221> NAME/KEY: misc_feature
<222> LOCATION: (6)..(6)
<223> OTHER INFORMATION: /note="2'-OMe modified nucleotide"
<220> FEATURE:
<221> NAME/KEY: misc_feature
<222> LOCATION: (7)..(7)
<223> OTHER INFORMATION: /note="2'-F modified nucleotide"
<220> FEATURE:
<221> NAME/KEY: misc_feature
<222> LOCATION: (8)..(8)
<223> OTHER INFORMATION: /note="2'-OMe modified nucleotide"
<220> FEATURE:
<221> NAME/KEY: misc_feature
<222> LOCATION: (9)..(9)
<223> OTHER INFORMATION: /note="2'-OMe modified nucleotide"
<220> FEATURE:
<221> NAME/KEY: misc_feature
<222> LOCATION: (10)..(10)
<223> OTHER INFORMATION: /note="2'-F modified nucleotide"
<220> FEATURE:
<221> NAME/KEY: misc_feature
<222> LOCATION: (11)..(11)
<223> OTHER INFORMATION: /note="2'-OMe modified nucleotide"
<220> FEATURE:
<221> NAME/KEY: misc_feature
<222> LOCATION: (12)..(12)
<223> OTHER INFORMATION: /note="2'-OMe modified nucleotide"
<220> FEATURE:
<221> NAME/KEY: misc_feature
<222> LOCATION: (13)..(13)
<223> OTHER INFORMATION: /note="2'-OMe modified nucleotide"
<220> FEATURE:
<221> NAME/KEY: misc_feature
<222> LOCATION: (14)..(14)
<223> OTHER INFORMATION: /note="2'-F modified nucleotide"
<220> FEATURE:
<221> NAME/KEY: misc_feature
<222> LOCATION: (15)..(15)
<223> OTHER INFORMATION: /note="2'-OMe modified nucleotide"
<220> FEATURE:
<221> NAME/KEY: misc_feature
<222> LOCATION: (16)..(16)
<223> OTHER INFORMATION: /note="2'-OMe modified nucleotide"
<220> FEATURE:
<221> NAME/KEY: misc_feature
<222> LOCATION: (17)..(17)
<223> OTHER INFORMATION: /note="2'-OMe modified nucleotide"
<220> FEATURE:
<221> NAME/KEY: misc_feature
<222> LOCATION: (18)..(18)
<223> OTHER INFORMATION: /note="2'-OMe modified nucleotide"
<220> FEATURE:
<221> NAME/KEY: misc_feature
<222> LOCATION: (19)..(19)
<223> OTHER INFORMATION: /note="2'-OMe modified nucleotide"
<220> FEATURE:
<221> NAME/KEY: misc_feature
<222> LOCATION: (20)..(20)
<223> OTHER INFORMATION: /note="2'-OMe modified nucleotide with a
3'-phosphorothioate linkage"
<220> FEATURE:
<221> NAME/KEY: misc_feature
<222> LOCATION: (21)..(21)
<223> OTHER INFORMATION: /note="2'-OMe modified nucleotide with a
3'-phosphorothioate linkage"
<220> FEATURE:
<221> NAME/KEY: misc_feature
<222> LOCATION: (22)..(22)
<223> OTHER INFORMATION: /note="2'-OMe modified nucleotide"

<400> SEQUENCE: 175
uguaguucuu cucaguuccu gg 22

<210> SEQ ID NO 176
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: misc_feature
<222> LOCATION: (1)..(1)
<223> OTHER INFORMATION: /note="2'-OMe modified nucleotide with a
3'-phosphorothioate linkage"
<220> FEATURE:
<221> NAME/KEY: misc_feature
<222> LOCATION: (2)..(2)
<223> OTHER INFORMATION: /note="2'-OMe modified nucleotide"
<220> FEATURE:
<221> NAME/KEY: misc_feature
<222> LOCATION: (3)..(3)
<223> OTHER INFORMATION: /note="2'-OMe modified nucleotide"
<220> FEATURE:
<221> NAME/KEY: misc_feature
<222> LOCATION: (4)..(4)
<223> OTHER INFORMATION: /note="2'-OMe modified nucleotide"
<220> FEATURE:
<221> NAME/KEY: misc_feature
<222> LOCATION: (5)..(5)
<223> OTHER INFORMATION: /note="2'-OMe modified nucleotide"
<220> FEATURE:
<221> NAME/KEY: misc_feature
<222> LOCATION: (6)..(6)
<223> OTHER INFORMATION: /note="2'-OMe modified nucleotide"
<220> FEATURE:
<221> NAME/KEY: misc_feature
<222> LOCATION: (7)..(7)
<223> OTHER INFORMATION: /note="2'-OMe modified nucleotide"
<220> FEATURE:
<221> NAME/KEY: misc_feature
<222> LOCATION: (8)..(8)
<223> OTHER INFORMATION: /note="2'-F modified nucleotide"
<220> FEATURE:
<221> NAME/KEY: misc_feature
<222> LOCATION: (9)..(9)
<223> OTHER INFORMATION: /note="2'-F modified nucleotide"
<220> FEATURE:
<221> NAME/KEY: misc_feature
<222> LOCATION: (10)..(10)
<223> OTHER INFORMATION: /note="2'-F modified nucleotide"
<220> FEATURE:
<221> NAME/KEY: misc_feature
<222> LOCATION: (11)..(11)
<223> OTHER INFORMATION: /note="2'-F modified nucleotide"
<220> FEATURE:
<221> NAME/KEY: misc_feature
<222> LOCATION: (12)..(12)
<223> OTHER INFORMATION: /note="2'-OMe modified nucleotide"
<220> FEATURE:
<221> NAME/KEY: misc_feature
<222> LOCATION: (13)..(13)
<223> OTHER INFORMATION: /note="2'-OMe modified nucleotide"
<220> FEATURE:
<221> NAME/KEY: misc_feature
<222> LOCATION: (14)..(14)
<223> OTHER INFORMATION: /note="2'-OMe modified nucleotide"
<220> FEATURE:
<221> NAME/KEY: misc_feature
<222> LOCATION: (15)..(15)
<223> OTHER INFORMATION: /note="2'-OMe modified nucleotide"
<220> FEATURE:
<221> NAME/KEY: misc_feature
<222> LOCATION: (16)..(16)
<223> OTHER INFORMATION: /note="2'-OMe modified nucleotide"
<220> FEATURE:
<221> NAME/KEY: misc_feature
<222> LOCATION: (17)..(17)
<223> OTHER INFORMATION: /note="2'-OMe modified nucleotide"
<220> FEATURE:
<221> NAME/KEY: misc_feature
<222> LOCATION: (18)..(18)
<223> OTHER INFORMATION: /note="2'-OMe modified nucleotide"
<220> FEATURE:
<221> NAME/KEY: misc_feature
<222> LOCATION: (19)..(19)
<223> OTHER INFORMATION: /note="2'-OMe modified nucleotide"
<220> FEATURE:
<221> NAME/KEY: misc_feature
<222> LOCATION: (20)..(20)
<223> OTHER INFORMATION: /note="2'-OMe modified nucleotide"
<220> FEATURE:
<221> NAME/KEY: misc_feature
<222> LOCATION: (21)..(21)
<223> OTHER INFORMATION: /note="2'-OMe modified nucleotide"
<220> FEATURE:
<221> NAME/KEY: misc_feature
<222> LOCATION: (22)..(22)
<223> OTHER INFORMATION: /note="2'-OMe modified nucleotide"
<220> FEATURE:
<221> NAME/KEY: misc_feature
<222> LOCATION: (23)..(23)
<223> OTHER INFORMATION: /note="2'-OMe modified nucleotide"
<220> FEATURE:
<221> NAME/KEY: misc_feature
<222> LOCATION: (24)..(24)
<223> OTHER INFORMATION: /note="2'-OMe modified nucleotide"
<220> FEATURE:
<221> NAME/KEY: misc_feature
<222> LOCATION: (25)..(25)
<223> OTHER INFORMATION: /note="2'-OMe modified nucleotide"
<220> FEATURE:
<221> NAME/KEY: misc_feature
<222> LOCATION: (26)..(26)
<223> OTHER INFORMATION: /note="2'-OMe modified nucleotide"
<220> FEATURE:
<221> NAME/KEY: misc_feature
<222> LOCATION: (27)..(27)
<223> OTHER INFORMATION: /note="2'-OMe modified nucleotide"
<220> FEATURE:
<221> NAME/KEY: misc_feature
<222> LOCATION: (28)..(28)
<223> OTHER INFORMATION: /note="ademA-GalNAc"
<220> FEATURE:
<221> NAME/KEY: misc_feature
<222> LOCATION: (29)..(29)
<223> OTHER INFORMATION: /note="ademA-GalNAc"
<220> FEATURE:
<221> NAME/KEY: misc_feature
<222> LOCATION: (30)..(30)
<223> OTHER INFORMATION: /note="ademA-GalNAc"
<220> FEATURE:
<221> NAME/KEY: misc_feature
<222> LOCATION: (31)..(31)
<223> OTHER INFORMATION: /note="2'-OMe modified nucleotide"
<220> FEATURE:
<221> NAME/KEY: misc_feature
<222> LOCATION: (32)..(32)
<223> OTHER INFORMATION: /note="2'-OMe modified nucleotide"
<220> FEATURE:
<221> NAME/KEY: misc_feature
<222> LOCATION: (33)..(33)
<223> OTHER INFORMATION: /note="2'-OMe modified nucleotide"
<220> FEATURE:
<221> NAME/KEY: misc_feature
<222> LOCATION: (34)..(34)
<223> OTHER INFORMATION: /note="2'-OMe modified nucleotide"
<220> FEATURE:
<221> NAME/KEY: misc_feature
<222> LOCATION: (35)..(35)
<223> OTHER INFORMATION: /note="2'-OMe modified nucleotide"
<220> FEATURE:
<221> NAME/KEY: misc_feature
<222> LOCATION: (36)..(36)
<223> OTHER INFORMATION: /note="2'-OMe modified nucleotide"

<400> SEQUENCE: 176
gaacugagaa gaacuacaua gcagccgaaa ggcugc 36

<210> SEQ ID NO 177
<211> LENGTH: 22
<212> TYPE: RNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: misc_feature
<222> LOCATION: (1)..(1)
<223> OTHER INFORMATION: /note="MePhosphonate-4O-mUs"
<220> FEATURE:
<221> NAME/KEY: misc_feature
<222> LOCATION: (2)..(2)
<223> OTHER INFORMATION: /note="2'-F modified nucleotide with a
      3'-phosphorothioate linkage"
<220> FEATURE:
<221> NAME/KEY: misc_feature
<222> LOCATION: (3)..(3)
<223> OTHER INFORMATION: /note="2'-F modified nucleotide with a
      3'-phosphorothioate linkage"
<220> FEATURE:
<221> NAME/KEY: misc_feature
<222> LOCATION: (4)..(4)
<223> OTHER INFORMATION: /note="2'-F modified nucleotide"
<220> FEATURE:
<221> NAME/KEY: misc_feature
<222> LOCATION: (5)..(5)
<223> OTHER INFORMATION: /note="2'-F modified nucleotide"
<220> FEATURE:
<221> NAME/KEY: misc_feature
<222> LOCATION: (6)..(6)
<223> OTHER INFORMATION: /note="2'-OMe modified nucleotide"
<220> FEATURE:
<221> NAME/KEY: misc_feature
<222> LOCATION: (7)..(7)
<223> OTHER INFORMATION: /note="2'-F modified nucleotide"
<220> FEATURE:
<221> NAME/KEY: misc_feature
<222> LOCATION: (8)..(8)
<223> OTHER INFORMATION: /note="2'-OMe modified nucleotide"
<220> FEATURE:
<221> NAME/KEY: misc_feature
<222> LOCATION: (9)..(9)
<223> OTHER INFORMATION: /note="2'-OMe modified nucleotide"
<220> FEATURE:
<221> NAME/KEY: misc_feature
<222> LOCATION: (10)..(10)
<223> OTHER INFORMATION: /note="2'-F modified nucleotide"
<220> FEATURE:
<221> NAME/KEY: misc_feature
<222> LOCATION: (11)..(11)
<223> OTHER INFORMATION: /note="2'-OMe modified nucleotide"
<220> FEATURE:
<221> NAME/KEY: misc_feature
<222> LOCATION: (12)..(12)
<223> OTHER INFORMATION: /note="2'-OMe modified nucleotide"
<220> FEATURE:
<221> NAME/KEY: misc_feature
<222> LOCATION: (13)..(13)
<223> OTHER INFORMATION: /note="2'-OMe modified nucleotide"
<220> FEATURE:
<221> NAME/KEY: misc_feature
<222> LOCATION: (14)..(14)
<223> OTHER INFORMATION: /note="2'-F modified nucleotide"
<220> FEATURE:
<221> NAME/KEY: misc_feature
<222> LOCATION: (15)..(15)
<223> OTHER INFORMATION: /note="2'-OMe modified nucleotide"
<220> FEATURE:
<221> NAME/KEY: misc_feature
<222> LOCATION: (16)..(16)
<223> OTHER INFORMATION: /note="2'-OMe modified nucleotide"
<220> FEATURE:
<221> NAME/KEY: misc_feature
<222> LOCATION: (17)..(17)
<223> OTHER INFORMATION: /note="2'-OMe modified nucleotide"
<220> FEATURE:
<221> NAME/KEY: misc_feature
<222> LOCATION: (18)..(18)
<223> OTHER INFORMATION: /note="2'-OMe modified nucleotide"
```

<220> FEATURE:
<221> NAME/KEY: misc_feature
<222> LOCATION: (19)..(19)
<223> OTHER INFORMATION: /note="2'-OMe modified nucleotide"
<220> FEATURE:
<221> NAME/KEY: misc_feature
<222> LOCATION: (20)..(20)
<223> OTHER INFORMATION: /note="2'-OMe modified nucleotide with a 3'-phosphorothioate linkage"
<220> FEATURE:
<221> NAME/KEY: misc_feature
<222> LOCATION: (21)..(21)
<223> OTHER INFORMATION: /note="2'-OMe modified nucleotide with a 3'-phosphorothioate linkage"
<220> FEATURE:
<221> NAME/KEY: misc_feature
<222> LOCATION: (22)..(22)
<223> OTHER INFORMATION: /note="2'-OMe modified nucleotide"

<400> SEQUENCE: 177
uauguaguuc uucucaguuc gg 22

<210> SEQ ID NO 178
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: misc_feature
<222> LOCATION: (1)..(1)
<223> OTHER INFORMATION: /note="2'-OMe modified nucleotide with a 3'-phosphorothioate linkage"
<220> FEATURE:
<221> NAME/KEY: misc_feature
<222> LOCATION: (2)..(2)
<223> OTHER INFORMATION: /note="2'-OMe modified nucleotide"
<220> FEATURE:
<221> NAME/KEY: misc_feature
<222> LOCATION: (3)..(3)
<223> OTHER INFORMATION: /note="2'-OMe modified nucleotide"
<220> FEATURE:
<221> NAME/KEY: misc_feature
<222> LOCATION: (4)..(4)
<223> OTHER INFORMATION: /note="2'-OMe modified nucleotide"
<220> FEATURE:
<221> NAME/KEY: misc_feature
<222> LOCATION: (5)..(5)
<223> OTHER INFORMATION: /note="2'-OMe modified nucleotide"
<220> FEATURE:
<221> NAME/KEY: misc_feature
<222> LOCATION: (6)..(6)
<223> OTHER INFORMATION: /note="2'-OMe modified nucleotide"
<220> FEATURE:
<221> NAME/KEY: misc_feature
<222> LOCATION: (7)..(7)
<223> OTHER INFORMATION: /note="2'-OMe modified nucleotide"
<220> FEATURE:
<221> NAME/KEY: misc_feature
<222> LOCATION: (8)..(8)
<223> OTHER INFORMATION: /note="2'-F modified nucleotide"
<220> FEATURE:
<221> NAME/KEY: misc_feature
<222> LOCATION: (9)..(9)
<223> OTHER INFORMATION: /note="2'-F modified nucleotide"
<220> FEATURE:
<221> NAME/KEY: misc_feature
<222> LOCATION: (10)..(10)
<223> OTHER INFORMATION: /note="2'-F modified nucleotide"
<220> FEATURE:
<221> NAME/KEY: misc_feature
<222> LOCATION: (11)..(11)
<223> OTHER INFORMATION: /note="2'-F modified nucleotide"
<220> FEATURE:
<221> NAME/KEY: misc_feature
<222> LOCATION: (12)..(12)
<223> OTHER INFORMATION: /note="2'-OMe modified nucleotide"
<220> FEATURE:
<221> NAME/KEY: misc_feature
<222> LOCATION: (13)..(13)
<223> OTHER INFORMATION: /note="2'-OMe modified nucleotide"
<220> FEATURE:
<221> NAME/KEY: misc_feature
<222> LOCATION: (14)..(14)
<223> OTHER INFORMATION: /note="2'-OMe modified nucleotide"
<220> FEATURE:
<221> NAME/KEY: misc_feature
<222> LOCATION: (15)..(15)
<223> OTHER INFORMATION: /note="2'-OMe modified nucleotide"
<220> FEATURE:
<221> NAME/KEY: misc_feature
<222> LOCATION: (16)..(16)
<223> OTHER INFORMATION: /note="2'-OMe modified nucleotide"
<220> FEATURE:
<221> NAME/KEY: misc_feature
<222> LOCATION: (17)..(17)
<223> OTHER INFORMATION: /note="2'-OMe modified nucleotide"
<220> FEATURE:
<221> NAME/KEY: misc_feature
<222> LOCATION: (18)..(18)
<223> OTHER INFORMATION: /note="2'-OMe modified nucleotide"
<220> FEATURE:
<221> NAME/KEY: misc_feature
<222> LOCATION: (19)..(19)
<223> OTHER INFORMATION: /note="2'-OMe modified nucleotide"
<220> FEATURE:
<221> NAME/KEY: misc_feature
<222> LOCATION: (20)..(20)
<223> OTHER INFORMATION: /note="2'-OMe modified nucleotide"
<220> FEATURE:
<221> NAME/KEY: misc_feature
<222> LOCATION: (21)..(21)
<223> OTHER INFORMATION: /note="2'-OMe modified nucleotide"
<220> FEATURE:
<221> NAME/KEY: misc_feature
<222> LOCATION: (22)..(22)
<223> OTHER INFORMATION: /note="2'-OMe modified nucleotide"
<220> FEATURE:
<221> NAME/KEY: misc_feature
<222> LOCATION: (23)..(23)
<223> OTHER INFORMATION: /note="2'-OMe modified nucleotide"
<220> FEATURE:
<221> NAME/KEY: misc_feature
<222> LOCATION: (24)..(24)
<223> OTHER INFORMATION: /note="2'-OMe modified nucleotide"
<220> FEATURE:
<221> NAME/KEY: misc_feature
<222> LOCATION: (25)..(25)
<223> OTHER INFORMATION: /note="2'-OMe modified nucleotide"
<220> FEATURE:
<221> NAME/KEY: misc_feature
<222> LOCATION: (26)..(26)
<223> OTHER INFORMATION: /note="2'-OMe modified nucleotide"
<220> FEATURE:
<221> NAME/KEY: misc_feature
<222> LOCATION: (27)..(27)
<223> OTHER INFORMATION: /note="2'-OMe modified nucleotide"
<220> FEATURE:
<221> NAME/KEY: misc_feature
<222> LOCATION: (28)..(28)
<223> OTHER INFORMATION: /note="ademA-GalNAc"
<220> FEATURE:
<221> NAME/KEY: misc_feature
<222> LOCATION: (29)..(29)
<223> OTHER INFORMATION: /note="ademA-GalNAc"
<220> FEATURE:
<221> NAME/KEY: misc_feature
<222> LOCATION: (30)..(30)
<223> OTHER INFORMATION: /note="ademA-GalNAc"
<220> FEATURE:
<221> NAME/KEY: misc_feature
<222> LOCATION: (31)..(31)
<223> OTHER INFORMATION: /note="2'-OMe modified nucleotide"
<220> FEATURE:

```
<221> NAME/KEY: misc_feature
<222> LOCATION: (32)..(32)
<223> OTHER INFORMATION: /note="2'-OMe modified nucleotide"
<220> FEATURE:
<221> NAME/KEY: misc_feature
<222> LOCATION: (33)..(33)
<223> OTHER INFORMATION: /note="2'-OMe modified nucleotide"
<220> FEATURE:
<221> NAME/KEY: misc_feature
<222> LOCATION: (34)..(34)
<223> OTHER INFORMATION: /note="2'-OMe modified nucleotide"
<220> FEATURE:
<221> NAME/KEY: misc_feature
<222> LOCATION: (35)..(35)
<223> OTHER INFORMATION: /note="2'-OMe modified nucleotide"
<220> FEATURE:
<221> NAME/KEY: misc_feature
<222> LOCATION: (36)..(36)
<223> OTHER INFORMATION: /note="2'-OMe modified nucleotide"

<400> SEQUENCE: 178

ugagaagaac uacauauaaa gcagccgaaa ggcugc                              36


<210> SEQ ID NO 179
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: misc_feature
<222> LOCATION: (1)..(1)
<223> OTHER INFORMATION: /note="MePhosphonate-4O-mUs"
<220> FEATURE:
<221> NAME/KEY: misc_feature
<222> LOCATION: (2)..(2)
<223> OTHER INFORMATION: /note="2'-F modified nucleotide with a
      3'-phosphorothioate linkage"
<220> FEATURE:
<221> NAME/KEY: misc_feature
<222> LOCATION: (3)..(3)
<223> OTHER INFORMATION: /note="2'-F modified nucleotide with a
      3'-phosphorothioate linkage"
<220> FEATURE:
<221> NAME/KEY: misc_feature
<222> LOCATION: (4)..(4)
<223> OTHER INFORMATION: /note="2'-F modified nucleotide"
<220> FEATURE:
<221> NAME/KEY: misc_feature
<222> LOCATION: (5)..(5)
<223> OTHER INFORMATION: /note="2'-F modified nucleotide"
<220> FEATURE:
<221> NAME/KEY: misc_feature
<222> LOCATION: (6)..(6)
<223> OTHER INFORMATION: /note="2'-OMe modified nucleotide"
<220> FEATURE:
<221> NAME/KEY: misc_feature
<222> LOCATION: (7)..(7)
<223> OTHER INFORMATION: /note="2'-F modified nucleotide"
<220> FEATURE:
<221> NAME/KEY: misc_feature
<222> LOCATION: (8)..(8)
<223> OTHER INFORMATION: /note="2'-OMe modified nucleotide"
<220> FEATURE:
<221> NAME/KEY: misc_feature
<222> LOCATION: (9)..(9)
<223> OTHER INFORMATION: /note="2'-OMe modified nucleotide"
<220> FEATURE:
<221> NAME/KEY: misc_feature
<222> LOCATION: (10)..(10)
<223> OTHER INFORMATION: /note="2'-F modified nucleotide"
<220> FEATURE:
<221> NAME/KEY: misc_feature
<222> LOCATION: (11)..(11)
<223> OTHER INFORMATION: /note="2'-OMe modified nucleotide"
```

<220> FEATURE:
<221> NAME/KEY: misc_feature
<222> LOCATION: (12)..(12)
<223> OTHER INFORMATION: /note="2'-OMe modified nucleotide"
<220> FEATURE:
<221> NAME/KEY: misc_feature
<222> LOCATION: (13)..(13)
<223> OTHER INFORMATION: /note="2'-OMe modified nucleotide"
<220> FEATURE:
<221> NAME/KEY: misc_feature
<222> LOCATION: (14)..(14)
<223> OTHER INFORMATION: /note="2'-F modified nucleotide"
<220> FEATURE:
<221> NAME/KEY: misc_feature
<222> LOCATION: (15)..(15)
<223> OTHER INFORMATION: /note="2'-OMe modified nucleotide"
<220> FEATURE:
<221> NAME/KEY: misc_feature
<222> LOCATION: (16)..(16)
<223> OTHER INFORMATION: /note="2'-OMe modified nucleotide"
<220> FEATURE:
<221> NAME/KEY: misc_feature
<222> LOCATION: (17)..(17)
<223> OTHER INFORMATION: /note="2'-OMe modified nucleotide"
<220> FEATURE:
<221> NAME/KEY: misc_feature
<222> LOCATION: (18)..(18)
<223> OTHER INFORMATION: /note="2'-OMe modified nucleotide"
<220> FEATURE:
<221> NAME/KEY: misc_feature
<222> LOCATION: (19)..(19)
<223> OTHER INFORMATION: /note="2'-OMe modified nucleotide"
<220> FEATURE:
<221> NAME/KEY: misc_feature
<222> LOCATION: (20)..(20)
<223> OTHER INFORMATION: /note="2'-OMe modified nucleotide with a
3'-phosphorothioate linkage"
<220> FEATURE:
<221> NAME/KEY: misc_feature
<222> LOCATION: (21)..(21)
<223> OTHER INFORMATION: /note="2'-OMe modified nucleotide with a
3'-phosphorothioate linkage"
<220> FEATURE:
<221> NAME/KEY: misc_feature
<222> LOCATION: (22)..(22)
<223> OTHER INFORMATION: /note="2'-OMe modified nucleotide"

<400> SEQUENCE: 179
uuuauaugua guucuucuca gg 22

<210> SEQ ID NO 180
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: misc_feature
<222> LOCATION: (1)..(1)
<223> OTHER INFORMATION: /note="2'-OMe modified nucleotide with a
3'-phosphorothioate linkage"
<220> FEATURE:
<221> NAME/KEY: misc_feature
<222> LOCATION: (2)..(2)
<223> OTHER INFORMATION: /note="2'-OMe modified nucleotide"
<220> FEATURE:
<221> NAME/KEY: misc_feature
<222> LOCATION: (3)..(3)
<223> OTHER INFORMATION: /note="2'-OMe modified nucleotide"
<220> FEATURE:
<221> NAME/KEY: misc_feature
<222> LOCATION: (4)..(4)
<223> OTHER INFORMATION: /note="2'-OMe modified nucleotide"
<220> FEATURE:
<221> NAME/KEY: misc_feature
<222> LOCATION: (5)..(5)
<223> OTHER INFORMATION: /note="2'-OMe modified nucleotide"
<220> FEATURE:
<221> NAME/KEY: misc_feature
<222> LOCATION: (6)..(6)
<223> OTHER INFORMATION: /note="2'-OMe modified nucleotide"
<220> FEATURE:
<221> NAME/KEY: misc_feature
<222> LOCATION: (7)..(7)
<223> OTHER INFORMATION: /note="2'-OMe modified nucleotide"
<220> FEATURE:
<221> NAME/KEY: misc_feature
<222> LOCATION: (8)..(8)
<223> OTHER INFORMATION: /note="2'-F modified nucleotide"
<220> FEATURE:
<221> NAME/KEY: misc_feature
<222> LOCATION: (9)..(9)
<223> OTHER INFORMATION: /note="2'-F modified nucleotide"
<220> FEATURE:
<221> NAME/KEY: misc_feature
<222> LOCATION: (10)..(10)
<223> OTHER INFORMATION: /note="2'-F modified nucleotide"
<220> FEATURE:
<221> NAME/KEY: misc_feature
<222> LOCATION: (11)..(11)
<223> OTHER INFORMATION: /note="2'-F modified nucleotide"
<220> FEATURE:
<221> NAME/KEY: misc_feature
<222> LOCATION: (12)..(12)
<223> OTHER INFORMATION: /note="2'-OMe modified nucleotide"
<220> FEATURE:
<221> NAME/KEY: misc_feature
<222> LOCATION: (13)..(13)
<223> OTHER INFORMATION: /note="2'-OMe modified nucleotide"
<220> FEATURE:
<221> NAME/KEY: misc_feature
<222> LOCATION: (14)..(14)
<223> OTHER INFORMATION: /note="2'-OMe modified nucleotide"
<220> FEATURE:
<221> NAME/KEY: misc_feature
<222> LOCATION: (15)..(15)
<223> OTHER INFORMATION: /note="2'-OMe modified nucleotide"
<220> FEATURE:
<221> NAME/KEY: misc_feature
<222> LOCATION: (16)..(16)
<223> OTHER INFORMATION: /note="2'-OMe modified nucleotide"
<220> FEATURE:
<221> NAME/KEY: misc_feature
<222> LOCATION: (17)..(17)
<223> OTHER INFORMATION: /note="2'-OMe modified nucleotide"
<220> FEATURE:
<221> NAME/KEY: misc_feature
<222> LOCATION: (18)..(18)
<223> OTHER INFORMATION: /note="2'-OMe modified nucleotide"
<220> FEATURE:
<221> NAME/KEY: misc_feature
<222> LOCATION: (19)..(19)
<223> OTHER INFORMATION: /note="2'-OMe modified nucleotide"
<220> FEATURE:
<221> NAME/KEY: misc_feature
<222> LOCATION: (20)..(20)
<223> OTHER INFORMATION: /note="2'-OMe modified nucleotide"
<220> FEATURE:
<221> NAME/KEY: misc_feature
<222> LOCATION: (21)..(21)
<223> OTHER INFORMATION: /note="2'-OMe modified nucleotide"
<220> FEATURE:
<221> NAME/KEY: misc_feature
<222> LOCATION: (22)..(22)
<223> OTHER INFORMATION: /note="2'-OMe modified nucleotide"
<220> FEATURE:
<221> NAME/KEY: misc_feature
<222> LOCATION: (23)..(23)
<223> OTHER INFORMATION: /note="2'-OMe modified nucleotide"
<220> FEATURE:
<221> NAME/KEY: misc_feature
<222> LOCATION: (24)..(24)
<223> OTHER INFORMATION: /note="2'-OMe modified nucleotide"
<220> FEATURE:

```
<221> NAME/KEY: misc_feature
<222> LOCATION: (25)..(25)
<223> OTHER INFORMATION: /note="2'-OMe modified nucleotide"
<220> FEATURE:
<221> NAME/KEY: misc_feature
<222> LOCATION: (26)..(26)
<223> OTHER INFORMATION: /note="2'-OMe modified nucleotide"
<220> FEATURE:
<221> NAME/KEY: misc_feature
<222> LOCATION: (27)..(27)
<223> OTHER INFORMATION: /note="2'-OMe modified nucleotide"
<220> FEATURE:
<221> NAME/KEY: misc_feature
<222> LOCATION: (28)..(28)
<223> OTHER INFORMATION: /note="ademA-GalNAc"
<220> FEATURE:
<221> NAME/KEY: misc_feature
<222> LOCATION: (29)..(29)
<223> OTHER INFORMATION: /note="ademA-GalNAc"
<220> FEATURE:
<221> NAME/KEY: misc_feature
<222> LOCATION: (30)..(30)
<223> OTHER INFORMATION: /note="ademA-GalNAc"
<220> FEATURE:
<221> NAME/KEY: misc_feature
<222> LOCATION: (31)..(31)
<223> OTHER INFORMATION: /note="2'-OMe modified nucleotide"
<220> FEATURE:
<221> NAME/KEY: misc_feature
<222> LOCATION: (32)..(32)
<223> OTHER INFORMATION: /note="2'-OMe modified nucleotide"
<220> FEATURE:
<221> NAME/KEY: misc_feature
<222> LOCATION: (33)..(33)
<223> OTHER INFORMATION: /note="2'-OMe modified nucleotide"
<220> FEATURE:
<221> NAME/KEY: misc_feature
<222> LOCATION: (34)..(34)
<223> OTHER INFORMATION: /note="2'-OMe modified nucleotide"
<220> FEATURE:
<221> NAME/KEY: misc_feature
<222> LOCATION: (35)..(35)
<223> OTHER INFORMATION: /note="2'-OMe modified nucleotide"
<220> FEATURE:
<221> NAME/KEY: misc_feature
<222> LOCATION: (36)..(36)
<223> OTHER INFORMATION: /note="2'-OMe modified nucleotide"

<400> SEQUENCE: 180

gagaagaacu acauauaaaa gcagccgaaa ggcugc                          36


<210> SEQ ID NO 181
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: misc_feature
<222> LOCATION: (1)..(1)
<223> OTHER INFORMATION: /note="MePhosphonate-4O-mUs"
<220> FEATURE:
<221> NAME/KEY: misc_feature
<222> LOCATION: (2)..(2)
<223> OTHER INFORMATION: /note="2'-F modified nucleotide with a
      3'-phosphorothioate linkage"
<220> FEATURE:
<221> NAME/KEY: misc_feature
<222> LOCATION: (3)..(3)
<223> OTHER INFORMATION: /note="2'-F modified nucleotide with a
      3'-phosphorothioate linkage"
<220> FEATURE:
<221> NAME/KEY: misc_feature
<222> LOCATION: (4)..(4)
<223> OTHER INFORMATION: /note="2'-F modified nucleotide"
```

<220> FEATURE:
<221> NAME/KEY: misc_feature
<222> LOCATION: (5)..(5)
<223> OTHER INFORMATION: /note="2'-F modified nucleotide"
<220> FEATURE:
<221> NAME/KEY: misc_feature
<222> LOCATION: (6)..(6)
<223> OTHER INFORMATION: /note="2'-OMe modified nucleotide"
<220> FEATURE:
<221> NAME/KEY: misc_feature
<222> LOCATION: (7)..(7)
<223> OTHER INFORMATION: /note="2'-F modified nucleotide"
<220> FEATURE:
<221> NAME/KEY: misc_feature
<222> LOCATION: (8)..(8)
<223> OTHER INFORMATION: /note="2'-OMe modified nucleotide"
<220> FEATURE:
<221> NAME/KEY: misc_feature
<222> LOCATION: (9)..(9)
<223> OTHER INFORMATION: /note="2'-OMe modified nucleotide"
<220> FEATURE:
<221> NAME/KEY: misc_feature
<222> LOCATION: (10)..(10)
<223> OTHER INFORMATION: /note="2'-F modified nucleotide"
<220> FEATURE:
<221> NAME/KEY: misc_feature
<222> LOCATION: (11)..(11)
<223> OTHER INFORMATION: /note="2'-OMe modified nucleotide"
<220> FEATURE:
<221> NAME/KEY: misc_feature
<222> LOCATION: (12)..(12)
<223> OTHER INFORMATION: /note="2'-OMe modified nucleotide"
<220> FEATURE:
<221> NAME/KEY: misc_feature
<222> LOCATION: (13)..(13)
<223> OTHER INFORMATION: /note="2'-OMe modified nucleotide"
<220> FEATURE:
<221> NAME/KEY: misc_feature
<222> LOCATION: (14)..(14)
<223> OTHER INFORMATION: /note="2'-F modified nucleotide"
<220> FEATURE:
<221> NAME/KEY: misc_feature
<222> LOCATION: (15)..(15)
<223> OTHER INFORMATION: /note="2'-OMe modified nucleotide"
<220> FEATURE:
<221> NAME/KEY: misc_feature
<222> LOCATION: (16)..(16)
<223> OTHER INFORMATION: /note="2'-OMe modified nucleotide"
<220> FEATURE:
<221> NAME/KEY: misc_feature
<222> LOCATION: (17)..(17)
<223> OTHER INFORMATION: /note="2'-OMe modified nucleotide"
<220> FEATURE:
<221> NAME/KEY: misc_feature
<222> LOCATION: (18)..(18)
<223> OTHER INFORMATION: /note="2'-OMe modified nucleotide"
<220> FEATURE:
<221> NAME/KEY: misc_feature
<222> LOCATION: (19)..(19)
<223> OTHER INFORMATION: /note="2'-OMe modified nucleotide"
<220> FEATURE:
<221> NAME/KEY: misc_feature
<222> LOCATION: (20)..(20)
<223> OTHER INFORMATION: /note="2'-OMe modified nucleotide with a
3'-phosphorothioate linkage"
<220> FEATURE:
<221> NAME/KEY: misc_feature
<222> LOCATION: (21)..(21)
<223> OTHER INFORMATION: /note="2'-OMe modified nucleotide with a
3'-phosphorothioate linkage"
<220> FEATURE:
<221> NAME/KEY: misc_feature
<222> LOCATION: (22)..(22)
<223> OTHER INFORMATION: /note="2'-OMe modified nucleotide"

<400> SEQUENCE: 181
uuuuauaugu aguucuucuc gg 22

<210> SEQ ID NO 182
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: misc_feature
<222> LOCATION: (1)..(1)
<223> OTHER INFORMATION: /note="2'-OMe modified nucleotide with a
3'-phosphorothioate linkage"
<220> FEATURE:
<221> NAME/KEY: misc_feature
<222> LOCATION: (2)..(2)
<223> OTHER INFORMATION: /note="2'-OMe modified nucleotide"
<220> FEATURE:
<221> NAME/KEY: misc_feature
<222> LOCATION: (3)..(3)
<223> OTHER INFORMATION: /note="2'-OMe modified nucleotide"
<220> FEATURE:
<221> NAME/KEY: misc_feature
<222> LOCATION: (4)..(4)
<223> OTHER INFORMATION: /note="2'-OMe modified nucleotide"
<220> FEATURE:
<221> NAME/KEY: misc_feature
<222> LOCATION: (5)..(5)
<223> OTHER INFORMATION: /note="2'-OMe modified nucleotide"
<220> FEATURE:
<221> NAME/KEY: misc_feature
<222> LOCATION: (6)..(6)
<223> OTHER INFORMATION: /note="2'-OMe modified nucleotide"
<220> FEATURE:
<221> NAME/KEY: misc_feature
<222> LOCATION: (7)..(7)
<223> OTHER INFORMATION: /note="2'-OMe modified nucleotide"
<220> FEATURE:
<221> NAME/KEY: misc_feature
<222> LOCATION: (8)..(8)
<223> OTHER INFORMATION: /note="2'-F modified nucleotide"
<220> FEATURE:
<221> NAME/KEY: misc_feature
<222> LOCATION: (9)..(9)
<223> OTHER INFORMATION: /note="2'-F modified nucleotide"
<220> FEATURE:
<221> NAME/KEY: misc_feature
<222> LOCATION: (10)..(10)
<223> OTHER INFORMATION: /note="2'-F modified nucleotide"
<220> FEATURE:
<221> NAME/KEY: misc_feature
<222> LOCATION: (11)..(11)
<223> OTHER INFORMATION: /note="2'-F modified nucleotide"
<220> FEATURE:
<221> NAME/KEY: misc_feature
<222> LOCATION: (12)..(12)
<223> OTHER INFORMATION: /note="2'-OMe modified nucleotide"
<220> FEATURE:
<221> NAME/KEY: misc_feature
<222> LOCATION: (13)..(13)
<223> OTHER INFORMATION: /note="2'-OMe modified nucleotide"
<220> FEATURE:
<221> NAME/KEY: misc_feature
<222> LOCATION: (14)..(14)
<223> OTHER INFORMATION: /note="2'-OMe modified nucleotide"
<220> FEATURE:
<221> NAME/KEY: misc_feature
<222> LOCATION: (15)..(15)
<223> OTHER INFORMATION: /note="2'-OMe modified nucleotide"
<220> FEATURE:
<221> NAME/KEY: misc_feature
<222> LOCATION: (16)..(16)
<223> OTHER INFORMATION: /note="2'-OMe modified nucleotide"
<220> FEATURE:
<221> NAME/KEY: misc_feature
<222> LOCATION: (17)..(17)
<223> OTHER INFORMATION: /note="2'-OMe modified nucleotide"
<220> FEATURE:

<221> NAME/KEY: misc_feature
<222> LOCATION: (18)..(18)
<223> OTHER INFORMATION: /note="2'-OMe modified nucleotide"
<220> FEATURE:
<221> NAME/KEY: misc_feature
<222> LOCATION: (19)..(19)
<223> OTHER INFORMATION: /note="2'-OMe modified nucleotide"
<220> FEATURE:
<221> NAME/KEY: misc_feature
<222> LOCATION: (20)..(20)
<223> OTHER INFORMATION: /note="2'-OMe modified nucleotide"
<220> FEATURE:
<221> NAME/KEY: misc_feature
<222> LOCATION: (21)..(21)
<223> OTHER INFORMATION: /note="2'-OMe modified nucleotide"
<220> FEATURE:
<221> NAME/KEY: misc_feature
<222> LOCATION: (22)..(22)
<223> OTHER INFORMATION: /note="2'-OMe modified nucleotide"
<220> FEATURE:
<221> NAME/KEY: misc_feature
<222> LOCATION: (23)..(23)
<223> OTHER INFORMATION: /note="2'-OMe modified nucleotide"
<220> FEATURE:
<221> NAME/KEY: misc_feature
<222> LOCATION: (24)..(24)
<223> OTHER INFORMATION: /note="2'-OMe modified nucleotide"
<220> FEATURE:
<221> NAME/KEY: misc_feature
<222> LOCATION: (25)..(25)
<223> OTHER INFORMATION: /note="2'-OMe modified nucleotide"
<220> FEATURE:
<221> NAME/KEY: misc_feature
<222> LOCATION: (26)..(26)
<223> OTHER INFORMATION: /note="2'-OMe modified nucleotide"
<220> FEATURE:
<221> NAME/KEY: misc_feature
<222> LOCATION: (27)..(27)
<223> OTHER INFORMATION: /note="2'-OMe modified nucleotide"
<220> FEATURE:
<221> NAME/KEY: misc_feature
<222> LOCATION: (28)..(28)
<223> OTHER INFORMATION: /note="ademA-GalNAc"
<220> FEATURE:
<221> NAME/KEY: misc_feature
<222> LOCATION: (29)..(29)
<223> OTHER INFORMATION: /note="ademA-GalNAc"
<220> FEATURE:
<221> NAME/KEY: misc_feature
<222> LOCATION: (30)..(30)
<223> OTHER INFORMATION: /note="ademA-GalNAc"
<220> FEATURE:
<221> NAME/KEY: misc_feature
<222> LOCATION: (31)..(31)
<223> OTHER INFORMATION: /note="2'-OMe modified nucleotide"
<220> FEATURE:
<221> NAME/KEY: misc_feature
<222> LOCATION: (32)..(32)
<223> OTHER INFORMATION: /note="2'-OMe modified nucleotide"
<220> FEATURE:
<221> NAME/KEY: misc_feature
<222> LOCATION: (33)..(33)
<223> OTHER INFORMATION: /note="2'-OMe modified nucleotide"
<220> FEATURE:
<221> NAME/KEY: misc_feature
<222> LOCATION: (34)..(34)
<223> OTHER INFORMATION: /note="2'-OMe modified nucleotide"
<220> FEATURE:
<221> NAME/KEY: misc_feature
<222> LOCATION: (35)..(35)
<223> OTHER INFORMATION: /note="2'-OMe modified nucleotide"
<220> FEATURE:
<221> NAME/KEY: misc_feature
<222> LOCATION: (36)..(36)
<223> OTHER INFORMATION: /note="2'-OMe modified nucleotide"

<400> SEQUENCE: 182
agagguaaag aauaugucaa gcagccgaaa ggcugc 36

```
<210> SEQ ID NO 183
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: misc_feature
<222> LOCATION: (1)..(1)
<223> OTHER INFORMATION: /note="MePhosphonate-4O-mUs"
<220> FEATURE:
<221> NAME/KEY: misc_feature
<222> LOCATION: (2)..(2)
<223> OTHER INFORMATION: /note="2'-F modified nucleotide with a
      3'-phosphorothioate linkage"
<220> FEATURE:
<221> NAME/KEY: misc_feature
<222> LOCATION: (3)..(3)
<223> OTHER INFORMATION: /note="2'-F modified nucleotide with a
      3'-phosphorothioate linkage"
<220> FEATURE:
<221> NAME/KEY: misc_feature
<222> LOCATION: (4)..(4)
<223> OTHER INFORMATION: /note="2'-F modified nucleotide"
<220> FEATURE:
<221> NAME/KEY: misc_feature
<222> LOCATION: (5)..(5)
<223> OTHER INFORMATION: /note="2'-F modified nucleotide"
<220> FEATURE:
<221> NAME/KEY: misc_feature
<222> LOCATION: (6)..(6)
<223> OTHER INFORMATION: /note="2'-OMe modified nucleotide"
<220> FEATURE:
<221> NAME/KEY: misc_feature
<222> LOCATION: (7)..(7)
<223> OTHER INFORMATION: /note="2'-F modified nucleotide"
<220> FEATURE:
<221> NAME/KEY: misc_feature
<222> LOCATION: (8)..(8)
<223> OTHER INFORMATION: /note="2'-OMe modified nucleotide"
<220> FEATURE:
<221> NAME/KEY: misc_feature
<222> LOCATION: (9)..(9)
<223> OTHER INFORMATION: /note="2'-OMe modified nucleotide"
<220> FEATURE:
<221> NAME/KEY: misc_feature
<222> LOCATION: (10)..(10)
<223> OTHER INFORMATION: /note="2'-F modified nucleotide"
<220> FEATURE:
<221> NAME/KEY: misc_feature
<222> LOCATION: (11)..(11)
<223> OTHER INFORMATION: /note="2'-OMe modified nucleotide"
<220> FEATURE:
<221> NAME/KEY: misc_feature
<222> LOCATION: (12)..(12)
<223> OTHER INFORMATION: /note="2'-OMe modified nucleotide"
<220> FEATURE:
<221> NAME/KEY: misc_feature
<222> LOCATION: (13)..(13)
<223> OTHER INFORMATION: /note="2'-OMe modified nucleotide"
<220> FEATURE:
<221> NAME/KEY: misc_feature
<222> LOCATION: (14)..(14)
<223> OTHER INFORMATION: /note="2'-F modified nucleotide"
<220> FEATURE:
<221> NAME/KEY: misc_feature
<222> LOCATION: (15)..(15)
<223> OTHER INFORMATION: /note="2'-OMe modified nucleotide"
<220> FEATURE:
<221> NAME/KEY: misc_feature
<222> LOCATION: (16)..(16)
<223> OTHER INFORMATION: /note="2'-OMe modified nucleotide"
<220> FEATURE:
<221> NAME/KEY: misc_feature
<222> LOCATION: (17)..(17)
```

```
<223> OTHER INFORMATION: /note="2'-OMe modified nucleotide"
<220> FEATURE:
<221> NAME/KEY: misc_feature
<222> LOCATION: (18)..(18)
<223> OTHER INFORMATION: /note="2'-OMe modified nucleotide"
<220> FEATURE:
<221> NAME/KEY: misc_feature
<222> LOCATION: (19)..(19)
<223> OTHER INFORMATION: /note="2'-OMe modified nucleotide"
<220> FEATURE:
<221> NAME/KEY: misc_feature
<222> LOCATION: (20)..(20)
<223> OTHER INFORMATION: /note="2'-OMe modified nucleotide with a
      3'-phosphorothioate linkage"
<220> FEATURE:
<221> NAME/KEY: misc_feature
<222> LOCATION: (21)..(21)
<223> OTHER INFORMATION: /note="2'-OMe modified nucleotide with a
      3'-phosphorothioate linkage"
<220> FEATURE:
<221> NAME/KEY: misc_feature
<222> LOCATION: (22)..(22)
<223> OTHER INFORMATION: /note="2'-OMe modified nucleotide"

<400> SEQUENCE: 183

uugacauauu cuuuaccucu gg                                          22


<210> SEQ ID NO 184
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: misc_feature
<222> LOCATION: (1)..(1)
<223> OTHER INFORMATION: /note="2'-OMe modified nucleotide with a
      3'-phosphorothioate linkage"
<220> FEATURE:
<221> NAME/KEY: misc_feature
<222> LOCATION: (2)..(2)
<223> OTHER INFORMATION: /note="2'-OMe modified nucleotide"
<220> FEATURE:
<221> NAME/KEY: misc_feature
<222> LOCATION: (3)..(3)
<223> OTHER INFORMATION: /note="2'-OMe modified nucleotide"
<220> FEATURE:
<221> NAME/KEY: misc_feature
<222> LOCATION: (4)..(4)
<223> OTHER INFORMATION: /note="2'-OMe modified nucleotide"
<220> FEATURE:
<221> NAME/KEY: misc_feature
<222> LOCATION: (5)..(5)
<223> OTHER INFORMATION: /note="2'-OMe modified nucleotide"
<220> FEATURE:
<221> NAME/KEY: misc_feature
<222> LOCATION: (6)..(6)
<223> OTHER INFORMATION: /note="2'-OMe modified nucleotide"
<220> FEATURE:
<221> NAME/KEY: misc_feature
<222> LOCATION: (7)..(7)
<223> OTHER INFORMATION: /note="2'-OMe modified nucleotide"
<220> FEATURE:
<221> NAME/KEY: misc_feature
<222> LOCATION: (8)..(8)
<223> OTHER INFORMATION: /note="2'-F modified nucleotide"
<220> FEATURE:
<221> NAME/KEY: misc_feature
<222> LOCATION: (9)..(9)
<223> OTHER INFORMATION: /note="2'-F modified nucleotide"
<220> FEATURE:
<221> NAME/KEY: misc_feature
<222> LOCATION: (10)..(10)
<223> OTHER INFORMATION: /note="2'-F modified nucleotide"
<220> FEATURE:
```

<221> NAME/KEY: misc_feature
<222> LOCATION: (11)..(11)
<223> OTHER INFORMATION: /note="2'-F modified nucleotide"
<220> FEATURE:
<221> NAME/KEY: misc_feature
<222> LOCATION: (12)..(12)
<223> OTHER INFORMATION: /note="2'-OMe modified nucleotide"
<220> FEATURE:
<221> NAME/KEY: misc_feature
<222> LOCATION: (13)..(13)
<223> OTHER INFORMATION: /note="2'-OMe modified nucleotide"
<220> FEATURE:
<221> NAME/KEY: misc_feature
<222> LOCATION: (14)..(14)
<223> OTHER INFORMATION: /note="2'-OMe modified nucleotide"
<220> FEATURE:
<221> NAME/KEY: misc_feature
<222> LOCATION: (15)..(15)
<223> OTHER INFORMATION: /note="2'-OMe modified nucleotide"
<220> FEATURE:
<221> NAME/KEY: misc_feature
<222> LOCATION: (16)..(16)
<223> OTHER INFORMATION: /note="2'-OMe modified nucleotide"
<220> FEATURE:
<221> NAME/KEY: misc_feature
<222> LOCATION: (17)..(17)
<223> OTHER INFORMATION: /note="2'-OMe modified nucleotide"
<220> FEATURE:
<221> NAME/KEY: misc_feature
<222> LOCATION: (18)..(18)
<223> OTHER INFORMATION: /note="2'-OMe modified nucleotide"
<220> FEATURE:
<221> NAME/KEY: misc_feature
<222> LOCATION: (19)..(19)
<223> OTHER INFORMATION: /note="2'-OMe modified nucleotide"
<220> FEATURE:
<221> NAME/KEY: misc_feature
<222> LOCATION: (20)..(20)
<223> OTHER INFORMATION: /note="2'-OMe modified nucleotide"
<220> FEATURE:
<221> NAME/KEY: misc_feature
<222> LOCATION: (21)..(21)
<223> OTHER INFORMATION: /note="2'-OMe modified nucleotide"
<220> FEATURE:
<221> NAME/KEY: misc_feature
<222> LOCATION: (22)..(22)
<223> OTHER INFORMATION: /note="2'-OMe modified nucleotide"
<220> FEATURE:
<221> NAME/KEY: misc_feature
<222> LOCATION: (23)..(23)
<223> OTHER INFORMATION: /note="2'-OMe modified nucleotide"
<220> FEATURE:
<221> NAME/KEY: misc_feature
<222> LOCATION: (24)..(24)
<223> OTHER INFORMATION: /note="2'-OMe modified nucleotide"
<220> FEATURE:
<221> NAME/KEY: misc_feature
<222> LOCATION: (25)..(25)
<223> OTHER INFORMATION: /note="2'-OMe modified nucleotide"
<220> FEATURE:
<221> NAME/KEY: misc_feature
<222> LOCATION: (26)..(26)
<223> OTHER INFORMATION: /note="2'-OMe modified nucleotide"
<220> FEATURE:
<221> NAME/KEY: misc_feature
<222> LOCATION: (27)..(27)
<223> OTHER INFORMATION: /note="2'-OMe modified nucleotide"
<220> FEATURE:
<221> NAME/KEY: misc_feature
<222> LOCATION: (28)..(28)
<223> OTHER INFORMATION: /note="ademA-GalNAc"
<220> FEATURE:
<221> NAME/KEY: misc_feature
<222> LOCATION: (29)..(29)
<223> OTHER INFORMATION: /note="ademA-GalNAc"
<220> FEATURE:
<221> NAME/KEY: misc_feature
<222> LOCATION: (30)..(30)
<223> OTHER INFORMATION: /note="ademA-GalNAc"

<220> FEATURE:
<221> NAME/KEY: misc_feature
<222> LOCATION: (31)..(31)
<223> OTHER INFORMATION: /note="2'-OMe modified nucleotide"
<220> FEATURE:
<221> NAME/KEY: misc_feature
<222> LOCATION: (32)..(32)
<223> OTHER INFORMATION: /note="2'-OMe modified nucleotide"
<220> FEATURE:
<221> NAME/KEY: misc_feature
<222> LOCATION: (33)..(33)
<223> OTHER INFORMATION: /note="2'-OMe modified nucleotide"
<220> FEATURE:
<221> NAME/KEY: misc_feature
<222> LOCATION: (34)..(34)
<223> OTHER INFORMATION: /note="2'-OMe modified nucleotide"
<220> FEATURE:
<221> NAME/KEY: misc_feature
<222> LOCATION: (35)..(35)
<223> OTHER INFORMATION: /note="2'-OMe modified nucleotide"
<220> FEATURE:
<221> NAME/KEY: misc_feature
<222> LOCATION: (36)..(36)
<223> OTHER INFORMATION: /note="2'-OMe modified nucleotide"

<400> SEQUENCE: 184
aauaugucac uugaacucaa gcagccgaaa ggcugc 36

<210> SEQ ID NO 185
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: misc_feature
<222> LOCATION: (1)..(1)
<223> OTHER INFORMATION: /note="MePhosphonate-4O-mUs"
<220> FEATURE:
<221> NAME/KEY: misc_feature
<222> LOCATION: (2)..(2)
<223> OTHER INFORMATION: /note="2'-F modified nucleotide with a 3'-phosphorothioate linkage"
<220> FEATURE:
<221> NAME/KEY: misc_feature
<222> LOCATION: (3)..(3)
<223> OTHER INFORMATION: /note="2'-F modified nucleotide with a 3'-phosphorothioate linkage"
<220> FEATURE:
<221> NAME/KEY: misc_feature
<222> LOCATION: (4)..(4)
<223> OTHER INFORMATION: /note="2'-F modified nucleotide"
<220> FEATURE:
<221> NAME/KEY: misc_feature
<222> LOCATION: (5)..(5)
<223> OTHER INFORMATION: /note="2'-F modified nucleotide"
<220> FEATURE:
<221> NAME/KEY: misc_feature
<222> LOCATION: (6)..(6)
<223> OTHER INFORMATION: /note="2'-OMe modified nucleotide"
<220> FEATURE:
<221> NAME/KEY: misc_feature
<222> LOCATION: (7)..(7)
<223> OTHER INFORMATION: /note="2'-F modified nucleotide"
<220> FEATURE:
<221> NAME/KEY: misc_feature
<222> LOCATION: (8)..(8)
<223> OTHER INFORMATION: /note="2'-OMe modified nucleotide"
<220> FEATURE:
<221> NAME/KEY: misc_feature
<222> LOCATION: (9)..(9)
<223> OTHER INFORMATION: /note="2'-OMe modified nucleotide"
<220> FEATURE:
<221> NAME/KEY: misc_feature
<222> LOCATION: (10)..(10)

<223> OTHER INFORMATION: /note="2'-F modified nucleotide"
<220> FEATURE:
<221> NAME/KEY: misc_feature
<222> LOCATION: (11)..(11)
<223> OTHER INFORMATION: /note="2'-OMe modified nucleotide"
<220> FEATURE:
<221> NAME/KEY: misc_feature
<222> LOCATION: (12)..(12)
<223> OTHER INFORMATION: /note="2'-OMe modified nucleotide"
<220> FEATURE:
<221> NAME/KEY: misc_feature
<222> LOCATION: (13)..(13)
<223> OTHER INFORMATION: /note="2'-OMe modified nucleotide"
<220> FEATURE:
<221> NAME/KEY: misc_feature
<222> LOCATION: (14)..(14)
<223> OTHER INFORMATION: /note="2'-F modified nucleotide"
<220> FEATURE:
<221> NAME/KEY: misc_feature
<222> LOCATION: (15)..(15)
<223> OTHER INFORMATION: /note="2'-OMe modified nucleotide"
<220> FEATURE:
<221> NAME/KEY: misc_feature
<222> LOCATION: (16)..(16)
<223> OTHER INFORMATION: /note="2'-OMe modified nucleotide"
<220> FEATURE:
<221> NAME/KEY: misc_feature
<222> LOCATION: (17)..(17)
<223> OTHER INFORMATION: /note="2'-OMe modified nucleotide"
<220> FEATURE:
<221> NAME/KEY: misc_feature
<222> LOCATION: (18)..(18)
<223> OTHER INFORMATION: /note="2'-OMe modified nucleotide"
<220> FEATURE:
<221> NAME/KEY: misc_feature
<222> LOCATION: (19)..(19)
<223> OTHER INFORMATION: /note="2'-OMe modified nucleotide"
<220> FEATURE:
<221> NAME/KEY: misc_feature
<222> LOCATION: (20)..(20)
<223> OTHER INFORMATION: /note="2'-OMe modified nucleotide with a
3'-phosphorothioate linkage"
<220> FEATURE:
<221> NAME/KEY: misc_feature
<222> LOCATION: (21)..(21)
<223> OTHER INFORMATION: /note="2'-OMe modified nucleotide with a
3'-phosphorothioate linkage"
<220> FEATURE:
<221> NAME/KEY: misc_feature
<222> LOCATION: (22)..(22)
<223> OTHER INFORMATION: /note="2'-OMe modified nucleotide"

<400> SEQUENCE: 185
uugaguucaa gugacauauu gg 22

<210> SEQ ID NO 186
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: misc_feature
<222> LOCATION: (1)..(1)
<223> OTHER INFORMATION: /note="2'-OMe modified nucleotide with a
3'-phosphorothioate linkage"
<220> FEATURE:
<221> NAME/KEY: misc_feature
<222> LOCATION: (2)..(2)
<223> OTHER INFORMATION: /note="2'-OMe modified nucleotide"
<220> FEATURE:
<221> NAME/KEY: misc_feature
<222> LOCATION: (3)..(3)
<223> OTHER INFORMATION: /note="2'-OMe modified nucleotide"
<220> FEATURE:

-continued

<221> NAME/KEY: misc_feature
<222> LOCATION: (4)..(4)
<223> OTHER INFORMATION: /note="2'-OMe modified nucleotide"
<220> FEATURE:
<221> NAME/KEY: misc_feature
<222> LOCATION: (5)..(5)
<223> OTHER INFORMATION: /note="2'-OMe modified nucleotide"
<220> FEATURE:
<221> NAME/KEY: misc_feature
<222> LOCATION: (6)..(6)
<223> OTHER INFORMATION: /note="2'-OMe modified nucleotide"
<220> FEATURE:
<221> NAME/KEY: misc_feature
<222> LOCATION: (7)..(7)
<223> OTHER INFORMATION: /note="2'-OMe modified nucleotide"
<220> FEATURE:
<221> NAME/KEY: misc_feature
<222> LOCATION: (8)..(8)
<223> OTHER INFORMATION: /note="2'-F modified nucleotide"
<220> FEATURE:
<221> NAME/KEY: misc_feature
<222> LOCATION: (9)..(9)
<223> OTHER INFORMATION: /note="2'-F modified nucleotide"
<220> FEATURE:
<221> NAME/KEY: misc_feature
<222> LOCATION: (10)..(10)
<223> OTHER INFORMATION: /note="2'-F modified nucleotide"
<220> FEATURE:
<221> NAME/KEY: misc_feature
<222> LOCATION: (11)..(11)
<223> OTHER INFORMATION: /note="2'-F modified nucleotide"
<220> FEATURE:
<221> NAME/KEY: misc_feature
<222> LOCATION: (12)..(12)
<223> OTHER INFORMATION: /note="2'-OMe modified nucleotide"
<220> FEATURE:
<221> NAME/KEY: misc_feature
<222> LOCATION: (13)..(13)
<223> OTHER INFORMATION: /note="2'-OMe modified nucleotide"
<220> FEATURE:
<221> NAME/KEY: misc_feature
<222> LOCATION: (14)..(14)
<223> OTHER INFORMATION: /note="2'-OMe modified nucleotide"
<220> FEATURE:
<221> NAME/KEY: misc_feature
<222> LOCATION: (15)..(15)
<223> OTHER INFORMATION: /note="2'-OMe modified nucleotide"
<220> FEATURE:
<221> NAME/KEY: misc_feature
<222> LOCATION: (16)..(16)
<223> OTHER INFORMATION: /note="2'-OMe modified nucleotide"
<220> FEATURE:
<221> NAME/KEY: misc_feature
<222> LOCATION: (17)..(17)
<223> OTHER INFORMATION: /note="2'-OMe modified nucleotide"
<220> FEATURE:
<221> NAME/KEY: misc_feature
<222> LOCATION: (18)..(18)
<223> OTHER INFORMATION: /note="2'-OMe modified nucleotide"
<220> FEATURE:
<221> NAME/KEY: misc_feature
<222> LOCATION: (19)..(19)
<223> OTHER INFORMATION: /note="2'-OMe modified nucleotide"
<220> FEATURE:
<221> NAME/KEY: misc_feature
<222> LOCATION: (20)..(20)
<223> OTHER INFORMATION: /note="2'-OMe modified nucleotide"
<220> FEATURE:
<221> NAME/KEY: misc_feature
<222> LOCATION: (21)..(21)
<223> OTHER INFORMATION: /note="2'-OMe modified nucleotide"
<220> FEATURE:
<221> NAME/KEY: misc_feature
<222> LOCATION: (22)..(22)
<223> OTHER INFORMATION: /note="2'-OMe modified nucleotide"
<220> FEATURE:
<221> NAME/KEY: misc_feature
<222> LOCATION: (23)..(23)
<223> OTHER INFORMATION: /note="2'-OMe modified nucleotide"

<220> FEATURE:
<221> NAME/KEY: misc_feature
<222> LOCATION: (24)..(24)
<223> OTHER INFORMATION: /note="2'-OMe modified nucleotide"
<220> FEATURE:
<221> NAME/KEY: misc_feature
<222> LOCATION: (25)..(25)
<223> OTHER INFORMATION: /note="2'-OMe modified nucleotide"
<220> FEATURE:
<221> NAME/KEY: misc_feature
<222> LOCATION: (26)..(26)
<223> OTHER INFORMATION: /note="2'-OMe modified nucleotide"
<220> FEATURE:
<221> NAME/KEY: misc_feature
<222> LOCATION: (27)..(27)
<223> OTHER INFORMATION: /note="2'-OMe modified nucleotide"
<220> FEATURE:
<221> NAME/KEY: misc_feature
<222> LOCATION: (28)..(28)
<223> OTHER INFORMATION: /note="ademA-GalNAc"
<220> FEATURE:
<221> NAME/KEY: misc_feature
<222> LOCATION: (29)..(29)
<223> OTHER INFORMATION: /note="ademA-GalNAc"
<220> FEATURE:
<221> NAME/KEY: misc_feature
<222> LOCATION: (30)..(30)
<223> OTHER INFORMATION: /note="ademA-GalNAc"
<220> FEATURE:
<221> NAME/KEY: misc_feature
<222> LOCATION: (31)..(31)
<223> OTHER INFORMATION: /note="2'-OMe modified nucleotide"
<220> FEATURE:
<221> NAME/KEY: misc_feature
<222> LOCATION: (32)..(32)
<223> OTHER INFORMATION: /note="2'-OMe modified nucleotide"
<220> FEATURE:
<221> NAME/KEY: misc_feature
<222> LOCATION: (33)..(33)
<223> OTHER INFORMATION: /note="2'-OMe modified nucleotide"
<220> FEATURE:
<221> NAME/KEY: misc_feature
<222> LOCATION: (34)..(34)
<223> OTHER INFORMATION: /note="2'-OMe modified nucleotide"
<220> FEATURE:
<221> NAME/KEY: misc_feature
<222> LOCATION: (35)..(35)
<223> OTHER INFORMATION: /note="2'-OMe modified nucleotide"
<220> FEATURE:
<221> NAME/KEY: misc_feature
<222> LOCATION: (36)..(36)
<223> OTHER INFORMATION: /note="2'-OMe modified nucleotide"

<400> SEQUENCE: 186
ugaaauauuu agaagagcaa gcagccgaaa ggcugc 36

<210> SEQ ID NO 187
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: misc_feature
<222> LOCATION: (1)..(1)
<223> OTHER INFORMATION: /note="MePhosphonate-4O-mUs"
<220> FEATURE:
<221> NAME/KEY: misc_feature
<222> LOCATION: (2)..(2)
<223> OTHER INFORMATION: /note="2'-F modified nucleotide with a
3'-phosphorothioate linkage"
<220> FEATURE:
<221> NAME/KEY: misc_feature
<222> LOCATION: (3)..(3)
<223> OTHER INFORMATION: /note="2'-F modified nucleotide with a

```
      3'-phosphorothioate linkage"
<220> FEATURE:
<221> NAME/KEY: misc_feature
<222> LOCATION: (4)..(4)
<223> OTHER INFORMATION: /note="2'-F modified nucleotide"
<220> FEATURE:
<221> NAME/KEY: misc_feature
<222> LOCATION: (5)..(5)
<223> OTHER INFORMATION: /note="2'-F modified nucleotide"
<220> FEATURE:
<221> NAME/KEY: misc_feature
<222> LOCATION: (6)..(6)
<223> OTHER INFORMATION: /note="2'-OMe modified nucleotide"
<220> FEATURE:
<221> NAME/KEY: misc_feature
<222> LOCATION: (7)..(7)
<223> OTHER INFORMATION: /note="2'-F modified nucleotide"
<220> FEATURE:
<221> NAME/KEY: misc_feature
<222> LOCATION: (8)..(8)
<223> OTHER INFORMATION: /note="2'-OMe modified nucleotide"
<220> FEATURE:
<221> NAME/KEY: misc_feature
<222> LOCATION: (9)..(9)
<223> OTHER INFORMATION: /note="2'-OMe modified nucleotide"
<220> FEATURE:
<221> NAME/KEY: misc_feature
<222> LOCATION: (10)..(10)
<223> OTHER INFORMATION: /note="2'-F modified nucleotide"
<220> FEATURE:
<221> NAME/KEY: misc_feature
<222> LOCATION: (11)..(11)
<223> OTHER INFORMATION: /note="2'-OMe modified nucleotide"
<220> FEATURE:
<221> NAME/KEY: misc_feature
<222> LOCATION: (12)..(12)
<223> OTHER INFORMATION: /note="2'-OMe modified nucleotide"
<220> FEATURE:
<221> NAME/KEY: misc_feature
<222> LOCATION: (13)..(13)
<223> OTHER INFORMATION: /note="2'-OMe modified nucleotide"
<220> FEATURE:
<221> NAME/KEY: misc_feature
<222> LOCATION: (14)..(14)
<223> OTHER INFORMATION: /note="2'-F modified nucleotide"
<220> FEATURE:
<221> NAME/KEY: misc_feature
<222> LOCATION: (15)..(15)
<223> OTHER INFORMATION: /note="2'-OMe modified nucleotide"
<220> FEATURE:
<221> NAME/KEY: misc_feature
<222> LOCATION: (16)..(16)
<223> OTHER INFORMATION: /note="2'-OMe modified nucleotide"
<220> FEATURE:
<221> NAME/KEY: misc_feature
<222> LOCATION: (17)..(17)
<223> OTHER INFORMATION: /note="2'-OMe modified nucleotide"
<220> FEATURE:
<221> NAME/KEY: misc_feature
<222> LOCATION: (18)..(18)
<223> OTHER INFORMATION: /note="2'-OMe modified nucleotide"
<220> FEATURE:
<221> NAME/KEY: misc_feature
<222> LOCATION: (19)..(19)
<223> OTHER INFORMATION: /note="2'-OMe modified nucleotide"
<220> FEATURE:
<221> NAME/KEY: misc_feature
<222> LOCATION: (20)..(20)
<223> OTHER INFORMATION: /note="2'-OMe modified nucleotide with a
      3'-phosphorothioate linkage"
<220> FEATURE:
<221> NAME/KEY: misc_feature
<222> LOCATION: (21)..(21)
<223> OTHER INFORMATION: /note="2'-OMe modified nucleotide with a
      3'-phosphorothioate linkage"
<220> FEATURE:
<221> NAME/KEY: misc_feature
<222> LOCATION: (22)..(22)
<223> OTHER INFORMATION: /note="2'-OMe modified nucleotide"
```

<400> SEQUENCE: 187
uugcucuucu aaauauuuca gg 22

<210> SEQ ID NO 188
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: misc_feature
<222> LOCATION: (1)..(1)
<223> OTHER INFORMATION: /note="2'-OMe modified nucleotide with a 3'-phosphorothioate linkage"
<220> FEATURE:
<221> NAME/KEY: misc_feature
<222> LOCATION: (2)..(2)
<223> OTHER INFORMATION: /note="2'-OMe modified nucleotide"
<220> FEATURE:
<221> NAME/KEY: misc_feature
<222> LOCATION: (3)..(3)
<223> OTHER INFORMATION: /note="2'-OMe modified nucleotide"
<220> FEATURE:
<221> NAME/KEY: misc_feature
<222> LOCATION: (4)..(4)
<223> OTHER INFORMATION: /note="2'-OMe modified nucleotide"
<220> FEATURE:
<221> NAME/KEY: misc_feature
<222> LOCATION: (5)..(5)
<223> OTHER INFORMATION: /note="2'-OMe modified nucleotide"
<220> FEATURE:
<221> NAME/KEY: misc_feature
<222> LOCATION: (6)..(6)
<223> OTHER INFORMATION: /note="2'-OMe modified nucleotide"
<220> FEATURE:
<221> NAME/KEY: misc_feature
<222> LOCATION: (7)..(7)
<223> OTHER INFORMATION: /note="2'-OMe modified nucleotide"
<220> FEATURE:
<221> NAME/KEY: misc_feature
<222> LOCATION: (8)..(8)
<223> OTHER INFORMATION: /note="2'-F modified nucleotide"
<220> FEATURE:
<221> NAME/KEY: misc_feature
<222> LOCATION: (9)..(9)
<223> OTHER INFORMATION: /note="2'-F modified nucleotide"
<220> FEATURE:
<221> NAME/KEY: misc_feature
<222> LOCATION: (10)..(10)
<223> OTHER INFORMATION: /note="2'-F modified nucleotide"
<220> FEATURE:
<221> NAME/KEY: misc_feature
<222> LOCATION: (11)..(11)
<223> OTHER INFORMATION: /note="2'-F modified nucleotide"
<220> FEATURE:
<221> NAME/KEY: misc_feature
<222> LOCATION: (12)..(12)
<223> OTHER INFORMATION: /note="2'-OMe modified nucleotide"
<220> FEATURE:
<221> NAME/KEY: misc_feature
<222> LOCATION: (13)..(13)
<223> OTHER INFORMATION: /note="2'-OMe modified nucleotide"
<220> FEATURE:
<221> NAME/KEY: misc_feature
<222> LOCATION: (14)..(14)
<223> OTHER INFORMATION: /note="2'-OMe modified nucleotide"
<220> FEATURE:
<221> NAME/KEY: misc_feature
<222> LOCATION: (15)..(15)
<223> OTHER INFORMATION: /note="2'-OMe modified nucleotide"
<220> FEATURE:
<221> NAME/KEY: misc_feature
<222> LOCATION: (16)..(16)
<223> OTHER INFORMATION: /note="2'-OMe modified nucleotide"

<220> FEATURE:
<221> NAME/KEY: misc_feature
<222> LOCATION: (17)..(17)
<223> OTHER INFORMATION: /note="2'-OMe modified nucleotide"
<220> FEATURE:
<221> NAME/KEY: misc_feature
<222> LOCATION: (18)..(18)
<223> OTHER INFORMATION: /note="2'-OMe modified nucleotide"
<220> FEATURE:
<221> NAME/KEY: misc_feature
<222> LOCATION: (19)..(19)
<223> OTHER INFORMATION: /note="2'-OMe modified nucleotide"
<220> FEATURE:
<221> NAME/KEY: misc_feature
<222> LOCATION: (20)..(20)
<223> OTHER INFORMATION: /note="2'-OMe modified nucleotide"
<220> FEATURE:
<221> NAME/KEY: misc_feature
<222> LOCATION: (21)..(21)
<223> OTHER INFORMATION: /note="2'-OMe modified nucleotide"
<220> FEATURE:
<221> NAME/KEY: misc_feature
<222> LOCATION: (22)..(22)
<223> OTHER INFORMATION: /note="2'-OMe modified nucleotide"
<220> FEATURE:
<221> NAME/KEY: misc_feature
<222> LOCATION: (23)..(23)
<223> OTHER INFORMATION: /note="2'-OMe modified nucleotide"
<220> FEATURE:
<221> NAME/KEY: misc_feature
<222> LOCATION: (24)..(24)
<223> OTHER INFORMATION: /note="2'-OMe modified nucleotide"
<220> FEATURE:
<221> NAME/KEY: misc_feature
<222> LOCATION: (25)..(25)
<223> OTHER INFORMATION: /note="2'-OMe modified nucleotide"
<220> FEATURE:
<221> NAME/KEY: misc_feature
<222> LOCATION: (26)..(26)
<223> OTHER INFORMATION: /note="2'-OMe modified nucleotide"
<220> FEATURE:
<221> NAME/KEY: misc_feature
<222> LOCATION: (27)..(27)
<223> OTHER INFORMATION: /note="2'-OMe modified nucleotide"
<220> FEATURE:
<221> NAME/KEY: misc_feature
<222> LOCATION: (28)..(28)
<223> OTHER INFORMATION: /note="ademA-GalNAc"
<220> FEATURE:
<221> NAME/KEY: misc_feature
<222> LOCATION: (29)..(29)
<223> OTHER INFORMATION: /note="ademA-GalNAc"
<220> FEATURE:
<221> NAME/KEY: misc_feature
<222> LOCATION: (30)..(30)
<223> OTHER INFORMATION: /note="ademA-GalNAc"
<220> FEATURE:
<221> NAME/KEY: misc_feature
<222> LOCATION: (31)..(31)
<223> OTHER INFORMATION: /note="2'-OMe modified nucleotide"
<220> FEATURE:
<221> NAME/KEY: misc_feature
<222> LOCATION: (32)..(32)
<223> OTHER INFORMATION: /note="2'-OMe modified nucleotide"
<220> FEATURE:
<221> NAME/KEY: misc_feature
<222> LOCATION: (33)..(33)
<223> OTHER INFORMATION: /note="2'-OMe modified nucleotide"
<220> FEATURE:
<221> NAME/KEY: misc_feature
<222> LOCATION: (34)..(34)
<223> OTHER INFORMATION: /note="2'-OMe modified nucleotide"
<220> FEATURE:
<221> NAME/KEY: misc_feature
<222> LOCATION: (35)..(35)
<223> OTHER INFORMATION: /note="2'-OMe modified nucleotide"
<220> FEATURE:
<221> NAME/KEY: misc_feature
<222> LOCATION: (36)..(36)

<223> OTHER INFORMATION: /note="2'-OMe modified nucleotide"

<400> SEQUENCE: 188
gaaauauuua gaagagcaaa gcagccgaaa ggcugc 36

<210> SEQ ID NO 189
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: misc_feature
<222> LOCATION: (1)..(1)
<223> OTHER INFORMATION: /note="MePhosphonate-4O-mUs"
<220> FEATURE:
<221> NAME/KEY: misc_feature
<222> LOCATION: (2)..(2)
<223> OTHER INFORMATION: /note="2'-F modified nucleotide with a 3'-phosphorothioate linkage"
<220> FEATURE:
<221> NAME/KEY: misc_feature
<222> LOCATION: (3)..(3)
<223> OTHER INFORMATION: /note="2'-F modified nucleotide with a 3'-phosphorothioate linkage"
<220> FEATURE:
<221> NAME/KEY: misc_feature
<222> LOCATION: (4)..(4)
<223> OTHER INFORMATION: /note="2'-F modified nucleotide"
<220> FEATURE:
<221> NAME/KEY: misc_feature
<222> LOCATION: (5)..(5)
<223> OTHER INFORMATION: /note="2'-F modified nucleotide"
<220> FEATURE:
<221> NAME/KEY: misc_feature
<222> LOCATION: (6)..(6)
<223> OTHER INFORMATION: /note="2'-OMe modified nucleotide"
<220> FEATURE:
<221> NAME/KEY: misc_feature
<222> LOCATION: (7)..(7)
<223> OTHER INFORMATION: /note="2'-F modified nucleotide"
<220> FEATURE:
<221> NAME/KEY: misc_feature
<222> LOCATION: (8)..(8)
<223> OTHER INFORMATION: /note="2'-OMe modified nucleotide"
<220> FEATURE:
<221> NAME/KEY: misc_feature
<222> LOCATION: (9)..(9)
<223> OTHER INFORMATION: /note="2'-OMe modified nucleotide"
<220> FEATURE:
<221> NAME/KEY: misc_feature
<222> LOCATION: (10)..(10)
<223> OTHER INFORMATION: /note="2'-F modified nucleotide"
<220> FEATURE:
<221> NAME/KEY: misc_feature
<222> LOCATION: (11)..(11)
<223> OTHER INFORMATION: /note="2'-OMe modified nucleotide"
<220> FEATURE:
<221> NAME/KEY: misc_feature
<222> LOCATION: (12)..(12)
<223> OTHER INFORMATION: /note="2'-OMe modified nucleotide"
<220> FEATURE:
<221> NAME/KEY: misc_feature
<222> LOCATION: (13)..(13)
<223> OTHER INFORMATION: /note="2'-OMe modified nucleotide"
<220> FEATURE:
<221> NAME/KEY: misc_feature
<222> LOCATION: (14)..(14)
<223> OTHER INFORMATION: /note="2'-F modified nucleotide"
<220> FEATURE:
<221> NAME/KEY: misc_feature
<222> LOCATION: (15)..(15)
<223> OTHER INFORMATION: /note="2'-OMe modified nucleotide"
<220> FEATURE:
<221> NAME/KEY: misc_feature
<222> LOCATION: (16)..(16)
<223> OTHER INFORMATION: /note="2'-OMe modified nucleotide"
<220> FEATURE:
<221> NAME/KEY: misc_feature
<222> LOCATION: (17)..(17)
<223> OTHER INFORMATION: /note="2'-OMe modified nucleotide"
<220> FEATURE:
<221> NAME/KEY: misc_feature
<222> LOCATION: (18)..(18)
<223> OTHER INFORMATION: /note="2'-OMe modified nucleotide"
<220> FEATURE:
<221> NAME/KEY: misc_feature
<222> LOCATION: (19)..(19)
<223> OTHER INFORMATION: /note="2'-OMe modified nucleotide"
<220> FEATURE:
<221> NAME/KEY: misc_feature
<222> LOCATION: (20)..(20)
<223> OTHER INFORMATION: /note="2'-OMe modified nucleotide with a
3'-phosphorothioate linkage"
<220> FEATURE:
<221> NAME/KEY: misc_feature
<222> LOCATION: (21)..(21)
<223> OTHER INFORMATION: /note="2'-OMe modified nucleotide with a
3'-phosphorothioate linkage"
<220> FEATURE:
<221> NAME/KEY: misc_feature
<222> LOCATION: (22)..(22)
<223> OTHER INFORMATION: /note="2'-OMe modified nucleotide"

<400> SEQUENCE: 189
uuugcucuuc uaaauauuuc gg 22

<210> SEQ ID NO 190
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: misc_feature
<222> LOCATION: (1)..(1)
<223> OTHER INFORMATION: /note="2'-OMe modified nucleotide with a
3'-phosphorothioate linkage"
<220> FEATURE:
<221> NAME/KEY: misc_feature
<222> LOCATION: (2)..(2)
<223> OTHER INFORMATION: /note="2'-OMe modified nucleotide"
<220> FEATURE:
<221> NAME/KEY: misc_feature
<222> LOCATION: (3)..(3)
<223> OTHER INFORMATION: /note="2'-OMe modified nucleotide"
<220> FEATURE:
<221> NAME/KEY: misc_feature
<222> LOCATION: (4)..(4)
<223> OTHER INFORMATION: /note="2'-OMe modified nucleotide"
<220> FEATURE:
<221> NAME/KEY: misc_feature
<222> LOCATION: (5)..(5)
<223> OTHER INFORMATION: /note="2'-OMe modified nucleotide"
<220> FEATURE:
<221> NAME/KEY: misc_feature
<222> LOCATION: (6)..(6)
<223> OTHER INFORMATION: /note="2'-OMe modified nucleotide"
<220> FEATURE:
<221> NAME/KEY: misc_feature
<222> LOCATION: (7)..(7)
<223> OTHER INFORMATION: /note="2'-OMe modified nucleotide"
<220> FEATURE:
<221> NAME/KEY: misc_feature
<222> LOCATION: (8)..(8)
<223> OTHER INFORMATION: /note="2'-F modified nucleotide"
<220> FEATURE:
<221> NAME/KEY: misc_feature
<222> LOCATION: (9)..(9)
<223> OTHER INFORMATION: /note="2'-F modified nucleotide"

-continued

<220> FEATURE:
<221> NAME/KEY: misc_feature
<222> LOCATION: (10)..(10)
<223> OTHER INFORMATION: /note="2'-F modified nucleotide"
<220> FEATURE:
<221> NAME/KEY: misc_feature
<222> LOCATION: (11)..(11)
<223> OTHER INFORMATION: /note="2'-F modified nucleotide"
<220> FEATURE:
<221> NAME/KEY: misc_feature
<222> LOCATION: (12)..(12)
<223> OTHER INFORMATION: /note="2'-OMe modified nucleotide"
<220> FEATURE:
<221> NAME/KEY: misc_feature
<222> LOCATION: (13)..(13)
<223> OTHER INFORMATION: /note="2'-OMe modified nucleotide"
<220> FEATURE:
<221> NAME/KEY: misc_feature
<222> LOCATION: (14)..(14)
<223> OTHER INFORMATION: /note="2'-OMe modified nucleotide"
<220> FEATURE:
<221> NAME/KEY: misc_feature
<222> LOCATION: (15)..(15)
<223> OTHER INFORMATION: /note="2'-OMe modified nucleotide"
<220> FEATURE:
<221> NAME/KEY: misc_feature
<222> LOCATION: (16)..(16)
<223> OTHER INFORMATION: /note="2'-OMe modified nucleotide"
<220> FEATURE:
<221> NAME/KEY: misc_feature
<222> LOCATION: (17)..(17)
<223> OTHER INFORMATION: /note="2'-OMe modified nucleotide"
<220> FEATURE:
<221> NAME/KEY: misc_feature
<222> LOCATION: (18)..(18)
<223> OTHER INFORMATION: /note="2'-OMe modified nucleotide"
<220> FEATURE:
<221> NAME/KEY: misc_feature
<222> LOCATION: (19)..(19)
<223> OTHER INFORMATION: /note="2'-OMe modified nucleotide"
<220> FEATURE:
<221> NAME/KEY: misc_feature
<222> LOCATION: (20)..(20)
<223> OTHER INFORMATION: /note="2'-OMe modified nucleotide"
<220> FEATURE:
<221> NAME/KEY: misc_feature
<222> LOCATION: (21)..(21)
<223> OTHER INFORMATION: /note="2'-OMe modified nucleotide"
<220> FEATURE:
<221> NAME/KEY: misc_feature
<222> LOCATION: (22)..(22)
<223> OTHER INFORMATION: /note="2'-OMe modified nucleotide"
<220> FEATURE:
<221> NAME/KEY: misc_feature
<222> LOCATION: (23)..(23)
<223> OTHER INFORMATION: /note="2'-OMe modified nucleotide"
<220> FEATURE:
<221> NAME/KEY: misc_feature
<222> LOCATION: (24)..(24)
<223> OTHER INFORMATION: /note="2'-OMe modified nucleotide"
<220> FEATURE:
<221> NAME/KEY: misc_feature
<222> LOCATION: (25)..(25)
<223> OTHER INFORMATION: /note="2'-OMe modified nucleotide"
<220> FEATURE:
<221> NAME/KEY: misc_feature
<222> LOCATION: (26)..(26)
<223> OTHER INFORMATION: /note="2'-OMe modified nucleotide"
<220> FEATURE:
<221> NAME/KEY: misc_feature
<222> LOCATION: (27)..(27)
<223> OTHER INFORMATION: /note="2'-OMe modified nucleotide"
<220> FEATURE:
<221> NAME/KEY: misc_feature
<222> LOCATION: (28)..(28)
<223> OTHER INFORMATION: /note="ademA-GalNAc"
<220> FEATURE:
<221> NAME/KEY: misc_feature
<222> LOCATION: (29)..(29)

<223> OTHER INFORMATION: /note="ademA-GalNAc"
<220> FEATURE:
<221> NAME/KEY: misc_feature
<222> LOCATION: (30)..(30)
<223> OTHER INFORMATION: /note="ademA-GalNAc"
<220> FEATURE:
<221> NAME/KEY: misc_feature
<222> LOCATION: (31)..(31)
<223> OTHER INFORMATION: /note="2'-OMe modified nucleotide"
<220> FEATURE:
<221> NAME/KEY: misc_feature
<222> LOCATION: (32)..(32)
<223> OTHER INFORMATION: /note="2'-OMe modified nucleotide"
<220> FEATURE:
<221> NAME/KEY: misc_feature
<222> LOCATION: (33)..(33)
<223> OTHER INFORMATION: /note="2'-OMe modified nucleotide"
<220> FEATURE:
<221> NAME/KEY: misc_feature
<222> LOCATION: (34)..(34)
<223> OTHER INFORMATION: /note="2'-OMe modified nucleotide"
<220> FEATURE:
<221> NAME/KEY: misc_feature
<222> LOCATION: (35)..(35)
<223> OTHER INFORMATION: /note="2'-OMe modified nucleotide"
<220> FEATURE:
<221> NAME/KEY: misc_feature
<222> LOCATION: (36)..(36)
<223> OTHER INFORMATION: /note="2'-OMe modified nucleotide"

<400> SEQUENCE: 190
agcaacuaac uaacuuaaua gcagccgaaa ggcugc 36

<210> SEQ ID NO 191
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: misc_feature
<222> LOCATION: (1)..(1)
<223> OTHER INFORMATION: /note="MePhosphonate-4O-mUs"
<220> FEATURE:
<221> NAME/KEY: misc_feature
<222> LOCATION: (2)..(2)
<223> OTHER INFORMATION: /note="2'-F modified nucleotide with a 3'-phosphorothioate linkage"
<220> FEATURE:
<221> NAME/KEY: misc_feature
<222> LOCATION: (3)..(3)
<223> OTHER INFORMATION: /note="2'-F modified nucleotide with a 3'-phosphorothioate linkage"
<220> FEATURE:
<221> NAME/KEY: misc_feature
<222> LOCATION: (4)..(4)
<223> OTHER INFORMATION: /note="2'-F modified nucleotide"
<220> FEATURE:
<221> NAME/KEY: misc_feature
<222> LOCATION: (5)..(5)
<223> OTHER INFORMATION: /note="2'-F modified nucleotide"
<220> FEATURE:
<221> NAME/KEY: misc_feature
<222> LOCATION: (6)..(6)
<223> OTHER INFORMATION: /note="2'-OMe modified nucleotide"
<220> FEATURE:
<221> NAME/KEY: misc_feature
<222> LOCATION: (7)..(7)
<223> OTHER INFORMATION: /note="2'-F modified nucleotide"
<220> FEATURE:
<221> NAME/KEY: misc_feature
<222> LOCATION: (8)..(8)
<223> OTHER INFORMATION: /note="2'-OMe modified nucleotide"
<220> FEATURE:
<221> NAME/KEY: misc_feature
<222> LOCATION: (9)..(9)
<223> OTHER INFORMATION: /note="2'-OMe modified nucleotide"
<220> FEATURE:
<221> NAME/KEY: misc_feature
<222> LOCATION: (10)..(10)
<223> OTHER INFORMATION: /note="2'-F modified nucleotide"
<220> FEATURE:
<221> NAME/KEY: misc_feature
<222> LOCATION: (11)..(11)
<223> OTHER INFORMATION: /note="2'-OMe modified nucleotide"
<220> FEATURE:
<221> NAME/KEY: misc_feature
<222> LOCATION: (12)..(12)
<223> OTHER INFORMATION: /note="2'-OMe modified nucleotide"
<220> FEATURE:
<221> NAME/KEY: misc_feature
<222> LOCATION: (13)..(13)
<223> OTHER INFORMATION: /note="2'-OMe modified nucleotide"
<220> FEATURE:
<221> NAME/KEY: misc_feature
<222> LOCATION: (14)..(14)
<223> OTHER INFORMATION: /note="2'-F modified nucleotide"
<220> FEATURE:
<221> NAME/KEY: misc_feature
<222> LOCATION: (15)..(15)
<223> OTHER INFORMATION: /note="2'-OMe modified nucleotide"
<220> FEATURE:
<221> NAME/KEY: misc_feature
<222> LOCATION: (16)..(16)
<223> OTHER INFORMATION: /note="2'-OMe modified nucleotide"
<220> FEATURE:
<221> NAME/KEY: misc_feature
<222> LOCATION: (17)..(17)
<223> OTHER INFORMATION: /note="2'-OMe modified nucleotide"
<220> FEATURE:
<221> NAME/KEY: misc_feature
<222> LOCATION: (18)..(18)
<223> OTHER INFORMATION: /note="2'-OMe modified nucleotide"
<220> FEATURE:
<221> NAME/KEY: misc_feature
<222> LOCATION: (19)..(19)
<223> OTHER INFORMATION: /note="2'-OMe modified nucleotide"
<220> FEATURE:
<221> NAME/KEY: misc_feature
<222> LOCATION: (20)..(20)
<223> OTHER INFORMATION: /note="2'-OMe modified nucleotide with a
3'-phosphorothioate linkage"
<220> FEATURE:
<221> NAME/KEY: misc_feature
<222> LOCATION: (21)..(21)
<223> OTHER INFORMATION: /note="2'-OMe modified nucleotide with a
3'-phosphorothioate linkage"
<220> FEATURE:
<221> NAME/KEY: misc_feature
<222> LOCATION: (22)..(22)
<223> OTHER INFORMATION: /note="2'-OMe modified nucleotide"

<400> SEQUENCE: 191
uauuaaguua guuaguugcu gg 22

<210> SEQ ID NO 192
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: misc_feature
<222> LOCATION: (1)..(1)
<223> OTHER INFORMATION: /note="2'-OMe modified nucleotide with a
3'-phosphorothioate linkage"
<220> FEATURE:
<221> NAME/KEY: misc_feature
<222> LOCATION: (2)..(2)
<223> OTHER INFORMATION: /note="2'-OMe modified nucleotide"

<220> FEATURE:
<221> NAME/KEY: misc_feature
<222> LOCATION: (3)..(3)
<223> OTHER INFORMATION: /note="2'-OMe modified nucleotide"
<220> FEATURE:
<221> NAME/KEY: misc_feature
<222> LOCATION: (4)..(4)
<223> OTHER INFORMATION: /note="2'-OMe modified nucleotide"
<220> FEATURE:
<221> NAME/KEY: misc_feature
<222> LOCATION: (5)..(5)
<223> OTHER INFORMATION: /note="2'-OMe modified nucleotide"
<220> FEATURE:
<221> NAME/KEY: misc_feature
<222> LOCATION: (6)..(6)
<223> OTHER INFORMATION: /note="2'-OMe modified nucleotide"
<220> FEATURE:
<221> NAME/KEY: misc_feature
<222> LOCATION: (7)..(7)
<223> OTHER INFORMATION: /note="2'-OMe modified nucleotide"
<220> FEATURE:
<221> NAME/KEY: misc_feature
<222> LOCATION: (8)..(8)
<223> OTHER INFORMATION: /note="2'-F modified nucleotide"
<220> FEATURE:
<221> NAME/KEY: misc_feature
<222> LOCATION: (9)..(9)
<223> OTHER INFORMATION: /note="2'-F modified nucleotide"
<220> FEATURE:
<221> NAME/KEY: misc_feature
<222> LOCATION: (10)..(10)
<223> OTHER INFORMATION: /note="2'-F modified nucleotide"
<220> FEATURE:
<221> NAME/KEY: misc_feature
<222> LOCATION: (11)..(11)
<223> OTHER INFORMATION: /note="2'-F modified nucleotide"
<220> FEATURE:
<221> NAME/KEY: misc_feature
<222> LOCATION: (12)..(12)
<223> OTHER INFORMATION: /note="2'-OMe modified nucleotide"
<220> FEATURE:
<221> NAME/KEY: misc_feature
<222> LOCATION: (13)..(13)
<223> OTHER INFORMATION: /note="2'-OMe modified nucleotide"
<220> FEATURE:
<221> NAME/KEY: misc_feature
<222> LOCATION: (14)..(14)
<223> OTHER INFORMATION: /note="2'-OMe modified nucleotide"
<220> FEATURE:
<221> NAME/KEY: misc_feature
<222> LOCATION: (15)..(15)
<223> OTHER INFORMATION: /note="2'-OMe modified nucleotide"
<220> FEATURE:
<221> NAME/KEY: misc_feature
<222> LOCATION: (16)..(16)
<223> OTHER INFORMATION: /note="2'-OMe modified nucleotide"
<220> FEATURE:
<221> NAME/KEY: misc_feature
<222> LOCATION: (17)..(17)
<223> OTHER INFORMATION: /note="2'-OMe modified nucleotide"
<220> FEATURE:
<221> NAME/KEY: misc_feature
<222> LOCATION: (18)..(18)
<223> OTHER INFORMATION: /note="2'-OMe modified nucleotide"
<220> FEATURE:
<221> NAME/KEY: misc_feature
<222> LOCATION: (19)..(19)
<223> OTHER INFORMATION: /note="2'-OMe modified nucleotide"
<220> FEATURE:
<221> NAME/KEY: misc_feature
<222> LOCATION: (20)..(20)
<223> OTHER INFORMATION: /note="2'-OMe modified nucleotide"
<220> FEATURE:
<221> NAME/KEY: misc_feature
<222> LOCATION: (21)..(21)
<223> OTHER INFORMATION: /note="2'-OMe modified nucleotide"
<220> FEATURE:
<221> NAME/KEY: misc_feature
<222> LOCATION: (22)..(22)

-continued

<223> OTHER INFORMATION: /note="2'-OMe modified nucleotide"
<220> FEATURE:
<221> NAME/KEY: misc_feature
<222> LOCATION: (23)..(23)
<223> OTHER INFORMATION: /note="2'-OMe modified nucleotide"
<220> FEATURE:
<221> NAME/KEY: misc_feature
<222> LOCATION: (24)..(24)
<223> OTHER INFORMATION: /note="2'-OMe modified nucleotide"
<220> FEATURE:
<221> NAME/KEY: misc_feature
<222> LOCATION: (25)..(25)
<223> OTHER INFORMATION: /note="2'-OMe modified nucleotide"
<220> FEATURE:
<221> NAME/KEY: misc_feature
<222> LOCATION: (26)..(26)
<223> OTHER INFORMATION: /note="2'-OMe modified nucleotide"
<220> FEATURE:
<221> NAME/KEY: misc_feature
<222> LOCATION: (27)..(27)
<223> OTHER INFORMATION: /note="2'-OMe modified nucleotide"
<220> FEATURE:
<221> NAME/KEY: misc_feature
<222> LOCATION: (28)..(28)
<223> OTHER INFORMATION: /note="ademA-GalNAc"
<220> FEATURE:
<221> NAME/KEY: misc_feature
<222> LOCATION: (29)..(29)
<223> OTHER INFORMATION: /note="ademA-GalNAc"
<220> FEATURE:
<221> NAME/KEY: misc_feature
<222> LOCATION: (30)..(30)
<223> OTHER INFORMATION: /note="ademA-GalNAc"
<220> FEATURE:
<221> NAME/KEY: misc_feature
<222> LOCATION: (31)..(31)
<223> OTHER INFORMATION: /note="2'-OMe modified nucleotide"
<220> FEATURE:
<221> NAME/KEY: misc_feature
<222> LOCATION: (32)..(32)
<223> OTHER INFORMATION: /note="2'-OMe modified nucleotide"
<220> FEATURE:
<221> NAME/KEY: misc_feature
<222> LOCATION: (33)..(33)
<223> OTHER INFORMATION: /note="2'-OMe modified nucleotide"
<220> FEATURE:
<221> NAME/KEY: misc_feature
<222> LOCATION: (34)..(34)
<223> OTHER INFORMATION: /note="2'-OMe modified nucleotide"
<220> FEATURE:
<221> NAME/KEY: misc_feature
<222> LOCATION: (35)..(35)
<223> OTHER INFORMATION: /note="2'-OMe modified nucleotide"
<220> FEATURE:
<221> NAME/KEY: misc_feature
<222> LOCATION: (36)..(36)
<223> OTHER INFORMATION: /note="2'-OMe modified nucleotide"

<400> SEQUENCE: 192
cuaacuuaau ucaaaaucaa gcagccgaaa ggcugc 36

<210> SEQ ID NO 193
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: misc_feature
<222> LOCATION: (1)..(1)
<223> OTHER INFORMATION: /note="MePhosphonate-4O-mUs"
<220> FEATURE:
<221> NAME/KEY: misc_feature
<222> LOCATION: (2)..(2)
<223> OTHER INFORMATION: /note="2'-F modified nucleotide with a 3'-phosphorothioate linkage"
<220> FEATURE:
<221> NAME/KEY: misc_feature
<222> LOCATION: (3)..(3)
<223> OTHER INFORMATION: /note="2'-F modified nucleotide with a
3'-phosphorothioate linkage"
<220> FEATURE:
<221> NAME/KEY: misc_feature
<222> LOCATION: (4)..(4)
<223> OTHER INFORMATION: /note="2'-F modified nucleotide"
<220> FEATURE:
<221> NAME/KEY: misc_feature
<222> LOCATION: (5)..(5)
<223> OTHER INFORMATION: /note="2'-F modified nucleotide"
<220> FEATURE:
<221> NAME/KEY: misc_feature
<222> LOCATION: (6)..(6)
<223> OTHER INFORMATION: /note="2'-OMe modified nucleotide"
<220> FEATURE:
<221> NAME/KEY: misc_feature
<222> LOCATION: (7)..(7)
<223> OTHER INFORMATION: /note="2'-F modified nucleotide"
<220> FEATURE:
<221> NAME/KEY: misc_feature
<222> LOCATION: (8)..(8)
<223> OTHER INFORMATION: /note="2'-OMe modified nucleotide"
<220> FEATURE:
<221> NAME/KEY: misc_feature
<222> LOCATION: (9)..(9)
<223> OTHER INFORMATION: /note="2'-OMe modified nucleotide"
<220> FEATURE:
<221> NAME/KEY: misc_feature
<222> LOCATION: (10)..(10)
<223> OTHER INFORMATION: /note="2'-F modified nucleotide"
<220> FEATURE:
<221> NAME/KEY: misc_feature
<222> LOCATION: (11)..(11)
<223> OTHER INFORMATION: /note="2'-OMe modified nucleotide"
<220> FEATURE:
<221> NAME/KEY: misc_feature
<222> LOCATION: (12)..(12)
<223> OTHER INFORMATION: /note="2'-OMe modified nucleotide"
<220> FEATURE:
<221> NAME/KEY: misc_feature
<222> LOCATION: (13)..(13)
<223> OTHER INFORMATION: /note="2'-OMe modified nucleotide"
<220> FEATURE:
<221> NAME/KEY: misc_feature
<222> LOCATION: (14)..(14)
<223> OTHER INFORMATION: /note="2'-F modified nucleotide"
<220> FEATURE:
<221> NAME/KEY: misc_feature
<222> LOCATION: (15)..(15)
<223> OTHER INFORMATION: /note="2'-OMe modified nucleotide"
<220> FEATURE:
<221> NAME/KEY: misc_feature
<222> LOCATION: (16)..(16)
<223> OTHER INFORMATION: /note="2'-OMe modified nucleotide"
<220> FEATURE:
<221> NAME/KEY: misc_feature
<222> LOCATION: (17)..(17)
<223> OTHER INFORMATION: /note="2'-OMe modified nucleotide"
<220> FEATURE:
<221> NAME/KEY: misc_feature
<222> LOCATION: (18)..(18)
<223> OTHER INFORMATION: /note="2'-OMe modified nucleotide"
<220> FEATURE:
<221> NAME/KEY: misc_feature
<222> LOCATION: (19)..(19)
<223> OTHER INFORMATION: /note="2'-OMe modified nucleotide"
<220> FEATURE:
<221> NAME/KEY: misc_feature
<222> LOCATION: (20)..(20)
<223> OTHER INFORMATION: /note="2'-OMe modified nucleotide with a
3'-phosphorothioate linkage"
<220> FEATURE:
<221> NAME/KEY: misc_feature
<222> LOCATION: (21)..(21)
<223> OTHER INFORMATION: /note="2'-OMe modified nucleotide with a 3'-phosphorothioate linkage"
<220> FEATURE:
<221> NAME/KEY: misc_feature
<222> LOCATION: (22)..(22)
<223> OTHER INFORMATION: /note="2'-OMe modified nucleotide"

<400> SEQUENCE: 193
uugauuuuga auuaaguuag gg 22

<210> SEQ ID NO 194
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: misc_feature
<222> LOCATION: (1)..(1)
<223> OTHER INFORMATION: /note="2'-OMe modified nucleotide with a 3'-phosphorothioate linkage"
<220> FEATURE:
<221> NAME/KEY: misc_feature
<222> LOCATION: (2)..(2)
<223> OTHER INFORMATION: /note="2'-OMe modified nucleotide"
<220> FEATURE:
<221> NAME/KEY: misc_feature
<222> LOCATION: (3)..(3)
<223> OTHER INFORMATION: /note="2'-OMe modified nucleotide"
<220> FEATURE:
<221> NAME/KEY: misc_feature
<222> LOCATION: (4)..(4)
<223> OTHER INFORMATION: /note="2'-OMe modified nucleotide"
<220> FEATURE:
<221> NAME/KEY: misc_feature
<222> LOCATION: (5)..(5)
<223> OTHER INFORMATION: /note="2'-OMe modified nucleotide"
<220> FEATURE:
<221> NAME/KEY: misc_feature
<222> LOCATION: (6)..(6)
<223> OTHER INFORMATION: /note="2'-OMe modified nucleotide"
<220> FEATURE:
<221> NAME/KEY: misc_feature
<222> LOCATION: (7)..(7)
<223> OTHER INFORMATION: /note="2'-OMe modified nucleotide"
<220> FEATURE:
<221> NAME/KEY: misc_feature
<222> LOCATION: (8)..(8)
<223> OTHER INFORMATION: /note="2'-F modified nucleotide"
<220> FEATURE:
<221> NAME/KEY: misc_feature
<222> LOCATION: (9)..(9)
<223> OTHER INFORMATION: /note="2'-F modified nucleotide"
<220> FEATURE:
<221> NAME/KEY: misc_feature
<222> LOCATION: (10)..(10)
<223> OTHER INFORMATION: /note="2'-F modified nucleotide"
<220> FEATURE:
<221> NAME/KEY: misc_feature
<222> LOCATION: (11)..(11)
<223> OTHER INFORMATION: /note="2'-F modified nucleotide"
<220> FEATURE:
<221> NAME/KEY: misc_feature
<222> LOCATION: (12)..(12)
<223> OTHER INFORMATION: /note="2'-OMe modified nucleotide"
<220> FEATURE:
<221> NAME/KEY: misc_feature
<222> LOCATION: (13)..(13)
<223> OTHER INFORMATION: /note="2'-OMe modified nucleotide"
<220> FEATURE:
<221> NAME/KEY: misc_feature
<222> LOCATION: (14)..(14)
<223> OTHER INFORMATION: /note="2'-OMe modified nucleotide"
<220> FEATURE:
<221> NAME/KEY: misc_feature
<222> LOCATION: (15)..(15)

<223> OTHER INFORMATION: /note="2'-OMe modified nucleotide"
<220> FEATURE:
<221> NAME/KEY: misc_feature
<222> LOCATION: (16)..(16)
<223> OTHER INFORMATION: /note="2'-OMe modified nucleotide"
<220> FEATURE:
<221> NAME/KEY: misc_feature
<222> LOCATION: (17)..(17)
<223> OTHER INFORMATION: /note="2'-OMe modified nucleotide"
<220> FEATURE:
<221> NAME/KEY: misc_feature
<222> LOCATION: (18)..(18)
<223> OTHER INFORMATION: /note="2'-OMe modified nucleotide"
<220> FEATURE:
<221> NAME/KEY: misc_feature
<222> LOCATION: (19)..(19)
<223> OTHER INFORMATION: /note="2'-OMe modified nucleotide"
<220> FEATURE:
<221> NAME/KEY: misc_feature
<222> LOCATION: (20)..(20)
<223> OTHER INFORMATION: /note="2'-OMe modified nucleotide"
<220> FEATURE:
<221> NAME/KEY: misc_feature
<222> LOCATION: (21)..(21)
<223> OTHER INFORMATION: /note="2'-OMe modified nucleotide"
<220> FEATURE:
<221> NAME/KEY: misc_feature
<222> LOCATION: (22)..(22)
<223> OTHER INFORMATION: /note="2'-OMe modified nucleotide"
<220> FEATURE:
<221> NAME/KEY: misc_feature
<222> LOCATION: (23)..(23)
<223> OTHER INFORMATION: /note="2'-OMe modified nucleotide"
<220> FEATURE:
<221> NAME/KEY: misc_feature
<222> LOCATION: (24)..(24)
<223> OTHER INFORMATION: /note="2'-OMe modified nucleotide"
<220> FEATURE:
<221> NAME/KEY: misc_feature
<222> LOCATION: (25)..(25)
<223> OTHER INFORMATION: /note="2'-OMe modified nucleotide"
<220> FEATURE:
<221> NAME/KEY: misc_feature
<222> LOCATION: (26)..(26)
<223> OTHER INFORMATION: /note="2'-OMe modified nucleotide"
<220> FEATURE:
<221> NAME/KEY: misc_feature
<222> LOCATION: (27)..(27)
<223> OTHER INFORMATION: /note="2'-OMe modified nucleotide"
<220> FEATURE:
<221> NAME/KEY: misc_feature
<222> LOCATION: (28)..(28)
<223> OTHER INFORMATION: /note="ademA-GalNAc"
<220> FEATURE:
<221> NAME/KEY: misc_feature
<222> LOCATION: (29)..(29)
<223> OTHER INFORMATION: /note="ademA-GalNAc"
<220> FEATURE:
<221> NAME/KEY: misc_feature
<222> LOCATION: (30)..(30)
<223> OTHER INFORMATION: /note="ademA-GalNAc"
<220> FEATURE:
<221> NAME/KEY: misc_feature
<222> LOCATION: (31)..(31)
<223> OTHER INFORMATION: /note="2'-OMe modified nucleotide"
<220> FEATURE:
<221> NAME/KEY: misc_feature
<222> LOCATION: (32)..(32)
<223> OTHER INFORMATION: /note="2'-OMe modified nucleotide"
<220> FEATURE:
<221> NAME/KEY: misc_feature
<222> LOCATION: (33)..(33)
<223> OTHER INFORMATION: /note="2'-OMe modified nucleotide"
<220> FEATURE:
<221> NAME/KEY: misc_feature
<222> LOCATION: (34)..(34)
<223> OTHER INFORMATION: /note="2'-OMe modified nucleotide"
<220> FEATURE:
<221> NAME/KEY: misc_feature
<222> LOCATION: (35)..(35)
<223> OTHER INFORMATION: /note="2'-OMe modified nucleotide"
<220> FEATURE:
<221> NAME/KEY: misc_feature
<222> LOCATION: (36)..(36)
<223> OTHER INFORMATION: /note="2'-OMe modified nucleotide"

<400> SEQUENCE: 194
gaaguaacuu cacuuaaaaa gcagccgaaa ggcugc 36

<210> SEQ ID NO 195
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: misc_feature
<222> LOCATION: (1)..(1)
<223> OTHER INFORMATION: /note="MePhosphonate-4O-mUs"
<220> FEATURE:
<221> NAME/KEY: misc_feature
<222> LOCATION: (2)..(2)
<223> OTHER INFORMATION: /note="2'-F modified nucleotide with a 3'-phosphorothioate linkage"
<220> FEATURE:
<221> NAME/KEY: misc_feature
<222> LOCATION: (3)..(3)
<223> OTHER INFORMATION: /note="2'-F modified nucleotide with a 3'-phosphorothioate linkage"
<220> FEATURE:
<221> NAME/KEY: misc_feature
<222> LOCATION: (4)..(4)
<223> OTHER INFORMATION: /note="2'-F modified nucleotide"
<220> FEATURE:
<221> NAME/KEY: misc_feature
<222> LOCATION: (5)..(5)
<223> OTHER INFORMATION: /note="2'-F modified nucleotide"
<220> FEATURE:
<221> NAME/KEY: misc_feature
<222> LOCATION: (6)..(6)
<223> OTHER INFORMATION: /note="2'-OMe modified nucleotide"
<220> FEATURE:
<221> NAME/KEY: misc_feature
<222> LOCATION: (7)..(7)
<223> OTHER INFORMATION: /note="2'-F modified nucleotide"
<220> FEATURE:
<221> NAME/KEY: misc_feature
<222> LOCATION: (8)..(8)
<223> OTHER INFORMATION: /note="2'-OMe modified nucleotide"
<220> FEATURE:
<221> NAME/KEY: misc_feature
<222> LOCATION: (9)..(9)
<223> OTHER INFORMATION: /note="2'-OMe modified nucleotide"
<220> FEATURE:
<221> NAME/KEY: misc_feature
<222> LOCATION: (10)..(10)
<223> OTHER INFORMATION: /note="2'-F modified nucleotide"
<220> FEATURE:
<221> NAME/KEY: misc_feature
<222> LOCATION: (11)..(11)
<223> OTHER INFORMATION: /note="2'-OMe modified nucleotide"
<220> FEATURE:
<221> NAME/KEY: misc_feature
<222> LOCATION: (12)..(12)
<223> OTHER INFORMATION: /note="2'-OMe modified nucleotide"
<220> FEATURE:
<221> NAME/KEY: misc_feature
<222> LOCATION: (13)..(13)
<223> OTHER INFORMATION: /note="2'-OMe modified nucleotide"
<220> FEATURE:
<221> NAME/KEY: misc_feature
<222> LOCATION: (14)..(14)
<223> OTHER INFORMATION: /note="2'-F modified nucleotide"
<220> FEATURE:

<221> NAME/KEY: misc_feature
<222> LOCATION: (15)..(15)
<223> OTHER INFORMATION: /note="2'-OMe modified nucleotide"
<220> FEATURE:
<221> NAME/KEY: misc_feature
<222> LOCATION: (16)..(16)
<223> OTHER INFORMATION: /note="2'-OMe modified nucleotide"
<220> FEATURE:
<221> NAME/KEY: misc_feature
<222> LOCATION: (17)..(17)
<223> OTHER INFORMATION: /note="2'-OMe modified nucleotide"
<220> FEATURE:
<221> NAME/KEY: misc_feature
<222> LOCATION: (18)..(18)
<223> OTHER INFORMATION: /note="2'-OMe modified nucleotide"
<220> FEATURE:
<221> NAME/KEY: misc_feature
<222> LOCATION: (19)..(19)
<223> OTHER INFORMATION: /note="2'-OMe modified nucleotide"
<220> FEATURE:
<221> NAME/KEY: misc_feature
<222> LOCATION: (20)..(20)
<223> OTHER INFORMATION: /note="2'-OMe modified nucleotide with a
3'-phosphorothioate linkage"
<220> FEATURE:
<221> NAME/KEY: misc_feature
<222> LOCATION: (21)..(21)
<223> OTHER INFORMATION: /note="2'-OMe modified nucleotide with a
3'-phosphorothioate linkage"
<220> FEATURE:
<221> NAME/KEY: misc_feature
<222> LOCATION: (22)..(22)
<223> OTHER INFORMATION: /note="2'-OMe modified nucleotide"

<400> SEQUENCE: 195
uuuuuaagug aaguuacuuc gg 22

<210> SEQ ID NO 196
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: misc_feature
<222> LOCATION: (1)..(1)
<223> OTHER INFORMATION: /note="2'-OMe modified nucleotide with a
3'-phosphorothioate linkage"
<220> FEATURE:
<221> NAME/KEY: misc_feature
<222> LOCATION: (2)..(2)
<223> OTHER INFORMATION: /note="2'-OMe modified nucleotide"
<220> FEATURE:
<221> NAME/KEY: misc_feature
<222> LOCATION: (3)..(3)
<223> OTHER INFORMATION: /note="2'-OMe modified nucleotide"
<220> FEATURE:
<221> NAME/KEY: misc_feature
<222> LOCATION: (4)..(4)
<223> OTHER INFORMATION: /note="2'-OMe modified nucleotide"
<220> FEATURE:
<221> NAME/KEY: misc_feature
<222> LOCATION: (5)..(5)
<223> OTHER INFORMATION: /note="2'-OMe modified nucleotide"
<220> FEATURE:
<221> NAME/KEY: misc_feature
<222> LOCATION: (6)..(6)
<223> OTHER INFORMATION: /note="2'-OMe modified nucleotide"
<220> FEATURE:
<221> NAME/KEY: misc_feature
<222> LOCATION: (7)..(7)
<223> OTHER INFORMATION: /note="2'-OMe modified nucleotide"
<220> FEATURE:
<221> NAME/KEY: misc_feature
<222> LOCATION: (8)..(8)

<223> OTHER INFORMATION: /note="2'-F modified nucleotide"
<220> FEATURE:
<221> NAME/KEY: misc_feature
<222> LOCATION: (9)..(9)
<223> OTHER INFORMATION: /note="2'-F modified nucleotide"
<220> FEATURE:
<221> NAME/KEY: misc_feature
<222> LOCATION: (10)..(10)
<223> OTHER INFORMATION: /note="2'-F modified nucleotide"
<220> FEATURE:
<221> NAME/KEY: misc_feature
<222> LOCATION: (11)..(11)
<223> OTHER INFORMATION: /note="2'-F modified nucleotide"
<220> FEATURE:
<221> NAME/KEY: misc_feature
<222> LOCATION: (12)..(12)
<223> OTHER INFORMATION: /note="2'-OMe modified nucleotide"
<220> FEATURE:
<221> NAME/KEY: misc_feature
<222> LOCATION: (13)..(13)
<223> OTHER INFORMATION: /note="2'-OMe modified nucleotide"
<220> FEATURE:
<221> NAME/KEY: misc_feature
<222> LOCATION: (14)..(14)
<223> OTHER INFORMATION: /note="2'-OMe modified nucleotide"
<220> FEATURE:
<221> NAME/KEY: misc_feature
<222> LOCATION: (15)..(15)
<223> OTHER INFORMATION: /note="2'-OMe modified nucleotide"
<220> FEATURE:
<221> NAME/KEY: misc_feature
<222> LOCATION: (16)..(16)
<223> OTHER INFORMATION: /note="2'-OMe modified nucleotide"
<220> FEATURE:
<221> NAME/KEY: misc_feature
<222> LOCATION: (17)..(17)
<223> OTHER INFORMATION: /note="2'-OMe modified nucleotide"
<220> FEATURE:
<221> NAME/KEY: misc_feature
<222> LOCATION: (18)..(18)
<223> OTHER INFORMATION: /note="2'-OMe modified nucleotide"
<220> FEATURE:
<221> NAME/KEY: misc_feature
<222> LOCATION: (19)..(19)
<223> OTHER INFORMATION: /note="2'-OMe modified nucleotide"
<220> FEATURE:
<221> NAME/KEY: misc_feature
<222> LOCATION: (20)..(20)
<223> OTHER INFORMATION: /note="2'-OMe modified nucleotide"
<220> FEATURE:
<221> NAME/KEY: misc_feature
<222> LOCATION: (21)..(21)
<223> OTHER INFORMATION: /note="2'-OMe modified nucleotide"
<220> FEATURE:
<221> NAME/KEY: misc_feature
<222> LOCATION: (22)..(22)
<223> OTHER INFORMATION: /note="2'-OMe modified nucleotide"
<220> FEATURE:
<221> NAME/KEY: misc_feature
<222> LOCATION: (23)..(23)
<223> OTHER INFORMATION: /note="2'-OMe modified nucleotide"
<220> FEATURE:
<221> NAME/KEY: misc_feature
<222> LOCATION: (24)..(24)
<223> OTHER INFORMATION: /note="2'-OMe modified nucleotide"
<220> FEATURE:
<221> NAME/KEY: misc_feature
<222> LOCATION: (25)..(25)
<223> OTHER INFORMATION: /note="2'-OMe modified nucleotide"
<220> FEATURE:
<221> NAME/KEY: misc_feature
<222> LOCATION: (26)..(26)
<223> OTHER INFORMATION: /note="2'-OMe modified nucleotide"
<220> FEATURE:
<221> NAME/KEY: misc_feature
<222> LOCATION: (27)..(27)
<223> OTHER INFORMATION: /note="2'-OMe modified nucleotide"
<220> FEATURE:
<221> NAME/KEY: misc_feature
<222> LOCATION: (28)..(28)
<223> OTHER INFORMATION: /note="ademA-GalNAc"
<220> FEATURE:
<221> NAME/KEY: misc_feature
<222> LOCATION: (29)..(29)
<223> OTHER INFORMATION: /note="ademA-GalNAc"
<220> FEATURE:
<221> NAME/KEY: misc_feature
<222> LOCATION: (30)..(30)
<223> OTHER INFORMATION: /note="ademA-GalNAc"
<220> FEATURE:
<221> NAME/KEY: misc_feature
<222> LOCATION: (31)..(31)
<223> OTHER INFORMATION: /note="2'-OMe modified nucleotide"
<220> FEATURE:
<221> NAME/KEY: misc_feature
<222> LOCATION: (32)..(32)
<223> OTHER INFORMATION: /note="2'-OMe modified nucleotide"
<220> FEATURE:
<221> NAME/KEY: misc_feature
<222> LOCATION: (33)..(33)
<223> OTHER INFORMATION: /note="2'-OMe modified nucleotide"
<220> FEATURE:
<221> NAME/KEY: misc_feature
<222> LOCATION: (34)..(34)
<223> OTHER INFORMATION: /note="2'-OMe modified nucleotide"
<220> FEATURE:
<221> NAME/KEY: misc_feature
<222> LOCATION: (35)..(35)
<223> OTHER INFORMATION: /note="2'-OMe modified nucleotide"
<220> FEATURE:
<221> NAME/KEY: misc_feature
<222> LOCATION: (36)..(36)
<223> OTHER INFORMATION: /note="2'-OMe modified nucleotide"

<400> SEQUENCE: 196
uuuuguagaa aaacaagaua gcagccgaaa ggcugc 36

<210> SEQ ID NO 197
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: misc_feature
<222> LOCATION: (1)..(1)
<223> OTHER INFORMATION: /note="MePhosphonate-4O-mUs"
<220> FEATURE:
<221> NAME/KEY: misc_feature
<222> LOCATION: (2)..(2)
<223> OTHER INFORMATION: /note="2'-F modified nucleotide with a
3'-phosphorothioate linkage"
<220> FEATURE:
<221> NAME/KEY: misc_feature
<222> LOCATION: (3)..(3)
<223> OTHER INFORMATION: /note="2'-F modified nucleotide with a
3'-phosphorothioate linkage"
<220> FEATURE:
<221> NAME/KEY: misc_feature
<222> LOCATION: (4)..(4)
<223> OTHER INFORMATION: /note="2'-F modified nucleotide"
<220> FEATURE:
<221> NAME/KEY: misc_feature
<222> LOCATION: (5)..(5)
<223> OTHER INFORMATION: /note="2'-F modified nucleotide"
<220> FEATURE:
<221> NAME/KEY: misc_feature
<222> LOCATION: (6)..(6)
<223> OTHER INFORMATION: /note="2'-OMe modified nucleotide"
<220> FEATURE:
<221> NAME/KEY: misc_feature
<222> LOCATION: (7)..(7)
<223> OTHER INFORMATION: /note="2'-F modified nucleotide"
<220> FEATURE:

-continued

<221> NAME/KEY: misc_feature
<222> LOCATION: (8)..(8)
<223> OTHER INFORMATION: /note="2'-OMe modified nucleotide"
<220> FEATURE:
<221> NAME/KEY: misc_feature
<222> LOCATION: (9)..(9)
<223> OTHER INFORMATION: /note="2'-OMe modified nucleotide"
<220> FEATURE:
<221> NAME/KEY: misc_feature
<222> LOCATION: (10)..(10)
<223> OTHER INFORMATION: /note="2'-F modified nucleotide"
<220> FEATURE:
<221> NAME/KEY: misc_feature
<222> LOCATION: (11)..(11)
<223> OTHER INFORMATION: /note="2'-OMe modified nucleotide"
<220> FEATURE:
<221> NAME/KEY: misc_feature
<222> LOCATION: (12)..(12)
<223> OTHER INFORMATION: /note="2'-OMe modified nucleotide"
<220> FEATURE:
<221> NAME/KEY: misc_feature
<222> LOCATION: (13)..(13)
<223> OTHER INFORMATION: /note="2'-OMe modified nucleotide"
<220> FEATURE:
<221> NAME/KEY: misc_feature
<222> LOCATION: (14)..(14)
<223> OTHER INFORMATION: /note="2'-F modified nucleotide"
<220> FEATURE:
<221> NAME/KEY: misc_feature
<222> LOCATION: (15)..(15)
<223> OTHER INFORMATION: /note="2'-OMe modified nucleotide"
<220> FEATURE:
<221> NAME/KEY: misc_feature
<222> LOCATION: (16)..(16)
<223> OTHER INFORMATION: /note="2'-OMe modified nucleotide"
<220> FEATURE:
<221> NAME/KEY: misc_feature
<222> LOCATION: (17)..(17)
<223> OTHER INFORMATION: /note="2'-OMe modified nucleotide"
<220> FEATURE:
<221> NAME/KEY: misc_feature
<222> LOCATION: (18)..(18)
<223> OTHER INFORMATION: /note="2'-OMe modified nucleotide"
<220> FEATURE:
<221> NAME/KEY: misc_feature
<222> LOCATION: (19)..(19)
<223> OTHER INFORMATION: /note="2'-OMe modified nucleotide"
<220> FEATURE:
<221> NAME/KEY: misc_feature
<222> LOCATION: (20)..(20)
<223> OTHER INFORMATION: /note="2'-OMe modified nucleotide with a
3'-phosphorothioate linkage"
<220> FEATURE:
<221> NAME/KEY: misc_feature
<222> LOCATION: (21)..(21)
<223> OTHER INFORMATION: /note="2'-OMe modified nucleotide with a
3'-phosphorothioate linkage"
<220> FEATURE:
<221> NAME/KEY: misc_feature
<222> LOCATION: (22)..(22)
<223> OTHER INFORMATION: /note="2'-OMe modified nucleotide"

<400> SEQUENCE: 197
uaucuuguuu uucuacaaaa gg 22

<210> SEQ ID NO 198
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: misc_feature
<222> LOCATION: (1)..(1)
<223> OTHER INFORMATION: /note="2'-OMe modified nucleotide with a 3'-phosphorothioate linkage"
<220> FEATURE:
<221> NAME/KEY: misc_feature
<222> LOCATION: (2)..(2)
<223> OTHER INFORMATION: /note="2'-OMe modified nucleotide"
<220> FEATURE:
<221> NAME/KEY: misc_feature
<222> LOCATION: (3)..(3)
<223> OTHER INFORMATION: /note="2'-OMe modified nucleotide"
<220> FEATURE:
<221> NAME/KEY: misc_feature
<222> LOCATION: (4)..(4)
<223> OTHER INFORMATION: /note="2'-OMe modified nucleotide"
<220> FEATURE:
<221> NAME/KEY: misc_feature
<222> LOCATION: (5)..(5)
<223> OTHER INFORMATION: /note="2'-OMe modified nucleotide"
<220> FEATURE:
<221> NAME/KEY: misc_feature
<222> LOCATION: (6)..(6)
<223> OTHER INFORMATION: /note="2'-OMe modified nucleotide"
<220> FEATURE:
<221> NAME/KEY: misc_feature
<222> LOCATION: (7)..(7)
<223> OTHER INFORMATION: /note="2'-OMe modified nucleotide"
<220> FEATURE:
<221> NAME/KEY: misc_feature
<222> LOCATION: (8)..(8)
<223> OTHER INFORMATION: /note="2'-F modified nucleotide"
<220> FEATURE:
<221> NAME/KEY: misc_feature
<222> LOCATION: (9)..(9)
<223> OTHER INFORMATION: /note="2'-F modified nucleotide"
<220> FEATURE:
<221> NAME/KEY: misc_feature
<222> LOCATION: (10)..(10)
<223> OTHER INFORMATION: /note="2'-F modified nucleotide"
<220> FEATURE:
<221> NAME/KEY: misc_feature
<222> LOCATION: (11)..(11)
<223> OTHER INFORMATION: /note="2'-F modified nucleotide"
<220> FEATURE:
<221> NAME/KEY: misc_feature
<222> LOCATION: (12)..(12)
<223> OTHER INFORMATION: /note="2'-OMe modified nucleotide"
<220> FEATURE:
<221> NAME/KEY: misc_feature
<222> LOCATION: (13)..(13)
<223> OTHER INFORMATION: /note="2'-OMe modified nucleotide"
<220> FEATURE:
<221> NAME/KEY: misc_feature
<222> LOCATION: (14)..(14)
<223> OTHER INFORMATION: /note="2'-OMe modified nucleotide"
<220> FEATURE:
<221> NAME/KEY: misc_feature
<222> LOCATION: (15)..(15)
<223> OTHER INFORMATION: /note="2'-OMe modified nucleotide"
<220> FEATURE:
<221> NAME/KEY: misc_feature
<222> LOCATION: (16)..(16)
<223> OTHER INFORMATION: /note="2'-OMe modified nucleotide"
<220> FEATURE:
<221> NAME/KEY: misc_feature
<222> LOCATION: (17)..(17)
<223> OTHER INFORMATION: /note="2'-OMe modified nucleotide"
<220> FEATURE:
<221> NAME/KEY: misc_feature
<222> LOCATION: (18)..(18)
<223> OTHER INFORMATION: /note="2'-OMe modified nucleotide"
<220> FEATURE:
<221> NAME/KEY: misc_feature
<222> LOCATION: (19)..(19)
<223> OTHER INFORMATION: /note="2'-OMe modified nucleotide"
<220> FEATURE:
<221> NAME/KEY: misc_feature
<222> LOCATION: (20)..(20)
<223> OTHER INFORMATION: /note="2'-OMe modified nucleotide"
<220> FEATURE:
<221> NAME/KEY: misc_feature
<222> LOCATION: (21)..(21)
<223> OTHER INFORMATION: /note="2'-OMe modified nucleotide"
<220> FEATURE:
<221> NAME/KEY: misc_feature
<222> LOCATION: (22)..(22)
<223> OTHER INFORMATION: /note="2'-OMe modified nucleotide"
<220> FEATURE:
<221> NAME/KEY: misc_feature
<222> LOCATION: (23)..(23)
<223> OTHER INFORMATION: /note="2'-OMe modified nucleotide"
<220> FEATURE:
<221> NAME/KEY: misc_feature
<222> LOCATION: (24)..(24)
<223> OTHER INFORMATION: /note="2'-OMe modified nucleotide"
<220> FEATURE:
<221> NAME/KEY: misc_feature
<222> LOCATION: (25)..(25)
<223> OTHER INFORMATION: /note="2'-OMe modified nucleotide"
<220> FEATURE:
<221> NAME/KEY: misc_feature
<222> LOCATION: (26)..(26)
<223> OTHER INFORMATION: /note="2'-OMe modified nucleotide"
<220> FEATURE:
<221> NAME/KEY: misc_feature
<222> LOCATION: (27)..(27)
<223> OTHER INFORMATION: /note="2'-OMe modified nucleotide"
<220> FEATURE:
<221> NAME/KEY: misc_feature
<222> LOCATION: (28)..(28)
<223> OTHER INFORMATION: /note="ademA-GalNAc"
<220> FEATURE:
<221> NAME/KEY: misc_feature
<222> LOCATION: (29)..(29)
<223> OTHER INFORMATION: /note="ademA-GalNAc"
<220> FEATURE:
<221> NAME/KEY: misc_feature
<222> LOCATION: (30)..(30)
<223> OTHER INFORMATION: /note="ademA-GalNAc"
<220> FEATURE:
<221> NAME/KEY: misc_feature
<222> LOCATION: (31)..(31)
<223> OTHER INFORMATION: /note="2'-OMe modified nucleotide"
<220> FEATURE:
<221> NAME/KEY: misc_feature
<222> LOCATION: (32)..(32)
<223> OTHER INFORMATION: /note="2'-OMe modified nucleotide"
<220> FEATURE:
<221> NAME/KEY: misc_feature
<222> LOCATION: (33)..(33)
<223> OTHER INFORMATION: /note="2'-OMe modified nucleotide"
<220> FEATURE:
<221> NAME/KEY: misc_feature
<222> LOCATION: (34)..(34)
<223> OTHER INFORMATION: /note="2'-OMe modified nucleotide"
<220> FEATURE:
<221> NAME/KEY: misc_feature
<222> LOCATION: (35)..(35)
<223> OTHER INFORMATION: /note="2'-OMe modified nucleotide"
<220> FEATURE:
<221> NAME/KEY: misc_feature
<222> LOCATION: (36)..(36)
<223> OTHER INFORMATION: /note="2'-OMe modified nucleotide"

<400> SEQUENCE: 198
uuuguagaaa aacaagauaa gcagccgaaa ggcugc 36

<210> SEQ ID NO 199
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: misc_feature
<222> LOCATION: (1)..(1)

<223> OTHER INFORMATION: /note="MePhosphonate-4O-mUs"
<220> FEATURE:
<221> NAME/KEY: misc_feature
<222> LOCATION: (2)..(2)
<223> OTHER INFORMATION: /note="2'-F modified nucleotide with a 3'-phosphorothioate linkage"
<220> FEATURE:
<221> NAME/KEY: misc_feature
<222> LOCATION: (3)..(3)
<223> OTHER INFORMATION: /note="2'-F modified nucleotide with a 3'-phosphorothioate linkage"
<220> FEATURE:
<221> NAME/KEY: misc_feature
<222> LOCATION: (4)..(4)
<223> OTHER INFORMATION: /note="2'-F modified nucleotide"
<220> FEATURE:
<221> NAME/KEY: misc_feature
<222> LOCATION: (5)..(5)
<223> OTHER INFORMATION: /note="2'-F modified nucleotide"
<220> FEATURE:
<221> NAME/KEY: misc_feature
<222> LOCATION: (6)..(6)
<223> OTHER INFORMATION: /note="2'-OMe modified nucleotide"
<220> FEATURE:
<221> NAME/KEY: misc_feature
<222> LOCATION: (7)..(7)
<223> OTHER INFORMATION: /note="2'-F modified nucleotide"
<220> FEATURE:
<221> NAME/KEY: misc_feature
<222> LOCATION: (8)..(8)
<223> OTHER INFORMATION: /note="2'-OMe modified nucleotide"
<220> FEATURE:
<221> NAME/KEY: misc_feature
<222> LOCATION: (9)..(9)
<223> OTHER INFORMATION: /note="2'-OMe modified nucleotide"
<220> FEATURE:
<221> NAME/KEY: misc_feature
<222> LOCATION: (10)..(10)
<223> OTHER INFORMATION: /note="2'-F modified nucleotide"
<220> FEATURE:
<221> NAME/KEY: misc_feature
<222> LOCATION: (11)..(11)
<223> OTHER INFORMATION: /note="2'-OMe modified nucleotide"
<220> FEATURE:
<221> NAME/KEY: misc_feature
<222> LOCATION: (12)..(12)
<223> OTHER INFORMATION: /note="2'-OMe modified nucleotide"
<220> FEATURE:
<221> NAME/KEY: misc_feature
<222> LOCATION: (13)..(13)
<223> OTHER INFORMATION: /note="2'-OMe modified nucleotide"
<220> FEATURE:
<221> NAME/KEY: misc_feature
<222> LOCATION: (14)..(14)
<223> OTHER INFORMATION: /note="2'-F modified nucleotide"
<220> FEATURE:
<221> NAME/KEY: misc_feature
<222> LOCATION: (15)..(15)
<223> OTHER INFORMATION: /note="2'-OMe modified nucleotide"
<220> FEATURE:
<221> NAME/KEY: misc_feature
<222> LOCATION: (16)..(16)
<223> OTHER INFORMATION: /note="2'-OMe modified nucleotide"
<220> FEATURE:
<221> NAME/KEY: misc_feature
<222> LOCATION: (17)..(17)
<223> OTHER INFORMATION: /note="2'-OMe modified nucleotide"
<220> FEATURE:
<221> NAME/KEY: misc_feature
<222> LOCATION: (18)..(18)
<223> OTHER INFORMATION: /note="2'-OMe modified nucleotide"
<220> FEATURE:
<221> NAME/KEY: misc_feature
<222> LOCATION: (19)..(19)
<223> OTHER INFORMATION: /note="2'-OMe modified nucleotide"
<220> FEATURE:
<221> NAME/KEY: misc_feature
<222> LOCATION: (20)..(20)
<223> OTHER INFORMATION: /note="2'-OMe modified nucleotide with a

```
      3'-phosphorothioate linkage"
<220> FEATURE:
<221> NAME/KEY: misc_feature
<222> LOCATION: (21)..(21)
<223> OTHER INFORMATION: /note="2'-OMe modified nucleotide with a
      3'-phosphorothioate linkage"
<220> FEATURE:
<221> NAME/KEY: misc_feature
<222> LOCATION: (22)..(22)
<223> OTHER INFORMATION: /note="2'-OMe modified nucleotide"

<400> SEQUENCE: 199

uuaucuuguu uuucuacaaa gg                                            22


<210> SEQ ID NO 200
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: misc_feature
<222> LOCATION: (1)..(1)
<223> OTHER INFORMATION: /note="2'-OMe modified nucleotide with a
      3'-phosphorothioate linkage"
<220> FEATURE:
<221> NAME/KEY: misc_feature
<222> LOCATION: (2)..(2)
<223> OTHER INFORMATION: /note="2'-OMe modified nucleotide"
<220> FEATURE:
<221> NAME/KEY: misc_feature
<222> LOCATION: (3)..(3)
<223> OTHER INFORMATION: /note="2'-OMe modified nucleotide"
<220> FEATURE:
<221> NAME/KEY: misc_feature
<222> LOCATION: (4)..(4)
<223> OTHER INFORMATION: /note="2'-OMe modified nucleotide"
<220> FEATURE:
<221> NAME/KEY: misc_feature
<222> LOCATION: (5)..(5)
<223> OTHER INFORMATION: /note="2'-OMe modified nucleotide"
<220> FEATURE:
<221> NAME/KEY: misc_feature
<222> LOCATION: (6)..(6)
<223> OTHER INFORMATION: /note="2'-OMe modified nucleotide"
<220> FEATURE:
<221> NAME/KEY: misc_feature
<222> LOCATION: (7)..(7)
<223> OTHER INFORMATION: /note="2'-OMe modified nucleotide"
<220> FEATURE:
<221> NAME/KEY: misc_feature
<222> LOCATION: (8)..(8)
<223> OTHER INFORMATION: /note="2'-F modified nucleotide"
<220> FEATURE:
<221> NAME/KEY: misc_feature
<222> LOCATION: (9)..(9)
<223> OTHER INFORMATION: /note="2'-F modified nucleotide"
<220> FEATURE:
<221> NAME/KEY: misc_feature
<222> LOCATION: (10)..(10)
<223> OTHER INFORMATION: /note="2'-F modified nucleotide"
<220> FEATURE:
<221> NAME/KEY: misc_feature
<222> LOCATION: (11)..(11)
<223> OTHER INFORMATION: /note="2'-F modified nucleotide"
<220> FEATURE:
<221> NAME/KEY: misc_feature
<222> LOCATION: (12)..(12)
<223> OTHER INFORMATION: /note="2'-OMe modified nucleotide"
<220> FEATURE:
<221> NAME/KEY: misc_feature
<222> LOCATION: (13)..(13)
<223> OTHER INFORMATION: /note="2'-OMe modified nucleotide"
<220> FEATURE:
<221> NAME/KEY: misc_feature
```

<222> LOCATION: (14)..(14)
<223> OTHER INFORMATION: /note="2'-OMe modified nucleotide"
<220> FEATURE:
<221> NAME/KEY: misc_feature
<222> LOCATION: (15)..(15)
<223> OTHER INFORMATION: /note="2'-OMe modified nucleotide"
<220> FEATURE:
<221> NAME/KEY: misc_feature
<222> LOCATION: (16)..(16)
<223> OTHER INFORMATION: /note="2'-OMe modified nucleotide"
<220> FEATURE:
<221> NAME/KEY: misc_feature
<222> LOCATION: (17)..(17)
<223> OTHER INFORMATION: /note="2'-OMe modified nucleotide"
<220> FEATURE:
<221> NAME/KEY: misc_feature
<222> LOCATION: (18)..(18)
<223> OTHER INFORMATION: /note="2'-OMe modified nucleotide"
<220> FEATURE:
<221> NAME/KEY: misc_feature
<222> LOCATION: (19)..(19)
<223> OTHER INFORMATION: /note="2'-OMe modified nucleotide"
<220> FEATURE:
<221> NAME/KEY: misc_feature
<222> LOCATION: (20)..(20)
<223> OTHER INFORMATION: /note="2'-OMe modified nucleotide"
<220> FEATURE:
<221> NAME/KEY: misc_feature
<222> LOCATION: (21)..(21)
<223> OTHER INFORMATION: /note="2'-OMe modified nucleotide"
<220> FEATURE:
<221> NAME/KEY: misc_feature
<222> LOCATION: (22)..(22)
<223> OTHER INFORMATION: /note="2'-OMe modified nucleotide"
<220> FEATURE:
<221> NAME/KEY: misc_feature
<222> LOCATION: (23)..(23)
<223> OTHER INFORMATION: /note="2'-OMe modified nucleotide"
<220> FEATURE:
<221> NAME/KEY: misc_feature
<222> LOCATION: (24)..(24)
<223> OTHER INFORMATION: /note="2'-OMe modified nucleotide"
<220> FEATURE:
<221> NAME/KEY: misc_feature
<222> LOCATION: (25)..(25)
<223> OTHER INFORMATION: /note="2'-OMe modified nucleotide"
<220> FEATURE:
<221> NAME/KEY: misc_feature
<222> LOCATION: (26)..(26)
<223> OTHER INFORMATION: /note="2'-OMe modified nucleotide"
<220> FEATURE:
<221> NAME/KEY: misc_feature
<222> LOCATION: (27)..(27)
<223> OTHER INFORMATION: /note="2'-OMe modified nucleotide"
<220> FEATURE:
<221> NAME/KEY: misc_feature
<222> LOCATION: (28)..(28)
<223> OTHER INFORMATION: /note="ademA-GalNAc"
<220> FEATURE:
<221> NAME/KEY: misc_feature
<222> LOCATION: (29)..(29)
<223> OTHER INFORMATION: /note="ademA-GalNAc"
<220> FEATURE:
<221> NAME/KEY: misc_feature
<222> LOCATION: (30)..(30)
<223> OTHER INFORMATION: /note="ademA-GalNAc"
<220> FEATURE:
<221> NAME/KEY: misc_feature
<222> LOCATION: (31)..(31)
<223> OTHER INFORMATION: /note="2'-OMe modified nucleotide"
<220> FEATURE:
<221> NAME/KEY: misc_feature
<222> LOCATION: (32)..(32)
<223> OTHER INFORMATION: /note="2'-OMe modified nucleotide"
<220> FEATURE:
<221> NAME/KEY: misc_feature
<222> LOCATION: (33)..(33)
<223> OTHER INFORMATION: /note="2'-OMe modified nucleotide"
<220> FEATURE:

<221> NAME/KEY: misc_feature
<222> LOCATION: (34)..(34)
<223> OTHER INFORMATION: /note="2'-OMe modified nucleotide"
<220> FEATURE:
<221> NAME/KEY: misc_feature
<222> LOCATION: (35)..(35)
<223> OTHER INFORMATION: /note="2'-OMe modified nucleotide"
<220> FEATURE:
<221> NAME/KEY: misc_feature
<222> LOCATION: (36)..(36)
<223> OTHER INFORMATION: /note="2'-OMe modified nucleotide"

<400> SEQUENCE: 200
uuguagaaaa acaagauaaa gcagccgaaa ggcugc 36

<210> SEQ ID NO 201
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: misc_feature
<222> LOCATION: (1)..(1)
<223> OTHER INFORMATION: /note="MePhosphonate-4O-mUs"
<220> FEATURE:
<221> NAME/KEY: misc_feature
<222> LOCATION: (2)..(2)
<223> OTHER INFORMATION: /note="2'-F modified nucleotide with a 3'-phosphorothioate linkage"
<220> FEATURE:
<221> NAME/KEY: misc_feature
<222> LOCATION: (3)..(3)
<223> OTHER INFORMATION: /note="2'-F modified nucleotide with a 3'-phosphorothioate linkage"
<220> FEATURE:
<221> NAME/KEY: misc_feature
<222> LOCATION: (4)..(4)
<223> OTHER INFORMATION: /note="2'-F modified nucleotide"
<220> FEATURE:
<221> NAME/KEY: misc_feature
<222> LOCATION: (5)..(5)
<223> OTHER INFORMATION: /note="2'-F modified nucleotide"
<220> FEATURE:
<221> NAME/KEY: misc_feature
<222> LOCATION: (6)..(6)
<223> OTHER INFORMATION: /note="2'-OMe modified nucleotide"
<220> FEATURE:
<221> NAME/KEY: misc_feature
<222> LOCATION: (7)..(7)
<223> OTHER INFORMATION: /note="2'-F modified nucleotide"
<220> FEATURE:
<221> NAME/KEY: misc_feature
<222> LOCATION: (8)..(8)
<223> OTHER INFORMATION: /note="2'-OMe modified nucleotide"
<220> FEATURE:
<221> NAME/KEY: misc_feature
<222> LOCATION: (9)..(9)
<223> OTHER INFORMATION: /note="2'-OMe modified nucleotide"
<220> FEATURE:
<221> NAME/KEY: misc_feature
<222> LOCATION: (10)..(10)
<223> OTHER INFORMATION: /note="2'-F modified nucleotide"
<220> FEATURE:
<221> NAME/KEY: misc_feature
<222> LOCATION: (11)..(11)
<223> OTHER INFORMATION: /note="2'-OMe modified nucleotide"
<220> FEATURE:
<221> NAME/KEY: misc_feature
<222> LOCATION: (12)..(12)
<223> OTHER INFORMATION: /note="2'-OMe modified nucleotide"
<220> FEATURE:
<221> NAME/KEY: misc_feature
<222> LOCATION: (13)..(13)
<223> OTHER INFORMATION: /note="2'-OMe modified nucleotide"

```
<220> FEATURE:
<221> NAME/KEY: misc_feature
<222> LOCATION: (14)..(14)
<223> OTHER INFORMATION: /note="2'-F modified nucleotide"
<220> FEATURE:
<221> NAME/KEY: misc_feature
<222> LOCATION: (15)..(15)
<223> OTHER INFORMATION: /note="2'-OMe modified nucleotide"
<220> FEATURE:
<221> NAME/KEY: misc_feature
<222> LOCATION: (16)..(16)
<223> OTHER INFORMATION: /note="2'-OMe modified nucleotide"
<220> FEATURE:
<221> NAME/KEY: misc_feature
<222> LOCATION: (17)..(17)
<223> OTHER INFORMATION: /note="2'-OMe modified nucleotide"
<220> FEATURE:
<221> NAME/KEY: misc_feature
<222> LOCATION: (18)..(18)
<223> OTHER INFORMATION: /note="2'-OMe modified nucleotide"
<220> FEATURE:
<221> NAME/KEY: misc_feature
<222> LOCATION: (19)..(19)
<223> OTHER INFORMATION: /note="2'-OMe modified nucleotide"
<220> FEATURE:
<221> NAME/KEY: misc_feature
<222> LOCATION: (20)..(20)
<223> OTHER INFORMATION: /note="2'-OMe modified nucleotide with a
      3'-phosphorothioate linkage"
<220> FEATURE:
<221> NAME/KEY: misc_feature
<222> LOCATION: (21)..(21)
<223> OTHER INFORMATION: /note="2'-OMe modified nucleotide with a
      3'-phosphorothioate linkage"
<220> FEATURE:
<221> NAME/KEY: misc_feature
<222> LOCATION: (22)..(22)
<223> OTHER INFORMATION: /note="2'-OMe modified nucleotide"

<400> SEQUENCE: 201

uuuaucuugu uuucuacaa gg                                              22


<210> SEQ ID NO 202
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: misc_feature
<222> LOCATION: (1)..(1)
<223> OTHER INFORMATION: /note="2'-OMe modified nucleotide with a
      3'-phosphorothioate linkage"
<220> FEATURE:
<221> NAME/KEY: misc_feature
<222> LOCATION: (2)..(2)
<223> OTHER INFORMATION: /note="2'-OMe modified nucleotide"
<220> FEATURE:
<221> NAME/KEY: misc_feature
<222> LOCATION: (3)..(3)
<223> OTHER INFORMATION: /note="2'-OMe modified nucleotide"
<220> FEATURE:
<221> NAME/KEY: misc_feature
<222> LOCATION: (4)..(4)
<223> OTHER INFORMATION: /note="2'-OMe modified nucleotide"
<220> FEATURE:
<221> NAME/KEY: misc_feature
<222> LOCATION: (5)..(5)
<223> OTHER INFORMATION: /note="2'-OMe modified nucleotide"
<220> FEATURE:
<221> NAME/KEY: misc_feature
<222> LOCATION: (6)..(6)
<223> OTHER INFORMATION: /note="2'-OMe modified nucleotide"
<220> FEATURE:
<221> NAME/KEY: misc_feature
```

<222> LOCATION: (7)..(7)
<223> OTHER INFORMATION: /note="2'-OMe modified nucleotide"
<220> FEATURE:
<221> NAME/KEY: misc_feature
<222> LOCATION: (8)..(8)
<223> OTHER INFORMATION: /note="2'-F modified nucleotide"
<220> FEATURE:
<221> NAME/KEY: misc_feature
<222> LOCATION: (9)..(9)
<223> OTHER INFORMATION: /note="2'-F modified nucleotide"
<220> FEATURE:
<221> NAME/KEY: misc_feature
<222> LOCATION: (10)..(10)
<223> OTHER INFORMATION: /note="2'-F modified nucleotide"
<220> FEATURE:
<221> NAME/KEY: misc_feature
<222> LOCATION: (11)..(11)
<223> OTHER INFORMATION: /note="2'-F modified nucleotide"
<220> FEATURE:
<221> NAME/KEY: misc_feature
<222> LOCATION: (12)..(12)
<223> OTHER INFORMATION: /note="2'-OMe modified nucleotide"
<220> FEATURE:
<221> NAME/KEY: misc_feature
<222> LOCATION: (13)..(13)
<223> OTHER INFORMATION: /note="2'-OMe modified nucleotide"
<220> FEATURE:
<221> NAME/KEY: misc_feature
<222> LOCATION: (14)..(14)
<223> OTHER INFORMATION: /note="2'-OMe modified nucleotide"
<220> FEATURE:
<221> NAME/KEY: misc_feature
<222> LOCATION: (15)..(15)
<223> OTHER INFORMATION: /note="2'-OMe modified nucleotide"
<220> FEATURE:
<221> NAME/KEY: misc_feature
<222> LOCATION: (16)..(16)
<223> OTHER INFORMATION: /note="2'-OMe modified nucleotide"
<220> FEATURE:
<221> NAME/KEY: misc_feature
<222> LOCATION: (17)..(17)
<223> OTHER INFORMATION: /note="2'-OMe modified nucleotide"
<220> FEATURE:
<221> NAME/KEY: misc_feature
<222> LOCATION: (18)..(18)
<223> OTHER INFORMATION: /note="2'-OMe modified nucleotide"
<220> FEATURE:
<221> NAME/KEY: misc_feature
<222> LOCATION: (19)..(19)
<223> OTHER INFORMATION: /note="2'-OMe modified nucleotide"
<220> FEATURE:
<221> NAME/KEY: misc_feature
<222> LOCATION: (20)..(20)
<223> OTHER INFORMATION: /note="2'-OMe modified nucleotide"
<220> FEATURE:
<221> NAME/KEY: misc_feature
<222> LOCATION: (21)..(21)
<223> OTHER INFORMATION: /note="2'-OMe modified nucleotide"
<220> FEATURE:
<221> NAME/KEY: misc_feature
<222> LOCATION: (22)..(22)
<223> OTHER INFORMATION: /note="2'-OMe modified nucleotide"
<220> FEATURE:
<221> NAME/KEY: misc_feature
<222> LOCATION: (23)..(23)
<223> OTHER INFORMATION: /note="2'-OMe modified nucleotide"
<220> FEATURE:
<221> NAME/KEY: misc_feature
<222> LOCATION: (24)..(24)
<223> OTHER INFORMATION: /note="2'-OMe modified nucleotide"
<220> FEATURE:
<221> NAME/KEY: misc_feature
<222> LOCATION: (25)..(25)
<223> OTHER INFORMATION: /note="2'-OMe modified nucleotide"
<220> FEATURE:
<221> NAME/KEY: misc_feature
<222> LOCATION: (26)..(26)
<223> OTHER INFORMATION: /note="2'-OMe modified nucleotide"
<220> FEATURE:

<221> NAME/KEY: misc_feature
<222> LOCATION: (27)..(27)
<223> OTHER INFORMATION: /note="2'-OMe modified nucleotide"
<220> FEATURE:
<221> NAME/KEY: misc_feature
<222> LOCATION: (28)..(28)
<223> OTHER INFORMATION: /note="ademA-GalNAc"
<220> FEATURE:
<221> NAME/KEY: misc_feature
<222> LOCATION: (29)..(29)
<223> OTHER INFORMATION: /note="ademA-GalNAc"
<220> FEATURE:
<221> NAME/KEY: misc_feature
<222> LOCATION: (30)..(30)
<223> OTHER INFORMATION: /note="ademA-GalNAc"
<220> FEATURE:
<221> NAME/KEY: misc_feature
<222> LOCATION: (31)..(31)
<223> OTHER INFORMATION: /note="2'-OMe modified nucleotide"
<220> FEATURE:
<221> NAME/KEY: misc_feature
<222> LOCATION: (32)..(32)
<223> OTHER INFORMATION: /note="2'-OMe modified nucleotide"
<220> FEATURE:
<221> NAME/KEY: misc_feature
<222> LOCATION: (33)..(33)
<223> OTHER INFORMATION: /note="2'-OMe modified nucleotide"
<220> FEATURE:
<221> NAME/KEY: misc_feature
<222> LOCATION: (34)..(34)
<223> OTHER INFORMATION: /note="2'-OMe modified nucleotide"
<220> FEATURE:
<221> NAME/KEY: misc_feature
<222> LOCATION: (35)..(35)
<223> OTHER INFORMATION: /note="2'-OMe modified nucleotide"
<220> FEATURE:
<221> NAME/KEY: misc_feature
<222> LOCATION: (36)..(36)
<223> OTHER INFORMATION: /note="2'-OMe modified nucleotide"

<400> SEQUENCE: 202
guagaaaaac aagauaauaa gcagccgaaa ggcugc 36

<210> SEQ ID NO 203
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: misc_feature
<222> LOCATION: (1)..(1)
<223> OTHER INFORMATION: /note="MePhosphonate-4O-mUs"
<220> FEATURE:
<221> NAME/KEY: misc_feature
<222> LOCATION: (2)..(2)
<223> OTHER INFORMATION: /note="2'-F modified nucleotide with a
3'-phosphorothioate linkage"
<220> FEATURE:
<221> NAME/KEY: misc_feature
<222> LOCATION: (3)..(3)
<223> OTHER INFORMATION: /note="2'-F modified nucleotide with a
3'-phosphorothioate linkage"
<220> FEATURE:
<221> NAME/KEY: misc_feature
<222> LOCATION: (4)..(4)
<223> OTHER INFORMATION: /note="2'-F modified nucleotide"
<220> FEATURE:
<221> NAME/KEY: misc_feature
<222> LOCATION: (5)..(5)
<223> OTHER INFORMATION: /note="2'-F modified nucleotide"
<220> FEATURE:
<221> NAME/KEY: misc_feature
<222> LOCATION: (6)..(6)
<223> OTHER INFORMATION: /note="2'-OMe modified nucleotide"

<220> FEATURE:
<221> NAME/KEY: misc_feature
<222> LOCATION: (7)..(7)
<223> OTHER INFORMATION: /note="2'-F modified nucleotide"
<220> FEATURE:
<221> NAME/KEY: misc_feature
<222> LOCATION: (8)..(8)
<223> OTHER INFORMATION: /note="2'-OMe modified nucleotide"
<220> FEATURE:
<221> NAME/KEY: misc_feature
<222> LOCATION: (9)..(9)
<223> OTHER INFORMATION: /note="2'-OMe modified nucleotide"
<220> FEATURE:
<221> NAME/KEY: misc_feature
<222> LOCATION: (10)..(10)
<223> OTHER INFORMATION: /note="2'-F modified nucleotide"
<220> FEATURE:
<221> NAME/KEY: misc_feature
<222> LOCATION: (11)..(11)
<223> OTHER INFORMATION: /note="2'-OMe modified nucleotide"
<220> FEATURE:
<221> NAME/KEY: misc_feature
<222> LOCATION: (12)..(12)
<223> OTHER INFORMATION: /note="2'-OMe modified nucleotide"
<220> FEATURE:
<221> NAME/KEY: misc_feature
<222> LOCATION: (13)..(13)
<223> OTHER INFORMATION: /note="2'-OMe modified nucleotide"
<220> FEATURE:
<221> NAME/KEY: misc_feature
<222> LOCATION: (14)..(14)
<223> OTHER INFORMATION: /note="2'-F modified nucleotide"
<220> FEATURE:
<221> NAME/KEY: misc_feature
<222> LOCATION: (15)..(15)
<223> OTHER INFORMATION: /note="2'-OMe modified nucleotide"
<220> FEATURE:
<221> NAME/KEY: misc_feature
<222> LOCATION: (16)..(16)
<223> OTHER INFORMATION: /note="2'-OMe modified nucleotide"
<220> FEATURE:
<221> NAME/KEY: misc_feature
<222> LOCATION: (17)..(17)
<223> OTHER INFORMATION: /note="2'-OMe modified nucleotide"
<220> FEATURE:
<221> NAME/KEY: misc_feature
<222> LOCATION: (18)..(18)
<223> OTHER INFORMATION: /note="2'-OMe modified nucleotide"
<220> FEATURE:
<221> NAME/KEY: misc_feature
<222> LOCATION: (19)..(19)
<223> OTHER INFORMATION: /note="2'-OMe modified nucleotide"
<220> FEATURE:
<221> NAME/KEY: misc_feature
<222> LOCATION: (20)..(20)
<223> OTHER INFORMATION: /note="2'-OMe modified nucleotide with a
3'-phosphorothioate linkage"
<220> FEATURE:
<221> NAME/KEY: misc_feature
<222> LOCATION: (21)..(21)
<223> OTHER INFORMATION: /note="2'-OMe modified nucleotide with a
3'-phosphorothioate linkage"
<220> FEATURE:
<221> NAME/KEY: misc_feature
<222> LOCATION: (22)..(22)
<223> OTHER INFORMATION: /note="2'-OMe modified nucleotide"

<400> SEQUENCE: 203
uuauuaucuu guuuuucuac gg 22

<210> SEQ ID NO 204
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence:

Synthetic oligonucleotide"
<220> FEATURE:
<221> NAME/KEY: misc_feature
<222> LOCATION: (1)..(1)
<223> OTHER INFORMATION: /note="2'-OMe modified nucleotide with a 3'-phosphorothioate linkage"
<220> FEATURE:
<221> NAME/KEY: misc_feature
<222> LOCATION: (2)..(2)
<223> OTHER INFORMATION: /note="2'-OMe modified nucleotide"
<220> FEATURE:
<221> NAME/KEY: misc_feature
<222> LOCATION: (3)..(3)
<223> OTHER INFORMATION: /note="2'-OMe modified nucleotide"
<220> FEATURE:
<221> NAME/KEY: misc_feature
<222> LOCATION: (4)..(4)
<223> OTHER INFORMATION: /note="2'-OMe modified nucleotide"
<220> FEATURE:
<221> NAME/KEY: misc_feature
<222> LOCATION: (5)..(5)
<223> OTHER INFORMATION: /note="2'-OMe modified nucleotide"
<220> FEATURE:
<221> NAME/KEY: misc_feature
<222> LOCATION: (6)..(6)
<223> OTHER INFORMATION: /note="2'-OMe modified nucleotide"
<220> FEATURE:
<221> NAME/KEY: misc_feature
<222> LOCATION: (7)..(7)
<223> OTHER INFORMATION: /note="2'-OMe modified nucleotide"
<220> FEATURE:
<221> NAME/KEY: misc_feature
<222> LOCATION: (8)..(8)
<223> OTHER INFORMATION: /note="2'-F modified nucleotide"
<220> FEATURE:
<221> NAME/KEY: misc_feature
<222> LOCATION: (9)..(9)
<223> OTHER INFORMATION: /note="2'-F modified nucleotide"
<220> FEATURE:
<221> NAME/KEY: misc_feature
<222> LOCATION: (10)..(10)
<223> OTHER INFORMATION: /note="2'-F modified nucleotide"
<220> FEATURE:
<221> NAME/KEY: misc_feature
<222> LOCATION: (11)..(11)
<223> OTHER INFORMATION: /note="2'-F modified nucleotide"
<220> FEATURE:
<221> NAME/KEY: misc_feature
<222> LOCATION: (12)..(12)
<223> OTHER INFORMATION: /note="2'-OMe modified nucleotide"
<220> FEATURE:
<221> NAME/KEY: misc_feature
<222> LOCATION: (13)..(13)
<223> OTHER INFORMATION: /note="2'-OMe modified nucleotide"
<220> FEATURE:
<221> NAME/KEY: misc_feature
<222> LOCATION: (14)..(14)
<223> OTHER INFORMATION: /note="2'-OMe modified nucleotide"
<220> FEATURE:
<221> NAME/KEY: misc_feature
<222> LOCATION: (15)..(15)
<223> OTHER INFORMATION: /note="2'-OMe modified nucleotide"
<220> FEATURE:
<221> NAME/KEY: misc_feature
<222> LOCATION: (16)..(16)
<223> OTHER INFORMATION: /note="2'-OMe modified nucleotide"
<220> FEATURE:
<221> NAME/KEY: misc_feature
<222> LOCATION: (17)..(17)
<223> OTHER INFORMATION: /note="2'-OMe modified nucleotide"
<220> FEATURE:
<221> NAME/KEY: misc_feature
<222> LOCATION: (18)..(18)
<223> OTHER INFORMATION: /note="2'-OMe modified nucleotide"
<220> FEATURE:
<221> NAME/KEY: misc_feature
<222> LOCATION: (19)..(19)
<223> OTHER INFORMATION: /note="2'-OMe modified nucleotide"
<220> FEATURE:

<221> NAME/KEY: misc_feature
<222> LOCATION: (20)..(20)
<223> OTHER INFORMATION: /note="2'-OMe modified nucleotide"
<220> FEATURE:
<221> NAME/KEY: misc_feature
<222> LOCATION: (21)..(21)
<223> OTHER INFORMATION: /note="2'-OMe modified nucleotide"
<220> FEATURE:
<221> NAME/KEY: misc_feature
<222> LOCATION: (22)..(22)
<223> OTHER INFORMATION: /note="2'-OMe modified nucleotide"
<220> FEATURE:
<221> NAME/KEY: misc_feature
<222> LOCATION: (23)..(23)
<223> OTHER INFORMATION: /note="2'-OMe modified nucleotide"
<220> FEATURE:
<221> NAME/KEY: misc_feature
<222> LOCATION: (24)..(24)
<223> OTHER INFORMATION: /note="2'-OMe modified nucleotide"
<220> FEATURE:
<221> NAME/KEY: misc_feature
<222> LOCATION: (25)..(25)
<223> OTHER INFORMATION: /note="2'-OMe modified nucleotide"
<220> FEATURE:
<221> NAME/KEY: misc_feature
<222> LOCATION: (26)..(26)
<223> OTHER INFORMATION: /note="2'-OMe modified nucleotide"
<220> FEATURE:
<221> NAME/KEY: misc_feature
<222> LOCATION: (27)..(27)
<223> OTHER INFORMATION: /note="2'-OMe modified nucleotide"
<220> FEATURE:
<221> NAME/KEY: misc_feature
<222> LOCATION: (28)..(28)
<223> OTHER INFORMATION: /note="ademA-GalNAc"
<220> FEATURE:
<221> NAME/KEY: misc_feature
<222> LOCATION: (29)..(29)
<223> OTHER INFORMATION: /note="ademA-GalNAc"
<220> FEATURE:
<221> NAME/KEY: misc_feature
<222> LOCATION: (30)..(30)
<223> OTHER INFORMATION: /note="ademA-GalNAc"
<220> FEATURE:
<221> NAME/KEY: misc_feature
<222> LOCATION: (31)..(31)
<223> OTHER INFORMATION: /note="2'-OMe modified nucleotide"
<220> FEATURE:
<221> NAME/KEY: misc_feature
<222> LOCATION: (32)..(32)
<223> OTHER INFORMATION: /note="2'-OMe modified nucleotide"
<220> FEATURE:
<221> NAME/KEY: misc_feature
<222> LOCATION: (33)..(33)
<223> OTHER INFORMATION: /note="2'-OMe modified nucleotide"
<220> FEATURE:
<221> NAME/KEY: misc_feature
<222> LOCATION: (34)..(34)
<223> OTHER INFORMATION: /note="2'-OMe modified nucleotide"
<220> FEATURE:
<221> NAME/KEY: misc_feature
<222> LOCATION: (35)..(35)
<223> OTHER INFORMATION: /note="2'-OMe modified nucleotide"
<220> FEATURE:
<221> NAME/KEY: misc_feature
<222> LOCATION: (36)..(36)
<223> OTHER INFORMATION: /note="2'-OMe modified nucleotide"

<400> SEQUENCE: 204
uagaaaaaca agauaauaga gcagccgaaa ggcugc 36

<210> SEQ ID NO 205
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: misc_feature
<222> LOCATION: (1)..(1)
<223> OTHER INFORMATION: /note="MePhosphonate-4O-mUs"
<220> FEATURE:
<221> NAME/KEY: misc_feature
<222> LOCATION: (2)..(2)
<223> OTHER INFORMATION: /note="2'-F modified nucleotide with a
      3'-phosphorothioate linkage"
<220> FEATURE:
<221> NAME/KEY: misc_feature
<222> LOCATION: (3)..(3)
<223> OTHER INFORMATION: /note="2'-F modified nucleotide with a
      3'-phosphorothioate linkage"
<220> FEATURE:
<221> NAME/KEY: misc_feature
<222> LOCATION: (4)..(4)
<223> OTHER INFORMATION: /note="2'-F modified nucleotide"
<220> FEATURE:
<221> NAME/KEY: misc_feature
<222> LOCATION: (5)..(5)
<223> OTHER INFORMATION: /note="2'-F modified nucleotide"
<220> FEATURE:
<221> NAME/KEY: misc_feature
<222> LOCATION: (6)..(6)
<223> OTHER INFORMATION: /note="2'-OMe modified nucleotide"
<220> FEATURE:
<221> NAME/KEY: misc_feature
<222> LOCATION: (7)..(7)
<223> OTHER INFORMATION: /note="2'-F modified nucleotide"
<220> FEATURE:
<221> NAME/KEY: misc_feature
<222> LOCATION: (8)..(8)
<223> OTHER INFORMATION: /note="2'-OMe modified nucleotide"
<220> FEATURE:
<221> NAME/KEY: misc_feature
<222> LOCATION: (9)..(9)
<223> OTHER INFORMATION: /note="2'-OMe modified nucleotide"
<220> FEATURE:
<221> NAME/KEY: misc_feature
<222> LOCATION: (10)..(10)
<223> OTHER INFORMATION: /note="2'-F modified nucleotide"
<220> FEATURE:
<221> NAME/KEY: misc_feature
<222> LOCATION: (11)..(11)
<223> OTHER INFORMATION: /note="2'-OMe modified nucleotide"
<220> FEATURE:
<221> NAME/KEY: misc_feature
<222> LOCATION: (12)..(12)
<223> OTHER INFORMATION: /note="2'-OMe modified nucleotide"
<220> FEATURE:
<221> NAME/KEY: misc_feature
<222> LOCATION: (13)..(13)
<223> OTHER INFORMATION: /note="2'-OMe modified nucleotide"
<220> FEATURE:
<221> NAME/KEY: misc_feature
<222> LOCATION: (14)..(14)
<223> OTHER INFORMATION: /note="2'-F modified nucleotide"
<220> FEATURE:
<221> NAME/KEY: misc_feature
<222> LOCATION: (15)..(15)
<223> OTHER INFORMATION: /note="2'-OMe modified nucleotide"
<220> FEATURE:
<221> NAME/KEY: misc_feature
<222> LOCATION: (16)..(16)
<223> OTHER INFORMATION: /note="2'-OMe modified nucleotide"
<220> FEATURE:
<221> NAME/KEY: misc_feature
<222> LOCATION: (17)..(17)
<223> OTHER INFORMATION: /note="2'-OMe modified nucleotide"
<220> FEATURE:
<221> NAME/KEY: misc_feature
<222> LOCATION: (18)..(18)
<223> OTHER INFORMATION: /note="2'-OMe modified nucleotide"
<220> FEATURE:
<221> NAME/KEY: misc_feature
<222> LOCATION: (19)..(19)

<223> OTHER INFORMATION: /note="2'-OMe modified nucleotide"
<220> FEATURE:
<221> NAME/KEY: misc_feature
<222> LOCATION: (20)..(20)
<223> OTHER INFORMATION: /note="2'-OMe modified nucleotide with a 3'-phosphorothioate linkage"
<220> FEATURE:
<221> NAME/KEY: misc_feature
<222> LOCATION: (21)..(21)
<223> OTHER INFORMATION: /note="2'-OMe modified nucleotide with a 3'-phosphorothioate linkage"
<220> FEATURE:
<221> NAME/KEY: misc_feature
<222> LOCATION: (22)..(22)
<223> OTHER INFORMATION: /note="2'-OMe modified nucleotide"

<400> SEQUENCE: 205
ucuauuaucu uguuuuucua gg 22

<210> SEQ ID NO 206
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: misc_feature
<222> LOCATION: (1)..(1)
<223> OTHER INFORMATION: /note="2'-OMe modified nucleotide with a 3'-phosphorothioate linkage"
<220> FEATURE:
<221> NAME/KEY: misc_feature
<222> LOCATION: (2)..(2)
<223> OTHER INFORMATION: /note="2'-OMe modified nucleotide"
<220> FEATURE:
<221> NAME/KEY: misc_feature
<222> LOCATION: (3)..(3)
<223> OTHER INFORMATION: /note="2'-OMe modified nucleotide"
<220> FEATURE:
<221> NAME/KEY: misc_feature
<222> LOCATION: (4)..(4)
<223> OTHER INFORMATION: /note="2'-OMe modified nucleotide"
<220> FEATURE:
<221> NAME/KEY: misc_feature
<222> LOCATION: (5)..(5)
<223> OTHER INFORMATION: /note="2'-OMe modified nucleotide"
<220> FEATURE:
<221> NAME/KEY: misc_feature
<222> LOCATION: (6)..(6)
<223> OTHER INFORMATION: /note="2'-OMe modified nucleotide"
<220> FEATURE:
<221> NAME/KEY: misc_feature
<222> LOCATION: (7)..(7)
<223> OTHER INFORMATION: /note="2'-OMe modified nucleotide"
<220> FEATURE:
<221> NAME/KEY: misc_feature
<222> LOCATION: (8)..(8)
<223> OTHER INFORMATION: /note="2'-F modified nucleotide"
<220> FEATURE:
<221> NAME/KEY: misc_feature
<222> LOCATION: (9)..(9)
<223> OTHER INFORMATION: /note="2'-F modified nucleotide"
<220> FEATURE:
<221> NAME/KEY: misc_feature
<222> LOCATION: (10)..(10)
<223> OTHER INFORMATION: /note="2'-F modified nucleotide"
<220> FEATURE:
<221> NAME/KEY: misc_feature
<222> LOCATION: (11)..(11)
<223> OTHER INFORMATION: /note="2'-F modified nucleotide"
<220> FEATURE:
<221> NAME/KEY: misc_feature
<222> LOCATION: (12)..(12)
<223> OTHER INFORMATION: /note="2'-OMe modified nucleotide"
<220> FEATURE:

<221> NAME/KEY: misc_feature
<222> LOCATION: (13)..(13)
<223> OTHER INFORMATION: /note="2'-OMe modified nucleotide"
<220> FEATURE:
<221> NAME/KEY: misc_feature
<222> LOCATION: (14)..(14)
<223> OTHER INFORMATION: /note="2'-OMe modified nucleotide"
<220> FEATURE:
<221> NAME/KEY: misc_feature
<222> LOCATION: (15)..(15)
<223> OTHER INFORMATION: /note="2'-OMe modified nucleotide"
<220> FEATURE:
<221> NAME/KEY: misc_feature
<222> LOCATION: (16)..(16)
<223> OTHER INFORMATION: /note="2'-OMe modified nucleotide"
<220> FEATURE:
<221> NAME/KEY: misc_feature
<222> LOCATION: (17)..(17)
<223> OTHER INFORMATION: /note="2'-OMe modified nucleotide"
<220> FEATURE:
<221> NAME/KEY: misc_feature
<222> LOCATION: (18)..(18)
<223> OTHER INFORMATION: /note="2'-OMe modified nucleotide"
<220> FEATURE:
<221> NAME/KEY: misc_feature
<222> LOCATION: (19)..(19)
<223> OTHER INFORMATION: /note="2'-OMe modified nucleotide"
<220> FEATURE:
<221> NAME/KEY: misc_feature
<222> LOCATION: (20)..(20)
<223> OTHER INFORMATION: /note="2'-OMe modified nucleotide"
<220> FEATURE:
<221> NAME/KEY: misc_feature
<222> LOCATION: (21)..(21)
<223> OTHER INFORMATION: /note="2'-OMe modified nucleotide"
<220> FEATURE:
<221> NAME/KEY: misc_feature
<222> LOCATION: (22)..(22)
<223> OTHER INFORMATION: /note="2'-OMe modified nucleotide"
<220> FEATURE:
<221> NAME/KEY: misc_feature
<222> LOCATION: (23)..(23)
<223> OTHER INFORMATION: /note="2'-OMe modified nucleotide"
<220> FEATURE:
<221> NAME/KEY: misc_feature
<222> LOCATION: (24)..(24)
<223> OTHER INFORMATION: /note="2'-OMe modified nucleotide"
<220> FEATURE:
<221> NAME/KEY: misc_feature
<222> LOCATION: (25)..(25)
<223> OTHER INFORMATION: /note="2'-OMe modified nucleotide"
<220> FEATURE:
<221> NAME/KEY: misc_feature
<222> LOCATION: (26)..(26)
<223> OTHER INFORMATION: /note="2'-OMe modified nucleotide"
<220> FEATURE:
<221> NAME/KEY: misc_feature
<222> LOCATION: (27)..(27)
<223> OTHER INFORMATION: /note="2'-OMe modified nucleotide"
<220> FEATURE:
<221> NAME/KEY: misc_feature
<222> LOCATION: (28)..(28)
<223> OTHER INFORMATION: /note="ademA-GalNAc"
<220> FEATURE:
<221> NAME/KEY: misc_feature
<222> LOCATION: (29)..(29)
<223> OTHER INFORMATION: /note="ademA-GalNAc"
<220> FEATURE:
<221> NAME/KEY: misc_feature
<222> LOCATION: (30)..(30)
<223> OTHER INFORMATION: /note="ademA-GalNAc"
<220> FEATURE:
<221> NAME/KEY: misc_feature
<222> LOCATION: (31)..(31)
<223> OTHER INFORMATION: /note="2'-OMe modified nucleotide"
<220> FEATURE:
<221> NAME/KEY: misc_feature
<222> LOCATION: (32)..(32)
<223> OTHER INFORMATION: /note="2'-OMe modified nucleotide"

<220> FEATURE:
<221> NAME/KEY: misc_feature
<222> LOCATION: (33)..(33)
<223> OTHER INFORMATION: /note="2'-OMe modified nucleotide"
<220> FEATURE:
<221> NAME/KEY: misc_feature
<222> LOCATION: (34)..(34)
<223> OTHER INFORMATION: /note="2'-OMe modified nucleotide"
<220> FEATURE:
<221> NAME/KEY: misc_feature
<222> LOCATION: (35)..(35)
<223> OTHER INFORMATION: /note="2'-OMe modified nucleotide"
<220> FEATURE:
<221> NAME/KEY: misc_feature
<222> LOCATION: (36)..(36)
<223> OTHER INFORMATION: /note="2'-OMe modified nucleotide"

<400> SEQUENCE: 206
agaaaaacaa gauaauagca gcagccgaaa ggcugc 36

<210> SEQ ID NO 207
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: misc_feature
<222> LOCATION: (1)..(1)
<223> OTHER INFORMATION: /note="MePhosphonate-4O-mUs"
<220> FEATURE:
<221> NAME/KEY: misc_feature
<222> LOCATION: (2)..(2)
<223> OTHER INFORMATION: /note="2'-F modified nucleotide with a
3'-phosphorothioate linkage"
<220> FEATURE:
<221> NAME/KEY: misc_feature
<222> LOCATION: (3)..(3)
<223> OTHER INFORMATION: /note="2'-F modified nucleotide with a
3'-phosphorothioate linkage"
<220> FEATURE:
<221> NAME/KEY: misc_feature
<222> LOCATION: (4)..(4)
<223> OTHER INFORMATION: /note="2'-F modified nucleotide"
<220> FEATURE:
<221> NAME/KEY: misc_feature
<222> LOCATION: (5)..(5)
<223> OTHER INFORMATION: /note="2'-F modified nucleotide"
<220> FEATURE:
<221> NAME/KEY: misc_feature
<222> LOCATION: (6)..(6)
<223> OTHER INFORMATION: /note="2'-OMe modified nucleotide"
<220> FEATURE:
<221> NAME/KEY: misc_feature
<222> LOCATION: (7)..(7)
<223> OTHER INFORMATION: /note="2'-F modified nucleotide"
<220> FEATURE:
<221> NAME/KEY: misc_feature
<222> LOCATION: (8)..(8)
<223> OTHER INFORMATION: /note="2'-OMe modified nucleotide"
<220> FEATURE:
<221> NAME/KEY: misc_feature
<222> LOCATION: (9)..(9)
<223> OTHER INFORMATION: /note="2'-OMe modified nucleotide"
<220> FEATURE:
<221> NAME/KEY: misc_feature
<222> LOCATION: (10)..(10)
<223> OTHER INFORMATION: /note="2'-F modified nucleotide"
<220> FEATURE:
<221> NAME/KEY: misc_feature
<222> LOCATION: (11)..(11)
<223> OTHER INFORMATION: /note="2'-OMe modified nucleotide"
<220> FEATURE:
<221> NAME/KEY: misc_feature
<222> LOCATION: (12)..(12)

<223> OTHER INFORMATION: /note="2'-OMe modified nucleotide"
<220> FEATURE:
<221> NAME/KEY: misc_feature
<222> LOCATION: (13)..(13)
<223> OTHER INFORMATION: /note="2'-OMe modified nucleotide"
<220> FEATURE:
<221> NAME/KEY: misc_feature
<222> LOCATION: (14)..(14)
<223> OTHER INFORMATION: /note="2'-F modified nucleotide"
<220> FEATURE:
<221> NAME/KEY: misc_feature
<222> LOCATION: (15)..(15)
<223> OTHER INFORMATION: /note="2'-OMe modified nucleotide"
<220> FEATURE:
<221> NAME/KEY: misc_feature
<222> LOCATION: (16)..(16)
<223> OTHER INFORMATION: /note="2'-OMe modified nucleotide"
<220> FEATURE:
<221> NAME/KEY: misc_feature
<222> LOCATION: (17)..(17)
<223> OTHER INFORMATION: /note="2'-OMe modified nucleotide"
<220> FEATURE:
<221> NAME/KEY: misc_feature
<222> LOCATION: (18)..(18)
<223> OTHER INFORMATION: /note="2'-OMe modified nucleotide"
<220> FEATURE:
<221> NAME/KEY: misc_feature
<222> LOCATION: (19)..(19)
<223> OTHER INFORMATION: /note="2'-OMe modified nucleotide"
<220> FEATURE:
<221> NAME/KEY: misc_feature
<222> LOCATION: (20)..(20)
<223> OTHER INFORMATION: /note="2'-OMe modified nucleotide with a
3'-phosphorothioate linkage"
<220> FEATURE:
<221> NAME/KEY: misc_feature
<222> LOCATION: (21)..(21)
<223> OTHER INFORMATION: /note="2'-OMe modified nucleotide with a
3'-phosphorothioate linkage"
<220> FEATURE:
<221> NAME/KEY: misc_feature
<222> LOCATION: (22)..(22)
<223> OTHER INFORMATION: /note="2'-OMe modified nucleotide"

<400> SEQUENCE: 207
ugcuauuauc uuguuuuucu gg 22

<210> SEQ ID NO 208
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: misc_feature
<222> LOCATION: (1)..(1)
<223> OTHER INFORMATION: /note="2'-OMe modified nucleotide with a
3'-phosphorothioate linkage"
<220> FEATURE:
<221> NAME/KEY: misc_feature
<222> LOCATION: (2)..(2)
<223> OTHER INFORMATION: /note="2'-OMe modified nucleotide"
<220> FEATURE:
<221> NAME/KEY: misc_feature
<222> LOCATION: (3)..(3)
<223> OTHER INFORMATION: /note="2'-OMe modified nucleotide"
<220> FEATURE:
<221> NAME/KEY: misc_feature
<222> LOCATION: (4)..(4)
<223> OTHER INFORMATION: /note="2'-OMe modified nucleotide"
<220> FEATURE:
<221> NAME/KEY: misc_feature
<222> LOCATION: (5)..(5)
<223> OTHER INFORMATION: /note="2'-OMe modified nucleotide"
<220> FEATURE:

<221> NAME/KEY: misc_feature
<222> LOCATION: (6)..(6)
<223> OTHER INFORMATION: /note="2'-OMe modified nucleotide"
<220> FEATURE:
<221> NAME/KEY: misc_feature
<222> LOCATION: (7)..(7)
<223> OTHER INFORMATION: /note="2'-OMe modified nucleotide"
<220> FEATURE:
<221> NAME/KEY: misc_feature
<222> LOCATION: (8)..(8)
<223> OTHER INFORMATION: /note="2'-F modified nucleotide"
<220> FEATURE:
<221> NAME/KEY: misc_feature
<222> LOCATION: (9)..(9)
<223> OTHER INFORMATION: /note="2'-F modified nucleotide"
<220> FEATURE:
<221> NAME/KEY: misc_feature
<222> LOCATION: (10)..(10)
<223> OTHER INFORMATION: /note="2'-F modified nucleotide"
<220> FEATURE:
<221> NAME/KEY: misc_feature
<222> LOCATION: (11)..(11)
<223> OTHER INFORMATION: /note="2'-F modified nucleotide"
<220> FEATURE:
<221> NAME/KEY: misc_feature
<222> LOCATION: (12)..(12)
<223> OTHER INFORMATION: /note="2'-OMe modified nucleotide"
<220> FEATURE:
<221> NAME/KEY: misc_feature
<222> LOCATION: (13)..(13)
<223> OTHER INFORMATION: /note="2'-OMe modified nucleotide"
<220> FEATURE:
<221> NAME/KEY: misc_feature
<222> LOCATION: (14)..(14)
<223> OTHER INFORMATION: /note="2'-OMe modified nucleotide"
<220> FEATURE:
<221> NAME/KEY: misc_feature
<222> LOCATION: (15)..(15)
<223> OTHER INFORMATION: /note="2'-OMe modified nucleotide"
<220> FEATURE:
<221> NAME/KEY: misc_feature
<222> LOCATION: (16)..(16)
<223> OTHER INFORMATION: /note="2'-OMe modified nucleotide"
<220> FEATURE:
<221> NAME/KEY: misc_feature
<222> LOCATION: (17)..(17)
<223> OTHER INFORMATION: /note="2'-OMe modified nucleotide"
<220> FEATURE:
<221> NAME/KEY: misc_feature
<222> LOCATION: (18)..(18)
<223> OTHER INFORMATION: /note="2'-OMe modified nucleotide"
<220> FEATURE:
<221> NAME/KEY: misc_feature
<222> LOCATION: (19)..(19)
<223> OTHER INFORMATION: /note="2'-OMe modified nucleotide"
<220> FEATURE:
<221> NAME/KEY: misc_feature
<222> LOCATION: (20)..(20)
<223> OTHER INFORMATION: /note="2'-OMe modified nucleotide"
<220> FEATURE:
<221> NAME/KEY: misc_feature
<222> LOCATION: (21)..(21)
<223> OTHER INFORMATION: /note="2'-OMe modified nucleotide"
<220> FEATURE:
<221> NAME/KEY: misc_feature
<222> LOCATION: (22)..(22)
<223> OTHER INFORMATION: /note="2'-OMe modified nucleotide"
<220> FEATURE:
<221> NAME/KEY: misc_feature
<222> LOCATION: (23)..(23)
<223> OTHER INFORMATION: /note="2'-OMe modified nucleotide"
<220> FEATURE:
<221> NAME/KEY: misc_feature
<222> LOCATION: (24)..(24)
<223> OTHER INFORMATION: /note="2'-OMe modified nucleotide"
<220> FEATURE:
<221> NAME/KEY: misc_feature
<222> LOCATION: (25)..(25)
<223> OTHER INFORMATION: /note="2'-OMe modified nucleotide"

<220> FEATURE:
<221> NAME/KEY: misc_feature
<222> LOCATION: (26)..(26)
<223> OTHER INFORMATION: /note="2'-OMe modified nucleotide"
<220> FEATURE:
<221> NAME/KEY: misc_feature
<222> LOCATION: (27)..(27)
<223> OTHER INFORMATION: /note="2'-OMe modified nucleotide"
<220> FEATURE:
<221> NAME/KEY: misc_feature
<222> LOCATION: (28)..(28)
<223> OTHER INFORMATION: /note="ademA-GalNAc"
<220> FEATURE:
<221> NAME/KEY: misc_feature
<222> LOCATION: (29)..(29)
<223> OTHER INFORMATION: /note="ademA-GalNAc"
<220> FEATURE:
<221> NAME/KEY: misc_feature
<222> LOCATION: (30)..(30)
<223> OTHER INFORMATION: /note="ademA-GalNAc"
<220> FEATURE:
<221> NAME/KEY: misc_feature
<222> LOCATION: (31)..(31)
<223> OTHER INFORMATION: /note="2'-OMe modified nucleotide"
<220> FEATURE:
<221> NAME/KEY: misc_feature
<222> LOCATION: (32)..(32)
<223> OTHER INFORMATION: /note="2'-OMe modified nucleotide"
<220> FEATURE:
<221> NAME/KEY: misc_feature
<222> LOCATION: (33)..(33)
<223> OTHER INFORMATION: /note="2'-OMe modified nucleotide"
<220> FEATURE:
<221> NAME/KEY: misc_feature
<222> LOCATION: (34)..(34)
<223> OTHER INFORMATION: /note="2'-OMe modified nucleotide"
<220> FEATURE:
<221> NAME/KEY: misc_feature
<222> LOCATION: (35)..(35)
<223> OTHER INFORMATION: /note="2'-OMe modified nucleotide"
<220> FEATURE:
<221> NAME/KEY: misc_feature
<222> LOCATION: (36)..(36)
<223> OTHER INFORMATION: /note="2'-OMe modified nucleotide"

<400> SEQUENCE: 208
aaaaacaaga uaauagcaua gcagccgaaa ggcugc 36

<210> SEQ ID NO 209
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: misc_feature
<222> LOCATION: (1)..(1)
<223> OTHER INFORMATION: /note="MePhosphonate-4O-mUs"
<220> FEATURE:
<221> NAME/KEY: misc_feature
<222> LOCATION: (2)..(2)
<223> OTHER INFORMATION: /note="2'-F modified nucleotide with a
3'-phosphorothioate linkage"
<220> FEATURE:
<221> NAME/KEY: misc_feature
<222> LOCATION: (3)..(3)
<223> OTHER INFORMATION: /note="2'-F modified nucleotide with a
3'-phosphorothioate linkage"
<220> FEATURE:
<221> NAME/KEY: misc_feature
<222> LOCATION: (4)..(4)
<223> OTHER INFORMATION: /note="2'-F modified nucleotide"
<220> FEATURE:
<221> NAME/KEY: misc_feature
<222> LOCATION: (5)..(5)

<223> OTHER INFORMATION: /note="2'-F modified nucleotide"
<220> FEATURE:
<221> NAME/KEY: misc_feature
<222> LOCATION: (6)..(6)
<223> OTHER INFORMATION: /note="2'-OMe modified nucleotide"
<220> FEATURE:
<221> NAME/KEY: misc_feature
<222> LOCATION: (7)..(7)
<223> OTHER INFORMATION: /note="2'-F modified nucleotide"
<220> FEATURE:
<221> NAME/KEY: misc_feature
<222> LOCATION: (8)..(8)
<223> OTHER INFORMATION: /note="2'-OMe modified nucleotide"
<220> FEATURE:
<221> NAME/KEY: misc_feature
<222> LOCATION: (9)..(9)
<223> OTHER INFORMATION: /note="2'-OMe modified nucleotide"
<220> FEATURE:
<221> NAME/KEY: misc_feature
<222> LOCATION: (10)..(10)
<223> OTHER INFORMATION: /note="2'-F modified nucleotide"
<220> FEATURE:
<221> NAME/KEY: misc_feature
<222> LOCATION: (11)..(11)
<223> OTHER INFORMATION: /note="2'-OMe modified nucleotide"
<220> FEATURE:
<221> NAME/KEY: misc_feature
<222> LOCATION: (12)..(12)
<223> OTHER INFORMATION: /note="2'-OMe modified nucleotide"
<220> FEATURE:
<221> NAME/KEY: misc_feature
<222> LOCATION: (13)..(13)
<223> OTHER INFORMATION: /note="2'-OMe modified nucleotide"
<220> FEATURE:
<221> NAME/KEY: misc_feature
<222> LOCATION: (14)..(14)
<223> OTHER INFORMATION: /note="2'-F modified nucleotide"
<220> FEATURE:
<221> NAME/KEY: misc_feature
<222> LOCATION: (15)..(15)
<223> OTHER INFORMATION: /note="2'-OMe modified nucleotide"
<220> FEATURE:
<221> NAME/KEY: misc_feature
<222> LOCATION: (16)..(16)
<223> OTHER INFORMATION: /note="2'-OMe modified nucleotide"
<220> FEATURE:
<221> NAME/KEY: misc_feature
<222> LOCATION: (17)..(17)
<223> OTHER INFORMATION: /note="2'-OMe modified nucleotide"
<220> FEATURE:
<221> NAME/KEY: misc_feature
<222> LOCATION: (18)..(18)
<223> OTHER INFORMATION: /note="2'-OMe modified nucleotide"
<220> FEATURE:
<221> NAME/KEY: misc_feature
<222> LOCATION: (19)..(19)
<223> OTHER INFORMATION: /note="2'-OMe modified nucleotide"
<220> FEATURE:
<221> NAME/KEY: misc_feature
<222> LOCATION: (20)..(20)
<223> OTHER INFORMATION: /note="2'-OMe modified nucleotide with a 3'-phosphorothioate linkage"
<220> FEATURE:
<221> NAME/KEY: misc_feature
<222> LOCATION: (21)..(21)
<223> OTHER INFORMATION: /note="2'-OMe modified nucleotide with a 3'-phosphorothioate linkage"
<220> FEATURE:
<221> NAME/KEY: misc_feature
<222> LOCATION: (22)..(22)
<223> OTHER INFORMATION: /note="2'-OMe modified nucleotide"

<400> SEQUENCE: 209
uaugcuauua ucuuguuuuu gg 22

<210> SEQ ID NO 210
<211> LENGTH: 36

<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: misc_feature
<222> LOCATION: (1)..(1)
<223> OTHER INFORMATION: /note="2'-OMe modified nucleotide with a 3'-phosphorothioate linkage"
<220> FEATURE:
<221> NAME/KEY: misc_feature
<222> LOCATION: (2)..(2)
<223> OTHER INFORMATION: /note="2'-OMe modified nucleotide"
<220> FEATURE:
<221> NAME/KEY: misc_feature
<222> LOCATION: (3)..(3)
<223> OTHER INFORMATION: /note="2'-OMe modified nucleotide"
<220> FEATURE:
<221> NAME/KEY: misc_feature
<222> LOCATION: (4)..(4)
<223> OTHER INFORMATION: /note="2'-OMe modified nucleotide"
<220> FEATURE:
<221> NAME/KEY: misc_feature
<222> LOCATION: (5)..(5)
<223> OTHER INFORMATION: /note="2'-OMe modified nucleotide"
<220> FEATURE:
<221> NAME/KEY: misc_feature
<222> LOCATION: (6)..(6)
<223> OTHER INFORMATION: /note="2'-OMe modified nucleotide"
<220> FEATURE:
<221> NAME/KEY: misc_feature
<222> LOCATION: (7)..(7)
<223> OTHER INFORMATION: /note="2'-OMe modified nucleotide"
<220> FEATURE:
<221> NAME/KEY: misc_feature
<222> LOCATION: (8)..(8)
<223> OTHER INFORMATION: /note="2'-F modified nucleotide"
<220> FEATURE:
<221> NAME/KEY: misc_feature
<222> LOCATION: (9)..(9)
<223> OTHER INFORMATION: /note="2'-F modified nucleotide"
<220> FEATURE:
<221> NAME/KEY: misc_feature
<222> LOCATION: (10)..(10)
<223> OTHER INFORMATION: /note="2'-F modified nucleotide"
<220> FEATURE:
<221> NAME/KEY: misc_feature
<222> LOCATION: (11)..(11)
<223> OTHER INFORMATION: /note="2'-F modified nucleotide"
<220> FEATURE:
<221> NAME/KEY: misc_feature
<222> LOCATION: (12)..(12)
<223> OTHER INFORMATION: /note="2'-OMe modified nucleotide"
<220> FEATURE:
<221> NAME/KEY: misc_feature
<222> LOCATION: (13)..(13)
<223> OTHER INFORMATION: /note="2'-OMe modified nucleotide"
<220> FEATURE:
<221> NAME/KEY: misc_feature
<222> LOCATION: (14)..(14)
<223> OTHER INFORMATION: /note="2'-OMe modified nucleotide"
<220> FEATURE:
<221> NAME/KEY: misc_feature
<222> LOCATION: (15)..(15)
<223> OTHER INFORMATION: /note="2'-OMe modified nucleotide"
<220> FEATURE:
<221> NAME/KEY: misc_feature
<222> LOCATION: (16)..(16)
<223> OTHER INFORMATION: /note="2'-OMe modified nucleotide"
<220> FEATURE:
<221> NAME/KEY: misc_feature
<222> LOCATION: (17)..(17)
<223> OTHER INFORMATION: /note="2'-OMe modified nucleotide"
<220> FEATURE:
<221> NAME/KEY: misc_feature
<222> LOCATION: (18)..(18)
<223> OTHER INFORMATION: /note="2'-OMe modified nucleotide"

<220> FEATURE:
<221> NAME/KEY: misc_feature
<222> LOCATION: (19)..(19)
<223> OTHER INFORMATION: /note="2'-OMe modified nucleotide"
<220> FEATURE:
<221> NAME/KEY: misc_feature
<222> LOCATION: (20)..(20)
<223> OTHER INFORMATION: /note="2'-OMe modified nucleotide"
<220> FEATURE:
<221> NAME/KEY: misc_feature
<222> LOCATION: (21)..(21)
<223> OTHER INFORMATION: /note="2'-OMe modified nucleotide"
<220> FEATURE:
<221> NAME/KEY: misc_feature
<222> LOCATION: (22)..(22)
<223> OTHER INFORMATION: /note="2'-OMe modified nucleotide"
<220> FEATURE:
<221> NAME/KEY: misc_feature
<222> LOCATION: (23)..(23)
<223> OTHER INFORMATION: /note="2'-OMe modified nucleotide"
<220> FEATURE:
<221> NAME/KEY: misc_feature
<222> LOCATION: (24)..(24)
<223> OTHER INFORMATION: /note="2'-OMe modified nucleotide"
<220> FEATURE:
<221> NAME/KEY: misc_feature
<222> LOCATION: (25)..(25)
<223> OTHER INFORMATION: /note="2'-OMe modified nucleotide"
<220> FEATURE:
<221> NAME/KEY: misc_feature
<222> LOCATION: (26)..(26)
<223> OTHER INFORMATION: /note="2'-OMe modified nucleotide"
<220> FEATURE:
<221> NAME/KEY: misc_feature
<222> LOCATION: (27)..(27)
<223> OTHER INFORMATION: /note="2'-OMe modified nucleotide"
<220> FEATURE:
<221> NAME/KEY: misc_feature
<222> LOCATION: (28)..(28)
<223> OTHER INFORMATION: /note="ademA-GalNAc"
<220> FEATURE:
<221> NAME/KEY: misc_feature
<222> LOCATION: (29)..(29)
<223> OTHER INFORMATION: /note="ademA-GalNAc"
<220> FEATURE:
<221> NAME/KEY: misc_feature
<222> LOCATION: (30)..(30)
<223> OTHER INFORMATION: /note="ademA-GalNAc"
<220> FEATURE:
<221> NAME/KEY: misc_feature
<222> LOCATION: (31)..(31)
<223> OTHER INFORMATION: /note="2'-OMe modified nucleotide"
<220> FEATURE:
<221> NAME/KEY: misc_feature
<222> LOCATION: (32)..(32)
<223> OTHER INFORMATION: /note="2'-OMe modified nucleotide"
<220> FEATURE:
<221> NAME/KEY: misc_feature
<222> LOCATION: (33)..(33)
<223> OTHER INFORMATION: /note="2'-OMe modified nucleotide"
<220> FEATURE:
<221> NAME/KEY: misc_feature
<222> LOCATION: (34)..(34)
<223> OTHER INFORMATION: /note="2'-OMe modified nucleotide"
<220> FEATURE:
<221> NAME/KEY: misc_feature
<222> LOCATION: (35)..(35)
<223> OTHER INFORMATION: /note="2'-OMe modified nucleotide"
<220> FEATURE:
<221> NAME/KEY: misc_feature
<222> LOCATION: (36)..(36)
<223> OTHER INFORMATION: /note="2'-OMe modified nucleotide"

<400> SEQUENCE: 210
aacagcauag ucaaauaaaa gcagccgaaa ggcugc 36

<210> SEQ ID NO 211

<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: misc_feature
<222> LOCATION: (1)..(1)
<223> OTHER INFORMATION: /note="MePhosphonate-4O-mUs"
<220> FEATURE:
<221> NAME/KEY: misc_feature
<222> LOCATION: (2)..(2)
<223> OTHER INFORMATION: /note="2'-F modified nucleotide with a
3'-phosphorothioate linkage"
<220> FEATURE:
<221> NAME/KEY: misc_feature
<222> LOCATION: (3)..(3)
<223> OTHER INFORMATION: /note="2'-F modified nucleotide with a
3'-phosphorothioate linkage"
<220> FEATURE:
<221> NAME/KEY: misc_feature
<222> LOCATION: (4)..(4)
<223> OTHER INFORMATION: /note="2'-F modified nucleotide"
<220> FEATURE:
<221> NAME/KEY: misc_feature
<222> LOCATION: (5)..(5)
<223> OTHER INFORMATION: /note="2'-F modified nucleotide"
<220> FEATURE:
<221> NAME/KEY: misc_feature
<222> LOCATION: (6)..(6)
<223> OTHER INFORMATION: /note="2'-OMe modified nucleotide"
<220> FEATURE:
<221> NAME/KEY: misc_feature
<222> LOCATION: (7)..(7)
<223> OTHER INFORMATION: /note="2'-F modified nucleotide"
<220> FEATURE:
<221> NAME/KEY: misc_feature
<222> LOCATION: (8)..(8)
<223> OTHER INFORMATION: /note="2'-OMe modified nucleotide"
<220> FEATURE:
<221> NAME/KEY: misc_feature
<222> LOCATION: (9)..(9)
<223> OTHER INFORMATION: /note="2'-OMe modified nucleotide"
<220> FEATURE:
<221> NAME/KEY: misc_feature
<222> LOCATION: (10)..(10)
<223> OTHER INFORMATION: /note="2'-F modified nucleotide"
<220> FEATURE:
<221> NAME/KEY: misc_feature
<222> LOCATION: (11)..(11)
<223> OTHER INFORMATION: /note="2'-OMe modified nucleotide"
<220> FEATURE:
<221> NAME/KEY: misc_feature
<222> LOCATION: (12)..(12)
<223> OTHER INFORMATION: /note="2'-OMe modified nucleotide"
<220> FEATURE:
<221> NAME/KEY: misc_feature
<222> LOCATION: (13)..(13)
<223> OTHER INFORMATION: /note="2'-OMe modified nucleotide"
<220> FEATURE:
<221> NAME/KEY: misc_feature
<222> LOCATION: (14)..(14)
<223> OTHER INFORMATION: /note="2'-F modified nucleotide"
<220> FEATURE:
<221> NAME/KEY: misc_feature
<222> LOCATION: (15)..(15)
<223> OTHER INFORMATION: /note="2'-OMe modified nucleotide"
<220> FEATURE:
<221> NAME/KEY: misc_feature
<222> LOCATION: (16)..(16)
<223> OTHER INFORMATION: /note="2'-OMe modified nucleotide"
<220> FEATURE:
<221> NAME/KEY: misc_feature
<222> LOCATION: (17)..(17)
<223> OTHER INFORMATION: /note="2'-OMe modified nucleotide"
<220> FEATURE:
<221> NAME/KEY: misc_feature
<222> LOCATION: (18)..(18)
<223> OTHER INFORMATION: /note="2'-OMe modified nucleotide"
<220> FEATURE:
<221> NAME/KEY: misc_feature
<222> LOCATION: (19)..(19)
<223> OTHER INFORMATION: /note="2'-OMe modified nucleotide"
<220> FEATURE:
<221> NAME/KEY: misc_feature
<222> LOCATION: (20)..(20)
<223> OTHER INFORMATION: /note="2'-OMe modified nucleotide with a 3'-phosphorothioate linkage"
<220> FEATURE:
<221> NAME/KEY: misc_feature
<222> LOCATION: (21)..(21)
<223> OTHER INFORMATION: /note="2'-OMe modified nucleotide with a 3'-phosphorothioate linkage"
<220> FEATURE:
<221> NAME/KEY: misc_feature
<222> LOCATION: (22)..(22)
<223> OTHER INFORMATION: /note="2'-OMe modified nucleotide"

<400> SEQUENCE: 211
uuuuauuuga cuaugcuguu gg 22

<210> SEQ ID NO 212
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: misc_feature
<222> LOCATION: (1)..(1)
<223> OTHER INFORMATION: /note="2'-OMe modified nucleotide with a 3'-phosphorothioate linkage"
<220> FEATURE:
<221> NAME/KEY: misc_feature
<222> LOCATION: (2)..(2)
<223> OTHER INFORMATION: /note="2'-OMe modified nucleotide"
<220> FEATURE:
<221> NAME/KEY: misc_feature
<222> LOCATION: (3)..(3)
<223> OTHER INFORMATION: /note="2'-OMe modified nucleotide"
<220> FEATURE:
<221> NAME/KEY: misc_feature
<222> LOCATION: (4)..(4)
<223> OTHER INFORMATION: /note="2'-OMe modified nucleotide"
<220> FEATURE:
<221> NAME/KEY: misc_feature
<222> LOCATION: (5)..(5)
<223> OTHER INFORMATION: /note="2'-OMe modified nucleotide"
<220> FEATURE:
<221> NAME/KEY: misc_feature
<222> LOCATION: (6)..(6)
<223> OTHER INFORMATION: /note="2'-OMe modified nucleotide"
<220> FEATURE:
<221> NAME/KEY: misc_feature
<222> LOCATION: (7)..(7)
<223> OTHER INFORMATION: /note="2'-OMe modified nucleotide"
<220> FEATURE:
<221> NAME/KEY: misc_feature
<222> LOCATION: (8)..(8)
<223> OTHER INFORMATION: /note="2'-F modified nucleotide"
<220> FEATURE:
<221> NAME/KEY: misc_feature
<222> LOCATION: (9)..(9)
<223> OTHER INFORMATION: /note="2'-F modified nucleotide"
<220> FEATURE:
<221> NAME/KEY: misc_feature
<222> LOCATION: (10)..(10)
<223> OTHER INFORMATION: /note="2'-F modified nucleotide"
<220> FEATURE:
<221> NAME/KEY: misc_feature
<222> LOCATION: (11)..(11)
<223> OTHER INFORMATION: /note="2'-F modified nucleotide"

<220> FEATURE:
<221> NAME/KEY: misc_feature
<222> LOCATION: (12)..(12)
<223> OTHER INFORMATION: /note="2'-OMe modified nucleotide"
<220> FEATURE:
<221> NAME/KEY: misc_feature
<222> LOCATION: (13)..(13)
<223> OTHER INFORMATION: /note="2'-OMe modified nucleotide"
<220> FEATURE:
<221> NAME/KEY: misc_feature
<222> LOCATION: (14)..(14)
<223> OTHER INFORMATION: /note="2'-OMe modified nucleotide"
<220> FEATURE:
<221> NAME/KEY: misc_feature
<222> LOCATION: (15)..(15)
<223> OTHER INFORMATION: /note="2'-OMe modified nucleotide"
<220> FEATURE:
<221> NAME/KEY: misc_feature
<222> LOCATION: (16)..(16)
<223> OTHER INFORMATION: /note="2'-OMe modified nucleotide"
<220> FEATURE:
<221> NAME/KEY: misc_feature
<222> LOCATION: (17)..(17)
<223> OTHER INFORMATION: /note="2'-OMe modified nucleotide"
<220> FEATURE:
<221> NAME/KEY: misc_feature
<222> LOCATION: (18)..(18)
<223> OTHER INFORMATION: /note="2'-OMe modified nucleotide"
<220> FEATURE:
<221> NAME/KEY: misc_feature
<222> LOCATION: (19)..(19)
<223> OTHER INFORMATION: /note="2'-OMe modified nucleotide"
<220> FEATURE:
<221> NAME/KEY: misc_feature
<222> LOCATION: (20)..(20)
<223> OTHER INFORMATION: /note="2'-OMe modified nucleotide"
<220> FEATURE:
<221> NAME/KEY: misc_feature
<222> LOCATION: (21)..(21)
<223> OTHER INFORMATION: /note="2'-OMe modified nucleotide"
<220> FEATURE:
<221> NAME/KEY: misc_feature
<222> LOCATION: (22)..(22)
<223> OTHER INFORMATION: /note="2'-OMe modified nucleotide"
<220> FEATURE:
<221> NAME/KEY: misc_feature
<222> LOCATION: (23)..(23)
<223> OTHER INFORMATION: /note="2'-OMe modified nucleotide"
<220> FEATURE:
<221> NAME/KEY: misc_feature
<222> LOCATION: (24)..(24)
<223> OTHER INFORMATION: /note="2'-OMe modified nucleotide"
<220> FEATURE:
<221> NAME/KEY: misc_feature
<222> LOCATION: (25)..(25)
<223> OTHER INFORMATION: /note="2'-OMe modified nucleotide"
<220> FEATURE:
<221> NAME/KEY: misc_feature
<222> LOCATION: (26)..(26)
<223> OTHER INFORMATION: /note="2'-OMe modified nucleotide"
<220> FEATURE:
<221> NAME/KEY: misc_feature
<222> LOCATION: (27)..(27)
<223> OTHER INFORMATION: /note="2'-OMe modified nucleotide"
<220> FEATURE:
<221> NAME/KEY: misc_feature
<222> LOCATION: (28)..(28)
<223> OTHER INFORMATION: /note="ademA-GalNAc"
<220> FEATURE:
<221> NAME/KEY: misc_feature
<222> LOCATION: (29)..(29)
<223> OTHER INFORMATION: /note="ademA-GalNAc"
<220> FEATURE:
<221> NAME/KEY: misc_feature
<222> LOCATION: (30)..(30)
<223> OTHER INFORMATION: /note="ademA-GalNAc"
<220> FEATURE:
<221> NAME/KEY: misc_feature
<222> LOCATION: (31)..(31)

<223> OTHER INFORMATION: /note="2'-OMe modified nucleotide"
<220> FEATURE:
<221> NAME/KEY: misc_feature
<222> LOCATION: (32)..(32)
<223> OTHER INFORMATION: /note="2'-OMe modified nucleotide"
<220> FEATURE:
<221> NAME/KEY: misc_feature
<222> LOCATION: (33)..(33)
<223> OTHER INFORMATION: /note="2'-OMe modified nucleotide"
<220> FEATURE:
<221> NAME/KEY: misc_feature
<222> LOCATION: (34)..(34)
<223> OTHER INFORMATION: /note="2'-OMe modified nucleotide"
<220> FEATURE:
<221> NAME/KEY: misc_feature
<222> LOCATION: (35)..(35)
<223> OTHER INFORMATION: /note="2'-OMe modified nucleotide"
<220> FEATURE:
<221> NAME/KEY: misc_feature
<222> LOCATION: (36)..(36)
<223> OTHER INFORMATION: /note="2'-OMe modified nucleotide"

<400> SEQUENCE: 212
acagaaauuu cucuaucuua gcagccgaaa ggcugc 36

<210> SEQ ID NO 213
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: misc_feature
<222> LOCATION: (1)..(1)
<223> OTHER INFORMATION: /note="MePhosphonate-4O-mUs"
<220> FEATURE:
<221> NAME/KEY: misc_feature
<222> LOCATION: (2)..(2)
<223> OTHER INFORMATION: /note="2'-F modified nucleotide with a 3'-phosphorothioate linkage"
<220> FEATURE:
<221> NAME/KEY: misc_feature
<222> LOCATION: (3)..(3)
<223> OTHER INFORMATION: /note="2'-F modified nucleotide with a 3'-phosphorothioate linkage"
<220> FEATURE:
<221> NAME/KEY: misc_feature
<222> LOCATION: (4)..(4)
<223> OTHER INFORMATION: /note="2'-F modified nucleotide"
<220> FEATURE:
<221> NAME/KEY: misc_feature
<222> LOCATION: (5)..(5)
<223> OTHER INFORMATION: /note="2'-F modified nucleotide"
<220> FEATURE:
<221> NAME/KEY: misc_feature
<222> LOCATION: (6)..(6)
<223> OTHER INFORMATION: /note="2'-OMe modified nucleotide"
<220> FEATURE:
<221> NAME/KEY: misc_feature
<222> LOCATION: (7)..(7)
<223> OTHER INFORMATION: /note="2'-F modified nucleotide"
<220> FEATURE:
<221> NAME/KEY: misc_feature
<222> LOCATION: (8)..(8)
<223> OTHER INFORMATION: /note="2'-OMe modified nucleotide"
<220> FEATURE:
<221> NAME/KEY: misc_feature
<222> LOCATION: (9)..(9)
<223> OTHER INFORMATION: /note="2'-OMe modified nucleotide"
<220> FEATURE:
<221> NAME/KEY: misc_feature
<222> LOCATION: (10)..(10)
<223> OTHER INFORMATION: /note="2'-F modified nucleotide"
<220> FEATURE:
<221> NAME/KEY: misc_feature
<222> LOCATION: (11)..(11)
<223> OTHER INFORMATION: /note="2'-OMe modified nucleotide"
<220> FEATURE:
<221> NAME/KEY: misc_feature
<222> LOCATION: (12)..(12)
<223> OTHER INFORMATION: /note="2'-OMe modified nucleotide"
<220> FEATURE:
<221> NAME/KEY: misc_feature
<222> LOCATION: (13)..(13)
<223> OTHER INFORMATION: /note="2'-OMe modified nucleotide"
<220> FEATURE:
<221> NAME/KEY: misc_feature
<222> LOCATION: (14)..(14)
<223> OTHER INFORMATION: /note="2'-F modified nucleotide"
<220> FEATURE:
<221> NAME/KEY: misc_feature
<222> LOCATION: (15)..(15)
<223> OTHER INFORMATION: /note="2'-OMe modified nucleotide"
<220> FEATURE:
<221> NAME/KEY: misc_feature
<222> LOCATION: (16)..(16)
<223> OTHER INFORMATION: /note="2'-OMe modified nucleotide"
<220> FEATURE:
<221> NAME/KEY: misc_feature
<222> LOCATION: (17)..(17)
<223> OTHER INFORMATION: /note="2'-OMe modified nucleotide"
<220> FEATURE:
<221> NAME/KEY: misc_feature
<222> LOCATION: (18)..(18)
<223> OTHER INFORMATION: /note="2'-OMe modified nucleotide"
<220> FEATURE:
<221> NAME/KEY: misc_feature
<222> LOCATION: (19)..(19)
<223> OTHER INFORMATION: /note="2'-OMe modified nucleotide"
<220> FEATURE:
<221> NAME/KEY: misc_feature
<222> LOCATION: (20)..(20)
<223> OTHER INFORMATION: /note="2'-OMe modified nucleotide with a
3'-phosphorothioate linkage"
<220> FEATURE:
<221> NAME/KEY: misc_feature
<222> LOCATION: (21)..(21)
<223> OTHER INFORMATION: /note="2'-OMe modified nucleotide with a
3'-phosphorothioate linkage"
<220> FEATURE:
<221> NAME/KEY: misc_feature
<222> LOCATION: (22)..(22)
<223> OTHER INFORMATION: /note="2'-OMe modified nucleotide"

<400> SEQUENCE: 213
uaagauagag aaauuucugu gg 22

<210> SEQ ID NO 214
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: misc_feature
<222> LOCATION: (1)..(1)
<223> OTHER INFORMATION: /note="2'-OMe modified nucleotide with a
3'-phosphorothioate linkage"
<220> FEATURE:
<221> NAME/KEY: misc_feature
<222> LOCATION: (2)..(2)
<223> OTHER INFORMATION: /note="2'-OMe modified nucleotide"
<220> FEATURE:
<221> NAME/KEY: misc_feature
<222> LOCATION: (3)..(3)
<223> OTHER INFORMATION: /note="2'-OMe modified nucleotide"
<220> FEATURE:
<221> NAME/KEY: misc_feature
<222> LOCATION: (4)..(4)
<223> OTHER INFORMATION: /note="2'-OMe modified nucleotide"

<220> FEATURE:
<221> NAME/KEY: misc_feature
<222> LOCATION: (5)..(5)
<223> OTHER INFORMATION: /note="2'-OMe modified nucleotide"
<220> FEATURE:
<221> NAME/KEY: misc_feature
<222> LOCATION: (6)..(6)
<223> OTHER INFORMATION: /note="2'-OMe modified nucleotide"
<220> FEATURE:
<221> NAME/KEY: misc_feature
<222> LOCATION: (7)..(7)
<223> OTHER INFORMATION: /note="2'-OMe modified nucleotide"
<220> FEATURE:
<221> NAME/KEY: misc_feature
<222> LOCATION: (8)..(8)
<223> OTHER INFORMATION: /note="2'-F modified nucleotide"
<220> FEATURE:
<221> NAME/KEY: misc_feature
<222> LOCATION: (9)..(9)
<223> OTHER INFORMATION: /note="2'-F modified nucleotide"
<220> FEATURE:
<221> NAME/KEY: misc_feature
<222> LOCATION: (10)..(10)
<223> OTHER INFORMATION: /note="2'-F modified nucleotide"
<220> FEATURE:
<221> NAME/KEY: misc_feature
<222> LOCATION: (11)..(11)
<223> OTHER INFORMATION: /note="2'-F modified nucleotide"
<220> FEATURE:
<221> NAME/KEY: misc_feature
<222> LOCATION: (12)..(12)
<223> OTHER INFORMATION: /note="2'-OMe modified nucleotide"
<220> FEATURE:
<221> NAME/KEY: misc_feature
<222> LOCATION: (13)..(13)
<223> OTHER INFORMATION: /note="2'-OMe modified nucleotide"
<220> FEATURE:
<221> NAME/KEY: misc_feature
<222> LOCATION: (14)..(14)
<223> OTHER INFORMATION: /note="2'-OMe modified nucleotide"
<220> FEATURE:
<221> NAME/KEY: misc_feature
<222> LOCATION: (15)..(15)
<223> OTHER INFORMATION: /note="2'-OMe modified nucleotide"
<220> FEATURE:
<221> NAME/KEY: misc_feature
<222> LOCATION: (16)..(16)
<223> OTHER INFORMATION: /note="2'-OMe modified nucleotide"
<220> FEATURE:
<221> NAME/KEY: misc_feature
<222> LOCATION: (17)..(17)
<223> OTHER INFORMATION: /note="2'-OMe modified nucleotide"
<220> FEATURE:
<221> NAME/KEY: misc_feature
<222> LOCATION: (18)..(18)
<223> OTHER INFORMATION: /note="2'-OMe modified nucleotide"
<220> FEATURE:
<221> NAME/KEY: misc_feature
<222> LOCATION: (19)..(19)
<223> OTHER INFORMATION: /note="2'-OMe modified nucleotide"
<220> FEATURE:
<221> NAME/KEY: misc_feature
<222> LOCATION: (20)..(20)
<223> OTHER INFORMATION: /note="2'-OMe modified nucleotide"
<220> FEATURE:
<221> NAME/KEY: misc_feature
<222> LOCATION: (21)..(21)
<223> OTHER INFORMATION: /note="2'-OMe modified nucleotide"
<220> FEATURE:
<221> NAME/KEY: misc_feature
<222> LOCATION: (22)..(22)
<223> OTHER INFORMATION: /note="2'-OMe modified nucleotide"
<220> FEATURE:
<221> NAME/KEY: misc_feature
<222> LOCATION: (23)..(23)
<223> OTHER INFORMATION: /note="2'-OMe modified nucleotide"
<220> FEATURE:
<221> NAME/KEY: misc_feature
<222> LOCATION: (24)..(24)

<223> OTHER INFORMATION: /note="2'-OMe modified nucleotide"
<220> FEATURE:
<221> NAME/KEY: misc_feature
<222> LOCATION: (25)..(25)
<223> OTHER INFORMATION: /note="2'-OMe modified nucleotide"
<220> FEATURE:
<221> NAME/KEY: misc_feature
<222> LOCATION: (26)..(26)
<223> OTHER INFORMATION: /note="2'-OMe modified nucleotide"
<220> FEATURE:
<221> NAME/KEY: misc_feature
<222> LOCATION: (27)..(27)
<223> OTHER INFORMATION: /note="2'-OMe modified nucleotide"
<220> FEATURE:
<221> NAME/KEY: misc_feature
<222> LOCATION: (28)..(28)
<223> OTHER INFORMATION: /note="ademA-GalNAc"
<220> FEATURE:
<221> NAME/KEY: misc_feature
<222> LOCATION: (29)..(29)
<223> OTHER INFORMATION: /note="ademA-GalNAc"
<220> FEATURE:
<221> NAME/KEY: misc_feature
<222> LOCATION: (30)..(30)
<223> OTHER INFORMATION: /note="ademA-GalNAc"
<220> FEATURE:
<221> NAME/KEY: misc_feature
<222> LOCATION: (31)..(31)
<223> OTHER INFORMATION: /note="2'-OMe modified nucleotide"
<220> FEATURE:
<221> NAME/KEY: misc_feature
<222> LOCATION: (32)..(32)
<223> OTHER INFORMATION: /note="2'-OMe modified nucleotide"
<220> FEATURE:
<221> NAME/KEY: misc_feature
<222> LOCATION: (33)..(33)
<223> OTHER INFORMATION: /note="2'-OMe modified nucleotide"
<220> FEATURE:
<221> NAME/KEY: misc_feature
<222> LOCATION: (34)..(34)
<223> OTHER INFORMATION: /note="2'-OMe modified nucleotide"
<220> FEATURE:
<221> NAME/KEY: misc_feature
<222> LOCATION: (35)..(35)
<223> OTHER INFORMATION: /note="2'-OMe modified nucleotide"
<220> FEATURE:
<221> NAME/KEY: misc_feature
<222> LOCATION: (36)..(36)
<223> OTHER INFORMATION: /note="2'-OMe modified nucleotide"

<400> SEQUENCE: 214
ugaaugaaau aagaaaugua gcagccgaaa ggcugc 36

<210> SEQ ID NO 215
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: misc_feature
<222> LOCATION: (1)..(1)
<223> OTHER INFORMATION: /note="MePhosphonate-4O-mUs"
<220> FEATURE:
<221> NAME/KEY: misc_feature
<222> LOCATION: (2)..(2)
<223> OTHER INFORMATION: /note="2'-F modified nucleotide with a 3'-phosphorothioate linkage"
<220> FEATURE:
<221> NAME/KEY: misc_feature
<222> LOCATION: (3)..(3)
<223> OTHER INFORMATION: /note="2'-F modified nucleotide with a 3'-phosphorothioate linkage"
<220> FEATURE:
<221> NAME/KEY: misc_feature

```
<222> LOCATION: (4)..(4)
<223> OTHER INFORMATION: /note="2'-F modified nucleotide"
<220> FEATURE:
<221> NAME/KEY: misc_feature
<222> LOCATION: (5)..(5)
<223> OTHER INFORMATION: /note="2'-F modified nucleotide"
<220> FEATURE:
<221> NAME/KEY: misc_feature
<222> LOCATION: (6)..(6)
<223> OTHER INFORMATION: /note="2'-OMe modified nucleotide"
<220> FEATURE:
<221> NAME/KEY: misc_feature
<222> LOCATION: (7)..(7)
<223> OTHER INFORMATION: /note="2'-F modified nucleotide"
<220> FEATURE:
<221> NAME/KEY: misc_feature
<222> LOCATION: (8)..(8)
<223> OTHER INFORMATION: /note="2'-OMe modified nucleotide"
<220> FEATURE:
<221> NAME/KEY: misc_feature
<222> LOCATION: (9)..(9)
<223> OTHER INFORMATION: /note="2'-OMe modified nucleotide"
<220> FEATURE:
<221> NAME/KEY: misc_feature
<222> LOCATION: (10)..(10)
<223> OTHER INFORMATION: /note="2'-F modified nucleotide"
<220> FEATURE:
<221> NAME/KEY: misc_feature
<222> LOCATION: (11)..(11)
<223> OTHER INFORMATION: /note="2'-OMe modified nucleotide"
<220> FEATURE:
<221> NAME/KEY: misc_feature
<222> LOCATION: (12)..(12)
<223> OTHER INFORMATION: /note="2'-OMe modified nucleotide"
<220> FEATURE:
<221> NAME/KEY: misc_feature
<222> LOCATION: (13)..(13)
<223> OTHER INFORMATION: /note="2'-OMe modified nucleotide"
<220> FEATURE:
<221> NAME/KEY: misc_feature
<222> LOCATION: (14)..(14)
<223> OTHER INFORMATION: /note="2'-F modified nucleotide"
<220> FEATURE:
<221> NAME/KEY: misc_feature
<222> LOCATION: (15)..(15)
<223> OTHER INFORMATION: /note="2'-OMe modified nucleotide"
<220> FEATURE:
<221> NAME/KEY: misc_feature
<222> LOCATION: (16)..(16)
<223> OTHER INFORMATION: /note="2'-OMe modified nucleotide"
<220> FEATURE:
<221> NAME/KEY: misc_feature
<222> LOCATION: (17)..(17)
<223> OTHER INFORMATION: /note="2'-OMe modified nucleotide"
<220> FEATURE:
<221> NAME/KEY: misc_feature
<222> LOCATION: (18)..(18)
<223> OTHER INFORMATION: /note="2'-OMe modified nucleotide"
<220> FEATURE:
<221> NAME/KEY: misc_feature
<222> LOCATION: (19)..(19)
<223> OTHER INFORMATION: /note="2'-OMe modified nucleotide"
<220> FEATURE:
<221> NAME/KEY: misc_feature
<222> LOCATION: (20)..(20)
<223> OTHER INFORMATION: /note="2'-OMe modified nucleotide with a
      3'-phosphorothioate linkage"
<220> FEATURE:
<221> NAME/KEY: misc_feature
<222> LOCATION: (21)..(21)
<223> OTHER INFORMATION: /note="2'-OMe modified nucleotide with a
      3'-phosphorothioate linkage"
<220> FEATURE:
<221> NAME/KEY: misc_feature
<222> LOCATION: (22)..(22)
<223> OTHER INFORMATION: /note="2'-OMe modified nucleotide"

<400> SEQUENCE: 215
```

uacauuucuu auuucauuca gg 22

<210> SEQ ID NO 216
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: misc_feature
<222> LOCATION: (1)..(1)
<223> OTHER INFORMATION: /note="2'-OMe modified nucleotide with a 3'-phosphorothioate linkage"
<220> FEATURE:
<221> NAME/KEY: misc_feature
<222> LOCATION: (2)..(2)
<223> OTHER INFORMATION: /note="2'-OMe modified nucleotide"
<220> FEATURE:
<221> NAME/KEY: misc_feature
<222> LOCATION: (3)..(3)
<223> OTHER INFORMATION: /note="2'-OMe modified nucleotide"
<220> FEATURE:
<221> NAME/KEY: misc_feature
<222> LOCATION: (4)..(4)
<223> OTHER INFORMATION: /note="2'-OMe modified nucleotide"
<220> FEATURE:
<221> NAME/KEY: misc_feature
<222> LOCATION: (5)..(5)
<223> OTHER INFORMATION: /note="2'-OMe modified nucleotide"
<220> FEATURE:
<221> NAME/KEY: misc_feature
<222> LOCATION: (6)..(6)
<223> OTHER INFORMATION: /note="2'-OMe modified nucleotide"
<220> FEATURE:
<221> NAME/KEY: misc_feature
<222> LOCATION: (7)..(7)
<223> OTHER INFORMATION: /note="2'-OMe modified nucleotide"
<220> FEATURE:
<221> NAME/KEY: misc_feature
<222> LOCATION: (8)..(8)
<223> OTHER INFORMATION: /note="2'-F modified nucleotide"
<220> FEATURE:
<221> NAME/KEY: misc_feature
<222> LOCATION: (9)..(9)
<223> OTHER INFORMATION: /note="2'-F modified nucleotide"
<220> FEATURE:
<221> NAME/KEY: misc_feature
<222> LOCATION: (10)..(10)
<223> OTHER INFORMATION: /note="2'-F modified nucleotide"
<220> FEATURE:
<221> NAME/KEY: misc_feature
<222> LOCATION: (11)..(11)
<223> OTHER INFORMATION: /note="2'-F modified nucleotide"
<220> FEATURE:
<221> NAME/KEY: misc_feature
<222> LOCATION: (12)..(12)
<223> OTHER INFORMATION: /note="2'-OMe modified nucleotide"
<220> FEATURE:
<221> NAME/KEY: misc_feature
<222> LOCATION: (13)..(13)
<223> OTHER INFORMATION: /note="2'-OMe modified nucleotide"
<220> FEATURE:
<221> NAME/KEY: misc_feature
<222> LOCATION: (14)..(14)
<223> OTHER INFORMATION: /note="2'-OMe modified nucleotide"
<220> FEATURE:
<221> NAME/KEY: misc_feature
<222> LOCATION: (15)..(15)
<223> OTHER INFORMATION: /note="2'-OMe modified nucleotide"
<220> FEATURE:
<221> NAME/KEY: misc_feature
<222> LOCATION: (16)..(16)
<223> OTHER INFORMATION: /note="2'-OMe modified nucleotide"
<220> FEATURE:
<221> NAME/KEY: misc_feature
<222> LOCATION: (17)..(17)

<223> OTHER INFORMATION: /note="2'-OMe modified nucleotide"
<220> FEATURE:
<221> NAME/KEY: misc_feature
<222> LOCATION: (18)..(18)
<223> OTHER INFORMATION: /note="2'-OMe modified nucleotide"
<220> FEATURE:
<221> NAME/KEY: misc_feature
<222> LOCATION: (19)..(19)
<223> OTHER INFORMATION: /note="2'-OMe modified nucleotide"
<220> FEATURE:
<221> NAME/KEY: misc_feature
<222> LOCATION: (20)..(20)
<223> OTHER INFORMATION: /note="2'-OMe modified nucleotide"
<220> FEATURE:
<221> NAME/KEY: misc_feature
<222> LOCATION: (21)..(21)
<223> OTHER INFORMATION: /note="2'-OMe modified nucleotide"
<220> FEATURE:
<221> NAME/KEY: misc_feature
<222> LOCATION: (22)..(22)
<223> OTHER INFORMATION: /note="2'-OMe modified nucleotide"
<220> FEATURE:
<221> NAME/KEY: misc_feature
<222> LOCATION: (23)..(23)
<223> OTHER INFORMATION: /note="2'-OMe modified nucleotide"
<220> FEATURE:
<221> NAME/KEY: misc_feature
<222> LOCATION: (24)..(24)
<223> OTHER INFORMATION: /note="2'-OMe modified nucleotide"
<220> FEATURE:
<221> NAME/KEY: misc_feature
<222> LOCATION: (25)..(25)
<223> OTHER INFORMATION: /note="2'-OMe modified nucleotide"
<220> FEATURE:
<221> NAME/KEY: misc_feature
<222> LOCATION: (26)..(26)
<223> OTHER INFORMATION: /note="2'-OMe modified nucleotide"
<220> FEATURE:
<221> NAME/KEY: misc_feature
<222> LOCATION: (27)..(27)
<223> OTHER INFORMATION: /note="2'-OMe modified nucleotide"
<220> FEATURE:
<221> NAME/KEY: misc_feature
<222> LOCATION: (28)..(28)
<223> OTHER INFORMATION: /note="ademA-GalNAc"
<220> FEATURE:
<221> NAME/KEY: misc_feature
<222> LOCATION: (29)..(29)
<223> OTHER INFORMATION: /note="ademA-GalNAc"
<220> FEATURE:
<221> NAME/KEY: misc_feature
<222> LOCATION: (30)..(30)
<223> OTHER INFORMATION: /note="ademA-GalNAc"
<220> FEATURE:
<221> NAME/KEY: misc_feature
<222> LOCATION: (31)..(31)
<223> OTHER INFORMATION: /note="2'-OMe modified nucleotide"
<220> FEATURE:
<221> NAME/KEY: misc_feature
<222> LOCATION: (32)..(32)
<223> OTHER INFORMATION: /note="2'-OMe modified nucleotide"
<220> FEATURE:
<221> NAME/KEY: misc_feature
<222> LOCATION: (33)..(33)
<223> OTHER INFORMATION: /note="2'-OMe modified nucleotide"
<220> FEATURE:
<221> NAME/KEY: misc_feature
<222> LOCATION: (34)..(34)
<223> OTHER INFORMATION: /note="2'-OMe modified nucleotide"
<220> FEATURE:
<221> NAME/KEY: misc_feature
<222> LOCATION: (35)..(35)
<223> OTHER INFORMATION: /note="2'-OMe modified nucleotide"
<220> FEATURE:
<221> NAME/KEY: misc_feature
<222> LOCATION: (36)..(36)
<223> OTHER INFORMATION: /note="2'-OMe modified nucleotide"

<400> SEQUENCE: 216

-continued

```
acccagcaac ucucaaguua gcagccgaaa ggcugc                            36


<210> SEQ ID NO 217
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: misc_feature
<222> LOCATION: (1)..(1)
<223> OTHER INFORMATION: /note="MePhosphonate-4O-mUs"
<220> FEATURE:
<221> NAME/KEY: misc_feature
<222> LOCATION: (2)..(2)
<223> OTHER INFORMATION: /note="2'-F modified nucleotide with a
      3'-phosphorothioate linkage"
<220> FEATURE:
<221> NAME/KEY: misc_feature
<222> LOCATION: (3)..(3)
<223> OTHER INFORMATION: /note="2'-F modified nucleotide with a
      3'-phosphorothioate linkage"
<220> FEATURE:
<221> NAME/KEY: misc_feature
<222> LOCATION: (4)..(4)
<223> OTHER INFORMATION: /note="2'-F modified nucleotide"
<220> FEATURE:
<221> NAME/KEY: misc_feature
<222> LOCATION: (5)..(5)
<223> OTHER INFORMATION: /note="2'-F modified nucleotide"
<220> FEATURE:
<221> NAME/KEY: misc_feature
<222> LOCATION: (6)..(6)
<223> OTHER INFORMATION: /note="2'-OMe modified nucleotide"
<220> FEATURE:
<221> NAME/KEY: misc_feature
<222> LOCATION: (7)..(7)
<223> OTHER INFORMATION: /note="2'-F modified nucleotide"
<220> FEATURE:
<221> NAME/KEY: misc_feature
<222> LOCATION: (8)..(8)
<223> OTHER INFORMATION: /note="2'-OMe modified nucleotide"
<220> FEATURE:
<221> NAME/KEY: misc_feature
<222> LOCATION: (9)..(9)
<223> OTHER INFORMATION: /note="2'-OMe modified nucleotide"
<220> FEATURE:
<221> NAME/KEY: misc_feature
<222> LOCATION: (10)..(10)
<223> OTHER INFORMATION: /note="2'-F modified nucleotide"
<220> FEATURE:
<221> NAME/KEY: misc_feature
<222> LOCATION: (11)..(11)
<223> OTHER INFORMATION: /note="2'-OMe modified nucleotide"
<220> FEATURE:
<221> NAME/KEY: misc_feature
<222> LOCATION: (12)..(12)
<223> OTHER INFORMATION: /note="2'-OMe modified nucleotide"
<220> FEATURE:
<221> NAME/KEY: misc_feature
<222> LOCATION: (13)..(13)
<223> OTHER INFORMATION: /note="2'-OMe modified nucleotide"
<220> FEATURE:
<221> NAME/KEY: misc_feature
<222> LOCATION: (14)..(14)
<223> OTHER INFORMATION: /note="2'-F modified nucleotide"
<220> FEATURE:
<221> NAME/KEY: misc_feature
<222> LOCATION: (15)..(15)
<223> OTHER INFORMATION: /note="2'-OMe modified nucleotide"
<220> FEATURE:
<221> NAME/KEY: misc_feature
<222> LOCATION: (16)..(16)
<223> OTHER INFORMATION: /note="2'-OMe modified nucleotide"
<220> FEATURE:
```

<221> NAME/KEY: misc_feature
<222> LOCATION: (17)..(17)
<223> OTHER INFORMATION: /note="2'-OMe modified nucleotide"
<220> FEATURE:
<221> NAME/KEY: misc_feature
<222> LOCATION: (18)..(18)
<223> OTHER INFORMATION: /note="2'-OMe modified nucleotide"
<220> FEATURE:
<221> NAME/KEY: misc_feature
<222> LOCATION: (19)..(19)
<223> OTHER INFORMATION: /note="2'-OMe modified nucleotide"
<220> FEATURE:
<221> NAME/KEY: misc_feature
<222> LOCATION: (20)..(20)
<223> OTHER INFORMATION: /note="2'-OMe modified nucleotide with a 3'-phosphorothioate linkage"
<220> FEATURE:
<221> NAME/KEY: misc_feature
<222> LOCATION: (21)..(21)
<223> OTHER INFORMATION: /note="2'-OMe modified nucleotide with a 3'-phosphorothioate linkage"
<220> FEATURE:
<221> NAME/KEY: misc_feature
<222> LOCATION: (22)..(22)
<223> OTHER INFORMATION: /note="2'-OMe modified nucleotide"

<400> SEQUENCE: 217
uaacuugaga guugcugggu gg 22

<210> SEQ ID NO 218
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: misc_feature
<222> LOCATION: (1)..(1)
<223> OTHER INFORMATION: /note="2'-OMe modified nucleotide with a 3'-phosphorothioate linkage"
<220> FEATURE:
<221> NAME/KEY: misc_feature
<222> LOCATION: (2)..(2)
<223> OTHER INFORMATION: /note="2'-OMe modified nucleotide"
<220> FEATURE:
<221> NAME/KEY: misc_feature
<222> LOCATION: (3)..(3)
<223> OTHER INFORMATION: /note="2'-OMe modified nucleotide"
<220> FEATURE:
<221> NAME/KEY: misc_feature
<222> LOCATION: (4)..(4)
<223> OTHER INFORMATION: /note="2'-OMe modified nucleotide"
<220> FEATURE:
<221> NAME/KEY: misc_feature
<222> LOCATION: (5)..(5)
<223> OTHER INFORMATION: /note="2'-OMe modified nucleotide"
<220> FEATURE:
<221> NAME/KEY: misc_feature
<222> LOCATION: (6)..(6)
<223> OTHER INFORMATION: /note="2'-OMe modified nucleotide"
<220> FEATURE:
<221> NAME/KEY: misc_feature
<222> LOCATION: (7)..(7)
<223> OTHER INFORMATION: /note="2'-OMe modified nucleotide"
<220> FEATURE:
<221> NAME/KEY: misc_feature
<222> LOCATION: (8)..(8)
<223> OTHER INFORMATION: /note="2'-F modified nucleotide"
<220> FEATURE:
<221> NAME/KEY: misc_feature
<222> LOCATION: (9)..(9)
<223> OTHER INFORMATION: /note="2'-F modified nucleotide"
<220> FEATURE:
<221> NAME/KEY: misc_feature
<222> LOCATION: (10)..(10)

<223> OTHER INFORMATION: /note="2'-F modified nucleotide"
<220> FEATURE:
<221> NAME/KEY: misc_feature
<222> LOCATION: (11)..(11)
<223> OTHER INFORMATION: /note="2'-F modified nucleotide"
<220> FEATURE:
<221> NAME/KEY: misc_feature
<222> LOCATION: (12)..(12)
<223> OTHER INFORMATION: /note="2'-OMe modified nucleotide"
<220> FEATURE:
<221> NAME/KEY: misc_feature
<222> LOCATION: (13)..(13)
<223> OTHER INFORMATION: /note="2'-OMe modified nucleotide"
<220> FEATURE:
<221> NAME/KEY: misc_feature
<222> LOCATION: (14)..(14)
<223> OTHER INFORMATION: /note="2'-OMe modified nucleotide"
<220> FEATURE:
<221> NAME/KEY: misc_feature
<222> LOCATION: (15)..(15)
<223> OTHER INFORMATION: /note="2'-OMe modified nucleotide"
<220> FEATURE:
<221> NAME/KEY: misc_feature
<222> LOCATION: (16)..(16)
<223> OTHER INFORMATION: /note="2'-OMe modified nucleotide"
<220> FEATURE:
<221> NAME/KEY: misc_feature
<222> LOCATION: (17)..(17)
<223> OTHER INFORMATION: /note="2'-OMe modified nucleotide"
<220> FEATURE:
<221> NAME/KEY: misc_feature
<222> LOCATION: (18)..(18)
<223> OTHER INFORMATION: /note="2'-OMe modified nucleotide"
<220> FEATURE:
<221> NAME/KEY: misc_feature
<222> LOCATION: (19)..(19)
<223> OTHER INFORMATION: /note="2'-OMe modified nucleotide"
<220> FEATURE:
<221> NAME/KEY: misc_feature
<222> LOCATION: (20)..(20)
<223> OTHER INFORMATION: /note="2'-OMe modified nucleotide"
<220> FEATURE:
<221> NAME/KEY: misc_feature
<222> LOCATION: (21)..(21)
<223> OTHER INFORMATION: /note="2'-OMe modified nucleotide"
<220> FEATURE:
<221> NAME/KEY: misc_feature
<222> LOCATION: (22)..(22)
<223> OTHER INFORMATION: /note="2'-OMe modified nucleotide"
<220> FEATURE:
<221> NAME/KEY: misc_feature
<222> LOCATION: (23)..(23)
<223> OTHER INFORMATION: /note="2'-OMe modified nucleotide"
<220> FEATURE:
<221> NAME/KEY: misc_feature
<222> LOCATION: (24)..(24)
<223> OTHER INFORMATION: /note="2'-OMe modified nucleotide"
<220> FEATURE:
<221> NAME/KEY: misc_feature
<222> LOCATION: (25)..(25)
<223> OTHER INFORMATION: /note="2'-OMe modified nucleotide"
<220> FEATURE:
<221> NAME/KEY: misc_feature
<222> LOCATION: (26)..(26)
<223> OTHER INFORMATION: /note="2'-OMe modified nucleotide"
<220> FEATURE:
<221> NAME/KEY: misc_feature
<222> LOCATION: (27)..(27)
<223> OTHER INFORMATION: /note="2'-OMe modified nucleotide"
<220> FEATURE:
<221> NAME/KEY: misc_feature
<222> LOCATION: (28)..(28)
<223> OTHER INFORMATION: /note="ademA-GalNAc"
<220> FEATURE:
<221> NAME/KEY: misc_feature
<222> LOCATION: (29)..(29)
<223> OTHER INFORMATION: /note="ademA-GalNAc"
<220> FEATURE:
<221> NAME/KEY: misc_feature -continued
<222> LOCATION: (30)..(30)
<223> OTHER INFORMATION: /note="ademA-GalNAc"
<220> FEATURE:
<221> NAME/KEY: misc_feature
<222> LOCATION: (31)..(31)
<223> OTHER INFORMATION: /note="2'-OMe modified nucleotide"
<220> FEATURE:
<221> NAME/KEY: misc_feature
<222> LOCATION: (32)..(32)
<223> OTHER INFORMATION: /note="2'-OMe modified nucleotide"
<220> FEATURE:
<221> NAME/KEY: misc_feature
<222> LOCATION: (33)..(33)
<223> OTHER INFORMATION: /note="2'-OMe modified nucleotide"
<220> FEATURE:
<221> NAME/KEY: misc_feature
<222> LOCATION: (34)..(34)
<223> OTHER INFORMATION: /note="2'-OMe modified nucleotide"
<220> FEATURE:
<221> NAME/KEY: misc_feature
<222> LOCATION: (35)..(35)
<223> OTHER INFORMATION: /note="2'-OMe modified nucleotide"
<220> FEATURE:
<221> NAME/KEY: misc_feature
<222> LOCATION: (36)..(36)
<223> OTHER INFORMATION: /note="2'-OMe modified nucleotide"

<400> SEQUENCE: 218
cccagcaacu cucaaguuua gcagccgaaa ggcugc 36

<210> SEQ ID NO 219
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: misc_feature
<222> LOCATION: (1)..(1)
<223> OTHER INFORMATION: /note="MePhosphonate-4O-mUs"
<220> FEATURE:
<221> NAME/KEY: misc_feature
<222> LOCATION: (2)..(2)
<223> OTHER INFORMATION: /note="2'-F modified nucleotide with a
3'-phosphorothioate linkage"
<220> FEATURE:
<221> NAME/KEY: misc_feature
<222> LOCATION: (3)..(3)
<223> OTHER INFORMATION: /note="2'-F modified nucleotide with a
3'-phosphorothioate linkage"
<220> FEATURE:
<221> NAME/KEY: misc_feature
<222> LOCATION: (4)..(4)
<223> OTHER INFORMATION: /note="2'-F modified nucleotide"
<220> FEATURE:
<221> NAME/KEY: misc_feature
<222> LOCATION: (5)..(5)
<223> OTHER INFORMATION: /note="2'-F modified nucleotide"
<220> FEATURE:
<221> NAME/KEY: misc_feature
<222> LOCATION: (6)..(6)
<223> OTHER INFORMATION: /note="2'-OMe modified nucleotide"
<220> FEATURE:
<221> NAME/KEY: misc_feature
<222> LOCATION: (7)..(7)
<223> OTHER INFORMATION: /note="2'-F modified nucleotide"
<220> FEATURE:
<221> NAME/KEY: misc_feature
<222> LOCATION: (8)..(8)
<223> OTHER INFORMATION: /note="2'-OMe modified nucleotide"
<220> FEATURE:
<221> NAME/KEY: misc_feature
<222> LOCATION: (9)..(9)
<223> OTHER INFORMATION: /note="2'-OMe modified nucleotide"
<220> FEATURE:

<221> NAME/KEY: misc_feature
<222> LOCATION: (10)..(10)
<223> OTHER INFORMATION: /note="2'-F modified nucleotide"
<220> FEATURE:
<221> NAME/KEY: misc_feature
<222> LOCATION: (11)..(11)
<223> OTHER INFORMATION: /note="2'-OMe modified nucleotide"
<220> FEATURE:
<221> NAME/KEY: misc_feature
<222> LOCATION: (12)..(12)
<223> OTHER INFORMATION: /note="2'-OMe modified nucleotide"
<220> FEATURE:
<221> NAME/KEY: misc_feature
<222> LOCATION: (13)..(13)
<223> OTHER INFORMATION: /note="2'-OMe modified nucleotide"
<220> FEATURE:
<221> NAME/KEY: misc_feature
<222> LOCATION: (14)..(14)
<223> OTHER INFORMATION: /note="2'-F modified nucleotide"
<220> FEATURE:
<221> NAME/KEY: misc_feature
<222> LOCATION: (15)..(15)
<223> OTHER INFORMATION: /note="2'-OMe modified nucleotide"
<220> FEATURE:
<221> NAME/KEY: misc_feature
<222> LOCATION: (16)..(16)
<223> OTHER INFORMATION: /note="2'-OMe modified nucleotide"
<220> FEATURE:
<221> NAME/KEY: misc_feature
<222> LOCATION: (17)..(17)
<223> OTHER INFORMATION: /note="2'-OMe modified nucleotide"
<220> FEATURE:
<221> NAME/KEY: misc_feature
<222> LOCATION: (18)..(18)
<223> OTHER INFORMATION: /note="2'-OMe modified nucleotide"
<220> FEATURE:
<221> NAME/KEY: misc_feature
<222> LOCATION: (19)..(19)
<223> OTHER INFORMATION: /note="2'-OMe modified nucleotide"
<220> FEATURE:
<221> NAME/KEY: misc_feature
<222> LOCATION: (20)..(20)
<223> OTHER INFORMATION: /note="2'-OMe modified nucleotide with a
3'-phosphorothioate linkage"
<220> FEATURE:
<221> NAME/KEY: misc_feature
<222> LOCATION: (21)..(21)
<223> OTHER INFORMATION: /note="2'-OMe modified nucleotide with a
3'-phosphorothioate linkage"
<220> FEATURE:
<221> NAME/KEY: misc_feature
<222> LOCATION: (22)..(22)
<223> OTHER INFORMATION: /note="2'-OMe modified nucleotide"

<400> SEQUENCE: 219
uaaacuugag aguugcuggg gg 22

<210> SEQ ID NO 220
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: misc_feature
<222> LOCATION: (1)..(1)
<223> OTHER INFORMATION: /note="2'-OMe modified nucleotide with a
3'-phosphorothioate linkage"
<220> FEATURE:
<221> NAME/KEY: misc_feature
<222> LOCATION: (2)..(2)
<223> OTHER INFORMATION: /note="2'-OMe modified nucleotide"
<220> FEATURE:
<221> NAME/KEY: misc_feature
<222> LOCATION: (3)..(3)

<223> OTHER INFORMATION: /note="2'-OMe modified nucleotide"
<220> FEATURE:
<221> NAME/KEY: misc_feature
<222> LOCATION: (4)..(4)
<223> OTHER INFORMATION: /note="2'-OMe modified nucleotide"
<220> FEATURE:
<221> NAME/KEY: misc_feature
<222> LOCATION: (5)..(5)
<223> OTHER INFORMATION: /note="2'-OMe modified nucleotide"
<220> FEATURE:
<221> NAME/KEY: misc_feature
<222> LOCATION: (6)..(6)
<223> OTHER INFORMATION: /note="2'-OMe modified nucleotide"
<220> FEATURE:
<221> NAME/KEY: misc_feature
<222> LOCATION: (7)..(7)
<223> OTHER INFORMATION: /note="2'-OMe modified nucleotide"
<220> FEATURE:
<221> NAME/KEY: misc_feature
<222> LOCATION: (8)..(8)
<223> OTHER INFORMATION: /note="2'-F modified nucleotide"
<220> FEATURE:
<221> NAME/KEY: misc_feature
<222> LOCATION: (9)..(9)
<223> OTHER INFORMATION: /note="2'-F modified nucleotide"
<220> FEATURE:
<221> NAME/KEY: misc_feature
<222> LOCATION: (10)..(10)
<223> OTHER INFORMATION: /note="2'-F modified nucleotide"
<220> FEATURE:
<221> NAME/KEY: misc_feature
<222> LOCATION: (11)..(11)
<223> OTHER INFORMATION: /note="2'-F modified nucleotide"
<220> FEATURE:
<221> NAME/KEY: misc_feature
<222> LOCATION: (12)..(12)
<223> OTHER INFORMATION: /note="2'-OMe modified nucleotide"
<220> FEATURE:
<221> NAME/KEY: misc_feature
<222> LOCATION: (13)..(13)
<223> OTHER INFORMATION: /note="2'-OMe modified nucleotide"
<220> FEATURE:
<221> NAME/KEY: misc_feature
<222> LOCATION: (14)..(14)
<223> OTHER INFORMATION: /note="2'-OMe modified nucleotide"
<220> FEATURE:
<221> NAME/KEY: misc_feature
<222> LOCATION: (15)..(15)
<223> OTHER INFORMATION: /note="2'-OMe modified nucleotide"
<220> FEATURE:
<221> NAME/KEY: misc_feature
<222> LOCATION: (16)..(16)
<223> OTHER INFORMATION: /note="2'-OMe modified nucleotide"
<220> FEATURE:
<221> NAME/KEY: misc_feature
<222> LOCATION: (17)..(17)
<223> OTHER INFORMATION: /note="2'-OMe modified nucleotide"
<220> FEATURE:
<221> NAME/KEY: misc_feature
<222> LOCATION: (18)..(18)
<223> OTHER INFORMATION: /note="2'-OMe modified nucleotide"
<220> FEATURE:
<221> NAME/KEY: misc_feature
<222> LOCATION: (19)..(19)
<223> OTHER INFORMATION: /note="2'-OMe modified nucleotide"
<220> FEATURE:
<221> NAME/KEY: misc_feature
<222> LOCATION: (20)..(20)
<223> OTHER INFORMATION: /note="2'-OMe modified nucleotide"
<220> FEATURE:
<221> NAME/KEY: misc_feature
<222> LOCATION: (21)..(21)
<223> OTHER INFORMATION: /note="2'-OMe modified nucleotide"
<220> FEATURE:
<221> NAME/KEY: misc_feature
<222> LOCATION: (22)..(22)
<223> OTHER INFORMATION: /note="2'-OMe modified nucleotide"
<220> FEATURE:
<221> NAME/KEY: misc_feature
<222> LOCATION: (23)..(23)
<223> OTHER INFORMATION: /note="2'-OMe modified nucleotide"
<220> FEATURE:
<221> NAME/KEY: misc_feature
<222> LOCATION: (24)..(24)
<223> OTHER INFORMATION: /note="2'-OMe modified nucleotide"
<220> FEATURE:
<221> NAME/KEY: misc_feature
<222> LOCATION: (25)..(25)
<223> OTHER INFORMATION: /note="2'-OMe modified nucleotide"
<220> FEATURE:
<221> NAME/KEY: misc_feature
<222> LOCATION: (26)..(26)
<223> OTHER INFORMATION: /note="2'-OMe modified nucleotide"
<220> FEATURE:
<221> NAME/KEY: misc_feature
<222> LOCATION: (27)..(27)
<223> OTHER INFORMATION: /note="2'-OMe modified nucleotide"
<220> FEATURE:
<221> NAME/KEY: misc_feature
<222> LOCATION: (28)..(28)
<223> OTHER INFORMATION: /note="ademA-GalNAc"
<220> FEATURE:
<221> NAME/KEY: misc_feature
<222> LOCATION: (29)..(29)
<223> OTHER INFORMATION: /note="ademA-GalNAc"
<220> FEATURE:
<221> NAME/KEY: misc_feature
<222> LOCATION: (30)..(30)
<223> OTHER INFORMATION: /note="ademA-GalNAc"
<220> FEATURE:
<221> NAME/KEY: misc_feature
<222> LOCATION: (31)..(31)
<223> OTHER INFORMATION: /note="2'-OMe modified nucleotide"
<220> FEATURE:
<221> NAME/KEY: misc_feature
<222> LOCATION: (32)..(32)
<223> OTHER INFORMATION: /note="2'-OMe modified nucleotide"
<220> FEATURE:
<221> NAME/KEY: misc_feature
<222> LOCATION: (33)..(33)
<223> OTHER INFORMATION: /note="2'-OMe modified nucleotide"
<220> FEATURE:
<221> NAME/KEY: misc_feature
<222> LOCATION: (34)..(34)
<223> OTHER INFORMATION: /note="2'-OMe modified nucleotide"
<220> FEATURE:
<221> NAME/KEY: misc_feature
<222> LOCATION: (35)..(35)
<223> OTHER INFORMATION: /note="2'-OMe modified nucleotide"
<220> FEATURE:
<221> NAME/KEY: misc_feature
<222> LOCATION: (36)..(36)
<223> OTHER INFORMATION: /note="2'-OMe modified nucleotide"

<400> SEQUENCE: 220
ccagcaacuc ucaaguuuua gcagccgaaa ggcugc 36

<210> SEQ ID NO 221
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: misc_feature
<222> LOCATION: (1)..(1)
<223> OTHER INFORMATION: /note="MePhosphonate-4O-mUs"
<220> FEATURE:
<221> NAME/KEY: misc_feature
<222> LOCATION: (2)..(2)
<223> OTHER INFORMATION: /note="2'-F modified nucleotide with a 3'-phosphorothioate linkage"
<220> FEATURE:
<221> NAME/KEY: misc_feature
<222> LOCATION: (3)..(3)
<223> OTHER INFORMATION: /note="2'-F modified nucleotide with a
3'-phosphorothioate linkage"
<220> FEATURE:
<221> NAME/KEY: misc_feature
<222> LOCATION: (4)..(4)
<223> OTHER INFORMATION: /note="2'-F modified nucleotide"
<220> FEATURE:
<221> NAME/KEY: misc_feature
<222> LOCATION: (5)..(5)
<223> OTHER INFORMATION: /note="2'-F modified nucleotide"
<220> FEATURE:
<221> NAME/KEY: misc_feature
<222> LOCATION: (6)..(6)
<223> OTHER INFORMATION: /note="2'-OMe modified nucleotide"
<220> FEATURE:
<221> NAME/KEY: misc_feature
<222> LOCATION: (7)..(7)
<223> OTHER INFORMATION: /note="2'-F modified nucleotide"
<220> FEATURE:
<221> NAME/KEY: misc_feature
<222> LOCATION: (8)..(8)
<223> OTHER INFORMATION: /note="2'-OMe modified nucleotide"
<220> FEATURE:
<221> NAME/KEY: misc_feature
<222> LOCATION: (9)..(9)
<223> OTHER INFORMATION: /note="2'-OMe modified nucleotide"
<220> FEATURE:
<221> NAME/KEY: misc_feature
<222> LOCATION: (10)..(10)
<223> OTHER INFORMATION: /note="2'-F modified nucleotide"
<220> FEATURE:
<221> NAME/KEY: misc_feature
<222> LOCATION: (11)..(11)
<223> OTHER INFORMATION: /note="2'-OMe modified nucleotide"
<220> FEATURE:
<221> NAME/KEY: misc_feature
<222> LOCATION: (12)..(12)
<223> OTHER INFORMATION: /note="2'-OMe modified nucleotide"
<220> FEATURE:
<221> NAME/KEY: misc_feature
<222> LOCATION: (13)..(13)
<223> OTHER INFORMATION: /note="2'-OMe modified nucleotide"
<220> FEATURE:
<221> NAME/KEY: misc_feature
<222> LOCATION: (14)..(14)
<223> OTHER INFORMATION: /note="2'-F modified nucleotide"
<220> FEATURE:
<221> NAME/KEY: misc_feature
<222> LOCATION: (15)..(15)
<223> OTHER INFORMATION: /note="2'-OMe modified nucleotide"
<220> FEATURE:
<221> NAME/KEY: misc_feature
<222> LOCATION: (16)..(16)
<223> OTHER INFORMATION: /note="2'-OMe modified nucleotide"
<220> FEATURE:
<221> NAME/KEY: misc_feature
<222> LOCATION: (17)..(17)
<223> OTHER INFORMATION: /note="2'-OMe modified nucleotide"
<220> FEATURE:
<221> NAME/KEY: misc_feature
<222> LOCATION: (18)..(18)
<223> OTHER INFORMATION: /note="2'-OMe modified nucleotide"
<220> FEATURE:
<221> NAME/KEY: misc_feature
<222> LOCATION: (19)..(19)
<223> OTHER INFORMATION: /note="2'-OMe modified nucleotide"
<220> FEATURE:
<221> NAME/KEY: misc_feature
<222> LOCATION: (20)..(20)
<223> OTHER INFORMATION: /note="2'-OMe modified nucleotide with a
3'-phosphorothioate linkage"
<220> FEATURE:
<221> NAME/KEY: misc_feature
<222> LOCATION: (21)..(21)
<223> OTHER INFORMATION: /note="2'-OMe modified nucleotide with a
3'-phosphorothioate linkage"
<220> FEATURE:
<221> NAME/KEY: misc_feature
<222> LOCATION: (22)..(22)
<223> OTHER INFORMATION: /note="2'-OMe modified nucleotide"

<400> SEQUENCE: 221
uaaaacuuga gaguugcugg gg 22

<210> SEQ ID NO 222
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: misc_feature
<222> LOCATION: (1)..(1)
<223> OTHER INFORMATION: /note="2'-OMe modified nucleotide with a
3'-phosphorothioate linkage"
<220> FEATURE:
<221> NAME/KEY: misc_feature
<222> LOCATION: (2)..(2)
<223> OTHER INFORMATION: /note="2'-OMe modified nucleotide"
<220> FEATURE:
<221> NAME/KEY: misc_feature
<222> LOCATION: (3)..(3)
<223> OTHER INFORMATION: /note="2'-OMe modified nucleotide"
<220> FEATURE:
<221> NAME/KEY: misc_feature
<222> LOCATION: (4)..(4)
<223> OTHER INFORMATION: /note="2'-OMe modified nucleotide"
<220> FEATURE:
<221> NAME/KEY: misc_feature
<222> LOCATION: (5)..(5)
<223> OTHER INFORMATION: /note="2'-OMe modified nucleotide"
<220> FEATURE:
<221> NAME/KEY: misc_feature
<222> LOCATION: (6)..(6)
<223> OTHER INFORMATION: /note="2'-OMe modified nucleotide"
<220> FEATURE:
<221> NAME/KEY: misc_feature
<222> LOCATION: (7)..(7)
<223> OTHER INFORMATION: /note="2'-OMe modified nucleotide"
<220> FEATURE:
<221> NAME/KEY: misc_feature
<222> LOCATION: (8)..(8)
<223> OTHER INFORMATION: /note="2'-F modified nucleotide"
<220> FEATURE:
<221> NAME/KEY: misc_feature
<222> LOCATION: (9)..(9)
<223> OTHER INFORMATION: /note="2'-F modified nucleotide"
<220> FEATURE:
<221> NAME/KEY: misc_feature
<222> LOCATION: (10)..(10)
<223> OTHER INFORMATION: /note="2'-F modified nucleotide"
<220> FEATURE:
<221> NAME/KEY: misc_feature
<222> LOCATION: (11)..(11)
<223> OTHER INFORMATION: /note="2'-F modified nucleotide"
<220> FEATURE:
<221> NAME/KEY: misc_feature
<222> LOCATION: (12)..(12)
<223> OTHER INFORMATION: /note="2'-OMe modified nucleotide"
<220> FEATURE:
<221> NAME/KEY: misc_feature
<222> LOCATION: (13)..(13)
<223> OTHER INFORMATION: /note="2'-OMe modified nucleotide"
<220> FEATURE:
<221> NAME/KEY: misc_feature
<222> LOCATION: (14)..(14)
<223> OTHER INFORMATION: /note="2'-OMe modified nucleotide"
<220> FEATURE:
<221> NAME/KEY: misc_feature
<222> LOCATION: (15)..(15)
<223> OTHER INFORMATION: /note="2'-OMe modified nucleotide"
<220> FEATURE:
<221> NAME/KEY: misc_feature -continued
<222> LOCATION: (16)..(16)
<223> OTHER INFORMATION: /note="2'-OMe modified nucleotide"
<220> FEATURE:
<221> NAME/KEY: misc_feature
<222> LOCATION: (17)..(17)
<223> OTHER INFORMATION: /note="2'-OMe modified nucleotide"
<220> FEATURE:
<221> NAME/KEY: misc_feature
<222> LOCATION: (18)..(18)
<223> OTHER INFORMATION: /note="2'-OMe modified nucleotide"
<220> FEATURE:
<221> NAME/KEY: misc_feature
<222> LOCATION: (19)..(19)
<223> OTHER INFORMATION: /note="2'-OMe modified nucleotide"
<220> FEATURE:
<221> NAME/KEY: misc_feature
<222> LOCATION: (20)..(20)
<223> OTHER INFORMATION: /note="2'-OMe modified nucleotide"
<220> FEATURE:
<221> NAME/KEY: misc_feature
<222> LOCATION: (21)..(21)
<223> OTHER INFORMATION: /note="2'-OMe modified nucleotide"
<220> FEATURE:
<221> NAME/KEY: misc_feature
<222> LOCATION: (22)..(22)
<223> OTHER INFORMATION: /note="2'-OMe modified nucleotide"
<220> FEATURE:
<221> NAME/KEY: misc_feature
<222> LOCATION: (23)..(23)
<223> OTHER INFORMATION: /note="2'-OMe modified nucleotide"
<220> FEATURE:
<221> NAME/KEY: misc_feature
<222> LOCATION: (24)..(24)
<223> OTHER INFORMATION: /note="2'-OMe modified nucleotide"
<220> FEATURE:
<221> NAME/KEY: misc_feature
<222> LOCATION: (25)..(25)
<223> OTHER INFORMATION: /note="2'-OMe modified nucleotide"
<220> FEATURE:
<221> NAME/KEY: misc_feature
<222> LOCATION: (26)..(26)
<223> OTHER INFORMATION: /note="2'-OMe modified nucleotide"
<220> FEATURE:
<221> NAME/KEY: misc_feature
<222> LOCATION: (27)..(27)
<223> OTHER INFORMATION: /note="2'-OMe modified nucleotide"
<220> FEATURE:
<221> NAME/KEY: misc_feature
<222> LOCATION: (28)..(28)
<223> OTHER INFORMATION: /note="ademA-GalNAc"
<220> FEATURE:
<221> NAME/KEY: misc_feature
<222> LOCATION: (29)..(29)
<223> OTHER INFORMATION: /note="ademA-GalNAc"
<220> FEATURE:
<221> NAME/KEY: misc_feature
<222> LOCATION: (30)..(30)
<223> OTHER INFORMATION: /note="ademA-GalNAc"
<220> FEATURE:
<221> NAME/KEY: misc_feature
<222> LOCATION: (31)..(31)
<223> OTHER INFORMATION: /note="2'-OMe modified nucleotide"
<220> FEATURE:
<221> NAME/KEY: misc_feature
<222> LOCATION: (32)..(32)
<223> OTHER INFORMATION: /note="2'-OMe modified nucleotide"
<220> FEATURE:
<221> NAME/KEY: misc_feature
<222> LOCATION: (33)..(33)
<223> OTHER INFORMATION: /note="2'-OMe modified nucleotide"
<220> FEATURE:
<221> NAME/KEY: misc_feature
<222> LOCATION: (34)..(34)
<223> OTHER INFORMATION: /note="2'-OMe modified nucleotide"
<220> FEATURE:
<221> NAME/KEY: misc_feature
<222> LOCATION: (35)..(35)
<223> OTHER INFORMATION: /note="2'-OMe modified nucleotide"
<220> FEATURE:

<221> NAME/KEY: misc_feature
<222> LOCATION: (36)..(36)
<223> OTHER INFORMATION: /note="2'-OMe modified nucleotide"

<400> SEQUENCE: 222
aagauauacu ccauagugaa gcagccgaaa ggcugc 36

<210> SEQ ID NO 223
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: misc_feature
<222> LOCATION: (1)..(1)
<223> OTHER INFORMATION: /note="MePhosphonate-4O-mUs"
<220> FEATURE:
<221> NAME/KEY: misc_feature
<222> LOCATION: (2)..(2)
<223> OTHER INFORMATION: /note="2'-F modified nucleotide with a 3'-phosphorothioate linkage"
<220> FEATURE:
<221> NAME/KEY: misc_feature
<222> LOCATION: (3)..(3)
<223> OTHER INFORMATION: /note="2'-F modified nucleotide with a 3'-phosphorothioate linkage"
<220> FEATURE:
<221> NAME/KEY: misc_feature
<222> LOCATION: (4)..(4)
<223> OTHER INFORMATION: /note="2'-F modified nucleotide"
<220> FEATURE:
<221> NAME/KEY: misc_feature
<222> LOCATION: (5)..(5)
<223> OTHER INFORMATION: /note="2'-F modified nucleotide"
<220> FEATURE:
<221> NAME/KEY: misc_feature
<222> LOCATION: (6)..(6)
<223> OTHER INFORMATION: /note="2'-OMe modified nucleotide"
<220> FEATURE:
<221> NAME/KEY: misc_feature
<222> LOCATION: (7)..(7)
<223> OTHER INFORMATION: /note="2'-F modified nucleotide"
<220> FEATURE:
<221> NAME/KEY: misc_feature
<222> LOCATION: (8)..(8)
<223> OTHER INFORMATION: /note="2'-OMe modified nucleotide"
<220> FEATURE:
<221> NAME/KEY: misc_feature
<222> LOCATION: (9)..(9)
<223> OTHER INFORMATION: /note="2'-OMe modified nucleotide"
<220> FEATURE:
<221> NAME/KEY: misc_feature
<222> LOCATION: (10)..(10)
<223> OTHER INFORMATION: /note="2'-F modified nucleotide"
<220> FEATURE:
<221> NAME/KEY: misc_feature
<222> LOCATION: (11)..(11)
<223> OTHER INFORMATION: /note="2'-OMe modified nucleotide"
<220> FEATURE:
<221> NAME/KEY: misc_feature
<222> LOCATION: (12)..(12)
<223> OTHER INFORMATION: /note="2'-OMe modified nucleotide"
<220> FEATURE:
<221> NAME/KEY: misc_feature
<222> LOCATION: (13)..(13)
<223> OTHER INFORMATION: /note="2'-OMe modified nucleotide"
<220> FEATURE:
<221> NAME/KEY: misc_feature
<222> LOCATION: (14)..(14)
<223> OTHER INFORMATION: /note="2'-F modified nucleotide"
<220> FEATURE:
<221> NAME/KEY: misc_feature
<222> LOCATION: (15)..(15)
<223> OTHER INFORMATION: /note="2'-OMe modified nucleotide"

```
<220> FEATURE:
<221> NAME/KEY: misc_feature
<222> LOCATION: (16)..(16)
<223> OTHER INFORMATION: /note="2'-OMe modified nucleotide"
<220> FEATURE:
<221> NAME/KEY: misc_feature
<222> LOCATION: (17)..(17)
<223> OTHER INFORMATION: /note="2'-OMe modified nucleotide"
<220> FEATURE:
<221> NAME/KEY: misc_feature
<222> LOCATION: (18)..(18)
<223> OTHER INFORMATION: /note="2'-OMe modified nucleotide"
<220> FEATURE:
<221> NAME/KEY: misc_feature
<222> LOCATION: (19)..(19)
<223> OTHER INFORMATION: /note="2'-OMe modified nucleotide"
<220> FEATURE:
<221> NAME/KEY: misc_feature
<222> LOCATION: (20)..(20)
<223> OTHER INFORMATION: /note="2'-OMe modified nucleotide with a
      3'-phosphorothioate linkage"
<220> FEATURE:
<221> NAME/KEY: misc_feature
<222> LOCATION: (21)..(21)
<223> OTHER INFORMATION: /note="2'-OMe modified nucleotide with a
      3'-phosphorothioate linkage"
<220> FEATURE:
<221> NAME/KEY: misc_feature
<222> LOCATION: (22)..(22)
<223> OTHER INFORMATION: /note="2'-OMe modified nucleotide"

<400> SEQUENCE: 223

uucacuaugg aguauaucuu gg                                          22


<210> SEQ ID NO 224
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: misc_feature
<222> LOCATION: (1)..(1)
<223> OTHER INFORMATION: /note="2'-OMe modified nucleotide with a
      3'-phosphorothioate linkage"
<220> FEATURE:
<221> NAME/KEY: misc_feature
<222> LOCATION: (2)..(2)
<223> OTHER INFORMATION: /note="2'-OMe modified nucleotide"
<220> FEATURE:
<221> NAME/KEY: misc_feature
<222> LOCATION: (3)..(3)
<223> OTHER INFORMATION: /note="2'-OMe modified nucleotide"
<220> FEATURE:
<221> NAME/KEY: misc_feature
<222> LOCATION: (4)..(4)
<223> OTHER INFORMATION: /note="2'-OMe modified nucleotide"
<220> FEATURE:
<221> NAME/KEY: misc_feature
<222> LOCATION: (5)..(5)
<223> OTHER INFORMATION: /note="2'-OMe modified nucleotide"
<220> FEATURE:
<221> NAME/KEY: misc_feature
<222> LOCATION: (6)..(6)
<223> OTHER INFORMATION: /note="2'-OMe modified nucleotide"
<220> FEATURE:
<221> NAME/KEY: misc_feature
<222> LOCATION: (7)..(7)
<223> OTHER INFORMATION: /note="2'-OMe modified nucleotide"
<220> FEATURE:
<221> NAME/KEY: misc_feature
<222> LOCATION: (8)..(8)
<223> OTHER INFORMATION: /note="2'-F modified nucleotide"
<220> FEATURE:
<221> NAME/KEY: misc_feature
```

<222> LOCATION: (9)..(9)
<223> OTHER INFORMATION: /note="2'-F modified nucleotide"
<220> FEATURE:
<221> NAME/KEY: misc_feature
<222> LOCATION: (10)..(10)
<223> OTHER INFORMATION: /note="2'-F modified nucleotide"
<220> FEATURE:
<221> NAME/KEY: misc_feature
<222> LOCATION: (11)..(11)
<223> OTHER INFORMATION: /note="2'-F modified nucleotide"
<220> FEATURE:
<221> NAME/KEY: misc_feature
<222> LOCATION: (12)..(12)
<223> OTHER INFORMATION: /note="2'-OMe modified nucleotide"
<220> FEATURE:
<221> NAME/KEY: misc_feature
<222> LOCATION: (13)..(13)
<223> OTHER INFORMATION: /note="2'-OMe modified nucleotide"
<220> FEATURE:
<221> NAME/KEY: misc_feature
<222> LOCATION: (14)..(14)
<223> OTHER INFORMATION: /note="2'-OMe modified nucleotide"
<220> FEATURE:
<221> NAME/KEY: misc_feature
<222> LOCATION: (15)..(15)
<223> OTHER INFORMATION: /note="2'-OMe modified nucleotide"
<220> FEATURE:
<221> NAME/KEY: misc_feature
<222> LOCATION: (16)..(16)
<223> OTHER INFORMATION: /note="2'-OMe modified nucleotide"
<220> FEATURE:
<221> NAME/KEY: misc_feature
<222> LOCATION: (17)..(17)
<223> OTHER INFORMATION: /note="2'-OMe modified nucleotide"
<220> FEATURE:
<221> NAME/KEY: misc_feature
<222> LOCATION: (18)..(18)
<223> OTHER INFORMATION: /note="2'-OMe modified nucleotide"
<220> FEATURE:
<221> NAME/KEY: misc_feature
<222> LOCATION: (19)..(19)
<223> OTHER INFORMATION: /note="2'-OMe modified nucleotide"
<220> FEATURE:
<221> NAME/KEY: misc_feature
<222> LOCATION: (20)..(20)
<223> OTHER INFORMATION: /note="2'-OMe modified nucleotide"
<220> FEATURE:
<221> NAME/KEY: misc_feature
<222> LOCATION: (21)..(21)
<223> OTHER INFORMATION: /note="2'-OMe modified nucleotide"
<220> FEATURE:
<221> NAME/KEY: misc_feature
<222> LOCATION: (22)..(22)
<223> OTHER INFORMATION: /note="2'-OMe modified nucleotide"
<220> FEATURE:
<221> NAME/KEY: misc_feature
<222> LOCATION: (23)..(23)
<223> OTHER INFORMATION: /note="2'-OMe modified nucleotide"
<220> FEATURE:
<221> NAME/KEY: misc_feature
<222> LOCATION: (24)..(24)
<223> OTHER INFORMATION: /note="2'-OMe modified nucleotide"
<220> FEATURE:
<221> NAME/KEY: misc_feature
<222> LOCATION: (25)..(25)
<223> OTHER INFORMATION: /note="2'-OMe modified nucleotide"
<220> FEATURE:
<221> NAME/KEY: misc_feature
<222> LOCATION: (26)..(26)
<223> OTHER INFORMATION: /note="2'-OMe modified nucleotide"
<220> FEATURE:
<221> NAME/KEY: misc_feature
<222> LOCATION: (27)..(27)
<223> OTHER INFORMATION: /note="2'-OMe modified nucleotide"
<220> FEATURE:
<221> NAME/KEY: misc_feature
<222> LOCATION: (28)..(28)
<223> OTHER INFORMATION: /note="ademA-GalNAc"
<220> FEATURE:

<221> NAME/KEY: misc_feature
<222> LOCATION: (29)..(29)
<223> OTHER INFORMATION: /note="ademA-GalNAc"
<220> FEATURE:
<221> NAME/KEY: misc_feature
<222> LOCATION: (30)..(30)
<223> OTHER INFORMATION: /note="ademA-GalNAc"
<220> FEATURE:
<221> NAME/KEY: misc_feature
<222> LOCATION: (31)..(31)
<223> OTHER INFORMATION: /note="2'-OMe modified nucleotide"
<220> FEATURE:
<221> NAME/KEY: misc_feature
<222> LOCATION: (32)..(32)
<223> OTHER INFORMATION: /note="2'-OMe modified nucleotide"
<220> FEATURE:
<221> NAME/KEY: misc_feature
<222> LOCATION: (33)..(33)
<223> OTHER INFORMATION: /note="2'-OMe modified nucleotide"
<220> FEATURE:
<221> NAME/KEY: misc_feature
<222> LOCATION: (34)..(34)
<223> OTHER INFORMATION: /note="2'-OMe modified nucleotide"
<220> FEATURE:
<221> NAME/KEY: misc_feature
<222> LOCATION: (35)..(35)
<223> OTHER INFORMATION: /note="2'-OMe modified nucleotide"
<220> FEATURE:
<221> NAME/KEY: misc_feature
<222> LOCATION: (36)..(36)
<223> OTHER INFORMATION: /note="2'-OMe modified nucleotide"

<400> SEQUENCE: 224
auauacucca uagugaagca gcagccgaaa ggcugc 36

<210> SEQ ID NO 225
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: misc_feature
<222> LOCATION: (1)..(1)
<223> OTHER INFORMATION: /note="MePhosphonate-4O-mUs"
<220> FEATURE:
<221> NAME/KEY: misc_feature
<222> LOCATION: (2)..(2)
<223> OTHER INFORMATION: /note="2'-F modified nucleotide with a 3'-phosphorothioate linkage"
<220> FEATURE:
<221> NAME/KEY: misc_feature
<222> LOCATION: (3)..(3)
<223> OTHER INFORMATION: /note="2'-F modified nucleotide with a 3'-phosphorothioate linkage"
<220> FEATURE:
<221> NAME/KEY: misc_feature
<222> LOCATION: (4)..(4)
<223> OTHER INFORMATION: /note="2'-F modified nucleotide"
<220> FEATURE:
<221> NAME/KEY: misc_feature
<222> LOCATION: (5)..(5)
<223> OTHER INFORMATION: /note="2'-F modified nucleotide"
<220> FEATURE:
<221> NAME/KEY: misc_feature
<222> LOCATION: (6)..(6)
<223> OTHER INFORMATION: /note="2'-OMe modified nucleotide"
<220> FEATURE:
<221> NAME/KEY: misc_feature
<222> LOCATION: (7)..(7)
<223> OTHER INFORMATION: /note="2'-F modified nucleotide"
<220> FEATURE:
<221> NAME/KEY: misc_feature
<222> LOCATION: (8)..(8)
<223> OTHER INFORMATION: /note="2'-OMe modified nucleotide"

-continued

<220> FEATURE:
<221> NAME/KEY: misc_feature
<222> LOCATION: (9)..(9)
<223> OTHER INFORMATION: /note="2'-OMe modified nucleotide"
<220> FEATURE:
<221> NAME/KEY: misc_feature
<222> LOCATION: (10)..(10)
<223> OTHER INFORMATION: /note="2'-F modified nucleotide"
<220> FEATURE:
<221> NAME/KEY: misc_feature
<222> LOCATION: (11)..(11)
<223> OTHER INFORMATION: /note="2'-OMe modified nucleotide"
<220> FEATURE:
<221> NAME/KEY: misc_feature
<222> LOCATION: (12)..(12)
<223> OTHER INFORMATION: /note="2'-OMe modified nucleotide"
<220> FEATURE:
<221> NAME/KEY: misc_feature
<222> LOCATION: (13)..(13)
<223> OTHER INFORMATION: /note="2'-OMe modified nucleotide"
<220> FEATURE:
<221> NAME/KEY: misc_feature
<222> LOCATION: (14)..(14)
<223> OTHER INFORMATION: /note="2'-F modified nucleotide"
<220> FEATURE:
<221> NAME/KEY: misc_feature
<222> LOCATION: (15)..(15)
<223> OTHER INFORMATION: /note="2'-OMe modified nucleotide"
<220> FEATURE:
<221> NAME/KEY: misc_feature
<222> LOCATION: (16)..(16)
<223> OTHER INFORMATION: /note="2'-OMe modified nucleotide"
<220> FEATURE:
<221> NAME/KEY: misc_feature
<222> LOCATION: (17)..(17)
<223> OTHER INFORMATION: /note="2'-OMe modified nucleotide"
<220> FEATURE:
<221> NAME/KEY: misc_feature
<222> LOCATION: (18)..(18)
<223> OTHER INFORMATION: /note="2'-OMe modified nucleotide"
<220> FEATURE:
<221> NAME/KEY: misc_feature
<222> LOCATION: (19)..(19)
<223> OTHER INFORMATION: /note="2'-OMe modified nucleotide"
<220> FEATURE:
<221> NAME/KEY: misc_feature
<222> LOCATION: (20)..(20)
<223> OTHER INFORMATION: /note="2'-OMe modified nucleotide with a
3'-phosphorothioate linkage"
<220> FEATURE:
<221> NAME/KEY: misc_feature
<222> LOCATION: (21)..(21)
<223> OTHER INFORMATION: /note="2'-OMe modified nucleotide with a
3'-phosphorothioate linkage"
<220> FEATURE:
<221> NAME/KEY: misc_feature
<222> LOCATION: (22)..(22)
<223> OTHER INFORMATION: /note="2'-OMe modified nucleotide"

<400> SEQUENCE: 225
ugcuucacua uggaguauau gg 22

<210> SEQ ID NO 226
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: misc_feature
<222> LOCATION: (1)..(1)
<223> OTHER INFORMATION: /note="2'-OMe modified nucleotide with a
3'-phosphorothioate linkage"
<220> FEATURE:
<221> NAME/KEY: misc_feature
<222> LOCATION: (2)..(2)
<223> OTHER INFORMATION: /note="2'-OMe modified nucleotide"
<220> FEATURE:
<221> NAME/KEY: misc_feature
<222> LOCATION: (3)..(3)
<223> OTHER INFORMATION: /note="2'-OMe modified nucleotide"
<220> FEATURE:
<221> NAME/KEY: misc_feature
<222> LOCATION: (4)..(4)
<223> OTHER INFORMATION: /note="2'-OMe modified nucleotide"
<220> FEATURE:
<221> NAME/KEY: misc_feature
<222> LOCATION: (5)..(5)
<223> OTHER INFORMATION: /note="2'-OMe modified nucleotide"
<220> FEATURE:
<221> NAME/KEY: misc_feature
<222> LOCATION: (6)..(6)
<223> OTHER INFORMATION: /note="2'-OMe modified nucleotide"
<220> FEATURE:
<221> NAME/KEY: misc_feature
<222> LOCATION: (7)..(7)
<223> OTHER INFORMATION: /note="2'-OMe modified nucleotide"
<220> FEATURE:
<221> NAME/KEY: misc_feature
<222> LOCATION: (8)..(8)
<223> OTHER INFORMATION: /note="2'-F modified nucleotide"
<220> FEATURE:
<221> NAME/KEY: misc_feature
<222> LOCATION: (9)..(9)
<223> OTHER INFORMATION: /note="2'-F modified nucleotide"
<220> FEATURE:
<221> NAME/KEY: misc_feature
<222> LOCATION: (10)..(10)
<223> OTHER INFORMATION: /note="2'-F modified nucleotide"
<220> FEATURE:
<221> NAME/KEY: misc_feature
<222> LOCATION: (11)..(11)
<223> OTHER INFORMATION: /note="2'-F modified nucleotide"
<220> FEATURE:
<221> NAME/KEY: misc_feature
<222> LOCATION: (12)..(12)
<223> OTHER INFORMATION: /note="2'-OMe modified nucleotide"
<220> FEATURE:
<221> NAME/KEY: misc_feature
<222> LOCATION: (13)..(13)
<223> OTHER INFORMATION: /note="2'-OMe modified nucleotide"
<220> FEATURE:
<221> NAME/KEY: misc_feature
<222> LOCATION: (14)..(14)
<223> OTHER INFORMATION: /note="2'-OMe modified nucleotide"
<220> FEATURE:
<221> NAME/KEY: misc_feature
<222> LOCATION: (15)..(15)
<223> OTHER INFORMATION: /note="2'-OMe modified nucleotide"
<220> FEATURE:
<221> NAME/KEY: misc_feature
<222> LOCATION: (16)..(16)
<223> OTHER INFORMATION: /note="2'-OMe modified nucleotide"
<220> FEATURE:
<221> NAME/KEY: misc_feature
<222> LOCATION: (17)..(17)
<223> OTHER INFORMATION: /note="2'-OMe modified nucleotide"
<220> FEATURE:
<221> NAME/KEY: misc_feature
<222> LOCATION: (18)..(18)
<223> OTHER INFORMATION: /note="2'-OMe modified nucleotide"
<220> FEATURE:
<221> NAME/KEY: misc_feature
<222> LOCATION: (19)..(19)
<223> OTHER INFORMATION: /note="2'-OMe modified nucleotide"
<220> FEATURE:
<221> NAME/KEY: misc_feature
<222> LOCATION: (20)..(20)
<223> OTHER INFORMATION: /note="2'-OMe modified nucleotide"
<220> FEATURE:
<221> NAME/KEY: misc_feature
<222> LOCATION: (21)..(21)
<223> OTHER INFORMATION: /note="2'-OMe modified nucleotide"
<220> FEATURE:

<221> NAME/KEY: misc_feature
<222> LOCATION: (22)..(22)
<223> OTHER INFORMATION: /note="2'-OMe modified nucleotide"
<220> FEATURE:
<221> NAME/KEY: misc_feature
<222> LOCATION: (23)..(23)
<223> OTHER INFORMATION: /note="2'-OMe modified nucleotide"
<220> FEATURE:
<221> NAME/KEY: misc_feature
<222> LOCATION: (24)..(24)
<223> OTHER INFORMATION: /note="2'-OMe modified nucleotide"
<220> FEATURE:
<221> NAME/KEY: misc_feature
<222> LOCATION: (25)..(25)
<223> OTHER INFORMATION: /note="2'-OMe modified nucleotide"
<220> FEATURE:
<221> NAME/KEY: misc_feature
<222> LOCATION: (26)..(26)
<223> OTHER INFORMATION: /note="2'-OMe modified nucleotide"
<220> FEATURE:
<221> NAME/KEY: misc_feature
<222> LOCATION: (27)..(27)
<223> OTHER INFORMATION: /note="2'-OMe modified nucleotide"
<220> FEATURE:
<221> NAME/KEY: misc_feature
<222> LOCATION: (28)..(28)
<223> OTHER INFORMATION: /note="ademA-GalNAc"
<220> FEATURE:
<221> NAME/KEY: misc_feature
<222> LOCATION: (29)..(29)
<223> OTHER INFORMATION: /note="ademA-GalNAc"
<220> FEATURE:
<221> NAME/KEY: misc_feature
<222> LOCATION: (30)..(30)
<223> OTHER INFORMATION: /note="ademA-GalNAc"
<220> FEATURE:
<221> NAME/KEY: misc_feature
<222> LOCATION: (31)..(31)
<223> OTHER INFORMATION: /note="2'-OMe modified nucleotide"
<220> FEATURE:
<221> NAME/KEY: misc_feature
<222> LOCATION: (32)..(32)
<223> OTHER INFORMATION: /note="2'-OMe modified nucleotide"
<220> FEATURE:
<221> NAME/KEY: misc_feature
<222> LOCATION: (33)..(33)
<223> OTHER INFORMATION: /note="2'-OMe modified nucleotide"
<220> FEATURE:
<221> NAME/KEY: misc_feature
<222> LOCATION: (34)..(34)
<223> OTHER INFORMATION: /note="2'-OMe modified nucleotide"
<220> FEATURE:
<221> NAME/KEY: misc_feature
<222> LOCATION: (35)..(35)
<223> OTHER INFORMATION: /note="2'-OMe modified nucleotide"
<220> FEATURE:
<221> NAME/KEY: misc_feature
<222> LOCATION: (36)..(36)
<223> OTHER INFORMATION: /note="2'-OMe modified nucleotide"

<400> SEQUENCE: 226
uacuccauag ugaagcaaua gcagccgaaa ggcugc 36

<210> SEQ ID NO 227
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: misc_feature
<222> LOCATION: (1)..(1)
<223> OTHER INFORMATION: /note="MePhosphonate-4O-mUs"
<220> FEATURE:
<221> NAME/KEY: misc_feature
<222> LOCATION: (2)..(2)
<223> OTHER INFORMATION: /note="2'-F modified nucleotide with a
3'-phosphorothioate linkage"
<220> FEATURE:
<221> NAME/KEY: misc_feature
<222> LOCATION: (3)..(3)
<223> OTHER INFORMATION: /note="2'-F modified nucleotide with a
3'-phosphorothioate linkage"
<220> FEATURE:
<221> NAME/KEY: misc_feature
<222> LOCATION: (4)..(4)
<223> OTHER INFORMATION: /note="2'-F modified nucleotide"
<220> FEATURE:
<221> NAME/KEY: misc_feature
<222> LOCATION: (5)..(5)
<223> OTHER INFORMATION: /note="2'-F modified nucleotide"
<220> FEATURE:
<221> NAME/KEY: misc_feature
<222> LOCATION: (6)..(6)
<223> OTHER INFORMATION: /note="2'-OMe modified nucleotide"
<220> FEATURE:
<221> NAME/KEY: misc_feature
<222> LOCATION: (7)..(7)
<223> OTHER INFORMATION: /note="2'-F modified nucleotide"
<220> FEATURE:
<221> NAME/KEY: misc_feature
<222> LOCATION: (8)..(8)
<223> OTHER INFORMATION: /note="2'-OMe modified nucleotide"
<220> FEATURE:
<221> NAME/KEY: misc_feature
<222> LOCATION: (9)..(9)
<223> OTHER INFORMATION: /note="2'-OMe modified nucleotide"
<220> FEATURE:
<221> NAME/KEY: misc_feature
<222> LOCATION: (10)..(10)
<223> OTHER INFORMATION: /note="2'-F modified nucleotide"
<220> FEATURE:
<221> NAME/KEY: misc_feature
<222> LOCATION: (11)..(11)
<223> OTHER INFORMATION: /note="2'-OMe modified nucleotide"
<220> FEATURE:
<221> NAME/KEY: misc_feature
<222> LOCATION: (12)..(12)
<223> OTHER INFORMATION: /note="2'-OMe modified nucleotide"
<220> FEATURE:
<221> NAME/KEY: misc_feature
<222> LOCATION: (13)..(13)
<223> OTHER INFORMATION: /note="2'-OMe modified nucleotide"
<220> FEATURE:
<221> NAME/KEY: misc_feature
<222> LOCATION: (14)..(14)
<223> OTHER INFORMATION: /note="2'-F modified nucleotide"
<220> FEATURE:
<221> NAME/KEY: misc_feature
<222> LOCATION: (15)..(15)
<223> OTHER INFORMATION: /note="2'-OMe modified nucleotide"
<220> FEATURE:
<221> NAME/KEY: misc_feature
<222> LOCATION: (16)..(16)
<223> OTHER INFORMATION: /note="2'-OMe modified nucleotide"
<220> FEATURE:
<221> NAME/KEY: misc_feature
<222> LOCATION: (17)..(17)
<223> OTHER INFORMATION: /note="2'-OMe modified nucleotide"
<220> FEATURE:
<221> NAME/KEY: misc_feature
<222> LOCATION: (18)..(18)
<223> OTHER INFORMATION: /note="2'-OMe modified nucleotide"
<220> FEATURE:
<221> NAME/KEY: misc_feature
<222> LOCATION: (19)..(19)
<223> OTHER INFORMATION: /note="2'-OMe modified nucleotide"
<220> FEATURE:
<221> NAME/KEY: misc_feature
<222> LOCATION: (20)..(20)
<223> OTHER INFORMATION: /note="2'-OMe modified nucleotide with a
3'-phosphorothioate linkage"
<220> FEATURE:
<221> NAME/KEY: misc_feature
<222> LOCATION: (21)..(21)
<223> OTHER INFORMATION: /note="2'-OMe modified nucleotide with a 3'-phosphorothioate linkage"
<220> FEATURE:
<221> NAME/KEY: misc_feature
<222> LOCATION: (22)..(22)
<223> OTHER INFORMATION: /note="2'-OMe modified nucleotide"

<400> SEQUENCE: 227
uauugcuuca cuauggagua gg 22

<210> SEQ ID NO 228
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: misc_feature
<222> LOCATION: (1)..(1)
<223> OTHER INFORMATION: /note="2'-OMe modified nucleotide with a 3'-phosphorothioate linkage"
<220> FEATURE:
<221> NAME/KEY: misc_feature
<222> LOCATION: (2)..(2)
<223> OTHER INFORMATION: /note="2'-OMe modified nucleotide"
<220> FEATURE:
<221> NAME/KEY: misc_feature
<222> LOCATION: (3)..(3)
<223> OTHER INFORMATION: /note="2'-OMe modified nucleotide"
<220> FEATURE:
<221> NAME/KEY: misc_feature
<222> LOCATION: (4)..(4)
<223> OTHER INFORMATION: /note="2'-OMe modified nucleotide"
<220> FEATURE:
<221> NAME/KEY: misc_feature
<222> LOCATION: (5)..(5)
<223> OTHER INFORMATION: /note="2'-OMe modified nucleotide"
<220> FEATURE:
<221> NAME/KEY: misc_feature
<222> LOCATION: (6)..(6)
<223> OTHER INFORMATION: /note="2'-OMe modified nucleotide"
<220> FEATURE:
<221> NAME/KEY: misc_feature
<222> LOCATION: (7)..(7)
<223> OTHER INFORMATION: /note="2'-OMe modified nucleotide"
<220> FEATURE:
<221> NAME/KEY: misc_feature
<222> LOCATION: (8)..(8)
<223> OTHER INFORMATION: /note="2'-F modified nucleotide"
<220> FEATURE:
<221> NAME/KEY: misc_feature
<222> LOCATION: (9)..(9)
<223> OTHER INFORMATION: /note="2'-F modified nucleotide"
<220> FEATURE:
<221> NAME/KEY: misc_feature
<222> LOCATION: (10)..(10)
<223> OTHER INFORMATION: /note="2'-F modified nucleotide"
<220> FEATURE:
<221> NAME/KEY: misc_feature
<222> LOCATION: (11)..(11)
<223> OTHER INFORMATION: /note="2'-F modified nucleotide"
<220> FEATURE:
<221> NAME/KEY: misc_feature
<222> LOCATION: (12)..(12)
<223> OTHER INFORMATION: /note="2'-OMe modified nucleotide"
<220> FEATURE:
<221> NAME/KEY: misc_feature
<222> LOCATION: (13)..(13)
<223> OTHER INFORMATION: /note="2'-OMe modified nucleotide"
<220> FEATURE:
<221> NAME/KEY: misc_feature
<222> LOCATION: (14)..(14)
<223> OTHER INFORMATION: /note="2'-OMe modified nucleotide"
<220> FEATURE:

-continued

<221> NAME/KEY: misc_feature
<222> LOCATION: (15)..(15)
<223> OTHER INFORMATION: /note="2'-OMe modified nucleotide"
<220> FEATURE:
<221> NAME/KEY: misc_feature
<222> LOCATION: (16)..(16)
<223> OTHER INFORMATION: /note="2'-OMe modified nucleotide"
<220> FEATURE:
<221> NAME/KEY: misc_feature
<222> LOCATION: (17)..(17)
<223> OTHER INFORMATION: /note="2'-OMe modified nucleotide"
<220> FEATURE:
<221> NAME/KEY: misc_feature
<222> LOCATION: (18)..(18)
<223> OTHER INFORMATION: /note="2'-OMe modified nucleotide"
<220> FEATURE:
<221> NAME/KEY: misc_feature
<222> LOCATION: (19)..(19)
<223> OTHER INFORMATION: /note="2'-OMe modified nucleotide"
<220> FEATURE:
<221> NAME/KEY: misc_feature
<222> LOCATION: (20)..(20)
<223> OTHER INFORMATION: /note="2'-OMe modified nucleotide"
<220> FEATURE:
<221> NAME/KEY: misc_feature
<222> LOCATION: (21)..(21)
<223> OTHER INFORMATION: /note="2'-OMe modified nucleotide"
<220> FEATURE:
<221> NAME/KEY: misc_feature
<222> LOCATION: (22)..(22)
<223> OTHER INFORMATION: /note="2'-OMe modified nucleotide"
<220> FEATURE:
<221> NAME/KEY: misc_feature
<222> LOCATION: (23)..(23)
<223> OTHER INFORMATION: /note="2'-OMe modified nucleotide"
<220> FEATURE:
<221> NAME/KEY: misc_feature
<222> LOCATION: (24)..(24)
<223> OTHER INFORMATION: /note="2'-OMe modified nucleotide"
<220> FEATURE:
<221> NAME/KEY: misc_feature
<222> LOCATION: (25)..(25)
<223> OTHER INFORMATION: /note="2'-OMe modified nucleotide"
<220> FEATURE:
<221> NAME/KEY: misc_feature
<222> LOCATION: (26)..(26)
<223> OTHER INFORMATION: /note="2'-OMe modified nucleotide"
<220> FEATURE:
<221> NAME/KEY: misc_feature
<222> LOCATION: (27)..(27)
<223> OTHER INFORMATION: /note="2'-OMe modified nucleotide"
<220> FEATURE:
<221> NAME/KEY: misc_feature
<222> LOCATION: (28)..(28)
<223> OTHER INFORMATION: /note="ademA-GalNAc"
<220> FEATURE:
<221> NAME/KEY: misc_feature
<222> LOCATION: (29)..(29)
<223> OTHER INFORMATION: /note="ademA-GalNAc"
<220> FEATURE:
<221> NAME/KEY: misc_feature
<222> LOCATION: (30)..(30)
<223> OTHER INFORMATION: /note="ademA-GalNAc"
<220> FEATURE:
<221> NAME/KEY: misc_feature
<222> LOCATION: (31)..(31)
<223> OTHER INFORMATION: /note="2'-OMe modified nucleotide"
<220> FEATURE:
<221> NAME/KEY: misc_feature
<222> LOCATION: (32)..(32)
<223> OTHER INFORMATION: /note="2'-OMe modified nucleotide"
<220> FEATURE:
<221> NAME/KEY: misc_feature
<222> LOCATION: (33)..(33)
<223> OTHER INFORMATION: /note="2'-OMe modified nucleotide"
<220> FEATURE:
<221> NAME/KEY: misc_feature
<222> LOCATION: (34)..(34)
<223> OTHER INFORMATION: /note="2'-OMe modified nucleotide"

<220> FEATURE:
<221> NAME/KEY: misc_feature
<222> LOCATION: (35)..(35)
<223> OTHER INFORMATION: /note="2'-OMe modified nucleotide"
<220> FEATURE:
<221> NAME/KEY: misc_feature
<222> LOCATION: (36)..(36)
<223> OTHER INFORMATION: /note="2'-OMe modified nucleotide"

<400> SEQUENCE: 228
auagugaagc aaucuaauua gcagccgaaa ggcugc 36

<210> SEQ ID NO 229
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: misc_feature
<222> LOCATION: (1)..(1)
<223> OTHER INFORMATION: /note="MePhosphonate-4O-mUs"
<220> FEATURE:
<221> NAME/KEY: misc_feature
<222> LOCATION: (2)..(2)
<223> OTHER INFORMATION: /note="2'-F modified nucleotide with a 3'-phosphorothioate linkage"
<220> FEATURE:
<221> NAME/KEY: misc_feature
<222> LOCATION: (3)..(3)
<223> OTHER INFORMATION: /note="2'-F modified nucleotide with a 3'-phosphorothioate linkage"
<220> FEATURE:
<221> NAME/KEY: misc_feature
<222> LOCATION: (4)..(4)
<223> OTHER INFORMATION: /note="2'-F modified nucleotide"
<220> FEATURE:
<221> NAME/KEY: misc_feature
<222> LOCATION: (5)..(5)
<223> OTHER INFORMATION: /note="2'-F modified nucleotide"
<220> FEATURE:
<221> NAME/KEY: misc_feature
<222> LOCATION: (6)..(6)
<223> OTHER INFORMATION: /note="2'-OMe modified nucleotide"
<220> FEATURE:
<221> NAME/KEY: misc_feature
<222> LOCATION: (7)..(7)
<223> OTHER INFORMATION: /note="2'-F modified nucleotide"
<220> FEATURE:
<221> NAME/KEY: misc_feature
<222> LOCATION: (8)..(8)
<223> OTHER INFORMATION: /note="2'-OMe modified nucleotide"
<220> FEATURE:
<221> NAME/KEY: misc_feature
<222> LOCATION: (9)..(9)
<223> OTHER INFORMATION: /note="2'-OMe modified nucleotide"
<220> FEATURE:
<221> NAME/KEY: misc_feature
<222> LOCATION: (10)..(10)
<223> OTHER INFORMATION: /note="2'-F modified nucleotide"
<220> FEATURE:
<221> NAME/KEY: misc_feature
<222> LOCATION: (11)..(11)
<223> OTHER INFORMATION: /note="2'-OMe modified nucleotide"
<220> FEATURE:
<221> NAME/KEY: misc_feature
<222> LOCATION: (12)..(12)
<223> OTHER INFORMATION: /note="2'-OMe modified nucleotide"
<220> FEATURE:
<221> NAME/KEY: misc_feature
<222> LOCATION: (13)..(13)
<223> OTHER INFORMATION: /note="2'-OMe modified nucleotide"
<220> FEATURE:
<221> NAME/KEY: misc_feature
<222> LOCATION: (14)..(14)

<223> OTHER INFORMATION: /note="2'-F modified nucleotide"
<220> FEATURE:
<221> NAME/KEY: misc_feature
<222> LOCATION: (15)..(15)
<223> OTHER INFORMATION: /note="2'-OMe modified nucleotide"
<220> FEATURE:
<221> NAME/KEY: misc_feature
<222> LOCATION: (16)..(16)
<223> OTHER INFORMATION: /note="2'-OMe modified nucleotide"
<220> FEATURE:
<221> NAME/KEY: misc_feature
<222> LOCATION: (17)..(17)
<223> OTHER INFORMATION: /note="2'-OMe modified nucleotide"
<220> FEATURE:
<221> NAME/KEY: misc_feature
<222> LOCATION: (18)..(18)
<223> OTHER INFORMATION: /note="2'-OMe modified nucleotide"
<220> FEATURE:
<221> NAME/KEY: misc_feature
<222> LOCATION: (19)..(19)
<223> OTHER INFORMATION: /note="2'-OMe modified nucleotide"
<220> FEATURE:
<221> NAME/KEY: misc_feature
<222> LOCATION: (20)..(20)
<223> OTHER INFORMATION: /note="2'-OMe modified nucleotide with a 3'-phosphorothioate linkage"
<220> FEATURE:
<221> NAME/KEY: misc_feature
<222> LOCATION: (21)..(21)
<223> OTHER INFORMATION: /note="2'-OMe modified nucleotide with a 3'-phosphorothioate linkage"
<220> FEATURE:
<221> NAME/KEY: misc_feature
<222> LOCATION: (22)..(22)
<223> OTHER INFORMATION: /note="2'-OMe modified nucleotide"

<400> SEQUENCE: 229
uaauuagauu gcuucacuau gg 22

<210> SEQ ID NO 230
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: misc_feature
<222> LOCATION: (1)..(1)
<223> OTHER INFORMATION: /note="2'-OMe modified nucleotide with a 3'-phosphorothioate linkage"
<220> FEATURE:
<221> NAME/KEY: misc_feature
<222> LOCATION: (2)..(2)
<223> OTHER INFORMATION: /note="2'-OMe modified nucleotide"
<220> FEATURE:
<221> NAME/KEY: misc_feature
<222> LOCATION: (3)..(3)
<223> OTHER INFORMATION: /note="2'-OMe modified nucleotide"
<220> FEATURE:
<221> NAME/KEY: misc_feature
<222> LOCATION: (4)..(4)
<223> OTHER INFORMATION: /note="2'-OMe modified nucleotide"
<220> FEATURE:
<221> NAME/KEY: misc_feature
<222> LOCATION: (5)..(5)
<223> OTHER INFORMATION: /note="2'-OMe modified nucleotide"
<220> FEATURE:
<221> NAME/KEY: misc_feature
<222> LOCATION: (6)..(6)
<223> OTHER INFORMATION: /note="2'-OMe modified nucleotide"
<220> FEATURE:
<221> NAME/KEY: misc_feature
<222> LOCATION: (7)..(7)
<223> OTHER INFORMATION: /note="2'-OMe modified nucleotide"
<220> FEATURE:

<221> NAME/KEY: misc_feature
<222> LOCATION: (8)..(8)
<223> OTHER INFORMATION: /note="2'-F modified nucleotide"
<220> FEATURE:
<221> NAME/KEY: misc_feature
<222> LOCATION: (9)..(9)
<223> OTHER INFORMATION: /note="2'-F modified nucleotide"
<220> FEATURE:
<221> NAME/KEY: misc_feature
<222> LOCATION: (10)..(10)
<223> OTHER INFORMATION: /note="2'-F modified nucleotide"
<220> FEATURE:
<221> NAME/KEY: misc_feature
<222> LOCATION: (11)..(11)
<223> OTHER INFORMATION: /note="2'-F modified nucleotide"
<220> FEATURE:
<221> NAME/KEY: misc_feature
<222> LOCATION: (12)..(12)
<223> OTHER INFORMATION: /note="2'-OMe modified nucleotide"
<220> FEATURE:
<221> NAME/KEY: misc_feature
<222> LOCATION: (13)..(13)
<223> OTHER INFORMATION: /note="2'-OMe modified nucleotide"
<220> FEATURE:
<221> NAME/KEY: misc_feature
<222> LOCATION: (14)..(14)
<223> OTHER INFORMATION: /note="2'-OMe modified nucleotide"
<220> FEATURE:
<221> NAME/KEY: misc_feature
<222> LOCATION: (15)..(15)
<223> OTHER INFORMATION: /note="2'-OMe modified nucleotide"
<220> FEATURE:
<221> NAME/KEY: misc_feature
<222> LOCATION: (16)..(16)
<223> OTHER INFORMATION: /note="2'-OMe modified nucleotide"
<220> FEATURE:
<221> NAME/KEY: misc_feature
<222> LOCATION: (17)..(17)
<223> OTHER INFORMATION: /note="2'-OMe modified nucleotide"
<220> FEATURE:
<221> NAME/KEY: misc_feature
<222> LOCATION: (18)..(18)
<223> OTHER INFORMATION: /note="2'-OMe modified nucleotide"
<220> FEATURE:
<221> NAME/KEY: misc_feature
<222> LOCATION: (19)..(19)
<223> OTHER INFORMATION: /note="2'-OMe modified nucleotide"
<220> FEATURE:
<221> NAME/KEY: misc_feature
<222> LOCATION: (20)..(20)
<223> OTHER INFORMATION: /note="2'-OMe modified nucleotide"
<220> FEATURE:
<221> NAME/KEY: misc_feature
<222> LOCATION: (21)..(21)
<223> OTHER INFORMATION: /note="2'-OMe modified nucleotide"
<220> FEATURE:
<221> NAME/KEY: misc_feature
<222> LOCATION: (22)..(22)
<223> OTHER INFORMATION: /note="2'-OMe modified nucleotide"
<220> FEATURE:
<221> NAME/KEY: misc_feature
<222> LOCATION: (23)..(23)
<223> OTHER INFORMATION: /note="2'-OMe modified nucleotide"
<220> FEATURE:
<221> NAME/KEY: misc_feature
<222> LOCATION: (24)..(24)
<223> OTHER INFORMATION: /note="2'-OMe modified nucleotide"
<220> FEATURE:
<221> NAME/KEY: misc_feature
<222> LOCATION: (25)..(25)
<223> OTHER INFORMATION: /note="2'-OMe modified nucleotide"
<220> FEATURE:
<221> NAME/KEY: misc_feature
<222> LOCATION: (26)..(26)
<223> OTHER INFORMATION: /note="2'-OMe modified nucleotide"
<220> FEATURE:
<221> NAME/KEY: misc_feature
<222> LOCATION: (27)..(27)
<223> OTHER INFORMATION: /note="2'-OMe modified nucleotide"

<220> FEATURE:
<221> NAME/KEY: misc_feature
<222> LOCATION: (28)..(28)
<223> OTHER INFORMATION: /note="ademA-GalNAc"
<220> FEATURE:
<221> NAME/KEY: misc_feature
<222> LOCATION: (29)..(29)
<223> OTHER INFORMATION: /note="ademA-GalNAc"
<220> FEATURE:
<221> NAME/KEY: misc_feature
<222> LOCATION: (30)..(30)
<223> OTHER INFORMATION: /note="ademA-GalNAc"
<220> FEATURE:
<221> NAME/KEY: misc_feature
<222> LOCATION: (31)..(31)
<223> OTHER INFORMATION: /note="2'-OMe modified nucleotide"
<220> FEATURE:
<221> NAME/KEY: misc_feature
<222> LOCATION: (32)..(32)
<223> OTHER INFORMATION: /note="2'-OMe modified nucleotide"
<220> FEATURE:
<221> NAME/KEY: misc_feature
<222> LOCATION: (33)..(33)
<223> OTHER INFORMATION: /note="2'-OMe modified nucleotide"
<220> FEATURE:
<221> NAME/KEY: misc_feature
<222> LOCATION: (34)..(34)
<223> OTHER INFORMATION: /note="2'-OMe modified nucleotide"
<220> FEATURE:
<221> NAME/KEY: misc_feature
<222> LOCATION: (35)..(35)
<223> OTHER INFORMATION: /note="2'-OMe modified nucleotide"
<220> FEATURE:
<221> NAME/KEY: misc_feature
<222> LOCATION: (36)..(36)
<223> OTHER INFORMATION: /note="2'-OMe modified nucleotide"

<400> SEQUENCE: 230
ucaaaaugga agguuauaca gcagccgaaa ggcugc 36

<210> SEQ ID NO 231
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: misc_feature
<222> LOCATION: (1)..(1)
<223> OTHER INFORMATION: /note="MePhosphonate-4O-mUs"
<220> FEATURE:
<221> NAME/KEY: misc_feature
<222> LOCATION: (2)..(2)
<223> OTHER INFORMATION: /note="2'-F modified nucleotide with a
3'-phosphorothioate linkage"
<220> FEATURE:
<221> NAME/KEY: misc_feature
<222> LOCATION: (3)..(3)
<223> OTHER INFORMATION: /note="2'-F modified nucleotide with a
3'-phosphorothioate linkage"
<220> FEATURE:
<221> NAME/KEY: misc_feature
<222> LOCATION: (4)..(4)
<223> OTHER INFORMATION: /note="2'-F modified nucleotide"
<220> FEATURE:
<221> NAME/KEY: misc_feature
<222> LOCATION: (5)..(5)
<223> OTHER INFORMATION: /note="2'-F modified nucleotide"
<220> FEATURE:
<221> NAME/KEY: misc_feature
<222> LOCATION: (6)..(6)
<223> OTHER INFORMATION: /note="2'-OMe modified nucleotide"
<220> FEATURE:
<221> NAME/KEY: misc_feature
<222> LOCATION: (7)..(7)

<223> OTHER INFORMATION: /note="2'-F modified nucleotide"
<220> FEATURE:
<221> NAME/KEY: misc_feature
<222> LOCATION: (8)..(8)
<223> OTHER INFORMATION: /note="2'-OMe modified nucleotide"
<220> FEATURE:
<221> NAME/KEY: misc_feature
<222> LOCATION: (9)..(9)
<223> OTHER INFORMATION: /note="2'-OMe modified nucleotide"
<220> FEATURE:
<221> NAME/KEY: misc_feature
<222> LOCATION: (10)..(10)
<223> OTHER INFORMATION: /note="2'-F modified nucleotide"
<220> FEATURE:
<221> NAME/KEY: misc_feature
<222> LOCATION: (11)..(11)
<223> OTHER INFORMATION: /note="2'-OMe modified nucleotide"
<220> FEATURE:
<221> NAME/KEY: misc_feature
<222> LOCATION: (12)..(12)
<223> OTHER INFORMATION: /note="2'-OMe modified nucleotide"
<220> FEATURE:
<221> NAME/KEY: misc_feature
<222> LOCATION: (13)..(13)
<223> OTHER INFORMATION: /note="2'-OMe modified nucleotide"
<220> FEATURE:
<221> NAME/KEY: misc_feature
<222> LOCATION: (14)..(14)
<223> OTHER INFORMATION: /note="2'-F modified nucleotide"
<220> FEATURE:
<221> NAME/KEY: misc_feature
<222> LOCATION: (15)..(15)
<223> OTHER INFORMATION: /note="2'-OMe modified nucleotide"
<220> FEATURE:
<221> NAME/KEY: misc_feature
<222> LOCATION: (16)..(16)
<223> OTHER INFORMATION: /note="2'-OMe modified nucleotide"
<220> FEATURE:
<221> NAME/KEY: misc_feature
<222> LOCATION: (17)..(17)
<223> OTHER INFORMATION: /note="2'-OMe modified nucleotide"
<220> FEATURE:
<221> NAME/KEY: misc_feature
<222> LOCATION: (18)..(18)
<223> OTHER INFORMATION: /note="2'-OMe modified nucleotide"
<220> FEATURE:
<221> NAME/KEY: misc_feature
<222> LOCATION: (19)..(19)
<223> OTHER INFORMATION: /note="2'-OMe modified nucleotide"
<220> FEATURE:
<221> NAME/KEY: misc_feature
<222> LOCATION: (20)..(20)
<223> OTHER INFORMATION: /note="2'-OMe modified nucleotide with a
3'-phosphorothioate linkage"
<220> FEATURE:
<221> NAME/KEY: misc_feature
<222> LOCATION: (21)..(21)
<223> OTHER INFORMATION: /note="2'-OMe modified nucleotide with a
3'-phosphorothioate linkage"
<220> FEATURE:
<221> NAME/KEY: misc_feature
<222> LOCATION: (22)..(22)
<223> OTHER INFORMATION: /note="2'-OMe modified nucleotide"

<400> SEQUENCE: 231
uguauaaccu uccauuuuga gg 22

<210> SEQ ID NO 232
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: misc_feature
<222> LOCATION: (1)..(1)
<223> OTHER INFORMATION: /note="2'-OMe modified nucleotide with a
3'-phosphorothioate linkage"
<220> FEATURE:
<221> NAME/KEY: misc_feature
<222> LOCATION: (2)..(2)
<223> OTHER INFORMATION: /note="2'-OMe modified nucleotide"
<220> FEATURE:
<221> NAME/KEY: misc_feature
<222> LOCATION: (3)..(3)
<223> OTHER INFORMATION: /note="2'-OMe modified nucleotide"
<220> FEATURE:
<221> NAME/KEY: misc_feature
<222> LOCATION: (4)..(4)
<223> OTHER INFORMATION: /note="2'-OMe modified nucleotide"
<220> FEATURE:
<221> NAME/KEY: misc_feature
<222> LOCATION: (5)..(5)
<223> OTHER INFORMATION: /note="2'-OMe modified nucleotide"
<220> FEATURE:
<221> NAME/KEY: misc_feature
<222> LOCATION: (6)..(6)
<223> OTHER INFORMATION: /note="2'-OMe modified nucleotide"
<220> FEATURE:
<221> NAME/KEY: misc_feature
<222> LOCATION: (7)..(7)
<223> OTHER INFORMATION: /note="2'-OMe modified nucleotide"
<220> FEATURE:
<221> NAME/KEY: misc_feature
<222> LOCATION: (8)..(8)
<223> OTHER INFORMATION: /note="2'-F modified nucleotide"
<220> FEATURE:
<221> NAME/KEY: misc_feature
<222> LOCATION: (9)..(9)
<223> OTHER INFORMATION: /note="2'-F modified nucleotide"
<220> FEATURE:
<221> NAME/KEY: misc_feature
<222> LOCATION: (10)..(10)
<223> OTHER INFORMATION: /note="2'-F modified nucleotide"
<220> FEATURE:
<221> NAME/KEY: misc_feature
<222> LOCATION: (11)..(11)
<223> OTHER INFORMATION: /note="2'-F modified nucleotide"
<220> FEATURE:
<221> NAME/KEY: misc_feature
<222> LOCATION: (12)..(12)
<223> OTHER INFORMATION: /note="2'-OMe modified nucleotide"
<220> FEATURE:
<221> NAME/KEY: misc_feature
<222> LOCATION: (13)..(13)
<223> OTHER INFORMATION: /note="2'-OMe modified nucleotide"
<220> FEATURE:
<221> NAME/KEY: misc_feature
<222> LOCATION: (14)..(14)
<223> OTHER INFORMATION: /note="2'-OMe modified nucleotide"
<220> FEATURE:
<221> NAME/KEY: misc_feature
<222> LOCATION: (15)..(15)
<223> OTHER INFORMATION: /note="2'-OMe modified nucleotide"
<220> FEATURE:
<221> NAME/KEY: misc_feature
<222> LOCATION: (16)..(16)
<223> OTHER INFORMATION: /note="2'-OMe modified nucleotide"
<220> FEATURE:
<221> NAME/KEY: misc_feature
<222> LOCATION: (17)..(17)
<223> OTHER INFORMATION: /note="2'-OMe modified nucleotide"
<220> FEATURE:
<221> NAME/KEY: misc_feature
<222> LOCATION: (18)..(18)
<223> OTHER INFORMATION: /note="2'-OMe modified nucleotide"
<220> FEATURE:
<221> NAME/KEY: misc_feature
<222> LOCATION: (19)..(19)
<223> OTHER INFORMATION: /note="2'-OMe modified nucleotide"
<220> FEATURE:
<221> NAME/KEY: misc_feature
<222> LOCATION: (20)..(20)
<223> OTHER INFORMATION: /note="2'-OMe modified nucleotide"

<220> FEATURE:
<221> NAME/KEY: misc_feature
<222> LOCATION: (21)..(21)
<223> OTHER INFORMATION: /note="2'-OMe modified nucleotide"
<220> FEATURE:
<221> NAME/KEY: misc_feature
<222> LOCATION: (22)..(22)
<223> OTHER INFORMATION: /note="2'-OMe modified nucleotide"
<220> FEATURE:
<221> NAME/KEY: misc_feature
<222> LOCATION: (23)..(23)
<223> OTHER INFORMATION: /note="2'-OMe modified nucleotide"
<220> FEATURE:
<221> NAME/KEY: misc_feature
<222> LOCATION: (24)..(24)
<223> OTHER INFORMATION: /note="2'-OMe modified nucleotide"
<220> FEATURE:
<221> NAME/KEY: misc_feature
<222> LOCATION: (25)..(25)
<223> OTHER INFORMATION: /note="2'-OMe modified nucleotide"
<220> FEATURE:
<221> NAME/KEY: misc_feature
<222> LOCATION: (26)..(26)
<223> OTHER INFORMATION: /note="2'-OMe modified nucleotide"
<220> FEATURE:
<221> NAME/KEY: misc_feature
<222> LOCATION: (27)..(27)
<223> OTHER INFORMATION: /note="2'-OMe modified nucleotide"
<220> FEATURE:
<221> NAME/KEY: misc_feature
<222> LOCATION: (28)..(28)
<223> OTHER INFORMATION: /note="ademA-GalNAc"
<220> FEATURE:
<221> NAME/KEY: misc_feature
<222> LOCATION: (29)..(29)
<223> OTHER INFORMATION: /note="ademA-GalNAc"
<220> FEATURE:
<221> NAME/KEY: misc_feature
<222> LOCATION: (30)..(30)
<223> OTHER INFORMATION: /note="ademA-GalNAc"
<220> FEATURE:
<221> NAME/KEY: misc_feature
<222> LOCATION: (31)..(31)
<223> OTHER INFORMATION: /note="2'-OMe modified nucleotide"
<220> FEATURE:
<221> NAME/KEY: misc_feature
<222> LOCATION: (32)..(32)
<223> OTHER INFORMATION: /note="2'-OMe modified nucleotide"
<220> FEATURE:
<221> NAME/KEY: misc_feature
<222> LOCATION: (33)..(33)
<223> OTHER INFORMATION: /note="2'-OMe modified nucleotide"
<220> FEATURE:
<221> NAME/KEY: misc_feature
<222> LOCATION: (34)..(34)
<223> OTHER INFORMATION: /note="2'-OMe modified nucleotide"
<220> FEATURE:
<221> NAME/KEY: misc_feature
<222> LOCATION: (35)..(35)
<223> OTHER INFORMATION: /note="2'-OMe modified nucleotide"
<220> FEATURE:
<221> NAME/KEY: misc_feature
<222> LOCATION: (36)..(36)
<223> OTHER INFORMATION: /note="2'-OMe modified nucleotide"

<400> SEQUENCE: 232
aaauggaagg uuauacucua gcagccgaaa ggcugc 36

<210> SEQ ID NO 233
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:

<221> NAME/KEY: misc_feature
<222> LOCATION: (1)..(1)
<223> OTHER INFORMATION: /note="MePhosphonate-4O-mUs"
<220> FEATURE:
<221> NAME/KEY: misc_feature
<222> LOCATION: (2)..(2)
<223> OTHER INFORMATION: /note="2'-F modified nucleotide with a 3'-phosphorothioate linkage"
<220> FEATURE:
<221> NAME/KEY: misc_feature
<222> LOCATION: (3)..(3)
<223> OTHER INFORMATION: /note="2'-F modified nucleotide with a 3'-phosphorothioate linkage"
<220> FEATURE:
<221> NAME/KEY: misc_feature
<222> LOCATION: (4)..(4)
<223> OTHER INFORMATION: /note="2'-F modified nucleotide"
<220> FEATURE:
<221> NAME/KEY: misc_feature
<222> LOCATION: (5)..(5)
<223> OTHER INFORMATION: /note="2'-F modified nucleotide"
<220> FEATURE:
<221> NAME/KEY: misc_feature
<222> LOCATION: (6)..(6)
<223> OTHER INFORMATION: /note="2'-OMe modified nucleotide"
<220> FEATURE:
<221> NAME/KEY: misc_feature
<222> LOCATION: (7)..(7)
<223> OTHER INFORMATION: /note="2'-F modified nucleotide"
<220> FEATURE:
<221> NAME/KEY: misc_feature
<222> LOCATION: (8)..(8)
<223> OTHER INFORMATION: /note="2'-OMe modified nucleotide"
<220> FEATURE:
<221> NAME/KEY: misc_feature
<222> LOCATION: (9)..(9)
<223> OTHER INFORMATION: /note="2'-OMe modified nucleotide"
<220> FEATURE:
<221> NAME/KEY: misc_feature
<222> LOCATION: (10)..(10)
<223> OTHER INFORMATION: /note="2'-F modified nucleotide"
<220> FEATURE:
<221> NAME/KEY: misc_feature
<222> LOCATION: (11)..(11)
<223> OTHER INFORMATION: /note="2'-OMe modified nucleotide"
<220> FEATURE:
<221> NAME/KEY: misc_feature
<222> LOCATION: (12)..(12)
<223> OTHER INFORMATION: /note="2'-OMe modified nucleotide"
<220> FEATURE:
<221> NAME/KEY: misc_feature
<222> LOCATION: (13)..(13)
<223> OTHER INFORMATION: /note="2'-OMe modified nucleotide"
<220> FEATURE:
<221> NAME/KEY: misc_feature
<222> LOCATION: (14)..(14)
<223> OTHER INFORMATION: /note="2'-F modified nucleotide"
<220> FEATURE:
<221> NAME/KEY: misc_feature
<222> LOCATION: (15)..(15)
<223> OTHER INFORMATION: /note="2'-OMe modified nucleotide"
<220> FEATURE:
<221> NAME/KEY: misc_feature
<222> LOCATION: (16)..(16)
<223> OTHER INFORMATION: /note="2'-OMe modified nucleotide"
<220> FEATURE:
<221> NAME/KEY: misc_feature
<222> LOCATION: (17)..(17)
<223> OTHER INFORMATION: /note="2'-OMe modified nucleotide"
<220> FEATURE:
<221> NAME/KEY: misc_feature
<222> LOCATION: (18)..(18)
<223> OTHER INFORMATION: /note="2'-OMe modified nucleotide"
<220> FEATURE:
<221> NAME/KEY: misc_feature
<222> LOCATION: (19)..(19)
<223> OTHER INFORMATION: /note="2'-OMe modified nucleotide"
<220> FEATURE:
<221> NAME/KEY: misc_feature
<222> LOCATION: (20)..(20)
<223> OTHER INFORMATION: /note="2'-OMe modified nucleotide with a
3'-phosphorothioate linkage"
<220> FEATURE:
<221> NAME/KEY: misc_feature
<222> LOCATION: (21)..(21)
<223> OTHER INFORMATION: /note="2'-OMe modified nucleotide with a
3'-phosphorothioate linkage"
<220> FEATURE:
<221> NAME/KEY: misc_feature
<222> LOCATION: (22)..(22)
<223> OTHER INFORMATION: /note="2'-OMe modified nucleotide"

<400> SEQUENCE: 233
uagaguauaa ccuuccauuu gg 22

<210> SEQ ID NO 234
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: misc_feature
<222> LOCATION: (1)..(1)
<223> OTHER INFORMATION: /note="2'-OMe modified nucleotide with a
3'-phosphorothioate linkage"
<220> FEATURE:
<221> NAME/KEY: misc_feature
<222> LOCATION: (2)..(2)
<223> OTHER INFORMATION: /note="2'-OMe modified nucleotide"
<220> FEATURE:
<221> NAME/KEY: misc_feature
<222> LOCATION: (3)..(3)
<223> OTHER INFORMATION: /note="2'-OMe modified nucleotide"
<220> FEATURE:
<221> NAME/KEY: misc_feature
<222> LOCATION: (4)..(4)
<223> OTHER INFORMATION: /note="2'-OMe modified nucleotide"
<220> FEATURE:
<221> NAME/KEY: misc_feature
<222> LOCATION: (5)..(5)
<223> OTHER INFORMATION: /note="2'-OMe modified nucleotide"
<220> FEATURE:
<221> NAME/KEY: misc_feature
<222> LOCATION: (6)..(6)
<223> OTHER INFORMATION: /note="2'-OMe modified nucleotide"
<220> FEATURE:
<221> NAME/KEY: misc_feature
<222> LOCATION: (7)..(7)
<223> OTHER INFORMATION: /note="2'-OMe modified nucleotide"
<220> FEATURE:
<221> NAME/KEY: misc_feature
<222> LOCATION: (8)..(8)
<223> OTHER INFORMATION: /note="2'-F modified nucleotide"
<220> FEATURE:
<221> NAME/KEY: misc_feature
<222> LOCATION: (9)..(9)
<223> OTHER INFORMATION: /note="2'-F modified nucleotide"
<220> FEATURE:
<221> NAME/KEY: misc_feature
<222> LOCATION: (10)..(10)
<223> OTHER INFORMATION: /note="2'-F modified nucleotide"
<220> FEATURE:
<221> NAME/KEY: misc_feature
<222> LOCATION: (11)..(11)
<223> OTHER INFORMATION: /note="2'-F modified nucleotide"
<220> FEATURE:
<221> NAME/KEY: misc_feature
<222> LOCATION: (12)..(12)
<223> OTHER INFORMATION: /note="2'-OMe modified nucleotide"
<220> FEATURE:
<221> NAME/KEY: misc_feature
<222> LOCATION: (13)..(13)
<223> OTHER INFORMATION: /note="2'-OMe modified nucleotide"

<220> FEATURE:
<221> NAME/KEY: misc_feature
<222> LOCATION: (14)..(14)
<223> OTHER INFORMATION: /note="2'-OMe modified nucleotide"
<220> FEATURE:
<221> NAME/KEY: misc_feature
<222> LOCATION: (15)..(15)
<223> OTHER INFORMATION: /note="2'-OMe modified nucleotide"
<220> FEATURE:
<221> NAME/KEY: misc_feature
<222> LOCATION: (16)..(16)
<223> OTHER INFORMATION: /note="2'-OMe modified nucleotide"
<220> FEATURE:
<221> NAME/KEY: misc_feature
<222> LOCATION: (17)..(17)
<223> OTHER INFORMATION: /note="2'-OMe modified nucleotide"
<220> FEATURE:
<221> NAME/KEY: misc_feature
<222> LOCATION: (18)..(18)
<223> OTHER INFORMATION: /note="2'-OMe modified nucleotide"
<220> FEATURE:
<221> NAME/KEY: misc_feature
<222> LOCATION: (19)..(19)
<223> OTHER INFORMATION: /note="2'-OMe modified nucleotide"
<220> FEATURE:
<221> NAME/KEY: misc_feature
<222> LOCATION: (20)..(20)
<223> OTHER INFORMATION: /note="2'-OMe modified nucleotide"
<220> FEATURE:
<221> NAME/KEY: misc_feature
<222> LOCATION: (21)..(21)
<223> OTHER INFORMATION: /note="2'-OMe modified nucleotide"
<220> FEATURE:
<221> NAME/KEY: misc_feature
<222> LOCATION: (22)..(22)
<223> OTHER INFORMATION: /note="2'-OMe modified nucleotide"
<220> FEATURE:
<221> NAME/KEY: misc_feature
<222> LOCATION: (23)..(23)
<223> OTHER INFORMATION: /note="2'-OMe modified nucleotide"
<220> FEATURE:
<221> NAME/KEY: misc_feature
<222> LOCATION: (24)..(24)
<223> OTHER INFORMATION: /note="2'-OMe modified nucleotide"
<220> FEATURE:
<221> NAME/KEY: misc_feature
<222> LOCATION: (25)..(25)
<223> OTHER INFORMATION: /note="2'-OMe modified nucleotide"
<220> FEATURE:
<221> NAME/KEY: misc_feature
<222> LOCATION: (26)..(26)
<223> OTHER INFORMATION: /note="2'-OMe modified nucleotide"
<220> FEATURE:
<221> NAME/KEY: misc_feature
<222> LOCATION: (27)..(27)
<223> OTHER INFORMATION: /note="2'-OMe modified nucleotide"
<220> FEATURE:
<221> NAME/KEY: misc_feature
<222> LOCATION: (28)..(28)
<223> OTHER INFORMATION: /note="ademA-GalNAc"
<220> FEATURE:
<221> NAME/KEY: misc_feature
<222> LOCATION: (29)..(29)
<223> OTHER INFORMATION: /note="ademA-GalNAc"
<220> FEATURE:
<221> NAME/KEY: misc_feature
<222> LOCATION: (30)..(30)
<223> OTHER INFORMATION: /note="ademA-GalNAc"
<220> FEATURE:
<221> NAME/KEY: misc_feature
<222> LOCATION: (31)..(31)
<223> OTHER INFORMATION: /note="2'-OMe modified nucleotide"
<220> FEATURE:
<221> NAME/KEY: misc_feature
<222> LOCATION: (32)..(32)
<223> OTHER INFORMATION: /note="2'-OMe modified nucleotide"
<220> FEATURE:
<221> NAME/KEY: misc_feature
<222> LOCATION: (33)..(33)

<223> OTHER INFORMATION: /note="2'-OMe modified nucleotide"
<220> FEATURE:
<221> NAME/KEY: misc_feature
<222> LOCATION: (34)..(34)
<223> OTHER INFORMATION: /note="2'-OMe modified nucleotide"
<220> FEATURE:
<221> NAME/KEY: misc_feature
<222> LOCATION: (35)..(35)
<223> OTHER INFORMATION: /note="2'-OMe modified nucleotide"
<220> FEATURE:
<221> NAME/KEY: misc_feature
<222> LOCATION: (36)..(36)
<223> OTHER INFORMATION: /note="2'-OMe modified nucleotide"

<400> SEQUENCE: 234
gaagguuaua cucuauaaaa gcagccgaaa ggcugc 36

<210> SEQ ID NO 235
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: misc_feature
<222> LOCATION: (1)..(1)
<223> OTHER INFORMATION: /note="MePhosphonate-4O-mUs"
<220> FEATURE:
<221> NAME/KEY: misc_feature
<222> LOCATION: (2)..(2)
<223> OTHER INFORMATION: /note="2'-F modified nucleotide with a 3'-phosphorothioate linkage"
<220> FEATURE:
<221> NAME/KEY: misc_feature
<222> LOCATION: (3)..(3)
<223> OTHER INFORMATION: /note="2'-F modified nucleotide with a 3'-phosphorothioate linkage"
<220> FEATURE:
<221> NAME/KEY: misc_feature
<222> LOCATION: (4)..(4)
<223> OTHER INFORMATION: /note="2'-F modified nucleotide"
<220> FEATURE:
<221> NAME/KEY: misc_feature
<222> LOCATION: (5)..(5)
<223> OTHER INFORMATION: /note="2'-F modified nucleotide"
<220> FEATURE:
<221> NAME/KEY: misc_feature
<222> LOCATION: (6)..(6)
<223> OTHER INFORMATION: /note="2'-OMe modified nucleotide"
<220> FEATURE:
<221> NAME/KEY: misc_feature
<222> LOCATION: (7)..(7)
<223> OTHER INFORMATION: /note="2'-F modified nucleotide"
<220> FEATURE:
<221> NAME/KEY: misc_feature
<222> LOCATION: (8)..(8)
<223> OTHER INFORMATION: /note="2'-OMe modified nucleotide"
<220> FEATURE:
<221> NAME/KEY: misc_feature
<222> LOCATION: (9)..(9)
<223> OTHER INFORMATION: /note="2'-OMe modified nucleotide"
<220> FEATURE:
<221> NAME/KEY: misc_feature
<222> LOCATION: (10)..(10)
<223> OTHER INFORMATION: /note="2'-F modified nucleotide"
<220> FEATURE:
<221> NAME/KEY: misc_feature
<222> LOCATION: (11)..(11)
<223> OTHER INFORMATION: /note="2'-OMe modified nucleotide"
<220> FEATURE:
<221> NAME/KEY: misc_feature
<222> LOCATION: (12)..(12)
<223> OTHER INFORMATION: /note="2'-OMe modified nucleotide"
<220> FEATURE:
<221> NAME/KEY: misc_feature
<222> LOCATION: (13)..(13)
<223> OTHER INFORMATION: /note="2'-OMe modified nucleotide"
<220> FEATURE:
<221> NAME/KEY: misc_feature
<222> LOCATION: (14)..(14)
<223> OTHER INFORMATION: /note="2'-F modified nucleotide"
<220> FEATURE:
<221> NAME/KEY: misc_feature
<222> LOCATION: (15)..(15)
<223> OTHER INFORMATION: /note="2'-OMe modified nucleotide"
<220> FEATURE:
<221> NAME/KEY: misc_feature
<222> LOCATION: (16)..(16)
<223> OTHER INFORMATION: /note="2'-OMe modified nucleotide"
<220> FEATURE:
<221> NAME/KEY: misc_feature
<222> LOCATION: (17)..(17)
<223> OTHER INFORMATION: /note="2'-OMe modified nucleotide"
<220> FEATURE:
<221> NAME/KEY: misc_feature
<222> LOCATION: (18)..(18)
<223> OTHER INFORMATION: /note="2'-OMe modified nucleotide"
<220> FEATURE:
<221> NAME/KEY: misc_feature
<222> LOCATION: (19)..(19)
<223> OTHER INFORMATION: /note="2'-OMe modified nucleotide"
<220> FEATURE:
<221> NAME/KEY: misc_feature
<222> LOCATION: (20)..(20)
<223> OTHER INFORMATION: /note="2'-OMe modified nucleotide with a
3'-phosphorothioate linkage"
<220> FEATURE:
<221> NAME/KEY: misc_feature
<222> LOCATION: (21)..(21)
<223> OTHER INFORMATION: /note="2'-OMe modified nucleotide with a
3'-phosphorothioate linkage"
<220> FEATURE:
<221> NAME/KEY: misc_feature
<222> LOCATION: (22)..(22)
<223> OTHER INFORMATION: /note="2'-OMe modified nucleotide"

<400> SEQUENCE: 235
uuuuauagag uauaaccuuc gg 22

<210> SEQ ID NO 236
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: misc_feature
<222> LOCATION: (1)..(1)
<223> OTHER INFORMATION: /note="2'-OMe modified nucleotide with a
3'-phosphorothioate linkage"
<220> FEATURE:
<221> NAME/KEY: misc_feature
<222> LOCATION: (2)..(2)
<223> OTHER INFORMATION: /note="2'-OMe modified nucleotide"
<220> FEATURE:
<221> NAME/KEY: misc_feature
<222> LOCATION: (3)..(3)
<223> OTHER INFORMATION: /note="2'-OMe modified nucleotide"
<220> FEATURE:
<221> NAME/KEY: misc_feature
<222> LOCATION: (4)..(4)
<223> OTHER INFORMATION: /note="2'-OMe modified nucleotide"
<220> FEATURE:
<221> NAME/KEY: misc_feature
<222> LOCATION: (5)..(5)
<223> OTHER INFORMATION: /note="2'-OMe modified nucleotide"
<220> FEATURE:
<221> NAME/KEY: misc_feature
<222> LOCATION: (6)..(6)
<223> OTHER INFORMATION: /note="2'-OMe modified nucleotide"

<220> FEATURE:
<221> NAME/KEY: misc_feature
<222> LOCATION: (7)..(7)
<223> OTHER INFORMATION: /note="2'-OMe modified nucleotide"
<220> FEATURE:
<221> NAME/KEY: misc_feature
<222> LOCATION: (8)..(8)
<223> OTHER INFORMATION: /note="2'-F modified nucleotide"
<220> FEATURE:
<221> NAME/KEY: misc_feature
<222> LOCATION: (9)..(9)
<223> OTHER INFORMATION: /note="2'-F modified nucleotide"
<220> FEATURE:
<221> NAME/KEY: misc_feature
<222> LOCATION: (10)..(10)
<223> OTHER INFORMATION: /note="2'-F modified nucleotide"
<220> FEATURE:
<221> NAME/KEY: misc_feature
<222> LOCATION: (11)..(11)
<223> OTHER INFORMATION: /note="2'-F modified nucleotide"
<220> FEATURE:
<221> NAME/KEY: misc_feature
<222> LOCATION: (12)..(12)
<223> OTHER INFORMATION: /note="2'-OMe modified nucleotide"
<220> FEATURE:
<221> NAME/KEY: misc_feature
<222> LOCATION: (13)..(13)
<223> OTHER INFORMATION: /note="2'-OMe modified nucleotide"
<220> FEATURE:
<221> NAME/KEY: misc_feature
<222> LOCATION: (14)..(14)
<223> OTHER INFORMATION: /note="2'-OMe modified nucleotide"
<220> FEATURE:
<221> NAME/KEY: misc_feature
<222> LOCATION: (15)..(15)
<223> OTHER INFORMATION: /note="2'-OMe modified nucleotide"
<220> FEATURE:
<221> NAME/KEY: misc_feature
<222> LOCATION: (16)..(16)
<223> OTHER INFORMATION: /note="2'-OMe modified nucleotide"
<220> FEATURE:
<221> NAME/KEY: misc_feature
<222> LOCATION: (17)..(17)
<223> OTHER INFORMATION: /note="2'-OMe modified nucleotide"
<220> FEATURE:
<221> NAME/KEY: misc_feature
<222> LOCATION: (18)..(18)
<223> OTHER INFORMATION: /note="2'-OMe modified nucleotide"
<220> FEATURE:
<221> NAME/KEY: misc_feature
<222> LOCATION: (19)..(19)
<223> OTHER INFORMATION: /note="2'-OMe modified nucleotide"
<220> FEATURE:
<221> NAME/KEY: misc_feature
<222> LOCATION: (20)..(20)
<223> OTHER INFORMATION: /note="2'-OMe modified nucleotide"
<220> FEATURE:
<221> NAME/KEY: misc_feature
<222> LOCATION: (21)..(21)
<223> OTHER INFORMATION: /note="2'-OMe modified nucleotide"
<220> FEATURE:
<221> NAME/KEY: misc_feature
<222> LOCATION: (22)..(22)
<223> OTHER INFORMATION: /note="2'-OMe modified nucleotide"
<220> FEATURE:
<221> NAME/KEY: misc_feature
<222> LOCATION: (23)..(23)
<223> OTHER INFORMATION: /note="2'-OMe modified nucleotide"
<220> FEATURE:
<221> NAME/KEY: misc_feature
<222> LOCATION: (24)..(24)
<223> OTHER INFORMATION: /note="2'-OMe modified nucleotide"
<220> FEATURE:
<221> NAME/KEY: misc_feature
<222> LOCATION: (25)..(25)
<223> OTHER INFORMATION: /note="2'-OMe modified nucleotide"
<220> FEATURE:
<221> NAME/KEY: misc_feature
<222> LOCATION: (26)..(26)

<223> OTHER INFORMATION: /note="2'-OMe modified nucleotide"
<220> FEATURE:
<221> NAME/KEY: misc_feature
<222> LOCATION: (27)..(27)
<223> OTHER INFORMATION: /note="2'-OMe modified nucleotide"
<220> FEATURE:
<221> NAME/KEY: misc_feature
<222> LOCATION: (28)..(28)
<223> OTHER INFORMATION: /note="ademA-GalNAc"
<220> FEATURE:
<221> NAME/KEY: misc_feature
<222> LOCATION: (29)..(29)
<223> OTHER INFORMATION: /note="ademA-GalNAc"
<220> FEATURE:
<221> NAME/KEY: misc_feature
<222> LOCATION: (30)..(30)
<223> OTHER INFORMATION: /note="ademA-GalNAc"
<220> FEATURE:
<221> NAME/KEY: misc_feature
<222> LOCATION: (31)..(31)
<223> OTHER INFORMATION: /note="2'-OMe modified nucleotide"
<220> FEATURE:
<221> NAME/KEY: misc_feature
<222> LOCATION: (32)..(32)
<223> OTHER INFORMATION: /note="2'-OMe modified nucleotide"
<220> FEATURE:
<221> NAME/KEY: misc_feature
<222> LOCATION: (33)..(33)
<223> OTHER INFORMATION: /note="2'-OMe modified nucleotide"
<220> FEATURE:
<221> NAME/KEY: misc_feature
<222> LOCATION: (34)..(34)
<223> OTHER INFORMATION: /note="2'-OMe modified nucleotide"
<220> FEATURE:
<221> NAME/KEY: misc_feature
<222> LOCATION: (35)..(35)
<223> OTHER INFORMATION: /note="2'-OMe modified nucleotide"
<220> FEATURE:
<221> NAME/KEY: misc_feature
<222> LOCATION: (36)..(36)
<223> OTHER INFORMATION: /note="2'-OMe modified nucleotide"

<400> SEQUENCE: 236
aagguuauac ucuauaaaaa gcagccgaaa ggcugc 36

<210> SEQ ID NO 237
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: misc_feature
<222> LOCATION: (1)..(1)
<223> OTHER INFORMATION: /note="MePhosphonate-4O-mUs"
<220> FEATURE:
<221> NAME/KEY: misc_feature
<222> LOCATION: (2)..(2)
<223> OTHER INFORMATION: /note="2'-F modified nucleotide with a 3'-phosphorothioate linkage"
<220> FEATURE:
<221> NAME/KEY: misc_feature
<222> LOCATION: (3)..(3)
<223> OTHER INFORMATION: /note="2'-F modified nucleotide with a 3'-phosphorothioate linkage"
<220> FEATURE:
<221> NAME/KEY: misc_feature
<222> LOCATION: (4)..(4)
<223> OTHER INFORMATION: /note="2'-F modified nucleotide"
<220> FEATURE:
<221> NAME/KEY: misc_feature
<222> LOCATION: (5)..(5)
<223> OTHER INFORMATION: /note="2'-F modified nucleotide"
<220> FEATURE:
<221> NAME/KEY: misc_feature
<222> LOCATION: (6)..(6)
<223> OTHER INFORMATION: /note="2'-OMe modified nucleotide"
<220> FEATURE:
<221> NAME/KEY: misc_feature
<222> LOCATION: (7)..(7)
<223> OTHER INFORMATION: /note="2'-F modified nucleotide"
<220> FEATURE:
<221> NAME/KEY: misc_feature
<222> LOCATION: (8)..(8)
<223> OTHER INFORMATION: /note="2'-OMe modified nucleotide"
<220> FEATURE:
<221> NAME/KEY: misc_feature
<222> LOCATION: (9)..(9)
<223> OTHER INFORMATION: /note="2'-OMe modified nucleotide"
<220> FEATURE:
<221> NAME/KEY: misc_feature
<222> LOCATION: (10)..(10)
<223> OTHER INFORMATION: /note="2'-F modified nucleotide"
<220> FEATURE:
<221> NAME/KEY: misc_feature
<222> LOCATION: (11)..(11)
<223> OTHER INFORMATION: /note="2'-OMe modified nucleotide"
<220> FEATURE:
<221> NAME/KEY: misc_feature
<222> LOCATION: (12)..(12)
<223> OTHER INFORMATION: /note="2'-OMe modified nucleotide"
<220> FEATURE:
<221> NAME/KEY: misc_feature
<222> LOCATION: (13)..(13)
<223> OTHER INFORMATION: /note="2'-OMe modified nucleotide"
<220> FEATURE:
<221> NAME/KEY: misc_feature
<222> LOCATION: (14)..(14)
<223> OTHER INFORMATION: /note="2'-F modified nucleotide"
<220> FEATURE:
<221> NAME/KEY: misc_feature
<222> LOCATION: (15)..(15)
<223> OTHER INFORMATION: /note="2'-OMe modified nucleotide"
<220> FEATURE:
<221> NAME/KEY: misc_feature
<222> LOCATION: (16)..(16)
<223> OTHER INFORMATION: /note="2'-OMe modified nucleotide"
<220> FEATURE:
<221> NAME/KEY: misc_feature
<222> LOCATION: (17)..(17)
<223> OTHER INFORMATION: /note="2'-OMe modified nucleotide"
<220> FEATURE:
<221> NAME/KEY: misc_feature
<222> LOCATION: (18)..(18)
<223> OTHER INFORMATION: /note="2'-OMe modified nucleotide"
<220> FEATURE:
<221> NAME/KEY: misc_feature
<222> LOCATION: (19)..(19)
<223> OTHER INFORMATION: /note="2'-OMe modified nucleotide"
<220> FEATURE:
<221> NAME/KEY: misc_feature
<222> LOCATION: (20)..(20)
<223> OTHER INFORMATION: /note="2'-OMe modified nucleotide with a 3'-phosphorothioate linkage"
<220> FEATURE:
<221> NAME/KEY: misc_feature
<222> LOCATION: (21)..(21)
<223> OTHER INFORMATION: /note="2'-OMe modified nucleotide with a 3'-phosphorothioate linkage"
<220> FEATURE:
<221> NAME/KEY: misc_feature
<222> LOCATION: (22)..(22)
<223> OTHER INFORMATION: /note="2'-OMe modified nucleotide"

<400> SEQUENCE: 237
uuuuuauaga guauaaccuu gg 22

<210> SEQ ID NO 238
<211> LENGTH: 36
<212> TYPE: RNA
<213> ORGANISM: Artificial Sequence
<220> FEATURE:

<221> NAME/KEY: source
<223> OTHER INFORMATION: /note="Description of Artificial Sequence: Synthetic oligonucleotide"
<220> FEATURE:
<221> NAME/KEY: misc_feature
<222> LOCATION: (1)..(1)
<223> OTHER INFORMATION: /note="2'-OMe modified nucleotide with a 3'-phosphorothioate linkage"
<220> FEATURE:
<221> NAME/KEY: misc_feature
<222> LOCATION: (2)..(2)
<223> OTHER INFORMATION: /note="2'-OMe modified nucleotide"
<220> FEATURE:
<221> NAME/KEY: misc_feature
<222> LOCATION: (3)..(3)
<223> OTHER INFORMATION: /note="2'-OMe modified nucleotide"
<220> FEATURE:
<221> NAME/KEY: misc_feature
<222> LOCATION: (4)..(4)
<223> OTHER INFORMATION: /note="2'-OMe modified nucleotide"
<220> FEATURE:
<221> NAME/KEY: misc_feature
<222> LOCATION: (5)..(5)
<223> OTHER INFORMATION: /note="2'-OMe modified nucleotide"
<220> FEATURE:
<221> NAME/KEY: misc_feature
<222> LOCATION: (6)..(6)
<223> OTHER INFORMATION: /note="2'-OMe modified nucleotide"
<220> FEATURE:
<221> NAME/KEY: misc_feature
<222> LOCATION: (7)..(7)
<223> OTHER INFORMATION: /note="2'-OMe modified nucleotide"
<220> FEATURE:
<221> NAME/KEY: misc_feature
<222> LOCATION: (8)..(8)
<223> OTHER INFORMATION: /note="2'-F modified nucleotide"
<220> FEATURE:
<221> NAME/KEY: misc_feature
<222> LOCATION: (9)..(9)
<223> OTHER INFORMATION: /note="2'-F modified nucleotide"
<220> FEATURE:
<221> NAME/KEY: misc_feature
<222> LOCATION: (10)..(10)
<223> OTHER INFORMATION: /note="2'-F modified nucleotide"
<220> FEATURE:
<221> NAME/KEY: misc_feature
<222> LOCATION: (11)..(11)
<223> OTHER INFORMATION: /note="2'-F modified nucleotide"
<220> FEATURE:
<221> NAME/KEY: misc_feature
<222> LOCATION: (12)..(12)
<223> OTHER INFORMATION: /note="2'-OMe modified nucleotide"
<220> FEATURE:
<221> NAME/KEY: misc_feature
<222> LOCATION: (13)..(13)
<223> OTHER INFORMATION: /note="2'-OMe modified nucleotide"
<220> FEATURE:
<221> NAME/KEY: misc_feature
<222> LOCATION: (14)..(14)
<223> OTHER INFORMATION: /note="2'-OMe modified nucleotide"
<220> FEATURE:
<221> NAME/KEY: misc_feature
<222> LOCATION: (15)..(15)
<223> OTHER INFORMATION: /note="2'-OMe modified nucleotide"
<220> FEATURE:
<221> NAME/KEY: misc_feature
<222> LOCATION: (16)..(16)
<223> OTHER INFORMATION: /note="2'-OMe modified nucleotide"
<220> FEATURE:
<221> NAME/KEY: misc_feature
<222> LOCATION: (17)..(17)
<223> OTHER INFORMATION: /note="2'-OMe modified nucleotide"
<220> FEATURE:
<221> NAME/KEY: misc_feature
<222> LOCATION: (18)..(18)
<223> OTHER INFORMATION: /note="2'-OMe modified nucleotide"
<220> FEATURE:
<221> NAME/KEY: misc_feature
<222> LOCATION: (19)..(19)

<223> OTHER INFORMATION: /note="2'-OMe modified nucleotide"
<220> FEATURE:
<221> NAME/KEY: misc_feature
<222> LOCATION: (20)..(20)
<223> OTHER INFORMATION: /note="2'-OMe modified nucleotide"
<220> FEATURE:
<221> NAME/KEY: misc_feature
<222> LOCATION: (21)..(21)
<223> OTHER INFORMATION: /note="2'-OMe modified nucleotide"
<220> FEATURE:
<221> NAME/KEY: misc_feature
<222> LOCATION: (22)..(22)
<223> OTHER INFORMATION: /note="2'-OMe modified nucleotide"
<220> FEATURE:
<221> NAME/KEY: misc_feature
<222> LOCATION: (23)..(23)
<223> OTHER INFORMATION: /note="2'-OMe modified nucleotide"
<220> FEATURE:
<221> NAME/KEY: misc_feature
<222> LOCATION: (24)..(24)
<223> OTHER INFORMATION: /note="2'-OMe modified nucleotide"
<220> FEATURE:
<221> NAME/KEY: misc_feature
<222> LOCATION: (25)..(25)
<223> OTHER INFORMATION: /note="2'-OMe modified nucleotide"
<220> FEATURE:
<221> NAME/KEY: misc_feature
<222> LOCATION: (26)..(26)
<223> OTHER INFORMATION: /note="2'-OMe modified nucleotide"
<220> FEATURE:
<221> NAME/KEY: misc_feature
<222> LOCATION: (27)..(27)
<223> OTHER INFORMATION: /note="2'-OMe modified nucleotide"
<220> FEATURE:
<221> NAME/KEY: misc_feature
<222> LOCATION: (28)..(28)
<223> OTHER INFORMATION: /note="ademA-GalNAc"
<220> FEATURE:
<221> NAME/KEY: misc_feature
<222> LOCATION: (29)..(29)
<223> OTHER INFORMATION: /note="ademA-GalNAc"
<220> FEATURE:
<221> NAME/KEY: misc_feature
<222> LOCATION: (30)..(30)
<223> OTHER INFORMATION: /note="ademA-GalNAc"
<220> FEATURE:
<221> NAME/KEY: misc_feature
<222> LOCATION: (31)..(31)
<223> OTHER INFORMATION: /note="2'-OMe modified nucleotide"
<220> FEATURE:
<221> NAME/KEY: misc_feature
<222> LOCATION: (32)..(32)
<223> OTHER INFORMATION: /note="2'-OMe modified nucleotide"
<220> FEATURE:
<221> NAME/KEY: misc_feature
<222> LOCATION: (33)..(33)
<223> OTHER INFORMATION: /note="2'-OMe modified nucleotide"
<220> FEATURE:
<221> NAME/KEY: misc_feature
<222> LOCATION: (34)..(34)
<223> OTHER INFORMATION: /note="2'-OMe modified nucleotide"
<220> FEATURE:
<221> NAME/KEY: misc_feature
<222> LOCATION: (35)..(35)
<223> OTHER INFORMATION: /note="2'-OMe modified nucleotide"
<220> FEATURE:
<221> NAME/KEY: misc_feature
<222> LOCATION: (36)..(36)
<223> OTHER INFORMATION: /note="2'-OMe modified nucleotide"

<400> SEQUENCE: 238
agguuauacu cuauaaaaua gcagccgaaa ggcugc 36

<210> SEQ ID NO 239
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: misc_feature
<222> LOCATION: (1)..(1)
<223> OTHER INFORMATION: /note="MePhosphonate-4O-mUs"
<220> FEATURE:
<221> NAME/KEY: misc_feature
<222> LOCATION: (2)..(2)
<223> OTHER INFORMATION: /note="2'-F modified nucleotide with a
3'-phosphorothioate linkage"
<220> FEATURE:
<221> NAME/KEY: misc_feature
<222> LOCATION: (3)..(3)
<223> OTHER INFORMATION: /note="2'-F modified nucleotide with a
3'-phosphorothioate linkage"
<220> FEATURE:
<221> NAME/KEY: misc_feature
<222> LOCATION: (4)..(4)
<223> OTHER INFORMATION: /note="2'-F modified nucleotide"
<220> FEATURE:
<221> NAME/KEY: misc_feature
<222> LOCATION: (5)..(5)
<223> OTHER INFORMATION: /note="2'-F modified nucleotide"
<220> FEATURE:
<221> NAME/KEY: misc_feature
<222> LOCATION: (6)..(6)
<223> OTHER INFORMATION: /note="2'-OMe modified nucleotide"
<220> FEATURE:
<221> NAME/KEY: misc_feature
<222> LOCATION: (7)..(7)
<223> OTHER INFORMATION: /note="2'-F modified nucleotide"
<220> FEATURE:
<221> NAME/KEY: misc_feature
<222> LOCATION: (8)..(8)
<223> OTHER INFORMATION: /note="2'-OMe modified nucleotide"
<220> FEATURE:
<221> NAME/KEY: misc_feature
<222> LOCATION: (9)..(9)
<223> OTHER INFORMATION: /note="2'-OMe modified nucleotide"
<220> FEATURE:
<221> NAME/KEY: misc_feature
<222> LOCATION: (10)..(10)
<223> OTHER INFORMATION: /note="2'-F modified nucleotide"
<220> FEATURE:
<221> NAME/KEY: misc_feature
<222> LOCATION: (11)..(11)
<223> OTHER INFORMATION: /note="2'-OMe modified nucleotide"
<220> FEATURE:
<221> NAME/KEY: misc_feature
<222> LOCATION: (12)..(12)
<223> OTHER INFORMATION: /note="2'-OMe modified nucleotide"
<220> FEATURE:
<221> NAME/KEY: misc_feature
<222> LOCATION: (13)..(13)
<223> OTHER INFORMATION: /note="2'-OMe modified nucleotide"
<220> FEATURE:
<221> NAME/KEY: misc_feature
<222> LOCATION: (14)..(14)
<223> OTHER INFORMATION: /note="2'-F modified nucleotide"
<220> FEATURE:
<221> NAME/KEY: misc_feature
<222> LOCATION: (15)..(15)
<223> OTHER INFORMATION: /note="2'-OMe modified nucleotide"
<220> FEATURE:
<221> NAME/KEY: misc_feature
<222> LOCATION: (16)..(16)
<223> OTHER INFORMATION: /note="2'-OMe modified nucleotide"
<220> FEATURE:
<221> NAME/KEY: misc_feature
<222> LOCATION: (17)..(17)
<223> OTHER INFORMATION: /note="2'-OMe modified nucleotide"
<220> FEATURE:
<221> NAME/KEY: misc_feature
<222> LOCATION: (18)..(18)
<223> OTHER INFORMATION: /note="2'-OMe modified nucleotide"
<220> FEATURE:

```
<221> NAME/KEY: misc_feature
<222> LOCATION: (19)..(19)
<223> OTHER INFORMATION: /note="2'-OMe modified nucleotide"
<220> FEATURE:
<221> NAME/KEY: misc_feature
<222> LOCATION: (20)..(20)
<223> OTHER INFORMATION: /note="2'-OMe modified nucleotide with a
      3'-phosphorothioate linkage"
<220> FEATURE:
<221> NAME/KEY: misc_feature
<222> LOCATION: (21)..(21)
<223> OTHER INFORMATION: /note="2'-OMe modified nucleotide with a
      3'-phosphorothioate linkage"
<220> FEATURE:
<221> NAME/KEY: misc_feature
<222> LOCATION: (22)..(22)
<223> OTHER INFORMATION: /note="2'-OMe modified nucleotide"

<400> SEQUENCE: 239

uauuuuauag aguauaaccu gg                                          22


<210> SEQ ID NO 240
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: misc_feature
<222> LOCATION: (1)..(1)
<223> OTHER INFORMATION: /note="2'-OMe modified nucleotide with a
      3'-phosphorothioate linkage"
<220> FEATURE:
<221> NAME/KEY: misc_feature
<222> LOCATION: (2)..(2)
<223> OTHER INFORMATION: /note="2'-OMe modified nucleotide"
<220> FEATURE:
<221> NAME/KEY: misc_feature
<222> LOCATION: (3)..(3)
<223> OTHER INFORMATION: /note="2'-OMe modified nucleotide"
<220> FEATURE:
<221> NAME/KEY: misc_feature
<222> LOCATION: (4)..(4)
<223> OTHER INFORMATION: /note="2'-OMe modified nucleotide"
<220> FEATURE:
<221> NAME/KEY: misc_feature
<222> LOCATION: (5)..(5)
<223> OTHER INFORMATION: /note="2'-OMe modified nucleotide"
<220> FEATURE:
<221> NAME/KEY: misc_feature
<222> LOCATION: (6)..(6)
<223> OTHER INFORMATION: /note="2'-OMe modified nucleotide"
<220> FEATURE:
<221> NAME/KEY: misc_feature
<222> LOCATION: (7)..(7)
<223> OTHER INFORMATION: /note="2'-OMe modified nucleotide"
<220> FEATURE:
<221> NAME/KEY: misc_feature
<222> LOCATION: (8)..(8)
<223> OTHER INFORMATION: /note="2'-F modified nucleotide"
<220> FEATURE:
<221> NAME/KEY: misc_feature
<222> LOCATION: (9)..(9)
<223> OTHER INFORMATION: /note="2'-F modified nucleotide"
<220> FEATURE:
<221> NAME/KEY: misc_feature
<222> LOCATION: (10)..(10)
<223> OTHER INFORMATION: /note="2'-F modified nucleotide"
<220> FEATURE:
<221> NAME/KEY: misc_feature
<222> LOCATION: (11)..(11)
<223> OTHER INFORMATION: /note="2'-F modified nucleotide"
<220> FEATURE:
<221> NAME/KEY: misc_feature
<222> LOCATION: (12)..(12)
```

<223> OTHER INFORMATION: /note="2'-OMe modified nucleotide"
<220> FEATURE:
<221> NAME/KEY: misc_feature
<222> LOCATION: (13)..(13)
<223> OTHER INFORMATION: /note="2'-OMe modified nucleotide"
<220> FEATURE:
<221> NAME/KEY: misc_feature
<222> LOCATION: (14)..(14)
<223> OTHER INFORMATION: /note="2'-OMe modified nucleotide"
<220> FEATURE:
<221> NAME/KEY: misc_feature
<222> LOCATION: (15)..(15)
<223> OTHER INFORMATION: /note="2'-OMe modified nucleotide"
<220> FEATURE:
<221> NAME/KEY: misc_feature
<222> LOCATION: (16)..(16)
<223> OTHER INFORMATION: /note="2'-OMe modified nucleotide"
<220> FEATURE:
<221> NAME/KEY: misc_feature
<222> LOCATION: (17)..(17)
<223> OTHER INFORMATION: /note="2'-OMe modified nucleotide"
<220> FEATURE:
<221> NAME/KEY: misc_feature
<222> LOCATION: (18)..(18)
<223> OTHER INFORMATION: /note="2'-OMe modified nucleotide"
<220> FEATURE:
<221> NAME/KEY: misc_feature
<222> LOCATION: (19)..(19)
<223> OTHER INFORMATION: /note="2'-OMe modified nucleotide"
<220> FEATURE:
<221> NAME/KEY: misc_feature
<222> LOCATION: (20)..(20)
<223> OTHER INFORMATION: /note="2'-OMe modified nucleotide"
<220> FEATURE:
<221> NAME/KEY: misc_feature
<222> LOCATION: (21)..(21)
<223> OTHER INFORMATION: /note="2'-OMe modified nucleotide"
<220> FEATURE:
<221> NAME/KEY: misc_feature
<222> LOCATION: (22)..(22)
<223> OTHER INFORMATION: /note="2'-OMe modified nucleotide"
<220> FEATURE:
<221> NAME/KEY: misc_feature
<222> LOCATION: (23)..(23)
<223> OTHER INFORMATION: /note="2'-OMe modified nucleotide"
<220> FEATURE:
<221> NAME/KEY: misc_feature
<222> LOCATION: (24)..(24)
<223> OTHER INFORMATION: /note="2'-OMe modified nucleotide"
<220> FEATURE:
<221> NAME/KEY: misc_feature
<222> LOCATION: (25)..(25)
<223> OTHER INFORMATION: /note="2'-OMe modified nucleotide"
<220> FEATURE:
<221> NAME/KEY: misc_feature
<222> LOCATION: (26)..(26)
<223> OTHER INFORMATION: /note="2'-OMe modified nucleotide"
<220> FEATURE:
<221> NAME/KEY: misc_feature
<222> LOCATION: (27)..(27)
<223> OTHER INFORMATION: /note="2'-OMe modified nucleotide"
<220> FEATURE:
<221> NAME/KEY: misc_feature
<222> LOCATION: (28)..(28)
<223> OTHER INFORMATION: /note="ademA-GalNAc"
<220> FEATURE:
<221> NAME/KEY: misc_feature
<222> LOCATION: (29)..(29)
<223> OTHER INFORMATION: /note="ademA-GalNAc"
<220> FEATURE:
<221> NAME/KEY: misc_feature
<222> LOCATION: (30)..(30)
<223> OTHER INFORMATION: /note="ademA-GalNAc"
<220> FEATURE:
<221> NAME/KEY: misc_feature
<222> LOCATION: (31)..(31)
<223> OTHER INFORMATION: /note="2'-OMe modified nucleotide"
<220> FEATURE:
<221> NAME/KEY: misc_feature
<222> LOCATION: (32)..(32)
<223> OTHER INFORMATION: /note="2'-OMe modified nucleotide"
<220> FEATURE:
<221> NAME/KEY: misc_feature
<222> LOCATION: (33)..(33)
<223> OTHER INFORMATION: /note="2'-OMe modified nucleotide"
<220> FEATURE:
<221> NAME/KEY: misc_feature
<222> LOCATION: (34)..(34)
<223> OTHER INFORMATION: /note="2'-OMe modified nucleotide"
<220> FEATURE:
<221> NAME/KEY: misc_feature
<222> LOCATION: (35)..(35)
<223> OTHER INFORMATION: /note="2'-OMe modified nucleotide"
<220> FEATURE:
<221> NAME/KEY: misc_feature
<222> LOCATION: (36)..(36)
<223> OTHER INFORMATION: /note="2'-OMe modified nucleotide"

<400> SEQUENCE: 240
auucagaaag cuuugaauga gcagccgaaa ggcugc 36

<210> SEQ ID NO 241
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: misc_feature
<222> LOCATION: (1)..(1)
<223> OTHER INFORMATION: /note="MePhosphonate-4O-mUs"
<220> FEATURE:
<221> NAME/KEY: misc_feature
<222> LOCATION: (2)..(2)
<223> OTHER INFORMATION: /note="2'-F modified nucleotide with a 3'-phosphorothioate linkage"
<220> FEATURE:
<221> NAME/KEY: misc_feature
<222> LOCATION: (3)..(3)
<223> OTHER INFORMATION: /note="2'-F modified nucleotide with a 3'-phosphorothioate linkage"
<220> FEATURE:
<221> NAME/KEY: misc_feature
<222> LOCATION: (4)..(4)
<223> OTHER INFORMATION: /note="2'-F modified nucleotide"
<220> FEATURE:
<221> NAME/KEY: misc_feature
<222> LOCATION: (5)..(5)
<223> OTHER INFORMATION: /note="2'-F modified nucleotide"
<220> FEATURE:
<221> NAME/KEY: misc_feature
<222> LOCATION: (6)..(6)
<223> OTHER INFORMATION: /note="2'-OMe modified nucleotide"
<220> FEATURE:
<221> NAME/KEY: misc_feature
<222> LOCATION: (7)..(7)
<223> OTHER INFORMATION: /note="2'-F modified nucleotide"
<220> FEATURE:
<221> NAME/KEY: misc_feature
<222> LOCATION: (8)..(8)
<223> OTHER INFORMATION: /note="2'-OMe modified nucleotide"
<220> FEATURE:
<221> NAME/KEY: misc_feature
<222> LOCATION: (9)..(9)
<223> OTHER INFORMATION: /note="2'-OMe modified nucleotide"
<220> FEATURE:
<221> NAME/KEY: misc_feature
<222> LOCATION: (10)..(10)
<223> OTHER INFORMATION: /note="2'-F modified nucleotide"
<220> FEATURE:
<221> NAME/KEY: misc_feature
<222> LOCATION: (11)..(11)
<223> OTHER INFORMATION: /note="2'-OMe modified nucleotide"
<220> FEATURE:

```
<221> NAME/KEY: misc_feature
<222> LOCATION: (12)..(12)
<223> OTHER INFORMATION: /note="2'-OMe modified nucleotide"
<220> FEATURE:
<221> NAME/KEY: misc_feature
<222> LOCATION: (13)..(13)
<223> OTHER INFORMATION: /note="2'-OMe modified nucleotide"
<220> FEATURE:
<221> NAME/KEY: misc_feature
<222> LOCATION: (14)..(14)
<223> OTHER INFORMATION: /note="2'-F modified nucleotide"
<220> FEATURE:
<221> NAME/KEY: misc_feature
<222> LOCATION: (15)..(15)
<223> OTHER INFORMATION: /note="2'-OMe modified nucleotide"
<220> FEATURE:
<221> NAME/KEY: misc_feature
<222> LOCATION: (16)..(16)
<223> OTHER INFORMATION: /note="2'-OMe modified nucleotide"
<220> FEATURE:
<221> NAME/KEY: misc_feature
<222> LOCATION: (17)..(17)
<223> OTHER INFORMATION: /note="2'-OMe modified nucleotide"
<220> FEATURE:
<221> NAME/KEY: misc_feature
<222> LOCATION: (18)..(18)
<223> OTHER INFORMATION: /note="2'-OMe modified nucleotide"
<220> FEATURE:
<221> NAME/KEY: misc_feature
<222> LOCATION: (19)..(19)
<223> OTHER INFORMATION: /note="2'-OMe modified nucleotide"
<220> FEATURE:
<221> NAME/KEY: misc_feature
<222> LOCATION: (20)..(20)
<223> OTHER INFORMATION: /note="2'-OMe modified nucleotide with a
      3'-phosphorothioate linkage"
<220> FEATURE:
<221> NAME/KEY: misc_feature
<222> LOCATION: (21)..(21)
<223> OTHER INFORMATION: /note="2'-OMe modified nucleotide with a
      3'-phosphorothioate linkage"
<220> FEATURE:
<221> NAME/KEY: misc_feature
<222> LOCATION: (22)..(22)
<223> OTHER INFORMATION: /note="2'-OMe modified nucleotide"

<400> SEQUENCE: 241

ucauucaaag cuuucugaau gg                                            22


<210> SEQ ID NO 242
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: misc_feature
<222> LOCATION: (1)..(1)
<223> OTHER INFORMATION: /note="2'-OMe modified nucleotide with a
      3'-phosphorothioate linkage"
<220> FEATURE:
<221> NAME/KEY: misc_feature
<222> LOCATION: (2)..(2)
<223> OTHER INFORMATION: /note="2'-OMe modified nucleotide"
<220> FEATURE:
<221> NAME/KEY: misc_feature
<222> LOCATION: (3)..(3)
<223> OTHER INFORMATION: /note="2'-F modified nucleotide"
<220> FEATURE:
<221> NAME/KEY: misc_feature
<222> LOCATION: (4)..(4)
<223> OTHER INFORMATION: /note="2'-OMe modified nucleotide"
<220> FEATURE:
<221> NAME/KEY: misc_feature
<222> LOCATION: (5)..(5)
```

<223> OTHER INFORMATION: /note="2'-OMe modified nucleotide"
<220> FEATURE:
<221> NAME/KEY: misc_feature
<222> LOCATION: (6)..(6)
<223> OTHER INFORMATION: /note="2'-OMe modified nucleotide"
<220> FEATURE:
<221> NAME/KEY: misc_feature
<222> LOCATION: (7)..(7)
<223> OTHER INFORMATION: /note="2'-OMe modified nucleotide"
<220> FEATURE:
<221> NAME/KEY: misc_feature
<222> LOCATION: (8)..(8)
<223> OTHER INFORMATION: /note="2'-F modified nucleotide"
<220> FEATURE:
<221> NAME/KEY: misc_feature
<222> LOCATION: (9)..(9)
<223> OTHER INFORMATION: /note="2'-OMe modified nucleotide"
<220> FEATURE:
<221> NAME/KEY: misc_feature
<222> LOCATION: (10)..(10)
<223> OTHER INFORMATION: /note="2'-F modified nucleotide"
<220> FEATURE:
<221> NAME/KEY: misc_feature
<222> LOCATION: (11)..(11)
<223> OTHER INFORMATION: /note="2'-OMe modified nucleotide"
<220> FEATURE:
<221> NAME/KEY: misc_feature
<222> LOCATION: (12)..(12)
<223> OTHER INFORMATION: /note="2'-F modified nucleotide"
<220> FEATURE:
<221> NAME/KEY: misc_feature
<222> LOCATION: (13)..(13)
<223> OTHER INFORMATION: /note="2'-F modified nucleotide"
<220> FEATURE:
<221> NAME/KEY: misc_feature
<222> LOCATION: (14)..(14)
<223> OTHER INFORMATION: /note="2'-OMe modified nucleotide"
<220> FEATURE:
<221> NAME/KEY: misc_feature
<222> LOCATION: (15)..(15)
<223> OTHER INFORMATION: /note="2'-OMe modified nucleotide"
<220> FEATURE:
<221> NAME/KEY: misc_feature
<222> LOCATION: (16)..(16)
<223> OTHER INFORMATION: /note="2'-OMe modified nucleotide"
<220> FEATURE:
<221> NAME/KEY: misc_feature
<222> LOCATION: (17)..(17)
<223> OTHER INFORMATION: /note="2'-F modified nucleotide"
<220> FEATURE:
<221> NAME/KEY: misc_feature
<222> LOCATION: (18)..(18)
<223> OTHER INFORMATION: /note="2'-OMe modified nucleotide"
<220> FEATURE:
<221> NAME/KEY: misc_feature
<222> LOCATION: (19)..(19)
<223> OTHER INFORMATION: /note="2'-OMe modified nucleotide"
<220> FEATURE:
<221> NAME/KEY: misc_feature
<222> LOCATION: (20)..(20)
<223> OTHER INFORMATION: /note="2'-OMe modified nucleotide"
<220> FEATURE:
<221> NAME/KEY: misc_feature
<222> LOCATION: (21)..(21)
<223> OTHER INFORMATION: /note="2'-OMe modified nucleotide"
<220> FEATURE:
<221> NAME/KEY: misc_feature
<222> LOCATION: (22)..(22)
<223> OTHER INFORMATION: /note="2'-OMe modified nucleotide"
<220> FEATURE:
<221> NAME/KEY: misc_feature
<222> LOCATION: (23)..(23)
<223> OTHER INFORMATION: /note="2'-OMe modified nucleotide"
<220> FEATURE:
<221> NAME/KEY: misc_feature
<222> LOCATION: (24)..(24)
<223> OTHER INFORMATION: /note="2'-OMe modified nucleotide"
<220> FEATURE:
<221> NAME/KEY: misc_feature

```
<222> LOCATION: (25)..(25)
<223> OTHER INFORMATION: /note="2'-OMe modified nucleotide"
<220> FEATURE:
<221> NAME/KEY: misc_feature
<222> LOCATION: (26)..(26)
<223> OTHER INFORMATION: /note="2'-OMe modified nucleotide"
<220> FEATURE:
<221> NAME/KEY: misc_feature
<222> LOCATION: (27)..(27)
<223> OTHER INFORMATION: /note="2'-OMe modified nucleotide"
<220> FEATURE:
<221> NAME/KEY: misc_feature
<222> LOCATION: (28)..(28)
<223> OTHER INFORMATION: /note="ademA-GalNAc"
<220> FEATURE:
<221> NAME/KEY: misc_feature
<222> LOCATION: (29)..(29)
<223> OTHER INFORMATION: /note="ademA-GalNAc"
<220> FEATURE:
<221> NAME/KEY: misc_feature
<222> LOCATION: (30)..(30)
<223> OTHER INFORMATION: /note="ademA-GalNAc"
<220> FEATURE:
<221> NAME/KEY: misc_feature
<222> LOCATION: (31)..(31)
<223> OTHER INFORMATION: /note="2'-OMe modified nucleotide"
<220> FEATURE:
<221> NAME/KEY: misc_feature
<222> LOCATION: (32)..(32)
<223> OTHER INFORMATION: /note="2'-OMe modified nucleotide"
<220> FEATURE:
<221> NAME/KEY: misc_feature
<222> LOCATION: (33)..(33)
<223> OTHER INFORMATION: /note="2'-OMe modified nucleotide"
<220> FEATURE:
<221> NAME/KEY: misc_feature
<222> LOCATION: (34)..(34)
<223> OTHER INFORMATION: /note="2'-OMe modified nucleotide"
<220> FEATURE:
<221> NAME/KEY: misc_feature
<222> LOCATION: (35)..(35)
<223> OTHER INFORMATION: /note="2'-OMe modified nucleotide"
<220> FEATURE:
<221> NAME/KEY: misc_feature
<222> LOCATION: (36)..(36)
<223> OTHER INFORMATION: /note="2'-OMe modified nucleotide"

<400> SEQUENCE: 242

aaaucaagau uugcuaugua gcagccgaaa ggcugc                              36


<210> SEQ ID NO 243
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: misc_feature
<222> LOCATION: (1)..(1)
<223> OTHER INFORMATION: /note="MePhosphonate-4O-mUs"
<220> FEATURE:
<221> NAME/KEY: misc_feature
<222> LOCATION: (2)..(2)
<223> OTHER INFORMATION: /note="2'-F modified nucleotide with a
      3'-phosphorothioate linkage"
<220> FEATURE:
<221> NAME/KEY: misc_feature
<222> LOCATION: (3)..(3)
<223> OTHER INFORMATION: /note="2'-F modified nucleotide with a
      3'-phosphorothioate linkage"
<220> FEATURE:
<221> NAME/KEY: misc_feature
<222> LOCATION: (4)..(4)
<223> OTHER INFORMATION: /note="2'-OMe modified nucleotide"
<220> FEATURE:
```

<221> NAME/KEY: misc_feature
<222> LOCATION: (5)..(5)
<223> OTHER INFORMATION: /note="2'-F modified nucleotide"
<220> FEATURE:
<221> NAME/KEY: misc_feature
<222> LOCATION: (6)..(6)
<223> OTHER INFORMATION: /note="2'-OMe modified nucleotide"
<220> FEATURE:
<221> NAME/KEY: misc_feature
<222> LOCATION: (7)..(7)
<223> OTHER INFORMATION: /note="2'-F modified nucleotide"
<220> FEATURE:
<221> NAME/KEY: misc_feature
<222> LOCATION: (8)..(8)
<223> OTHER INFORMATION: /note="2'-OMe modified nucleotide"
<220> FEATURE:
<221> NAME/KEY: misc_feature
<222> LOCATION: (9)..(9)
<223> OTHER INFORMATION: /note="2'-OMe modified nucleotide"
<220> FEATURE:
<221> NAME/KEY: misc_feature
<222> LOCATION: (10)..(10)
<223> OTHER INFORMATION: /note="2'-OMe modified nucleotide"
<220> FEATURE:
<221> NAME/KEY: misc_feature
<222> LOCATION: (11)..(11)
<223> OTHER INFORMATION: /note="2'-OMe modified nucleotide"
<220> FEATURE:
<221> NAME/KEY: misc_feature
<222> LOCATION: (12)..(12)
<223> OTHER INFORMATION: /note="2'-F modified nucleotide"
<220> FEATURE:
<221> NAME/KEY: misc_feature
<222> LOCATION: (13)..(13)
<223> OTHER INFORMATION: /note="2'-OMe modified nucleotide"
<220> FEATURE:
<221> NAME/KEY: misc_feature
<222> LOCATION: (14)..(14)
<223> OTHER INFORMATION: /note="2'-F modified nucleotide"
<220> FEATURE:
<221> NAME/KEY: misc_feature
<222> LOCATION: (15)..(15)
<223> OTHER INFORMATION: /note="2'-OMe modified nucleotide"
<220> FEATURE:
<221> NAME/KEY: misc_feature
<222> LOCATION: (16)..(16)
<223> OTHER INFORMATION: /note="2'-F modified nucleotide"
<220> FEATURE:
<221> NAME/KEY: misc_feature
<222> LOCATION: (17)..(17)
<223> OTHER INFORMATION: /note="2'-OMe modified nucleotide"
<220> FEATURE:
<221> NAME/KEY: misc_feature
<222> LOCATION: (18)..(18)
<223> OTHER INFORMATION: /note="2'-OMe modified nucleotide"
<220> FEATURE:
<221> NAME/KEY: misc_feature
<222> LOCATION: (19)..(19)
<223> OTHER INFORMATION: /note="2'-F modified nucleotide"
<220> FEATURE:
<221> NAME/KEY: misc_feature
<222> LOCATION: (20)..(20)
<223> OTHER INFORMATION: /note="2'-OMe modified nucleotide with a
3'-phosphorothioate linkage"
<220> FEATURE:
<221> NAME/KEY: misc_feature
<222> LOCATION: (21)..(21)
<223> OTHER INFORMATION: /note="2'-OMe modified nucleotide with a
3'-phosphorothioate linkage"
<220> FEATURE:
<221> NAME/KEY: misc_feature
<222> LOCATION: (22)..(22)
<223> OTHER INFORMATION: /note="2'-OMe modified nucleotide"

<400> SEQUENCE: 243
uacauagcaa aucuugauuu gg 22

<210> SEQ ID NO 244
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: misc_feature
<222> LOCATION: (1)..(1)
<223> OTHER INFORMATION: /note="2'-OMe modified nucleotide with a 3'-phosphorothioate linkage"
<220> FEATURE:
<221> NAME/KEY: misc_feature
<222> LOCATION: (2)..(2)
<223> OTHER INFORMATION: /note="2'-OMe modified nucleotide"
<220> FEATURE:
<221> NAME/KEY: misc_feature
<222> LOCATION: (3)..(3)
<223> OTHER INFORMATION: /note="2'-F modified nucleotide"
<220> FEATURE:
<221> NAME/KEY: misc_feature
<222> LOCATION: (4)..(4)
<223> OTHER INFORMATION: /note="2'-OMe modified nucleotide"
<220> FEATURE:
<221> NAME/KEY: misc_feature
<222> LOCATION: (5)..(5)
<223> OTHER INFORMATION: /note="2'-OMe modified nucleotide"
<220> FEATURE:
<221> NAME/KEY: misc_feature
<222> LOCATION: (6)..(6)
<223> OTHER INFORMATION: /note="2'-OMe modified nucleotide"
<220> FEATURE:
<221> NAME/KEY: misc_feature
<222> LOCATION: (7)..(7)
<223> OTHER INFORMATION: /note="2'-OMe modified nucleotide"
<220> FEATURE:
<221> NAME/KEY: misc_feature
<222> LOCATION: (8)..(8)
<223> OTHER INFORMATION: /note="2'-F modified nucleotide"
<220> FEATURE:
<221> NAME/KEY: misc_feature
<222> LOCATION: (9)..(9)
<223> OTHER INFORMATION: /note="2'-OMe modified nucleotide"
<220> FEATURE:
<221> NAME/KEY: misc_feature
<222> LOCATION: (10)..(10)
<223> OTHER INFORMATION: /note="2'-F modified nucleotide"
<220> FEATURE:
<221> NAME/KEY: misc_feature
<222> LOCATION: (11)..(11)
<223> OTHER INFORMATION: /note="2'-OMe modified nucleotide"
<220> FEATURE:
<221> NAME/KEY: misc_feature
<222> LOCATION: (12)..(12)
<223> OTHER INFORMATION: /note="2'-F modified nucleotide"
<220> FEATURE:
<221> NAME/KEY: misc_feature
<222> LOCATION: (13)..(13)
<223> OTHER INFORMATION: /note="2'-F modified nucleotide"
<220> FEATURE:
<221> NAME/KEY: misc_feature
<222> LOCATION: (14)..(14)
<223> OTHER INFORMATION: /note="2'-OMe modified nucleotide"
<220> FEATURE:
<221> NAME/KEY: misc_feature
<222> LOCATION: (15)..(15)
<223> OTHER INFORMATION: /note="2'-OMe modified nucleotide"
<220> FEATURE:
<221> NAME/KEY: misc_feature
<222> LOCATION: (16)..(16)
<223> OTHER INFORMATION: /note="2'-OMe modified nucleotide"
<220> FEATURE:
<221> NAME/KEY: misc_feature
<222> LOCATION: (17)..(17)
<223> OTHER INFORMATION: /note="2'-F modified nucleotide"
<220> FEATURE:
<221> NAME/KEY: misc_feature -continued
<222> LOCATION: (18)..(18)
<223> OTHER INFORMATION: /note="2'-OMe modified nucleotide"
<220> FEATURE:
<221> NAME/KEY: misc_feature
<222> LOCATION: (19)..(19)
<223> OTHER INFORMATION: /note="2'-OMe modified nucleotide"
<220> FEATURE:
<221> NAME/KEY: misc_feature
<222> LOCATION: (20)..(20)
<223> OTHER INFORMATION: /note="2'-OMe modified nucleotide"
<220> FEATURE:
<221> NAME/KEY: misc_feature
<222> LOCATION: (21)..(21)
<223> OTHER INFORMATION: /note="2'-OMe modified nucleotide"
<220> FEATURE:
<221> NAME/KEY: misc_feature
<222> LOCATION: (22)..(22)
<223> OTHER INFORMATION: /note="2'-OMe modified nucleotide"
<220> FEATURE:
<221> NAME/KEY: misc_feature
<222> LOCATION: (23)..(23)
<223> OTHER INFORMATION: /note="2'-OMe modified nucleotide"
<220> FEATURE:
<221> NAME/KEY: misc_feature
<222> LOCATION: (24)..(24)
<223> OTHER INFORMATION: /note="2'-OMe modified nucleotide"
<220> FEATURE:
<221> NAME/KEY: misc_feature
<222> LOCATION: (25)..(25)
<223> OTHER INFORMATION: /note="2'-OMe modified nucleotide"
<220> FEATURE:
<221> NAME/KEY: misc_feature
<222> LOCATION: (26)..(26)
<223> OTHER INFORMATION: /note="2'-OMe modified nucleotide"
<220> FEATURE:
<221> NAME/KEY: misc_feature
<222> LOCATION: (27)..(27)
<223> OTHER INFORMATION: /note="2'-OMe modified nucleotide"
<220> FEATURE:
<221> NAME/KEY: misc_feature
<222> LOCATION: (28)..(28)
<223> OTHER INFORMATION: /note="ademA-GalNAc"
<220> FEATURE:
<221> NAME/KEY: misc_feature
<222> LOCATION: (29)..(29)
<223> OTHER INFORMATION: /note="ademA-GalNAc"
<220> FEATURE:
<221> NAME/KEY: misc_feature
<222> LOCATION: (30)..(30)
<223> OTHER INFORMATION: /note="ademA-GalNAc"
<220> FEATURE:
<221> NAME/KEY: misc_feature
<222> LOCATION: (31)..(31)
<223> OTHER INFORMATION: /note="2'-OMe modified nucleotide"
<220> FEATURE:
<221> NAME/KEY: misc_feature
<222> LOCATION: (32)..(32)
<223> OTHER INFORMATION: /note="2'-OMe modified nucleotide"
<220> FEATURE:
<221> NAME/KEY: misc_feature
<222> LOCATION: (33)..(33)
<223> OTHER INFORMATION: /note="2'-OMe modified nucleotide"
<220> FEATURE:
<221> NAME/KEY: misc_feature
<222> LOCATION: (34)..(34)
<223> OTHER INFORMATION: /note="2'-OMe modified nucleotide"
<220> FEATURE:
<221> NAME/KEY: misc_feature
<222> LOCATION: (35)..(35)
<223> OTHER INFORMATION: /note="2'-OMe modified nucleotide"
<220> FEATURE:
<221> NAME/KEY: misc_feature
<222> LOCATION: (36)..(36)
<223> OTHER INFORMATION: /note="2'-OMe modified nucleotide"

<400> SEQUENCE: 244
cucaacauau uugaucagua gcagccgaaa ggcugc 36

<210> SEQ ID NO 245
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: misc_feature
<222> LOCATION: (1)..(1)
<223> OTHER INFORMATION: /note="MePhosphonate-4O-mUs"
<220> FEATURE:
<221> NAME/KEY: misc_feature
<222> LOCATION: (2)..(2)
<223> OTHER INFORMATION: /note="2'-F modified nucleotide with a 3'-phosphorothioate linkage"
<220> FEATURE:
<221> NAME/KEY: misc_feature
<222> LOCATION: (3)..(3)
<223> OTHER INFORMATION: /note="2'-F modified nucleotide with a 3'-phosphorothioate linkage"
<220> FEATURE:
<221> NAME/KEY: misc_feature
<222> LOCATION: (4)..(4)
<223> OTHER INFORMATION: /note="2'-OMe modified nucleotide"
<220> FEATURE:
<221> NAME/KEY: misc_feature
<222> LOCATION: (5)..(5)
<223> OTHER INFORMATION: /note="2'-F modified nucleotide"
<220> FEATURE:
<221> NAME/KEY: misc_feature
<222> LOCATION: (6)..(6)
<223> OTHER INFORMATION: /note="2'-OMe modified nucleotide"
<220> FEATURE:
<221> NAME/KEY: misc_feature
<222> LOCATION: (7)..(7)
<223> OTHER INFORMATION: /note="2'-F modified nucleotide"
<220> FEATURE:
<221> NAME/KEY: misc_feature
<222> LOCATION: (8)..(8)
<223> OTHER INFORMATION: /note="2'-OMe modified nucleotide"
<220> FEATURE:
<221> NAME/KEY: misc_feature
<222> LOCATION: (9)..(9)
<223> OTHER INFORMATION: /note="2'-OMe modified nucleotide"
<220> FEATURE:
<221> NAME/KEY: misc_feature
<222> LOCATION: (10)..(10)
<223> OTHER INFORMATION: /note="2'-OMe modified nucleotide"
<220> FEATURE:
<221> NAME/KEY: misc_feature
<222> LOCATION: (11)..(11)
<223> OTHER INFORMATION: /note="2'-OMe modified nucleotide"
<220> FEATURE:
<221> NAME/KEY: misc_feature
<222> LOCATION: (12)..(12)
<223> OTHER INFORMATION: /note="2'-F modified nucleotide"
<220> FEATURE:
<221> NAME/KEY: misc_feature
<222> LOCATION: (13)..(13)
<223> OTHER INFORMATION: /note="2'-OMe modified nucleotide"
<220> FEATURE:
<221> NAME/KEY: misc_feature
<222> LOCATION: (14)..(14)
<223> OTHER INFORMATION: /note="2'-F modified nucleotide"
<220> FEATURE:
<221> NAME/KEY: misc_feature
<222> LOCATION: (15)..(15)
<223> OTHER INFORMATION: /note="2'-OMe modified nucleotide"
<220> FEATURE:
<221> NAME/KEY: misc_feature
<222> LOCATION: (16)..(16)
<223> OTHER INFORMATION: /note="2'-F modified nucleotide"
<220> FEATURE:
<221> NAME/KEY: misc_feature
<222> LOCATION: (17)..(17)
<223> OTHER INFORMATION: /note="2'-OMe modified nucleotide"

<220> FEATURE:
<221> NAME/KEY: misc_feature
<222> LOCATION: (18)..(18)
<223> OTHER INFORMATION: /note="2'-OMe modified nucleotide"
<220> FEATURE:
<221> NAME/KEY: misc_feature
<222> LOCATION: (19)..(19)
<223> OTHER INFORMATION: /note="2'-F modified nucleotide"
<220> FEATURE:
<221> NAME/KEY: misc_feature
<222> LOCATION: (20)..(20)
<223> OTHER INFORMATION: /note="2'-OMe modified nucleotide with a 3'-phosphorothioate linkage"
<220> FEATURE:
<221> NAME/KEY: misc_feature
<222> LOCATION: (21)..(21)
<223> OTHER INFORMATION: /note="2'-OMe modified nucleotide with a 3'-phosphorothioate linkage"
<220> FEATURE:
<221> NAME/KEY: misc_feature
<222> LOCATION: (22)..(22)
<223> OTHER INFORMATION: /note="2'-OMe modified nucleotide"

<400> SEQUENCE: 245
uacugaucaa auauguugag gg 22

<210> SEQ ID NO 246
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: misc_feature
<222> LOCATION: (1)..(1)
<223> OTHER INFORMATION: /note="2'-OMe modified nucleotide with a 3'-phosphorothioate linkage"
<220> FEATURE:
<221> NAME/KEY: misc_feature
<222> LOCATION: (2)..(2)
<223> OTHER INFORMATION: /note="2'-OMe modified nucleotide"
<220> FEATURE:
<221> NAME/KEY: misc_feature
<222> LOCATION: (3)..(3)
<223> OTHER INFORMATION: /note="2'-F modified nucleotide"
<220> FEATURE:
<221> NAME/KEY: misc_feature
<222> LOCATION: (4)..(4)
<223> OTHER INFORMATION: /note="2'-OMe modified nucleotide"
<220> FEATURE:
<221> NAME/KEY: misc_feature
<222> LOCATION: (5)..(5)
<223> OTHER INFORMATION: /note="2'-OMe modified nucleotide"
<220> FEATURE:
<221> NAME/KEY: misc_feature
<222> LOCATION: (6)..(6)
<223> OTHER INFORMATION: /note="2'-OMe modified nucleotide"
<220> FEATURE:
<221> NAME/KEY: misc_feature
<222> LOCATION: (7)..(7)
<223> OTHER INFORMATION: /note="2'-OMe modified nucleotide"
<220> FEATURE:
<221> NAME/KEY: misc_feature
<222> LOCATION: (8)..(8)
<223> OTHER INFORMATION: /note="2'-F modified nucleotide"
<220> FEATURE:
<221> NAME/KEY: misc_feature
<222> LOCATION: (9)..(9)
<223> OTHER INFORMATION: /note="2'-OMe modified nucleotide"
<220> FEATURE:
<221> NAME/KEY: misc_feature
<222> LOCATION: (10)..(10)
<223> OTHER INFORMATION: /note="2'-F modified nucleotide"
<220> FEATURE:
<221> NAME/KEY: misc_feature
<222> LOCATION: (11)..(11)
<223> OTHER INFORMATION: /note="2'-OMe modified nucleotide"
<220> FEATURE:
<221> NAME/KEY: misc_feature
<222> LOCATION: (12)..(12)
<223> OTHER INFORMATION: /note="2'-F modified nucleotide"
<220> FEATURE:
<221> NAME/KEY: misc_feature
<222> LOCATION: (13)..(13)
<223> OTHER INFORMATION: /note="2'-F modified nucleotide"
<220> FEATURE:
<221> NAME/KEY: misc_feature
<222> LOCATION: (14)..(14)
<223> OTHER INFORMATION: /note="2'-OMe modified nucleotide"
<220> FEATURE:
<221> NAME/KEY: misc_feature
<222> LOCATION: (15)..(15)
<223> OTHER INFORMATION: /note="2'-OMe modified nucleotide"
<220> FEATURE:
<221> NAME/KEY: misc_feature
<222> LOCATION: (16)..(16)
<223> OTHER INFORMATION: /note="2'-OMe modified nucleotide"
<220> FEATURE:
<221> NAME/KEY: misc_feature
<222> LOCATION: (17)..(17)
<223> OTHER INFORMATION: /note="2'-F modified nucleotide"
<220> FEATURE:
<221> NAME/KEY: misc_feature
<222> LOCATION: (18)..(18)
<223> OTHER INFORMATION: /note="2'-OMe modified nucleotide"
<220> FEATURE:
<221> NAME/KEY: misc_feature
<222> LOCATION: (19)..(19)
<223> OTHER INFORMATION: /note="2'-OMe modified nucleotide"
<220> FEATURE:
<221> NAME/KEY: misc_feature
<222> LOCATION: (20)..(20)
<223> OTHER INFORMATION: /note="2'-OMe modified nucleotide"
<220> FEATURE:
<221> NAME/KEY: misc_feature
<222> LOCATION: (21)..(21)
<223> OTHER INFORMATION: /note="2'-OMe modified nucleotide"
<220> FEATURE:
<221> NAME/KEY: misc_feature
<222> LOCATION: (22)..(22)
<223> OTHER INFORMATION: /note="2'-OMe modified nucleotide"
<220> FEATURE:
<221> NAME/KEY: misc_feature
<222> LOCATION: (23)..(23)
<223> OTHER INFORMATION: /note="2'-OMe modified nucleotide"
<220> FEATURE:
<221> NAME/KEY: misc_feature
<222> LOCATION: (24)..(24)
<223> OTHER INFORMATION: /note="2'-OMe modified nucleotide"
<220> FEATURE:
<221> NAME/KEY: misc_feature
<222> LOCATION: (25)..(25)
<223> OTHER INFORMATION: /note="2'-OMe modified nucleotide"
<220> FEATURE:
<221> NAME/KEY: misc_feature
<222> LOCATION: (26)..(26)
<223> OTHER INFORMATION: /note="2'-OMe modified nucleotide"
<220> FEATURE:
<221> NAME/KEY: misc_feature
<222> LOCATION: (27)..(27)
<223> OTHER INFORMATION: /note="2'-OMe modified nucleotide"
<220> FEATURE:
<221> NAME/KEY: misc_feature
<222> LOCATION: (28)..(28)
<223> OTHER INFORMATION: /note="ademA-GalNAc"
<220> FEATURE:
<221> NAME/KEY: misc_feature
<222> LOCATION: (29)..(29)
<223> OTHER INFORMATION: /note="ademA-GalNAc"
<220> FEATURE:
<221> NAME/KEY: misc_feature
<222> LOCATION: (30)..(30)
<223> OTHER INFORMATION: /note="ademA-GalNAc"
<220> FEATURE:

<221> NAME/KEY: misc_feature
<222> LOCATION: (31)..(31)
<223> OTHER INFORMATION: /note="2'-OMe modified nucleotide"
<220> FEATURE:
<221> NAME/KEY: misc_feature
<222> LOCATION: (32)..(32)
<223> OTHER INFORMATION: /note="2'-OMe modified nucleotide"
<220> FEATURE:
<221> NAME/KEY: misc_feature
<222> LOCATION: (33)..(33)
<223> OTHER INFORMATION: /note="2'-OMe modified nucleotide"
<220> FEATURE:
<221> NAME/KEY: misc_feature
<222> LOCATION: (34)..(34)
<223> OTHER INFORMATION: /note="2'-OMe modified nucleotide"
<220> FEATURE:
<221> NAME/KEY: misc_feature
<222> LOCATION: (35)..(35)
<223> OTHER INFORMATION: /note="2'-OMe modified nucleotide"
<220> FEATURE:
<221> NAME/KEY: misc_feature
<222> LOCATION: (36)..(36)
<223> OTHER INFORMATION: /note="2'-OMe modified nucleotide"

<400> SEQUENCE: 246
guggagaaaa caaccuaaaa gcagccgaaa ggcugc 36

<210> SEQ ID NO 247
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: misc_feature
<222> LOCATION: (1)..(1)
<223> OTHER INFORMATION: /note="MePhosphonate-4O-mUs"
<220> FEATURE:
<221> NAME/KEY: misc_feature
<222> LOCATION: (2)..(2)
<223> OTHER INFORMATION: /note="2'-F modified nucleotide with a 3'-phosphorothioate linkage"
<220> FEATURE:
<221> NAME/KEY: misc_feature
<222> LOCATION: (3)..(3)
<223> OTHER INFORMATION: /note="2'-F modified nucleotide with a 3'-phosphorothioate linkage"
<220> FEATURE:
<221> NAME/KEY: misc_feature
<222> LOCATION: (4)..(4)
<223> OTHER INFORMATION: /note="2'-OMe modified nucleotide"
<220> FEATURE:
<221> NAME/KEY: misc_feature
<222> LOCATION: (5)..(5)
<223> OTHER INFORMATION: /note="2'-F modified nucleotide"
<220> FEATURE:
<221> NAME/KEY: misc_feature
<222> LOCATION: (6)..(6)
<223> OTHER INFORMATION: /note="2'-OMe modified nucleotide"
<220> FEATURE:
<221> NAME/KEY: misc_feature
<222> LOCATION: (7)..(7)
<223> OTHER INFORMATION: /note="2'-F modified nucleotide"
<220> FEATURE:
<221> NAME/KEY: misc_feature
<222> LOCATION: (8)..(8)
<223> OTHER INFORMATION: /note="2'-OMe modified nucleotide"
<220> FEATURE:
<221> NAME/KEY: misc_feature
<222> LOCATION: (9)..(9)
<223> OTHER INFORMATION: /note="2'-OMe modified nucleotide"
<220> FEATURE:
<221> NAME/KEY: misc_feature
<222> LOCATION: (10)..(10)
<223> OTHER INFORMATION: /note="2'-OMe modified nucleotide"

<220> FEATURE:
<221> NAME/KEY: misc_feature
<222> LOCATION: (11)..(11)
<223> OTHER INFORMATION: /note="2'-OMe modified nucleotide"
<220> FEATURE:
<221> NAME/KEY: misc_feature
<222> LOCATION: (12)..(12)
<223> OTHER INFORMATION: /note="2'-F modified nucleotide"
<220> FEATURE:
<221> NAME/KEY: misc_feature
<222> LOCATION: (13)..(13)
<223> OTHER INFORMATION: /note="2'-OMe modified nucleotide"
<220> FEATURE:
<221> NAME/KEY: misc_feature
<222> LOCATION: (14)..(14)
<223> OTHER INFORMATION: /note="2'-F modified nucleotide"
<220> FEATURE:
<221> NAME/KEY: misc_feature
<222> LOCATION: (15)..(15)
<223> OTHER INFORMATION: /note="2'-OMe modified nucleotide"
<220> FEATURE:
<221> NAME/KEY: misc_feature
<222> LOCATION: (16)..(16)
<223> OTHER INFORMATION: /note="2'-F modified nucleotide"
<220> FEATURE:
<221> NAME/KEY: misc_feature
<222> LOCATION: (17)..(17)
<223> OTHER INFORMATION: /note="2'-OMe modified nucleotide"
<220> FEATURE:
<221> NAME/KEY: misc_feature
<222> LOCATION: (18)..(18)
<223> OTHER INFORMATION: /note="2'-OMe modified nucleotide"
<220> FEATURE:
<221> NAME/KEY: misc_feature
<222> LOCATION: (19)..(19)
<223> OTHER INFORMATION: /note="2'-F modified nucleotide"
<220> FEATURE:
<221> NAME/KEY: misc_feature
<222> LOCATION: (20)..(20)
<223> OTHER INFORMATION: /note="2'-OMe modified nucleotide with a
3'-phosphorothioate linkage"
<220> FEATURE:
<221> NAME/KEY: misc_feature
<222> LOCATION: (21)..(21)
<223> OTHER INFORMATION: /note="2'-OMe modified nucleotide with a
3'-phosphorothioate linkage"
<220> FEATURE:
<221> NAME/KEY: misc_feature
<222> LOCATION: (22)..(22)
<223> OTHER INFORMATION: /note="2'-OMe modified nucleotide"

<400> SEQUENCE: 247
uuuuagguug uuuucuccac gg 22

<210> SEQ ID NO 248
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 248

Cys Arg Glu Lys Ala
1 5